US007060444B1

(12) United States Patent
McCabe et al.

(10) Patent No.: US 7,060,444 B1
(45) Date of Patent: Jun. 13, 2006

(54) ZONE 3 NECROSIS ASSOCIATED MARKERS AND METHOD OF USE THEREOF

(75) Inventors: Denise A. McCabe, Bethel, CT (US); Oswald R. Crasta, Clinton, CT (US); Darius M. Dziuda, Bethany, CT (US); Craig L. Hyde, Old Lyme, CT (US); Robert Gerwien, Branford, CT (US)

(73) Assignee: CuraGen Corporation, New Haven, CT (US)

( * ) Notice: Subject to any disclaimer, the term of this patent is extended or adjusted under 35 U.S.C. 154(b) by 247 days.

(21) Appl. No.: 10/663,418

(22) Filed: Sep. 15, 2003

Related U.S. Application Data

(60) Provisional application No. 60/410,763, filed on Sep. 13, 2002.

(51) Int. Cl.
*C12Q 1/68* (2006.01)
*G01N 33/48* (2006.01)
*G01N 33/50* (2006.01)
*C07H 21/02* (2006.01)
*C07H 21/04* (2006.01)

(52) U.S. Cl. .............................. 435/6; 702/19; 702/20; 536/24.31

(58) Field of Classification Search .................... 435/6; 702/19, 20; 536/24.31
See application file for complete search history.

*Primary Examiner*—David Guzo
*Assistant Examiner*—Michael Burkhardt
(74) *Attorney, Agent, or Firm*—Daniel K. Rieger; George M. Yahwak; CuraGen Corporation

(57) ABSTRACT

Disclosed are methods of identifying toxic agents, e.g., hepatotoxic agents, using differential gene expression.

10 Claims, 2 Drawing Sheets

SEQUENCE LISTING

<160> NUMBER OF SEQ ID NOS: 171

<210> SEQ ID NO 1
<211> LENGTH: 2018
<212> TYPE: DNA
<213> ORGANISM: Rattus norvegicus

<400> SEQUENCE: 1
tttttttttt tttttttttt gaaggttttc aaccggcatg tttttattaa tgaaatggaa 60

-continued

```
tggaagcagt cagaacagag attacagaat tacagaatgg atcagttatc tgttaagttt    120
tacagggctg gtgtgtgttg tttctgccta agggtcctgc tcaaaagatc ttggaatcca    180
cttgggaagc atcttagata tagatggttg ctgtgtcact tatgatacgg tccctgaatg    240
gttctatgtc actcgtggag gtggtgtcct atccccctat ctgaaatgag attgacgtcg    300
ggtgactttc tcttcgctgc agtgactcct gtgcgcctgt aatgcgacag gcacgtagga    360
aatgtgttca ggatttactg tggacttctc ctttcttcct tctaggtaaa attctaaagc    420
gtagttttgt aactgtgaaa tgctatctgt gactccattt tgtctaacta gcaccaatca    480
caggtgtaag ccggcatcaa cacaaacgct ggtttagaga tgccttctcc ttccgggtgc    540
acactgtggc ccggacctgg aggaattcgc cccgaaccgc tggcctgtgg ctactgtgcg    600
gatttgaatt tttgtttttc gaagagcgct ctcagctgct gctcagtggt ggcttccttc    660
tgctgcatca gctctgctgc ccctttcgtc actccccaag catccggctt ggacatcgaa    720
ggattgtacg gtctgccgga agctattcga agattctgcc agtattcttt cctggccctt    780
gccctgatcc agggtttggt gtgcatgtcc aaaccacttc cccagctgcc atgtttttct    840
gaagctggtg gtaaaaatcc cctttctggg gcgagctcct ctgcaatggc cctgatgtgg    900
tagggctcaa atccgcagca gccgccaatg tacctgaccc ccaggttgta ggcctctctg    960
gcgtattttt gaatatccca tctggtggca actctgggtt ccaatccaaa ggggaattct   1020
gggagatcaa taaatccctg tttgccacag tcaggggtgt ggtaggccag gggctggctc   1080
atcaagtaag ccttcagccg agctgcttcc agaccctcct tcatgagctt tattgtctgc   1140
aagctggtgc tggggtcgaa gtggcagttc acaccgacaa tggcggcacc tgcttttacc   1200
aaacgcactg cgcactctcc aggagacacg ccatgtagat ctccttcagg tccgatgcac   1260
atggtagccg ctataggctt cccggatgtt tttaaggcct cgactgccca cacggcttct   1320
tcaacatgtt caaaatactc tgcaatgagg aagtccacat tcttcttcat gaagacctca   1380
agctgttggt gaaatatctt tttaacttcc gtctcactct tgcagctgag gtaggaaggt   1440
gtctgactca cacctcctgc aaccaatgca tccccttcgt cagcaacttg ccgtgcaatg   1500
tcacaagcag cttcattgac cttctgccca gatatcttct ctgccacgta gttccctcgg   1560
ttttccagct tgtcctcact tgcatagaaa gtgaaggtct gcatgacgtt cgatccagct   1620
ctgaggaact cccgatgaag ctgccgaact gcctcggggt gctccaccgc agcctctggg   1680
gtccagggtc cagcctttac gtagcccctc ttttccagtg caaagacaaa tcccccatct   1740
ccgatcacga cttcgccagc atttaagcgt tctaagattc ccctcttggc cttcttgccg   1800
gcaatcggtg ccatctttcc ggtgtcctga gtggcgctga acgcagctgc ggactggaca   1860
ggagcggtct ccagcaaagg cttgactgct gagccgcttc tggcctcttt atatacagca   1920
gctaggattc cccagccttg accgggtcca acacatggcc tcaggcgggg aacacgccca   1980
ccagcctttg aaacaggcct ggggctagct gggaattc                            2018
```

<210> SEQ ID NO 2
<211> LENGTH: 1984
<212> TYPE: DNA
<213> ORGANISM: Rattus norvegicus

<400> SEQUENCE: 2

```
gacatggcac cagccggagg cccacgagtc aagaagggta tcttggagcg tctggacagc     60
ggggaggttg tggttgggga cggcggcttt ctcttcactc tggaaaagag aggctttgtg    120
aaggcaggac tttggactcc agaagcagtg gtagagtatc caagtgcagt tcgtcagctt    180
```

-continued

```
cacacagaat tcttgagagc gggagccgat gtcttgcaga cattcacctt ttcggctgct    240

gaagacagaa tggaaagcaa gtgggaagct gtgaatgcag ctgcctgtga cctggcccag    300

gaggtggctg atggaggggc tgctttggtg gcagggggca tctgccagac atcactgtac    360

aagtaccaca aggatgaaac tagaattaaa aacattttcc gactacagct aggtgttttt    420

gccaggaaaa atgtggactt cttgattgca gagtattttg agcatgtgga agaagccgtg    480

tgggctgtgg aagtcttgag agaggtgggg gcacctgtgg ctgtgaccat gtgcatcggc    540

ccagaggggg acatgcacgg cgtgacaccg ggagagtgtg cggtgagact gtctcgtgca    600

ggggcgaaca tcattggggt aaactgccgg tttgggcctg gaccagctta caggaccatg    660

agctcatgaa ggagggcctc agggattgcg gcctactagc tcaccttatg gtccagtgct    720

tgggttttct cacactggga ctgtggcaag ggagggttgt ggacttcctg atatcctttt    780

cgcctggggc aagagttgcc accagatggg atattcaaaa atacgccaga gaggcctaca    840

acctgggggt caggtacatt ggcggctgct gcggatttga gccctaccac atcaggggcc    900

attgcagagg agctcgcccc agaaagggga tttttgccac cagcttcaga aaaacatggc    960

atctggggaa gtggtttgga catgcacacc aaaccctgga tcagagcaag ggctagacgg   1020

gaatactggg aaactctgtt gccagcttcg ggaagacctt tctgtccttc cctatcaaag   1080

ccagatgctt gagaagccat gaaagagacc tctgaagtga cagaaaggag gaaacagcct   1140

caagccccat ctggaatctt cctggctgct gtcctcagcc cgttcttctg gctgttgagc   1200

atcgatgagc tgtcgtccct tccaattgag tgacatatca ctcctgagta tgcccactag   1260

atgcggtgga gatgcagagg catccggacc ccacgcccca ccccctcccc tcacacactt   1320

actctctgcc tagtaatgcc acagagcttc catccccatc caaaggtcat caggcatggc   1380

tatcagttgg ctctcagggt ggatttgaca ttctcagatg attagaagtt ggcaagaagc   1440

aaccttggtg aataactctg gtgtctaaac tctgtacttg agttacagtc tcagtagagg   1500

agacgccaaa gctgttgcga gtgacggcag aattattgaa cagtcatgat gcttggcttt   1560

caaaggcgat tatcgcttta aggtcttaga attagtaagt gcatctttat aaccaggcat   1620

agctagatca taaactactg atggccaagg accatagaac gtgcttctta ccttcctctc   1680

tagttagcat tacgacaaac ataatcacca acgctcaggg aaacacttgc tgattcaagt   1740

aaaatgcatg aaccttggaa gacctttcta gaagtcagag atcaagttca tcttgttcta   1800

gcactttcca cattcatgtt tggtttgtat gctgcgccct acttttgttt tttgctacaa   1860

tgtaacaaat tagtgagtaa ccattagtga aattgcgaat aattttcctt ttctaaattt   1920

tgatttcttt ggaacattga tttaaaaaaa atagtgtgtt gcttgtcaaa aaaaaaaaaa   1980

aaaa                                                                1984
```

<210> SEQ ID NO 3
<211> LENGTH: 2510
<212> TYPE: DNA
<213> ORGANISM: Rattus norvegicus

<400> SEQUENCE: 3

```
ccatagcgaa gacttcatga agactgtccc aggcatgctg tgacacaaac tacagaaggt     60

gggaaaagat ctttgtggtc aaaccatccg gaccttggct accgcagaca gaacaatact    120

gaccgcattc actcatacac agttctcggc acctcccagt gctcagagca gaccctcaag    180

gagatgagca gatccaggat ggggagccca atgcaccgag tgtccctggg ggacacctgg    240
```

-continued

```
agctggcaag tgcacccgga catagacagc gaaaggcact caccgtcctt cagtgtggag    300
cgactcacca acatccttga tggaggcctc ccaaacaccg tgctgcgaag aaaagtcgaa    360
agcatcatac aaagtgaccc agtgtttaat ttgaagaagc tttacttcat gacccgagag    420
gagctatatg aggatgcgat tcaaaagaga ttccatctcg agaagctagc ctggagcctg    480
ggctggtcag aagatggtcc tgaacgcatt tatgctaaca gagtccttga tggaaacgtc    540
aacttaagct tacatggtgt tgccatgaat gctatccgaa gcctgggctc agatgaacag    600
attgctaaat ggggccaact ctgcaaaaac ttccaaatca tcacaacata cgcccagaca    660
gagctgggac acgggacata cctacagggc ctggagactg aagccaccta tgatgaagcc    720
aggcaggagc ttgtgataca cagccctacg atgacttcca ccaagtggtg gcctggggac    780
ttgggatggt cggtcaccca tgctgtggtc ctagcccagt tgacctgctt aggagtccgg    840
cacggcatgc acgccttcat tgtgcccatt cggagcctag aggatcacac cccactgcca    900
ggaatcacag ttggggacat aggccccaag atgggtttgg aacacataga caatggcttc    960
ctgcaactga accacgtgcg ggttcccaga gaaaacatgc tcagtcgctt tgcagaggtc   1020
ttgccagatg gtacctacca gaggcttggg acgccacaga gcaattatct tggcatgttg   1080
gtgacccggg tgcagctgct gtgtaaagga atcctaccct ccctccagaa ggcttgcatc   1140
attgccacgc gctactcagt aatccgccat cagtctcgac ttcggcccag tgacccagag   1200
gcaaaaatcc tggaatacca gacgcagcag cagaaactcc ttcctcagct tgctgtgagc   1260
tatgccttcc acttcacggc caccagcctc tcagaattct tccacagctc ctacagtgct   1320
attctgaaga gagacttcag cctcctgcct gagctccatg cattgagcac tggtatgaag   1380
gccacgtttg cagacttctg tgcccagggc gccgagatct gtcgcagagc ttgcgggggc   1440
catggctact caaagctgag cggcctgccg acactggttg ctcgagcaac agcctcttgc   1500
acatatgagg gtgagaatac ggtgctctac ctgcaagtgg ccaggtttct gatgaagagc   1560
tatctgcagg ctcaagcgtc cccaggcgcc acaccacaga agcctctccc tcagtccgtc   1620
atgtatattg ccacacaaag gccagccagg tgctcagccc agactgcagc tgacttccgc   1680
tgcccagatg tctataccac agcctgggca tatgtgtcta ccaggctcat aagagatgca   1740
gcacaccgta cacagaccct catgaagtcc ggggttgacc agcatgatgc ctggaatcaa   1800
actactgtca tccaccttca ggctgctaag gctcactgct acttcatcac tgtgaagaat   1860
ttcaaggaag ctgtggagaa actagacaag gaaccagaga ttcagcgtgt gctccaacgc   1920
ctctgtgacc tctatgcctt acacggtgtt ctgactaact caggggactt tctgcatgat   1980
ggcttcctgt ctggggccca ggtggacatg gccagagaag ccttcctaga cctgcttccc   2040
ttgatccgga aggatgccat cttgttaacc gatgcttttg acttctcgga ccattgttta   2100
aactcggcac ttggctgtta tgatggacac gtctacgaac gcctgtttga gtgggctcag   2160
aagtacccag ccaatactca ggagaaccct gcctataaga agtatatccg accactgatg   2220
ctcggctgga gacacaagat gtgaaaagtc aaaggatttg ggaccgagaa gcaccacggc   2280
cttactatgg cacatataca tagagaattt aaagcacggg gggggggggg gggggggtgc   2340
tgctcggtta aatcaggtag taaattggta catgaatgga tggtcatcct attagtctac   2400
tattgagcat gtttgaaact ttcccttgtc catctatagc atgtatttgg ctaaatgcta   2460
aaatttttgt tttacataca ggaaaagcta ataaacttgt cagttacaaa              2510
```

<210> SEQ ID NO 4
<211> LENGTH: 4601

-continued

<212> TYPE: DNA
<213> ORGANISM: Rattus norvegicus

<400> SEQUENCE: 4

```
tttttttttt tttttttttt tttttttttt tttttttttt taacaatgag acatatacag     60
ctttatttaa cctgtaaaaa gtcacactct gcagagtgac acctttctta tctcagcaga    120
aagcaaggag tgtgtgaaaa accttttcct caggttggga accgtatgac cctggctggg    180
ctcacatgtg gatccttcca gagtccttgt gtgtggcagc ttcttcccag aggtctccct    240
ggctggtgtg acccctcacc aacaacagac agggggggcaa aatatttcta cctggacaag   300
gctgccctga gattgtccct ttccctccta ttaagggaca ttacatgctt aagaccttcc    360
cagaaaagtc accttcaagg tgacttggct ttcatcatgt ctgctgacac ttaggctcca    420
cttatttacc atgatggtgt gtgctaacgg tccttcctct tccaataacc tcaccatcga    480
tggcatttta aatatcactc tgttctctgg gaccgaggga tggagaaccg ctctccctca    540
gaccaggttt tgactcagga gctgggtttt attttgaaga aacttcccta catgagtcat    600
gagcaaggga aatggatgtg gggagggag gaggggctct gagggaggag tacgaatgga     660
ggaaagaaaa gaatgtcatt ggcgagggag agcatggcac agcccagggc ttccctctct    720
tccctccacc tccttccttt cttcctgcag acggggaact ccagtccctc tcagatggga    780
actgagttca ccctggttcc caacgcatac ggtttcagct tcgcttctgt ttagcatcac    840
ctttctctgt ctttatcgtc aatcattacg cgtttggttt cccacggctt ctacacactt    900
ccatggccga gaaatggcgg ttgcccatgg gcagcaggtc cagttcattc ttcacaggtg    960
ggaagttgtt tctcagccaa gaagctgatc tttctggcac attccaccgt ggtcaacctc   1020
tgtttcccct ttgaccctgg tccttttcat tcctctcctc ccctaggaac atcgagttct   1080
catgccatta ccgacggtga ctggttcatc tggaccctca tcgagtggat gctgctaaga   1140
atcttcttct gatggcctgc caaggtgacc cctattctca ggaggtcttc tgatgtcatc   1200
tgggtgacca gctggaggga ggtgaagcca gcggtgagga agctgtccct gtactggacc   1260
attttgatgg cacttagcca gtcatccacg gtggtaaagg ccgtgaagtc tgggatagag   1320
cggtcaagca ggggttggga aggcacagcg gtgatggttg ccacagtctt gagactagct   1380
gggttccgga tcatcttgtc cagggtgttg acgatctctg caaaacgggg ccggctattt   1440
cgatccttct gccaacagtc cagcatgagc tggtgcaggg cagctgggca gtccatagga   1500
gggggcagcc ggtagtcctg ctcaatggca ttgatgacat cttgattgga catatcccag   1560
taaggtctct ctccaaatga cattacttcc cacatgacaa tcccgtagct ccagacatcg   1620
ctggctgacg taaacttgcg gtaggcgatg gcctctggag ctgtccatct aacaggtatc   1680
ttccctccca aggagctggt gtaggtgggg tctgaggtgt catcctggag gtagcgagag   1740
aggccaaagt cagacacttt gcacaccagg ttgctgttca ccagaatgtt cctagcagcc   1800
aggtcccggt gcacataatt catctcagat aggtacttca tgccagcagc gatgcccctc   1860
agcatcccca caagctggat cacggtgaac tgtccgtcat tttgccggag gaaagagtct   1920
aaagcgccat tctccatgaa ctccgtaatg atcatgacag gtcggctctt ggtgacaaca   1980
ccctctaggc gaatgatgtt gggatggtca aactggccca tgatgctcgc ctcgctcaga   2040
aaatcccgac gctgtttctc tgagtaccca gctttcaggg tcttgatggc cacatagatt   2100
tccctcttgc ctggcagctt caatcggccc ttgtacactt ctccaaactc ccctgctccg   2160
atgacctctt caattttcac aaaagacaca tcaatctcct tggcaaactc ccggacagct   2220
```

-continued

```
tcattagggt cctcataagt gaacgggtca atgtagatct tcatccctgg ggagcctcgg   2280
cctgtgctgt aatgctgaag tttatcactg tacacagcct ctttgctgta agctcgtttc   2340
ctgctgcaga caatggagat agccaccaga gacacaacaa atacaacccc agctgctgca   2400
gagccagcga tcaggggtag ctgctctctc agctccgact tgtaatcatc atctgtcaga   2460
gtctggaagc acatcttgcc actgaacttg ccatagccag ccacggttcg agctcgtacc   2520
tggaccacat acaccatgcc gggccgtagc ccatcgatac gtgccgtgtt ggtctggctc   2580
ctggccatgg aagagttgaa ctcattgtgc tccttctcat agtaccggat ctcatagtcc   2640
aggatgatgc cattaggctg ctccggctga ggccatgaca aggtgatgct cctcatggtg   2700
gcactgacct ggtgcatgat aggaacagtg gagggggcag cttggtttgt ggtgatgttg   2760
acagagacat gctgtggggg gaagggactc ttgctagaga ctccattgat ggcctggata   2820
tcaaaagtgt atggggtgtg ggcccatagg ctactgatag agacacgaca ctcagtcaag   2880
cccagctgtc tgggtacaaa ctccacattg tcatcgcagc gggagcaact ccggcggtct   2940
gctctgcact tcttgcagat gatgttgtag gtcacatcat ctcgcccacc ggtctctctt   3000
ggagggtgcc actctagaat gatagatgtc tcattcacaa tggagatgac atttcgaggg   3060
cctgatggga cactagtgca cgccacttct gggggatcaa agtctgctcg gtaatagcca   3120
gtccggcagg tgcagatggg agacgcctct gaaggggagc ggctgttgga ggggcagtgg   3180
gagcagcctt cagcttcctg gctggccttg aaggttcccg caggacaggc cttgcaggcc   3240
acgctgttct caggttcata gccagcctta caggtgcagc gcccaatggg caccatccac   3300
tctccatctc cattgcagta gagttttatg ggcacatcca cttcttctgc attagggatg   3360
catgtgcccc gagcaatcac cagagatgtg ctctctgctc ctgtcatggt ttctgggaac   3420
actgcaaaat tttgcacaat gctgggacac tttttgaaga agacacggac agaaagtaga   3480
gacatacagg ctccataatc ctggaaagcg aggtaaaaac cattcctagt aagaggccca   3540
aagctcctga cttctgtgtt gaccttcatc aaccttcccc caaaatccac ctgggagaag   3600
ctctcatctg cagcaatggt gtcaactttg aggtaggggg cttcagacca gaaggctgac   3660
ttcttggtgg caatgacaga gtcagtctca tagtagtata agttgaaggt ctctttgcag   3720
gagcctggga catttggaag gctgctgcag tccctcacag tgaagcgcat ctctgtatag   3780
atgcgatggg cgccccgtct gttgataaag gtggtaagca gccagttgtt ctggttgggt   3840
tcaaagacgt tgcacacttg gtaagtacgg atggtgttca ggttttcatc gtagccactg   3900
acttcttccc acccagaggc agggttggcc gtccatccca actctgcagt ggcagtcctt   3960
gtgtccatca atgtttcttc catcgcggcc actgcagatg ccaggaggaa cagcagcagg   4020
caatccaggg ccatcgccgg ccagcggccc ccaggccgag ccccagcgga gacgcgccgc   4080
gtcccagggc gccgctgcgc tcccggcggg tggcttctcc gtgtcctttc gcgctctggc   4140
cgggaccgga ctccccggag cgcggcgtgg gcgtgggcgg gagtgtgcgc gcgtggggcg   4200
gtgcgggcgc gcgtggatgt gggtgtgcat gtgtgtgtgt gtgtttatgg gagaggtggg   4260
tgtgtgcgtg cgtgtgtgag agagggtgag ggagagcgag ccaaaccata aaaagatgga   4320
gggggagttg tgggtgggcg accctgctag tttcatagct ggcattcttg gggctggaaa   4380
ccccatggca caagacgtta ggatggctgg tctgctcaac cactgtgccg tgtgtgaggg   4440
gtctctcggc ttgtgtctct atcctgctct cattgagtcg gatgacctgt acagctctgt   4500
ctaccatgga ggatgtattg tgaagtctct gtgctaagga ctcacgtttg ggtgctttgg   4560
agatgaaatg gatgacatgt acactggata tccccctcgt g                       4601
```

-continued

<210> SEQ ID NO 5
<211> LENGTH: 902
<212> TYPE: DNA
<213> ORGANISM: Rattus norvegicus

<400> SEQUENCE: 5

```
ccccccctcg aggtgttttc tttcatttca ttccttgtct ttagggcttt ttttttttc      60
aaggtctcat tatttatttg ttactcttta aagacttatt tttgactgga ctcagattta    120
gaagtagaag ctctcagcga agacagccta cgtctcttgg caatctgttc ctggcgcttc    180
tctttggctt ccttcattct cttggccaaa agtttagcat attctgcagc ctcctccttg    240
tttttcttag tgcgttgctt cttcagagca atacgtcggc gtttgtgttg caggacacgg    300
ggagtaacaa gacgctgaat cttgggcgct ttggtcctgg gcttcttacc ttctttgttt    360
aagggctttc tgacaacata ctggcggaca tcatcttctt tggagagatt aaaaagcttt    420
cggattctac tagctctttt aggtcccaac cgacgaggca cagtggtatc tgtcagtcct    480
ggaatatcct tctctccttt ttttacaata accaagttga gaacactcag gttggcatcc    540
acaatgcatc ctcggacaga cttgcgcttc ctctctccag ttctcctagg tctataacaa    600
gaatgcccct tactcaaaag caggcgcact ctgccatggg tcaaaacgcc ttgcttcatg    660
ggaaaacctt gtttgtcatt cccaccgctg atccggacca cataaccctt ccactcttca    720
ccaagagcat cagcagctac ttctgtggcc atgcgcttct catagaacgt acgaagcttg    780
cgttcgtcat ccacttctat gagtttctga cagccagtgg cagggaagga gatattcagc    840
ttcatcttga cacagccgac cgcctaggag gcgtgttacc attctgatgt tggagcggcc    900
gc                                                                   902
```

<210> SEQ ID NO 6
<211> LENGTH: 2560
<212> TYPE: DNA
<213> ORGANISM: Rattus norvegicus

<400> SEQUENCE: 6

```
agttgcttca gtgtcccggt gcggttagtc acgtttcgtg cgtgctcatt ctgccaagat     60
gcctgaggaa acccagaccc aagaccaacc aatggaggaa gaggaggtcg aaacctttgc    120
ctttcaggca gaaattgccc agttaatgtc cttgatcatc aacactttct actcgaacaa    180
agagatcttt ctgagggagc tcatttccaa ctcctcagac gctctggata agatcagata    240
cgagagcttg accgacccta gtaaactgga ctcggggaag gagctgcaca ttaatctcat    300
tcccaacaag caagaccgaa ccctcactat tgtggatact ggcattggaa tgaccaaggc    360
tgacttgatc aataaccttg gcactattgc caagtcaggc accaaagcct tcatggaggc    420
tttgcaggct ggtgcagata tctctatgat tggccagttt ggtgttggtt tttactctgc    480
gtatttggtt gctgagaaag tgactgtcat caccaagcat aatgatgacg agcagtacgc    540
ctgggagtcc tcagctggag gatccttcac tgtgaggaca gacacaggtg aaccaatggg    600
tcgtggaaca aaggttatct tgcatctaaa agaagaccaa actgagtatt tggaggaaag    660
gagaataaaa gaaattgtga agaaacattc tcagtttatt ggctacccca ttactctctt    720
tgtggagaag gaacgtgaca aggaagtcag tgatgatgag gctgaagaaa aggaagagaa    780
agaggaagag aaagaaaaag aagaaaagga gtctgatgac aagcctgaaa tagaagatgt    840
tggttctgat gaagaagaag aagagaagaa ggatggtgac aagaagaaaa agaagaagat    900
```

-continued

```
aaaggaaaag tacattgatc aagaagaact caacaaaaca aagccgatct ggaccagaaa    960

tcctgatgac attacgaatg aagaatacgg agagttctac aagagcttaa ccaacgactg   1020

ggaagaacat ttggcagtaa agcatttttc tgttgaagga caattagaat tccgggctct   1080

tctttttgtc ccaagacgcg ctccttttga tctatttgaa aacagaaaga aaaagaacaa   1140

catcaagttg tatgttcgca gagtttttat catggataac tgtgaggagt taatccccga   1200

gtatctgaat ttcatcagag gggtggtgga ttctgaggat ctccctctaa atatttcccg   1260

tgaaatgctg caacaaagca aaattctgaa agttatcagg aagaatttgg tcaagaaatg   1320

cctagaacta tttactgaac tggctgaaga taaagagaac tacaaaaagt tttatgagca   1380

gttctcaaaa aatataaagc ttggaattca tgaagactct caaaatcgga agaagctttc   1440

agagctgttg agatactaca catctgcttc tggggatgag atggtttctc tgaaggacta   1500

ctgcaccaga atgaaggaaa accagaagca catctatttt atcacaggtg agaccaagga   1560

ccaggttgct aactcagcct ttgtggaacg tctccgaaag catggcttag aagtaatcta   1620

tatgattgag cccattgatg agtattgtgt gcaacagctg aaggaatttg agggcaagac   1680

cttggtgtca gttaccaaag aaggactgga acttccagaa gatgaagagg aaaagaagaa   1740

acaggaagag aaaaagacaa aatttgagaa cctctgcaaa attatgaagg atattttaga   1800

gaaaaaggtt gaaaaggtgg ttgtgtcaaa ccgattggtg acatccccat gctgtattgt   1860

cacaagcaca tatggctgga cagcaaacat ggagagaatc atgaaagctc aagccctcag   1920

agacaactca acaatgggtt acatggcagc aaagaaacac ctggagataa accctgatca   1980

ctccattatt gaaaccttaa ggcaaaaggc agaggctgac aagaatgaca agtctgtgaa   2040

agatctggtc atcttgctgt acgaaacagc actcctgtct tccggcttca gtctggaaga   2100

tccccagacc catgctaaca ggatctacag gatgatcaag cttggtctag gtattgatga   2160

ggatgatcct actgtggatg ataccagtgc tgctgtaact gaagaaatgc cacccctgga   2220

aggagatgat gacacatcac gcatggaaga agtagactag gcttcaccag aactatgtgt   2280

ttgatgctta ccttcattcc ttctgataat atattttcca tgatttttgt ttatttttgt   2340

taacatttaa aacatctgtg tggcatgaaa actaggggaa ggtaaaaatt tctacatgtg   2400

atactgtgat actataggtt tgactcaaga ggttgataga acgtttgttg taagacgtaa   2460

tgtaacctac ggtacttgtt aactatgggg gtctgaaagt gtttagctgt tgagctggat   2520

tcctttagta gaccaaatta agatgactta agtttcatct                         2560


<210> SEQ ID NO 7
<211> LENGTH: 1567
<212> TYPE: DNA
<213> ORGANISM: Rattus norvegicus

<400> SEQUENCE: 7

ttgctcctcc ttgctctcct cgtgggcttc ttgttactct tagtcagggg acacccaaag     60

tcccgtggca acttcccacc aggacctcgt ccccttcccc tcttggggaa cctcctgcag    120

ttggacagag gggcctcct caattccttc atgcagcttc gagaaaaata tggagatgtg    180

ttcacagtac acctgggacc aaggcctgtg gtcatgctat gtgggacaga caccataaag    240

gaggctctgg tgggccaagc tgaggatttc tctggtcggg gaacaatcgc tgtgattgag    300

ccaatcttca aggaatatgg tgtgatcttt gccaatgggg aacgctggaa ggcccttcgg    360

cgattctctc tggctaccat gagagacttt gggatgggaa agaggagtgt ggaagaacgg    420

attcaggagg aagcccaatg tttggtggag gaactgcgga aatcccaggg agccccactg    480
```

-continued

```
gatcccacct tcctcttcca gtgcatcaca gccaacatca tctgctccat tgtgtttgga    540

gagcgctttg actacacaga ccgccagttc ctgcgcctgt tggagctgtt ctaccggacc    600

ttttccctcc taagttcatt ctccagccag gtgtttgagt tcttctctgg gttcctgaaa    660

tactttcctg gtgcccacag acaaatctcc aaaaacctcc aggaaatcct cgattacatt    720

ggccatattg tggagaagca cagggccacc ttagacccaa gcgctccacg agacttcatc    780

gacacttacc ttctgcgcat ggagaaggag aagtcgaacc accacacaga gttccatcat    840

gagaacctca tgatctccct gctctctctc ttctttgctg gcactgagac cagcagcacc    900

acactccgct atggtttcct gctgatgctc aagtaccccc atgtcgcaga gaaagtccaa    960

aaggagattg atcaggtgat cggctcacac cggctaccaa cccttgatga ccgcagtaaa   1020

atgccataca ctgatgcagt tatccacgag attcagaggt tttcagatct tgtccctatt   1080

ggagtaccac acagagtcac caaagacacc atgttccgag ggtacctgct tcccaagaac   1140

actgaagtgt accccatcct gagttcagct ctccatgacc cacagtactt tgaccaccca   1200

gacagcttca atcctgaaca cttcctggat gccaatgggg cactgaaaaa gagtgaagct   1260

ttcatgccct tctccacagg aaagcgcatt tgtcttggcg aaggcattgc ccgaaatgaa   1320

ttgttcctct tcttcaccac catcctccag aacttctctg tgtcaagcca tttggctccc   1380

aaggacattg acctcacgcc caaggagagt ggcattggaa aaatacctcc aacgtaccag   1440

atctgcttct cagctcggtg atccggctga ggcagccagg tgccccagtt ctgttgggaa   1500

tggcctcatg tttctgcctc tggggacct gctgaaaacc aggctccaag gccactgctc    1560

cacatct                                                             1567
```

<210> SEQ ID NO 8
<211> LENGTH: 1686
<212> TYPE: DNA
<213> ORGANISM: Rattus norvegicus

<400> SEQUENCE: 8

```
cccagtgccc ttttgtcctg tgtatctgtt tcgtggtgtc cttgccaaca tctatggtgt     60

gggtaaggga atgaggagtg aatagccaaa gcaggaggcg tgaacatctg aagttgcata    120

actgagtgta ggggcagatt cagcataaaa gatcctgctg gagagcatgc actgaagtct    180

accgtggtta caccaggacc atggagccca gtatcttgct cctccttgct ctccttgtgg    240

gcttcttgtt actcttagtc aggggacacc caaagtcccg tggcaacttc ccaccaggac    300

ctcgtcccct tcccctcttg gggaacctcc tgcagttgga cagaggaggc ctcctcaatt    360

ccttcatgca gcttcgcgaa aaatatggag atgtgttcac agtacacctg ggaccaaggc    420

ctgtggtcat gctatgtggg acagacacca taaaggaggc tctggtgggc caagctgagg    480

atttctctgg tcggggaaca atcgctgtga ttgagccaat cttcaaggaa tatggtgtga    540

tctttgccaa tggggaacgc tggaaggccc ttcggcgatt ctctctggct accatgagag    600

actttgggat gggaaagagg agtgtggaag aacggattca ggaggaagcc caatgtttgg    660

tggaggaact gcggaaatcc cagggagccc cactggatcc caccttcctc ttccagtgca    720

tcacagccaa catcatctgc tccattgtgt ttggagagcg ctttgactac acagaccgcc    780

agttcctgcg cctgttggag ctgttctacc ggaccttttc cctcctaagt tcattctcca    840

gccaggtgtt tgagttcttc tctgggttcc tgaaatactt tcctggtgcc cacagacaaa    900

tctccaaaaa cctccaggaa atcctcgatt acattggcca tattgtggag aagcacaggg    960
```

-continued ccaccttaga ccccagcgct ccacgagact tcatcgacac ttaccttctg cgcatggaga 1020
aggagaagtc gaaccaccac acagagttcc atcatgagaa cctcatgatc tccctgctct 1080
ctctcttctt tgctggcact gagaccggca gcaccacact ccgctatggt ttcctgctca 1140
tgctcaagta cccccatgtc acagtgaaag tccaaaagga gattgatcag gtgattggct 1200
ctcacaggcc accatccctt gatgatcgta ccaaaatgcc atacactgat gcagtcatcc 1260
acgagattca gaggtttgca gatcttgccc caattggttt accacacaga gtcaccaaag 1320
acaccatgtt ccgagggtac ctgctcccca agaacactga ggtgtatccc atcctgagtt 1380
cagctctcca tgacccacag tactttgacc atccagacac cttcaatcct gagcacttcc 1440
tggatgccga tgggacactg aaaaagagtg aagcttttat gcccttctcc acaggaaagc 1500
gcatttgtct tggcgaaggc attgcccgaa atgaattgtt cctcttcttc accaccatcc 1560
tccagaactt ctctgtgtca agccatttgg ctcccaagga cattgacctc acgcccatgg 1620
agagtggcat tgcaaaaata cctccaacgt accagatctg cttctcagct cggtgatcgg 1680
gctgag 1686

<210> SEQ ID NO 9
<211> LENGTH: 1476
<212> TYPE: DNA
<213> ORGANISM: Rattus norvegicus

<400> SEQUENCE: 9
atggagccca gtatcttgct cctccttgct ctccttgtgg gcttcttgtt actcttagtc 60
aggggacacc caaagtcccg tggcaacttc ccaccaggac ctcgtcccct tcccctcttg 120
gggaacctcc tgcagttgga cagaggaggc ctcctcaatt ccttcatgca gcttcgcgaa 180
aaatatggag atgtgttcac agtacacctg ggaccaaggc ctgtggtcat gctatgtggg 240
acagacacca taaaggaggc tctggtgggc caagctgagg atttctctgg tcggggaaca 300
atcgctgtga ttgagccaat cttcaaggaa tatggtgtga tctttgccaa tggggaacgc 360
tggaaggccc ttcggcgatt ctctctggct accatgagag actttgggat gggaaagagg 420
agtgtggaag aacggattca ggaggaagcc caatgtttgg tggaggaact gcggaaatcc 480
cagggagccc cactggatcc caccttcctc ttccagtgca tcacagccaa catcatctgc 540
tccattgtgt ttggagagcg ctttgactac acagaccgcc agttcctgcg cctgttggag 600
ctgttctacc ggaccttttc cctcctaagt tcattctcca gccaggtgtt tgagttcttc 660
tctgggttcc tgaaatactt tcctggtgcc cacagacaaa tctccaaaaa cctccaggaa 720
atcctcgatt acattggcca tattgtggag aagcacaggg ccaccttaga ccccagcgct 780
ccacgagact tcatcgacac ttaccttctg cgcatggaga aggagaagtc gaaccaccac 840
acagagttcc atcatgagaa cctcatgatc tccctgctct ctctcttctt tgctggcact 900
gagaccggca gcaccacact ccgctatggt ttcctgctca tgctcaagta cccccatgtc 960
acagtgaaag tccaaaagga gattgatcag gtgattggct ctcacaggcc accatccctt 1020
gatgatcgta ccaaaatgcc atacactgat gcagtcatcc acgagattca gaggtttgca 1080
gatcttgccc caattggttt accacacaga gtcaccaaag acaccatgtt ccgagggtac 1140
ctgctcccca agaacactga ggtgtatccc atcctgagtt cagctctcca tgacccacag 1200
tactttgacc atccagacac cttcaatcct gagcacttcc tggatgccga tgggacactg 1260
aaaaagagtg aagcttttat gcccttctcc acaggaaagc gcatttgtct tggcgaaggc 1320
attgcccgaa atgaattgtt cctcttcttc accaccatcc tccagaactt ctctgtgtca 1380

-continued

```
agccatttgg ctcccaagga cattgacctc acgcccatgg agagtggcat tgcaaaaata   1440

cctccaacgt accagatctg cttctcagct cggtga                             1476
```

<210> SEQ ID NO 10
<211> LENGTH: 1476
<212> TYPE: DNA
<213> ORGANISM: Rattus norvegicus

<400> SEQUENCE: 10

```
atggagccca gtatcttgct cctccttgct ctccttgtgg gcttcttgtt actcttagtc     60

aggggacacc caaagtcccg tggcaacttc ccaccaggac ctcgtcccct tcccctcttg    120

gggaacctcc tgcagttgga cagagggggc ctcctcaatt ccttcatgca gcttcgagaa    180

aaatatggag atgtgttcac agtacacctg ggaccaaggc ctgtggtcat gctatgtggg    240

acagacacca taaaggaggc tctggtgggc caacctgagg atttctctgg tcggggaaca    300

atcgctgtga ttgagccaat cttcaaggaa tatggtgtga tctttgccaa tggggaacgc    360

tggaaggccc ttcggcgatt ctctctggct accatgagag actttgggat gggaaagagg    420

agtgtggaag aacggattca ggaggaagcc caatgtttgg tggaggaact gcggaaatcc    480

cagggagccc cactggatcc caccttcctc ttccagtgca tcacagccaa catcatctgc    540

tccattgtgt ttggagagcg ctttgactac acagaccgcc agttcctgcg cctgttggag    600

ctgttctacc ggaggttttc cctcctaagt tcattctcca gccaggtgtt tgagttcttc    660

tctgggttcc tgaaatactt tcctggtgcc cacagacaaa tctccaaaaa cctccaggaa    720

atcctcgatt acattggcca tattgtggag aagcacaggg ccaccttaga cccaagcgct    780

ccacgagact tcatcgacac ttaccttctg cgcatggaga aggagaagtc gaaccaccac    840

acagagttcc atcatgagaa cctcatgatc tccctgctct ctctcttctt tgctggcact    900

gagaccagca gcaccacact ccgctatggt ttcctgctga tgctcaagta cccccatgtc    960

gcagagaaag tccaaaagga ggttgatcag gtgatcggtt cacaccggct accaaccctt   1020

gatgaccgca gtaaaatgcc atacactgat gcagttatcc atgagattca taggttttca   1080

gatcttgtcc ctattggagt accacacaga gtcaccaaag acaccatgtt ccgagggtac   1140

ctgcttccca agaacactga agtgtacccc atccggagtt cagctctcca tgacccacag   1200

tactttgacc acccagacag cttcaatcct gaacacttcc tggacgttaa cggggcactg   1260

aaaaagagtg aagctttcat gcccttctcc acaggaaagc acatttgtct tggcgaaggc   1320

attgcccgaa atgaattgtt cctcttcttc accaccatcc tccagaactt ctctgtgtca   1380

agccatttgg ctcccaagga cattgacctc acgcccaagg agagtggcat tggaaaaata   1440

cctccaacgt accagatctg cttctcagct cggtga                             1476
```

<210> SEQ ID NO 11
<211> LENGTH: 1760
<212> TYPE: DNA
<213> ORGANISM: Rattus norvegicus

<400> SEQUENCE: 11

```
cccagtgccc ttttgtcctg tgtatctgtt tcgtggtgtc cttgccaaca tgtatggtgt     60

gggtaaggga atgaggagtg aatagctaaa gcaggaggcg tgaacatctg aagttgcata    120

actgagtgga ggggcggatt cagcataaaa gatcctgctg gagagcatgc actgaagtct    180

accgtggtta caccaggacc atggagccca gtatcttgct cctccttgct ctccttgtgg    240
```

-continued

```
gcttcttgtt actcttagtc aggggacacc caaagtcccg tggcaacttc ccaccaggac    300
ctcgtcccct tcccctcttg gggaacctcc tgcagttgga cagagggggc ctcctcaatt    360
ccttcatgca gcttcgagaa aaatatggag atgtgttcac agtacacctg ggaccaaggc    420
ctgtggtcat gctatgtggg acagacacca taaaggaggc tctggtgggc caacctgagg    480
atttctctgg tcggggaaca atcgctgtga ttgagccaat cttcaaggaa tatggtgtga    540
tctttgccaa tggggaacgc tggaaggccc ttcggcgatt ctctctggct accatgagag    600
actttgggat gggaaagagg agtgtggaag aacggattca ggaggaagcc caatgtttgg    660
tggaggaact gcggaaatcc cagggagccc cactggatcc caccttcctc ttccagtgca    720
tcacagccaa catcatctgc tccattgtgt ttggagagcg ctttgactac acagaccgcc    780
agttcctgcg cctgttggag ctgttctacc ggaggttttc cctcctaagt tcattctcca    840
gccaggtgtt tgagttcttc tctgggttcc tgaaatactt tcctggtgcc cacagacaaa    900
tctccaaaaa cctccaggaa atcctcgatt acattggcca tattgtggag aagcacaggg    960
ccaccttaga cccaagcgct ccacgagact tcatcgacac ttaccttctg cgcatggaga   1020
aggagaagtc gaaccaccac acagagttcc atcatgagaa cctcatgatc tccctgctct   1080
ctctcttctt tgctggcact gagaccagca gcaccacact ccgctatggt ttcctgctga   1140
tgctcaagta cccccatgtc gcagagaaag tccaaaagga ggttgatcag gtgatcggtt   1200
cacaccggct accaaccctt gatgaccgca gtaaaatgcc atacactgat gcagttatcc   1260
atgagattca taggttttca gatcttgtcc ctattggagt accacacaga gtcaccaaag   1320
acaccatgtt ccgagggtac ctgcttccca agaacactga agtgtacccc atccggagtt   1380
cagctctcca tgacccacag tactttgacc acccagacag cttcaatcct gaacacttcc   1440
tggacgttaa cggggcactg aaaaagagtg aagctttcat gcccttctcc acaggaaagc   1500
acatttgtct tggcgaaggc attgcccgaa atgaattgtt cctcttcttc accaccatcc   1560
tccagaactt ctctgtgtca agccatttgg ctcccaagga cattgacctc acgcccaagg   1620
agagtggcat tggaaaaata cctccaacgt accagatctg cttctcagct cggtgatccg   1680
gctgaggcag ccatgtgccc cagttctgtt gggaatggcc tcatgtttct gcctctgggg   1740
gacctgctga aaaccaggct                                                1760
```

<210> SEQ ID NO 12
<211> LENGTH: 1733
<212> TYPE: DNA
<213> ORGANISM: Rattus norvegicus

<400> SEQUENCE: 12

```
gacttgggag gaaccagggc ctacacttag ccctggtaaa cagcagagca tgctgggata     60
attcttccca gaaaaggaaa agcaggcact tctgttccca gggaaaacaa caggagcact    120
ttggacctcc ctgctgcagt caggagtcat gtggctggaa cttgtcctgg cttcccttct    180
gggctttgtc atctactggt ttgtctcccg ggacaaggag gaaaccttac cactaggaga    240
tggatggtgg gggccagggt caaagccatc agccaaagaa gatgagagca tccggccctt    300
caaggtggaa acatcagatg aggagatcaa ggacttacac cagaggatag ataggttccg    360
ggcatcccca cctttggagg gcagccgctt ccactatggc ttcaactcca actacatgaa    420
gaaagtggtg tcctactgga ggaacgagtt tgactggagg aagcaggtgg agatcctcaa    480
ccagtaccct cacttcaaga ccaagatcga agggcttgac atccacttca tccatgtgaa    540
gcctccccag ctgccctcag ggcgcacccc aaagcccttg ctgatggtgc atggctggcc    600
```

-continued

```
tggatccttc tatgagtttt acaagatcat cccactactg actgacccca agtcccacgg     660
tctgagtgac gagcacgtgt ttgaagtcat ctgtccctcg attcctggct atggctactc     720
agaggcatcc agcaagaaag gtttaaattc ggtggccact gcgaggattt tctacaagct     780
gatgacacgg ctgggcttcc agaaattcta cattcaaggc ggggactggg ggtccctcat     840
ctgcaccaac atggcccaga tggttcccaa ccacgtgaaa ggcctgcact taaatatggc     900
tttcatttcg agaagttttt acaccatgac tcctctcctg ggccaacgct tcgggagatt     960
ccttggctac acagagaagg atatcgagct cttgtacccc tataaggaga aggttttcta    1020
cagcatcatg agggagagtg gctacttaca catccaagcc accaagccag acactgtggg    1080
ctgtgctctc aatgactctc ccgtgggcct ggctgcctac atcttagaga agttctccac    1140
ctggaccaag tcagagtacc gtgaactgga ggatggaggc ctggagagga agttctccct    1200
ggatgatctg ctggttaaca tcatgatcta ctggacgaca ggaaccattg tctcctccca    1260
acgctactac aaggagaatt tgggccaggg catcatggtc cataaacatg aggggatgaa    1320
ggtctttgtg cccactggct tttcagcctt cccttccgag ctactgcatg ccccagaaaa    1380
gtgggtgaag gtcaagtacc ccaaactcat ctcctattcc tacatggaac gtgggggcca    1440
ctttgctgcc tttgaagagc ccaagcttct ggcccaggac atccgcaagt tcgtgtccct    1500
ggctgagctg cagtagtgac actggatacc aactgtggct ttagcagcag ccctggttcc    1560
tcccaagtca cacttatgga agatgacccc tttctgagga ataagtttgt tccctgacca    1620
cactcgagga cccagactta aactccacag agtcgtatgt tacccccata tgcttcacct    1680
cactacatag ctgtgttagc tacatggctt taatgataaa tggatttatt tct           1733
```

<210> SEQ ID NO 13
<211> LENGTH: 1574
<212> TYPE: DNA
<213> ORGANISM: Rattus norvegicus

<400> SEQUENCE: 13

```
tgagccaatc ttcaaggaat atggtgtgtt ctttgccaat ggggaacgct ggaaggccct      60
tcggcgattc tctctggcta ccatgagaga ctttgggatg ggaaagagga gtgtggaaga     120
acggattcag gaggaagccc aatgtttggt ggaggaactg cggaaatccc agggagcccc     180
actggatccc accttcctct tccagtgcat cacagccaac atcatctgct ccattgtgtt     240
tggagagcgc tttgactaca cagaccgcca gttcctgcgc ctgttggagc tgttctaccg     300
gaccttttcc ctcctaagtt cattctccag ccaggtgttt gagttcttct ctgggttcct     360
gaaatacttt cctggtgccc acagacaaat ctccaaaaac ctccaggaaa tcctcgatta     420
cattggccat attgtggaga agcacagggc caccttagac ccccagcgctc cacgagactt     480
catcgacact taccttctgc gcatggagaa agtgagtcct gcatggatga gagaggagaa     540
gtcgaaccac cacacagagt tccatcatga gaacctcatg atctccctgc tctctctctt     600
ctttgctggc actgagaccg gcagcaccac actccgctat ggtttcctgc tcatgctcaa     660
gtacccccat gtcacagaga aagtccaaaa ggagattgat caggtgattg gctctcacag     720
gccaccatcc cttgatgatc gtaccaaaat gccatacact gatgcagtca tccacgagat     780
tcagagattt gcagatcttg ccccaattgg tttaccacac agagtcacca aagacaccat     840
gttccgaggg tacctgctcc ccaagaacac tgaggtgtat cccatcctga gttcagctct     900
ccatgaccca cagtactttg accatccaga caccttcaat cctgagcact tcctggatgc     960
```

-continued

```
cgatgggaca ctgaaaaaga gtgaagcttt tatgcccttc tccacaggaa agcgcatttg   1020

tcttggcgaa ggcattgccc gaaatgaatt gttcctcttc ttcaccacca tcctccagaa   1080

cttctctgtg tcaagccatt tggctcccaa ggacattgac ctcacgccca aggagagtgg   1140

cattgcaaaa atacctccaa cataccagat ctgcttctca gctcggtgat cgggctgagg   1200

cagccaggtg ccccagttct gttgggaatg gcctcatgtt tctgcctctg gggggacctgc  1260

tgaaaaccag gctcaaggcc actgctcaca tcttcctatt gcagttctcc aaagtcccaa   1320

ggcttgttct tattcctgtg aatggcactg aagaagtcaa tcgactgtct tattttgaca   1380

tgtgaacaga gatttcatga gtacacatct catgctgagt cacttccctc ttcctcctaa   1440

tagcccacgt ccccacttat cagccctcca tggtctgtga tctgtgctaa tggactctgt   1500

atatggtctc agtgctatgt ctacagactt acatagtatg tatggttcag gtaaacagaa   1560

tcacagagtg tgtg                                                      1574
```

<210> SEQ ID NO 14
<211> LENGTH: 1473
<212> TYPE: DNA
<213> ORGANISM: Rattus norvegicus

<400> SEQUENCE: 14

```
atggaaccta gtgtcctact tctccttgct gtcctcctca gcttcttgct actcctggtc     60

aggggccatg caaagatcca tggtcgtctt ccaccaggac cctgccctgt accccttttg    120

ggaaatctct tgcagatgga cagaagaggc ctcctcaagt cttttattca gcttcaagaa    180

aaatatggag atgtgttcac agtgcactta ggactgaggc cagtggtcgt gttatgtggg    240

acacagacca taagagaggc tctggtggac catgctgagg ctttctctgg ccgggggaca    300

attgctgggc ttgagccagt tttccaggac tatggtatat tcttttccag tggagaacag    360

tggaagaccc ttcgacgatt ctctatggcc accatgagag actttgggat gagaaagaag    420

agtgtggagg agagaataaa ggaagaatcc caatgtttgg tggaggaact gaagaaatac    480

cagggagccc ccctggatcc caccttcctt ttccagtgca tcacatccaa catcatctgc    540

tccattgtct ttggagagtg ctttgactac acagatcacc aattcctgca cctgctggat    600

ctgatgtatc agacgttttc actcttaagc tcaatcttca gtcaggtatt tgaactcttc    660

cctggtgtcc tgaagtactt tcctggtgcc cacagacaaa tctccagaaa cctccatgaa    720

atcctggact tcattggcca gagtgtggag aagcacaggg ccactttgga cccaaatgct    780

ccacgagact ttatatatac ttaccttctg cacatggaga aaaagtcaaa ccattataca    840

gagttccatc actggaacct actgtcgtct gtactctctc tcttctttgc tggcactgag    900

actagcagca ccacactccg ctatggcttc ctgatcatgc tcaagtaccc tcatatcaca    960

gagaaagtcc aaaaagagat tgattgtgtg attggctcac accggctacc taccctggat   1020

gaccgcagca aaatgccata caccgaggca gttatccatg agattcagag attttcagat   1080

cttgccccta ttggaacacc acacagagtc atcaaagaca ccattttccg agggtacctg   1140

ctccctaaga acactgaggt gttccccatc ctgagttcag ttctccatga tccacagtac   1200

tttgaacaac cagacatctt caatcttcag cactttctgg atgccaatgg ggcactgaag   1260

ataattgaag cttttctgcc cttctccaca ggaaagcgaa tttgtcttgg tgaaagcatt   1320

gcccgcaatg aattgttcct tttcttcact accatcctcc agaacttctc cgtgtccagc   1380

cctgtggctc ctaaagacat tgatctcact cccaaagaga gtggtattgg aagaataccc   1440

caagtgtacc agatctgctt cttggcccac tga                                 1473
```

-continued

<210> SEQ ID NO 15
<211> LENGTH: 1269
<212> TYPE: DNA
<213> ORGANISM: Rattus norvegicus

<400> SEQUENCE: 15
gaattccgcg gccgccaacg tcctctctta cccgccacct tcttctgcca cctctaccac 60
ggtcaccatg tcgcaagccc ggcctgccac tgtgctgggt gccatggaga tgggtcgccg 120
catggatgtg acctccagct ccgcgtcggt gcgcgccttc ctgcagcgcg gccacacgga 180
gatagacacc gccttcgtgt atgcgaacgg tcagtctgag accatcctag gagacctggg 240
gctcggactg ggccgcagcg gctgcaaagt aaaaattgcc accaaggctg ccccaatgtt 300
tgggaagaca ctgaagccag ccgatgttcg gttccagctg gagacgtcac tgaagaggct 360
gcagtgtccc cgggtggacc tcttctattt acactttcca gaccacggca ctcctataga 420
ggagaccctg caggcctgcc accacgtgca tcaggagggc aagtttgtgg agcttggtct 480
gtccaactat gtctcctggg aagtggctga gatttgtacc ctctgcaaga aaaatggctg 540
gatcatgcca actgtgtacc agggcatgta caacgccatc accaggcagg tggagactga 600
gctcttcccc tgcctcagac acttcggact aaggttctac gccttcaacc ctttggctgg 660
gggcctgctg actggcagat ataaatacca ggataaggat gggaagaatc ctgagagccg 720
cttctttggg aatccatttt ctcaactgta catggaccgc tactggaagg aggaacactt 780
caatggcatc gccttggtgg agaaggctct gaagactacc tatggcccca ctgcccccag 840
tatgatctca gctgccgtac ggtggatgta ccatcactca cagctcaagg gcacccaagg 900
ggatgcagtc attctgggca tgtccagtct ggaacaactg gagcagaact tggccttggt 960
cgaggaaggg cctctggagc cagctgttgt ggatgccttt gaccaagcct ggaacctagt 1020
tgcccacgag tgtcccaact atttccgcta agatacatct gccttgggga tggcgcagct 1080
tactgcctgc cccgccttgt cctgggctcg atctgatctg gttctttcct ttttagacag 1140
gtcactgtct ttttcttccc tgctttctat acagccagtt gctttcaaag tgagagctgg 1200
ctgagcccca atacctcctg ctgaataaaa ctgttccctg tcacagcctg ggctacaact 1260
ggcggccga 1269

<210> SEQ ID NO 16
<211> LENGTH: 1177
<212> TYPE: DNA
<213> ORGANISM: Rattus norvegicus

<400> SEQUENCE: 16
tttttttttt ttttttttct accttctacc ttttattgtc acgtgaacca tggtcctaca 60
ggctgctgac aagcttggct gagcagggat cccaggggcg tcggcaggac atgaggaagg 120
gttgctggga gggcttggcc tcttccttga gaagacagca aatgtatcca gcctagatta 180
agggtagggc atcccctatc cctgtcagtg ggcctagatc tcagagcccc acattaaaga 240
ctgctaatgg gtcagaaatg ggggtccctt agatgggggt aggcagcaag gccctccctc 300
cagtgttctc attctgttcc ggtttcattt gttgtgtcca gggacggtga agcagatacc 360
agtctcaagc cccagggtgc aggaagacgg gaaatggggt gtgatgttag ggagtgtaag 420
aagggctgag gagcagggga gctgccgccg tgcagagctg gcttctgtct tcacaagaac 480
atttggccca tatcctgctt ggtcactccc aggccagaag atgggtcttc catgtccagt 540

-continued

```
ggctctttag gtggagtctg ggtgggctgc ttctcctcca gggagttctt gctcatttca    600

aacaacagcc actgtttcat ccagctctca aagaccttcc agtccagacc attcatagag    660

ttcttaaggt gcttcagatt ctccgggaag ctccccttca gctgtgggta gttcacgggt    720

ccagacttcg taagcaggtg catcacgtgg tcctgggtca tgttgccata cttggtaaca    780

ttcttcacgg gcgcttggag catgttatcc atggacagtg ggcgcatcag caagggagta    840

gccatgcgca tcgggctcac aggtttggca gatttcggaa gcttcatgcg aaggttctcc    900

agttgcaggt tctgggaggt gacggtcagc ttgtccaggc ggccctgctg ctggtacagg    960

aagtaagcag tggtggcctg cccagccaag agcagagcca ccaggacaga gacactggtg   1020

tacaggactc cacggttgca attgctttct ggggctctag cacgctggcc caggatgggc   1080

agctgctcat ggttagagat gaggtcgcgc tggtcatcca tgactctagc ctctagcttt   1140

tcccccaagt gctgctggtg ctgctgctgc tgctgct                            1177
```

<210> SEQ ID NO 17
<211> LENGTH: 1373
<212> TYPE: DNA
<213> ORGANISM: Rattus norvegicus

<400> SEQUENCE: 17

```
tttttttttt tttttgttct accttctacc ttttattgtc acgtgaacca tggtcctaca     60

ggctgctgac aagcttggct gagcagggat cccaggggcg tcggcaggac atgaggaagg    120

gttgctggga gggcttggcc tcttccttga gaagacagca aatgtatcca gcctagatta    180

agggtagggc atcccctatc cctgtcagtg ggcctagatc tcagagcccc acattaaaga    240

ctgctaatgg gtcagaaatg ggggtccctt agatgggggt aggcagcaag gccctccctc    300

cagtgttctc attctgttcc ggtttcattt gttgtgtcca gggacggtga agcagatacc    360

agtctcaagc cccagggtgc aggaagacgg gaaatggggt gtgatgttag ggagtgtaag    420

aagggctgag gagcagggga gctgccgccg tgcagagctg gcttctgtct tcacaagaac    480

atttggccca tatcctgctt ggtcactccc aggccagaag atgggtcttc catgtccagt    540

ggctcactgc agttatggcg cccgcggctc ttggtgtgag ggacctcagt gccgttgggg    600

aacacacacc agcagtagcc agtgctccca tggcactgga gtggcatata gttaccgttc    660

tcatcacact tgggacggaa cgcccccggg tggacatcag ggatgtggct gacttcttcc    720

tggcacttgg tcaatacttt aggtggagtc tgggtgggct gcttctcctc cagggagttc    780

ttgctcattt caaacaacag ccactgtttc atccagctct caaagacctt ccagtccaga    840

ccattcatag agttcttaag gtgcttcaga ttctccggga agctcccctt cagctgtggg    900

tagttcacgg gtccagactt cgtaagcagg tgcatcacgt ggtcctgggt catgttgcca    960

tacttggtaa cattcttcac gggcgcttgg agcatgttat ccatggacag tgggcgcatc   1020

agcaagggag tagccatgcg catcgggctc acaggtttgg cagatttcgg aagcttcatg   1080

cgaaggttct ccagttgcag gttctgggag gtgacggtca gcttgtccag gcggccctgc   1140

tgctggtaca ggaagtaagc agtggtggcc tgcccagcca agagcagagc caccaggaca   1200

gagacactgg tgtacaggac tccacggttg caattgcttt ctggggctct agcacgctgg   1260

cccaggatgg gcagctgctc atggttagag atgaggtcgc gctggtcatc catgactcta   1320

gcctctagct tttcccccaa gtgctgctgg tgctgctgct gctgctgctg ctg          1373
```

<210> SEQ ID NO 18
<211> LENGTH: 1044

-continued

<212> TYPE: DNA
<213> ORGANISM: Rattus norvegicus

<400> SEQUENCE: 18
cggcacgagg cgcgctcggc gctgtcagtt cgtcccgctg cccctcggcc cttgctgctg 60
gctctgacgg cgaccgacgg cgggcggggc ccgggttcgc ggccgagcgg cgccggtgag 120
ggcgcggagg aggcgcacag cgggaggagg agccgtgagc ctggcacgga gcggccgcgg 180
ccatggcgta cgcctatctc ttcaagtaca tcatcatcgg cgacacaggt gttggtaaat 240
cgtgcttatt gctacagttt acagacaaga ggtttcagcc ggtgcatgac ctcacaattg 300
gtgtagagtt tggtgctcga atgataacca ttgatgggaa acagataaaa ctccagatct 360
gggatacagc agggcaggag tcctttcgtt ctatcacaag gtcatattac agaggtgcag 420
cgggggcttt actagtgtat gatattacaa ggagagacac gttcaaccac ttgacaacct 480
ggttagaaga cgcccgtcag cattccaatt ccaacatggt catcatgctt attggaaata 540
aaagtgactt agaatctagg agagaagtga aaaaggaaga aggtgaagct tttgcacgag 600
agcatggact tatcttcatg gaaacttctg ccaagactgc ttctaatgta gaggaggcat 660
ttattaacac agcaaaagaa atttatgaaa aaatccaaga aggggtcttt gacattaata 720
atgaggcaaa cggcatcaaa attggccctc agcatgctgc taccaatgca tctcacggag 780
gcaaccaagg agggcagcag gcagggggag gctgctgctg agtctgctgt tgccggctag 840
ctgcccagtg gagccacgca ctctgtcacc ctctctcctc atgctcagct gagacatgaa 900
actattgaaa tggctttgtg tcacaggaga ctttaatcct tcagattctt gtataacttt 960
gaataaatgg ttaatgttca cttaaaaaga cagattttgg agattgtatt catatctatt 1020
tgcatttgat ttctaggtca attg 1044

<210> SEQ ID NO 19
<211> LENGTH: 1403
<212> TYPE: DNA
<213> ORGANISM: Rattus norvegicus

<400> SEQUENCE: 19
tttttttttt tttttttttt tttttttttt tttttttttt tttttttttt tttttttcta 60
aagtaaaaat ggtttattca cgacacatat gaggaagtgt ctcatgtcac agacggtacg 120
tccaactccc tggaatgttc atttctttgg cataaaggag agaatgaggg gaaagccagg 180
caaaggcagc taagatgggg gatgggtcgg cagctctgtc gtcatcttca cagggaggag 240
ttcaggggtc cattagtggc aggctgattc tctagaacat taggttgggg cacaggtagg 300
gccacttctg ggcaatccac catgccaagc ccttcagtcg tccccaccac acaggtacag 360
cagcgccttc tggtagtcac ccttagtgtc ttgctggatg aagtagtaca gggatttgcc 420
atatttcctc ttgaattcag atctgatttt caacatgtcc acttcactgc gagagaccat 480
gattctaatc aggaccttgt ctcgagtccc cttgcccttc atggagtcat acagccggtc 540
agcaaagtac aggggcttgt tctgaatgca ctgaaccagg ttcaggaagg cgttctccag 600
gtctcctttg acctctttcc tgatgctctc cagcatgtca taaggactgt agctcttgta 660
cctttcgaac actttctgga ggtggcacac actgcgctca gtcatgatgc tgatccactt 720
ggggacatcg gttcctttcc tcttcacccc agcatcatag agctcccggg catcctggtc 780
aatcagctcg tagtcaataa cagaaccatc ctctgcccgt ttaccctttg caagggcgac 840
caacagcttt cggaattctc cagatgtgtc agagatgatg tccttctcca gatcggtctt 900

-continued

```
gtacatttcc ttatacactc ggttaatctc ctgcagctcc tggttggttc ttgagcagat    960

gatctcgatg agggagtcct catcagtccc caggcccttc atggaggctt tgagctcaga   1020

ggcatcgtac tgagcaggtg tcttcaacag gcctaacatc acggtctcca ggtgaccaga   1080

caaggccgac ttcatcgccg atggcagttc ctttttggtc ctcctctggt aggcgaaggc   1140

aatgtcctgc ctctgtgcat tgctgcggtt agtcagaatg ttgacaatgg tgacctcgtc   1200

cacgcctttg gtcttgattg ctgtttcaat gttcaaagca tccctctcag cgtcgaagtt   1260

ggtgtagggt ttgaccgacc cataggcact tgggggtgta gaatgctgag aatcaccctc   1320

caagctgagc ttgcacagga tttcgtggac agtagacatt ttgaaaaaaa agctgggccg   1380

ggcacctatt gcagagagcc tcc                                           1403
```

```
<210> SEQ ID NO 20
<211> LENGTH: 5060
<212> TYPE: DNA
<213> ORGANISM: Rattus norvegicus

<400> SEQUENCE: 20

gggatgacat agagtacaac attcagagaa gttaactatt aagtcgtcag gatgaaaggt     60

caggaggcag gcctttaact gggctgtgag aatggagaaa gcacggtgca ctttaacatc    120

tgctttccca gaggaaaaag taaaggagaa acagtacaat catagaagag tcttcgtaac    180

agaagcgcga ggagagcatt atggacaagt tctgcaactc tactttttgg gatctctcat    240

tactggaaag tccagaggct gacctgcctc tttgttttga gcaaactgtt ctggtgtgga    300

ttcccttggg ctttctttgg ctcctggctc cttggcaact ttacagcgtg tacagatcca    360

ggaccaagag atcttctata accaaattct accttgccaa gcaggtgttc gtcgtgtttc    420

ttcttatttt agcagccata gacctgtctc ttgcgctcac agaagatact ggacaagcca    480

cagttcctcc tgtcagatat acgaatccaa tcctctacct gtgcacatgg ctcctggttt    540

tggcagtcca gcacagcagg caatggtgtg tacgaaagaa ctcttggttc ctgtctctgt    600

tctggatcct ctcggtctta tgcggcgtat tccagtttca gactctgata cgagcactcc    660

tgaaggacag caagtccaac atggcctact cctacctgtt cttcgtctcc tacggtttcc    720

agattgtcct cctgattctt acagcctttt caggaccaag tgactcaaca caaactccat    780

cagtcacggc ttcctttctg agtagcatta catttagttg gtatgacagg actgttctga    840

aaggttacaa gcatccactg acactagaag atgtctggga tatcgatgaa gggtttaaaa    900

caaggtcagt caccagcaag tttgaggcgg ccatgacaaa ggacctgcag aaagccaggc    960

aggcttttca gaggcggctg cagaagtccc agcggaaacc tgaggccaca ctacacggac   1020

tgaacaagaa gcagagtcag agccaagacg ttctcgtcct ggaagaagcg aaaaagaagt   1080

ctgagaagac caccaaagac tatcccaaat cgtggttgat caagtctctc ttcaaaacct   1140

tccacgtagt gatcctgaaa tcatttatac tgaaattaat acatgacctt ttggtgtttc   1200

tgaatcctca gctgctgaag ttgctgatcg gtttcgtgaa gagctctaac tcatacgtgt   1260

ggtttggcta tatctgtgca atcctaatgt ttgctgtgac tctcatccaa tctttctgcc   1320

ttcagtctta ctttcaacat tgttttgtgt tgggaatgtg cgtacggaca accgtcatgt   1380

cttcgatata taagaaggca ttgaccctat ctaacttggc taggaagcag tacaccattg   1440

gagagacggt gaacttgatg tctgtagatt cccagaagct aatggatgcg accaactaca   1500

tgcagttggt gtggtcaagt gttatacaga ttactttgtc catcttcttc ctgtggagag   1560

agttgggacc gtccatctta gcaggtgttg ggttatggt tctcctaatc ccagttaatg   1620
```

-continued

```
gagttctggc taccaagatc agaaatattc aggtccaaaa tatgaagaat aaagacaaac   1680
gtttaaaaat catgaatgag attctcagtg gaatcaagat cctgaaatac tttgcctggg   1740
agccttcatt tcaagagcaa gtccagggca ttcggaagaa agaactcaag aacttgctgc   1800
ggttcggcca gctgcagagt ctgctgatct tcattttaca gataactcca atcctggtgt   1860
ctgtggtcac attttctgtc tatgtcctgg tggatagcgc caatgttttg aatgcggaga   1920
aggcatttac ctccatcacc ctcttcaata tcctacgctt ccctctgtcc atgcttccca   1980
tggtgacctc atcgatcctc caggccagtg tttctgtgga ccggctggag aggtatttgg   2040
gaggagacga tttagacaca tctgccattc gccgcgtcag caattttgat aaagctgtga   2100
agttttcaga ggcctctttt acttgggacc cggacttgga agccacaatc caagatgtga   2160
acctggacat aaagccaggc caactggtgg ctgtggtggg cactgtaggc tctgggaaat   2220
cctctttggt atcagccatg ctgggagaaa tggaaaacgt tcacgggcac atcaccatcc   2280
agggatccac agcctatgtc cctcagcagt cctggattca gaatggaacc atcaaagaca   2340
acatcctgtt tgggtccgaa tacaatgaaa agaagtacca gcaagttctc aaagcatgcg   2400
ctctcctccc agacttggaa atattgcctg gaggagacat ggctgagatc ggagagaagg   2460
ggataaatct cagtggtggt cagaagcagc gagtcagcct ggccagagct gcctatcaag   2520
atgctgacat ctatattctg gacgatcccc tgtcggctgt ggatgctcat gtgggaaaac   2580
acattttcaa caaggttgtg ggccccaacg gcctgttggc tggcaagacg agaatctttg   2640
ttactcatgg tattcacttc cttccccaag tggatgagat tgtagttctg ggaaaaggca   2700
ccatcttaga gaaaggatcc tatcgtgacc tgttggacaa gaagggagtg tttgctagga   2760
actggaagac cttcatgaag cattcagggc ctgaaggaga ggccacagtc aataatgaca   2820
gtgaggcgga agacgacgat gatgggctga ttcccaccat ggaggaaatc cctgaggatg   2880
cagcttcctt ggccatgaga agagaaaata gtcttcgccg tacactgagc cgcagctcta   2940
ggtccagcag ccgacgtggg aagtccctca aaaactcctt gaagattaaa aatgtgaatg   3000
tcttgaagga gaaggaaaaa gaagtggaag gacaaaaact aattaagaaa gaatttgtgg   3060
aaaccgggaa ggtcaagttc tccatctacc tgaagtatct acaggcagta gggtggtggt   3120
ccatactttt catcatcctt ttctacggat tgaataatgt tgcttttatc ggctctaacc   3180
tctggctgag tgcttggacc agtgactctg acaacttgaa tgggaccaac aattcgtctt   3240
ctcataggga catgagaatt ggggtctttg gagctctggg attagcacaa ggtatatgtt   3300
tgcttatttc aactctgtgg agcatatatg cttgcagaaa tgcatcaaaa gctttgcacg   3360
ggcagctgtt aaccaacatc ctccgggcac ccatgaggtt ttttgacaca actcccacag   3420
gccggattgt gaacagattt tctggtgata tttctactgt ggacgacttg ctcccccaga   3480
cacttcgaag ctggatgatg tgtttctttg gcatcgctgg cactcttgtc atgatctgca   3540
tggccacccc agtcttcgct atcatcatca ttcctctcag cattctttat atttcggtgc   3600
aggtttttta tgtggctact tcccgccagc tgagacggtt ggattctgtc accaaatctc   3660
cgatctattc tcacttcagt gagactgtca caggtttgcc cattatccgt gcctttgagc   3720
accagcagcg atttctagct tggaatgaga agcagattga catcaaccag aaatgtgtct   3780
tttcctggat tacctccaac aggtggcttg caattcggct ggagctggtt ggaaacttgg   3840
tcgtcttctg ttccgccttg ctgctggtta tttatagaaa aaccttaacc ggggacgttg   3900
tgggctttgt tctgtccaac gccctcaata tcacacaaac cttgaactgg ctagtgagga   3960
```

-continued

```
tgacgtcaga agcagagacc aacattgtgg cagttgagcg aataagtgaa tacataaatg   4020

tagagaatga ggcgccctgg gtgactgaca agaggcctcc ggcagactgg cccagacatg   4080

gtgagatcca gtttaacaac tatcaagtgc ggtatcggcc ggagctggat ctggtactga   4140

aagggatcac ttgtaacatc aagagcggag agaaggtcgg cgtagtgggc aggactgggg   4200

ctgggaaatc atccctcaca aactgcctct tcagaatctt agagtctgcg gggggccaga   4260

tcatcattga tgggatagat gttgcctcca ttggactgca cgaccttcga gagaggctga   4320

ccatcattcc ccaggacccc attttgttct cggggagtct gaggatgaat ctcgaccctt   4380

tcaacaaata ttcagatgag gaggtttgga gggccctgga gttggctcac ctcagatcct   4440

ttgtgtctgg cctacagctt gggttgttat ccgaagtgac agagggtggt gacaacctga   4500

gcatagggca gaggcagctc ctatgcctgg gcagggctgt gcttcgaaaa tccaaaatcc   4560

tggtcctgga tgaagccacg gctgcagtgg atctcgagac ggatagcctc attcagacga   4620

ccatccgaaa ggagttctcc cagtgcacgg tcatcaccat cgctcacagg ctgcacacca   4680

tcatggacag tgacaagata atggtcctag acaacgggaa gattgtcgag tatggcagtc   4740

ctgaagaact gctgtccaac agaggttcct tctatctgat ggccaaggaa gccggcattg   4800

aaaatgtgaa tcacacagag ctctagcagc tggttccgtg gctggcggac tataagaaca   4860

gtttctatta tttgctttgg tttctgtgac tgtgctctag gtgcaaagac acatattttg   4920

ttcccgttgc tcaggctggc ctcaaactct aaggctccag caatctctgg tctcagccag   4980

agacctgtaa aaatagacac ttcaaagatt atcatgaata aatatttaaa taaatagtaa   5040

aaaaaaaaaa aaaaaaaaaa                                               5060
```

<210> SEQ ID NO 21
<211> LENGTH: 775
<212> TYPE: DNA
<213> ORGANISM: Rattus norvegicus

<400> SEQUENCE: 21

```
gaattctctg ggcccatccg ttgttctcaa tggacatgac ctccaggaag ctaaagtcca     60

ggtcgtgacc aaagccaagg ttgtagagcg ggaatctgcc ccggatagcg ttgcggacat    120

tcttgaggat ctgggaacgg tccgtctccc cttcagtggg ctctccgtcg gtcaacatga    180

taagaattga ggcagggctg ctgagttctg ggtggcttcc ttgagctctg tttaagatct    240

cgattcctcg gagcaagcct ccattcaggt ttgtggctcc agccaaagaa aagcgcctca    300

caaagtcttg ggctgcttgc aaattggcgt gagacgcggg taccagtgag cccttccatg    360

actgcacttg agacccaaag aggaccaggt caaagttgtc tactggcttc atgtccccca    420

atatcttaag gagcgcctcc tttgtctgct tcactttctg gccttccatg gacccactga    480

tatcaatcac aaaaaccagg ttcttgctca tgttggtcag gttttggggg gcaaagaaat    540

gtgtaaagta attgttggcc accaggaggt cacagagctt gtctcggttc acatcgtagg    600

tcaccttgaa gtctccattc agcaaggagg tagagcacgt ggggcaggac tgctgctggc    660

tcacagtggg gcggaagagc acatgaccct tcttccccga gaaagacttc ttgatggttt    720

gagcacttga ctggtgatga cgtagtgggc aaagcgagag gtgactttgc aattg         775
```

<210> SEQ ID NO 22
<211> LENGTH: 1561
<212> TYPE: DNA
<213> ORGANISM: Rattus norvegicus

<400> SEQUENCE: 22

-continued

```
ttttttttttt ttttttttac tgtatatgta atttaattca aattggaaca atgacgtaga     60
tatataagcc acaatccatg aaagtcttgg aggaaaacat aggagcagtt atttctgtac    120
ttgattttag tggtgagatt cttagctgtg gcatggatac acatgatcag aacagtatta    180
aataaggaga acgtcactga aaagagcaat ctgtgtgcat caaagaacat tatcaagaaa    240
gcaaagaagc aatgtgtata aaacgtccct aataggtaaa tctacataga taaagagaag    300
attggtggtt agacaaccag agggaggaag aatggagagt cactgagtaa tggttacagt    360
gtgtttgaaa ggggataaag ataagatcgt ggcctgattt tacccataaa ttgttgattc    420
tttacacaag aataatggtt agaggaatga gccacaatag cagatattat ccaaccatta    480
atgaaactta tgaccacttc ttaaattttt atttattttt ttaaaattta cttgtttctg    540
cataactttg agtgatgtta catgcttata caggatgctg gggccagtag tagccaaata    600
aaggcatcaa gacatgggtg gaaactggaa tttccagagg ttgtaagcag ccatgtgggt    660
ggtgggaaat gtccctgtgt cctttgcaag atcagcaact tttcctagta tctgtccttc    720
tctccagcat tcttacacat tgattcagtt ctaccaggct gtaagttatt ggctataagt    780
tatgagtatc agcggcatag caaaggctat atggcatcat tagacataac ctgcaaaagg    840
gcacaaatgc attcaggata gggagagctg aatgcaggca tcataagatc aggctggcag    900
gaagaaagta tcctcatctt ggaacatggt ttccccctac ttgcccatcc tgacagagct    960
ttggagtggt ggagatactg aagagaggac tctccccatg tagtaaatgt gtctttatgg   1020
agatgagaac ctgccacaga acagaatgct gctggttttg ttgtgcttga tgaagaaaag   1080
gaaggggtgg tcagcacaga atgttgggac aaaagcagca cagcagtatt ctatgacagc   1140
ggaggctgct gcagcctctg tgccttcctc attgacctcc actacgctct tgtgaacaat   1200
cttggacaca cacaggtttc tctctggaga cattgctgat aagtcagcct tggcctcttg   1260
gaagacatcc actattccca agcgctgaaa cacagactcc atgtcataat cctcttgcag   1320
tttaaatttt ggaaggaaaa cctcaacatt agtgttcttc ataaagtctg ggttggtcca   1380
ggctgttaac ttctcaaaag tgagattgct ttccaccttg ctgaggtccc cgtcattatc   1440
tgggagtagg accacgaagc tcagctccat tccttcatat ggcatcatga gcacttgcgc   1500
ctgcacctcg ttcacatggg caaggttata tgtgtcctca caacacatca tctgcactag   1560
t                                                                   1561
```

<210> SEQ ID NO 23
<211> LENGTH: 2320
<212> TYPE: DNA
<213> ORGANISM: Rattus norvegicus

<400> SEQUENCE: 23

```
gtatttcata aaacagagag gatcgcagga ggccggcact ctgactcctg gtggatggga     60
ctagggagtc agagtcaagc cctgactggc tgagggcggg cgctccgagt cagcatggaa    120
agtctctgcg gggtcctggt atttctgctg ctggctgcag gactgccgct ccaggcggcc    180
aagcggttcc gtgatgtgct gggccatgag cagtatccgg atcacatgag ggagaacaac    240
caattacgtg gctggtcttc agatgaaaat gaatgggatg aacagctgta tccagtgtgg    300
aggaggggag agggcagatg gaaggactcc tgggaaggag gccgtgtgca ggcagcccta    360
accagtgatt caccggcctt ggtgggttcc aatatcacct tcgtagtgaa cctggtgttc    420
cccagatgcc agaaggaaga tgccaacggc aatatcgtct atgagaggaa ctgcagaagt    480
```

-continued

```
gatttggagc tggcttctga cccgtatgtc tacaactgga ccacaggggc agacgatgag    540

gactgggaag acaacaccag ccaaggccag cacctcaggt tccccgacgg gaagcccttc    600

cctcgccccc acggacggaa gaaatggaac ttcgtctacg tcttccacac acttggtcag    660

tattttcaaa agctgggtca gtgttcagca cgagtttcta taaacacagt caacttgaca    720

gttggccctc aggtcatgga agtgattgtc tttcgaagac acggccgggc atacattccc    780

atctccaaag tgaaagacgt gtatgtgata acagatcaga tccctatatt cgtgaccatg    840

taccagaaga atgaccggaa ctcgtctgat gaaaccttcc tcagagacct ccccattttc    900

ttcgatgtcc tcattcacga tcccagtcat ttcctcaact actctgccat ttcctacaag    960

tggaactttg ggacaacac tggcctgttt gtctccaaca atcacacttt gaatcacacg   1020

tatgtgctca atggaacctt caactttaac ctcaccgtgc aaactgcagt gccgggacca   1080

tgcccctcac ccacaccttc gccttcttct tcgacttctc cttcgcctgc atcttcgcct   1140

tcacccacat tatcaacacc tagtccctct ttaatgccta ctggctacaa atccatggag   1200

ctgagtgaca tttccaatga aaactgccga ataaacagat atggttactt cagagccacc   1260

atcacaattg tagatggaat cctagaagtc aacatcatcc aggtagcaga tgtcccaatc   1320

cccacactgc agcctgacaa ctcactgatg gacttcattg tgacctgcaa aggggccact   1380

cccacggaag cctgtacgat catctctgac cccacctgcc agatcgccca gaacagggtg   1440

tgcagcccgg tggctgtgga tgagctgtgc ctcctgtccg tgaggagagc cttcaatggg   1500

tccggcacgt actgtgtgaa tttcactctg ggagacgatg caagcctggc cctcaccagc   1560

gccctgatct ctatccctgg caaagaccta ggctcccctc tgagaacagt gaatggtgtc   1620

ctgatctcca ttggctgcct ggccatgttt gtcaccatgg ttaccatctt gctgtacaaa   1680

aaacacaaga cgtacaagcc aataggaaac tgcaccagga acgtggtcaa gggcaaaggc   1740

ctgagtgttt ttctcagcca tgcaaaagcc ccgttctccc gaggagaccg ggagaaggat   1800

ccactgctcc aggacaagcc atggatgctc taagtcttca ctctcacttc tgactgggaa   1860

cccactcttc tgtgcatgta tgtgagctgt gcagaagtac atgactggta gctgttgttt   1920

tctacggatt attgtaaaat gtatatcatg gtttagggag tgtagttaat tggcatttta   1980

gtgaagggat gggaagacag tatttcttcg catctgtatt gtggttttta tactgttaat   2040

agggtgggca cattgtgtct gaagggggag ggggaggtca ctgctactta aggtcctagg   2100

ttaactggga gaggatgccc caggctcctt agatttctac acaagatgtg cctgaaccca   2160

gctagtcctg acctaaaggc catgcttcat caactctatc tcagctcatt gaacatacct   2220

gagcgcctga tggaattata atggaaccaa gcttgttgta tggtgtgtgt gtgtacataa   2280

gatactcatt aaaaagacag tctattaaaa aaaaaaaaaa                          2320
```

<210> SEQ ID NO 24
<211> LENGTH: 241
<212> TYPE: DNA
<213> ORGANISM: Rattus norvegicus

<400> SEQUENCE: 24

```
gaattcttgc agttacagag tatggctgtt gtctactcgg gagctcccag atcctcataa     60

ctcagggacg tgtccctatt tatggacaaa aaagtttgac gccaggtcgg gcctacatga    120

gctcttctct accctgcaag tccccagtgt atctgaggaa ggtgtattct gtcagagaag    180

caaggaagat caatgcacac ctttagtctc agccccatag gaggcagagt caagcagatc    240

t                                                                    241
```

<210> SEQ ID NO 25
<211> LENGTH: 283
<212> TYPE: DNA
<213> ORGANISM: Rattus norvegicus

<400> SEQUENCE: 25
aagctttata gtcaggcaca gctggctgtt gccaggcaac tgtggggcag agcatacctg 60
gctgttgcca agtagctgtg gggtggagct tagacagaat cccaacagat agtatagttg 120
gagagggttt cagtctgtca cagtggggag gcaggggcag tagttgagtt catggtgacc 180
agatcttgtg atggaggaaa tttacatcat catcccaggc tagaaagcag tgagcagggc 240
agagacagga gcaggttatc accttggaag acctgacact agt 283

<210> SEQ ID NO 26
<211> LENGTH: 642
<212> TYPE: DNA
<213> ORGANISM: Rattus norvegicus

<400> SEQUENCE: 26
ttgcggccgc ccaagtctgc cacttcaaca ctgtatctaa aacttgaaag gcactgtcaa 60
aaaccctggt gggttcctag ctttagggat ccatcgttag agtcagtaaa catggcaact 120
ctgcctccgg gcatgtgata cgtcgccagc agaggcttgc tagcccttgc cacacaacgc 180
tcagcttact caaagcactg ccaagacatg gctgccctga gacggttgtc tgggctcctt 240
ccttcctata ccttagggcg ccccccttcac agcactgggt aagcaatcag cccctcccgg 300
agaggagaag ggaaggtaaa agacaaaggt atgttttaca ctatgcaaaa cgttccagag 360
ggggaagatg aacgaagtaa caagtatcca acacagggtt ttaaaaagca acgacatttc 420
aaatgagctt gtatgggaga aagaaaagca ggttttcagg aaaaatccaa acacattcag 480
gtgtgtcttt taagtcatga gtttatcatt tattctaagt tcattgggag gaaaactgga 540
gactatcagc atagctgtct tactggggaa ggcattccca gtgaataaac atctccctta 600
cctgagctct tggcgagaga ttctgcccag cttgactctc tc 642

<210> SEQ ID NO 27
<211> LENGTH: 866
<212> TYPE: DNA
<213> ORGANISM: Rattus norvegicus

<400> SEQUENCE: 27
tttttttttt tttttttcca gaaatttgcc cattctttta tttgaaggca aaaattccca 60
tggaagtctg gatgaagaga gagacaaagg cttatagaaa ataaattgaa taactagaga 120
ttctctggat ccagacatag ttggttgata aatttgttac ctatttctca ttgtatttca 180
cattatttag acatagttct tgacatctct gttttgcata ctgtctctgg ccaagagttt 240
tggtcttcct ttctaaatat caagaggaaa aatggcagaa caaaccagta atgttacatg 300
gcatgtggtt cctgagtata taatcaagca ttagcagcag ttgtagttat ctgaatataa 360
tgcatagata taatacatga ccgaagagac acaccgattt aaacaaccaa tgtcaacact 420
gaaacaaaga attttaatgc taaggcaccc aatcacggtg tctttcagtt atttgttgtt 480
ttctttagga gactggccat acacagcagg gattcaaaat tgtggcttgc agtcatgaat 540
caacatttgc atttgagtaa cttacccatc ttctttatgc ttccacaaac atagtttcag 600
ttgggataat cactgaggtg tgcacagccc tttcttcctg tagtttaggc aatatccaag 660

-continued

```
gctgtagaac ttggggtaag gtgtaatggt gtcacaggag gagacatcta ctcactgtta    720

aatgttgctc tgatgtaggt tggccatagc tccccatacg atctcacagg gaagccgatg    780

ggtaatagca gcaggaagat catggtctac ataactgact ctggaacttc ttgacttata    840

acttattact ttttgggttt cttttc                                         866
```

<210> SEQ ID NO 28
<211> LENGTH: 629
<212> TYPE: DNA
<213> ORGANISM: Rattus norvegicus

<400> SEQUENCE: 28

```
agggaacccg gtttctgagg ttaagaacct ggtatgaggt agaaagcaga atcggacctt     60

aggcactcga gcgtcgtgtc gaagaaacat taaatagaat agaggagtaa aggggatgtt    120

tcggataagc gctaggtcga gtcaaagaag tcttgcaaga agagttaagg gagcaagaat    180

ttctagaagc atctagataa ggagtcgtag catactgacg ttactagtaa taagtagggt    240

gagtcggaga atcatgcgct cgatggtcat aagatagtat ctatcgagga gtgtaggagg    300

cctcgtcctt cggcggaaaa gtaacgcgta gcggttaaga atcttgtcgt tcattatctt    360

aagggtaagg agccatcagt ttagaagtcg ttcccgcggt agtaagttcg cgtcgatttt    420

aataagactt tagattgcgt cgtttagtcg acgtagtaga cggttaatag taacggtctt    480

acttccttaa gcgtttcgct agttcttaag cttaattcgg ctactctaga ttttaccttt    540

ggggttaagt ttccgttagc gttgttggaa tcggttttgc ctgcggggtg gacgcccgtc    600

taggagaacg cattcgctac gaacggtgc                                      629
```

<210> SEQ ID NO 29
<211> LENGTH: 1145
<212> TYPE: DNA
<213> ORGANISM: Rattus norvegicus

<400> SEQUENCE: 29

```
ttttttttt ttttttgat ggccagtgac agtttttgct ttttttatat ttataaacaa     60

aaccaacctc ccccccaagt aactccccaa acaaacaaaa aaccagatta aataaaattt    120

acagtgaacc cagcaaacat ctgtatgtgc aattaaatac tgtgtctgtt actgtggtgg    180

cacgaacctc aaacaaacaa tatacaagtg ttctggggtt ggatcagggg tcgggggagt    240

cccaagtttt aactctgtgg ggtttgggga gacaaggtgg ggaattgaac gaatggggaa    300

atcaatttat ttttcttaat tctgtccata taaatatatt catgaagacc aaaagaggga    360

agggcagttg ggctggtgat gaagtgggag aaggggaggg cagagccctc tcaactctac    420

tcagccaaaa atatgaaaca aattaatttc atggtgggag aagagattta aaaaatgata    480

gaagatggga aggaggggga gacagaaggg gaccaaccag ggaaaagggg gacccatggc    540

aagggagtcc catgtcaagg agtcctgtgc cggtgtgaga atctgtctgc ttctctcttc    600

agccataatg tggtaagctc tggcccaatc cgccttcggc tcccggcttg gcccttgctc    660

ctattgtgcc agcccctccc gcctccagct attgagagct agctcgctcc aggatcctca    720

ggtcgtagtt ctttttagct actcgaagtt tgaagcgact cacagagttg ttgaggcgaa    780

gggaggcatt gtgggcagcc aggggactgg ggaacacagc cactatagtg tacaaggcag    840

cgaggtccgc atggcggcca ttctcagcag tcccactgtt gtcccccccca cctgcaccag    900

gcaacccctg agcatcctta agccactgga tcttggcacc agacatggca agctgtgtga    960

agagtttgtc tgcctctgtg cgggtgattc cttccgggag atcagtcacc tccagtaccc   1020
```

-continued ttcccagcac aacatccgct gtccccaggt cagtggaggc agacttgagt gcttgtctct 1080
tgcctcggtt tccatgcttc aatccactct gtccctggtg caccgtatac gttgactggc 1140
catgg 1145

<210> SEQ ID NO 30
<211> LENGTH: 3087
<212> TYPE: DNA
<213> ORGANISM: Rattus norvegicus

<400> SEQUENCE: 30
tttttttttt tttttttcac atgtcaacaa ctgctagcta ctattaaaat actgtcaccc 60
aaggaggtgg aatgtttaac agaaaatagg ctttaacaat tcatactggt cctcaataac 120
tgcagatgac tagttcaagc caactgcaaa actgagcaag aaatgcagct tgaagaacag 180
gacaataaaa tttaatcttg caacttgata gacttggagg cattccggtc aatgtagaag 240
accttgcggg cctcagagtt aaagcccagg ccagcccta ggctgtactt ccagctcatg 300
gcccggtcgt agtcctgctg cagactctgc tggagcgtat ctgaagactt cttgtccagg 360
gccatgttgg acctgacagt catgctggga ggacggttga atgacgggga tagatgctta 420
aagccgccca taagtttcag gaaattttag tttctgtttc ttcattttca aagcccgcag 480
tgtcccactg gccaaactgg gttccctgat ctatgcaggc ctcatccata ttgccttttt 540
tttccagtac cacctccaag tctgtgtctg actcctcttt ttcctcctgc caggggtctt 600
cctttactcc gctctctttt ctcctcttct ttttcttcct tttcacagcc agcccttcac 660
caactggctg ctccaccttt tttttggatt tcactttctt cttcccaggg gccttcaggc 720
tgtctatcgg gatgaaatcc aacgcttcac ttctgactga cttcttattc cctttcttca 780
agctgttctc catggagatc ttggagttga ccgggaggat gtctccctcc tgatgagtct 840
ttttcttctt cttctttttc atgctgtgat ctctggggct cccctgcttc cttttgtgcc 900
ccaaggccgc ctgctcttcg gcctctgccc cctctaagca tgagtgcaaa gcatccccag 960
cctcagggat ccaagagtcc tggggaggaa aagcttccat gtccggaagc ttcttctcct 1020
tcctgtgctt tttaggcttc ctaccagctt tgcttacctc cttggcatgc ttggagtctg 1080
gggaagtctt cagccctgag ccttgggagg caacctttga taaggacttc cgcctcttct 1140
ttttcttctc tctgatgagg ccttctgctg actgctcaag gacctgcctt ctaaggctag 1200
gtgactttat ctgtcttgtc catgtaggct catccttgcc caggtactca tccaagtgtg 1260
tgctacagga cttttttctc ttctttctct tgcccagtga catctcaggg acctgcacct 1320
cacccacatt gttaaaaggg gatgtagccc ttggaggaga aacatctatg aagtaatcat 1380
tattgtttaa gactgagtac tgagtctctg gttctgagac atttgccacc ttctttttct 1440
tcttcttctt tttcttcttc tctgggagcc gtgggcccag gtcttctttc tgagtcttgt 1500
tgaccattac tggtctatta gcaggccaag catccccacg tgagcacccg cgcagccgcg 1560
acccggaagt cagcttcgaa tttctggccc gccccctcga aatcgttctc cttccgggtc 1620
gcagcttcgc ggcgccctgg gttgctgtag aaacggcgtc catggccgtg cctagacaag 1680
catccagcct cagcgtgctg cgtgaggaga cgggaggcgc tgcggactcg ccggtcacta 1740
cacgaatgcc cgggctcgca gggtcgcctg ggtcccccga agttctcgtg ttacccgcgc 1800
aggtcgccga gcctccgggg aagaacctgt gggagcagat ctgcgaggag tatgaagccg 1860
agcagcctac ctttccggaa ggatataaag tgaagtttag tttcctgcct tgcccggaat 1920

-continued

```
gctacgcttt cacgtggcca tcttccccgc agttgttgac atgcctagtg accgtgacct   1980

ctgacacccg ttttcccact tttgccagga tctgtatttt aacttacttc agagtcctct   2040

tagttgtctt ggtttggggg tggtttgggg gtgttgggat aacagatggg gcaaggctgt   2100

agccctactg agctgtttcc agaggccgtt gtcaggaagg atttccagtg ttacagcccc   2160

agagtataac agcagcgccc tgttagctta atggtcccca ttggttctgt ggctgcggct   2220

caccaggatt ctcccattca aaaggcccag acatggctga cagcctcctc tgtaggtctg   2280

actgacaagc taccacgcgt cttaggtaaa tagtaaagcc tttattttct tgttaagaac   2340

agcattttga aaataaaacc tatctgccca tgcttaacaa cctttaaagt ctgtgatatt   2400

ttatatacag ccctgtacat actgattgtc tggaaatttc ttaaacagtt tttgtttata   2460

agtatgcaag tcagccagga tgaggggaag agtgagggta cattataaaa tacacattaa   2520

tacatttaat aaatatatat tatctatcaa aaacgagcca tagctcttaa tgaataaagc   2580

acctgccaag ggctctcatc agctcacagt tgctacatcc ttggatgtgt aaatgccagt   2640

gccccccttct actttgccat ttggcaaatt caaaagacaa ctcttccacc accctgcact   2700

tgttccctgg ccttgacctc ctctgtgtgg gggtggggca gacaacaacc agatcttaac   2760

tttagaaaca gctgacacat tggagcccct cccctctgcc attgtcctgc taccttggca   2820

actgactcca gacctctatg gagtcttcac tcaggagggg acagagcggt ggttatagtc   2880

ccaatatggt attagtaccc gggcatgcca agttgtgctt gcagtttggg gttattcaca   2940

gatgactttc tagaccattt tccccaacca agtgttgggt gtatcaacac ttaaacaggt   3000

gccatgggat tatgcatttc agccttgctc tgtcagaagc tggctgccac agtatctggg   3060

tggagttgcc tcgtggtcct cctcgtg                                      3087
```

<210> SEQ ID NO 31
<211> LENGTH: 434
<212> TYPE: DNA
<213> ORGANISM: Rattus norvegicus

<400> SEQUENCE: 31

```
tgtacaatgg gggataaaag tgtcaaatga gatgttgcta tagtttcatt tcttttgccg     60

tgatagagca ccctgacaaa aagcagcacg agaggaaatg tatctggctt acgattccat    120

gttaaagccc gtcattgatg aggtgggtcg gggagtcaag gtaagactgt aaacagctag    180

tcaatcacat ccacagtcag agacagaagg acacaaattc atggatactt gctcctttgc    240

actcagctca gtttctccac tcttacacag ttttaaatgc cctgcctagg gagtgatgcc    300

acccacagtg ggctggatgt tcccacatca gttatgacaa tctcccacct catgcccata    360

ggccaaccca atgtagacaa tctctcattg agactctctt cccaggccat gtcaagctga    420

cagttatagc tagc                                                      434
```

<210> SEQ ID NO 32
<211> LENGTH: 221
<212> TYPE: DNA
<213> ORGANISM: Rattus norvegicus

<400> SEQUENCE: 32

```
agatctctta agtgaaaata gaaaaatgat tactaacgag aagatagacg cctacaacga     60

agctgcagtc agcattctga acagcagcac caggacatcc aagtccaatg tcaagatgtt    120

cagtgtttcc aaactcatcg cccaagaaac catcatggag tctttgggtg gcttacacct    180

tcctgaatca agcagagaaa ctagtgcaat gattctcatg a                        221
```

-continued

<210> SEQ ID NO 33
<211> LENGTH: 581
<212> TYPE: DNA
<213> ORGANISM: Rattus norvegicus

<400> SEQUENCE: 33
tcatgactcc cagcattgac attcccctac aatagggctt tgagccttca caaaaccaag 60
ggcctctcct gccattgttg ctcaacaagg ccatcctctg cttgatatgc ctctcgagtc 120
atgggtcatt ccatgtgtaa tctttggtgg tttagtacct ggcagctctg catggttgat 180
attgttgttc ttactatgga gtgacaagcc tgttctgctt gttcaattat ttgtctaact 240
ccttagttga gtaccctgtt tgcagtccaa tggttgggtg tcagaatctg cctctgtatt 300
tgtcaggctc tggcagaggc tctcaggaga cagctatatc tggctccttt cagccagcac 360
ttcttggcat tagcaataat gtctaggttt gatgactata aatgggatgg atccctaggt 420
gtgatagttt ctggatggcc tttccttcag tcactgctcc acattaggtc ttgatatttc 480
ctccttattt tgtttccctt tctgccccat cgttgtgccc ttttgataga ttttgcagtt 540
tagaaataca atttacgtgc aggtttattg cattcagatc t 581

<210> SEQ ID NO 34
<211> LENGTH: 221
<212> TYPE: DNA
<213> ORGANISM: Rattus norvegicus

<400> SEQUENCE: 34
tcatgatgaa gaaatgggtt ctcggcaata ggcaaaggca ggatgagagc agaggggtcc 60
atgggggtcg aaggctgccc atgggggtgg ttctatgctc tgaccatttt gagatgaact 120
aataatgttc cggcagtggc tatcccctaa caaagatcac aagccgccta gtggagggaa 180
tggaatctga actctggtac cagcctccaa gatccagatc t 221

<210> SEQ ID NO 35
<211> LENGTH: 370
<212> TYPE: DNA
<213> ORGANISM: Rattus norvegicus

<400> SEQUENCE: 35
gaattcacta gaccagcata ttgctctatg ctgcctttcc agcgctgtac tgcctgtagt 60
ggaacagact cttggagtcc acagtacgag ctttctgcac agcctcagca aaaagtttgg 120
tcacctggaa attggtgagc agagcaattc cactgtccac agctgtcctc cgaatcacat 180
aattatcatg gacaaatttg gtgttgttat tggggaggtt aatcactagg tcaatgcttc 240
cgtctcttat caactttctg atggaagaga ggctgggatt ctgtccttcc tgagatggcc 300
aagccactgg ggtggcagga acattgttgg cgttgagcca gtctgatgtg gcttctgtgg 360
caaaaagctt 370

<210> SEQ ID NO 36
<211> LENGTH: 1404
<212> TYPE: DNA
<213> ORGANISM: Rattus norvegicus

<400> SEQUENCE: 36
ctagtccccg cagcctagcg cgggcggcgg cgggcgatgg aggagagcag agccccgggc 60
cccgccgtcc tccagcgcgc tccgctgcaa ccccgcagct gagcccagag gctccggccc 120

-continued

```
tgtgcgccct accgcggccc cgccactatg gccggcgtgt gggcgccgga gcactcggtt    180

gaagcgcaca gcaaccagtc aagtgctgcc gacggctgcg gctctgtgtc cgtggccttc    240

cccatcacca tgatggtcac tggcttcgtg ggcaacgcgc tggccatgtt gcttgtgtcg    300

cgcagctata gacgccggga gagcaaacgc aaaaagtctt tcctgctgtg cattggctgg    360

ctggcgctca ccgacttggt ggggcagctc ctgaccagtc cggtggtcat cctcgtgtac    420

ctgtcgcagc gacgctggga gcaactcgac ccatcggggc gcctgtgcac cttcttcggg    480

ctgaccatga cagtgttcgg actgtcctcg ctcttggtgg ccagcgccat ggccgtggag    540

cgcgccctgg ctatccgtgc gccgcactgg tatgccagcc acatgaagac tcgcgccacg    600

cgcgcggtac tgctgggtgt gtggctgtct gtgctcgcct tcgcgctgct gcctgtgctg    660

ggcgtgggcc gctacagcgt gcagtggccc ggcacgtggt gcttcatcag caccgggccg    720

gcgggcaacg agacggactc tgcgcgggag ccgggcagcg tggcctttgc ctccgccttc    780

gcctgtctag gcttgctggc tctggtggtg acctttgcct gcaacctggc gaccatcaaa    840

gccctggtgt cccgctgccg ggccaaagcc gccgcctcgc agtccagcgc ccagtggggc    900

cggatcacca cggagacggc tatccagctt atggggatca tgtgtgtact gtccgtctgc    960

tggtcgccgc tattgataat gatgctgaaa atgatcttca atcagatgtc agtagagcaa   1020

tgcaagacgc agatgggaaa ggagaaggag tgcaattcct tcctaatcgc cgttcgcctg   1080

gcttcgctga accagatctt ggatccctgg gtttatctgc tgctaagaaa gatccttctt   1140

cgaaagttct gccagatcag ggaccacacc aactatgctt ccagctctac ctccttgccc   1200

tgcccaggct tctcagtcct gatgtggagt gaccagctag aaagatgatg aacaacctga   1260

agcggagttt cattgcaata cctgcttccc tgagtatgag aatttcttcc cccagggaag   1320

gataactgaa tcattttgga ttgtatcttc tttcggcctc atattttaag ttttccttgc   1380

cattaaacac accgagacaa gctt                                          1404
```

<210> SEQ ID NO 37
<211> LENGTH: 443
<212> TYPE: DNA
<213> ORGANISM: Rattus norvegicus

<400> SEQUENCE: 37

```
agatctctac accgcaaaag gtctcttccg tgctgcggtg cccagcggtg cgtccactgg     60

catctacgag gccctagaac tccgagacaa tgataagacc cgcttcatgg ggaagggtgt    120

ctcaaaggct gttgagcaca tcaataaaac tattgcacct gctctggtta gcaagaaact    180

gaatgttgtg gagcaggaga agattgacca gctgatgatc gagatggacg gcacagagaa    240

taaatctaag tttggcgcac atgccatcct gggagtgtcc ctggctgtct gcaaggctgg    300

tgccgtggag aaggggggtgc ccctttaccg tcacattgcc gacttggccg gcaaccctga    360

agtcatcctg ccggtcccag ctttcaatgt gatcaacggc ggttctcatg ctggcgacaa    420

gttggccatg caagagttca tga                                            443
```

<210> SEQ ID NO 38
<211> LENGTH: 1381
<212> TYPE: DNA
<213> ORGANISM: Rattus norvegicus
<220> FEATURE:
<221> NAME/KEY: misc_feature
<222> LOCATION: (1379)..(1379)
<223> OTHER INFORMATION: Wherein n may be a, c, g or t

<400> SEQUENCE: 38

-continued

```
gggcccctcc tgctcgctgc tgctggaggc gtttcggcga tattacaact atatttttgg     60
tttctacaag agacatcatg gccctgctaa atttcaagat aaaccacagt tagagaagct    120
tctggtcttc attaacctcg aaccgcagtg tgatgccttc cctagtatgt catcagatga    180
gtcctattct ctacttgtac aagaaccagt agctctcctc aaggccaacg aagtttgggg    240
agcactaaga ggtttggaga cctttagcca gttggtttac caggacgctt atgggacttt    300
taccatcaat gaatccacta ttgctgattc tccaagattc cctcatagag gaattctaat    360
tgatacatcc agacactacc tgcctgtgaa gacaattttt aaaactctgg atgtcatggc    420
ttttaataag tttaacgtcc ttcactggca catagtggac gaccagtctt tcccttatca    480
gagtatcact tttcctgagc taagcaacaa gggaagctat tctttgtctc atgtctatac    540
accaaacgac atccatatgg tacttgaata tgcccggctc cgagggattc gagtcatacc    600
agaattcgat agccccggcc atacacagtc ttgggggaaa ggtcagaaaa accttctaac    660
tccatgtttc attcaaaaaa ttagaactca aaaggttgga cctgtagacc caagtctaaa    720
tacaacatac gtattctttg acacattctt caaagaaatc agcagggtgt ttccagacca    780
gtttatccac ttgggaggag atgaagtgga atttgaatgt tgggcatcaa atccaaacat    840
ccaaaatttc atgaagaaaa agggctttgg caacaatttt agaagactag aatcctttta    900
tatcaaaaag taagtcatct gaaagcctaa tcaccactgt tttcatacaa gtccaagctg    960
cgacttagct ctctgcttta cttctcatct tccccactgc ttgcaagagt ggagccaaga   1020
acacctagga ggcagtaagc attttgcagt aactactgaa atagagggag aagccatgcg   1080
cccgctagga gctctggctg ccctttgtct tttgcactat ccaggggctg gaactcactc   1140
cctttgtcct gagtgacctg ggcatctct gctccttaca cagtgcagtg acatttccaa   1200
cattccacag ccagggaatt ggtactgaag tggtggctgc cttgttagaa aacacagaca   1260
gaccacttcc caaaagtttg gtggacagtc tgttctctaa gaatcagcac atttttcccc   1320
atagggacca gaccacactt aggcatcatg ggccatgtgg agttgcaaat ctcttttana   1380
a                                                                   1381
```

<210> SEQ ID NO 39
<211> LENGTH: 2229
<212> TYPE: DNA
<213> ORGANISM: Rattus norvegicus

<400> SEQUENCE: 39

```
tttttttttt ttccagagca gaggtctttt ttaatcaatc acaaagtact ttaaaatctc     60
ataggggaca gccttgaatc atctatccac gctgattgta ccggtaagta gaacaggata    120
agagcaattc gccagctgca gcacagtctg gtacacgagc agcccggggc cagccatgcc    180
tggcgttaca atgtgctctc acaaaagtaa ctcatggaac tcaacgtgaa gtcgcgcttt    240
tttttttttg gttctttttt ttccggagct ggggaccgaa cccagggcct tgcgcttcct    300
aggcaagcgc tctaccactg agctaaatcc ccaacccctg aagtcgagct ttaaataata    360
acctgagtta aattcccagg gaaaggaggg cactgactcc tacaggctgc tctctgacct    420
ccacaagtcc caggatacat ctgagcccgt cccacacaaa ctagcactca atatggaact    480
tttattcatg tgatttctgt acatcaggga gtacaagagt aaacctttac aaatggtgct    540
gattttacca caataaatga caaaaccaaa gcagtgtctg gtgacagtgg cagggcttta    600
aggttcaaac ccagccaaga agtttgttac gatttccttc agctttgcat ccgactgttc    660
```

-continued

```
tgagattttc ccatcagacc tgatattgcc caagaggctc tggtgctggc tcacaacatg    720
agacaagaaa gcactctcga actttgtgat cttactgggc tccagtttat caagataacc    780
ccggacgcct gcatagatga cagccacctg ttcttcaata gccatgggag agtactgtcc    840
ttgctttagc agctcggtca ggcgcacgcc acggctcaag agctgctgag tggcagcatc    900
cagatcagaa ccaaactggg caaaagcagc gacctcccgg tactgggcca actccagctt    960
catggtgcct gccacctgct tcatggctct ggtctgggcg gcagatccga cacgggacac   1020
agacaagccc acattaatgg cagggcggat gcctttatag aacaattctg tttccaagaa   1080
gatctgtcca tcggtgatgg aaataacgtt tgttggaatg taggcggaca catcaccagc   1140
ctgtgtttca atgactggta aggcagtcaa agagccacca ccaaaggaat cgttcatctt   1200
ggctgctctc tccagcaggc gagagtgtag gtaaaacaca tcaccgggat aggcctctcg   1260
acccgggggt cggcggagca gcagagacat ctggcggtaa gcaacagcct gcttggataa   1320
gtcgtcatag atgatcagag cgtgcttgcc attatctcgg aaatactctc ccatggagca   1380
gccggagtaa ggagccaagt actgaagcgg ggcagcatca gaggcagtgg ctgacaccac   1440
aatggtgtac ttcatggcat ctgcgtctgt cagtctcttc accaactgag caacggtgga   1500
ccgtttctga ccaatagcaa cgtagatgca gtacagtttc ttcttctcgt cagtcccatc   1560
attgaaacgc ttctggttga tgattgtgtc aatagcaatc gaggttttcc cggtctgtct   1620
gtctccaata atcagctcac gctgacctcg gccaatcggc accaggctat ccacagcctt   1680
gatgcccgtc tgcattggtt cccgcacaga gattcggggg ataattccag gggctttcag   1740
gcccactcgt ctgcgaatct tggaaccaac tggacccttc ccatcaatgg catttcccag   1800
ggcatcaact acacggccca acagttcatc gccaactgga acgtccacga tggctcctgt   1860
tctcttcacg atatcacctt ctttaattag cttgtcattc ccaaacacga caactccaac   1920
attgtcgggt tccaagttca gggacatacc ctttaagccg gaagaaaact ctaccatctc   1980
ctcagcttga acgttcctca gtccatgcac tcgggcaata ccatcaccaa tgcttaagac   2040
acggccagtc tcttcaaggt caacagaagt atcagctcca aggatccgct cctcgagaat   2100
ggaggacatc tcggcagtgc cagtcttctg aagtcgagtg ttagaggcat ggagatttct   2160
tgtaccaaca aaagatgacc ccaaggcatt tttggagacc agtcccgccc gtcgagggag   2220
ggcacggcg                                                           2229
```

<210> SEQ ID NO 40
<211> LENGTH: 4651
<212> TYPE: DNA
<213> ORGANISM: Rattus norvegicus

<400> SEQUENCE: 40

```
tttttttttt ttttttttgc ttgtttgttt gtttgtttac ttcatgaaat gaaaacagga     60
aagcatatta aaactcaaaa caatgaaaca gaaaacataa aaggtagtct aatagtcaga    120
aaacactggt aaactagcgt gtgttaagta tcagggacat atttatacaa aaaagtaagt    180
ctgagggaaa attctaccca gtcattcttc tcccagtccc agtaagtaac aaagtggctt    240
atcctattgt acctgccatg gtttaatgct gtacaagtgt ggcctgctga gcacatccag    300
gacttcttgt gcatgtagtt atcttgccat ggaagtgtct tgatgcagag ctgctagaac    360
caactgtctg gtcagttggc tccaggcaac tctgtgtaat acacgctacg ggcaagcttc    420
ttcctttatg gaagagtgca tgaatcaaat caataaagac aagaatccca gagttcccta    480
tgtcagcaag cgccataggt ctgttttttt tccccctatg tacctcacca tgaggcaacc    540
```

-continued

```
ttctgttcca aaaggacaat gttctcgatg gatacctttc agtggaatct tcacagttcg    600
aagaccaata gatatacctt caacttccca aagagcatca ggggaggggc ccacttcttg    660
gctcagtgac aaagcccgtc agagttatgc tttaaagcca gtctgagggt ttgacatttg    720
acacaatgtg gacatggctg tcaggagcag aggtgctgcc atggcttggt cctgggcctc    780
tggaaagtcc ggtttgtaac tggtacaatg cctcttcaat gtcatgctcc actaaactca    840
ctgcttggcg gtgccacccg caggtactct gcattttcag ctgtggggcc cttaaagatg    900
ccattcggct tggcttcttt gggaaagaag tcctgctggt agtcagggtt gtccaggctc    960
atttggtggc tgcctttctg gatccagagg gcagagctgt caaacccact actgaggcag   1020
gtcggctggg cagtgttgag atactcaggg ttgctcaccg cattgctatg ggattttga   1080
taatgcaggt ctcttccagg agctggatgc aggggctgat tgtgatagac tgggttctgc   1140
acagagccag ccggcctctt gggaacagat tggtttatat attcaggcac gggaaggaat   1200
gtgtcatcta tgttgtcctc tgtcaggacg ctggtgggat cggagctata ccgttgcaag   1260
aaggcgtctt ctttgacacg gcagctccca tttctattaa tgcaagccac agtggaactg   1320
ttgctatttg cactcagaga gctcaagagt ggagtccgtg acgtggatgg gctgttgaag   1380
aagccttgct gtgggatgag gtattcatca gcatcaacta cgtcttccat gtcctcctcc   1440
tccatcaggg ctcggtaaaa gttggagtct gtagggctcg gcaaatgcat cctttcatcc   1500
ccctggataa caaggtagcg ctgtgggtct ctggccattt tggagaattc gagaatcaac   1560
tctcggaact ttgggtggct atcagcatct atcatccagc acttgaccat gatcatgtag   1620
acgtcgatgg tgcagatagg tggctgtgga aggcgctctc ctttctctag gatggatgag   1680
atctcacttg cagggatccc atcataaggc ttggacccaa aggtcatcag ttcccacacg   1740
gtgactccat agctccagac gtcgctttgg tgtgtataaa ttcggtgtaa aattgattcc   1800
aaagccatcc acttgatagg cactttgccc ccctctgcat ggtattcttt ctcctcagca   1860
ccaagcagtt tggccagtcc aaaatctgtg atcttgacat gctgtggtgt ctttaccagt   1920
acattcctgg ctgccaagtc acggtgtacc aaacgccggt cttccaggta gttcatgccc   1980
tttgcaatct gcacacacca gttgagtagg tactgggagc caatgttgtc cttatgttct   2040
cggacatagt ccaggaggca accatagggc atgagttgtg taatgagctg gacagtggag   2100
gtcagacaga tgcccaggag gcggcataca tgagggttgt ccacactggc catcacgtag   2160
gcttcatcaa ggatttcctt gttggctttg ggagatgtgg cttctcttaa ctccttgatg   2220
gccacaggga ttttcacttt ctcgccttct gggatccaga gacccttata cactgtgcca   2280
aatgctcctg aacccagaac tttgatcttt ttgaattctg tttcctttaa tatcctcaag   2340
tgggcttggt tcggagcttc tccgctgggt gtgagaggtt ccacgagctc tctctcttga   2400
agcaggcggc gtagtgtacg ttttcggaca agctgacgtc gacgcatgaa gaggccgatc   2460
ccaagggcca ccactactat gaagaggagg ccacccacaa tcccagtggc gatggatggg   2520
atctttggcc cttctggttg ttgacatcct ttaaggcctg gcccagcaca tccataggta   2580
cagtttgcat ggcagaggtg gcagacgtta ttggcatctg caaacttcca gaccagggtg   2640
ttgttctccc ccatgatgcc cgaagggcag gtcttgacac agtggggacc atcaacatag   2700
tgggcacact tgatgcagtt gtctggcccc cggcctgtac aggtgatgtt catggtctgg   2760
ggcagacatt ctggatggca ctggatgcat tcagaatttt ccacaaactc cctcggttcc   2820
ccctccagga tgttgcactt gtccacgcac tccctgcctc tgctcacatt ctggcaggag   2880
```

-continued

```
acacagtccg tgggctcagg gccccagcag ccttccgagg agcataaagg attacagacg   2940

tggttcgtgg ccttgcagtc cttttcagct ctgttgttca tgattttggt cttttgattg   3000

ggcgtcccga agagtttttt ccagtttata gtgtttgcgt agcacaaatt tcggttccca   3060

gaaataatca catccccatc actgatctcc ttgagggaac gcaaccccag cgatgttatg   3120

ttcaggccga caaccgccag agaaaactga ccatgttgct ttgttctgcc acgaattatt   3180

tctaggttct caaaagcatg gaggtcagtc cagttttcag gccaagcctg aatcagcaaa   3240

aaccctgtta tttccttcac agttttgaga atttctagtt cccgtgggtc tagaggagga   3300

gtgcgggtga aagaatcccc cttaaaggcc actggcagga tgtggaggtc cccactgatg   3360

gcagtgcagt acttgaagtg tttgatgttt gtagcattta tggagagtgt gtctttaaat   3420

tcaccaatgc ctatgccatt gcaaactttg cggcagggcc cgtcacattt tttacacttg   3480

ctgactccat cttcttctac ttcatagtag tctggcccac aggcccggac acacgagccg   3540

tgatctgtca ccacgtagtt tctggggcat ttcttcacac aggtggcacc aaagctgtac   3600

ttcccctcag ggttgacatc catctggtac gtggtggggt tgtacagcat gagtggtggg   3660

caggtgtctt tgcacgtggc ttcatctcgg aacctgtggc agaccagaca gtcactctct   3720

ctgggccctg tacaccctgc ggcacactgg ttgtggcagc agtcgctagg ggacctgcca   3780

cgacaacgcc gggaacattg ctgggcgcag atgattttgg tcaatttctg gcagttctcc   3840

tctcctcttc cccagcagct tccattggga cagctcggat cacatttcgg gcagcccgtc   3900

aggtggcgct gtacgtccat tgacatgttg ctcagaaaga catcttggac gatgtccctc   3960

cactggatgg tctccatatt gcagaggatg gggttgttgc taaatcgcac agcaccgatc   4020

agaatttcct gtaagttccg catgggcagt tccctaagcc cagttttgtt ggttccatag   4080

ttggacagga cggctaaggc gtaggtgttt tcgtagagag catttcccct gatgatctgc   4140

aggttctcca aagggattct ctccacggtg ttcagggcaa tgagaacata gccagccacc   4200

tcctggatgg tctttaagaa ggaaaggtca taattccttt gcacataggt gatttccaag   4260

tttccaagga ccacttcaca gttgttgaac atcctctgga ggctcagaaa gtggtcttca   4320

aaggtgccta gttgggtgag cctgttactt gtgccttggc aaactttctt ttcctccagc   4380

gccccacctg cggcgcagag cgcagccagc agcagcagta gcttggttct cgcagtccct   4440

gagggtcgca tcccggctcg gcagtcgttg gctctggctc tccgggatta atccgagtca   4500

gactgagtcc cacggtcgtg cccggtgact gcgtcggcaa cgacgacggg acccggactc   4560

agactcgcgt ccaggtgacc cgtcgcctgt cttggtggcg gtagcctccg ggactggctc   4620

cagacgctcg agcccaggaa gagcgcacag t                                  4651
```

<210> SEQ ID NO 41
<211> LENGTH: 1726
<212> TYPE: DNA
<213> ORGANISM: Rattus norvegicus

<400> SEQUENCE: 41

```
tccgatctga gcagacagct acagccaaca gatggcgtgt aagtttggag ctgtcactga     60

cttaaggtgc cttatgtctt agccttccct aatgtaaggt gggtgggcat aactggaaca    120

agtctgttaa gacttgctct gaggaggctg acagttcagt aggtgacatg taggaaggat    180

tcagggcagg gaggaaccac tgcatctttc atccgacaca gtagttactg actaaacaac    240

agtgagcact tgagtgcact gagtgcaact gtgcagggcc tggtgcagga gaactctctg    300

gactgaagaa ttccgtgaaa gtataaaagc cactacgacc agaactgccc ctcggaacgg    360
```

-continued

```
ctcaaaggag tcaagagtgg gtaagctgag acgggctgga gacaggacca gggtcaagaa    420
ctggggggac accgacatct gaacgcgtcc agtcctctga gcccttgtcc tgaccaattt    480
aagatctgta tcctggctgg aatcgagcag tctcttcaaa aatgagttct ttgagcttct    540
ccttaggtaa gtcgtccagc tccatgtcaa acttgaatgg tgcttcagca atgggctcat    600
cacttgggtc ataatactgc tccaggtacg ggtgggccag agcctgttca acttcaatcc    660
tcttgtgagg gttaaatgtc aacattttat ccagtaaatc cagagctttg gagtcagcgt    720
ttgggaacaa cctgttccac ggcaccttat ttttgtgcgg gagagaaagc aaatagtttc    780
tagcttttaa atttattata caattcagat cttcctgtga tggagatcca agaataccca    840
ggatgtgatt cagctggtca aggtaatgct ttcctgggaa gataggcctg ttggatagca    900
tctctgccag gatgcagccc acagaccaaa tatcaatgga cttggtataa cccttggaat    960
tcaacataat ttctggagct ctgtaccaac gcgtggctac atactctgtc aagaaccctg   1020
tatgatcatg gtctggatct gcaacacggg caaggccaaa gtcacagatc ttgagatcac   1080
aagtggtgtt cagcaggagg ttggaaggct tgaggtcacg gtgcagaaca ttagctgaat   1140
gtatatactt taatcctctc aggatctgat aaagaaaata gcagatatga tacttgctga   1200
ggtgctgtgt cttcaagagc ttgtaaagat ctgtctccat gaggtcctgt actatatata   1260
catctttcat ctgctcaatg gttggtgccc ggatgatgtc attgatgccg atgatgttct   1320
catgtctgaa gcgcagtagg atttttatct ctctcagggt tctctgacag taggtctggt   1380
gctcaaaagg actgattttc ttgatagcaa ctcgaacttt gttgagatta tcataagcag   1440
aacaaaccat gccgtaggcg ccttctccga tgtacgagag attagtgtag cgcggcccca   1500
cgtcgaacac ctgcccgcgg accatctccg ggcccgccgc cgccgccgcc gccatgttgg   1560
ctgcacagcc tccgccgcgt tgggctcgac gcttcgcgtt accgctcgac ttgtgctgcg   1620
cttcccacag gaaccgcgcc gccgcccgtg tagccggctg gcggcgatcg ggaacgagga   1680
gggaggacaa cacagaagag agaactaacc gccggtagaa ccacgg                  1726
```

<210> SEQ ID NO 42
<211> LENGTH: 526
<212> TYPE: DNA
<213> ORGANISM: Rattus norvegicus

<400> SEQUENCE: 42

```
gtgcacagag ggactcaac ggtgtgccgc tgctcagact acatctggcc cacaaatgtt     60
cttctagagc caccagaatt taagattatt ggctttaagg accacataaa tgtgatgatg    120
gagtttccac ctgccactta caagctattc ggggaaagct tatggaaaag actggagtct    180
acatccttcg tcatcgagga acagacagag gacagcatta gggtgcacaa gccccaaatg    240
aataatgtca ctgggaactt cacgtatgtc cttagagact tacttccaaa gacaaactac    300
tgtgtgtctg tttattttga tgatacacct gtaataaaat ctcccttaaa atgcaccgtc    360
cttcagcctg accaggaatc aggtatggct aggcttttaa aatttgcact gttgttttga    420
tggaaaactt gctgaaagaa aaaaaaaaac tcaagttctg gtacactaaa tgtacttctt    480
ccaataaatg cacatcactg agctgtttaa aaaaaaaaaa aaaaaa                  526
```

<210> SEQ ID NO 43
<211> LENGTH: 3520
<212> TYPE: DNA
<213> ORGANISM: Rattus norvegicus -continued

<400> SEQUENCE: 43

```
tttttttttt ttttttgac aagataaaga gtctttattg acatagagct ccacgtgacc     60
tcttctgtcc tgccctcctt gcaaacatac taggtgtccc aaaggtaggg acacgagcag    120
acagtcctga gcctggtccc gtcctccaga atgcagtcag actgcagtct gccatctgcc    180
atccctatca tctggccacc aaccagaacc agccccacag ttcccttgtg gtctcgcctt    240
ggctgccagt ggtggtgtcc actgggacct gccactaggc tgctgtgttt gtttactggg    300
atcccacttc cacatcctgg gagccctggc ttctggccac atgtgggtaa ctggcagtga    360
ctttgggcaa tcaagtttgc gttcttgttg ctttccacaa ctgggccaag ctgggacagc    420
aggctctgct tctagtctca gtccgagctg ttcaatgaat agcctccttg gggcagtatc    480
taccctccct taactcaaaa tttccactag ttagggcctc ccaagccact gccaggccag    540
ctgcgagttt ctaggaccag cttccagctg gagaacccga cagctatgcc aggactgctg    600
tgagccttgg gcaaacggtc tattgggtgg acagaatggg cctgagcagg tagggcaaca    660
agagctagga gagcccaggg cttaagaata tcagcactgc tgtgggagaa agcaaaatga    720
gtccctgaat cccttgtgag ggaggagagc ccaggccaac ggtaggggag acagccaggc    780
tctgaacttc tagggtcagg ccaagttcac atcttcactt caccattctt tcgatttctg    840
ggaaacctgc cagctgggct gtctctcagg aagcacttcc ctggcttgga ggaaccccgg    900
ccttagcaca gacctcagca acaacagcac actcacctaa gacacagtga cgcccagagt    960
gcccacaggt acctcagtag tctggctggg aacaggagag tggccagggc ccttgcccac   1020
ccctgacaaa ttggagggtg tcctgggtgc taaggtgagg ttggcttcct gtgacatttc   1080
cccaggacag ctctccaagg tccccgagag attccccaag gatggtgatt tttcatcata   1140
gcaacagccg cagccagggc tagcaacgac atggatctga ccatcttcct cctggctgtg   1200
gtgttgcttc aggtggccac acagatggca ggtgagggac gagtacacaa tgccaaggcc   1260
caggtcatcc ccaaagggct tgggcacctg ctctgaagga ggaggggcct tcagccaggt   1320
gcctcctttg agccccagct ctagaccaag gcattctggg gtgctattgg gtggggctga   1380
gttcagggga ctgggtggca gctccatgtc cagtccgaag gtgaataagg gcatggagtt   1440
gggggactgg ttaggaacag ggttctggaa gggcttgtac cctccacatc cactgtcagt   1500
ccctgctgct gctgtgtccg tgcagacgcc actgctgctg agcaggctcg agaaagcctt   1560
gtaaccagtg tctccagaag gcccgacacc aggcacccac ctggcctggg acgcaccctg   1620
cttcactgcc tgcacaaact cttggtagcc actggtaggg gctggggtgg agccagctgt   1680
cccgtgctgc aggacactca tgtgaaggat ctgctcccag ctctccgctt gctgcattgg   1740
tggccctgaa gaatgggggt caaccgggct cagaagatcc ccttcttcca gatgtccagc   1800
ctgcttctgt tctgaagcca gctctccagg atttggggcg gggctggaga agtcactaaa   1860
actccggtag gcaggattgt ctgaaatgac aaggggggacc tgtgtgcagg ctgtgccagt   1920
tgctctctca gggtctgggt gtggaggctg ctgccctgtg acctggcatg tggtctcact   1980
gggccccgtg gggaagcagg cccaggacgt agaagcttgc ccactttctg aaggcagaag   2040
ggaggatgac tctgccatgc tcgactggcc aacgcctcca ttctcagccc ccagcaagtc   2100
tgaaaacagg ttctcagtga gccgggccat gatgtctgcc tgactctcct ggaagccccc   2160
tccgctgttc tcaggtgaca tgctcaggtc ccctttgacc atctcatcct cttcctcctc   2220
cacattctgt actggggcct caaacagctc catacagcgc accacactga catgaacgtt   2280
ctctggccag aggacggtcc tgctgacctc cgcaggatac cagcctgctt tttcaggact   2340
```

-continued ctggagaggc ttggttttgg cagccttcgg ggattctctc tctttcttca ctctatgctc 2400
cagcaagcag ggcagcagct tggttagaca agtcttccag tgccggctct tggttgactc 2460
ctggcttcgg gtctgcttct cccagaggga caccttcgtg tcctgaatga tgatggctgc 2520
taagggactg cgtgctggag tgggaatctg gtcccaccat atcttcttaa tcttgataat 2580
gctgaagtaa caggtcaggc aaaacaatag gatgcagatg caggagatgc tgacacccag 2640
cgggaggcgc tgcagcaggg gcagctggaa gtggttgtac cacgtgatgc tgggactcca 2700
ctcactccag atgccaggga agctctggga caagaccctc acacgtgccc tatagcgcac 2760
ccctgatgtt agggtgttga ctgggaagct cagcttgggt tccgtgtagg tcacattata 2820
gactttgaat tccgccgggt tgtcctctct ggagatgttg accatgcaga tgaggccttt 2880
gtgcaggaag ttgttcgatg ggtatgggtt gctccacatc agcagcaggc cattggagac 2940
attggtgtgg agtgtgaggt tgtctggagc tgggggcttc acattgtcac taggcttgaa 3000
ggagccttgc cacagctgtc cccgctcaga ccacagttcc agccagtatg tgtctgcctg 3060
gatcggctcc tctatggcca tttggcacac acacacggtg tcggcactgt tcttgggggt 3120
gcatgtgagg ttttcagaga actcgaagag cagcctgtag tccaggagga gctgagaact 3180
gcagtccaca gtgctatcca gctgccactc acacgtagaa gtgcggatgt agtcagagaa 3240
gcaggtgggg tcacccagga ccttgatgcc cccagagcca gtcacccata gcaaaatcag 3300
acagctcacg gaggacagga acttggtgca aagccgcccc attgcggaca caaaggtgcc 3360
tgggctatac agggagagac tggaatgcag ctcagtggca gcgtacctgg cccccagatc 3420
ctgggctccc tctccagcac ctgtgtgttc aggctccacg cgccgtgcgg ggctttcctg 3480
cgcgaaggac ctcgcccggt ttcctacgcc gcccggacgc 3520

<210> SEQ ID NO 44
<211> LENGTH: 390
<212> TYPE: DNA
<213> ORGANISM: Rattus norvegicus

<400> SEQUENCE: 44
gtgcactaag aatgacaaac ttgctgtgtg ccacaaagat cttgggtggc tggttggtgg 60
ccagtggtca ggttggcctc acactgctcc aagtagaaga gcagcagctg tcggtctgaa 120
ggccccagtc cccctgtccg ccccggcaca aggggctggg ctggtgtcca gttggccagg 180
tcatggtcta tgggacgaga cacctcctgc tccagtcgct caaactgttt cagctgctgc 240
agctccagtt ggccttttcc ctgtcgcacg atgttgccct tttccagcag ttccttctgg 300
gtcttctcaa attcctcctt cccctgcaga tgaacgtagt catagtcctc catccaaccc 360
ccttcactgt tctcatactg gccatccgga 390

<210> SEQ ID NO 45
<211> LENGTH: 383
<212> TYPE: DNA
<213> ORGANISM: Rattus norvegicus

<400> SEQUENCE: 45
tctagacttt aacaacaagc gtgatgaaca cccagagaaa tgcaggagtc ggactaagaa 60
catgatgtgg tacggtgtcc ttgggaccaa agaactgctt cacagaacct acaggaacct 120
ggaacaaaag gtcctgctgg agtgtgatgg gcgcccgatt cccctcccaa gtcttcaggg 180
aattgctgtc ctcaacattc ccagctatgc tggagggacc aacttctggg ggggcaccaa 240

-continued

```
ggaagatgat acttttgcag ctccatcatt cgatgataag attctggagg tggtcgctgt    300

gttcggcagc atgcagatgg ctgtgtctcg tgtaattaag ctacaacatc atcgaattgc    360

ccagtgtcgc acagtgaaga tct                                            383
```

<210> SEQ ID NO 46
<211> LENGTH: 2870
<212> TYPE: DNA
<213> ORGANISM: Rattus norvegicus

<400> SEQUENCE: 46

```
tttttttttt tttttttaa ccaagaggag gaatataatt gtgataggaa actaagaatc      60

atgaagctca ctacaaaaga caaacactac tgaaacatgt tgtgctggcc ttgacacacg    120

caggcagact gtcgcctagc tctgaggcag agggtcaagg ttgacacagg gctcggagga    180

aatatttacc agagagaatg tggtgattca tttatcagtc cagagatcgc aagtataaaa    240

cttcaagata taagaaggat caaattatat catgtatgtg attcaattta aaatgtctta    300

gccctcttac attatattat ctggattata actgtaaaaa aaatcaaatt acattcatat    360

gaaactttta tcaaaagaaa tcaaatccat ttttatgaaa ctttatagta caattatttt    420

tagttggtct ttccttaggt cacagtattt ataattccat ttacatctgt ataattttta    480

aaattaaaaa acaaaagcaa atcaatagaa atctaagttt tcttttgtaa aactctcttc    540

agtctccagg ccggcaccac atgacagtgt tgacttgtcc tccagacatg gacaactccc    600

aggatccctg gcttacgaac cattcaggcc tcgactcatt aggaatgctt tttggtttgg    660

ctcacgttgc aagaaattct ggagcatgtc catgccgtcc agggaccccc caggcttcag    720

gattaagttt ctgtatttca ttccaacctc tggattcatg atcccctctt ttttaaaaca    780

gctgtgaaac atgtccatgg aaaacacttc actccaaaga tatccataat attggccatc    840

ataccctcct gccaagtgtc caaaagtagc tggcatattt gtgcctggcg tagctgcaac    900

tcccagaatt tctgtgcagt atttagcgta ttcgctcgcg gcatccagag tcgcattggt    960

atggagagat tggtcaactt tgctcaaaac aatttggcgc agcgtcagaa gacctgtgtt   1020

gaccagccta gaagcaacaa gcttctcgag cagctcgtct gtgatagggt gtccatcttt   1080

ataatgcttt gacagttttc gcagggaatc aacgtcccac acccagtttt caagcatttg   1140

tgatggcacc tctacaaagt cagtttccac gtttgttcca ctgaatcgtg caaagtcagt   1200

ctgcgcacag atctgatgca tgacgtgacc gaactcgtgg aagtaagtcc gcacttcatc   1260

atgtctcagg agagagggcc gacctgctac aggctgagag aagttgacca ccagggcggc   1320

cacagacatc atccgactgc catcagggag aaggcagcct ggctggagac cgaagcaggc   1380

tgcatggttg tattttcctt cccttggata gaggtccagg tagaactgcc ccaggacctc   1440

tcctgtagct ttatccttca cagtgtaaag tgaaacgctc ttattccaaa catgagcatc   1500

gggcacttgt tcaaatgaaa gtcccagcag ctcctggtag atgcttagca agccttccgt   1560

gaccacctca atggggaagt actccttaag ggactcctgg tccaccgagt acttgagctc   1620

ctctgtctgt gtcatgtagt aatggaggtc ccatgcattg atcttcccgt cgtattcaaa   1680

acctcgctct tcacattcct tcttcttcag gctcaaaata aactcccgtt ctgcctcacc   1740

caagggtttc aatttctggc ttaaatcatc tagaaaggcg gccacgcggc tggtgctctt   1800

cgcagtgttc agttcaagga caaagtcagc atgggtgtta tagcccagca gcttggccac   1860

ttgagctcgc agcgggagga gctgttgcag aattgcggtg ttttcctgtt tgcacctggt   1920

atgaaaagcc atttccatct tccttcgagt ttcagggaca cagcatttct tcatgacagg   1980
```

-continued

```
gaagtagtga ggatacttta aggtaacttt gtacttgtct tcatctgttt tttctaaact   2040
gtcaatgaag tcatcaggaa gagcaccaag ttcagccttg gagaatacaa gggaagtgtc   2100
gtcctcattg aggttcttgt tgaagtcaat gcatagctca ctcattctct tcttcattga   2160
tttgatttca tttcttatgt gttctgaaag atggagtcca ttcctttttc ccattttaat   2220
tgacttttcc aagtatcgcc tggcttcagg ctttatcttc tccaaatcgc atgtttcttg   2280
taaatgaaca attctctgaa acacatcttc tctcatgctc atctcaatat caaaacgaga   2340
aagctttttg tctgcttctg tgcttgcagc ccgcacttct ctgtcagatg acacgtgctg   2400
agggaagtcc agcatggtcc tttccactat gtacgtcact tctatgtcag ccagcacctg   2460
cagacagttc tcataagtta cttctttcag ggcgattgtc cccacggtgt cgtacacctg   2520
cttggtctgt gctatgagct gctctgtcct cgtcttgatc tgctctggag aaaggtccca   2580
tctgagaaca ttcctgccag ccgcagtgta ggaagacata gcttgaagag gagaagccag   2640
ctcctttccc agtgtcattg tcagctgaag cctggagcca ccagctctgt ggaggcctcg   2700
cagagtcgaa aggcacaggg tgatcatggg cacgccggga ggccggcagc agctggcgcg   2760
tcgtcctccc gcttgtaggt gcaggaggca ggcggtggtg tctgcgggcc cggaagccag   2820
gagtgggcca agccgaggag accagatctc gagacggagg ccgtcagtcc              2870
```

<210> SEQ ID NO 47
<211> LENGTH: 5127
<212> TYPE: DNA
<213> ORGANISM: Rattus norvegicus

<400> SEQUENCE: 47

```
tttttttttt tttgtttata tgccaacata taccttgtgc tagaaatact ttatggggtt     60
acaactcttt atatacaatt ttttttgagg cagtatctct gatggagagc ataacttgta    120
aagagcttgt gtgtgcttcc gtgctccaaa atgataggaa atccactttg agaagacaac    180
ttatttgatt ttaaaaaaac aaaaaacaaaa acaaaaacag aaacaaaacc gcaccaatgc    240
acagccagag gctccgctgg aactgataca gaaccgcgca aacgccgtga ttataagtaa    300
cattttccag ggtggtcaag gctaacgtac aatattatac acctggcact gatgtttgcc    360
attggtcagc aactggcaaa atttgtttct atgtataaat ttatttttaa acattatctc    420
tggcctgaca tatcttcact atttataaaa acatttagac agtgagctca cgttgaataa    480
ctaggtctac tgtgttctgg aagctcttca gtagtaaaac agctttttcg tgttccatat    540
gcacaaaact gtgtccattt gcctgaagga ttttatcccc gggctgtaga aggttggatg    600
ctggtccatc aggctgaacc ctagtaacaa agataccctt gtcggaaggt ttgaaaggat    660
ttccttgccc actaattcca ccgctgatac taaatccaag cccagggttc ttttctattc    720
tcacacagaa ctgctcggga taaccgtcca tactcctctg ccctttcgtt tgaattaagc    780
accgtccagg ctggggtccc cgggtggcct gtgatgaggg gatctggatg ggcagtggcg    840
actggaactg ctgaatggtc actttgttga tgttcccttc atatggctgc tgctcccggc    900
tgcggtgctg aaggctctgt gaccccatca gggtctgaat gtggctgcct gcctttttag    960
taatggtgtc cggaggtaca tcccgcctcc caagtgggta aggattccat tggccactag   1020
gagagacatc ttcttgtcca ttgtctaaaa tgttgctttg ctgggacggg gtcctgtcta   1080
accttctagc ttctatatgt ctaagcagct gctgtctcca gtctgccggc attttgccac   1140
agctctcctc tcccttcaca ggggtgggcc ttgtctttat atcactgtta tctgatgtct   1200
```

-continued

```
tgtcaccata gttacccaag ttatagtcag atggtatttt ttccaggagg gctgccatgg   1260
taggcctagc tgaaactggc ctggtttggg aggccccgta actctctgtg ctgtagctcc   1320
tggcagacag tggcctcctc tgggtaaggt ttttagcagg aaaacttccc gcctgcgctt   1380
tcacttcttg atatgaaggg tgctcatctt cgtacctgcc attcctcttg aggaattggg   1440
gatcagtcat tgaaacgctg ctctggcctt ccagccctcc cctataggct gctcggccat   1500
acctgtcacc agggggcagc tcgtggggct cactgaccct tctgaacatg gccatctctg   1560
tggagctggc cagggagtca gccctcctta ggaagcctgc cctgggcccc tggctggcga   1620
actgagcatt caccatggca tcctcattta cagatggttg ggaaaaggag aacatctgct   1680
ccatgggtgg gtatcctcta taggctctgg ggctgacgag atccttggcg atgtttttac   1740
cgggctgttg tacatactca gaattgtgtg caaaaggggg tgggatcctc ttctctgctt   1800
ttacttccac cgctccttgt ggattgaagc tttggtcaaa ctgatagacc ttcttagtca   1860
tagatgcttt ttgttggggt gggcctttac tacttccgta catgagcatt tcgtcatcca   1920
gcatgggtac cgactggctc ctggacatac tggacatgcc gtgctctggt cccaagaact   1980
tgtctggccg ctcgtggctt cctaagtgat cgcttccaga ggcatagttt tccagtggaa   2040
tgttatagac cttgtaggta ccgacgtcaa tctcatcaat actctgggac tttttgaact   2100
tgttggactt tatatctttc atgagcgggg aaagcctctc cgtgcttttg ctaattgcaa   2160
taacaccttt agacgaatct gggcggcagt ggatttgaga aaagacatta ccgagactcc   2220
ggttgggggt ggggtcgtgg tactcccatg gcactcccgg agaaaaggga cctggtgtct   2280
ctgtaggctc cttcatgtgg tcttttcttt caggcaaggg actggtagta ggggttgttt   2340
ctaatttgga gggaaaagca gtcctgtcct caaatggact gggggttctg gtccaattct   2400
gccagggatt ggaaggaggc acttctgttt ctggtgtgtg tctgtgggtg gactgctcca   2460
gttccagggg aacaccgaca atcctttctt gcctgattaa aggcctgcgc ccatgagcag   2520
gtacgcttct agccttggag cttaagagag ggttattgtt ggcattctcg cctgtggctt   2580
cctcggagac aaaacctgtg ttatcgtaat gggagccatc ggtccagttg tcagggaaag   2640
catcactcat tggcagccga tcaggacgct gggggaggtt ccctggaggg acagcctccc   2700
gttgggtgag taatggcttt gcatctagag gctgtgggaa aggtggtgca atcctgttac   2760
cccacaaaga gttatgcacg gcatctttag ttgttggctg caaggacccc actttcaccc   2820
gggtgttgga ggatgctgag gaagcctggg agggcgagta gtctgagtag gtgcctgagg   2880
agacactgtt attcagacag tgagttttgt caacttcaga ctcatcagtt gattcttttt   2940
tgtccttccc tagcagaaca agtttgggtg ggtacagagg ggtctcagct aatgaagggt   3000
gaagttcccc aatcctcatt tcattagctg gatgaacaaa agaatcctcc actgtaatct   3060
cctttggggc caccggccac ttgtgttcaa acttttcttt cacagtttgc tccgtgttag   3120
ctgttgggtt tgcgttctca acgcgcactc catggcttgg cttacccacc agattttgaa   3180
cagattttac catgttcttt aaatcctccg ggtaaggagt tggatatcgt tttaggttta   3240
tttcaacctg tctgccactt agagagggaa gagtggtgga ttgggctgcc actggtaatg   3300
gagcacacat gctcctctcc tgctggaggc cacttataca accccatgcc agctggggggt   3360
cactctgggg gacgggcata tcttggatct gctgatcaca cctggcccat ggtgtgcagc   3420
aatcgccaga cagcctggca ggttggagag taatcccacg ctggcccctg tcccaggggg   3480
cttggcagga gagagcctta actttcccag cactttcgtc atcttctttt ttatcctcaa   3540
attcaaaggc aacagtcatg cgctgttgtc tctgctcctc ccacagggtg gggttgaagc   3600
```

-continued

```
tgtcgctgtc tgactggaaa tcttcatcac cacggggctg ctggggaaac atgtagttgg   3660
tcagtaccct ttgcttggtt tctggatggg cttctgtttg cagagggatg agggccttgg   3720
actgattgtc agaaagccac aatgctgcaa gctctttgag tttggtgaag gagaatggca   3780
agttcttcaa cctattatca cttagattta agactcgaag tctctgcatc tgcccgattt   3840
cttcaggaag aaattctagc ttattggagc gtagagacat aacggtgacg ttcttacagc   3900
ttccaatttc tctgggcaac tctgggagga aattctcgtc cacagctaag gttcgcaggc   3960
tgtgcaggta accaatggtg ggagggaggg actccagctc attgcaactg cagtcgaatt   4020
cttctaataa agataagttt ccgattgtgt tgggtagcat tgtaagctga ttgtcatcta   4080
cttttagagt tgttaacttt ttcagcaatc ctatagagtc cggcagctgt tgcaacatat   4140
tggatgatag taagaggtcc tcgagggctt cacatccaga aatatccatg tcaaccgttt   4200
ctatcctgtt ttttgacata tccaggtata ccaacatctt taacttccct atagacccag   4260
gcagcacttg caatgcgttg ttatccatcc acagctccct caaattctga atttgatcca   4320
gaacttcagg cagctcgctg aattcattat tgcctaggtc aagtctttcc agctgggcca   4380
gcttgtgcat tgactttggt agagttttca agtgattttc tcttaactcc aagattcgca   4440
atttgacaag tcttccaaaa ttagctggaa gaaattcgag gaaggcgtca ttcaggtaga   4500
gctgggtcag gttaagaagc tgcgtgaagc catcgggtag tttagaaatg ggattgacac   4560
tggcttcaat aatggttaaa cacttacagc actttatgtt ttctggaaat tcttgtacac   4620
cgtttttact gatgtcgagt tctttcagat taactaggct agcaatggag gtcggcagac   4680
ttgagaggtc attatcagga atgcttagtt tccttagagc ttgacagttg aacaattgct   4740
tgggtagctc ctcaatctga ttggcatcta gatagagctc ttctagtgta cgttcgaagt   4800
tgaagacctc cttgggtacc tgttgcaggc tgcagtggga gtaatccaac accgagatga   4860
tctcttcctc gccacggaag cagcggcatg gcaccaggcg gccgatgagc ttccgtttgg   4920
tggtcatctc caggcactgc attgctagtc actcctgtct ctgaagactt ctaggctgtg   4980
ggcactttga cttgcattct tttcatgtag cgggctcact cttcttcagg cctcttccga   5040
agtgctgcac gggcctcctt acaaggactt ctctgatatt gtgggggatt ccttccccgt   5100
attaggttct ccatcatcgc agaagca                                       5127
```

<210> SEQ ID NO 48
<211> LENGTH: 1768
<212> TYPE: DNA
<213> ORGANISM: Rattus norvegicus
<220> FEATURE:
<221> NAME/KEY: misc_feature
<222> LOCATION: (893)..(893)
<223> OTHER INFORMATION: Wherein n may be a, c, g or t

<400> SEQUENCE: 48

```
tttttttttt tttttttttt actagtaagg tatttactag gaaatgatac aaacagccag     60
gaaaagggtg catcgcagaa cagggtctgt gcgtataaga tgggtatttc ccctttgtca    120
cgtcattttt tccatgaaga tgcgcttaag ataggaaggg taaagtaccg acacgtggca    180
ggccccgggt ttagggaagg gaacgtgaga gagacgtcaa tggaggccca caacagtgaa    240
acccctggaa gagggccaga gcagtcccct ggtgcagtac tcagcgaatg cgcatacaca    300
actggaaagg ccttggcaaa ttgcccagcc ctgagctgag cggggtcagg tcgatgtcct    360
caggctccac cagcggatgc aacgtgaagt tctggagaat ggaggtgagg tatatgaaca    420
```

-continued

```
gctccatgcg tgccagtggc tctcccagac acagtcggcg tcccgccgaa aatggcatga    480

aggcggggct cttcttgaag gattgattgg catccagaaa atgctcagga ttgaactcct    540

gaggggtctt gaattggtcg gagtcatagt gcacggtgtt aaggagcgtg atgacatctg    600

tgcccttggg tatcaggaag cccctgaaag gtgtgtcccg aatgacgcgg tggggcaggt    660

tcatggggat gacgtctgca aagcgctgca cttcgtggat caccgcgtct gtgtaaggca    720

tggatgcacg gtcctccagc gtgggcatcc gcgaacgtcc caccacacaa tcaatctctt    780

cctgcacacg ggcttgcact ttggggtact tcataagaat gaggaaggca tggcgtaaag    840

tggtgcccac agtctccgtt ccaccaaaga gcaggttgtg tgtggtcatc agnagggtgt    900

ccatattgaa gtggctcagt gggtcttgct tctcctgtac catttttgtg aggaagcagt    960

cgatgaagtc ccggggagag ttggggtcca gggagtcctg gtgctcgcgg acgctgcggg   1020

cgatgagatc tttcatgccc ccaaagttcc ggaacacgcg tctgtgcggc ccaggcaccc   1080

agtccaggag actcgggaag atgttgtaca tctcgcccca ggggctgctc ataatctgga   1140

agttgtcatt gataaagtgg ataatggtga gcagccgttc atcgtcataa tcgaagcgac   1200

tgccgaagat gacagagcaa ataatgttgg agaccgagcg gctcaggata aacacggggt   1260

caaagggctt gccttccgtt ttccgcagca cgtccagcag gaagctgcct tcttccagga   1320

tccgctcctc gatgcttctt tttcccatgc caaagttcct caggatttgg acagagaacc   1380

ttcggaggat cttccagcgt tctccatcgg agaaggcgat gccgttgccc ttggtgaagt   1440

tgaaaaagat ggggtatgag cctcggccac tgaactcctc ccctttgtcc acaagagcct   1500

ccttcacagt ttgatatccg ctgaggacaa tcacacgcct gggccccagg tacaccgtga   1560

acactgaccc atagtccttg ctaagcttgg tgagtgaggt cagcaagtct tgggagcgaa   1620

gctgcagcag gtttcctagg attgggagag gcttgggtcc tggagggagc tggcccttgc   1680

cccatgaggt gaaggtcagg gacagagaga tgacagccag gaggagaagc aagatggctg   1740

tgctcacacc atccatagtg aaggcagc                                      1768
```

<210> SEQ ID NO 49
<211> LENGTH: 367
<212> TYPE: DNA
<213> ORGANISM: Rattus norvegicus

<400> SEQUENCE: 49

```
actatatgat cctgtttaca tgaaccatac atactaggca aacctgtaga catagaattc     60

agaccttata catagtccaa tagcatagat cacagagcat ggagacctga taaatgggga    120

ctgaggctgt tgggaagaag tgaggaatga ctcagcaacc ttgggcctgg tctccagcag    180

gtctcccaga atcagaaaaa tggggccatt ttgaacagaa gtgagtcggc tgactgcctc    240

agcacaatca gcgggctaca aagcaaatct tgtacactga gtctacaagc aacactctct    300

gctatggatt cctgctcatg ctcaagtacc ctcatgttgc agagaaagtc caaaaggaga    360

ttgatca                                                             367
```

<210> SEQ ID NO 50
<211> LENGTH: 217
<212> TYPE: DNA
<213> ORGANISM: Rattus norvegicus

<400> SEQUENCE: 50

```
gccggctcaa aggtctctgc gagcgcattg gtgttttcaa tgacaatctt gcgtgccaag     60

tcttctccca aaaaggcgaa ttcatccagc atttcattgg tggttctgaa atgcgctttt    120
```

ggcagtggcg ctggctgggc atcttctccg tgcccaatgg tccggttgat catagcccct 180
tgaccgagac tacggacaat gatctcccga tagatct 217

<210> SEQ ID NO 51
<211> LENGTH: 1034
<212> TYPE: DNA
<213> ORGANISM: Rattus norvegicus

<400> SEQUENCE: 51
gaacacagac aaggatgtat gtgtgggttc agcagcccac agcatttctg ctcctgggac 60
tctcacttgg agttacagtg aagctcaact gtgttaaaga tacctacccc agtggtcaca 120
agtgctgtcg tgagtgccag ccaggccatg gtatggtgag ccgctgtgat cacaccaggg 180
acactgtatg tcatccatgt gagcctggct tctacaatga ggctgtcaat tacgacacct 240
gcaagcagtg tacacagtgc aaccaccgaa gtggaagtga actcaagcag aactgcacac 300
ctactgagga tactgtctgc cagtgtagac caggcaccca accccggcaa gacagcagcc 360
acaagcttgg agttgactgt gttccctgcc cccctggcca cttttctcca ggcagcaacc 420
aagcctgcaa gccctggacc aattgtacct tatctggaaa gcagatccgc cacccagcca 480
gtaacagctt ggacacagtc tgtgaagaca gaagcctcct ggccacactg ctctgggaga 540
cccagcgcac tacattcagg ccaaccactg tcccgtccac cacagtctgg cccaggactt 600
ctcagttgcc ctctacaccc accttggtgg ctcctgaggg ccctgcattt gctgttatcc 660
taggcctagg cctgggcttg ctggctccct tgactgtcct gctagccttg tacctgctcc 720
gaaaggcttg gagatcgccc aacactccca aaccttgttg ggaaaacagc ttcaggaccc 780
ctatccagga ggagcagacc gacacacact ttactctagc caagatctga gcaataccac 840
aggagtggat tttatggggc acagacagcc catatcctga tgcctgcctg ccagggccct 900
ccacaccgtt ctaggcgctg ggctggctgt gcactctccc atgtatgctg tgcatactac 960
ctgcctggtg gcactcctaa taaacatgct cgcagctgtg agtctgtcac tggccctaaa 1020
aaaaaaaaaa aaaa 1034

<210> SEQ ID NO 52
<211> LENGTH: 528
<212> TYPE: DNA
<213> ORGANISM: Rattus norvegicus

<400> SEQUENCE: 52
tttttttttt ttttttttcc ggggtcaaga tatttactcg atgctttcag gtttgaattc 60
aggggctcag caagggggag gggcagggaa gggacacaca gggcatcttc caatcactgt 120
gacttctggc aggtctcgat gtcttcattg ccagtggtga ctgatcagtt gggacatggg 180
gagaagtcct gtgccctcca cgtctccatt gaaatcttct tctgatattt atgcacatca 240
ttgctccggt ccccgtcaaa gtttccacag gccccacaca acatggccgc ataatgctca 300
tcaaccatca cattcagatg cccatccttt ccaagccaca cctggactcc ggccttctgg 360
tggacaaaca tggatccgtc tgagatcttc ctcacagaca cagatgttaa cacagtagct 420
gggagatcca actcggagac cattcaccca tgcacccttg cttgggatca cagtcaccat 480
gccatcctgg aagaagatgt ggaccttgct cacgatcttg tcattgtt 528

<210> SEQ ID NO 53
<211> LENGTH: 4743
<212> TYPE: DNA

-continued

<213> ORGANISM: Rattus norvegicus

<400> SEQUENCE: 53

```
tttttttttt ttttttttgt tggtttggtt tgtttttgga gacagggttt ctctgtgtag     60
tcctggctac cctggaacta actctgtaga tgagactggc ctctgactca agagatctgc    120
ctatttctgt gaggattcaa agtgttcatc gcaatgcccg gcttagaaaa tgagtcttga    180
aatggcactc agaagggtgg atgtggcctt ttgaacgggc aagtaacaca ggtaaaatga    240
aaacacaaca ggtgcagaag cctgatcaac actcaccgcc cagacacctt tcaaacaagg    300
agctaagtca atgaggtaga accccaaatc ctccacctag gcgctgacag gcttaaagac    360
cccattgccc cacacagccc tccctccttt gtaaggtcac tgagggtaca ggacctgggc    420
agagacccag agcaaacaga aatgaaagaa caggctttgt accctgaaga gaggaacagg    480
aggttttcaa ctcaaggtaa ctggatggca gcatttgccg gcttcgagtg ctgagtggac    540
acacgtgcag aaatgacgtg agatgacacg cttagtaaaa cgatgataca ctttactcgc    600
acaacctgaa cctctactaa aacccagcca gccacaagct gtttgctatc ctttattaag    660
aggtcccaca ttcttgcggg actccagcca aaccagacag gtcccctaaa tatagcagga    720
ggcctggagg ggaagggaat gacttaggat cccaccacac caccctggaa acagaactcc    780
accacagaca gacggacaga cggacggaca agagccgggg aggagaaccc acctcactct    840
tggttctctc cccgttgcat ccactcaaaa agaaagtcaa acactggcta tgcagacccc    900
agcccaccca cccacccata gcagcgtttg tgggactccc ccctgaaacg ggtagcccca    960
agacaacttc ctatggttct tccctgactt tggtttgctc ctggcaactc cgcgccctct   1020
tccttccctc agcctccagc tctctctcag catcttctac cacctactcg gaccttccct   1080
ctctcttgct ctctgctttc tggtctccct gccacgggct tcttggggaa gcagcgggca   1140
cctttctcct agcaagggcc ccactaggcc ctgtctgccc agcgtgggac tcacacagcc   1200
gccccactct ctttgaggtc aggggctgag cgctgccttc gcattcgtgg aggggtagtg   1260
tatggtgggt agcggggccc tggccgctgg gctgggtaag gttggggctg ttggggataa   1320
gagttgtgct tctggggccg taagtgctgg ggttctggct gtgtagaacc ccctccccga   1380
gatcggctcc ctccatctag ggaattcctg cgaggacggt ggggccttcg gggacttgga   1440
ggtctgcggt taggggggagg aggggggtgca gtgacctctt caggggggttg gggacctggg   1500
gcctcaccac tccccattcc tggccaggac tccctgtgct gagggttgct cttgaagggg   1560
aagcgcagct tgcaatcatg cgggggtaca aagcgagctg gggcctgcg tagtccccca    1620
ccccggcccc cggagccctg cagtccctgc agccgcagct gctcctgctt gagccagcga   1680
aggcgaccgc gacggaaggc agggtcctct tccatcagtc ttgacacacg ctcccagctg   1740
gactggggtg gtgaggaggg ccggacagct ggtgagtggt cattggacac tgcctcctct   1800
actgcctctg acccttcggg tggggcccag gtgaccaaac cagattcttc attatcatcc   1860
tcaagatcct gggtcaacgg gataaccctc tccatgcgga gcatccggtc ccgcagggcc   1920
tgcagctccc ggtccttgct gctgttttgc agcttcactt cctgcagaat tcctgtcagc   1980
ttgtcaatat gagcccggag gtcttctacc tctgccccac gggctccttc ctcaccacca   2040
cctccaccac ctccacatcc ttcttcttca cccacagtat cccagacatc cctggccaca   2100
gctctccagg cgtctccagg accctcaggc ttgccgtagg tccggcacag ctccctcatc   2160
ttgagagcag ccagagcttc aatctctgcc cgtccgtgac ggaagtcggc cagggccacc   2220
tcatagcaga tctccttcac tgcttgcatc ttcaggtcag ccatggtggc ccaccggggg   2280
```

-continued

```
tctttgccct ggagccgccg tcgctgaggg atctggtaaa ctcttcgagg ggccctgcgc   2340

ttcccactgc tgggcaggcc acagcgcttg acgatggtct ggactgtgtt agggggcagc   2400

tcgtcccgca aggaggaaat cagccgccag ctttcttcac aagagcgctt gtcagagtct   2460

tccccactgt cagaatctgc atacagccgc tgctgctcca gcaaaaggtc agcctcttcc   2520

ttttctttcc ggtactgatt ctccaagtct tgtagcctct tctccatctc tagcttgatg   2580

tctatgcctt gctgctccag ccagtccttc tgagcaaagt tccagtccac aggctcagag   2640

ggaggtcctg ggggtggggg gacccctcgc tctcgttcca gccgtgcttg ctccgggtga   2700

ttgaagcgga acacatggtt cttgcccatt acaatcctgt tgcctgactt cagcaccagc   2760

ggctccgtca caagcttccc attgacatat gtctcagctc cttcacaagg ttccaatgtg   2820

accatcactt ctccatcagg ctgagggatg ctgcggaaga ggcagtgctg ctcccggatg   2880

aactggccag tcaacttgat gtccacatct acctggccaa ccctggtgac gccatctttg   2940

atgtggtaga gaaggcattc agacatcaag ggtcctcat tcagatttac caggtgggga   3000

gtcttttttg gagagaagac acccacagta cgccatcctc ccggagagcc catctcagcc   3060

agcaatgctt ctctctccat cctcagagct tctgtcttac ggagcttctc ctcccaagtc   3120

tcattcagct cagctataat tttctctgtt tcctgcagcc tctccatggc ctcctcaggc   3180

ccaatctggg gctcagcact gggtgaaaat gacggctcca gctcgccgtt atgtggagga   3240

ggagatgagg gtgaagctgg ggcaggggga gatgatgcag caggcagaac acctccagga   3300

ctcccctctt ccacctttag acctcctaga gcagaggctg aaagcccctg agccatcagc   3360

agttcccgca accgggccac ctcctcctgc agctcccgga taagccgggc attggggtcc   3420

tcattgatga cagcattgca tcggatctgt ttggtgcggt ctgcgtacct gagagtgctg   3480

agtgtctcct cgtaattgat gtcagcggga ctcagggctg caatcattgc tgtgcgtgag   3540

ttcccaccca aattctcctt gagtagccag gtaagcacag agtctctgta agggatgaag   3600

tccgacttcc gcttctttga ttgcaaatct gccagggctg agatcacctt ccctagagta   3660

gtcagggact tattgatgtt tgcaccttcc ttcagacgca tgccccgagc ccctgaggag   3720

tcggcccgct cgctcccggc aaggttcacc aagctgatct tactgacctt ttctgaatcc   3780

agtccagtaa gctggtcatg ggagcgctgg gtaaagacga tagtaaagac agcgtgggag   3840

cggctgctgg tttcgttcat gttggtggca gccacagttc ttgccttatt tccacagtcc   3900

atgaggtcag caatgtctgc ataggaagtc acagccaact tagacaggtc ttgtacatat   3960

gggcccagga tggggtgctc ccggacccgc agagagcccc gactcttggg gttcaagagg   4020

tctcgtactc gttcgcaata gatctccata tagctcacct ccacagagta ggaaagttga   4080

gcactctggt tcacattaac tcgagagaag aggtcctcgc agagctgagg tacaatgccc   4140

tgctgccccg gttcctgccg ccccatcatg gtgtaggact tgccagcccc cgtctgaccg   4200

taagcaaaga tgcacacgtt gtagccttca aaggcatgca gcagcatctc ctctcctatg   4260

tctcgataca cctgctgttg agatgcaaac tgtgggtcct ccaccgaagt atgtgaccag   4320

taagaatagt cgaatgaagc ttttaaaaac atcctgctct gtttgggatt aatgatggag   4380

gtggtgttgc cctgcatgct gaccacacac ttggcatcct ggctggtctc acgggcatta   4440

aagggccgaa ccctcactgc cactttcacg gaggcaccag ccatagcttc agaatctcct   4500

gccctcctca gctggtgtcc tggccccaga tcagcggggc tgtatcagtt ctggctgcca   4560

ccggccctcg tatgggaagc cccatcctac acttggggcc tggccacacc agcaaggctc   4620
```

-continued

```
ctcgcggcag actcccggca gagagcaaag ggacaatact ttgctggcga gtagtgctat   4680

gaactctgcg ctaccggtgt aagagacgca tcggggccag ttcggggctg cccccgcccc   4740

tcg                                                                 4743
```

<210> SEQ ID NO 54
<211> LENGTH: 2136
<212> TYPE: DNA
<213> ORGANISM: Rattus norvegicus

<400> SEQUENCE: 54

```
atgggaaaaa aagataaccc agggtgtgag cattctcgtg ccgaattcgg cacgagcagc     60

attcgggaaa ggcaaacagt ggctctgaag cggatgttga atttcaatgt gcctcatgtt    120

aaaaacagtc ctggagaacc cgtatggaag gtactcatct atgacagatt tggccaagat    180

atcatctctc ctctgctgtc tgtgaaggag ctgagagaca tgggcatcac cctgcatctc    240

cttttgcact cagaccgaga tccaattcga gatgttcctg cggtgtactt tgtgatgcca    300

accgaagaaa atattgacag actgtgccag gatcttcgaa atcagctcta tgaatcctat    360

tatttaaatt ttatttctgc gatttcaaga agtaaactgg aagacattgc aaatgcagca    420

ttggccgcta atgcagtcac acaggttgcc aaggtttttg accagtatct caattttatt    480

actttggaag aggacatgtt tgtattatgt aatcaaaata aggaacttgt ttcatatcgg    540

gccattaata ggccagatat cacagacaca gagatggaga ctgttatgga cactattgtt    600

gacagcctct tctgcttttt tgttacatta ggtgctgttc ccatcatccg atgctcaaga    660

ggaacggcag cagaaatggt ggcagtgaaa ctagataaaa aactgcggga gaatctaaga    720

gatgcaagaa acagcctttt tactggtgat ccacttggga ctggccagtt cagcttccaa    780

aggcccttat tagtccttgt ggacagaaac attgacttgg caacgcctct gcaccatacg    840

tggacatacc aagcgctggt acacgatgtc ctggatttcc acttaaacag agtaaatttg    900

gaagaatcta caggagtgga aaattctcca actggtgcta gaccaaagag gaaaaacaag    960

aagtcttacg atttaactcc agttgataaa ttttggcaga aacataaagg aagtccattc   1020

ccagaagtcg cagaatcagt ccaacaagaa ctagaatctt acagagcaca agaagatgag   1080

gtcaaacgac tgaagagcat tatgggccta gaaggagagg acgaaggagc catcagcatg   1140

ctttctgata acactgctaa gctcacatca gctgtcagtt ctttgccaga actccttgaa   1200

aaaaaaagac ttatcgatct ccatacaaat gtcgccactg ctgttttaga acacataaag   1260

gcaagaaaac tggatgtata ttttgaatat gaagaaaaaa taatgagcaa gactactctg   1320

gataagtccc ttctcgacgt catatctgac cctgacgcag ggactccgga agacaaaatg   1380

aggctgtttc ttatctacta cataagcgct cagcaggcac catctgaggt tgatttggag   1440

cagtataaaa aggctttaac agatgcagga tgcaacctta gccctttaca gtatatcaaa   1500

cagtggaagg cttttgccaa gatggcctca actcctgcca gctacggaaa cactaccact   1560

aaaccaatgg gtctcttgtc ccgagtcatg aatacaggat cccagtttgt gatggaaggc   1620

gtcaagaacc tggtattgaa gcagcagaat ctacctgtta ctcggatttt agacaatctc   1680

atggagatga agtcaaaccc cgagactgat gattacagat attttgatcc caaaatgctg   1740

cggagcaatg acagctcagt tcctaggaac aaaagtccat tccaagaggc cattgtcttt   1800

gtggtaggag gaggcaacta tattgagtat cagaatcttg ttgactacat aaagggaaag   1860

caaggcaagc atattttgta tggctgcagt gagattttta atgctacaca gttcataaaa   1920

cagctgtcac agcttggaca aaagtaacac agaagagtca taatgggtga tcagtgtgga   1980
```

cagatgtaaa aagccagacg tgtccttctc catagcagtg ccctaacagt gcaacctgcg 2040
gaatcagtca tttttaaaga aattctatac ttcatatact gtacaatgat taaaataata 2100
aaccatttca gaagtaaaaa aaaaaaaaaa aaaccc 2136

<210> SEQ ID NO 55
<211> LENGTH: 1739
<212> TYPE: DNA
<213> ORGANISM: Rattus norvegicus

<400> SEQUENCE: 55
ctcaggtttc tcacactcct ggtaatactg taaaacttta ccatggacca cagttccaag 60
gactcctgaa cacagtcttg gagttaagcc tgtgaacagc ccacgcttcc catcgatgcg 120
taacaagcga tggattccat atctctgcgt gtagcactaa atgatggtaa cttcattcct 180
gtactggggt ttggaaccac tgtgcctgag aaggttgcta aggatgaagt tatcaaggct 240
actaaaatag ctatagataa tggattccgc catttgact ctgcttattt gtacgaagta 300
gaagaggaag tgggccaagc cattagaagc aagattgaag acggcactgt gaagagagaa 360
gatatattct atacttcaaa gctttggagc actttccata gaccagagct ggtccgaact 420
tgcttggaaa agacactgaa aagcactcaa ctggactatg tggatcttta tattattcat 480
ttcccaatgg ctttgcagcc tggagatata tttttcccac gagatgagca tggaaaacta 540
ttgtttgaaa cagtggatat ctgtgacaca tgggaggcca tggaaaagtg taaggatgca 600
ggattggcca agtctattgg ggtgtccaac tttaactgca ggcagctgga gaggattctg 660
aataagccag ggctcaaata caagcctgtg tgcaaccagg tggaatgtca cctttatctc 720
aaccagagca aaatgctgga ctattgtaag tcaaaagaca tcattctggt ttcctactgc 780
acgctgggaa gttcacgaga caaaacatgg gtggatcaga aaagtccagt tctcctagat 840
gatccagttc tttgtgccat agcaaagaag tacaagcaaa ccccagccct agttgccctt 900
cgctaccagc tgcagcgtgg ggttgtgccc ctgatcagga gtttcaacgc gaagcggatc 960
aaagagctaa cacaggtttt tgaattccag ttggcttcag aggacatgaa agccctggat 1020
ggcttgaaca gaaatttcag atacaacaat gcaaaatatt ttgatgacca tcccaatcat 1080
ccatttactg atgaatagta acatggtgga ctttgtcagc atttctatcg gaagatctgt 1140
ttatgcattg tgatttgaaa gatatcttgg atactggtga ctgaatgcat cagaccactg 1200
tttctgttaa ttcacagtca gctggagcaa tgtccacagt gctatgaggg aagccatgtt 1260
tttgtcacac tctgaaatgg aacatcacgt tgcttttcct tgtgttttta aatattcatt 1320
tattttgctt tccatatatg aatattttcc ctacatgtat gtgtatctca tgaatgtcta 1380
tgtccatgca gggttgaaga gtgttgcagg tcacttggaa ccggagttac attgattatg 1440
gagttaccat gtgggtgctg ggagccaaac ctaggtcttc tgtgagacta gcaagtgcct 1500
ttgaatgctg agccatctca ttaggtccaa ccctaaagat ccttgcctgc cactatttct 1560
gtgatctcaa tgttttgttt tctcctgact tctgacacca agctgatttg ctagaagtct 1620
tgggcatgaa gtgggtgttg aggacagtta ttgcaaaggg atttctgggt gggagttgaa 1680
agaacgttca acattcaggg aattaattgt tcgaggttat tgattagtca atattcccc 1739

<210> SEQ ID NO 56
<211> LENGTH: 336
<212> TYPE: DNA
<213> ORGANISM: Rattus norvegicus -continued

<400> SEQUENCE: 56

```
gtgcacttgt ccgaggcacc tttgcagaca cagccctggg cacatttgga gcagcccacg     60
gggcagcagg agcagcagct cttcttgcag gaggtgcatt tgcagttctt gcagccgcag    120
gagctggagc aggtgcagga gccgccggtg gagcaggagc agttggggtc cattccgaga    180
tctggtgaat ctggagcaac ggtgtaagcg acaagaaggc agtttttttt tttttttttt    240
taaaataaac aggcttttat tttccacctg ctcggtacaa aacggggttt attaaactgg    300
gtggaggtgt acggcaagac tctgagttgg tccgga                              336
```

<210> SEQ ID NO 57
<211> LENGTH: 1937
<212> TYPE: DNA
<213> ORGANISM: Rattus norvegicus

<400> SEQUENCE: 57

```
tttttttttt ttttttttcc aaaacaaatt cttttataag ttgtcttgtc atgttttgtc     60
acagcagaaa gaaaagccac taagacactt gctaatcccc cgttctgttt ttttttctca    120
aaaccccaag atatatatat atatatatat atttacactc attttacata tgcaaaaata    180
gaaccagact cttctcccta aagacttccc tgaaaaacct actcagaacc ctgcaagtac    240
ctgatttctg tttattgagc ttctcttcca gaatcaaggg aataaagaca aaggtttatt    300
tttcttcact ccaatgcctc caggaccaac ctggcatggt tttcattcca ggagctagca    360
aaataaggga tgaaagttta ggtatcttgc ctgctaattt cagtttccta agggtggaga    420
cagctccgtg taaatgccca gtaaacaggt acttgttgag ctaagtcatc aaaggaggag    480
cagtgcccca gaataaattg acagttaatg atgtcaagta tcttaatgtt tatttttatt    540
ctttacatcc agcacttgaa gaaaagaaaa tgacatagtg ttttagaaac atagtccttc    600
atgattataa ctcatcaata ccttagaaca cacaaggaca ctgtgagtta atgactacac    660
taaaaaataa tgggaaattc agcataatta acaaaaatcc aagaggaaat ttcaggacct    720
tgatcagaag ctttcactaa gtgctggcac tatatgctac ttcatttcac taagtgctgg    780
cgctatgtgc tacttcattt cactaagtac tggtgctatg tgctacttca ctgtagacca    840
agcttcaggg caggctaaga aatcttaacc ctctgaagac atgatctaag aaatggggac    900
caagcacttg tagagaattg gtagccatca agaagtccct agtaaggaca gctatggaag    960
gagctggcca cctttaacct gaacctgtct taaaattaca aagcccatgg agcagtactt   1020
ataaacacaa gcatggtgag gttttgccat tctataaata atcttcagga ttccagctgg   1080
ggctctcttt tggcatgaga agcttcaggt aaaccagcag acataggatg acctattatt   1140
gatggacctt ctcaaagtac tcttttgaag ctgttggact tggcttgatc gtaggggact   1200
ctggtgtcca gttgggtggg cagacttctc catgggtctc cacaaactgg aacgccttta   1260
ccaaacggag tggttcttcc acacttcggc ccaccggaag gtcattgaca ctcaggtgct   1320
tgatgacacc attagggtca ataatgaaga gacctctgag cgcaatgcca gcactttcca   1380
acagtactcc gtagtctcgg gatatctgct tagttaagtc cgacaacagc gtgatgttca   1440
tgtggcccaa accaccattc tttcttggcg tgttgatcca ggcaagatga ctgaagtggg   1500
aatccacaga aaccgcaact acttcacagt ttacgtcatg aaactcattg gctttgtcac   1560
tgaaagcaac aatttctgta ggacacacaa atgtgaaatc caaagggtag aagaaaagca   1620
ccaagtattt ccccttaaag tcgtcgagac tcagctcttt gaactctcca ttgacaacag   1680
cagtaccttt aaaatggggc gcatgctggg tgacagcagg ggtgtggaat gaagaactgg   1740
```

-continued

```
tgctaaaggc aaactttgct tggggacagg cagaccacag catgtctgtc aagcaggttc   1800

ttctagaagc aacaggccta agaactgttg aggcagaaat actccggaaa atagtgctcg   1860

caggccgagc caccgaggac cagagcaacc ttcccgcagc tgccgccatc ttcagagaac   1920

gcaagagcca cgatagc                                                  1937
```

<210> SEQ ID NO 58
<211> LENGTH: 686
<212> TYPE: DNA
<213> ORGANISM: Rattus norvegicus

<400> SEQUENCE: 58

```
atgcccacat ttgtgaccag tacatgtttc tgcccaccat gttcgagact atcaaagtcc     60

agaggggtca tcaatccact tatcccaaat caaggtgcac caatcccatt tcaacgcctc    120

tgccagcccc ttatttccaa tgaacacaga caaagctggg ttaatcaagt caagtttttt    180

tattttattg tcagttacat gctttataga aaaaagtgtg gagaaccggt cagggttgta    240

caaaaaaaag gctaggttcc tacgttgttt tatttacacc attgtgagga cgccccccact    300

tcaggcgcag cagctgcact tgtccgaagc ctctttgcag atgcagccct gggagcactt    360

cgcacagccc acggggcagc aggaacagca gcttttcttg caggaggtgc atttgcattg    420

tttgcatttg caggagccag cgcaggagca ggatccatct gtggcacagg agcagttggg    480

gtccatggcg aatggaggcg gcagttggag atcaacgaga gatcgctgta gagttctagg    540

agcgtgatgg agagaagcac gcggagcgcg acctttatag cccagagtat tgggtcgcgc    600

gcaaaagctc cgcccgggtg gcggggcgcc acctgccctc ctccccactg cctgcacacg    660

cccttcttct ggctcaaggg aaatgg                                         686
```

<210> SEQ ID NO 59
<211> LENGTH: 1234
<212> TYPE: DNA
<213> ORGANISM: Rattus norvegicus

<400> SEQUENCE: 59

```
tttttttttt tttttttag gaaaagcgac tgctttaatg aattagacaa aatttcacat      60

gaaatcagaa tcctataatc cttcccttct gatcactaaa aaatgcaaga ttcattcgtt    120

acaagccatg tgcgattcgg acccctcgaa ggcagtgcag gtctgcggtc cagcctcagg    180

tgctgcacta tttcccattc tcagcgctga acattcgttc tgtgagcatc cgctccaact    240

ttatggcatc agcagcaaac ttgcggatcc catcagagag cttctccaca gccatttggt    300

cctcattgtg cagccaacgg aaggccttct cgtccagatg tatcttctcc aagtcactgg    360

tctgggctgc tttgacggaa agcgtgggtg ccagcttgct gctgtccttg agcagctccc    420

ccagaagctt gggtgagatg gtgaggaaat cacagcctgc cagcgctttg atctcacccg    480

tgttacggaa ggaagcaccc atgacaatgg tcttgtagcc aaactttttg tagtagttgt    540

agatttttgt gacactcttc accccagggt cctcctgggg ttcgtaggat ttcttgtctg    600

tgtttgccac atgccagtca aggatgcgcc ccacaaaggg agagatgagc gtcacgcccg    660

cttcagcgca ggccacggcc tgggcgaagg agaaaagcag tgtcatgttg cagtggatgc    720

catgctgctc ctccagctcc tttccggcct ggattccctc ccaggttgat gataacttga    780

tgagaattct gtccttgctg atcccagctt ctttgtaaag ctctatgatg cgcctggctc    840

gggccaccat ggcatcctta tcaaaggaaa gccttgcatc gacttctgtg gatacacggc    900
```

-continued

```
ctagaatctt ctttagtatt tctgccccaa acagcacaaa aagtttatca atggcatttt    960

taatctgctc ctcttgtggc ccacccagct tcttgccgta ggcaatggcc tcctccacca   1020

gctcttggta ggcaggcatc tgtgctgcag ccaggatcag ggatgggttg gtggtggcat   1080

cctggggctt gtactcatcg atggcgttga aatcacccgt gtcagccacc acggtggtga   1140

actgcttgag ctggtccaag gcggactcca tcctctggcg ctttaccggg gaccccgaca   1200

tggcgaaacg cgcacagctg aggcggtagc tggt                               1234
```

<210> SEQ ID NO 60
<211> LENGTH: 2514
<212> TYPE: DNA
<213> ORGANISM: Rattus norvegicus

<400> SEQUENCE: 60

```
gcactctcca gcctctcacc gacttttttt tcaaggagac aattttattt ttttaccaag     60

gctgaattta taccataaca tgggtaacag agggaggggg gaagtgtgaa acatttacac    120

aggccaaggg cacagtatac atgtagtcag ctgatgtcaa caggatgttg gtttttcaga    180

aagcttacag gtcatcacat tgggtatctt gatgtcagat gtatttctca gcaaggtcag    240

aactttatca tatcattatt catcctgacc accagatttg tattagtctt ctgcagctgg    300

ctggggattt tccatgaacc cagtcatact taattctaac cataacatca ataatggagg    360

gtttcaaggg cattgctccc aacatgtaat tacaaaaaga aaaaagatga tatatttccc    420

aaaaagagag acacattcaa atttcctctc aaactcccca catctgaatc atgatgatgc    480

ttttaaattg gttctcttct taccaacatt ccaaccttcc cacaagaact tgctctccag    540

gttcttggag ctctggttct tgggctgttg gagagaaccc tgggtctctt ggtcactcct    600

gccacaggtg ccctacctca aaactaagaa aaagggaaaa tctatggagt actttcttct    660

tcctcaaaga atatggggaa tattgactaa tcaataacct cgaacaatta attccctgaa    720

tgttgaacgt tctttcaact cccacccaga aatccctttg caataactgt cctcaacacc    780

cacttcatgc ccaagacttc tagcaaatca gcttggtgtc agaagtcagg agaaaacaaa    840

acattgagat cacagaaata gtggcaggca aggatcttta gggttggacc taatgagatg    900

gctcagcatt caaaggcact tgctagtctc acagaagacc taggtttggc tcccagcacc    960

cacatggtaa ctccataatc aatgtaactc cggttccaag tgacctgcaa cactcttcaa   1020

ccctgcatgg acatagacat tcatgagata cacatacatg tagggaaaat attcatatat   1080

ggaaagcaaa ataaatgaat atttaaaaac acaaggaaaa gcaacgtgat gttccatttc   1140

agagtgtgac aaaaacatgg cttccctcat agcactgtgg acattgctcc agctgactgt   1200

gaattaacag aaacagtggt ctgatgcatt cagtcaccag tatccaagat atctttcaaa   1260

tcacaatgca taaacagatc ttccgataga aatgctgaca aagtccacca tgttactatt   1320

catcagtaaa tggatgattg ggatggtcat caaaatattt tgcattgttg tatctgaaat   1380

ttctgttcaa gccatccagg gctttcatgt cctctgaagc caactggaat tcaaaaacct   1440

gtgttagctc tttgatccgc ttcgcgttga aactcctgat caggggcaca accccacgct   1500

gcagctggta gcgaagggca actagggctg gggtttgctt gtacttcttt gctatggcac   1560

aaagaactgg atcatctagg agaactggac ttttctgatc cacccatgtt ttgtctcgtg   1620

aacttcccag cgtgcagtag gaaaccagaa tgatgtcttt tgacttacaa tagtccagca   1680

ttttgctctg gttgagataa aggtgacatt ccacctggtt gcacacaggc ttgtatttga   1740

gccctggctt attcagaatc ttctccagct gcctgcggtt aaagttggac accccgatgg   1800
```

-continued

```
acttggccaa tcctgcatcc ttacacttct ccatggcctc ccatgtgtca cagatatcca   1860

ctgtttcaaa caatagtttt ccatgctcat ctcgtgggaa aaatatatct ccaggctgca   1920

aagccattgg gaaatgaata atataaagat ccacatagtc cagttgagtg cttttcagtg   1980

tcttttccaa gcaagttcgg accagctctg gtctatggaa agtgctccaa agctttgaag   2040

tatagaatat atcttctctc ttcacagtgc cgtcttcaat cttgcttcta atggcttggc   2100

ccacttcctc ttctacttcg tacaaataag cagagtcaaa atggcggaat ccattatcta   2160

tagctatttt agtagccttg ataacttcat ccttagcaac cttctcaggc acagtggttc   2220

caaaccccag tacaggaatg aagttaccat catttagtgc tacacgcaga gatatggaat   2280

ccatcgcttg ttactcatgc aaccaagcag gtcttgggtc tggcgagggt cttctgactg   2340

ttctgagaca gccctgtgtg aggaatgcac tttcacaggg ttggaggtac ttccaagacg   2400

ccataggaac cacacgtggg tcacagctat cagttcactg tgggcaagaa acctctttat   2460

ggccacctgg taacaaaaat ttttctgtct gtgaattttt tcttactatt taaa         2514
```

<210> SEQ ID NO 61
<211> LENGTH: 1086
<212> TYPE: DNA
<213> ORGANISM: Rattus norvegicus

<400> SEQUENCE: 61

```
ttttttttt ttttttttca cacagggttg cttttatttc cacatccaac ttgagcagag     60

gccctgccac aacctgaaca gctgtgaggt gctgggtgcc tccagagttt ctggcacagt    120

aagtgttggg tgtgcagact tcctgatggc cacatgacac tggcccacac aggaacagca    180

agtccatgaa tggaaatccc actgagctgg aagtggaggc tctggaaacc ccatgggcag    240

cagcaggagt taaaggagcc accaggaaca ctgcagtgag gctccaatgc agacagggct    300

gataaaaacc caaacagggc attgtgagag cagaggctcg agtgtccccg ctgaggaccc    360

ggggctgaag gcacagagct gtgtcgggat ggaagaaccc tgggtgcact cgcagtccag    420

agcacgaaag cacaggtgag aacccagccc gaggctctct gtgaagagtg tggccttgga    480

tcttgggcac ggcacagtga cacacagtgc tgaggtcact cctgacttcc cagaggaatg    540

acctcttcag tgacaaaaaa ctcaatggtc tcttcctccc agtcatccac gttgctgtcc    600

agctcgtcag tgtccacccc tccccgtagc tctagacgct cgttcttctg cttcatatag    660

agttcctggg ccatttttcg gtattgcctg aagtcctcca tcatggtccg ccttctttcc    720

accagttcct ttgaagcttt ggactggctc aagcgatcct tctgctcaaa gatcttagag    780

tatttcttca gatccttttt aatttgcttt atctgatcct gactgaggag tgttgggggc    840

cttggtctcc agagcagctg gcagaagcgg tccttgttgt tcttctggag aagacgacct    900

tggaaggtcc acagccaata agcattgtcc accttatggc tccaccacga cacagaggta    960

accacatagc ggccagttgg gtcccattcg acgtcggagg ccatgtagtg ctctgcaatg   1020

ttcatgacgg tgcagtctga agtgtcgaca aacgccaagg cgccattcat gctcctcagc   1080

ctcgtg                                                              1086
```

<210> SEQ ID NO 62
<211> LENGTH: 1362
<212> TYPE: DNA
<213> ORGANISM: Rattus norvegicus

<400> SEQUENCE: 62

-continued

```
ccaaaccaac aaggcagcca caggccgtcg gtgcctgccg ccttccacca ggggcccgcc     60
aagacaacct tccaccatgg ctttgaagag aatccacaag gaactgaacg acctggcgca    120
ggatccccca gcacagtgtt cagcaggtcc tgtcggggaa gatatgttcc attggcaagc    180
tacaatcatg ggccaaatg acagtcccta ccagggtgga gcattttttct tgacaattga    240
tttcccaaca gagtacccct tcaaaccacc taaggttgaa tttacaacaa gaatttatca    300
tccaaatgtt aacagtaatg gcagcatttg tcttgatatt cttcggtcac agtggtctcc    360
agcactaact atttcaaaag tacttttgtc catcagttct ctgttgtgtg atcccaatcc    420
cgatgatccc ttagtgcctg agattgctca gatctacaaa acagatagag acaagtacaa    480
cagaacagct cgggaatgga ctcagaagta tgccatgtga ctaaagagat tattggatcc    540
tctgcgaata aaagctaggg gaactctgaa agagaaagtc cttttgattc ccacttgact    600
gtttgctgtg aacccacgat gtaccggcct cgtcctccct ggtgcacggt cttcatctga    660
tacagtactg ttgcatgttg cacgcaccaa aaatactgtg tttctgtacc aacactgtct    720
cctagcagac gagccttctc caggcataac ctaggtgtga gattaaaagt tttccttatt    780
gacttaaatc tggataacaa ggtgtgagtg agggtggtgg gtacaagata ctgctcagaa    840
ggggtaaagg tccccaacct ataagacaat gagatggctt ttcagtggaa gccatttaca    900
gctaaatgtt taaatgaatg aaaagctagg tgaagaacat gaatgttcct gtactcattt    960
tattccaaaa gacctagagc ttaaatgaac attaaagcca accagactaa gccaacccac   1020
ctcctgtatt ttaaagtcta attggtcaac aaaaatagat cggcactatc ggtccataaa   1080
gtgtgcctgg ctttgttccc aaatccttta tacacggatg actcaaccta ttttctttca   1140
cactttctct ccatattctt tggtttactt gcggtttctc agttgattca tcactaatag   1200
ctcttatttt tattatatta actgcttaat ctatttggat gtaaaggtag acattcaact   1260
tgatgaaaaa agcttgtgta tagagaccta attgctcctc ttggagcttg tacagtcaag   1320
aatgatgcat ctgtgtaata aaccaattat tctagccatt at                      1362
```

```
<210> SEQ ID NO 63
<211> LENGTH: 796
<212> TYPE: DNA
<213> ORGANISM: Rattus norvegicus

<400> SEQUENCE: 63
```

```
tgtacactac ccctcacaaa ccacaagccg cagcaacatg gatgcccagt ctggagcagc     60
aacagccagg atgacctgga gccagggggg cttcggaaca gatgtgcacc cttcctgggt    120
gatgttttca gctttgtgag aaaccttact atcagaggag atggctagca atgttaccaa    180
caagacagat cctcgatcca tgaattcccg tgtattcatt gggaatctca acactctggt    240
ggtcaagaag tctgatgtgg aggccatctt ttcaaagtat ggcaaaattg tgggttgctc    300
tgtgcataag ggctttgcct ttgtccagta tgttaatgaa agaaatgccc gagctgctgt    360
agctggagag gatggcagaa tgattgctgg ccaggtttta gatattaacc tggctgcaga    420
gccaaaagtg aaccgaggaa aagcgggtgt gaaacgatct gcagcggaga tgtacggttc    480
ctcatttgac ttggactatg actttcaacg cgattattat gacaggatgt acagttaccc    540
agcacgtgtt cctcctcctc ctcccattgc tcgagctgtg gtgccttcca aacgccagcg    600
tgtgtcgggg aacacctcac gaaggggcaa aagtggattc aattcaaaga gtggacaacg    660
gggatcttct tccaaatctg gaaagttgaa aggtgatgac cttcaggcca ttaaaaagga    720
gctgactcag ataaaacaaa aagtggattc tctgctggaa agcctggaaa aaaaaaaaaa    780
```

-continued

```
aaaaacccct cgtgcc                                                  796

<210> SEQ ID NO 64
<211> LENGTH: 716
<212> TYPE: DNA
<213> ORGANISM: Rattus norvegicus
<220> FEATURE:
<221> NAME/KEY: misc_feature
<222> LOCATION: (111)..(111)
<223> OTHER INFORMATION: Wherein n may be a, c, g or t

<400> SEQUENCE: 64

tttttttttt ttttttttga ttttggccaa actttttatt tagtattttg tagttgttta     60
acacacactt aaatggtctt actcggggag ggggaaggga ggttcttgta nattcccaag    120
gaaaggtcag aaaagcaaaa tatggccagc atccatttgc tttttttgag gggggggggt    180
ttctgggtaa atagtacatg cctaggcatc tgatctcagc ttggtttgtt tgtttgaata    240
tatatatact gcgaacattg agatttcagt tggaagacac cctgaaatcc tcacacccca    300
ccaaccctct ctaatggcta gcttgtctgc acaggcaggg tgattcaact ctcaatggag    360
accaaaggac atctagatgg ctaaatgttt gtggaagatc ttggggttgc ttgcctcatt    420
tgctgggaaa aatcaggaag tggccttcag ggacactttt acttggaaaa ttacaacact    480
agttacaagt cacgggttac acatctaaca tttgcttgtt gaaagcaact cataatagca    540
aataaaatta aacatgtctt actttttccc tcacaagaac ataaaaatta ttaaggggaa    600
caggaaattt taaaaaggta acacaatttt tcctttagta gtccttgggt agtttatgac    660
agaaagtttc catttttttg tttgtttctt tgaatgggga ttgttggtcc ctcgtg        716

<210> SEQ ID NO 65
<211> LENGTH: 456
<212> TYPE: DNA
<213> ORGANISM: Rattus norvegicus

<400> SEQUENCE: 65

tgtacagttg ctagtttgag gctggtgttg atgttctgac aagagtggct cagccatggc     60
tcagtagagt cctcttctgg aagtttgaga aattctggct tacgggaaaa ggtttttctt    120
tcttttcaag atatgtccaa caaagtcctc ttcggtcagt aatttctgca gtgacgcctt    180
tcgtccgtcc tgtcagcaaa ctccaatcgc aacttgggag tccagtcaat aaagggttaa    240
gcgcacacaa gcgtggccaa ctagtaggtc cgagaggttc accggcaggc accgtactta    300
atatgcagag gggtgggctt cacgcctccc cgccgagcgc tcccacggtc gaggagttgg    360
tgggcaagga gatgaggttt aagtccaatg ggttaaaccc aaccccgaga gggttaaaac    420
tacccgatga cgctgccacg gaggggccga atccac                              456

<210> SEQ ID NO 66
<211> LENGTH: 1640
<212> TYPE: DNA
<213> ORGANISM: Rattus norvegicus

<400> SEQUENCE: 66

tttttttttt ttttttttca caccagatga cgaatgtata tgaaagttaa ttcattaaat     60
taaaaaaaaa aatcaaacat ttggggaggg tttttttttac aacgaataat tctatacaca   120
tgctatagac acggtttcta taaaacacac tatctacaat ctacttacat ttaattgtcc    180
tgctatttct agttcatgtg agatcagtca caagtgagtc agtttccctg cctgtagaga    240
```

-continued

```
ctgcgtcatc ccttaatacc agggtcagag gcactggccg agcaaaacaa gattgtaaga    300

atcttatcaa ctatcttgct tatgagaaca gacaccaggg gccaagtgct ctgaaccggc    360

tttggagtta aggcagcaat gtaaggtgtc acgtaaaaac caagtgtgct ctttgaaagc    420

attccatgga tccccaaatg ctggccccct ttctaagtgc acctctgaag tcgagggaac    480

agctacacat ttgggaaaag tcattcgaga acagccgccc aaaaccttta aagttatagt    540

ttaagcttca ggcaaaagtt caaattactt ctcacaaata gaaagaattc actttttaaa    600

aacgaagtca catttagcca ctttatcaaa acaacttaac accggtacgg aaaacgtacg    660

ctaaaccaaa agtatggttt caatgcacgc cgtgccaaat attttcaaaa cgctagaaga    720

atggtacttc tttctctcag aatttcccag tttgtctgta gcagaacggt attctaaagt    780

ccagtctctg aacatggtca cggccgatga ctgtcatcca gcattaaaat agcctttatc    840

accctcgatg tccacttcct ggtcggaatc ctctgagatc tctgattcag ggtcttccgg    900

agaggctggg gagggtgaac actgagaact gtccaaagag gcacctttat tctgttcact    960

gggcaagtct tggccctggt cacaggaagt gtccaaactg tccaactcat cctttttatt   1020

gctttgagga ttctcctgct tcagtcgtct ccatttagct ctgcgattct gaaaccaggt   1080

tttgacctgt ctctcgctga gctgcaacat cttggccaga cgctttctct caggtgggga   1140

gaggtatttc tgagtctcga acttcttctc cagctcgatg gtctggtcgt tggaaaacct   1200

cacttgaccg cctttccttt tgtgcagagg tcgctgtagg aaggggttcc agagcaaggg   1260

cttgcccagg gggtcgtggc ggagtagggc gtgcgtgtag tcgttcaccg tccgcgggaa   1320

cgggtacaga gggcctccga agccaccggg gccataggca gcggccagcg cggcggcggg   1380

gtgatgcgag aaggcggggt ggaccggcgt gggctcgtac accggggtcc ggtaggagga   1440

cacgaggctg gtgaaggagg agttggggga cggcagcgtg ggagtgggcg tgggagcggc   1500

gggcccgcga cccaggatgt cgtcgatgta gaaaggcgtc gggtgagcgg gctgcagcag   1560

cggcgtgggc gcgtacagcg ggactccgac ggcgggcgca gccgcgggcc ccgggtgcgg   1620

gaactgcatg gctgctccgc                                               1640
```

<210> SEQ ID NO 67
<211> LENGTH: 370
<212> TYPE: DNA
<213> ORGANISM: Rattus norvegicus

<400> SEQUENCE: 67

```
gctagcatct tttttctgcc acgaggtgcg ttttattttc atcaatcata caaatgattt     60

tccatatcac agggcaagct gagtgcctgg gtgtgttcac agtgtagctt gtcgcttgtg    120

tctgtccatc ttccccgtca gaatggggtc tcagaaatga tgaggtgagg tggagaaatc    180

ctcctaggct tgtaggaaat tttactcctc ttttcctgtt gaatggtctt ttggttggct    240

ggtgttcttc tcatgctctt tggttttctc cagtgtggct ttattgaagc ttgtgatttc    300

ccccatggat aacttgcctg ccattttctt agaactcttg gaatcttgct ctgagctcat    360

gctccaattg                                                           370
```

<210> SEQ ID NO 68
<211> LENGTH: 249
<212> TYPE: DNA
<213> ORGANISM: Rattus norvegicus

<400> SEQUENCE: 68

```
aagctttgga gctgctaggt gctacctatg tcgataagaa aagggatctg cttggagccc     60
```

-continued

```
tgaagcattg gagacgggca atggaactcc gccaccaggg tggggactac cttcctaagc    120

ctgaacccca gcaactggtt ctagcctatg actattccag ggaggtgagc acgccccaag    180

agttggaagc cctcatcaca gatcctgatg agatgcggat gcaggcactg ctgatacggg    240

agaggatcc                                                            249
```

```
<210> SEQ ID NO 69
<211> LENGTH: 1516
<212> TYPE: DNA
<213> ORGANISM: Rattus norvegicus

<400> SEQUENCE: 69

tttttttttt tttttctaag aagctgttct catctatgaa ccagatggca tctaccccat     60

ctgttggctg atcagtccga tctttatgcc actcctgtgc tttagtgagc acctggtgac    120

agtcatgatg gggggtgtct aggtcagggt ccgggagcag ggttgtaggg tttagactcg    180

taggggcagt ctgggatcac aaggaacaag tgggataccc ggcccacgcc aaggtccacc    240

gttcttcggg tagtccatga gtatcatttg ttgtcagtag ccccttgtac tcaaggtctt    300

ttgcttgaca ctagcccatt tggacgtagg agcacagagt gttgggcccc cgtattcaca    360

caacaactgg gcgggcttcc cttctatctt tttgcatagc cagcactcta ggaccaagag    420

gcttgccttc caggctgctg gagaggcccc tcttgttctt cctggggcag tccctgaccc    480

agtgtccttt ttctttgcat taggcacact gatctttagc caggaattct cttctgttgc    540

caggtactgt cttcctaggt tccctaacta ctgtggccag tatatgttcc tctcttgtct    600

tttatctctc tttagctctc tagcttcctc ttctttttgt ctcttttctt ccctagcttc    660

ctgctctttt taccttcttt tctctttctc tttgtttaac cttactttct ctgtaactta    720

tactaactct cagcaactta gcttaaccct tcaaatttct gtaactttct cttcataccc    780

tttccttatc ttagccagat tggtggggca ttttccagcc cctaggagac ccaccctcgg    840

agcctggggg cagacctgga gcactcccta ccttcagggg cattgaagtc aacagtcagg    900

agccttccat ccatgtctgg aacattcttt ctggcctcta gcaggattct gtctttcctc    960

agtggtaaag aagatctgta acagttacta acaagcatct cacgtgggat ggtgagaaaa   1020

caagaaggga atctagagga gagaggtcca ctgaagagga caaatagcat ttagtcacac   1080

agctaaacca ggaggccttt ttttggacaa aaaggccact gtaaatataa gcacaagctt   1140

tgtctatgaa acagaaaggc gagcagagag gcagcctagc tgttaccggc tgtctctctg   1200

ggcttagatt ttcccttaag gagtacctac ctcccttcag tgtcagcttg gtggctttgc   1260

ctctcaagag aaccagcctc caaatgacac taggcttcta gtaacaacta ataacaaaag   1320

gatggagaga tggttagaac ctgggtgcta gatactaagc agctgacaaa agaattgtaa   1380

ccagttcacc tggggctttc aggactttag taacagccct ttaccaaact gtctcagtgg   1440

gctataggcc catggaaaag aaaacattaa tcctgacctt gtccaccacc aaagcctgaa   1500

ttctaacctc gtgccg                                                   1516
```

```
<210> SEQ ID NO 70
<211> LENGTH: 2076
<212> TYPE: DNA
<213> ORGANISM: Rattus norvegicus

<400> SEQUENCE: 70

aaaaaaaaaa aaaaaaaaaa aaaaaaaaaa acagtctctc tgcatcttct tctacagcta     60
```

-continued

```
ttaggtgctg tccacttttc tgcacagacc ctgaaccacg catcaactta ttttctctgc    120

aacttacaat aactctctca gtgacttagc tttacccttc aagtttctgt aactttctct    180

tcatatcctt tccttatctt agccagatcc agattggcgg gggattttcc agcccctagg    240

agacccaccc tcggagcctg ggggagacct ggagcactcc ctaccttcag gggcattgaa    300

gtcaacagtc aggagccttc catccatgtc tggaacattc tttctggcct ctagcaggat    360

ctgtctttcc tcagtggtaa agaagatctg taacagttac taacaagcat ctcacgtggg    420

atggtgagaa aacaagaagg gaatctagag gagagaggtc cactgaagag gacaaatagc    480

atttagtcac acagctaaac caggaggcct tttttttgga caaaaaggcc actgtaaata    540

taagcacaag ctttgtctat gaaacagaaa ggcgagcaga gaggcagcct agctgttacc    600

ggctgtctct ctggacttag attttccctt aaggagtacc tacctccctt cagtgtcagc    660

ttggtggctt tgcctctcaa gagaaccagc ctccaaatga cactaggctt ctagtaacaa    720

ctaataacaa aaggatggag agatggttag aacctgggtg ctagatacta agcagctgac    780

aaaagaattg taaccagttc acctggggct ttcaggactt tagtaacagc cctttaccaa    840

actgtctcag tgggctatag gcccatggaa aagaaaacat taatcctgac tggcaaaaca    900

aagttcttca cagttgtaga ttctttgaaa ctattttagg ggctcttttt gtcccccaac    960

ctggggcatt ttaaccatag gggcaggaac tggctgctgt ggggatagga ccaaaggcac   1020

tctccatgtt aatgatgatc agtggagaaa agtaattttg atgttggaga ctactcctcc   1080

ttggatagga cagcagataa ggaggcttct taagactctt aatgagcgct ctcctacttg   1140

agcgaaattc ctttcctgtt ctgttttcct atagccccac tagctctcca gccttttttag   1200

tcattcttcc ttgacgattt ctaacacagc ctgtcctttt tttatagcct gttaacagca   1260

tttctgatct tttaggcagc tatcgactaa gtgccatacc gggtgaaact ccgcctttaa   1320

gattccttac tcccaaggaa aatttaaatc tttcccagtt catcacagct ggctgcgagc   1380

ataagcacag aataaaacac tatatgtttt tgttttgttt ttctttcctt ttttcactag   1440

gctggggccc gaacccaggg ccttgcgctt gctaggcaag agctctacca ctgagctaaa   1500

tccccaaccc ccaaaacact atgttttaaa aattaacttt ggctatcaac caacacactg   1560

ccactagagc ggggtctcta caaaattaag tttcttactc actaagcgtt aaggggacca   1620

agtaaaactc ttcgacgaac aaagcaaaca gtttcatgat ttcaaacaca gtcgtcggtc   1680

caagatttta aacacagtcg tcagtccaaa ttcaaacacg aaacaaaagt caaaaagaca   1740

ctaacagaca caacacgtcc agaaaaccac agtcaggtca caaagaagac aaacaattcc   1800

aacagtcaaa caagtaacaa gcagacgcgc cgcgcagctt cggtaccaaa ctgaaaccaa   1860

aaaattcaga cggagtcatc aagggtgcgg atccctccga aaacggacgg aggtgccacg   1920

gatccggatc tccctctcct ccaaccaccc ttggaacgtc ttccagggct gcgggggaga   1980

agtccgagct cgtcagctcc ttctctggcc cgcccagata gtccccagat ctgagcctat   2040

tgatcgatcg ttcacaggac aagacaccct cgtgcc                              2076
```

<210> SEQ ID NO 71
<211> LENGTH: 64
<212> TYPE: DNA
<213> ORGANISM: Rattus norvegicus

<400> SEQUENCE: 71

```
tcatgacctc attttaggac caagagctgt gttggtttct tagattgtta gctttttctc     60

taga                                                                  64
```

<210> SEQ ID NO 72
<211> LENGTH: 131
<212> TYPE: DNA
<213> ORGANISM: Rattus norvegicus

<400> SEQUENCE: 72
tctagaaaac ggaggctgtc tggatgcagt agtcatttgc tgcagaggtt ggggaagggg 60
aggccccatg tttctcctgt ggaaagaggg tgtggggctc tgggaaaagg ccactcttca 120
aacattcatg a 131

<210> SEQ ID NO 73
<211> LENGTH: 124
<212> TYPE: DNA
<213> ORGANISM: Rattus norvegicus

<400> SEQUENCE: 73
gctagcctta tgccagcctg ccactgtcaa catattctgt tcccattggt tacatgcttg 60
atacatacac tcttgtgttt ttggctaatt gagcttttta attctattgt aatattttca 120
attg 124

<210> SEQ ID NO 74
<211> LENGTH: 124
<212> TYPE: DNA
<213> ORGANISM: Rattus norvegicus

<400> SEQUENCE: 74
caattgaaaa tattacaata gaattaaaaa tctcaattag ccaaaaacac aagagtgtat 60
gtatcaagca tgtaaccaat gggaacagaa tatgttgaca gtggcaggct ggcataaggc 120
tagc 124

<210> SEQ ID NO 75
<211> LENGTH: 1252
<212> TYPE: DNA
<213> ORGANISM: Rattus norvegicus

<400> SEQUENCE: 75
tttttttttt tttttatgaa gacacgaaat gcatttattc acataacaaa aaacaaaaac 60
aaaaacgaaa aaaacactca ctccctcttc acttgaaatg tgtcagtaat gactcaaagt 120
gtcatgattt accaggtggt gaattcttct gacaaccagg tgaagaatta ggaaaacata 180
cagttccagt ctttatattc tgaccctaga aatcggttca tttgtagctc ttgggggtac 240
acagtaaagc aggcaagcaa ctgtccacac tgtttcattc cacatactta gtgagtgccc 300
ttattcaggg cctaacttca ctccaggcac aaaaacaagg caggattgcc tggtaagtct 360
gaacatgaga aaagaaaacg atttattaca caacagatat atccatttat gtgagtgttg 420
acatctagga attctctgct ttatagacaa ttagaagcag catcctttct ttagaatatt 480
tctatgccct cactaaaccc atgagtaagt atcttgcttg ggagtcatac ccagagctaa 540
ttacaattca atattctccc tgtacatgca atccttgaaa aacgttatat gtattttatc 600
tcattttcat aaaagaatta caaagacccc aaaaaggttt agtgtttgtt tgcatattaa 660
ggttgcaatt ctccagaaac ccaaagttcg gatagtatgt gacgttgtgc agacaatagt 720
ttacctcatg ctacaggcta taaatgtcag aacagagctt aaacactcac attagtgaac 780
gcattggcac tacttgtact ctttatttta agggctaaga aaaagcacac ttctactcag 840

-continued

```
ccctatggaa gttatcagtg agcacattct ctatcgctca ctgtacagta aactatgtac     900

aacaggcact ataacaaaca gaattttaga gtcaggtatg acatgaaact ttttcaattt     960

tttatattta cactgtgggt ttatcctcat cttaagatca gtttttcatt ttgttttgtt    1020

cttctgtttt tttggttttt tttctgccta aacggtatgc tcaagtagca tggataaatc    1080

ttccagaata tgcactgagt aactccttgg ctcttcccag agccttgcct tcagcacagc    1140

atgatgttaa aagatggtct cattgtagac atcaaagtag gtagaagaac aattgtgtct    1200

gtatcagagg ctctatgaag agacctggag tctcgaagtt ccttcttact ac            1252
```

<210> SEQ ID NO 76
<211> LENGTH: 1241
<212> TYPE: DNA
<213> ORGANISM: Rattus norvegicus

<400> SEQUENCE: 76

```
aaattttggc tggatccaca gcaagagtcc tcagtattat ttatttgttt tgttttgtgt      60

tctgttttgt ttttactgca acttgacaat aaaagatgtt tggcattgga agagaataga     120

acattaggtc tgggcccagc gctctgactc cgtcttgttt aatagtttaa cctgaagtcg     180

caagactggg ataaacagga gagctgacat gaaggacatc atcgcacatg tttcggctta     240

ctgtgtcaga actacacgtg cttggcctta tttctttgag cctgtggcag aagagtgtat     300

cgaggcagaa agcagaaagg tccaacctcc ctttctagaa aatgtccctt gatgtcctga     360

ttctcttcca ctagtcctca ctactaaagg tcctgtcacc tctcagtaac actgtgggcc     420

gggaaccaag cctcagggca caggcctttg ggagctgtat tagagttctc gagaagaata     480

aacagcactt gcagaaggaa ttcccagaag aagaatgact tacaggcttc tgtccagcta     540

atccaacagt gagcagaaag tccaaaaatc cagcagttcg ggccatgagg ctgggtgtct     600

cggctggtct tcagtagact ctggaatccc aatgacgtag gctctaacgc cagtgaagga     660

atggacttgc caacaaggtg aggccaagca ggcaaagagc aaaagctccc ttcgtcctgt     720

cctcaagtag acttctagca gaaggcgtgg cccagactag aggtgtgtct tcccacctca     780

agatcaggat taaagaagat ctactgactt caaattaagc aaaactccct cccaggtgtg     840

ccctctgtca ttagatttta gttcattcaa gatggagtca agttgacaac caagaatggc     900

catcaccggg gacactccac atataaactg tataccaagc ttcatatttc agacatgttt     960

cttaatgtca tccacgtctc cagcccctgt agtgtgtatg tgttgtattc tctgcagaat    1020

ttagcatgcc cgtgtttcct gtccttcaca taaacgcctt tgtgtgaagc ttgcttgatc    1080

ctccactccc ctctccagcc cccacccctg tgacactgcc cagtaataac tgttcgttgt    1140

ttacctgttg cttgtaagtg caagtattaa agcaatttga aagctaaact cacctgtaag    1200

actataataa atacctgtaa tccaataaaa aaaaaaaaaa a                        1241
```

<210> SEQ ID NO 77
<211> LENGTH: 396
<212> TYPE: DNA
<213> ORGANISM: Rattus norvegicus

<400> SEQUENCE: 77

```
tttttttttt tttttttaaa taataatgtt actgtcgtgt tggctgtata tcattgcata      60

tacttcagga aaagttttct tgttcttgct aaataacaaa gcacaattgg taagttccat     120

ggacagcagg ctccctcaga acgtagccag ttctgtgagg caccccatat cccaaggaca     180

agcttgtggc atgccagatg aacagcagcc ttggcttaca cgcacacctg tacataaaag     240
```

-continued

```
ctcatctttc caaccacgtg cagccaagag attaccacag acttgacaca gggaccctaa    300

caggctccta tagacagtcc tgccgctcca tgaagtgggg aaggaacaaa tgcagtgacc    360

gcatctaatg cacttccttt gaaaatgttt gcttat                              396
```

<210> SEQ ID NO 78
<211> LENGTH: 473
<212> TYPE: DNA
<213> ORGANISM: Rattus norvegicus

<400> SEQUENCE: 78

```
agatctgagc ggccgcccac ggtcctgatg acagaagagc tctcctcccc gaaaggggca     60

gtccggagcc caccagtgga taccgccagg aaggagataa aggcagctga gcacaatggt    120

gctccagaac gcacagagga gatgaggaca ccggagcccc tggaggaggg tctagcagag    180

gaagctggca gggctgagcg cagtgacagc aggggcagcc cacagggtgg ccggcgctat    240

gtgcaggtga tgggcagcgg gctgctggcg gagatgaagg ctaaacagga gcggagagca    300

gcatgtgcgc agaagaagct tggcaacgat gtcatctccc aggatccctc cagcccagtc    360

atgagcaaca cagagcgatt agatggaggg gcaacagtgc ctaaactgca accaggtctt    420

ccagaggccc gctttggttt gggaacacca gaaaagaatg ccaaagctga acc           473
```

<210> SEQ ID NO 79
<211> LENGTH: 1221
<212> TYPE: DNA
<213> ORGANISM: Rattus norvegicus

<400> SEQUENCE: 79

```
tttttttttt ttttgtttgt gaaagtacag aaaactttat tggaaatctc ttgattatat     60

ttccaagtgt agctctcatt tcctaacaaa gcactggagg aggggcttca cagccacctg    120

gtcccagcct gagcttggct gcgggagttg tctagagccc gtttcttcca ttgtgtagga    180

ctgaggggca caggccacct tgaaggatgc ttcgctcagc ttccctggcc tctttcttaa    240

gaatctggga cataaaggct gctgtctaga ggccactggc tgagccctga aaagaatccg    300

tgccctcacc cccttttag tgctggccct gggggtaaa tcctgttcag taggctatga     360

atgtgcccct gacccaaagg ctgcaatggc acttggccac cactgctggg cacatttctc    420

tgtggcagca aaagcatgca caggggaaag gctccagtgt tacatgcaga ttactaacag    480

cagttgagag ccacctgctc caatgcgtaa cggctgctgc cagtgaggat ccagggacaa    540

gaacaggaca ggctggcaga ggcacttgac tgactcaagc aacaatacct gaaggtttaa    600

gtcaaccata ggctcagctt tggtttctca aaagggaacc aatccagctt gtaagcccag    660

ggccatgtac agactctgga attagaggga gggagagagg gaggaacagc tccctagtcc    720

tgctccagct caggggctgg agcagcaggt tatacagtgc tcctctgggc accatgggca    780

acacacctct gaggagtcct cacactgaac acacctgaga cctcctgggc tgctagaaca    840

gagctagtca cattacagat gctgtgtcaa cagagtatgc tcggcaggag cacgcagcat    900

gccgggaagc ctgatgcctg ctcagttcca tacacacagt ttgagggggc tactttgcct    960

ttgccagacc cattgctgat ctctccttag gtgtgacagg aagatcctca gagcagtagc   1020

acaggttctg agtaatcttc accggaggcc tacagcccag agaaaccctc ctccttcccc   1080

agcagaactg ctaaccccaa acatacttct tttataaaat atctgatttc tctgacagta   1140

ataaatattt accatgttct atatccacgc agcagcgatc gagggaaaac gaggaggaaa   1200
```

-continued aaagatccta caggcggccg c 1221

<210> SEQ ID NO 80
<211> LENGTH: 695
<212> TYPE: DNA
<213> ORGANISM: Rattus norvegicus

<400> SEQUENCE: 80
tttttttttt ttttttttga ttgaaaatgt ttaatttgta aggcacacag tttatgatca 60
ttttaatatc taaaagaacg aaattaacag gactaaaacc tgattgtcga atcatttacc 120
aagtttggat gtcacgttgt aaaagcaggc ttaaaaagat gactccttac aaaggagtga 180
ggtggacctg ggtgggacag gctagacatg gccctgaaaa ccttcttggg tgacaaagaa 240
acagactact ggactgaagc cacagcttcc aagaaacaag aaaatgtagt ggccaccaca 300
ttgggctttg tttccttatg agacattttc cacctcatct cgggatctta ctgttaccct 360
tgcccaaact gcttatggca tgagggttcc agagcccagc gccccagcca agtgtacaaa 420
agacgtttcc tgtagagtgt gcctgtgagg gacaagcttg aggagtcctg tagagcgtcc 480
agacaagctc acatttcctc attcatggat gatgaagggg atgtcacaag cagaccagaa 540
actcctcaat gtctcaggaa aggaccgttt tccagagcgg cttacaagtg ggactttctg 600
ggtttccatc tggagtttgg ttttcctgct tggcctcaga ctgagataga agagcagtga 660
gacagaaagt agacagagaa tgagctagcc tccgg 695

<210> SEQ ID NO 81
<211> LENGTH: 771
<212> TYPE: DNA
<213> ORGANISM: Rattus norvegicus

<400> SEQUENCE: 81
tttttttttt tttttttaga ggttaaaggt gttcatttgc caaccggaca gcctgagttg 60
gatcccctga gcccccatgg tggaaggaaa ggattggctc ctgtaagttg tccactcttc 120
tgaagtatgt gcactgcggt gtgtacctgc ccacatacac aaacaggcta ggtagagaag 180
aaaagggaaa ccattaatag tcaacactga tacttatcaa aaatggcact agatggtgat 240
ggtttaaaag cttcacttag aagccaacag tgacagcaga gacagacctc tgttaaccat 300
tgcaggcaaa actgaaagac atgctcacac aggaagcaag cacaggcggc tttgttgacg 360
gcttagctga aacagactca agacaaagcg tgttaacaga cagacgcact tcacggtgac 420
acgaggggcc agctaccaag aagacattga ccccaaaaca tgtatacacg ccaacagaat 480
cccaaaaggc acagtgagaa aggacagaag gaaagttcga aatagaactt tgtgctgccg 540
aggtaggaga ttaacttccc ctggagattt ccacagtggc caaaacttcg gtgaggatat 600
ggaagacgga ggtaccatct gagcttgatc agactctcta aggtgtgata ttgcaaatag 660
tgcaagccaa acgactcagc gggcacatca caggttcaag accagcctga gaaacttagc 720
agggccctgt ctcaaaatta aaagaggttg tttttaagga ccagcctcgt g 771

<210> SEQ ID NO 82
<211> LENGTH: 2262
<212> TYPE: DNA
<213> ORGANISM: Rattus norvegicus

<400> SEQUENCE: 82
cacgagggat caccagatgc tgccaggtgc tggttgccaa ggttgaaatg agaagtttct 60
gttaactggg tacagagttt cagttttaca aggtgaagaa gttgggcaga cagatggtag 120

-continued

```
ggatggtcac acaaagatat gaatgtattt actgccactg aagcaacact aaggtggtta    180
atctgagaag ttatgtttat tatttaaagg actaaattgt caagctaact tcaataactg    240
ttttattttg tacaactgac atattcatat agatgacatc tctaaagatg tctttatcag    300
tatttaaaac tgtgttacat ctcttaggaa tttgacacac agtttcactt gtaaggccag    360
ataaccaatt gtagggtgcg ttattaccca gaatgtggtg ggtccaagag cttgaactca    420
cgatcaagtt tggtgacact tgcctttacc cactgagcct tctcatcaac ccaagtttcc    480
caggaattaa gtaatctgtt tccctaattc cccttaagca aacatggcag tcaagtgtac    540
agcaggagac aggttatgat ttgcatgatg taatttaata atgtaaccat ctttggggaa    600
tctaattagt accaaaagag aaaaaaaaaa ccaacaggaa acagctgtct ctctcacaca    660
gtgttgagag ctttccctcc cactcattgc caatcagtgt cctggtgtcc cctcaccctg    720
cctctgtctc tgcaacctgc cagcctccaa ctgaacagac ttccattcct gtgcaatcta    780
agtcagtctc tccagtctct tcctccctcc ctccctcgct ctccctctct cttataaagg    840
aaagaaagca ctcactgggt ataattgatg tctatatgca ggtgagggca ggtacaagat    900
aaggcaagac ctgtgattgg gcagtgaaaa aagaaaggcg ggggcagagg ttttgtaagg    960
caggagagat gaggaggtag aagaaccaag aaaaaggcag agaaggacga cccagatctg   1020
cgtggcttta accgggcaaa ggtagctatg aatatttcat aagggacaga tttatatagg   1080
acaatttgtc ttacctaggt gggcagttta catcaatacc aattggttgt gactttattg   1140
tgtggacgtt ttgtggactg agaatttgct gatatgaatc tgactgctaa attacaagct   1200
ttgggttttg attttaactg gctactggga gttgtgactg tagccacagg ggcagatgct   1260
gggattgtga gcagggttca cagcacagtc ccaggatggc agctgctgct gggcccagag   1320
aggagccagt gccaacatgg ggctagccat ggaggtggag agatcgctgg ggacagagaa   1380
gagcaggagg cagtgtggct tggtgcctgg tgccccaccc acccctgcat ccattttaat   1440
tatttactgc tacaactggg tgcttgcttt tagtttcaga gggttagtcc attagcatcc   1500
tgaggagaag catgcaggca ggcagacagg catggtgcta gaagggtagc tgagagcttt   1560
aaatcgtgat ccgcacgctg cagagagaga aaaaggaaac agagatggag ggatgactgt   1620
ccctggcaag gactttcaaa ccttaaaagc cacctctagg gacacacctc ttccaacaag   1680
gccacacccc tactccttcc caacagtcca ccaactgtga acaaagcatc caaatgtatg   1740
ggccgatggg gccattccta ttcaagccac ctcactgaag gaataaatta acatgtccca   1800
aagtattaaa tgtagtcatt tttctcagta ctgagacaaa atatctcaag aaataaaaaa   1860
acactgaagg acgtatttcg tttggctccc cctttaaaag aaacagtcca ccatggccgg   1920
gaaggcatgt ggctggtcag agtgcaccct catgcaggaa gcagagagtg ggggagtgct   1980
cctcgaagcc ttttcctttt tatttagcat gcaccccaag cccacaggag ctggctaacc   2040
cagcaagcct tgctggcctg gaagccaccc ccaacaacca tcatcacccc agtgcctccc   2100
tacagtgggg attatgagtt gccaccatgc tgtttttcac atgggtgcag gggatttgaa   2160
accacagcct cctgcttgta cagaaagcat cctgaggagc catctctctg gattcaccct   2220
tcacttttgg ctgactgggc ctgagctgga gtcacctggg ct                      2262
```

<210> SEQ ID NO 83
<211> LENGTH: 422
<212> TYPE: DNA
<213> ORGANISM: Rattus norvegicus -continued

<400> SEQUENCE: 83

```
tttttttttt tttttttggt ttgttttgtt ttgtttttct ttgcttttct aaggatagtt     60
taaaatacaa acaaattaaa gtatgtgata tgtcaacatg atcatgcccc tcccagacac    120
agcctttaac tgtccagctc aaataagaga aatgctgaag cttaagatgt ctttgtcctc    180
aggaagacat cacatgtgtg gttgtcctga cactgcacat ggcagcttcc ccacaacatg    240
ggcccttcgc cttcacactg acaagaagtg tatgcccttc acactgacaa gaactgtgtg    300
ctcactacaa cttgtattgg ttgtaccttc cccaaaagca gtaatgtatt tctcaagatg    360
tcctaaatca agtggagact ctcctctgga aggaactgga ctcagcctcg tgccgaattc    420
tt                                                                   422
```

<210> SEQ ID NO 84
<211> LENGTH: 445
<212> TYPE: DNA
<213> ORGANISM: Rattus norvegicus

<400> SEQUENCE: 84

```
tttttttttt tttttttcag acaaggatgg tttattgaat ggaccccctg agactgatca     60
atcagggcca gggccgcagc ctcagaattc aggggctgag ccatgactct gaccatttct    120
cagggccggc ttataaaggg aaaaccccac aaagccacaa tgagctcgca tgcaggtgct    180
gccggatggt tggctctgac tcaagccatt tcagacagaa cagctcatat ttacctttaa    240
tgtggtgggc catatgtaaa gctttgtgta atttattaag ttgaacaaac ctcacagcat    300
gaccttgctc tgagtcgagt cattttctgt atcaatgatg gcaggcatgg aacaaaatgg    360
ctatagctat gctaggtggg gtagacctca acaggataag aaactaaaaa gtaacaaaga    420
tgagaagaca attgggcatc ctggt                                          445
```

<210> SEQ ID NO 85
<211> LENGTH: 482
<212> TYPE: DNA
<213> ORGANISM: Rattus norvegicus

<400> SEQUENCE: 85

```
tctttttttt cggagctggg gaccgaaccc agggccttgc gcttcctagg caagcgctct     60
accactgagc taaatcccca gccccaggaa caagccttct taaacaacca ccccatctct    120
ccagtccctg atcaatattt tatgactacg tttactctgt aaaacaaagg attaaaatct    180
aatccgatta ccagtcttac tagacaaacc ttccaaatct gagttttctc aagtataaac    240
acttcacaac accttctgag aaatgtccac atcactcaaa gacaacacat ttgggaggtt    300
tttatgggct tcttttcata cagaaccttt caaagcttgt aaaacttcga acctagggac    360
atttgggagt tcttctcggt ctcacacaaa acggacttgc tttcaaagat cccttcggat    420
tctatttgac ttagcaaaaa cacagcgcaa aacacacccc tgtaagaaca aaggtgcaat    480
tg                                                                   482
```

<210> SEQ ID NO 86
<211> LENGTH: 784
<212> TYPE: DNA
<213> ORGANISM: Rattus norvegicus

<400> SEQUENCE: 86

```
agttcatgtg cattggtgtt tgctcacatg catgtctgtg acgtatgcct gtaggagggc     60
atcagatccc tgcaactgga gttattgaca gttgtgagct accatgtggg ctgtgggaat    120
```

```
taaacctcga aaagcagcca gtgctcttaa ccactgagcc atctttccag ccacctcaac    180

tcattcttaa atccacttaa gacatagagg aaacactatt ccttctattc tgtttgctga    240

tatctgtaaa agtagacaga cttgcagagt ggtggtggca gacaccttta atgtcagcac    300

tcaagaggca gaggaagaca gatctgagtt caaggctacc ctgatctaca gatagagttt    360

caggtcagtc agagctttat agagagacct gtctcaaaat acaaaaaaca aaaccaaatt    420

aagtagacag actcccactt acacgaaacg taaacactgt ttcacacact tcagaatcac    480

atttaaacta ccaatcaaca agaactgaca gaaccaatat caggaaacct catccatata    540

aagcaacgtc acagcaccaa gcagttaaca gcttttggct cgctctaatc gaggatccca    600

aacacaaatc ttacacagac atggggaggt acatcctaca tctcatctcg gtcgcagctc    660

atcgtcagtc ctagggatct tttgggtccc cacaaagatg gaggcatagc cttgctcttc    720

ttgcccgaca aggaggccag caggccagga agttaaactg ccaatacctg ccaatgctgg    780

tctc                                                                 784
```

<210> SEQ ID NO 87
<211> LENGTH: 486
<212> TYPE: DNA
<213> ORGANISM: Rattus norvegicus
<220> FEATURE:
<221> NAME/KEY: misc_feature
<222> LOCATION: (19)..(19)
<223> OTHER INFORMATION: Wherein n may be a, c, g or t
<220> FEATURE:
<221> NAME/KEY: misc_feature
<222> LOCATION: (22)..(22)
<223> OTHER INFORMATION: Wherein n may be a, c, g or t
<220> FEATURE:
<221> NAME/KEY: misc_feature
<222> LOCATION: (107)..(107)
<223> OTHER INFORMATION: Wherein n may be a, c, g or t

<400> SEQUENCE: 87

```
tttttttttt ttttttttana gnagctgtat tttctttata ttctgcatgg gatatgaaat     60

aggggttttg ctccacaggg agcctggtca atatagacag gatgtantca gggtgtgtct    120

tccaaggtca tctccatttc caggcagatg gaaaaaaaat catgaacaat catgttgatg    180

attttgaaag atgagtatag gcaatagcat gtgtcctctg tcctgagcaa cagatctcag    240

ggatgtgagg gtgtgcgctt tctggatggt tcaccatacg catcttcagc accaaggcta    300

tgcaagcttt gttcagtaag gcagaacatc aggaactcag gagagtggct cccggaaggt    360

gatcatgtgg cttgacccct gattatccat cttcctcacc aatggtttgc ttacattcga    420

agcttaaagc cttaaagtta acttcgtctt gtgatgctgt taaatgtttt caattacagc    480

acgatc                                                               486
```

<210> SEQ ID NO 88
<211> LENGTH: 921
<212> TYPE: DNA
<213> ORGANISM: Rattus norvegicus

<400> SEQUENCE: 88

```
tttttttttt tttttttaa gagaaacatt ttaatatctg caggctcacg caggattcaa     60

ctgtgtgtgg tacagtctag agtgacttgc ttctatttac ttccacacac ggtgactttc    120

gatgagatgg ttaagctgag cagtatacat tcctgaacag tgccaaggat cctgttttca    180

aacagcttta tcaatcgaaa catcctcaaa gagccattgg aggcagtgtg gctgggccat    240
```

-continued

```
ctgcactaaa atcgcttatt cagaaggtgt caaagcagcc gagggccttg agccacaggt    300

tgctggtgtt cacatctcag ctgggacgtg ataaagactg catgagctgc agatccgcaa    360

acagccttgc aggctggctc tgctcctgca aagtcaatgg agccacaagg tacttcttaa    420

tggtgtcatc tgttcaggtt ctccagggag ttaagggaag cactgtcttt gcacacagtc    480

tctatcacaa gggctctggc tagcagcatg agagttccct ctcagccagg ctgccacagt    540

gagccatcta ttgtcctcac tgcagagtgc acaggatgaa gatgtccact ttcctcatca    600

gacttgctga cagcctcatt tcctgccaaa cggatcagac cacactttca accctggtgg    660

ctgcacatct tcctggacga taccagctcg atttacagcc tgctccttct ggtattcttc    720

cagccgcaga aggggccgga agtagatagg gtagaaggcg gctccgacca tagagatgaa    780

gcctccgaat atgagcgcgg tgcgcaggtt ccgggccgcg gccatggtga gaaagggggc    840

tgcagggcgg gcgaaggccc ggcacgctcc gaaacccgac tcccagcctt aaggtcgcga    900

cccggctcgg aagaggcgga g                                              921
```

<210> SEQ ID NO 89
<211> LENGTH: 525
<212> TYPE: DNA
<213> ORGANISM: Rattus norvegicus

<400> SEQUENCE: 89

```
tttttttttt tttttttaca tttatgaatt tttaatactc ctgtcaagat cttacaagga     60

gaaattactt tgggaggtgg gtatggaggt tagaggtagg ttggaaagtg gatcatgatc    120

tcaaaatagt aaatgctagc tgagtggctt tcccagagag aagcgacatg ccctgacgag    180

actggagaac atgtgtaaag gagagcttat tttcaggtct ccgctggcct ccatcctctt    240

caaaaacctc agctcctggg ttctgctcaa cccacattct gtaatacttg ctcaagtagg    300

cctgtagcac cttgtaggat acagacagtt ccaaatggat gtccactcca gtctctggct    360

gctctattct gtacttctct tgaatcacag cttttatcca tgtaagtaga tgcctttacc    420

tgggcacttg aagttcagag gagacaggtc tttagataga aatgtgcaaa ttacttatgt    480

ggttattgac aatcaatgac tgttctcccg tagtctcccc tcgtg                    525
```

<210> SEQ ID NO 90
<211> LENGTH: 930
<212> TYPE: DNA
<213> ORGANISM: Rattus norvegicus

<400> SEQUENCE: 90

```
tttttttttt tttttttac ataaactatt ttatttaaat aaaaccagga ctgaccctct     60

cccacacgca ccagcacatg cactcgcaca atcatgtcct ccgtttctgt tcctcctgaa    120

cagccacctc aaaccccaca ggttttcatt gtgaccatcc ttgaaacctg aaaattggga    180

gatcccatgc gaaacactgg cactcttccc ccaaccctgg gcaagcattc tcctcatcct    240

cctggtggga caggagctca gctcttccaa ggcacccaga tctggtgtgg tttcccttca    300

cacaacccgg gaacaccaat acccagagct gctctttgag gctgggaccc ctcgcttcag    360

gtcaactcct ctcacacaac agaggaggct ttgtaaccat gcttaagcgc tctccaaagg    420

ttcctggcat aggtaccgtc tggtatgagg aagagcgaca gagagcaatt gagcaccaag    480

ttccctaatg ccaccctgaa ggagggtgcc aagctccagt tcagtctgta ccaagaaaaa    540

gcaagcctag cgccacacat ggggaaggtg gggatggcaa ggtctcagcc ttgagaatct    600

cacatctcta ccctccagca tagatcccat gagggaccca ctagcacctt ggcgattgta    660
```

-continued

```
agggctcagc ccaactggag acacaccaca caaacagtgg ccatttggag ttggcccaaa    720

tgcctgtgtc ggtaacaggg tttgactccc gcatctaaca ctgactgaag gacacacagc    780

acagcagcta aggtcacgag aggtgcactg acagaaggtg ttgtcttcca gaggcacatg    840

gacatttcac acactgctca caggcaagct gggacaggag aagagcacag gctgccaggg    900

actcagcagc gtatctaggg catgccctct                                     930
```

<210> SEQ ID NO 91
<211> LENGTH: 1060
<212> TYPE: DNA
<213> ORGANISM: Rattus norvegicus

<400> SEQUENCE: 91

```
ttttttttt ttttttttgg ggtttggtat catttatttt ttttcttaaa cccacttgta      60

gtttgggttc agctgggaag caggatatac gggtagaggg aaggggacgg tgcgagcagg    120

attggcccat agctttgggg gcaatctcca aaccctgctc cagggaggta ggtcctgttg    180

tcaggctccc agctggctca ggtgaggctc caaatggatc ttctggagca agtgtcctga    240

gcagaggaga atttccattc tctccaaccc acctcctcaa agacccagtc agaaggtttt    300

ccaacacagt gccaggcagt tgaggggaca tcaggccacg ggcaggcctg agtgggtggg    360

acaaggaaca ctgtctggct tctggttcca ggtaacaacc taggatgtgg ctacccagag    420

gctgccatct agagtgacct ccgggagctg cttctcttgc ttcctgggct gcctgggatc    480

caaacctgca gctgccctgg ttgcaaccag tggtatactt cccacccccc acccctcaga    540

caaaataaaa taaaataaaa tacaataaaa attagaataa ataccaatcg ggtcaacatt    600

tacatttaca caaatggaca agatgatccc ccaaaccgta gaagtttaca gactggatgg    660

gaaggatacg cagatgaaga tggttttggg gaggaagagg ttcgccgtgg tggttgatgg    720

tggggggtcc tggccctgtc caggggaggg ccagagccct gcaggaactg tggtctcaga    780

gcttaggcaa tacggccagt tcatgaggag aacagtgacc tgcaggccac ttgagtagaa    840

aacaaggacc aacttgtcct gacaggtagg ggagcctaaa aaggctcaat atgagatcgc    900

catggccagc aggacaccac agtttgggag aggcttcgcc tcctgttcat ccattcagag    960

gcggctttga taggccgtcc ctctggcagc gggagagcct ctggcctggg gaggtcaggg   1020

tctgtgggta cctgcaacgc ccctacttcc cctcgtgccg                         1060
```

<210> SEQ ID NO 92
<211> LENGTH: 1158
<212> TYPE: DNA
<213> ORGANISM: Rattus norvegicus

<400> SEQUENCE: 92

```
tggctcagtg gtcgagcaca gtaacaacat ggagattcta aaaacagaga aagagaaaag     60

caagaagata gtggagggag acaagaagaa aggctggggg gccagttttg ttatttttgt    120

tttggttcag ctatatgctc cacacttcca aagcagcaaa tgtgttgcat caccacccaa    180

acctgagaaa gctacagcat cactggcaag gacaagctag cgcacgggtg acatcctcta    240

accctgccat tgtaaattat acaactgcag tttccagcac acaccattgc ctccgacact    300

attggagagc ccgtgacact ccaaaaactg ctaaggcctt tacagtatct gaccttcaat    360

ggccccgaaa actggtaggc cgcttctccc cattccaacc caaaaattac atgcgagcaa    420

cggaagagaa aagcttttaa gcccgcgcgg acgaagagac cagcggacgc tgctgaagac    480
```

-continued

```
cacagaccag gtaagccagc tgaggctgga gtttattgcc gatgagcgct gagtcctggg    540

gaggagcggg gaaggataag gtcgggcagg atcaggacct tggctaggag aggcggcgcc    600

acgaaggcga ggccgggagg tgcagacaga caggcgcagg ccacggtggg ggcgggccag    660

gctatccagg cactcggtga gcggtctccg gcgtcgctcc cggagctggg tggcggctgt    720

ggcggcggct ccgcggcagt cctggctgcg gtcgtggccc accggaggcc ccaagcaagc    780

aggacgcggc gggaggcggg gcgggtggtg ctgctcgagc acacggagca gctgcagcgc    840

tgggcaaggg gtcggcgggg cccgcaggcg gccgcgtggg gacccagatg agcccgtagt    900

ataccgcaag caacacagca gccaaggata cacacaggaa gtaggcgcag acaggggcga    960

gccgcagcca tcgggcgcgg ggcccctcgc tcagccccgt accacctggg ctctcgccac   1020

cactgcccac gcagctcgag cccccgcatg cgctgcccac tcagcctgta ccgacccgc    1080

ccccaccccg ccgcttctag caagccacgc cccttctaga gtcacgccct atcagaccgc   1140

caccccctc gtgccgaa                                                  1158
```

<210> SEQ ID NO 93
<211> LENGTH: 1241
<212> TYPE: DNA
<213> ORGANISM: Rattus norvegicus

<400> SEQUENCE: 93

```
aaaaatctcg atgccctcaa ctgttaggtt aaagcctgac ctgtgtcact atgtgctgtg     60

acacgaacct aattcccaag tggacaggga cacctgagtg gcatttcgtg cttcagttcc    120

ttccctcatg attcttgctg ggtcctcttc actgaggctc tcccctgagt catatattta    180

ctggaaaggc tacctggaga gcctttgaat tgtgggcatt cctttttaat gtgtccctct    240

cttccacaga tgaaacagcg cttttctctt gagtctctgt catcctgtct cttccacttt    300

tcggctggtg tcctgacaag tttctcccgg cccaggtcaa cagctgccct cattggcttg    360

gctttggcag ctgtgcacgg tgcagccttg tcttcttttg ctgacacttc cttttctgtg    420

tacttgttct gaatttcttt gtcctctttg cttctttttt ctttgctctc tgtgtacctt    480

tggtttgggg tatcttcctg gtctcgccgc cgcctcactt ttctcctcat gggacagtcc    540

ttcatgaagt ggccaatttt ccccacagatc cggcagcacc tgtcatttgg ggccagttct    600

ccctcagtca ggacatccgg atcaaagaag tatgccagga tgtcctttgg aaatcctttg    660

actggaattc caaatactct tctaccattg ataaaagctt tcattataaa atttgtcatt    720

ttccttgata atccagcacc aagattgtgg ttcaaatcaa agggatcttc aatgacgatg    780

tattttgagg tccactgttt cttaaaagtt gtaagcagac tttttcttct gatgctgatt    840

acgtgttcct taaagtcaaa ctcctcagtg tagaagcgta gaagtcccaa ccacagctgc    900

ccaacagatt ctgtattttt tccatattct ggccaacaag tgggcagttc atttatttga    960

tcgaaaaagt agatattcca gccatcaaca agtatttctg gtttcttttc acctttgtat   1020

atctcctgaa gcacagggat gacagggggg gaccgctgct ggaggaagta cagcaccata   1080

agagtgtaag cgtatgatga caagctgcct ctggacgcgt caccgatgtc acacatcttt   1140

gtgaacactt tcatggtgta gcacaggtat ttcactctgg ggtcaatggc tgagtatgca   1200

aacaggagcc gcgtgttgtg aagagccagt gtgtcctcgt g                       1241
```

<210> SEQ ID NO 94
<211> LENGTH: 2695
<212> TYPE: DNA
<213> ORGANISM: Rattus norvegicus -continued

<400> SEQUENCE: 94

```
tttttttttt ttttttttcc aggagtccct tcggtccctg atagcgggag cctggacctc     60
tgaggccgag agggtgctgt gtccccggcc tccgagccga ggtggcccgg ctagggggcg    120
ccacggagtt tttttttttt tttctttttc ttttccagga gtcccttcgg tcccagccag    180
cgggaccata gacacttttg aggccgagag ggtgctgtgt ccccggcctc cgagccgagg    240
tggcccggct aggtggcgcc acggattttt tttttctttt ccaggagtcc cttcggtccc    300
tgatagcggg agcctggacc tctgaggccg agagggtgct gtgtccccgg cctccgagcc    360
gaggtggccc ggctaggggg cgcctccgag gctttatttt ttccaggatc ctccccggtc    420
cctgccagcg ggagcatgga cttctgaggc cgaggggaag ctgtgttcca ggctatctac    480
catggcctcc tcggtctgtg agcactcagg gttctaaggt cgaccagttg ttcctttgcg    540
gtccggttct ctttctacat ggggacctct tggggacacg tcaccgaaca tgacttccag    600
acgttccgtg tggcctgtca tgtttatccc tgtgtctttt acacttttca tctttgctat    660
ctgtccttat tgtacctgga gatatatgct gacacgctgt ccttttgact ctttttgtca    720
ttaaaggacg ttggaagagg cttgcaccaa ggctgtttgc ttgtccagcc ctagctcttt    780
tcttctgcgc atgggcctct tcgatgcttg aagcttagcg tccccccatg agtacgcgct    840
tcctgctttc ccgtgcttgc ttgcctgtgc tctgtggggc agctttatga caaccgtccc    900
gcgtgtcagg cgttcccgat ttccccgtgg tggttgtcgt ccgttaccgg taggagtcgt    960
tggtgccgag tgcgactgaa aggtttttcc cgtttggtgc tagtgacccc ctggcgtgct   1020
cctctgcggc cgaccggttt ttttatttgt tttttttttt tttgtttttt ttttgttttt   1080
ttttttgttt tttggaagga gttcccgaac ctccgctgct tggtggtgtg tccctttctt   1140
tcctgctgtg tgcctcccga gttgcacctt ttctccttcg aaggggattt tattttttta   1200
tttttatttt tttttttattt ttattttttt tgaaggagtt cccgaacctc cgctgcccgt   1260
tgagtcccgt tcttccacgc cacgtgcctc ccgagtgcaa cgcttccttt tttttctcgc   1320
cctcgagaag ggtaaatttt tttttttgtgt gtgtgtgtgg cagtgttagc gacttcttcc   1380
cgtgctctct ctcgctcttc tcgctcgtat tcccgtccag tgcgtgttag aaagctctca   1440
cgcccgttgt tcccgatgca tggcgtgtct cgctcccgtt ggatcgatgt ggtgctgccg   1500
cgttctcttc gggccggggc ctaagccgcg ccaggcgagg gacggacatt catggcgaat   1560
ggtcattcag cgcgaatggc gaccgctctt ctcgttctgc cagcgggccc ctcgtctctc   1620
ctccccattc ctttgcaggg tggtgtgtgg aagtcagggg tgcggctgtc cggcacgagc   1680
gctgacccgc gcacacttgc tgctgtggtt cgcggtgtcc ctgtggacgt gtcgggggcg   1740
cttgcccccca cgccgttcac tgcttcgcgg ccctcttccc ccgtgccggg ggaaggtggt   1800
agacccgctg cggtgcatac ccttcccgaa tggtgtgtgc acgcgccctg ctttgtgtga   1860
gccttgcggt gctcctggag cgttccgggc tttgaccacc aaggtgcccg cttctgagtt   1920
ggcggtggcg cttcccgctc cccggcgtgc ctcctgtgct ccatggtgct tgtgccttta   1980
cgctttccct tgtcctagtt gccggctttc tgcacggtga cagaaagggg gggggtcgag   2040
gagttgagtg tgcggttaaa aggctccttc cgttgggtga gcgcccaccc cgtgcctatg   2100
tttttggtgc cttcacccgc gggccctgcg cggttagggt ggtgctgagc gatcgcggct   2160
ggccctttttt aaagaccgga ctccctcaag tcaaggctcc tcctttgtgt gcgccttgaa   2220
gaggcctggc cctcggcggg gacctgtcgc aggtcccccc ggtccgcgaa tgctcaagaa   2280
```

-continued

```
gaccccggag aaagagacct ttgccgatac cgcagacccc ccaccagctg gcgcgtggtc   2340
cttcccgttc tgtcccgcgc ctgttgctcg tttcccgttg cgtgcacgga gcccttggct   2400
gctcgtcggt gttgggttcg tcccgccctc agtgaggaat ttgccttctc tagctatctt   2460
cggaaagggc tttacgatct ccgaggggct tctcccggat ggtcccctcg gctgcccgcc   2520
ctgacctcag ccttctgcgc gcagcgtttg ctctctcgcc taccgcgacc cgcgcctccc   2580
cgctccgagt acgaggaggg atcacgcggg acggggctct gtcgacctgc cgctgtgcgg   2640
agcttgtggg ggagattggg tttctggtgg caggtggcgg ggaagggccg tgcac        2695
```

<210> SEQ ID NO 95
<211> LENGTH: 2423
<212> TYPE: DNA
<213> ORGANISM: Rattus norvegicus

<400> SEQUENCE: 95

```
ttttttttt ttgtttttca agttgcacat tttaatttac aatgtttacc agtaaaaagg     60
attagttaca aaaaggaaag ctgtctgtac aaaataaggg ttttttttt tcacattcat    120
aaagagaacc cactgtgaat tcttaccttg tgaagtcaat actcaaacag ctcactttgg    180
taaaactatc ttggaaggac tagtaatcca ggcaagataa taaaattatc agcttcccaa    240
tcatgtccag gagaaagaat tttctgaaca ttttccctgt acagaaaagc tctctgtact    300
tgcagatcct tagaaaagcc agtgctctca ggagacagcc tggtaccagg acgaagcata    360
atctcctgct cactcaaatg gcaatccttc ctgaatctga cagacacaca tttatcatag    420
cctcaggtca gcaggagaac cagatggttc aggatcagcc tctctccact caatagttta    480
tcatataaat taaatatgga gaggtacaca tgagaaaggg ggagctcttt ttcaaactcc    540
cacttcctaa tataatacac atcacagttt taatgagcag agaagggtaa gtcaccctgg    600
tttgggcaca tttcctcaag ggaaaaacca aagtatcaaa agccttcaaa gcatactggc    660
ccgtcccact gcagccagca gcctgattcc agaatgaaag catacagtag ctgtaaagcc    720
ctggagcctt cagaaagctt tatttagtga taagctgagc tctgctggca aaagcccacc    780
tataaaaagg gagcaggtct gattcacaaa gtgtatacat gcatgaccca aggtaatgaa    840
gaccttcaaa tgcaaatgat cctaaagcta ttggaacctc taattacgag tgacccgttc    900
agatgtgcct ccattagcct taaaaactga ccaacacaca tctgaagagg cacttccctt    960
agcattaaca taaacacttg accagaaaag gcatggtcca aaaaacagtt aactaaaaat   1020
ttagagtcta aacctctctt ctccaccgac tgaatgaaca cacccgcaat gaggaccaaa   1080
cagaatcagt gcctccaggg acgtgtgtct gtctggccat gtgatcagga acctcctaac   1140
atagcacagc acagcacagc tgctctgggc acacaaagcc agttcacccc atgaagaaac   1200
acaagggatt gtgattaaac ccatcccctg tgtcaggagc aactccacta tggttttgat   1260
cactcagctc agagggatag gagtgcctag caacaagtcc taatcctcgt tactcccagt   1320
ccgggccctc actgactcag aggtgccttt gtgtataaat atgtgagagg cagcaaatgg   1380
cagcactgct gacaggctaa tgcaggcccc acagcggaga aagttcttcc tctgctgctc   1440
caatcttctc cctacagtta cagtcctgcc agtgatggcc aaggaccatg tgtgagccag   1500
ctctttgtga ccaagctttg gcaagtcagt aagtttgtca aaggcaaaat ccttctgtgg   1560
acaatgctag ctgcagctct ggggacgtgt gagagaggag agggtcctct gacgggattg   1620
gggacgtgtg agagaggaga gggtcctctg agaggatttg actcatcagc ccctcttgcc   1680
cagttcatta atcagaagga aggggagagg agaagacagc agaacatgag tcagttgtga   1740
```

-continued

```
aatctgcaca gctgacattt gctcttcaca gcagaaagga cttgaatgag aatcatgaaa   1800
cttgaggaac acttgtattt tccttcggga tttaaaaatg tgtcttgtac caaaagacta   1860
cattcagtgt gggtcaggtc caagagcggc agcaagagct cggccattaa gcgtgcccag   1920
cactgggagg agactgtcat ctgcttagca tggctggtga gcaggccagg gctgctcctc   1980
actggtctcc aagtcggaag ccctggcccc agttgtgtct cccacctccg ccattctgat   2040
cagcagctcg cctcatgctt gcagggggca caccgaagcc cgacacccct cctctcctgc   2100
tgggtagcca gcggtacaaa aactgaggtg tggacagaaa attccttcct cccaaatcca   2160
ttgggtatct gaacatcagg aagaaataaa gatgtccgac aaggtttcca atgagctcat   2220
tgatgaccga gcctccaatg atatagttga atccgaggat aacccaaggt aagtaacagg   2280
ccttaaatcg tgttccaaac caaaatgata caatcaggtc tctgttcagc tgggcccaga   2340
cgtaaagtac tgacatgatt agaggaatca tcagcaactg catatccatg gctaagccag   2400
taataacaat gcagatccag ttg                                           2423
```

<210> SEQ ID NO 96
<211> LENGTH: 610
<212> TYPE: DNA
<213> ORGANISM: Rattus norvegicus

<400> SEQUENCE: 96

```
aaatttcaag aggtcagagt ggggcttaga ttaagtaact aatgcacagc aaaacgctgt     60
gagattaggt gtgaaggagc tggctgccct cctgtctctt cccttctcta tcccacagga    120
gctacagaga gagcacagca gccagacgct ggccaaacag ggaacactct ttatgccaag    180
tcgcaaagat gacaagcggc atgaggagga cccagggccc tcctttgtgt ggaaggacgg    240
agaggttctg ggagggctgg gaagggtatg ggaggatcct ttgtgtggga ggattgagga    300
aggcctgggc aggctgggaa gggctaggac cgctctcctt tgtgttagag gtctgggaaa    360
gtctgggagg atcctccttt gtgtgggagg actgaggggc tctgggaggg ctgggagggc    420
cctcctttgc ttcacagttt tagatgttgt tccatctgct ctcggagttt gaatttctgg    480
atctttcctg agacagtgag aggatagcct tccacaaaca cgatgtatcg ggaatctta     540
aaatgggaaa tctttccttt gcagaaagct ttgatctcct cctccgtggt ggtctctccg    600
cctcgtgcca                                                          610
```

<210> SEQ ID NO 97
<211> LENGTH: 1047
<212> TYPE: DNA
<213> ORGANISM: Rattus norvegicus

<400> SEQUENCE: 97

```
gtaacccacc tccattctgt tcttcggacg cttgcgccag tgggtcaatt ttattttctt     60
tcaaaaataa aagtcgagtg cattcagaga cggccttaag gcaatacgcc tcatcttccc    120
acagtaaaga tggcgacgcc gtgagtaagt tacaagtaac tccacttccg caattttctt    180
gagccctggt ccaagatggc ggacgaggcc acccggcggg tcgtgtctga gatcccggtg    240
ctgaagacta acgccggacc ccgagatcgg gaattgtggg tgcagcgact aaaggaggaa    300
tatcagtccc ttatccggta tgtcgaaaac aacaagaatg cggacaatga ttggttccga    360
ctggagtcca acaaggaagg gacccggtgg tttggaaaat gctggtacat ccacgacttc    420
ctcaaatacg agtttgacat cgagtttgaa attcctatca catatcccac tactgctcca    480
```

-continued

```
gaaattgcag tccctgagct ggatgggaaa acggcaaaga tgtacagggg tggcaaaata    540

tgtctaactg atcatttcaa acctttgtgg gccaggaatg tgcccaagtt tggactagct    600

cacctcatgg ccctggggct gggtccttgg ctggcagtgg aagtccctga tctgattcag    660

aagggtgtga tccagcacaa agaaaaatgc aaccaatgaa ggatgaagct tctgaggcag    720

gacagaggga ctgttgctag actctgattc tgtttcctcc tttctcatga ttccttcaag    780

ggtcacctct ggccattaca aagtagctgg agggacaaat aacaaaaccc aacaaaaggg    840

caaggtcaca aagttgctaa attaagctgt acagagaggt gaaagatttg ggccttgaaa    900

gaggcggttt gtatcccttc tccaagcaga gccctggagg cattttggag acctggggtg    960

taactgacag catatagctt tttgatttct ggagacaacc tgtcaataaa agctgcttcc   1020

catggtgtga aaaaaaaaaa aaaaaaa                                       1047
```

<210> SEQ ID NO 98
<211> LENGTH: 1191
<212> TYPE: DNA
<213> ORGANISM: Rattus norvegicus

<400> SEQUENCE: 98

```
tttgctatct gcacagccca tcgagggacc tgaggtggca aaccctggac agtgggtcag     60

gcggcgctca cgtctggggt gacaggatga agcgggctgt gggctgtgtg gagcaccgtg    120

cacccctagc acctttgggt ttcttgtgga gttctcgccc cagacatcag tgcactggat    180

tgcaaaaggc aattcatctt ttattggatc aggagcgcca tttggagtgt gccattatgg    240

gaggctcgta gctgtctgtc cctcgtgccg aattcggcac gagcccccct tttttttttt    300

tttttttttt tttttttttt tttttttttt tgaattagca caaacgcatt tatttactaa    360

ccaaaggaat gatcctgggt aaaccaacgg tctgacatgg gtttcgggta aagtgtctat    420

gatgaaaagt catgaaaaat aaaaccaaag aagtgaagca gtgtggttct gtacgacctg    480

ctcattgaat tgagcttatt ccctcagcca gctgactgct gtccaggatg acgagttagc    540

cagtcctcat tgtaccttct catagacccg agtacagatg gcattgttca tgacgcactc    600

caccaccatc ttcccgtcct tcagttttct cgttatcgtg ctttctttcc cttcccactt    660

ctggtgctgg accagggcac cgtctgtgaa ggtgcagacc gtctcagttt tcctgccatc    720

agctgtggtt tcatcaaact tctctcccaa ggtgcaagaa aacacggtcg tcttcaccgt    780

gctctcagtt ttgacggtga ggttgttgcc gtcgagggta atgatgcagt ctggtttggc    840

catggcaccc atcttcctaa gagccagccc tactcctagt tccttcatgt agtcctcaaa    900

cccgtggctt tccaccagac gccacttccc ttccaggtcc ttaaggctgg ccatggcgag    960

cgggagagca caaaagcagc aaggagacgc ggtggcgggg gcgctgaggg aataagctca   1020

attcaatgag caggtcgtac agaaccacac tgcttcactt ctttggtttt atttttcatg   1080

acttttcatc atagacactt tacccgaaac ccatgtcaga ccgttggttt acccaggatc   1140

attcctttgg ttagtaaata aatgcgtttg tgctaaaaaa aaaaaaaaaa a            1191
```

<210> SEQ ID NO 99
<211> LENGTH: 384
<212> TYPE: DNA
<213> ORGANISM: Rattus norvegicus
<220> FEATURE:
<221> NAME/KEY: misc_feature
<222> LOCATION: (1)..(1)
<223> OTHER INFORMATION: Wherein n may be a, c, g or t

<400> SEQUENCE: 99

-continued

```
ncctagcaga acgcttgtta ggagtctgtg ggacaagata gcctctgata aaataaactc     60

taaacatgaa ctccttcaag aaaaaggact ggactccacc actgttcaat aaagtcacag    120

cgagggatgc tagaggcggt agacagaaat taagacattc tagatacggg gagtggccac    180

ttggttgggc caccacttgc cttagcatag gtaccatagg ctaagcatgg aaggcagtaa    240

gggtggatgt cattttaatg agagcagcaa atttagtaca tggtttatca aataaaaggt    300

aaaggagtcc aagatcaatc tgacaaatag atctatcagc tgaattgtaa tcttggggtg    360

gaggggtcag aggtccggca attg                                           384


<210> SEQ ID NO 100
<211> LENGTH: 181
<212> TYPE: DNA
<213> ORGANISM: Rattus norvegicus

<400> SEQUENCE: 100

caattgctgc tctaggatag tcagagtgtg ttctctgtct cctgggaaac agtggaccag     60

gaatgaaagc ttcaacctgg tacccagatt ttagatgttt tagggacaat cagtcaaatt    120

tttgtgtgaa tgtatgggtt tatatgacta taactgtgta agacagagaa atggatgtac    180

a                                                                    181


<210> SEQ ID NO 101
<211> LENGTH: 130
<212> TYPE: DNA
<213> ORGANISM: Rattus norvegicus

<400> SEQUENCE: 101

ccatggacat aactacctcc tgattaagtc cgttaattga gacctaatca gtctgttaga     60

ttattgaaac aggtcctgtt agcagactgc agggagaaaa cacggtcatg aaccaaagag    120

tgagtccgga                                                           130


<210> SEQ ID NO 102
<211> LENGTH: 50
<212> TYPE: DNA
<213> ORGANISM: Rattus norvegicus

<400> SEQUENCE: 102

aagcttcctc catttcccag tagtgccata cgctggcaac cataggatcc                50


<210> SEQ ID NO 103
<211> LENGTH: 296
<212> TYPE: DNA
<213> ORGANISM: Rattus norvegicus

<400> SEQUENCE: 103

aagcttcaac tgtctattta ttcacagtca cactggctga gatgtcctac actgtgtcca     60

gtgcaagtgc tgacactgga cattgatgtc ttcttctgta tcttagagga aaggtcggta    120

gaggtagagc ctggcttccg gcttgtcata catgacccct aagtgattat ttctactgta    180

ccttattctc agaggaattt tatcatgaaa ggggtccagg agtctcccca caaaccttag    240

gaacaccaat ctcagtcaga cagggatgtt ttgaatgcac acctaaagtc tgatca        296


<210> SEQ ID NO 104
<211> LENGTH: 321
<212> TYPE: DNA
<213> ORGANISM: Rattus norvegicus
```

-continued

<400> SEQUENCE: 104
gctagccatt tggtatttat tagataacaa gttagggaac tcatgccttg gaaaggtgtt 60
gttggttgct tgtagttctt tgtctggcac agggaagcta cagctattat ctcaataaaa 120
tagctgtccc ttggattttt ttttttaaa taattgctta ttcgagccaa catctaaata 180
aggtgcatgc attgtatttg cttgatacgt ttgttgtgtc tctttttctt cttctgtaag 240
tttcttcccc tccttatttt tctttcctcg tattgtattt actggaaaaa ccagatcgcg 300
cgccctgcag gcttctgtac a 321

<210> SEQ ID NO 105
<211> LENGTH: 92
<212> TYPE: DNA
<213> ORGANISM: Rattus norvegicus

<400> SEQUENCE: 105
agatctgaaa gttaggcaaa atataagagc agccctctga agaggggacc tgccagctca 60
cttgggactc aacattctac tgtagagcta gc 92

<210> SEQ ID NO 106
<211> LENGTH: 94
<212> TYPE: DNA
<213> ORGANISM: Rattus norvegicus

<400> SEQUENCE: 106
agatcttggg gtttcaggct tgtttggcat tcaattttac cttctgagcc caggagcgag 60
aatcttgaac taaagagggc ttgacagtgc tagc 94

<210> SEQ ID NO 107
<211> LENGTH: 343
<212> TYPE: DNA
<213> ORGANISM: Rattus norvegicus

<400> SEQUENCE: 107
caattgaaca gtagtctgta agtagtgcaa cactgtaaaa tgttctcttt agttcagaga 60
gaaaattccc aagcattatt ccaactgctg ctaaaataga tgttataatt atcagtttaa 120
tgccagttcc aaacccctaa ataagcaaat attactgtta ttgccagcaa cttcctgaaa 180
ctacacaaat tcagtgtatc cctccctccc tcttttcctt tcagtcatga agggagcaga 240
tacaacccag ggtccaagat aggtaagtga tccttagatg attttagata gcaggtggtg 300
caaactttta atcccagcac ttgggaggta aacaggtgga tcc 343

<210> SEQ ID NO 108
<211> LENGTH: 238
<212> TYPE: DNA
<213> ORGANISM: Rattus norvegicus
<220> FEATURE:
<221> NAME/KEY: misc_feature
<222> LOCATION: (1)..(1)
<223> OTHER INFORMATION: Wherein n may be a, c, g or t

<400> SEQUENCE: 108
nctaacaaag atggtttaga gatccaggtc accaatcctc ttctcagaca gacccatttc 60
tggggtcaac agccattact gcatgtagag taaagggaag taagacagag agagttcatg 120
ggcagtccta actggctgtg tggaaacagc tttccaattg ttctgggaat gaatgtagag 180
tcagtgtccc tgcatgggtc atgataagag tgcctgcaag tgaggcgctc acaagctt 238

-continued

<210> SEQ ID NO 109
<211> LENGTH: 247
<212> TYPE: DNA
<213> ORGANISM: Rattus norvegicus

<400> SEQUENCE: 109
ctcaggttgg ccttaaactc actatatact caaggatgag gttgaaccta tcttcctatc 60
tctgtctcct gagtgtactg ggattgtaca catgtgccac catacctggc ttacgtgatg 120
ttgtggatca aacccatggc tttatgtatg ctaagcaagc actttatcaa ctcaaccaca 180
attcatctct atattttaaa tgtaatattc ctaatatgtc tttacatttt ccagctacat 240
tcctagg 247

<210> SEQ ID NO 110
<211> LENGTH: 196
<212> TYPE: DNA
<213> ORGANISM: Rattus norvegicus

<400> SEQUENCE: 110
tgatcaagag tcccaaaccc agagagtctg ggtgctgac atctgaatgt ggctggcctg 60
ccctggctga ctgctttcag tgccagccac actgatgccc cttagccctc tggggttaat 120
ttaggaactt gggctcaggc caccgtcacc agcaatgaac tcacaaagaa tgagatgtgg 180
ctgttgattt cctagg 196

<210> SEQ ID NO 111
<211> LENGTH: 457
<212> TYPE: DNA
<213> ORGANISM: Rattus norvegicus

<400> SEQUENCE: 111
agatcttccg gagcaatggg gttcagcttt tgcagcgcct actggacacg ggagagactg 60
acctcatgct ggcagccctg cgcacactgg tcggcatttg ctctgagcac cagtctcgga 120
cagtggcgac cctgagtgtc ctaggaactc ggagagtcgt ctccatcctg ggtgtggaaa 180
accaggctgt gtcgctggca gcctgccacc tgctgcaggt tatgtttgat gccctcaagg 240
aaggtgtcaa gaaaggcttc cgaggcaaag aaggtgccat tatcgtggat cctgcccggg 300
agctgaaggt tctcatcagt aacctcttgg agcttctgac tgagatgggg gtctctggcc 360
aaggccggga caatgccctg accctcctca ttaaaatggt acctcggaag tcaccgaaag 420
atcccaacaa cagcctcaca ctctgggtca ttgatca 457

<210> SEQ ID NO 112
<211> LENGTH: 85
<212> TYPE: DNA
<213> ORGANISM: Rattus norvegicus

<400> SEQUENCE: 112
gctagcttaa gggttcttct gtaggccgcc tcatttcctg gtttaatttt actttatgta 60
tatgatgttg cctggatgta gatct 85

<210> SEQ ID NO 113
<211> LENGTH: 241
<212> TYPE: DNA
<213> ORGANISM: Rattus norvegicus

<400> SEQUENCE: 113
agatcttttt tgcttccctt ccttttattg atccttagga ataaatcctc ccaaactctg 60

-continued ttgtttttaa agttttttga aagacctgat ttttttttcca ttttctttgc ccttgcaaat 120
aaccatcagt gtaattagtt gtccatgctg caagggaata ctttgtgagg gaaataagca 180
agaattgagt gttgtttact aagaggtcac gcggatggtt tttgggtaat tatttactag 240
t 241

<210> SEQ ID NO 114
<211> LENGTH: 388
<212> TYPE: DNA
<213> ORGANISM: Rattus norvegicus

<400> SEQUENCE: 114
tccggagctg gggactgaac ccagggcctt gtgcttccta ggcaagcgct ctaccactga 60
gctaaatccc caaccccgtc aaaggccatt tttatcctca tcaaacaatt ataccttact 120
ttttgagttg gaaatgtaat tcagtaatag tctgttttcc tagtatgtac aaagtcttgg 180
gctccctcac taacaccaaa ggaaagggga aaaaagagct cacttctttg actttcagtg 240
gccttccact cagactatgc ttgtttagaa cttcggcagc ttttttcatg ctctcctcca 300
tcttgaactc aacaacacta taaaaaagaa aagccaaaaa caaatgaata aaaccagtct 360
tacttggaaa attgaacttg gaaaattt 388

<210> SEQ ID NO 115
<211> LENGTH: 444
<212> TYPE: DNA
<213> ORGANISM: Rattus norvegicus

<400> SEQUENCE: 115
tctagagaaa tatacataga cagcaaggct ggagttgagc caggcaacct aagctgggcc 60
accggagtca ggcagctgca gaaggtcacg tgagcaggcc cagtgctagc ctgtgacgga 120
gtgatgtaga cactcagcca caccagggag ccaatctcca agttgtcttg gctagactgt 180
ggactctgcc cttcatgggt ctgccacaca ggcattctgg aactgtctag ctagctcttg 240
gggaaacagc taaaaggact ttggcttttc tggggtttgc agggagggta acagtgtctg 300
cgcccttgtt ctctacttct gaatgtagta acctcaccct ctggggtagc atatgacagg 360
tacccaactc cttttcgtgg gcaagcctct ggcaggggag ctctttctgt tgcaatgtaa 420
cagaggcatt gcctctttca attg 444

<210> SEQ ID NO 116
<211> LENGTH: 135
<212> TYPE: DNA
<213> ORGANISM: Rattus norvegicus

<400> SEQUENCE: 116
gtgcacagaa gtatgtgttc tgggtcggag gaaagatggt aggtgtttgt cccaacacag 60
tgaaaaggaa cagacatgtg aagtcttcag actgtgggcc tttgatttac ccctcagttg 120
gtctatgtgt gtaca 135

<210> SEQ ID NO 117
<211> LENGTH: 246
<212> TYPE: DNA
<213> ORGANISM: Rattus norvegicus

<400> SEQUENCE: 117
caattgcatt gcaaaatttt aaaggttaca ttgaaaacac ttgaaaataa gccaccaata 60
aatgagatga cgataataag agcccctaaa taaagaggct aagaaggagt taagtgtaaa 120

-continued

```
ggaagaggga agaaatagtt aaggcattta taagacacta gaaagtctag aagagagaat    180

gttagcagta cggagtcaca gctaaaaatc tgcatcttgc cctttaaaac ccaagagaga    240

aagctt                                                               246


<210> SEQ ID NO 118
<211> LENGTH: 203
<212> TYPE: DNA
<213> ORGANISM: Rattus norvegicus

<400> SEQUENCE: 118

agatctgctg gtgtttgcct ccacagtggt gaggttgcat gtacatgccg accatgctcc     60

tatctttcac atgagtgctg tggaatgctc aggtcttagt gcttgtacaa gcaccttact    120

caactgaacc attgtcttag cccaatagtg aaacactgaa aagttatttt acccatgatc    180

agaagcttta acaatcaact agt                                            203


<210> SEQ ID NO 119
<211> LENGTH: 233
<212> TYPE: DNA
<213> ORGANISM: Rattus norvegicus

<400> SEQUENCE: 119

cctaggtctg ccagtgaata agaagacccc tccccggaaa gtcccgagtt tatgttccat     60

gcgctattca atagccttca tcgcacatat ctgcaacttc acattgatag cacagaattc    120

catcataagc atcaccatgg tagccatggt caacaacacg gaccagccat cccacctcaa    180

tagctctact gaatggtttc ctgatggttt aaacggtgat caacatgaag ctt          233


<210> SEQ ID NO 120
<211> LENGTH: 300
<212> TYPE: DNA
<213> ORGANISM: Rattus norvegicus

<400> SEQUENCE: 120

tgtacacagg tagtcttagg atttctgttg ctgaaaccgt gggaagggaa cagttcaatg     60

agtaaaacca agacagaagt caacctggtt agaagctgga ggcaggagaa gatgcagagg    120

ctgtggaggg gtgctgctta ctggcttgct ccccatggct tattcctgct ttcttataga    180

acccaggacc accggcccaa gggttacacc atctgtggtg atctgggccc tcctccatca    240

accactaatt aagaaagtgt ccaagtttgg ctatatctta cagagatgtt ttctcaattg    300


<210> SEQ ID NO 121
<211> LENGTH: 351
<212> TYPE: DNA
<213> ORGANISM: Rattus norvegicus

<400> SEQUENCE: 121

cctagggaat ttgccattgt ttagtttaag ctaacactcc aaaggtaatc tcctatttcc     60

tcttttcctt tctgtcctcc atgtggctgt catgggcatg cagcatacca gttctcaggt    120

gcctggaaca ctggccagtg ctctagccca gccactgtgc cctgaaatcc ttccctgtgt    180

tcaatgctac agcacatcct ccagactgcc tccccacccc cagcaaccga attgagcagg    240

gacactaaga cagtcctttg gagacttcca ctggtctgtt gaaactttgg ctgctctcac    300

agcatagctc ctcttagcct gtaacttagt gctgctcagg ctgactgatc a             351


<210> SEQ ID NO 122
```

-continued

<211> LENGTH: 889
<212> TYPE: DNA
<213> ORGANISM: Rattus norvegicus

<400> SEQUENCE: 122
tttttttttt tttttttaag gggccaagca gaagacaagc tgcctttatt atagttgatg 60
tcacagctct gcttgtaata gattcagccc cagaaacacc ccggttaaaa cagcacggtt 120
gacttcaatg gatagagtct ttggtaaggt gaaccagacc agggctgacc gacaatcttc 180
gggcccctgg cccaggggta gcctgtagtc ttacgtgagg cccagcatgg cctgaagttc 240
ccgagcttta tcatctggca gagagcccag ggctgtgtgg aagctgtcgc tgtgctgctt 300
ggccaggaac gtcagtagta gtagcagtgc ggccttggtg tctgggggga tcctgttgtc 360
tggcaggatc aggctgcaga tgcgcaggag ctctgaagcc acacccacaa cctggtcagg 420
gttgttctgg tgcaggaagc tgaagaggtg acctatagtg acccattcct ccatgtcttc 480
cttcaggggc agggcatgta gcagggtagc tagcacctgg ggctctgttt ttcctgccgg 540
actggccatc agcagacggg caagagcccc acagatgtta tcacggactc gatcatgccg 600
ctcccttgcc aggaggggca aaaggaggcc cagtagctta gggaagtggt cctgagcagg 660 gcagcccccca tgctctgcaa gtacgcccag cccaaagatg gcattgctcc gcacctcggg 720
gtctgcttcc cgggcattgt ttaacagcac aggaaacagc cgggacacaa attgggctga 780
ggcagcacct agaccctgaa tggattctgc cagtgtcccc actgcaaagg acttctctgc 840
cactgtacag ctctgtttcg tcttacacag caataatggc aacctcgtg 889

<210> SEQ ID NO 123
<211> LENGTH: 310
<212> TYPE: DNA
<213> ORGANISM: Rattus norvegicus

<400> SEQUENCE: 123
tgatcaaggg cgacacatct ggagactata agaaggccct gctgctcctc tgtggaggcg 60
aggatgactg aggagctgcc tggagtgccc tgggcccgcc tgctgcccac catcagcttc 120
cttcagcacc acgcctactt acgttcaatg cctgcctgcc tgccacgctg ccttactcac 180
acgagtgtgt gctaatgacc aaagctgtct cgaatgaaag cagtgttctg ctgttctgtc 240
tgacatagac cttcccacgt ctctcagtct agtatctcta agttgcgttt tctatcctct 300
tctaaagctt 310

<210> SEQ ID NO 124
<211> LENGTH: 1733
<212> TYPE: DNA
<213> ORGANISM: Rattus norvegicus

<400> SEQUENCE: 124
aagctctggt tgcttgacat tgttgtacat atagggtctc gagcccctta gagctcgtcc 60
agttctttct ctgattcctt caacgggggt cctattctca gttcagtggt ttgctgctgg 120
cattcacctc tgtatttgct gtattctggc tgtgtctctc aggagagatc tacatccggc 180
tcctgttggt ctgcacttct ttgcttcatc catcttgtct aattgggtgg ctgtatatgt 240
atgggccaca tgtggggcag gctctgaatg ggtgttcctt ctgcctctgt tttaatcttt 300
gcctctctct tccctgccaa gggtattctt gttccccttt taaagaagga gtgaagcatt 360
cacattttga tcatccgtct tgagtttcat ttgttctgtg catctagggt aattcaagca 420
tttgggctaa tagccactta tcaatgagtg cataccatgt atgtctttct gtgattgggt 480

-continued

```
tagctcactc aggatgatat tttccagttc caaccatttg cctacgaatt tcataaactc    540
gttgtttttg atagctgagt aatattccat tgtgtagatg taccacattt tctgtatcca    600
ttcctctgtt gaagggcatc tgggttcttt ccagcttctg gctattataa ataaggctgc    660
aatgaacata gtggagcacg tgtctctttt atatgttggg gcatcttttg ggtatatgcc    720
caagagaggt atagctggat cctcaggcag ttcaatgtcc aattttctga ggaacctcca    780
gactgatttc cagaatggtt gtaccagttt gcaatcccac caacaatgga ggagtgttcc    840
tctttctcca catcctcgcc agcatctgtt gtcccctgag tttttgatca tagccattct    900
cactggtgtg aggtgaaatc tcacggttgt tttgatttgc atttccctta tgactaaaga    960
tgttgaacat ttctttaggt gtttctcagc catttggcat tcctcagctg tgaattcttt   1020
gtttagctct gaaccccatt ttttaatagg gttatttgtt tccctgcggt ctaacttctt   1080
gagttctttg tatattttgg atataaggcc tctatctgtt gtaggattgg taaagatatt   1140
ttcccaatct gttggttgcc gttttgtcct aaccacagtg tcctttgcct tacagaagct   1200
ttgcagtttt atgagatccc atttgtcgat tcttgatctt agagcataag ccattggtgt   1260
tttgttcagg aaattttttc cagtgcccat gtgttccaga tgcttcccta gtttttcttc   1320
tattagtttg agtgtgtctg gtttgatgtg gaggtccttg atccacttgg acttaagctt   1380
tgtacagggt gataagcatg gatcgatctg cattcttcta catgttgccc tccagttgaa   1440
ccagcaccat ttgctgaaaa tgctatcttt tttccattgg atggttttgg ctcctttgtc   1500
aaaaatcaag tgaccatagg tgtgtgggtt catttctggg tcttcagttc tattccattg   1560
gtctatctgt ctgtctctgt accaatcacc atgcagtttt tatcactatt gctctgtaat   1620
actgcttgag ttcagggata gtgattcccc ctgaagtcct tttattgttg aggatagctt   1680
tagctatcct gggttttttg ttattccaga tgaatttgca aattgttctg tct           1733
```

<210> SEQ ID NO 125
<211> LENGTH: 350
<212> TYPE: DNA
<213> ORGANISM: Rattus norvegicus

<400> SEQUENCE: 125

```
tgatcacgct cagcccttgg taggacattc tacagagtct cttgctgccc ctccgtctgt     60
gccagtggta ccacacgggg cagcctccgt ggaagtttct agttcacagt atgcagctca    120
gagtgaaagt gtggtgcatc aagactccag tgtccctgga atgccagtac aaactccagg    180
cccagtccaa ggacagaatt acagtgtctg ggattcaaac caacagtctg tcagtgtaca    240
gccccagtat tctcctgccc aatctcaagc aaccatatat taccaaggac agacatgttc    300
aactgtctac ggtgtgacct ctccttattc acagacaact cctccaattg               350
```

<210> SEQ ID NO 126
<211> LENGTH: 254
<212> TYPE: DNA
<213> ORGANISM: Rattus norvegicus

<400> SEQUENCE: 126

```
gctagcatcg tgatggccaa gtgcatccct gtgctttttt cttttctaag aaagattgaa     60
aaccaacagt tcttccccaa cagctgccta aattttaagg ggtctgaccc ttacatttca    120
attgggggaa tgaagggggc ccaaccggct taattgctgt gggagagtga gtctggatgt    180
ctgagagagc accttgggag ggactcttcc tgcaatgctg taaatacgag taccgtttta    240
```

-continued ataaagcatg taca 254

<210> SEQ ID NO 127
<211> LENGTH: 1063
<212> TYPE: DNA
<213> ORGANISM: Rattus norvegicus

<400> SEQUENCE: 127
tttttttttt tttttttggc tcctgccatc ttttttattg gtctgggctg tgggctgggg 60
gaggcaggtg ggctcacatc tttatgcaag cagcaaggag acggttcaca tgctcaggag 120
actccaggaa ggccttgagc ttgggtcggg ctttgagacg cgctacatag gcggagagca 180
gggggaagtc tttcaagtaa ccagggaaca ggagctctag gttcagaagt aaatccagta 240
ggcggtagtc ggcgaaggag atctggtcac caacaatgaa gcattggcca cccttgttct 300
gggccagaag agtttcaaat ggcttcaggt gtcctggaag ctccttccta tattggccct 360
tgtcctcctt acagatatgg agatagtgcc atgcaatgcg cctgaacacg tcttccagtc 420
cgtcgttcac catgtccacc agtgctgcct cttgctggtc tttgccgtag agcccgaagg 480
agtggcccag gtgccgtagg atggcattcg attggtacag agtgagcttt ccatcctgga 540
acttggggat ctgcccaaac agacaggaag ccttgaatgt gccttgctcc caaacatcca 600
aggtcaccac ctcctccttc caactctggc cctggtcggc tagcagcatg cgcataacct 660
cacagcgccc agtgttgggg tgcaggatgg ggatgaggcc acagcgaaga gacccaccct 720
cagagcatcc tgggagagtt tgggagactg gaaagctgac aagtggacta aactagcttg 780
ggagcctcga agggagggaa aaaatgtggt ggtagaggcc atgtcctaac attatcttgg 840
caagccaaga cccagcccca ccggcacagg gaaggaggaa aagtgacaga cagtgtagct 900
gcctatggag gctaagaggt cagtcctggc cccaccaacc acaattgtag tcccgcccca 960
agtctcggtc ttgcccccaa cgtggtcttg gccacatccc tccagcacca gtgttgaggg 1020
ggccccagga gtgactatgg cttgtgccct tcatcttgaa aac 1063

<210> SEQ ID NO 128
<211> LENGTH: 374
<212> TYPE: DNA
<213> ORGANISM: Rattus norvegicus

<400> SEQUENCE: 128
gtgcaccagt acctgatgct gggagatgaa tggcttagcg ctgttctact tggaacatat 60
cactcctgcc agccgggcac taacaattat cacccaatcc aggacttaaa ctgtgataga 120
ctggctgatg tttgcctttg aatagagtgt cccaaaagat gggaccactg gtcagctgcc 180
atggactaga ttctccacct gttgggggca atctggtcac cttgctgccc aatccgacct 240
ggagccacca cagcacgagt gtcaagcact ggcagaagcc catgggtgga ggaaagacct 300
ctgcgactgg ctgattgacc cctgctgaaa gccgaggcta ccttgtccac agacgggaac 360
agttctcttc atga 374

<210> SEQ ID NO 129
<211> LENGTH: 5215
<212> TYPE: DNA
<213> ORGANISM: Rattus norvegicus

<400> SEQUENCE: 129
aagcaacctt aaaatgactg caccctccca gatttctttt acattaacta aaaagtctta 60
tcacacaatc tcataaaatt tatgtaattt catttaattt tagccacaaa tcatcaaaat 120

-continued

```
gacgaggatt ttgacagctt tcaaagtggt gaggacactg aagactggtt ttggctttac    180
caatgtgact gcacaccaaa aatggaaatt ttcaagacct ggcatcaggc tcctttctgt    240
caaggcacag acagcacaca ttgtcctgga agatggaact aagatgaaag gttactcctt    300
tggccatcca tcctctgttg ctggtgaagt ggtttttaat actggcctgg gagggtaccc    360
agaagctatt actgaccctg cctacaaagg acagattctc acaatggcca accctattat    420
tgggaatggt ggagctcctg atactacttc tctggatgaa ctgggactta gcaaatattt    480
ggagtctaat ggaatcaagg tttcaggttt gctggtgctg gattatagta aagactacaa    540
ccactggctg gctaccaaga gtttagggca atggctacag gaagaaaagg ttcctgcaat    600
ttatggagtg gacacaagaa tgctgactaa aataattcgg gataagggta ccatgcttgg    660
gaagattgaa tttgaaggtc agcctgtgga ttttgtggat ccaaataaac agaatttgat    720
tgctgaggtt tcaaccaagg atgtcaaagt gtacggcaaa ggaaacccca caaaagtggt    780
agctgtagac tgtgggatta aaaacaatgt aatccgcctg ctagtaaagc gaggagctga    840
agtgcactta gttccctgga accatgattt caccaagatg gagtatgatg ggattttgat    900
cgcgggagga ccggggaacc cagctcttgc agaaccacta attcagaatg ttcagaagat    960
tttggagagt gatcgcaagg agccattgtt tggaatcagt acaggaaact taataacagg   1020
attggctgct ggtgccaaaa cctacaagat gtccatggcc aacagagggc agaatcagcc   1080
tgttttgaat atcacaaaca aacaggcttt cattactgct cagaatcatt gctatgcctt   1140
ggacaacacc ctccctgctg gctggaaacc actttttgtg aatgtcaacg atcaaacaaa   1200
tgaggggatt atgcatgaga gcaaaccctt cttcgctgtg cagttccacc cagaggtcac   1260
cccggggcca atagacactg agtacctgtt tgattccttt ttctcactga taaagaaagg   1320
aaaagctacc accattacat cagtcttacc gaagccagca ctagttgcat ctcgggttga   1380
ggtttccaaa gtccttattc taggatcagg aggtctgtcc attggtcagg ctggagaatt   1440
tgattactca ggatctcaag ctgtaaaagc catgaaggaa gaaaatgtca aaactgttct   1500
gatgaaccca aacattgcat cagtccagac caatgaggtg ggcttaaagc aagcggatac   1560
tgtctacttt cttcccatca cccctcagtt tgtcacagag gtcatcaagg cagaacagcc   1620
agatgggtta attctgggca tgggtggcca gacagctctg aactgtggag tagaactatt   1680
caagagaggt gtgctcaagg aatatggtgt gaaagtcctg ggaacttcag ttgagtccat   1740
tatggctacg gaagacaggc agctgttttc agataaacta aatgagatca atgaaaagat   1800
tgctccaagt tttgcagtgg aatcgattga ggatgcactg aaggcagcag acaccattgg   1860
ctacccagtg atgatccgtt ccgcctatgc actgggtggg ttaggctcag gcatctgtcc   1920
caacagagag actttgatgg acctcagcac aaaggccttt gctatgacca accaaattct   1980
ggtggagaag tcagtgacag gttggaaaga aatagaatat gaagtggttc gagatgctga   2040
tgacaattgt gtcactgtct gtaacatgga aaatgttgat gccatgggtg ttcacacagg   2100
tgactcagtt gttgtggctc ctgcccagac actctccaat gccgagtttc agatgttgag   2160
acgtacttca atcaatgttg ttcgccactt gggcattgtg ggtgaatgca acattcagtt   2220
tgcccttcat cctacctcaa tggaatactg catcattgaa gtgaatgcca agatgtcccc   2280
gaactctgct ctggcctcca aaacgactgg ctacccattg gcattcattg ctgcaaagat   2340
tgccctagga atcccacttc caggaattaa gaacgtcgta tccgggaaga catcagcctg   2400
ttttgaacct agcctggatt acatggtcac caagattccc cgctgggatc ttgaccgttt   2460
```

-continued

```
tcatggaaca tctagccgaa ttggtagctc tatgaaaagt gtaggagagg tcatggctat   2520
tggtcgtacc tttgaggaga gtttccagaa agctttacgg atgtgccacc catctataga   2580
gggtttcact ccccgtctcc caatgaacaa agaatggcca tcgaatttag atcttagaaa   2640
agagttgtct gaaccaagca gcacgcgtat ctatgccatt gccaaggcca ttgatgacaa   2700
catgtccctt gatgagattg agaagctcac atacattgac aagtggtttt tgtataagat   2760
gcgtgatatt ttaaacatgg aaaagacact gaaaggcctc aacagtgagt ccatgacaga   2820
agaaaccctg aaaagggcaa aggagattgg gttctcagat aagcagattt caaaatgcct   2880
tgggctcact gaggcccaga caagggagct gaggttaaag aaaaacatcc acccttgggt   2940
taaacagatt gatacactgg ctgcagaata cccatcagta acaaactatc tctatgttac   3000
ctacaatggt caggagcatg atgtcaattt tgatgaccat ggaatgatgg tgctaggctg   3060
tggtccatat cacattggca gcagtgtgga atttgattgg tgtgctgtct ctagtatccg   3120
cacactgcgt caacttggca agaagacggt ggtggtgaat tgcaatcctg agactgtgag   3180
cacagacttt gatgagtgtg acaaactgta ctttgaagag ttgtccttgg agagaatcct   3240
agacatctac catcaggagg catgtggtgg ctgcatcata tcagttggag gccagattcc   3300
aaacaacctg gcagttcctc tatacaagaa tggtgtcaag atcatgggca caagcccccct   3360
gcagatcgac agggctgagg atcgctccat cttctcagct gtcttggatg agctgaaggt   3420
ggctcaggca ccttggaaag ctgttaatac tttgaatgaa gcactggaat ttgcaaagtc   3480
tgtggactac ccctgcttgt tgaggccttc ctatgttttg agtgggtctg ctatgaatgt   3540
ggtattctct gaggatgaga tgaaaaaatt cctagaagag gcgactagag tttctcaggc   3600
cacgccagtg gtgctgacaa aatttgttga aggggcccga gaagtagaaa tggacgctgt   3660
tggcaaagat ggaagggtta tctctcatgc catctctgaa catgttgaag atgcaggtgt   3720
ccactcggag aatgccactc tgatgctgcc cacacaaacc atcagccaag ggccattga    3780
aaaggtgaag gatgctaccc ggaagattgc aaaggctttt gccatctctg gtccattcaa   3840
cgtccaattt cttgtcaaag gaaatgatgt cttggtgaat gagtgtaact tgagagcttc   3900
tcgatccttc ccctctgttt ccaagactct tggggttgac ttcattgatg tggccaccaa   3960
ggtgttgatt ggagagaatg ttgatgagaa acatcttcca acattggacc atcccataat   4020
tcctgttgac tatgttgcaa ttaaggctcc catgttttcc tggccccggt tgagggatgc   4080
tgaccccatt ctgagatgtg agatggcttc cactggagag gtggcttgct ttggtgaagg   4140
tattcataca gccttcctaa aggcaatgct ttccacagga tttaagatac cccagaaagg   4200
catcctgata ggcatccagc aatcattccg gccaagattc cttggtgtgg ctgaacaatt   4260
acacaatgaa ggtttcaagc tgtttgccac ggaagccaca tcagactggc tcaacgccaa   4320
caatgtccct gccaacccag tggcatggcc gtctcaagaa ggacagaatc ccagcctctc   4380
ttccatcaga aaattgatta gagatggcag cattgaccta gtgattaacc ttcccaacaa   4440
caacactaaa tttgtccatg ataattatgt gattcggagg acagctgttg atagtggaat   4500
ccctctcctc actaattttc aggtgaccaa actttttgct gaagctgtgc agaaatctcg   4560
caaggtggac tccaagagtc ttttccacta caggcagtac agtgctggaa aagcagcata   4620
gagatgcaga caccccagcc ccattattaa atcaacctga gccacatgtt atataaagga   4680
actgattcac aactttctca gagatgaata ttgataacta aacttcattt cagtttactt   4740
tgttatgcct taatattctg tgtcttttgc aattaaattg tcagtcactt cttcaaaacc   4800
ttacagtcct tcctaaggtt actcttcatg agattcatcc atttactaat actgtatttt   4860
```

-continued

```
tggtggacta ggcttgccta tgtgcttatg tgtagctttt tactttttat ggtgtgatta   4920

atggtgatca aggtaggaaa agttgtgttc tattttcttg aactccttct atactttaag   4980

atactctatt tttaaaacac tatctgcaaa ctcaggacac tttaacaggg cagaatactc   5040

taaaaacttg ataaaattaa atatagattt aatttatgaa ccttccatca tgtgtttgtg   5100

tattgcttct ttttggatcc tcattctcac ccatttggct aatccaggaa tattgttatc   5160

ccttcccatt atattgaagt tgagaaatgt gacagagcat ttagagtatg aattc        5215
```

<210> SEQ ID NO 130
<211> LENGTH: 1857
<212> TYPE: DNA
<213> ORGANISM: Rattus norvegicus

<400> SEQUENCE: 130

```
ctgatccggg ccgggcggga agtcgggtcc cgaggctccg gctcggcaga ccgggcggaa     60

agcagccgag cggccatgga gctgtgcggg ctggggctgc cccggccgcc catgctgctg    120

gcgctgctgt tggcgacact gctggcggcg atgttggcgc tgctgactca ggtggcgctg    180

gtggtgcagg tggcggaggc ggctcgggcc ccgagcgtct cggccaagcc ggggccggcg    240

ctgtggcccc tgccgctctc ggtgaagatg accccgaacc tgctgcatct cgccccggag    300

aacttctaca tcagccacag ccccaattcc acggcgggcc cctcctgcac cctgctggag    360

gaagcgtttc gacgatatca tggctatatt tttggtttct acaagtggca tcatgaacct    420

gctgaattcc aggctaaaac ccaggttcag caacttcttg tctcaatcac ccttcagtca    480

gagtgtgatg ctttccccaa catatcttca gatgagtctt atactttact tgtgaaagaa    540

ccagtggctg tccttaaggc caacagagtt tggggagcat tacgaggttt agagaccttt    600

agccagttag tttatcaaga ttcttatgga actttcacca tcaatgaatc caccattatt    660

gattctccaa ggttttctca cagaggaatt ttgattgata catccagaca ttatctgcca    720

gttaagatta ttcttaaaac tctggatgcc atggctttta ataagtttaa tgttcttcac    780

tggcacatag ttgatgacca gtctttccca tatcagagca tcacttttcc tgagttaagc    840

aataaaggaa gctattcttt gtctcatgtt tatacaccaa atgatgtccg tatggtgatt    900

gaatatgcca gattacgagg aattcgagtc ctgccagaat ttgatacccc tgggcataca    960

ctatcttggg gaaaaggtca gaaagacctc ctgactccat gttacagtag acaaaacaag   1020

ttggactctt ttggacctat aaaccctact ctgaatacaa catacagctt ccttactaca   1080

tttttcaaag aaattagtga ggtgtttcca gatcaattca ttcatttggg aggagatgaa   1140

gtggaattta aatgttggga atcaaatcca aaaattcaag atttcatgag gcaaaaaggc   1200

tttggcacag attttaagaa actagaatct ttctacattc aaaaggtttt ggatattatt   1260

gcaaccataa acaagggatc cattgtctgg caggaggttt ttgatgataa agcaaagctt   1320

gcgccgggca caatagttga agtatggaaa gacagcgcat atcctgagga actcagtaga   1380

gtcacagcat ctggcttccc tgtaatcctt tctgctcctt ggtacttaga tttgattagc   1440

tatggacaag attggaggaa atactataaa gtggaacctc ttgattttgg cggtactcag   1500

aaacagaaac aacttttcat tggtggagaa gcttgtctat ggggagaata tgtggatgca   1560

actaacctca ctccaagatt atggcctcgg gcaagtgctg ttggtgagag actctggagt   1620

tccaaagatg tcagagatat ggatgacgcc tatgacagac tgacaaggca ccgctgcagg   1680

atggtcgaac gtggaatagc tgcacaacct ctttatgctg gatattgtaa ccatgagaac   1740
```

-continued

```
atgtaaaaaa tggaggggaa aaaggccaca gcaatctgta ctacaatcaa ctttattttg   1800

aaatcatgta aaataagata ttagactttt ttgaataaaa tatttttatt gattgaa      1857
```

<210> SEQ ID NO 131
<211> LENGTH: 1137
<212> TYPE: DNA
<213> ORGANISM: Rattus norvegicus

<400> SEQUENCE: 131

```
ggtgccttat gcggtgattt taatgatagg tgtcatatat aggacggagt aatctgttta     60

cattctgttc ttctcgatgc actcacaagc gggtaactag gtgacaagaa aacaaagatc    120

ttattcaaaa gaggtcttac agcaacccaa cgtctcatct tcccatagta aagatgacgg    180

cgccttgagg taagctacag gcaacaccac ttccgcgttt ctcttgcgcc ctggtccaag    240

atggcggatg aagccacgcg acgtgttgtg tctgagatcc cggtgctgaa gactaacgcc    300

ggaccccgag atcgtgagtt gtgggtgcag cgactgaagg aggaatatca gtcccttatc    360

cggtatgtgg agaacaacaa gaatgctgac aacgattggt tccgactgga gtccaacaag    420

gaaggaactc ggtggtttgg aaaatgctgg tatatccatg acctcctgaa atatgagttt    480

gacatcgagt ttgacattcc tatcacatat cctactactg ccccagaaat tgcagttcct    540

gagctggatg gaaagacagc aaagatgtac aggggtggca aatatgcct gacggatcat    600

ttcaaacctt tgtgggccag gaatgtgccc aaatttggac tagctcatct catggctctg    660

gggctgggtc catggctggc agtggaaatc cctgatctga ttcagaaggg cgtcatccac    720

cacaaagaga aatgcaacca atgaagaatc aagccactga ggcagggcag agggaccttt    780

gataggctac gatactattt tcctgtgcat cacacttaac tcatctaact gcttccccgg    840

acaccctcca cctctagttg ttactaagta gctgcagtag gcattgctgg ggaagaaaca    900

aacacacacc aaacagtact gctacttagt ttctaaggct gcacagggaa gggaaagact    960

gggctttgga caatctagag gtaatttata tccgccccca ggtggagcaa catgcgattc   1020

tggaggcacg gggtaactg aaagtgagta catatagtct ttctggtttc tggagataac   1080

ccatcaataa aagctgcttc ctctggtaaa aaaaaaaaaa aaaaaaaaaa aaaaaaa      1137
```

<210> SEQ ID NO 132
<211> LENGTH: 1883
<212> TYPE: DNA
<213> ORGANISM: Rattus norvegicus

<400> SEQUENCE: 132

```
gtcccagtca gtccggaggc tgcggctgca gaagtaccgc tgcggagtaa ctgcaaagat     60

gctgtccgtg cgcgttgctg cggccgtggt ccgcgccctt cctcggcggg ccggactggt    120

ctccagaaat gctttgggtt catctttcat tgctgcaagg aacttccatg cctctaacac    180

tcatcttcaa aagactggga ctgctgagat gtcctctatt cttgaagagc gtattcttgg    240

agctgatacc tctgttgatc ttgaagaaac tgggcgtgtc ttaagtattg gtgatggtat    300

tgcccgcgta catgggctga ggaatgttca agcagaagaa atggtagagt tttcttcagg    360

cttaaagggt atgtccttga acttggaacc tgacaatgtt ggtgttgtcg tgtttggaaa    420

tgataaacta attaaggaag gagatatagt gaagaggaca ggagccattg tggacgttcc    480

agttggtgag gagctgttgg gtcgtgtagt tgatgccctt ggtaatgcta ttgatggaaa    540

gggtccaatt ggttccaaga cgcgtaggcg agttggtctg aaagcccccg gtatcattcc    600

tcgaatttca gtgcgggaac caatgcagac tggcattaag gctgtggata gcttggtgcc    660
```

-continued

```
aattggtcgt ggtcagcgtg aactgattat tggtgaccga cagactggga aaacctcaat    720
tgctattgac acaatcatta accagaaacg tttcaatgat ggatctgatg aaaagaagaa    780
gctgtactgt atttatgttg ctattggtca aaagagatcc actgttgccc agttggtgaa    840
gagacttaca gatgcagatg ccatgaagta caccattgtg gtgtcggcta cggcctcgga    900
tgctgcccca cttcagtacc tggctcctta ctctggctgt tccatgggag agtattttag    960
agacaatggc aaacatgctt tgatcatcta tgacgactta tccaaacagg ctgttgctta   1020
ccgtcagatg tctctgttgc tccgccgacc ccctggtcgt gaggcctatc ctggtgatgt   1080
gttctaccta cactcccggt tgctggagag agcagccaaa atgaacgatg cttttggtgg   1140
tggctccttg actgctttgc cagtcataga aacacaggct ggtgatgtgt ctgcttacat   1200
tccaacaaat gtcatttcca tcactgacgg acagatcttc ttggaaacag aattgttcta   1260
caaaggtatc cgccctgcaa ttaacgttgg tctgtctgta tctcgtgtcg gatccgctgc   1320
ccaaaccagg gctatgaagc aggtagcagg taccatgaag ctggaattgg ctcagtatcg   1380
tgaggttgct gcttttgccc agttcggttc tgacctcgat gctgccactc aacaactttt   1440
gagtcgtggc gtgcgtctaa ctgagttgct gaagcaagga cagtattctc ccatggctat   1500
tgaagaacaa gtggctgtta tctatgcggg tgtaagggga tatcttgata aactggagcc   1560
cagcaagatt acaaagtttg agaatgcttt cttgtctcat gtcgtcagcc agcaccaagc   1620
cttgttgggc actatcaggg ctgatggaaa gatctcagaa caatcagatg caaagctgaa   1680
agagattgta acaaatttct tggctggatt tgaagcttaa actcctgtgg attcacatca   1740
aataccagtt cagttttgtc attgttctag taaattagtt ccatttgtaa aaggtttact   1800
ctcatactcc ttatgtacag aaatcacatg aaaaataaag gttccataat gcaaaaaaaa   1860
aaaaaaaaaa aaaaaaaaaa aaa                                           1883
```

<210> SEQ ID NO 133
<211> LENGTH: 3597
<212> TYPE: DNA
<213> ORGANISM: Rattus norvegicus

<400> SEQUENCE: 133

```
ggcgaatgga gcaggggcgc gcagataatt aaagatttac acacagctgg aagaaatcat     60
agagaagccg ggcgtggtgg ctcatgccta taatcccagc acttttggag gctgaggcgg    120
gcagatcact tgagatcagg agttcgagac cagcctggtg ccttggcatc tcccaatggg    180
gtggctttgc tctgggctcc tgttccctgt gagctgcctg gtcctgctgc aggtggcaag    240
ctctgggaac atgaaggtct tgcaggagcc cacctgcgtc tccgactaca tgagcatctc    300
tacttgcgag tggaagatga atggtcccac caattgcagc accgagctcc gcctgttgta    360
ccagctggtt tttctgctct ccgaagccca cacgtgtatc cctgagaaca acggaggcgc    420
ggggtgcgtg tgccacctgc tcatggatga cgtggtcagt gcggataact atacactgga    480
cctgtgggct gggcagcagc tgctgtggaa gggctccttc aagcccagcg agcatgtgaa    540
acccagggcc ccaggaaacc tgacagttca caccaatgtc tccgacactc tgctgctgac    600
ctggagcaac ccgtatcccc ctgacaatta cctgtataat catctcacct atgcagtcaa    660
catttggagt gaaaacgacc cggcagattt cagaatctat aacgtgacct acctagaacc    720
ctccctccgc atcgcagcca gcaccctgaa gtctgggatt tcctacaggg cacgggtgag    780
ggcctgggct cagtgctata acaccacctg gagtgagtgg agccccagca ccaagtggca    840
```

-continued

```
caactcctac agggagccct tcgagcagca cctcctgctg ggcgtcagcg tttcctgcat    900
tgtcatcctg gccgtctgcc tgttgtgcta tgtcagcatc accaagatta agaaagaatg    960
gtgggatcag attcccaacc cagcccgcag ccgcctcgtg gctataataa tccaggatgc   1020
tcaggggtca cagtgggaga agcggtcccg aggccaggaa ccagccaagt gcccacactg   1080
gaagaattgt cttaccaagc tcttgccctg ttttctggag cacaacatga aaagggatga   1140
agatcctcac aaggctgcca aagagatgcc tttccagggc tctggaaaat cagcatggtg   1200
cccagtggag atcagcaaga cagtcctctg gccagagagc atcagcgtgg tgcgatgtgt   1260
ggagttgttt gaggccccgg tggagtgtga ggaggaggag gaggtagagg aagaaaaagg   1320
gagcttctgt gcatcgcctg agagcagcag ggatgacttc caggagggaa gggagggcat   1380
tgtggcccgg ctaacagaga gcctgttcct ggacctgctc ggagaggaga atgggggctt   1440
ttgccagcag gacatggggg agtcatgcct tcttccacct tcgggaagta cgagtgctca   1500
catgccctgg gatgagttcc caagtgcagg gcccaaggag gcacctccct ggggcaagga   1560
gcagcctctc cacctggagc caagtcctcc tgccagcccg acccagagtc cagacaacct   1620
gacttgcaca gagacgcccc tcgtcatcgc aggcaaccct gcttaccgca gcttcagcaa   1680
ctccctgagc cagtcaccgt gtcccagaga gctgggtcca gacccactgc tggccagaca   1740
cctggaggaa gtagaacccg agatgccctg tgtcccccag ctctctgagc caaccactgt   1800
gccccaacct gagccagaaa cctgggagca gatcctccgc cgaaatgtcc tccagcatgg   1860
ggcagctgca gcccccgtct cggcccccac cagtggctat caggagtttg tacatgcggt   1920
ggagcagggt ggcacccagg ccagtgcggt ggtgggcttg ggtcccccag gagaggctgg   1980
ttacaaggcc ttctcaagcc tgcttgccag cagtgctgtg tccccagaga aatgtgggtt   2040
tggggctagc agtggggaag aggggtataa gcctttccaa gacctcattc ctggctgccc   2100
tggggaccct gccccagtcc ctgtcccctt gttcaccttt ggactggaca gggagccacc   2160
tcgcagtccg cagagctcac atctcccaag cagctcccca gagcacctgg gtctggagcc   2220
gggggaaaag gtagaggaca tgccaaagcc cccacttccc caggagcagg ccacagaccc   2280
ccttgtggac agcctgggca gtggcattgt ctactcagcc cttacctgcc acctgtgcgg   2340
ccacctgaaa cagtgtcatg gccaggagga tggtggccag acccctgtca tggccagtcc   2400
ttgctgtggc tgctgctgtg gagacaggtc ctcgcccccct acaacccccc tgagggcccc   2460
agacccctct ccaggtgggg ttccactgga ggccagtctg tgtccggcct ccctggcacc   2520
ctcgggcatc tcagagaaga gtaaatcctc atcatccttc catcctgccc ctggcaatgc   2580
tcagagctca agccagaccc ccaaaatcgt gaactttgtc tccgtgggac ccacatacat   2640
gagggtctct taggtgcatg tcctcttgtt gctgagtctg cagatgagga ctagggctta   2700
tccatgcctg ggaaatgcca cctcctggaa ggcagccagg ctggcagatt tccaaaagac   2760
ttgaagaacc atggtatgaa ggtgattggc cccactgacg ttggcctaac actgggctgc   2820
agagactgga ccccgcccag cattgggctg ggctcgccac atcccatgag agtagagggc   2880
actgggtcgc cgtgccccac ggcaggcccc tgcaggaaaa ctgaggccct tgggcacctc   2940
gacttgtgaa cgagttgttg gctgctccct ccacagcttc tgcagcagac tgtccctgtt   3000
gtaactgccc aaggcatgtt ttgcccacca gatcatggcc cacgtggagg cccacctgcc   3060
tctgtctcac tgaactagaa gccgagccta gaaactaaca cagccatcaa gggaatgact   3120
tgggcggcct tgggaaatcg atgagaaatt gaacttcagg gagggtggtc attgcctaga   3180
ggtgctcatt catttaacag agcttcctta ggttgatgct ggaggcagaa tcccggctgt   3240
```

-continued

```
caaggggtgt tcagttaagg ggagcaacag aggacatgaa aaattgctat gactaaagca   3300
gggacaattt gctgccaaac acccatgccc agctgtatgg ctgggggctc ctcgtatgca   3360
tggaaccccc agaataaata tgctcagcca ccctgtgggc cgggcaatcc agacagcagg   3420
cataaggcac cagttaccct gcatgttggc ccagacctca ggtgctaggg aaggcgggaa   3480
ccttgggttg agtaatgctc gtctgtgtgt tttagtttca tcacctgtta tctgtgtttg   3540
ctgaggagag tggaacagaa ggggtggagt tttgtataaa taaagtttct ttgtctc      3597
```

<210> SEQ ID NO 134
<211> LENGTH: 1569
<212> TYPE: DNA
<213> ORGANISM: Rattus norvegicus

<400> SEQUENCE: 134

```
gtttgacgat gagagtgatg gggaagaaga ggaggagctc atggatgagg atgtggaaga     60
agaggatgac tcagagatct cagggtacag cgtggagaat gccttcttcg atgagaagga    120
agacacctgt gctgccgtgg gggagatctc tgtgaacacc agtgtggcct tccttccata    180
catggaaagt gtctttgaag aagtatttaa actgctggag tgccctcacc tgaatgtgcg    240
gaaggcagcc catgaggctc tgggtcagtt ttgctgtgca ctgcacaagg cctgtcaaag    300
ctgcccctcg gaacccaaca ctgctgcttt gcaggctgcc ctggcccgag tcgtgccatc    360
ctacatgcag gcagtgaaca gggagcggga acgccaggtg gtgatggccg tgctggaggc    420
cctgacaggg gtgctccgca gctgtgggac cctcacactg aagcccccctg ggcgcctcgc    480
tgagctctgt ggcgtgctca aggctgtgct gcagaggaag acagcctgtc aggatactga    540
cgaggaggag gaagaggaag atgatgatca ggctgaatac gacgccatgt tgctggagca    600
cgctggagag gccatccctg ccctggcagc cgcggctggg ggagactcct ttgccccatt    660
ctttgccggt ttcctgccat tattggtgtg caagacaaaa cagggctgca cagtggcaga    720
gaagtccttt gcagtgggga ccttggcaga gactattcag ggcctgggtg ctgcctcagc    780
ccagtttgtg tctcggctgc tccctgtgct gttgagcacc gcccaagagg cagaccccga    840
ggtgcgaagc aatgccatct tcgggatggg cgtgctggca gagcatgggg gccaccctgc    900
ccaggaacac ttccccaagc tgctggagct ccttttttccc ctcctggcgc gggagcgaca    960
tgatcgtgtc cgtgacaaca tctgtggggc acttgcccgc ctgttgatgg ccagtcccac   1020
caggaaacca gagccccagg tgctggctgc cctactgcat gccctgccac tgaaggagga   1080
cttggaggag tgggtcacca ttgggcgcct cttcagcttc ctgtaccaga gcagccctga   1140
ccaggttata gatgtggctc ccgagcttct gcgtatctgc agcctcattc tggctgacaa   1200
caagatccca ccagacacca aggccgcact gttgctgctc ctgacgttcc tggccaaaca   1260
gcacaccgac agctttcaag cagctctggg ctcactgcct gttgacaagg ctcaggagct   1320
ccaggctgta ctgggcctct cctagactgc aggctgcagc cagtccagag agaatagagc   1380
ctgcccaggc cttaagacca cctctcagcc cagttcagtt ctgccttacc aaagattctg   1440
agactcatac ccatttggag ccagccccac ttgctgcctt acagggctgt ccctgaggct   1500
ggatctgtta caaatgagtc atgacatcat actgtaataa aagcagcttg ttttctgctt   1560
gaacaatag                                                           1569
```

<210> SEQ ID NO 135
<211> LENGTH: 3129
<212> TYPE: DNA

<213> ORGANISM: Rattus norvegicus

<400> SEQUENCE: 135
cccgcactaa agacgcttct tcccggcggg taggaatccc gccggcgagc cgaacagttc 60
cccgagcgca gcccgcggac caccacccgg ccgcacgggc cgcttttgtc ccccgcccgc 120
cgcttctgtc cgagaggccg cccgcgaggc gcatcctgac cgcgagcgtc gggtcccaga 180
gccgggcgcg gctggggccc gaggctagca tctctcggga gccgcaaggc gagagctgca 240
aagtttaatt agacacttca gaattttgat cacctaatgt tgatttcaga tgtaaaagtc 300
aagagaagac tctaaaaata gcaaagatgc ttttgagcca gaatgccttc atcttcagat 360
cacttaattt ggttctcatg gtgtatatca gcctcgtgtt tggtatttca tatgattcgc 420
ctgattacac agatgaatct tgcactttca agatatcatt gcgaaatttc cggtccatct 480
tatcatggga attaaaaaac cactccattg taccaactca ctatacattg ctgtatacaa 540
tcatgagtaa accagaagat ttgaaggtgg ttaagaactg tgcaaatacc acaagatcat 600
tttgtgacct cacagatgag tggagaagca cacacgaggc ctatgtcacc gtcctagaag 660
gattcagcgg gaacacaacg ttgttcagtt gctcacacaa tttctggctg gccatagaca 720
tgtcttttga accaccagag tttgagattg ttggttttac caaccacatt aatgtgatgg 780
tgaaatttcc atctattgtt gaggaagaat tacagtttga tttatctctc gtcattgaag 840
aacagtcaga gggaattgtt aagaagcata aacccgaaat aaaaggaaac atgagtggaa 900
atttcaccta tatcattgac aagttaattc caaacacgaa ctactgtgta tctgtttatt 960
tagagcacag tgatgagcaa gcagtaataa agtctccctt aaaatgcacc ctccttccac 1020
ctggccagga atcagaatca gcagaatctg ccaaaatagg aggaataatt actgtgtttt 1080
tgatagcatt ggtcttgaca agcaccatag tgacactgaa atggattggt tatatatgct 1140
taagaaatag cctccccaaa gtcttgaggc aaggtctcgc taagggctgg aatgcagtgg 1200
ctattcacag gtgcagtcat aatgcactac agtctgaaac tcctgagctc aaacagtcgt 1260
cctgcctaag cttccccagt agctgggatt acaagcgtgc atccctgtgc cccagtgatt 1320
aagttttatt atgtagaaaa taaagagcaa acagtacagc tgatatggac tctctctctc 1380
ttttttttt tttttaagaa ttttcataac tttttagcct ggccatttcc taacctgcca 1440
ccgttggaag ccatggatat ggtggaggtc atttacatca acagaaagaa gaaagtgtgg 1500
gattataatt atgatgatga aagtgatagc gatactgagg cagcgcccag gacaagtggc 1560
ggtggctata ccatgcatgg actgactgtc aggcctctgg gtcaggcctc tgccacctct 1620
acagaatccc agttgataga cccggagtcc gaggaggagc ctgacctgcc tgaggttgat 1680
gtggagctcc ccacgatgcc aaaggacagc cctcagcagt tggaactctt gagtgggccc 1740
tgtgagagga gaaagagtcc actccaggac ccttttcccg aagaggacta cagctccacg 1800
gaggggtctg gggcagaat taccttcaat gtggacttaa actctgtgtt tttgagagtt 1860
cttgatgacg aggacagtga cgacttagaa gcccctctga tgctatcgtc tcatctggaa 1920
gagatggttg acccagagga tcctgataat gtgcaatcaa accatttgct ggccagcggg 1980
gaagggacac agccaacctt tcccagcccc tcttcagagg gcctgtggtc cgaagatgct 2040
ccatctgatc aaagtgacac ttctgagtca gatgttgacc ttggggatgg ttatataatg 2100
agatgactcc aaaactattg aatgaacttg gacagacaag cacctacagg gttctttgtc 2160
tctgcatcct aacttgctgc cttatcgtct gcaagtgttc tccaagggaa ggaggaggaa 2220
actgtggtgt tcctttcttc caggtgacat cacctatgca cattcccagt atggggacca 2280

```
tagtatcatt cagtgcattg tttacatatt caaagtggtg cactttgaag gaagcacatg   2340

tgcacctttc ctttacacta atgcacttag gatgtttctg catcatgtct accagggagc   2400

agggttcccc acagtttcag aggtggtcca ggaccctatg atatttctct tctttcgttc   2460

tttttttttt ttttttgaga cagagtctcg ttctgtcgcc caagctggag cgcaatggtg   2520

tgatcttggc tcactgcaac atccgcctcc cgggttcagg tgattctcct gcctcagcct   2580

ccctcgcaag tagctgggat tacaggcgcc tgccaccatg cctagcaaat ttttgtattt   2640

ttagtggaga caggatttta ccatgttggc caggctggtc tcgaactcct gacctcaagt   2700

gatctgccct cctcagcctc gtaaagtgct gggattacag gggtgagccg ctgtgcctgg   2760

ctggccctgt gatatttctg tgaaataaat tgggccaggg tgggagcagg gaaagaaaag   2820

gaaaatagta gcaagagctg caaagcaggc aggaagggag gaggagagcc aggtgagcag   2880

tggagagaag gggggccctg cacaaggaaa cagggaagag ccatcgaagt ttcagtcggt   2940

gagccttggg cacctcaccc atgtcacatc ctgtctcctg caattggaat tccaccttgt   3000

ccagccctcc ccagttaaag tggggaagac agactttagg atcacgtgtg tgactaatac   3060

agaaaggaaa catggcgtcg gggagaggga taaaacctga atgccatatt ttaagttaaa   3120

aaaaaaaaa                                                           3129
```

<210> SEQ ID NO 136
<211> LENGTH: 2643
<212> TYPE: DNA
<213> ORGANISM: Rattus norvegicus

<400> SEQUENCE: 136

```
gccccggcgc cgccgccgcc cagaccggac gacaggccac ctcgtcggcg tccgcccgag     60

tccccgcctc gccgccaacg ccacaaccac cgcgcacggc cccctgactc cgtccagtat    120

tgatcgggag agccggagcg agctcttcgg ggagcagcga tgcgaccctc cgggacggcc    180

ggggcagcgc tcctggcgct gctggctgcg ctctgcccgg cgagtcgggc tctggaggaa    240

aagaaagttt gccaaggcac gagtaacaag ctcacgcagt tgggcacttt tgaagatcat    300

tttctcagcc tccagaggat gttcaataac tgtgaggtgg tccttgggaa tttggaaatt    360

acctatgtgc agaggaatta tgatctttcc ttcttaaaga ccatccagga ggtggctggt    420

tatgtcctca ttgccctcaa cacagtggag cgaattcctt tggaaaacct gcagatcatc    480

agaggaaata tgtactacga aaattcctat gccttagcag tcttatctaa ctatgatgca    540

aataaaaccg gactgaagga gctgcccatg agaaatttac aggaaatcct gcatggcgcc    600

gtgcggttca gcaacaaccc tgccctgtgc aacgtggaga gcatccagtg gcgggacata    660

gtcagcagtg actttctcag caacatgtcg atggacttcc agaaccacct gggcagctgc    720

caaaagtgtg atccaagctg tcccaatggg agctgctggg gtgcaggaga ggagaactgc    780

cagaaactga ccaaaatcat ctgtgcccag cagtgctccg ggcgctgccg tggcaagtcc    840

cccagtgact gctgccacaa ccagtgtgct gcaggctgca caggcccccg ggagagcgac    900

tgcctggtct gccgcaaatt ccgagacgaa gccacgtgca aggacacctg ccccccactc    960

atgctctaca accccaccac gtaccagatg gatgtgaacc ccgagggcaa atacagcttt   1020

ggtgccacct gcgtgaagaa gtgtccccgt aattatgtgg tgacagatca cggctcgtgc   1080

gtccgagcct gtggggccga cagctatgag atggaggaag acggcgtccg caagtgtaag   1140

aagtgcgaag ggccttgccg caaagtgtgt aacggaatag gtattggtga atttaaagac   1200
```

-continued

```
tcactctcca taaatgctac gaatattaaa cacttcaaaa actgcacctc catcagtggc   1260
gatctccaca tcctgccggt ggcatttagg ggtgactcct tcacacatac tcctcctctg   1320
gatccacagg aactggatat tctgaaaacc gtaaaggaaa tcacagggtt tttgctgatt   1380
caggcttggc ctgaaaacag gacggacctc catgcctttg agaacctaga aatcatacgc   1440
ggcaggacca agcaacatgg tcagttttct cttgcagtcg tcagcctgaa cataacatcc   1500
ttgggattac gctccctcaa ggagataagt gatggagatg tgataatttc aggaaacaaa   1560
aatttgtgct atgcaaatac aataaactgg aaaaaactgt ttgggacctc cggtcagaaa   1620
accaaaatta taagcaacag aggtgaaaac agctgcaagg ccacaggcca ggtctgccat   1680
gccttgtgct cccccgaggg ctgctggggc ccggagccca gggactgcgt ctcttgccgg   1740
aatgtcagcc gaggcaggga atgcgtggac aagtgcaacc ttctggaggg tgagccaagg   1800
gagtttgtgg agaactctga gtgcatacag tgccacccag agtgcctgcc tcaggccatg   1860
aacatcacct gcacaggacg gggaccagac aactgtatcc agtgtgccca ctacattgac   1920
ggcccccact gcgtcaagac ctgcccggca ggagtcatgg gagaaaacaa caccctggtc   1980
tggaagtacg cagacgccgg ccatgtgtgc cacctgtgcc atccaaactg cacctacgga   2040
tgcactgggc caggtcttga aggctgtcca acgaatggaa gctacatagt gtctcacttt   2100
ccaagatcat tctacaagat gtcagtgcac tgaaacatgc aggggcgtgt tgagtgtgga   2160
aggatcttga caagttgttt tgaagatagc attttgctaa gtccctgagg tcactggtcc   2220
tcaaagcggc atggcgcatg gcgtggctgg ttctgccaca tgccagctgt gtgacctctg   2280
agactccact tcttccgtgc tgaaaataaa gaaggagttt tactaaggac caaacaagat   2340
aatgaatgtg aaactgctcc atgaacccca aagaattatg cacatagatg cgatcattaa   2400
gatgcgaagc catcgagtta ccacctggca tgcttaaact gtaaagagtg ggtcaaagta   2460
aactgaattg gaaaatccaa agttatgcag aaaaacaata aaggagatag taaaaagggt   2520
taacgagcca gtccagggga agcgaagaag acaaaaagag tccttttctg ggccaagttt   2580
gataaattag gcctcccgac cctttgctct gttgctttat caactctact cggcaataac   2640
aat                                                                 2643
```

<210> SEQ ID NO 137
<211> LENGTH: 1514
<212> TYPE: DNA
<213> ORGANISM: Rattus norvegicus

<400> SEQUENCE: 137

```
gcccctccct ccgcccgccc gccggcccgc ccgtcagtct ggcaggcagg caggcaatcg     60
gtccgagtgg ctgtcggctc ttcagctctc ccgctcggcg tcttccttcc tcctcccggt    120
cagcgtcggc ggctgcaccg gcggcggcgc agtccctgcg ggaggggcga caagagctga    180
gcggcggccg ccgagcgtcg agctcagcgc ggcggaggcg gcggcggccc ggcagccaac    240
atggcggcgg cggcggcggc gggcgcgggc ccggagatgg tccgcgggca ggtgttcgac    300
gtggggccgc gctacaccaa cctctcgtac atcggcgagg gcgcctacgg catggtgtgc    360
tctgcttatg ataatgtcaa caaagttcga gtagctatca agaaaatcag cccctttgag    420
caccagacct actgccagag aaccctgagg gagataaaaa tcttactgcg cttcagacat    480
gagaacatca ttggaatcaa tgacattatt cgagcaccaa ccatcgagca aatgaaagat    540
gtatatatag tacaggacct catggaaaca gatctttaca agctcttgaa gacacaacac    600
ctcagcaatg accatatctg ctattttctc taccagatcc tcagagggtt aaaatatatc    660
```

-continued

```
cattcagcta acgttctgca ccgtgacctc aagccttcca acctgctgct caacaccacc    720
tgtgatctca agatctgtga ctttggcctg gcccgtgttg cagatccaga ccatgatcac    780
acagggttcc tgacagaata tgtggccaca cgttggtaca gggctccaga aattatgttg    840
aattccaagg gctacaccaa gtccattgat atttggtctg taggctgcat tctggcagaa    900
atgctttcta acaggcccat ctttccaggg aagcattatc ttgaccagct gaaccacatt    960
ttgggtattc ttggatcccc atcacaagaa gacctgaatt gtataataaa tttaaaagct   1020
aggaactatt tgctttctct tccacacaaa aataaggtgc catggaacag gctgttccca   1080
aatgctgact ccaaagctct ggacttattg gacaaaatgt tgacattcaa cccacacaag   1140
aggattgaag tagaacaggc tctggcccac ccatatctgg agcagtatta cgacccgagt   1200
gacgagccca tcgccgaagc accattcaag ttcgacatgg aattggatga cttgcctaag   1260
gaaaagctca aagaactaat ttttgaagag actgctagat tccagccagg atacagatct   1320
taaatttgtc aggtacctgg agtttaatac agtgagctct agcaagggag gcgctgcctt   1380
ttgtttctag aatattatgt tcctcaaggt ccattatttt gtattctttt ccaagctcct   1440
tattggaagg tattttttta aatttagaat taaaaattat ttagaaaaaa aaaaaaaaaa   1500
aaaaaaaaaa aaaa                                                     1514
```

<210> SEQ ID NO 138
<211> LENGTH: 2890
<212> TYPE: DNA
<213> ORGANISM: Rattus norvegicus

<400> SEQUENCE: 138

```
ggcacgaggg tggcctctgc ggctaggccg gctcgagact cccgggcgcc gaggcgctgc     60
cgcccgcctc gccgccccac gccgaaggac cacgcgcccg ccgccgccag cctctcagcg    120
ctcccatgat cgcccggtgc cttttggctg tgcgaagcct ccgcagagtt ggtggttcca    180
ggattttact cagaatgacg ttaggaagag aagtgatgtc tcctcttcag gcaatgtctt    240
cctatactgt ggctggcaga aatgttttaa gatgggatct ttcaccagag caaattaaaa    300
caagaactga ggagctcatt gtgcagacca aacaggtgta cgatgctgtt ggaatgctcg    360
gtattgagga agtaacttac gagaactgtc tgcaggcact ggcagatgta gaagtaaagt    420
atatagtgga aaggaccatg ctagactttc cccagcatgt atcctctgac aaagaagtac    480
gagcagcaag tacagaagca gacaaaagac tttctcgttt tgatattgag atgagcatga    540
gaggagatat atttgagaga attgttcatt tacaggaaac ctgtgatctg gggaagataa    600
aacctgaggc cagacgatac ttggaaaagt caattaaaat ggggaaaaga aatgggctcc    660
atcttcctga acaagtacag aatgaaatca aatcaatgaa gaaaagaatg agtgagctat    720
gtattgattt taacaaaaac ctcaatgagg atgatacctt ccttgtattt tccaaggctg    780
aacttggtgc tcttcctgat gatttcattg acagtttaga aaagacagat gatgacaagt    840
ataaaattac cttaaaatat ccacactatt tccctgtcat gaagaaatgt tgtatccctg    900
aaaccagaag aaggatggaa atggctttta atacaaggtg caaagaggaa aacaccataa    960
ttttgcagca gctactccca ctgcgaacca aggtggccaa actactcggt tatagcacac   1020
atgctgactt cgtccttgaa atgaacactg caaagagcac aagccgcgta acagcctttc   1080
tagatgattt aagccagaag ttaaaaccct tgggtgaagc agaacgagag tttattttga   1140
atttgaagaa aaaggaatgc aaagacaggg gttttgaata tgatgggaaa atcaatgcct   1200
```

-continued

```
gggatctata ttactacatg actcagacag aggaactcaa gtattccata gaccaagagt   1260
tcctcaagga atacttccca attgaggtgg tcactgaagg cttgctgaac acctaccagg   1320
agttgttggg actttcattt gaacaaatga cagatgctca tgtttggaac aagagtgtta   1380
cactttatac tgtgaaggat aaagctacag gagaagtatt gggacagttc tatttggacc   1440
tctatccaag ggaaggaaaa tacaatcatg cggcctgctt cggtctccag cctggctgcc   1500
ttctgcctga tggaagccgg atgatggcag tggctgccct cgtggtgaac ttctcacagc   1560
cagtggcagg tcgtccctct ctcctgagac acgacgaggt gaggacttac tttcatgagt   1620
ttggtcacgt gatgcatcag atttgtgcac agactgattt tgcacgattt agcggaacaa   1680
atgtggaaac tgactttgta gaggtgccat cgcaaatgct tgaaaattgg gtgtgggacg   1740
tcgattccct ccgaagattg tcaaaacatt ataaagatgg aagccctatt gcagacgatc   1800
tgcttgaaaa acttgttgct tctaggctgg tcaacacagg tcttctgacc ctgcgccaga   1860
ttgttttgag caaagttgat cagtctcttc ataccaacac atcgctggat gctgcaagtg   1920
aatatgccaa atactgctca gaaatattag gagttgcagc tactccaggc acaaatatgc   1980
cagctacctt tggacatttg gcaggggggat acgatggcca atattatgga tatctttgga   2040
gtgaagtatt ttccatggat atgttttaca gctgttttaa aaaagaaggg ataatgaatc   2100
cagaggttgg aatgaaatac agaaacctaa tcctgaaacc tgggggatct ctggacggca   2160
tggacatgct ccacaatttc ttgaaacgtg agccaaacca aaaagcgttc ctaatgagta   2220
gaggcctgca tgctccgtga actggggatc tttggtagcc gtccatgtct ggaggacaag   2280
tcgacatcac catgtgttac tggcctggaa actgaaggga gttttgcaag tgaaaattta   2340
gatttctatt gacatccttt tgttttctaa ttttaaaaat tataaagatg taaatggaat   2400
tataaatact gtgacctaag aaaagaccca ctagaaagta attgtactat aaaatttcat   2460
aaaactggat ttgatttctt tttatgaaag tttcatatga atgtaacttg attttttact   2520
attataatct agataatatg atataagagg gctaagaatt tttaaattga atcatatata   2580
tgatataatt tgatccttct tgtatcttga agttttgtac ttgggatttc tggactgata   2640
aatgaatcat cacattcttc tggtaaatat tttcttggag ctctgtgtca actttgatcc   2700
tttgtctccc aggaaggtgt gacctctcct ttgcctgcat acctcaaggc caggggaata   2760
tgcctcagtg atgcatttat ctttgtatat caggccgcat gattcccaac tttctgccac   2820
acttaaatta cgttcctcca tttcagtttt gtcttttctg tctaaagttc agtcaaagag   2880
tatcaaaaaa                                                          2890
```

<210> SEQ ID NO 139
<211> LENGTH: 1350
<212> TYPE: DNA
<213> ORGANISM: Rattus norvegicus

<400> SEQUENCE: 139

```
gcggccgcgt cgacgtgaca gccggtacgc ccgggtttgg gcaacctcga ttacgggcgg     60
cctccaggcc cgccagcagc gccccgcgcc gcccgcccgc gcccctgccg ccccccggtt    120
ccggccgcgg accccactct ctgccgttcc ggctgcggct ccgctgccgg tagcgccgtc    180
ccccgggacc acccttcggc tggcgccctc ccatgctctc ggccacccgg agggcttgcc    240
agctcctcct cctccacagc ctctttcccg tcccgaggat gggcaactcg gcctcgaaca    300
tcgtcagccc ccaggaggcc ttgccgggcc ggaaggaaca gacccctgta gcggccaaac    360
atcatgtcaa tggcaacaga acagtcgaac ctttcccaga gggaacacag atggctgtat    420
```

-continued

```
ttggaatggg atgtttctgg ggagctgaaa ggaaattctg ggtcttgaaa ggagtgtatt    480
caactcaagt tggttttgca ggaggctata cttcaaatcc tacttataaa gaagtctgct    540
cagaaaaaac tggccatgca gaagtcgtcc gagtggtgta ccagccagaa cacatgagtt    600
ttgaggaact gctcaaggtc ttctgggaga atcacgaccc gacccaaggt atgcgccagg    660
ggaacgacca tggcactcag taccgctcgg ccatctaccc gacctctgcc aagcaaatgg    720
aggcagccct gagctccaaa gagaactacc aaaaggttct ttcagagcac ggcttcggcc    780
ccatcactac cgacatccgg gagggacaga ctttctacta tgcggaagac taccaccagc    840
agtacctgag caagaacccc aatggctact gcggccttgg gggcaccggc gtgtcctgcc    900
cagtgggtat taaaaaataa ttgctcccca catggtgggc ctttgaggtt ccagtaaaaa    960
tgctttcaac aaattgggca atgcttgtgt gattcacaat cgtggcattt aaagtgcaca   1020
aagtacaaag gaatttatac agattgggtt taccgaagta taatctatag gaggcgcgat   1080
ggcaagttga taaaatgtga cttatctcct aataagttat ggtgggagtg gagctgtgcg   1140
gtttcctgtg tcttctgggg tctgagtgaa gatagcaggg atgctgtgtt caccctcctt   1200
ggtagaagct aaggtgtgag ctgggaggtt gctggacagg atgggggacc ccagaagtcc   1260
tttatctgtg ctctctgccc gccagtgcct tacaatttgc aaacgtgtat agcctcagtg   1320
actcattcgc tgaaatcctt cgctttacca                                    1350
```

<210> SEQ ID NO 140
<211> LENGTH: 1825
<212> TYPE: DNA
<213> ORGANISM: Rattus norvegicus

<400> SEQUENCE: 140

```
gcaggctcag cgcatcccag ccagtgtctc ctgcagctca gcagctgcct tcaccatgga     60
cagcataagc acagccatct tactcctgct cctggctctc gtctgtctgc tcctgaccct    120
aagctcaaga gataagggaa agctgcctcc gggacccaga cccctctcaa tcctgggaaa    180
cctgctgctg ctttgctccc aagacatgct gacttctctc actaagctga gcaaggagta    240
tggctccatg tacacagtgc acctgggacc caggcgggtg gtggtcctca gcgggtacca    300
agctgtgaag gaggccctgg tggaccaggg agaggagttt agtggccgcg gtgactaccc    360
tgcctttttc aactttacca agggcaatgg catcgccttc tccagtgggg atcgatggaa    420
ggtcctgaga cagttctcta tccagattct acggaatttc gggatgggga agagaagcat    480
tgaggagcga atcctagagg agggcagctt cctgctggcg gacgtgcgga aaactgaagg    540
cgagcccttt gaccccacgt ttgtgctgag tcgctcagtg tccaacatta tctgttccgt    600
gctcttcggc agccgcttcg actatgatga tgagcgtctg ctcaccatta tccgccttat    660
caatgacaac ttccaaatca tgagcagccc ctggggcgag ttgtacgaca tcctagaccc    720
cagattcccg agcctcctgg actgggtgcc tgggccgcac caacgcatct tccagaactt    780
caagtgcctg agagacctca tcgcccacag cgtccacgac caccaggcct cgtctccccg    840
ggacttcatc cagtgcttcc tcaccaagat ggcagaggag aaggaggacc cactgagcca    900
cttccacatg gataccctgc tgatgaccac acataacctg ctctttggcg gcaccaagac    960
ggtgagcacc acgctgcacc acgccttcct ggcactcatg aagtacccaa aagttcaagc   1020
ccgcgtgcag gaggagatcg acctcgtggt gggacgcgcg cggctgccgg cgctgaagga   1080
ccgcgcggcc atgccttaca cagacgcggt gatccacgag gtgcagcgct ttgcagacat   1140
```

-continued

```
catccccatg aacttgccgc accgcgtcac tagggacacg gcctttcgcg gcttcctgat   1200

acccaagggc accgatgtca tcaccctcct taacaccgtc cactacgacc ccagccagtt   1260

cctgacgccc caggagttca accccgagca ttttttggat gccaatcagt ccttcaagaa   1320

gagtccagcc ttcatgccct tctcagctgg gcgccgtctg tgcctgggag agctgctggc   1380

gcgcatggag ctctttctgt acctcaccgc catcctgcag agcttttcgc tgcagccgct   1440

gggtgcgccc gaggacatcg acctgacccc actcagctca ggtcttggca atttgccgcg   1500

gcctttccag ctgtgcctgc gcccgcgcta acgccccggc ccttccagat tcgcctgtga   1560

gcgatgaggc ccacccatgt gggttgctac gtccccttct tggtccacag tctgccctca   1620

tccctctggc agtcacgctg tcttccctgc atgctgtgcc tgccgcgtgc ccttccccca   1680

tccctccaat ctgtgccccg tctgcagggc agaggcagat gtggcatgtc tttttgtacc   1740

cacagagctt gttctatggc acgccctttt ctaggctttt tgtatcattt cttagtacat   1800

tgtaatagat tcaaaccagt cttgg                                         1825


<210> SEQ ID NO 141
<211> LENGTH: 1734
<212> TYPE: DNA
<213> ORGANISM: Rattus norvegicus

<400> SEQUENCE: 141

agttgctgtg gaggccctgg cacggctgca gcagggtgtg agcgccaccg ttgcccacct     60

tctggacctg gcaggcagcg ccggtgcgac tgggagctgg cgtagcccct ctgagccaca    120

ggagccgctg gtgcaggacc tgcaggctgc tgtggccgcc gtccagagtg ccgtccacga    180

gctgttggag tttgcccgca gcgcggtggg caatgctgcc cacacatctg accgtgccct    240

gcatgccaag cttagccggc agctgcagaa gatggaggac gtgcaccaga cgctggtggc    300

acatggtcag gccctcgacg ctggccgggg aggctctgga gccacccttg aggacctgga    360

ccggctggtg gcctgctcgc gggctgtgcc cgaggacgcc aagcagctgg cctccttcct    420

gcacggcaat gcctcactgc tcttcagacg gaccaaggcc actgccccgg ggcctgaggg    480

gggtggcacc ctgcacccca accccactga caagaccagc agcatccagt cacgacccct    540

gccctcaccc cctaagttca cctcccagga ctcgccagat gggcagtacg agaacagcga    600

ggggggctgg atggaggact atgactacgt ccacctacag gggaaggagg agtttgagaa    660

gacccagaag gagctgctgg aaaagggcag catcacgcgg cagggcaaga gccagctgga    720

gttgcagcag ctgaagcagt ttgaacgact ggaacaggag gtgtcacggc ccatagacca    780

cgacctggcc aactggacgc cagcccaacc cctggccccg gggcgaacag gcggcctggg    840

gccctcggac cggcagctgc tgctcttcta cctggagcag tgtgaggcca acctgaccac    900

actgaccaac gccgtggacg ccttctttac cgccgtggcc accaaccagc cgcccaagat    960

ctttgtggcg cacagcaagt tcgtcatcct cagcgcccac aagctggtgt tcatcgggga   1020

cacactgtca cggcaggcca aggctgctga cgtgcgcagc caggtgaccc actacagcaa   1080

cctgctgtgc gacctcctgc gcggcatcgt ggccaccacc aaggccgctg ccttgcagta   1140

cccatcgcct tccgcggccc aggacatggt ggagagggtc aaggagctgg gccacagcac   1200

ccagcagttc cgccgcgtcc taggccagct ggcagccgcc tgagggtggt gaccccagga   1260

gggaggcagg ggaggggtgc ggcggtccca gctccctggc tcccatgtca agagtcgctg   1320

tgccacaggc ttagggacag gaccccagct ctgcgtcggt cctggtgccc tggatgccca   1380

ggaatctgta tatatttatg gccgggcagg gtgtggggcc atgcctcctc aggagccgaa   1440
```

-continued gcccaggggc cggccagtgg ccttccccag catgcaccac gggcccgggt tgggtcacca 1500
gacggggctg gagtgtgagg gtcctgcagc ctgcaggacc tcgtgccacc ccgagggctg 1560
agcctggtcc cacgagggtg ccgtgtcccc tgacagggcc agtgcagttt ggtgtgtcct 1620
ccgcctttcc aggagaagaa cctgaagaac tatttttcgt tattggtttt ccaatcattt 1680
gactaagagt ctccatttaa ataaagtttt taaaaggaaa aaaaaaaaaa aaaa 1734

<210> SEQ ID NO 142
<211> LENGTH: 471
<212> TYPE: DNA
<213> ORGANISM: Rattus norvegicus

<400> SEQUENCE: 142
tttttttttt tttttttgcc ggtcggagac tcccgtctgc caaggttttt attgtggtcc 60
cgcggggcag gaggtatgca tggcatacgt aagcagagag ccggaggcag ccatcggcac 120
ctagaacggt gcagagttgg cccaggagcg tggcggggca ggcggcctgc acctgccctg 180
ctcgcccagc agaccctccg ggctccagcc tggcggggcc cagcgtccac cttggtgggc 240
ccaggtcaga tcttggccag ggtggagtgg gcgtcggcct gctcctcttg gatgggggtc 300
cggaaactgc ctcccccagg gggcttgtgg gcatcggggg gcagcctctg gtccctccgg 360
agcaggtaca gggccagcag gatgggcagg gggcccagca gccccagcac caggcccagg 420
cccaggatgg ggggaaccgc acgggccccg gggacctcca cgggccgggt g 471

<210> SEQ ID NO 143
<211> LENGTH: 6217
<212> TYPE: DNA
<213> ORGANISM: Rattus norvegicus

<400> SEQUENCE: 143
cgctcccgcc ccagctcgcg ctgcccgggc gggcgccggc cgctggcgcc gctactgctg 60
ccgcccccgg ggcgcgagtc cgccgcccgc cgcccgggca cccggcgagg ggcgggggca 120
gctccgaacc ggccccagat ccttcccgct tccgcctcac gcttcccgga aagcttgtcc 180
ctctccgccg agctgctccg ggagccccgc cgcgccgagg gtatctccca gagccccagc 240
tggtgtggcc aggccccagg agtaggatgg ggctccccct acgagggccg gtggcagcca 300
gaactgatac agcccccctg gtctggggcc aggacgccag ctgaggaggg caggagtgtc 360
tggagctatg gctggtgcct cggtgaaagt ggcagtgagg gttcggccct ttaacgcccg 420
tgagaccagc caggatgcca agtgtgtggt cagcatgcag ggcaacacca cctccatcat 480
caatcctaaa cagagcaagg atgcccccaa aagcttcacc tttgactact cctactggtc 540
acacacttcg acggaggacc cccagtttgc atctcagcag caagtgtatc gggacattgg 600
agaagagatg ctgctccacg cctttgaagg ctacaacgtg tgcatctttg cctatgggca 660
gaccggggct gggaaatcct ataccatgat ggggcgacag gagccagggc agcagggcat 720
cgtgccccag ctctgtgagg acctcttctc tcgcgttagt gagaaccaga gtgctcagct 780
atcctactct gtggaggtga gctatatgga gatctactgt gagcgggtac gagacctctt 840
gaaccccaag agtcggggtt ctctgcgggt ccgggagcac cccatcctgg gcccgtacgt 900
gcaggacctg tccaaattgg ctgtgacctc ctacgcagac attgctgacc tcatggactg 960
tggaaataaa gcacggactg tggctgccac caacatgaat gagaccagca gccgttccca 1020
tgccgtcttt accatcgtct tcacacagcg ctgccatgac cagctcacgg ggctggactc 1080

-continued

```
ggagaaggtc agtaagatca gtttggtgga ccttgctggg agtgagcgag ccgactcctc   1140

aggggcccgg ggcatgcgcc tgaaggaagg agccaacatc aataagtccc tgactacact   1200

agggaaagtg atctcggccc ttgcagatat gcaatcaaag aagcgaaagt cggattttat   1260

cccctacagg gactctgtgc tcacctggct gctcaaggaa aatttggggg ggaactcacg   1320

cacagccatg attgcagccc tgagccctgc tgacatcaat tacgaggaga ctctcagcac   1380

cctcaggtat gctgaccgca ccaagcaaat ccgctgcaat gccatcatca acgaggaccc   1440

taatgcccgg ctgattagag agctgcagga ggaagtagcc cggctgcggg aactgctgat   1500

ggctcaggga ctgtcagcct ctgctctgga aggcctgaag acggaagaag ggagtgtcag   1560

aggcgccctg ccagctgtgt catctccccc agctccagtt tcaccctcat cacccaccac   1620

acataatggg gagctggagc cgtcattctc ccccaacacg gagtcccaga ttgggcctga   1680

ggaagccatg gagaggctgc aggagacaga gaagattata gctgagctga acgagacatg   1740

ggaggagaag ctacgcaaga cagaagccct gaggatggag agagaagcat tgctggctga   1800

gatgggggtg gccgtccggg aggatggggg aactgtgggc gtcttctctc caaagaagac   1860

tccccacctg gtgaacctga acgaagaccc tctgatgtct gagtgtctgc tctaccacat   1920

caaagatggc gtcaccaggg tcggccaagt agatatggac atcaagctga ccggacagtt   1980

cattcgggag caacactgtc tgttccggag catcccccag ccagatggag aagtggtggt   2040

cactctggag ccttgtgaag gagctgagac atatgtgaat gggaagcttg tgacggagcc   2100

gctggtgctg aagtcaggga ataggattgt gatgggcaag aaccacgttt tccgcttcaa   2160

ccacccggag caggcaaggc tggaacggga acgagggggtc cccccacccc caggaccgcc   2220

ctctgagcca gtcgactgga actttgccca gaaggaactg ctggagcagc aaggcatcga   2280

cataaagctg gaaatggaga agaggctgca ggatctggag aatcagtacc ggaaagaaaa   2340

ggaagaagcc gatcttctgc tggagcagca gcgactgtat gcagactcgg acagcgggga   2400

tgactctgac aagcgctctt gtgaagagag ctggaggctc atctcctcct tgcgggagca   2460

gctgccgccc accacggtcc agaccattgt caaacgctgt ggtctgccca gcagtggcaa   2520

gcgcagggcc cctcgcaggg tttatcagat cccccagcga cgcaggctgc agggcaaaga   2580

cccccgctgg gccaccatgg ctgacctgaa gatgcaggcg gtgaaggaga tctgctacga   2640

ggtggccctg gctgacttcc gccacgggcg ggctgagatt gaggccctgg ccgccctcaa   2700

gatgcgggag ctgtgtcgca cctatggcaa gccagacggc cccggagacg cctggagggc   2760

tgtggcccgg gatgtctggg acactgtagg cgaggaggaa ggaggtggag ctggcagtgg   2820

tggtggcagt gaggagggag cccgaggggc ggaggtggag gacctccggg cccacatcga   2880

caagctgacg ggcattctgc aggaggtgaa gctgcagaac agcagcaagg accgggagct   2940

gcaggccctg cgggaccgca tgctccgcat ggagagggtc atccccctgg cccaggatca   3000

tgaggatgag aatgaagaag gtggtgaggt cccctgggcc ccgcctgaag gatcagaggc   3060

agcagaggag gcagccccca gtgaccgcat gccgtcagcc cggcccccct cgccgccact   3120

gtcaagctgg gagcgggtgt cacggctcat ggaggaggac cctgccttcc gtcgtggtcg   3180

tcttcgctgg ctcaagcagg agcagctacg gctgcaggga ctgcagggct ctgggggccg   3240

gggcgggggg ctgcgcaggc ccccagcccg ctttgtgccc cctcacgact gcaagctacg   3300

cttcccctc aagagcaacc cccagcaccg ggagtcttgg ccagggatgg ggagcgggga   3360

ggctccaact ccgctccaac cccctgagga ggtcactccc catccagcca cccctgcccg   3420

ccggcctccg agtccccgaa ggtcccacca tccccgcagg aactccctgg atggaggggg   3480
```

-continued

```
ccgatcccgg ggagcgggtt ctgcacagcc tgaaccccag cacttccagc ccaaaaagca   3540
caactcttat ccccagccac cccaacccta cccagcccag cggcccccag ggccccgcta   3600
ccccccatac actactcccc cacgaatgag acggcagcgt tctgcccctg acctcaagga   3660
gagtggggca gctgtgtgag tcccacatcc tgggcagagg gcctggtggg gccccttgct   3720
aggagaaggg aagacgcccg agacgctgct tccccagaag tgctggggca gggaggccca   3780
ggagatgaga gagaaggtcc gagtaggtga tagaagacaa gggggagacc gagccggagg   3840
ctgaggaaag gaagagggca cggagttgcc aggagcaaac caaagtgaag agagagatag   3900
gaagctgcct cggggccacc ccttgcaaag gggtgtgtc ccacaaacgc tgctatgggt    3960
ggggtggggg gctggggtgc tgcgtagcca gtgtttgact ttcttttcaa gtgggggaaa   4020
gtgggagagg actgagagtg aggcaagttc tccccagccc ctgtccgtct gtctgtctgt   4080
ctgtggtggt ttctgtttct tgggaggcat ggtaggatca taagtcattc ccctcccctt   4140
ccaggcctcc tgctatattt gggggacctg actggtttgg ctggagtccc atgaggatgt   4200
gggcccttta ataaaggata gcaaacaggg agcttgtggc ctgtttgttt tgggttttca   4260
tggaggtgta ggttatataa ggcaatggca caggtcttaa gcatacttat cagtgaagta   4320
ttgtatgtgt gctctgtgca ggcaccaccc agatctggat ataagaatgt ttccatcttg   4380
tcttcctgaa cttcaccctc ctgtctcttc cttcaggttg cgcagcccga tcttttcccc   4440
gctttttttt tttgggagac agggtcttgc tttgttgccc aggctggagg tacagtcttg   4500
gctcactgca gcctccgcct cctgagtagc tgggattaca ggcatgtgcc accacgcccg   4560
gctcattact gttttttttg tagtgacgag gtttcgccgt gttggccagg ctggtctcga   4620
actcctgatg acctcaagtg atccgcccgc cttggcctcc cagagtggtg ggattgcaga   4680
gacagtgatc ttgctatgct gcccaggctg gtctcaacct tatgggctca agtgatcctc   4740
ccacctcagc ctcccaaagt gctaggatta cctgcgtgag ctacagcgcc ctgcctgttc   4800
tgggcttctt gcagagcctc ttcagctgca gagaagcagc tctcctttct ccaagtccag   4860
agccaacagg acgaataatg aagctgttgg gaagatttac tgataataca tgtaaagggt   4920
ctagcacatt ttaggagctc aaggttggtg ccttcccttt ttctttactc tgaaccggat   4980
atgaggcctt gagaaagaag agaggcgctt gcaaaacgag gtgaggtctc aggcacagtg   5040
gctcacgcct gtaatcccag cactttagga gaccgaggcg ggcggatcat gaggtcagga   5100
gttcgagacc agcctggcca acatggtgaa agcccgtctc tactaaaaat acaaaaatta   5160
gacgggcatg gtggtgggca cctgtaatcc cggctacttg ggaggttgag ggaggagaat   5220
cgcttgaacc caggaggtgg aggttgcagt gagccgagac tgcaccattg cactccagcc   5280
tgggcaatag agcgagactc cgtctcaagc aagcaagcaa gcaaacaaac aaaataaaaa   5340
acgaggtcaa gtttcaaaag atgtcacccc caacctggca aaacttctcc tcaagccctg   5400
tcgttccact cttgtccgcc aggaggagaa aaggttccct cgaaggacgt ctttgcttgc   5460
gcgttcacgg agccttgaga acgagtggcc gaggggaccc ctgcggccct gcgcgcctaa   5520
gggaggacct gactcctttc agaagtagca tttcttcccc ttcgtgggtg ctcttgagtt   5580
ccaaagaaaa ggaagagaag ccttcattga gcagcttctt ctgccttagg gactgtgcta   5640
gggggtagat cgaccttagg ggaaacaatc cccgcttatt agaggaggtt ttggatcagg   5700
gtttgcttta tttgaaattt aacaaataca gaaaagcaga aggaagaaaa ttgaagtaat   5760
ccatgtttcc actgggcgcg gcggctcacg cctataatcc cagcactttg ggaggccaag   5820
```

-continued

```
gcgggcggat cacgaggtca ggagttcgag accagcctga ccaacatggt gaaacccccc   5880
gtctctacta aaattacaaa attagccggt cgtggtggca cacgcctgta atcccagcta   5940
ctcaggaggc tgaggcagga gaatcgcttg aacccgggag gcagaggttg cagtgagccg   6000
agattgcacc actgcactcc agcctgagca acagagtgag actccgttgt ctttaaaggc   6060
caatcccata gcaaatgaca gagactcact tgagtaagaa aggtttttga caagaaaacc   6120
cacagaagaa gaggtaagct gtggatataa gaaaggcact acaatctgta tttaaatcta   6180
attgcacact agataatata tgtatgaaaa attattt                            6217
```

<210> SEQ ID NO 144
<211> LENGTH: 2139
<212> TYPE: DNA
<213> ORGANISM: Rattus norvegicus

<400> SEQUENCE: 144

```
ccaagatggc ggcggcagac acagcagcag cagccagtat tcgggaaagg cagacagtgg     60
ctttgaagcg tatgttgaat ttcaatgtgc ctcatattaa aaacagcaca ggagaaccag    120
tatggaaggt actcatttat gacagatttg gccaagatat aatctctcct ctgctatctg    180
tgaaggagct aagagacatg ggaatcactc tgcatctgct tttacactct gatcgagatc    240
ctattccaga tgttcctgca gtatactttg taatgccaac tgaagaaaat attgacagaa    300
tgtgccagga tcttcgaaat caactatatg aatcatatta tttaaatttt atttctgcta    360
tttcaagaag taaactggaa gatattgcaa atgcagcgtt agcagctagt gcagtaacac    420
aagtagccaa ggtttttgac caatatctca attttattac tttggaagat gatatgtttg    480
tattatgtaa tcaaaataag gagcttgttt catatcgtgc cattaacagg ccagatatca    540
cagacacgga aatggaaact gttatggaca ctatagttga cagcctcttc tgcttttatg    600
gtactcgggg tgatgttcct ataatcagat gttcaagagg aacagcagca gaaatggtag    660
cagtgaaact agacaagaaa cttcgagaaa atctaagaga tgcaagaaac agtcttttta    720
caggtgatac acttggagct ggccaattca gcttccagag gcccttatta gtccttgttg    780
acagaaacat agatttggca actcctttac atcatacttg gacatatcaa gcattggtgc    840
acgatgtact ggatttccat ttaaacaggg ttaatttgga agaatcttca ggagtggaaa    900
actctccagc tggtgctaga ccaaagagaa aaaacaagaa gtcttatgat ttaactccgg    960
ttgataaatt ttggcaaaaa cataaaggaa gtccattccc agaagttgca gaatcagttc   1020
agcaagaact agaatcttac agagcacagg aagatgaggt caaacgactt aaaagcatta   1080
tgggactaga aggggaagat gaaggagcca taagtatgct ttctgacaat accgctaagc   1140
taacatcagc tgttagttct ttgccagaac tccttgagaa aaaaagactt attgatctcc   1200
atacaaatgt tgccactgct gttttagaac atataaaggc aagaaaattg gatgtatatt   1260
ttgaatatga agaaaaaata atgagcaaaa ctactctgga taaatctctt ctagatataa   1320
tatcagaccc tgatgcagga actccagaag ataacatgag gttgtttctt atctattata   1380
taagcacaca gcaagcacct tctgaggctg atttggagca atataaaaaa gctttaactg   1440
atgcaggaaa ccttaatcct ttacaatata tcaaacagtg gaaggctttt accaagatgg   1500
cctcagctcc ggccagctat ggcagcacta ccactaaacc aatgggtctt ttatcacgag   1560
tcatgaatac aggatcacag tttgtgatgg aaggagtgaa gaacctggtt ttgaaacagc   1620
aaaatctacc tgttactcgt attttggaca atcttatgga gatgaagtca aaccccgaaa   1680
ctgatgacta tagatatttt gatcccaaaa tgctgcgggg caatgacagc tcagttccca   1740
```

-continued

```
gaaataaaaa tccattccaa gaggccattg tttttgtggt gggaggaggc aactacattg   1800

aatatcagaa tcttgttgac tacataaagg ggaaacaagg caaacacatt ttatatggct   1860

gcagtgagct ttttaatgct acacagttca taaaacagtt gtcacaactt ggacaaaagt   1920

aacacagaag aaccttacta tgataatcta cttggaatgt ggataaatgt aaaaagaaga   1980

aaagttagaa gagcaatatg tttccttctc tgtaacagtg tcctaacagt gaaaatcaga   2040

gttatttgtt aatttttaag gaaattatat acttaatatg tattgattaa aagaaacatt   2100

tcagaaataa aatttcaaca ttgaaaaaaa aaaaaaaaa                          2139


<210> SEQ ID NO 145
<211> LENGTH: 2464
<212> TYPE: DNA
<213> ORGANISM: Rattus norvegicus

<400> SEQUENCE: 145

ggcacgaggc aggcttcatt tggagtcagg cctggctgtt gctcaggtga ccagcttgtg     60

tctctgggag ggcgctgctt tccccggcca cccggcgcga tgatccagaa tgtcggaaat    120

cacctgcgac ggctctcttt ggaaggagaa attgcagaac ccctgggctg gtttattatc    180

agcagcaatc tccaaacaag ccccaggggc tgtcagatcc cccacgggct ggctgtgtag    240

agtggaatca ccttcagcaa gtgtcggcct ctggaattct attcgggctt ggcctctgtg    300

ttctccaacc acacatcccg gaagtcagcc ttacgtgcgg ggaacgacag tgccatggca    360

gacggcgagg gataccggaa ccccacggag gtgcagatga gccagctggt gctgccctgc    420

cacaccaacc aacgtggtga gctgagcgtc gggcagctgc tcaagtggat tgacaccacg    480

gcttgcctgt ccgcggagag gcacgctggc tgcccctgtg tcacagcttc catggatgac    540

atctattttg agcacaccat tagtgttgga caagtggtga atatcaaggc caaggtgaac    600

cgggccttca actccagcat ggaggtgggc atccaggtgg cctcggagga cctgtgctct    660

gagaagcagt ggaatgtgtg caaggccttg gccaccttcg tggcccgccg agagatcacc    720

aaggtgaagc tgaagcagat cacgccgcgg acagaagagg agaagatgga gcacagtgtg    780

gcggctgagc gccggcgcat gcgccttgtc tatgcagaca ccatcaagga cctcctggcc    840

aactgcgcca ttcagggcga tctggagagc agagactgta gccgcatggt gccggctgag    900

aagacccgtg tggagagtgt ggagctggtc ctgcctcccc acgccaatca ccagggcaac    960

acctttgggg gccagatcat ggcctggatg gagaatgtgg ccaccattgc agccaggtga   1020

gggcagggtg tgctgcctct gcctcccctc ctttctcctc ctcctcccct tggctacctc   1080

cctctggagg ggaaacccca gcttggggtt ggcattcaag gcttcagaag cttggctgtt   1140

ctgaatcaga gaaatgaatt tttgtgaact gaccattcct tgttctacta aaaaagctag   1200

catcttttac atgggaaaca ccaggtctct tggcctggca ctagatcctc cccttgatct   1260

ggccctacct gcactccttc tagtatctat gttcccttca catcaagcct tctagtatct   1320

atgttcgctt cacatcaaac catttgctgt tctctgttcc catcctccac tttcccagcc   1380

cctgcctttg ctcctgatgt agcctcctgc cgtgcttccc ctactcttct ttgtctgcta   1440

atatcctgcc cacttcctcc ataaagccat ctctgactgt tcccttcttc taaggggtga   1500

aaattgtttt ctctcctcta acatctgttt ctgtccgggg cttgttctac cctaaatatc   1560

agggtatttt ttatagttat ggtaactgac cttcactaat tgacactctc acacctccaa   1620

gactttgctc ttgctgttcc ctctaccagg agtgcctttc ccaacccatg ccctttccag   1680
```

-continued

```
ccaggtggat tcctccttat tctttagagc ctggcttaaa tggcccctcc tccagtttaa   1740

cctgtgggag acagtgcata agcaatgctg ttttgggcag gcctggctat gagtgcagta   1800

agatcctgga ggagcctgat ggtcagggaa ggctgcctga aggaagagca cttcagctgg   1860

gacttgaatg ccaagtagct ttgggtaagg ggagggcttc tggatagtgg gaacagcagc   1920

taccaaggtg taaaagttgg aaggaaaatg ggaaaggggt ttacccaaag ccctgctttc   1980

ttctgtcccc tcaaacttgg cttctttcca gccatgcata gacctcagta ttctaaacta   2040

tgaaatggga ctttagttct gtgcctctgg gcagaactgc cactgggttg ggtggcagtg   2100

ggtgggtcag aatgtgtagt tccaggctgc gtctggggat gggaccaggg tagaaggccg   2160

gcccaagctg gcctagcatg gtggctcaca cctgtaatcc cagcgctttg ggaggctgag   2220

gccacttagg ccagaagttc aagaccagcc tgggaacaag gtaaaacctc atctctacta   2280

aaaatacaaa aattagccag gtgtggtggt gcgtgcctgt agtctcagct acttgggagg   2340

ctgaggcagg agagtcactt gaacccggga ggcggaggtt gcagtgagcc gagattgcac   2400

cactgcattc cagcctgggc aacagagtga aaccctgtct caaaaaaaaa aaaaaaaaaa   2460

aaaa                                                                 2464
```

<210> SEQ ID NO 146
<211> LENGTH: 1104
<212> TYPE: DNA
<213> ORGANISM: Rattus norvegicus

<400> SEQUENCE: 146

```
ggtcgcttgg tggctccgtc tgttgtccgt ccgcccgcgg gtgccatcat ggcggacgcg     60

gccagtcagg tgctcctggg ctccggtctc accatcctgt cccagccgct catgtacgtg    120

aaagtgctca tccaggtggg atatgagcct cttcctccaa caataggacg aaatattttt    180

gggcggcaag tgtgtcagct tcctggtctc tttagttatg ctcagcacat tgccagtatc    240

gatgggaggc gcgggttgtt cacaggctta actccaagac tgtgttcggg agtccttgga    300

actgtggtcc atggtaaagt tttacagcat taccaggaga gtgacaaggg tgaggagtta    360

ggacctggaa atgtacagaa agaagtctca tcttcctttg accacgttat caaggagaca    420

actcgagaga tgatcgctcg ttctgctgct accctcatca cacatccctt ccatgtgatc    480

actctgagat ctatggtaca gttcattggc agagaatcca agtactgtgg actttgtgat    540

tccataataa ccatctatcg ggaagagggc attctaggat tttcgcgggt tcttgttcct    600

cgccttctag gtgacatcct ttctttgtgg ctgtgtaact cactggccta cctcgtcaat    660

acctatgcac tggacagtgg ggtttctacc atgaatgaaa tgaagagtta ttctcaagct    720

gtcacaggat tttttgcgag tatgttgacc tatccctttg tgcttgtctc caatcttatg    780

gctgtcaaca actgtggtct tgctggtgga tgccctcctt actccccaat atatacgtct    840

tggatagact gttggtgcat gctacaaaaa gaggggaata tgagccgagg aaatagctta    900

tttttccgga aggtcccctt tgggaagact tattgttgtg acctgaaaat gttaatttga    960

agatgtgggg cagggacagt gacatttctg tagtcccaga tgcacagaat tatgggagag   1020

aatgttgatt tctatacagt gtggcgcgct tttttaataa tcatttaatc ttgggaaaat   1080

taaaaaaaaa aaaaaaaaaa aaaa                                          1104
```

<210> SEQ ID NO 147
<211> LENGTH: 186
<212> TYPE: DNA
<213> ORGANISM: Rattus norvegicus -continued

<400> SEQUENCE: 147

```
atggatccca actgctcctg cgccgccggt gactcctgca cctgcgccgg ctcctgcaaa     60
tgcaaagagt gcaaatgcac ctcctgcaag aaaagctgct gctcctgctg ccctgtgggc    120
tgtgccaagt gtgcccaggg ctgcatctgc aaaggggcgt cggacaagtg cagctgctgc    180
gcctga                                                               186
```

<210> SEQ ID NO 148
<211> LENGTH: 3152
<212> TYPE: DNA
<213> ORGANISM: Rattus norvegicus

<400> SEQUENCE: 148

```
aattccggcc gcgtcgacgg gagagtcggt agcgcggcgg ccgcggagcc ctgcgagtag     60
gcaagcgttg ggcccatgca ggacgcggag aacgtggcgg tgcccgaggc ggccgaggag    120
cgcgccgagc ccggccagca gcagccggcc gccgagccgc cgccagccga ggggctgctg    180
cggcccgcgg ggcccggcgc tccggaggcc gcggggaccg aggcctccag tgaggaggtg    240
gggatcgcgg aggccgggcc ggagcccgag gtgaggaccg agccggcggc cgaggcagag    300
gcggcctccg gcccgtccga gtcgccctcg ccgccggccg ccgaggagct gcccgggtcg    360
catgctgagc cccctgtccc ggcacagggc gaggccccag gagagcaggc tcgggacgag    420
cgctccgaca gccgggccca ggcggtgtcc gaggacgcgg gaggaaacga gggcagagcg    480
gccgaggccg aaccccgggc gctggagaac ggcgacgcgg acgagccctc cttcagcgac    540
cccgaggact tcgtggacga cgtgagcgag gaagaattac tgggagatgt actcaaagat    600
cggccccagg aagcagatgg aatcgattcg gtgattgtag tggacaatgt ccctcaggtg    660
ggacccgacc gacttgagaa actcaaaaat gtcatccaca agatcttttc caagtttggg    720
aaaatcacaa atgattttta tcctgaagag gatgggaaga caaaagggta tattttcctg    780
gagtacgcgt cccctgccca cgctgtggat gctgtgaaga acgccgacgg ctacaagctt    840
gacaagcagc acacattccg ggtcaacctc tttacggatt ttgacaagta tatgacgatc    900
agtgacgagt gggatattcc agagaaacag cctttcaaag acctggggaa cttacgttac    960
tggcttgaag aggcagaatg cagagatcag tacagtgtga tttttgagag tggagaccgc   1020
acttccatat tctggaatga cgtaaaagac cctgtctcaa ttgaagaaag agcgagatgg   1080
acagagacgt atgtgcgttg gtctcctaag ggcacctacc tggctacctt tcatcaaaga   1140
ggcattgctc tatggggggg agagaaattc aagcaaattc agagattcag ccaccaaggg   1200
gttcagctta ttgacttctc accttgtgaa aggtacctgg tgacctttag ccccctgatg   1260
gacacgcagg atgaccctca ggccataatc atctgggaca tccttacggg gcacaagaag   1320
aggggttttc actgtgagag ctcagcccat tggcctattt ttaagtggag ccatgatggc   1380
aaattctttg ccagaatgac cctggatacg cttagcatct atgaaactcc ttctatgggt   1440
cttttggaca agaagagttt gaagatctct gggataaaag acttttcttg gtctcctggt   1500
ggtaacataa tcgccttctg ggtgcctgaa gacaaagata ttccagccag ggtaaccctg   1560
atgcagctcc ctaccaggca agagatccga gtgaggaacc tgttcaatgt ggtggactgc   1620
aagctccatt ggcagaagaa cggagactac ttgtgtgtga aagtagatag gactccgaaa   1680
ggcacccagg gtgttgtcac aaattttgaa attttccgaa tgagggagaa acaggtacct   1740
gtggatgtgg tcgagatgaa agaaaccatc atagcctttg cctgggaacc aaatggaagt   1800
```

-continued

```
aagtttgctg tgctgcacgg agaggctccg cggatatctg tgtctttcta ccacgtcaaa   1860

aacaacggga agattgaact catcaagatg ttcgacaagc agcaggcgaa caccatcttc   1920

tggagccccc aaggacagtt cgtggtgttg gcgggcctga ggagtatgaa cggtgcctta   1980

gcgtttgtgg acacttcgga ctgcacggtc atgaacatcg cagagcacta catggcttcc   2040

gacgtcgaat gggatcctac tgggcgctac gtcgtcacct ctgtgtcctg gtggagccat   2100

aaggtggaca acgcgtactg gctgtggact ttccagggac gcctcctgca gaagaacaac   2160

aaggaccgct tctgccagct gctgtggcgg ccccggcctc ccacactcct gagccaggaa   2220

cagatcaagc aaattaaaaa ggatctgaag aaatactcta agatctttga acagaaggat   2280

cgtttgagtc agtccaaagc ctcaaaggaa ttggtggaga gaaggcgcac catgatggaa   2340

gatttccgga agtaccggaa aatggcccag gagctctata tggagcagaa aaacgagcgc   2400

ctggagttgc gaggaggggt ggacactgac gagctggaca gcaacgtgga cgactgggaa   2460

gaggagacca ttgagttctt cgtcactgaa gaaatcattc ccctcgggaa tcaggagtga   2520

cctggagcac tgtggggacg gactccgcct gctgttcccg cgctgagcta caggactccc   2580

gagtgtgagc cgcggttcct ctgttgcagc gcagccgtgt gtgctgtgga gccgaggccg   2640

tcctgcagga agccgcgtga ctcccgcctc ctccctgtgc tctctggctc tggactgtga   2700

ctgcgcctgg attctgccat tgcgacacat tttgtgcct ttcagcccct ggtgtctgca    2760

gtgggggatt taaggcaccc gcttccactt ctttcttgtt tggagttttc tgttggaacc   2820

gccggcgttg gctccgaaga cttagcgacg ccactggcgg caccttctcc tgcgcccagt   2880

gatgtttcca cggtgcctgt acacagccga gcagcatttc cgttgaagga cttgcatccc   2940

cattgcgggc agtgctggac gtgtcccgga gacccaccgg gaggcgccgc atgccttgta   3000

cccccaccgt gcaggttgtg gccggttttc tccgcaggtt gaacatggaa ataaaagcaa   3060

acttgtatgg aattcaaaaa aaaaaaaaaa aaaaaaaaaa aaaaaaaaaa aaaaaaaaaa   3120

aaaaaaaaaa aaaaaaaaaa aaaaaaaaaa aa                                 3152
```

```
<210> SEQ ID NO 149
<211> LENGTH: 1740
<212> TYPE: DNA
<213> ORGANISM: Rattus norvegicus

<400> SEQUENCE: 149

cgaagactga gcggttgtgg ccgcgttgcc gacctccagc agcagtcggc ttctctacgc     60

agaacccggg agtaggagac tcagaatcga atctcttctc cctccccttc ttgtgagatt    120

tttttgatct tcagctacat tttcggcttt gtgagaaacc ttaccatcaa acacgatggc    180

cagcaacgtt accaacaaga cagatcctcg ctccatgaac tcccgtgtat tcattgggaa    240

tctcaacact cttgtggtca agaaatctga tgtggaggca atcttttcga agtatggcaa    300

aattgtgggc tgctctgttc ataagggctt tgccttcgtt cagtatgtta atgagagaaa    360

tgcccgggct gctgtagcag gagaggatgg cagaatgatt gctggccagg ttttagatat    420

taacctggct gcagagccaa aagtgaaccg aggaaaagca ggtgtgaaac gatctgcagc    480

ggagatgtac ggctcctctt ttgacttgga ctatgacttt caacgggact attatgatag    540

gatgtacagt tacccagcac gtgtacctcc tcctcctcct attgctcggg ctgtagtgcc    600

ctcgaaacgt cagcgtgtat caggaaacac ttcacgaagg ggcaaaagtg gcttcaattc    660

taagagtgga cagcggggat cttccaagtc tggaaagttg aaaggagatg accttcaggc    720

cattaagaag gagctgaccc agataaaaca aaaagtggat tctctcctgg aaaacctgga    780
```

-continued

```
aaaaattgaa aaggaacaga gcaaacaagc agtagagatg aagaatgata agtcagaaga    840

ggagcagagc agcagctccg tgaagaaaga tgagactaat gtgaagatgg agtctgaggg    900

gggtgcagat gactctgctg aggaggggga cctactggat gatgatgata atgaagatcg    960

gggggatgac cagctggagt tgatcaagga tgatgaaaaa gaggctgagg aaggagagga   1020

tgacagagac agcgccaatg gcgaggatga ctcttaagca catagtgggg tttagaaatc   1080

ttatcccatt atttctttac ctaggcgctt gtctaagatc aaatttttca ccagatcctc   1140

tcccctagta tcttcagcac atgctcactg ttctccccat ccttgtcctt cccatgttca   1200

ttaattcata ttgccccgcg cctagtccca ttttcacttc ctttgacgct cctagtagtt   1260

ttgttaagtc ttaccctgta atttttgctt ttaattttga tacctcttta tgacttaaca   1320

ataaaaagga tgtatggttt ttatcaactg tctccaaaat aatctcttgt tatgcaggga   1380

gtacagttct tttcattcat acataagttc agtagttgct tccctaactg caaaggcaat   1440

ctcatttagt tgagtagctc ttgaaagcag ctttgagtta gaagtatgtg tgttacaccc   1500

tcacattagt gtgctgtgtg gggcagttca acacaaatgt aacaatgtat ttttgtgaat   1560

gagagttggc atgtcaaatg catcctctag aaaaataatt agtgttatag tcttaagatt   1620

tgttttctaa agttgatact gtgggttatt tttgtgaaca gcctgatgtt tgggaccttt   1680

tttcctcaaa ataaacaagt ccttattaaa ccaggaattt ggagaaaaaa aaaaaaaaaa   1740
```

<210> SEQ ID NO 150
<211> LENGTH: 3624
<212> TYPE: DNA
<213> ORGANISM: Rattus norvegicus

<400> SEQUENCE: 150

```
gcaggttggg agggaaagtc gggggaggac gcggaagagg agctgtggga agggggagga     60

gggagggagg aaaagaggag gagacggagg agaactgagc agagcagagc atcgagccaa    120

aggggagatg agtttgtctg tcctctgctg aggctacggc cgggcctagg gaactgggag    180

cttgggtgga agcgacaccc gtggaagtgg gaggaggtgg cgccgggact ttaacccctt    240

gtgggctctg cggcagggga tttaaccctt tgtggatctg gcccctcgga ggcagcgtca    300

tcggtagttt taacccottc ggggctgggt ttcacgcact ggacttaccc tcatcacctt    360

gctcaccaac tcctttattg gggtgctccg cttggaggtt tgaggcccac ctccgcccat    420

tacgtactgt tcctgccgct gcaccccctt ggacccgcta gctggccgca ctgtgggcgc    480

ttaacccttt actgacttga gctccccaga ttgcagttgg agtttgctga tagaaggact    540

agctaaaggc gtcactgcag gaattacaaa ctgaagagga ctctgttgga ctgttttttt    600

tttctttttc tttttttaa gaaaaaccca tttttttcct taaggactta ctagccaaaa    660

tttcttaaac ttcgaggact ctactagcca tggccgagcc attcttgtca gaatatcaac    720

accagcctca aactagcaac tgtacaggtg ctgctgctgt ccaggaagag ctgaaccctg    780

agcgcccccc aggcgcggag gagcgggtgc ccgaggagga cagtaggtgg caatcgagag    840

cgttccccca gttgggtggc cgtccggggc cggaggggga agggagcctg gaatcccaac    900

cacctcccctt gcagacccag gcctgtccag aatctagctg cctgagagag ggcgagaagg    960

gccagaatgg ggacgactcg tccgctggcg gcgacttccc gccgccggca gaagtggaac   1020

cgacgcccga ggccgagctg ctcgcccagc cttgtcatga ctccgaggcc agtaagttgg   1080

gggctcctgc cgcagggggc gaagaggagt ggggacagca gcagagacag ctggggaaga   1140
```

-continued aaaaacatag gagacgcccg tccaagaaga agcggcattg gaaaccgtac tacaagctga 1200
cctgggaaga gaagaaaaag ttcgacgaga aacagagcct tcgagcttca aggatccgag 1260
ccgagatgtt cgccaagggc cagccggtcg cgccctataa caccacgcag ttcctcatgg 1320
atgatcacga ccaggaggag ccggatctca aaaccggcct gtactccaag cgggccgccg 1380
ccaaatccga cgacaccagc gatgacgact tcatggaaga agggggtgag gaggatgggg 1440
gcagcgatgg gatgggaggg gacggcagcg agtttctgca gcgggacttc tcggagacgt 1500
acgagcggta ccacacggag agcctgcaga acatgagcaa gcaggagctc atcaaggagt 1560
acctggaact ggagaagtgc ctctcgcgca tggaggacga gaacaaccgg ctgcggctgg 1620
agagcaagcg gctgggtggc gacgacgcgc gtgtgcggga gctggagctg gagctggacc 1680
ggctgcgcgc cgagaacctc cagctgctga ccgagaacga actgcaccgg cagcaggagc 1740
gagcgccgct ttccaagttt ggagactaga ctgaaacttt tttgggggag ggggcaaagg 1800
ggacttttta cagtgatgga atgtaacatt atatacatgt gtatataaga cagtggacct 1860
ttttatgaca cataatcaga agagaaatcc ccctggcttt ggttggtttc gtaaatttag 1920
ctatatgtag cttgcgtgct ttctcctgtt cttttaatta tgtgaaactg aagagttgct 1980
tttcttgttt tcctttttag aagttttttt ccttaatgtg aaagtaattt gaccaagtta 2040
taatgcattt ttgtttttaa caaatcccct ccttaaacgg agctataagg tggccaaatc 2100
tgagaacaat taaattcatt ttagttataa taaatttaat atttgtaaat gtaacatagt 2160
ttcagtgtga tttctagagc taattcaaaa tagtattgat atattttatg tgactgcatt 2220
tttggggagg ggtaccgaaa tcgttaaatt tgtcagtttg caaaaatatc aatctttaat 2280
gggagaattt tcaatttgcc aatttttttcc ttgaatgggt ttaagtatgc tacaatatac 2340
agttcaggca aaatttaaga tgtaattatc ttcaatactt aagtgtgctt gctttctagt 2400
gccttggttt tctttcttga tgctggaaaa ataaacaaac cggtattgag tgtttaggcg 2460
agtggaaagt ggctacaatc caaaatttta aatttaactc tgcctcggcc attcaaaagt 2520
ctaataacaa aaaatgtaaa cctaatttgg cagtttgtta ggttagacaa ctgacagcct 2580
catttcattc ctacaagttg gttttcagta atctcttcct tccccccagt aaggctggaa 2640
gaggctcttg gcaaacttct tagcgcaagc aatggttaga ttaatttgtg aggcagctct 2700
ttaagacgtt cagaggtaag aaatactgga tttataaagc aaatggctgt ttgggggatt 2760
ccaaggattt acctaattgt ccaattctac gtgctctcta taccaaaaca aaaaaaaagc 2820
tatccacctt tccatgtggg tcaaactaaa attagaaatg tcccctcact gcagatcaaa 2880
tgtaaagctt ccagttaagg agctaaatga ggtcctcagc tgaatgagga accctgtaca 2940
tccccttgca cagccctatt ctaaatcgct taaactatgc tgatagctgc ttaggttctt 3000
gagtagttct gctcttaaac gtagggaggc cctgagaact aaattttgcc ccaaaataaa 3060
aacagaaatt atgagattgc ctcctgtcat tttggttaac ccagtccttc acctgccctg 3120
tgtcagtgtc ttctgagggc aattgcgttg ctcaaatcac tagcacagag gttccttaat 3180
ttggggcctt agaaaccatt gtgggccttg gggtccatga accccatgaa attatttgta 3240
gacttgtatg tacatttttc tggggagaag gttcaagaga ttcataagat tgtcaaactc 3300
cttgaaggtt cagaacctct gcagggaagg gggaagaaaa ccctcccatt aggaagcatg 3360
cttttgcagt taaatggcga tggtggaggt gatagggact tcaagagtaa aatgcacctt 3420
gtattgcata agaagcatac acaaatcaat aaatcaaggg agattatacc agtaggactg 3480
aatcagggcc ttcaaagctg gactgagttg gtcctgttct ggcacatatg gtccactgga 3540

```
gacaatgtat gattgagctt ttctttggtc taaaaattat attaaacatt tattttgaaa   3600
aaaaaaaaaa aaaaaaaaaa aaaa                                          3624
```

<210> SEQ ID NO 151
<211> LENGTH: 1825
<212> TYPE: DNA
<213> ORGANISM: Rattus norvegicus

<400> SEQUENCE: 151

```
ggggagctct gcgaggggcc ggagcgcggc ggagccatgc agtacccgca ccccgggccg     60
gcggcgggcg ccgtgggggt gccgctgtac gcgcccacgc cgctgctgca acccgcacac    120
ccgacgccct tttacatcga ggacatcctg ggccgcgggc ccgccgcgcc cacgcccgcc    180
cccacgctgc cgtcccccaa ctcctccttc accagcctcg tgtcccccta ccggaccccg    240
gtgtacgagc ccacgccgat ccatccagcc ttctcgcacc actccgccgc cgcgctggcc    300
gctgcctacg gacccggcgg cttcgggggc cctctgtacc ccttcccgcg gacggtgaac    360
gactacacgc acgccctgct ccgccacgac cccctgggca aacctctact ctggagcccc    420
ttcttgcaga ggcctctgca taaaaggaaa ggcggccagg tgagattctc caacgaccag    480
accatcgagc tggagaagaa attcgagacg cagaaatatc tctctccgcc cgagaggaag    540
cgtctggcca agatgctgca gctcagcgag agacaggtca aaacctggtt tcagaatcga    600
cgcgctaaat ggaggagact aaaacaggag aaccctcaaa gcaataaaaa agaagaactg    660
gaaagtttgg acagttcctg tgatcagagg caagatttgc ccagtgaaca gaataaaggt    720
gcttctttgg atagctctca atgttcgccc tcccctgcct cccaggaaga ccttgaatca    780
gagatttcag aggattctga tcaggaagtg gacattgagg gcgataaaag ctattttaat    840
gctggatgat gaccactggc attggcatgt tcagaaaact ggatttagga ataatgtttt    900
gctacagaaa atcttcatag aagaactgga aggctatata agaaagggaa tcaattctct    960
ggtattctgg aaacctaaaa atatttggtg cactgctcaa ttaacaaacc tacatggaga   1020
ccttaatttt gacttaacaa atagtttatg tactgctctt aggttgtttt gataaagtga   1080
cattatagtg attaaattct tccccccttta aaaaaacagt tagtggtttt cactatttat  1140
aaaaaattaa ttttgaactt tttgttaaat ttttaagtta tagctttaaa ggttttaata   1200
ggaccttctt gaacgacttt tctgtaatct gtttatctcc cacttaatgg aaaggcaaag   1260
gggtacccca aatccagagg tgcctacatt tcaggcagcc ttggagtatt ttaaaaggaa   1320
aacattcttt acttttatat gacattctta tactgctgtc tcaaatccaa aaacatttca   1380
gagctcttgt ctcagagatg tgtgttcttt ttgtcagaga tatggttgat gagaatctta   1440
aatgcttgtt ttgcactatc acttagtacc tgtttgacca aggtgttaag gggatagtac   1500
ctcccaattc aagcagagaa actgacctga ctaaagttaa tcgcagatga actagaagtc   1560
acaggttaat taaatgtaag tagattgtag atactgtttt atatcaaaca atgtttataa   1620
tgtgtatata gaattgttca ctgtaaaaaa aatggccaaa atgtgttttt tttttaataa   1680
gtaacttgac tataaaataa agccgtccgt gggacgactg acctcgtaaa aaaaaaaaaa   1740
aaaaaaaaaa aaaaaaaaaa aaaaaaaaaa aaaaaaaaaa aaaaaaaaaa aaaaaaaaaa   1800
aaaaaaaaaa aaaaaaaaaa aaaaa                                         1825
```

<210> SEQ ID NO 152
<211> LENGTH: 1795
<212> TYPE: DNA

<213> ORGANISM: Rattus norvegicus

<400> SEQUENCE: 152
acgcgtccgc ccacgcgtcc gcccacgcgt ccggtcgggg ccagagcgca ggtgtacctg 60
gcggccgtgc tggagcacct gaccgccgag atcctggagc tggctggcaa cccggcccgc 120
gacaagaaga cccgcatcat cctgcgccac ctgtagctgg ccattcgcaa cggcgaggag 180
cttaacaagc tgctgggcga agtcaccatc gcgcagggcg gtgtcctgcc caacattcag 240
ggcgtgcttc tgccccagaa gaccaagagc caccacaagg ccaagggtga aaaccattca 300
ctaggagagg agaaacacaa tggccaccaa gacagagttg agtcccacag caagggagag 360
caagaacgca caagatatgc aagtggatga gacactgatc cccaggaaag gtccaagttt 420
atgttctgct cgctatggaa tagccctcgt cttacatttc tgcaatttca caacgatagc 480
acaaaatgtc atcatgaaca tcaccatggt agccatggtc aacagcacaa gccctcaatc 540
ccagctcaat gattcctctg aggtgctgcc tgttgactca tttggtggcc taagtaaagc 600
cccaaagagt cttcctgcaa agtcctcaat acttgggggt cagtttgcaa tttgggaaaa 660
gtggggccct ccacaagaac gaagcagact ctgcagcatt gctttatcag gaatgttact 720
gggatgcttt actgccatcc tcataggtgg cttcattagt gaaacccttg ggtggccctt 780
tgtcttctat atctttggag gtgttggctg tgtctgctgc cttctctggt ttgttgtgat 840
ttatgatgac cccttttcct atccatggat aagcacctca gaaaaagaat acatcatatc 900
ctccttgaaa caacaggtcg ggtcttctaa gcagcctctt cccatcaaag ctatgctcag 960
atctctaccc atttggtcca tatgtttagg ctgtttcagc catcaatggt tagttagcac 1020
aatggttgta tacataccaa cttacatcag ctctgtgtac catgttaaca tcagagacaa 1080
tggacttcta tctgcccttc cttttattgt tgcctgggtc ataggcatgg tgggaggcta 1140
tctggcagat ttccttctaa ccaaaaaagtt tagactcatc actgtgagga aaattgccac 1200
aattttagga agtctcccct cttcagcact cattgtgtct ctgccttacc tcaattccgg 1260
ctatatcaca gcaactgcct tgctgacgct ctcttgcgga ttaagcacat tgtgtcagtc 1320
agggatttat atcaatgtct tagatattgc tccaaggtat tccagttttc tcatgggagc 1380
atcaagagga ttttcgagca tagcacctgt cattgtaccc actgtcagcg gatttcttct 1440
tagtcaggac cctgagtttg ggtggaggaa tgtcttcttc ttgctgtttg ccgttaacct 1500
gttaggacta ctcttctacc tcatatttgg agaagcagat gtccaagaat gggctaaaga 1560
gagaaaactc actcgtttat gaagttatcc caccttggat ggaaaagtca ttaggcaccg 1620
tattgcataa aatagaaggc ttccgtgatg aaaataccag tgaaaagatt tttttttcct 1680
gtggctcttt tcaattatga gatcagttca ttattttatt cagacttttt tttgagagaa 1740
atgtaagatg aataaaaatt caaataaaat gataactaag aaaaaaaaaa aaaaa 1795

<210> SEQ ID NO 153

<400> SEQUENCE: 153

000

<210> SEQ ID NO 154
<211> LENGTH: 5011
<212> TYPE: DNA
<213> ORGANISM: Rattus norvegicus

<400> SEQUENCE: 154

-continued

```
gtgccgggaa gtggctccag ggagaagagg cctcttccct cacccgctgt gggagctgcg     60
ccccgaaagc ctgccccggc acgtcgggct ctcctgaccc gccaagacca gagagccgtt    120
ggcgccctcc gcccgggcct gccggtccgt ttattttaag aagctttgtg cgcctgctgt    180
ggggatttct gatccaggct gcgaagaatt tcgaagtctg gaaaatagca actgtgtttg    240
tttctaaagg atcttctcct gacccagcat cgctcatcac aatgaagaac caagacaaaa    300
agaacggggc tgccaaacaa tccaatccaa aaagcagccc aggacaaccg gaagcaggac    360
ccgagggagc ccaggagcgg cccagccagg cggctcctgc agtagaagca gaaggtcccg    420
gcagcagcca ggctcctcgg aagccggagg gggctcaagc cagaacggct cagtctgggg    480
cccttcgtga tgtctctgag gagctgagcc gccaactgga agacatactg agcacatact    540
gtgtggacaa taaccagggg ggccccggcg aggatggggc acagggtgag ccggctgaac    600
ccgaagatgc agagaagtcc cggacctatg tggcaaggaa tggggagcct gaaccaactc    660
cagtagtcaa tggagagaag gaaccctcca agggggatcc aaacacagaa gagatccggc    720
agagtgacga ggtcggagac cgagaccatc gaaggccaca ggagaagaaa aaagccaagg    780
gtttggggaa ggagatcacg ttgctgatgc agacattgaa tactctgagt accccagagg    840
agaagctggc tgctctgtgc aagaagtatg ctgaactgct ggaggagcac cggaattcac    900
agaagcagat gaagctccta cagaaaaagc agagccagct ggtgcaagag aaggaccacc    960
tgcgcggtga gcacagcaag gccgtcctgg cccgcagcaa gcttgagagc ctatgccgtg   1020
agctgcagcg gcacaaccgc tccctcaagg aagaaggtgt gcagcgggcc cgggaggagg   1080
aggagaagcg caaggaggtg acctcgcact tccaggtgac actgaatgac attcagctgc   1140
agatggaaca gcacaatgag cgcaactcca agctgcgcca agagaacatg gagctggctg   1200
agaggctcaa gaagctgatt gagcagtatg agctgcgcga ggagcatatc gacaaagtct   1260
tcaaacacaa ggacctacaa cagcagctgg tggatgccaa gctccagcag gcccaggaga   1320
tgctaaagga ggcagaagag cggcaccagc gggagaagga ttttctcctg aaagaggcag   1380
tagagtccca gaggatgtgt gagctgatga agcagcaaga gacccacctg aagcaacagc   1440
ttgccctata cacagagaag tttgaggagt tccagaacac actttccaaa agcagcgagg   1500
tattcaccac attcaagcag gagatggaaa agatgactaa gaagatcaag aagctggaga   1560
aagaaaccac catgtaccgg tcccggtggg agagcagcaa caaggccctg cttgagatgg   1620
ctgaggagaa aacagtccgg gataaagaac tggagggcct gcaggtaaaa atccaacggc   1680
tggagaagct gtgccgggca ctgcagacag agcgcaatga cctgaacaag agggtacagg   1740
acctgagtgc tggtggccag ggctccctca ctgacagtgg ccctgagagg aggccagagg   1800
ggcctggggc tcaagcaccc agctccccca gggtcacaga agcgccttgc tacccaggag   1860
caccgagcac agaagcatca ggccagactg ggcctcaaga gcccacctcc gccagggcct   1920
agagagcctg gtgttgggtc atgctgggaa gggagcggca gcccagccag gcctggccca   1980
taaaaggctc ccatgctgag cagcccattg ctgaagccag gatgttctga cctggctggc   2040
atctggcact tgcaattttg gattttgtgg gtcagtttta cgtacatagg gcattttgca   2100
aggccttgca aatgcattta tacctgtaag tgtacagtgg gcttgcattg gggatggggg   2160
tgtgtacaga tgaagtcagt ggcttgtctg tgagctgaag agtcttgaga ggggctgtca   2220
tctgtagctg ccatcacagt gagttggcag aagtgacttg agcatttctc tgtctgattt   2280
gaggctcaga cccctccctg cccttcagag ctcaagacaa gtaatacacc caggtcttga   2340
ctgcatttgt cttgtgagca gggcttgctt ggtcagctca ggccctccta gctgctctgg   2400
```

-continued

```
aggctccttt gattctctag acctggaaaa ggtgtcccta ggcagagccc tggcagggcg   2460
ctcagagctg gggatttcct gcctggaaca agggacctgg agaatgtttt tgcgtgggat   2520
gatgtgctgg tcaggagccc cttgggcatc gcttcccctg ccctttggta gtgccaggac   2580
caggccaatg atgcttctca gtagccttat cattcacagg tgcctctcta gcctgcacaa   2640
atgattgaca agagatcacc caaaggatta tttctgaagg tgttttttttc tttatttctt   2700
tttctttttt tttttttttc tttttctttt ttttttgcac atgacagtgt ttgtattgag   2760
gaccttccaa ggaagaggga tgctgtagca gtggtgcctg ggtgcctggc ctccagtgtc   2820
ccacctcctt caccacccca cttggctcct ttgccatctt gatgctgagg tttcctgttt   2880
ggtgagatca ggttgtttgt ggtaaaagaa aggaaagggc ttctgatggc tttgccacaa   2940
gcttacctgt gggtttcagt cctgagaggc caccaccagt tcccatcagc actgtctcca   3000
tgcagcagtt gctgggtccc atgtccagct gcctctttgg cttcatgggt ttttctgctt   3060
cctgcccccca cccccacatg tgcaatcctc aagatttgtc ctgattctat ttcctggcac   3120
ctccctgcct gtccttgggg attctacttc ttcctgtgtg ggagcccata gctgttgtct   3180
aacaggtaag aaatgaaatt gaactattga ctgggcccca gaaatccata aaatggctgc   3240
agacagttgt ttctgtgtcc tgttctaccc ccactccagt acataactac tatgtactgt   3300
gtagagccat tctatatgct gaatgttctg ctgttgcaaa cttgccaggg tattagccag   3360
tgtttgtgcc aagcagtttt ctgggacaac agaatgactc agaccaagat ggataggatg   3420
gttagggctt tgcttcttgc tgtttttctt tgaagctagt tcattgtcct gcaggtccct   3480
tcatcttcca tacctagccc actcttttag cccttacctt aaatctctca gataagttgg   3540
ttcacaaaga atgttaagta ctgaatcatg tgtgactgag accagagatg gcaaatgaat   3600
ggcacaccat ttctccttct cctgccccag ggcaggtacc actgatctgc atcagagttg   3660
cctgctattc tctggtgtat ccttcacatc taggtgccct caagcagctg tgtgagtgtt   3720
gagatctctg ccatctctgg ctgagatact gctgtcctgt gaagtgtttc ccatgacctt   3780
tttcttcccc tttgaatccc tctgtctgga gtagtccttg cctcttcctg ctccagtagg   3840
gccttttccc taccccagcc cctgtgccag gctaagctgg tacaagagct gccaacctca   3900
cagagtgttt gctaggcgag agaggtgcag ggaagaggca gaggtatgca ccttcccccct   3960
tgaagagagg ggaaaggcct acagtggccc acataattgc ctgactcaca cttcagctac   4020
ctcttaatgc ctgtggaggg actggagctg ctggatccca gtgtggtggt gtaggaggcc   4080
acagtgagca ggtggcccca gctgggtttc ccaggtcagg aatgtgggcc ccaggcaagg   4140
tgcagccttt gctcacagct ccatccatgt ctagaccttc aggccagtct gcagatgagg   4200
ttccctacct ttttcttctc ttcattgacc aaatcaacca atcactacag ctgctctgct   4260
tctgctttcc aaagtagccc aggtcctggg ccagatgcag gggaggtgcc tatccatgag   4320
tgaaggccag tgtcttcctc acctgggtgg gtcccacact tgtgacctca gttttaggac   4380
caagatctgt gttggtttct tagattgcta gcttttcctc caggggacca cagcaggtga   4440
agctcaagag cgcatggctc tgctaatagt aaattgtttt cagggccttg tccagctgag   4500
agcttcatgt ccaccagatt ctgagaggtg tcagcagcac tttttttttt tatttgttgt   4560
ttgttttcca tgaggttatc ggaccatggg ctgagctcag gcactttctg taggagactg   4620
ttatttctgt aaagatggtt atttaaccct cctccacccc atcacggtgg ccctgagggc   4680
tgacccggag gccagtggag ctgcctggtg tccacggggg agggccaagg cctgctgagc   4740
```

-continued

```
tgattctcca gctgctgccc cagcctttcc gccttgcaca gcacagaggt ggtcacccca   4800

gggacagcca ggcacctgct cctcttgccc ttcctggggg aagggagctg ccttctgtcc   4860

ctgtaactgc tttccttatg gcccagcccg gccactcaga cttgtttgaa gctgcactgg   4920

cagctttttt gtctcctttg ggtattcaca acagccaggg acttgatttt gatgtatttt   4980

aaaccacatt aaataaagag tctgttgcct t                                  5011
```

<210> SEQ ID NO 155

<400> SEQUENCE: 155

000

<210> SEQ ID NO 156
<211> LENGTH: 3452
<212> TYPE: DNA
<213> ORGANISM: Rattus norvegicus

<400> SEQUENCE: 156

```
ggcacgaggc tttcaccccc cccccccggc cattaccgaa gcggatgaaa acaaacacta     60

acgatggcgg cgccgggaag cgaccggctg ctgggcttaa ggcgggagtg accgcttaac    120

cagtgaggga agcactgaag agcgccagtc gacgtgggtg cgacaactcg cggagtctta    180

ggagcaaaac gtctggggcc tgcgagccag gacccttctg aagccttagg tgtctatcgg    240

cgacgtgtac ggtcactgca gctccggagc gcggaaccct cagccaggag gcgcggctgg    300

tcggtcccag gtcccggcct ccgtaatgag agcccggaac cactctttgt gccgcagctt    360

cgcagcatct tggactcaag tgattctcct gcctcagcct cctgagtagc tgggactaca    420

gattcctata ggcaatggaa actgatctca attcccagga cagaaaggac ctggacaagt    480

ttattaaatt ttttgccctc aagactgtcc aagtgattgt ccaggctcgg cttggtgaaa    540

agatttgcac tcgttcatca tcttctccaa cgggttcaga ttggttcaac ttagcaatca    600

aagacatccc agaggttaca catgaagcaa agaaggcact ggcaggacag ctgcctgcag    660

tcgggaggtc catgtgtgtg gagatttcac ttaagacttc tgagggagat tccatggagc    720

tggaaatatg gtgtcttgaa atgaatgaaa agtgtgataa agaaatcaaa gtttcctaca    780

cggtgtacaa cagactgtca ttgctgctga agtcccttct tgctataact agggtgacac    840

cagcctatag gctctccagg aaacaagggc atgaatatgt catattatac aggatatatt    900

ttggagaagt tcagctgagt ggcttaggag aaggcttcca gacagttcgt gttgggacag    960

tgggcacccc tgtgggcacc atcactcttt cttgtgctta cagaattaac ttggcattca   1020

tgtctaccag gcaatttgag aggaccccac ctatcatggg gattattatt gatcactttg   1080

tggaccgtcc ctatcccagc tcctctccca tgcacccctg caattacaga actgctggtg   1140

aggacactgg agtaatatac ccgtctgtag aagactctca agaagtgtgt accacctctt   1200

tttccacctc ccaccatcc cagctgatgg ttcctgggaa ggaaggtggg gtaccccttg    1260

ctcccaacca gcctgtccat ggtacccagg ctgaccagga gagactggca acctgcaccc   1320

cttctgacag aacccactgt gctgccacac cctccagtag tgaggatact gaaaccgtat   1380

caaacagcag tgagggacgg gcctcccctc acgatgtctt ggagaccatc tttgtccgaa   1440

aagtgggggc ttttgtcaac aaacccatta accaggtgac cctgacgagt ttggatatac   1500

cctttgccat gtttgctccc aagaatttgg agctggagga taccgatcca atggtgaatc   1560

ctccagattc cccagagact gaatctcctc tccagggcag cctgccttgc agctggcccc   1620
```

-continued

```
ttccctgcct gctgtcacca tccactgttt gacattccag ctggtggcca agagattggt   1680

gtggaggcag aaagaggaag gagacagtgc caggaggaag aaggaaggag tcccttagct   1740

ctcttcattg tccccttac ttcctgctat cttcttctcc tcttcttctc tctcttgcct   1800

ctatgcctgt atttctggca atatgacagg cctgcctacc caagatcaga actccaaaac   1860

cactcccacc cctgaaggtc gggagggtct gagcagccct ggtggctgcc tgtgctcagg   1920

tcctcagctc catgggaaat aaaaatggca ccctgaatct ctaggatttt gtcacttgga   1980

gtcacagcaa agttctcttc ctcttgtccc cccgttgctg ctccttggtt atagaacatg   2040

gtaaatattt attactttca gagaaaccag atattttata gaggaaatat gtttgaggtg   2100

agttgttttt cacttggaga aggcggaggg ctcttcctgg gacggagacc tcctcctccg   2160

gaggttattg agaatccggg ctgctgcttt gaggatcttc ccaccataca gacagcgaga   2220

tccaagaaga gggctggccg ggggcaaagt cacctcccag tgtggctgca ctggaactga   2280

ctaaaggctt taccttggat agttgcgtat tcctggtgag agccttacat ctcccacagt   2340

ttctgcagag tgactgactc cattctggca gcccaggaag tcctgggtgc taaatgtgat   2400

ggccacatgt agtggttagg ggatgttgtg tgtgtccccc aactgcctgg gtacttgttc   2460

ctgatccctg gggctgtcct gtggagcttt tcctcctgct tgggcctagc taccatctcc   2520

ctctaatccc aggttctcta cactgccctg gggtttacca gctggattgg cttctggttg   2580

agaaatcaaa gctgggcgta tgattgactt aacccttcag gtattgttac ttgaataagt   2640

caagtgccta gcctcaccca cctatgatct gtcctttccc agcctcgctg gtagtcctgg   2700

tcaaggagat ctaggtctac tccattcctc ctggcccacc tggggcattc actggcagca   2760

gctgtgcttc agtggagcag gtggttctca gctgcttgtt agtatactgc atgtgacact   2820

gttcccacat acaaggctga cttctgagga ttggagcagg ctctggcggg gaccagagct   2880

ctgcgtgctg ctgctgccac caagaagtgt tagcagaagc agtagcagcc aactggccct   2940

cctgactttg gcccagagca catgcgtggc ttgctgaacc caggctcagg tttatcccca   3000

aggccccagc tttgagaagg gggaaggccc ctggtaagtt attgatgccc ccatatttca   3060

gctactgctc tctttccaag gccttgcatg gaaaggccta gccattgtct gaggcagcaa   3120

tctttggcat ctacaggtgg cagcagcctt tcaccagggc tccatctgtg aagagtctca   3180

gccatgactt tgagctgagc ttgggagaag taaagcaact gttaaggcca gcccttgccc   3240

ctcagacctg ccatgaaagg aatgagccct agactgactc ctgcagcacc cccgggacag   3300

gctgggacca gctgtttgtc tccaggtgtc agagtccctc ctcctcctcc aacctctcca   3360

acctactttg tttggaaata ccgagctaca cttcaaaatg tattcaaggg atttccaata   3420

aattttttc tgtaaaaaaa aaaaaaaaaa aa                                  3452
```

<210> SEQ ID NO 157
<211> LENGTH: 902
<212> TYPE: DNA
<213> ORGANISM: Rattus norvegicus

<400> SEQUENCE: 157

```
ggggagtgcc gggcggtcgg cgggtcaggg cagcccgggg cctgacgcca tgtcccggaa     60

cctgcgcacc gcgctcattt tcggcggctt catctccctg atcggcgccg ccttctatcc    120

catctacttc cggcccctaa tgagattgga ggagtacaag aaggaacaag ctataaatcg    180

ggctggaatt gttcaagagg atgtgcagcc accagggtta aaagtgtggt ctgatccatt    240

tggcaggaaa tgagagggct gtcatcagct ctgattaaga aaggagattt cttcatgctt    300
```

-continued

```
tcgattctgc atggggtaca gccagtcacc tcaccagaga atgacggctg gagaagaaaa    360
ctctgtaata ccataaataa gagtgcttgt aataaaagac tgtgcacaag gattaatatt    420
tcccttctta agtatcaaaa gaactctgga acaaattata ccattaggaa ggttttcatg    480
attcagttga ttttccaaaa atgaagctat ctcacccagc tgggtttgga ggagcaatct    540
gcttattatt ctgtcgttac cacttactca agcgagctgt gatatgaata caagcaacca    600
gtgggctcgg gaaggtccgg gtctcttctg ccatcttcca gataagagat ttcagtaaaa    660
aactgccatg ctgagctgcc ttatagagct cttcgaaaat gttcgagttg ataaagctct    720
ttgaggacaa ggtacttcgt gcacctcatg ctgaagattg caccgtgttg gaaaataaat    780
atgaagcaag tcaaactaga tgcatacact tgtgtagaaa tcaataatca attaatagaa    840
gtgaaaaaat agacattaaa atgatttatt tcaaaaaaaa aaaaaaaaaa aaaaaaaaaa    900
aa                                                                   902
```

<210> SEQ ID NO 158
<211> LENGTH: 5737
<212> TYPE: DNA
<213> ORGANISM: Rattus norvegicus

<400> SEQUENCE: 158

```
gtcagatcag ggatcatttt ttttccttcc tctactccct ccccccctacc cgcccctccc     60
tccctgtttc ccttccctcc ctccctcccc tctctgctgg gtctgtgcgc tggggcgccc    120
gatcccctcc gcagctggga cgctccgaac tcgaggcagg agtcggctct ccggagcctc    180
gtccctccct tcccccttccc tgccccttc ccccaccccc gactcgggct tggcgcggcg    240
gccagaggaa ccccgagtcc cggcccaggc ccctgagctg gagggatgga aaactcctct    300
gcagcatcag cctcctcgga ggcagggagc agccgctccc aggagatcga ggagctggag    360
cgcttcatcg acagctacgt gctggagtac caggtgcagg ggctgctggc tgacaagacg    420
gagggtgatg gcgagagcga gaggacccag tcccacatct cccagtggac agcggactgc    480
agcgaaccgc tggacagcag ctgttccttc tcccgagggc gagccccccc acagcagaat    540
ggcagcaaag acaactctct ggacatgctg ggcacggaca tctgggcggc caacaccttc    600
gattccttca gtggtgccac ctgggacctg cagccggaaa agctggactt cacccagttc    660
caccgcaaag tccgacacac gcccaagcag cccctgccac acatcgaccg cgaagggtgt    720
ggcaaaggga agctggaaga tggggatggc atcaacctga atgacatcga gaaggtcctt    780
ccagcctggc agggctacca cccgatgccc catgaagtgg agatcgcaca caccaagaag    840
ctgttccgca ggaggagaaa tgatcgaagg cggcagcaga gacctccggg gggcaacaag    900
ccccaacagc atggtgacca ccagccaggc agtgccaaac acaacaggga ccaccagaaa    960
tcctaccagg ggggctcagc accccacccc tcagggaggc ccactcacca tggctacagc   1020
cagaaccggc gctggcacca tggcaacatg aagcacccac caggcgacaa gggggaggca   1080
ggcgcacacc gcaatgccaa agagaccatg accatcgaga acccaaaact ggaggacact   1140
gcaggggaca ccgggcacag cagcctcgag gccccccgca gccctgacac cctggccccg   1200
gtggcttctg agcggctgcc cccacagcag tcagggggggc cagaggttga gacaaaacgt   1260
aaagacagta ttcttcccga gcgcatcggg gagcggccca aaattaccct gctccagtct   1320
tccaaagaca gactgcggcg aaggctaaag gaaaaggatg aagtggccgt ggagacgacc   1380
actccccagc agaacaagat ggacaagctg atcgagatcc tgaacagcat gcggaacaac   1440
```

-continued

```
agcagcgacg tggacaccaa gctcaccacc ttcatggagg aggcccagaa ctccaccaac   1500
tccgaggaga tgctgggcga gatcgtgcgc acaatctacc agaaggctgt gtccgaccgc   1560
agcttcgcct tcaccgctgc caagctctgc gacaagatgg cgctctttat ggtggagggg   1620
accaagttcc ggagcctgct cctcaacatg ctgcagaagg acttcacggt gcgcgaggag   1680
ctgcagcagc aggacgtgga gcgctggctg ggcttcatca ccttcctgtg tgaggtcttc   1740
ggcaccatgc gcagcagcac aggcgagccc ttccgtgtgc tcgtgtgccc catctacacc   1800
tgcctcaggg agctcttgca atctcaggat gtgaaggaag atgctgtcct ttgctgctct   1860
atggagctgc agagtacagg ccggctgctg gaggaacagc tgcctgagat gatgacagag   1920
ctcctggcca gcgcacggga caagatgctg tgcccctcgg agtccatgct gacccggtcg   1980
ctgctcctag aggtcatcga gctccacgct aacagctgga accctctgac gccccccatc   2040
acgcagtact acaacagaac catccagaaa ctgacagcct gacagccagg gggcctggca   2100
ggcggcccac gggcagctgg ggccctggtg cacagggcca gatggacagg cgggaggaca   2160
ggggtggccc tggcgggaga aagaaatggg gaggagggca ggcagagtcg gtggccagtc   2220
tggagccaga cggggaaggg agcaaatccc tgagaggagt gcccccgcac aagcccccca   2280
gcccgagcat gcaagctcac accaataagg gaagcatgtt tctttttcct ggtggccctg   2340
gccctcccct tcctcactcc cgcctctccc ctccccatca gacccatccc ccacggagct   2400
ttgtgtgagg gatctcatcg ctgtgactcc tcggagacct tggcagcctc gcacgccggg   2460
gcaccgcttg ggtcagaaag gacctcggaa ggctgaaaaa gtgggtcgga gacgggctcg   2520
cattgttccc gcatgctgtc agccgcagtc gccaactggc agcaggcgac gtgtagcaga   2580
tgtccgggag gacaaaggca ggcacggtcc ccaccagccg cccgtaattg acggcctttg   2640
tcagccatgg cagagctgac gctccacctc ccacctccaa gtcctcctca ctgcagcccc   2700
cacagcctca ggcctagggg gtcaggcgca gcgggggaga tggagtttgc agttccactt   2760
gcactctttt gtttattgtg ttttattttt caaaagtcgg ttgctttgaa gtctctttgg   2820
ccaatgaaaa tgcccgtgag gtgatcacac agtcagcact gttgaggacc cccggattag   2880
tgggagatca aacccagctc ccctctagaa gaaggattcg agccacagac agcttgccag   2940
tagccaatta gggtaattgg aaacttctgc ccccggcgggg ggtccccgct ggaatcctgt   3000
gttcctcgcc actggcttcc agcgcctctg ttttctcaaa gggctgatac tgtcaccact   3060
gggaccaagt taaacctggt cctggcccca ggggccttgt ggcaaacagg gcacagaacg   3120
agactggcaa attaaaacca aaattctaga tggtgtcttg cgctccacac gcaggtctta   3180
ctggggaaaa ggatgggagt gggggctccc caggactcga ttttagctaa tgcgctgtgt   3240
cactgcccca gctcggacgt agaagcccag ccctccgtga gctcttggga aaggggtgaa   3300
ttcactgggt catggaaggg acagtcaggt gaccagcggg gtcgccagat gaagcttccc   3360
agccgggaaa caagacgggg tttcttggca ggccctggtc ctggggagca ggccctgttg   3420
ttggctggag aggaaggtgt ggggtggaac aggtgtccac atagctccat ctctgggggc   3480
tggagcacac actttgatga gcccccccgg aaatgatgtc agagcctagc cgcttcctta   3540
tttgctcttt tattgaggcc gggcaggccc tgggtcactt tggaggcccc tcttggtcca   3600
cactggactg gccgggaggt gatgggcggg gaaggttctc gtgattgatt gattctgagt   3660
ctgagagtgg cgagtgggga gaggcttccc cagttctctc cagctttccc tgcagctgca   3720
acctgccctc tggtcccagg tgtggagcct ttgcctgtct ctaaaaagag cctgttggcg   3780
acaaggtgta gggggcacaa gtttacctga aacaggtcag tggtctctcc caagaagcgc   3840
```

-continued

```
acgccacctc tggtccctgg ccctgaaccc tgccttcttc ctccctccac ggtttcttcc   3900
cagactttct caagctcctc ctcactgccc ttcctcccca gcccagcctg ggaacacaga   3960
tgccccgcgg gtaggaggcc tcgagggagg agccgggctg atgcggggct gctcagggca   4020
ggccccaggg cgagcttgcc atcgtggcca ggcagcctcc acctgtgctt cagtggcccc   4080
tgcccccctg aagcatgtgg ggtttgtccg ctaggaggag gcaaggcccc cgaagagagg   4140
agagacctgg gagtgggagc tcaggtcagg gaggaggcag gggagtgggg tctcccagac   4200
ccaacggtga gctcagagca agcttcacgc aggacgctcc gaaacactgt gtggaggggg   4260
ctgtgttgtg ggcaccttgg ggcctgattc tccttcctcc gaacgggctc cttgatggcc   4320
tggccacagg ggcagctccc cattggctgt taggaccaga gtgtgaagaa gaagtgaaat   4380
ataaatatgt atacatatat aaatatattt ttaattacat gtcgtgtcac ggtggctcca   4440
gacatactgt ttgcctagtt tattccactg cttgaaagcg cttcctagcc aatctgaaca   4500
acaacacttt aagctgtttt tctaaatgca ggttgctgct ccttttttcag atatggaagg   4560
aaaacgttaa gactattttt tttttaaaga aacaacagtc aagcctaaaa tttgagaccc   4620
cgaggcagct tcccgaggga gactgctcag acaggaactg caggacagaa gtggatgccc   4680
cacagaccct ggccccctcc ccaagtccat cccctctctg tggcatgagg aaggccgcgt   4740
ccgagttgac ctctgaatgt atgtgatgag aggcagagct ggatattgca tttctaaggc   4800
ttgcattgct ttcccctcgc ccgcggttct tggcgcatgg aagaggcggt ccagccatct   4860
gatgttgatc ctgtctcagt ctccccactg cctgtcagga tgagttagtc attgtttttc   4920
tccgaggcgg cctgcttgcc acagccctgc tccccaaggc ctggtggctt tgccgaagct   4980
ctgggaccgc agccccagcg aggcccccaa cctcacccag acgaggccag gagccccgcc   5040
accctccacg ggatgtgcac cctcagaccc cattctctct gttcgtcctt ccttgaccag   5100
tctgtaaacc ttcactgttt ggggatcgtc ctgtccatcc atgtaaatgt aaatgttggc   5160
cgagtcggta tttattctga ttgattttta ttttattcta ttattttctc cgagggatga   5220
gggtgggggg tgtgggaagg gtaccacaga tcaggccggg gcagctgtag gggcgggggc   5280
ccagacagcc aggccgccac cagagcagcc ccatggggtg ccccagacgc gggcctccaa   5340
gaagccaagt cccagtctgt tttctggcat cagacaccgg cccgtgttcc ttgtcagaca   5400
gacagactct caggcctgcc tggggagtcg tgtccctcag ctgcagggca ctgtgttggg   5460
aaaccattgg ctgggccttt gaggacacag atcagaagaa agaaagacaa ctttcctctg   5520
cgcggaacac tcacacggaa gggctggccg cctccctgag ccggctggga gtggacgaca   5580
ggacctacct ccccagagca agggcctggg gcttcccgcc aaagctgccg cggaaccccg   5640
ctagtgcgac caccctccct ccgtcggtat gtcctgcttt ccagctgaac ccaaactaca   5700
agtgggttta aaaaaaataa acaccaccac caaaaac                             5737
```

<210> SEQ ID NO 159
<211> LENGTH: 3606
<212> TYPE: DNA
<213> ORGANISM: Rattus norvegicus

<400> SEQUENCE: 159

```
gccttctaaa gcctctgaat gcaattacat gtatttcaga acattctaaa gaagtaataa     60
atcatcatcc agatgtacaa acaaaagatg ataagctcaa aaactcagtt ttggcccaag    120
gtcctggtgc taccagttca gctgcaaata cctgtaaggt acagccactt actcttaaag    180
```

-continued

```
agactgctga aagttttgga agcccaccaa aagaagaaat gggaaatgaa cacatcagtg    240
tccaccctga aaactcagac tgtatccaag cagatgttaa ctctgatgat tacaagggtg    300
ataaagtata ccatccagaa acaggaagga aaaacgagaa agagaaagtt ggaaggaagg    360
gcaagcatct gttgactgtt gatcagaaac gtggagagca tgttgtctgt ggcagcacac    420
gtaataatga gtcagagagc actttggatt tagaaggctt ccaaaatccc acagctaaag    480
agtgtgaggg acttgccact ttagataaca aggctgatct tgatggagaa agtacagaag    540
gtactgagga actagaagac tctctaaacc actttaccca ctcagtacag ggccagacat    600
cagaaatgat tccctctgat gaagaggagg aggacgacga agaagaggag gaggaagaag    660
aacctaggct caccattaac caaagggaag atgaagatgg catggctaat gaagatgagt    720
tagacaacac ctacactggg tcaggggatg aggacgccct atctgaagag gatgatgagt    780
taggcgaagc tgctaagtat gaagacgtga aagaatgtgg aaaacatgta gaaagagctc    840
tcctagtgga acttaataaa ataagtctca aggaagaaaa tgtatgtgaa gaaaaaaatt    900
cacctgtgga tcagtctgat ttttttatg aattcagtaa acttatcttc accaaaggca    960
agtctcctac ggtagtgtgc agcttatgca aacgagaggg tcatctaaag aaggactgtc   1020
ctgaagactt caaaagaatc cagctagaac ctctgccacc attaacaccc aagtttttaa   1080
atatcttaga tcaagtctgt atccagtgtt ataaggattt ttctccaaca attatagaag   1140
atcaggctcg tgaacatatt cggcaaaacc tagaaagttt cataagacag gactttccag   1200
gaactaaatt gagcctgttt ggctcctcca aaaatggatt tgggttcaaa cagagtgacc   1260
ttgacgtctg tatgacaatt aatggacttg aaactgctga gggattggac tgtgtcagaa   1320
ctattgaaga attagcaaga gtcctcagaa aacattcagg tctgagaaac atcttaccta   1380
ttacaacagc aaaggtgcca attgtgaagt tcttccattt gagaagtggt ctggaagtag   1440
atatcagttt gtataacaca ttggcccttc ataacacaag gcttttatct gcttattccg   1500
ccattgatcc cagagtgaag tatttgtgct ataccatgaa agtatttaca aagatgtgtg   1560
atattggtga tgcatctaga ggcagcttat catcgtatgc atatactctt atggtgctat   1620
attttctcca gcagaggaat ccaccagtca ttcctgtcct tcaagagata tacaaaggtg   1680
aaaagaaacc tgaaatattt gttgatggct ggaatattta ttttttgat caaatagatg   1740
aactgcctac ctattggtca gaatgtggaa aaaatacaga atctgttggg cagttatggt   1800
tgggccttct tcgtttctac acagaggaat ttgattttaa agaacatgtt attagcatca   1860
ggagaaaaag tctgcttaca acttttaaga aacagtggac ctcaaaatac attgttattg   1920
aagatccctt tgatttgaat cataatcttg gagctggatt atcaaggaaa atgacaaatt   1980
ttataatgaa ggcttttatc aatggtagaa gagtatttgg tattcctgtc aagggatttc   2040
caaaggacta cccctcaaaa atggaatact tttttgatcc agatgtgtta actgaaggag   2100
agctggcccc aaatgataga tgttgtcgaa tttgtggaaa aatcggacac ttcatgaagg   2160
actgtcctat gaggagaaaa gtaagacggc ggcgagatca ggaagatgcc ctgaaccaaa   2220
gataccctga gaacaaggaa aaaagaagca aagaggacaa agaaattcac aacaagtaca   2280
cagaaaggga ggtgtcaaca aaagaagata agcccataca gtgcacacct cagaaagcca   2340
agccaatgcg ggcagctgct gacctgggga gggagaagat cctcaggcca ccagtagaaa   2400
aatggaagag acaggatgac aaagacttaa gagaaaaacg ttgtttttatt tgtggaagag   2460
aagggcacat taaaaaggaa tgcccacagt ttaaaggctc ttcaggtagc ctttccagta   2520
aatatatgac tcagggaaaa gcctcagcga agaggaccca gcaggaatca tgagggaagg   2580
```

-continued aaaatgcagc actctaaatg gccactcagg cgttcctatt cactcggaaa attaggttca 2640
tttcacagga cacagcagtg tagatcaggc ttcaacttaa catttaaggg aaatgtcaga 2700
ttttttttta atttaatgaa attgttaatg aggaaaaatt tttaatatag tcttatctac 2760
cacacatccc catagattta aggattttaa tagaaagtca tgatgtatgt atttaagcca 2820
cgttaaaaga aaaaatataa ctatggaccg gtattcagtg aatacagttt catggttttt 2880
aattctttca aagcacatta aaaatggtgt gctgataaac cccaagtaaa ttaacccttt 2940
ttccgtataa atccattttt tgttttgaag aggggaaatt atatttattg ttgtttactg 3000
aatcctggtg tgaaagcata tcagatatgt atgaactgct actgctgtac ttccgattta 3060
cggacatcat tttattgcta tttgtagacg tgataacatg aacatgagta cctatttatg 3120
tgggccttca gtggatgggc agtgccactc aggtctctgg ggtttccctc tctaatttta 3180
agtaaattga catataacta ctatgcttat aaaaatgaag taaggaaaac aagtagtcct 3240
gtttgccact aaaaacattt tcaaaggaaa aataaaatga aagtactttt tactttttat 3300
gatactcaga aattaggatg aagaactttt aaaattgctg aagatcaaag aggttatctc 3360
tgccagtcac aagtgtggct ggtgtcattc tgggtctgac tggagccctc ctggactgtt 3420
tctttaattt caaaagccct gcagacatag tacctggtca gaactatgcc tcggtttatt 3480
tatcattttg aaataaaatc aaaatttcaa cctgtaaaaa aaaaaaaaaa aaaaaaaaaa 3540
aaaaaaaaaa aaaaaaaaaa aaaaaaaaaa aaaaaaaaaa aaaaaaaaaa aaaaaaaaaa 3600
aaaaaa 3606

<210> SEQ ID NO 160
<211> LENGTH: 1203
<212> TYPE: DNA
<213> ORGANISM: Rattus norvegicus

<400> SEQUENCE: 160
ggcacgaggc cgccttctgc atcgcggctt cggcggcttc cacctagaca cctaacagtc 60
gcggagccgg ccgcgtcgtg agggggtcgg cacggggagt cgggcggtct tgtgcatctt 120
ggctacctgt gggtcgaaga tgtcggacat cggagactgg ttcaggagca tcccggcgat 180
cacgcgctat tggttcgccg ccaccgtcgc cgtgcccttg gtcggcaaac tcggcctcat 240
cagcccggcc tacctcttcc tctggcccga agccttcctt tatcgctttc agatttggag 300
gccaatcact gccacctttt atttccctgt gggtccagga actggatttc tttatttggt 360
caatttatat ttcttatatc agtattctac gcgacttgaa acaggagctt ttgatgggag 420
gccagcagac tatttattca tgctcctctt taactggatt tgcatcgtga ttactggctt 480
agcaatggat atgcagttgc tgatgattcc tctgatcatg tcagtacttt atgtctgggc 540
ccagctgaac agagacatga ttgtatcatt ttggtttgga acacgattta aggcctgcta 600
tttaccctgg gttatccttg gattcaacta tatcatcgga ggctcggtaa tcaatgagct 660
tattggaaat ctggttggac atctttattt tttcctaatg ttcagatacc caatggactt 720
gggaggaaga aattttctat ccacacctca gtttttgtac cgctggctgc ccagtaggag 780
aggaggagta tcaggatttg gtgtgccccc tgctagcatg aggcgagctg ctgatcagaa 840
tggcggaggc gggagacaca actggggcca gggctttcga cttggagacc agtgaagggg 900
cggcctcggg cagccgctcc tctcaagcca catttcctcc cagtgctggg tgcgcttaac 960
aactgcgttc tggctaacac tgttggacct gacccacact gaatgtagtc tttcagtacg 1020

-continued agacaaagtt tcttaaatcc cgaagaaaaa tataagtgtt ccacaagttt cacgattctc 1080
attcaagtcc ttactgctgt gaagaacaaa taccaactgt gcaaattgca aaactgaaaa 1140
aaaaaaaaaa aaaaaaaaaa aaaaaaaaaa aaaaaaaaaa aaaaaaaaaa aaaaaaaaaa 1200
aaa 1203

<210> SEQ ID NO 161

<400> SEQUENCE: 161

000

<210> SEQ ID NO 162
<211> LENGTH: 2703
<212> TYPE: DNA
<213> ORGANISM: Rattus norvegicus

<400> SEQUENCE: 162
cgcgccggga acagccagtc ggtgcctaac gcgagtgtat ctcgagagag aagcgatcaa 60
cagctgccgg tctgcgcctg cgcggcgacg gggcgtggcc gcgggcgagt ggggccaagg 120
aggcagccgg gagcgggggc gcaggtgtta ctggttgcgt cgggtcacgt gggcgcgcag 180
cagaccgcgg tgcagcccgt tcgctcacac aaagcccaga cgcggagaaa atggcggcag 240
gggtcgaagc ggcggcggag gtggcggcga cggagatcaa aatggaggaa gagagcggcg 300
cgcccggcgt gccgagcggc aacggggctc cgggccctaa gggtgaagga gaacgacctg 360
ctcagaatga gaagaggaag gagaaaaaca taaaaagagg aggcaatcgc tttgagccat 420
atgccaatcc aactaaaaga tacagagcct tcattacaaa catacctttt gatgtgaaat 480
ggcagtcact taaagacctg gttaaagaaa aagttggtga ggtaacatac gtggagctct 540
taatggacgc tgaaggaaag tcaaggggat gtgctgttgt tgaattcaag atggaagaga 600
gcatgaaaaa agctgcggaa gtcctaaaca agcatagtct gagcggaaga ccactgaaag 660
tcaaagaaga tcctgatggt gaacatgcca ggagagcaat gcaaaaggtg atggctacga 720
ctggtgggat gggtatggga ccaggtggcc caggaatgat tactatccca cccagtatcc 780
taaataatcc caacatccca aatgagatta tccatgcatt acaggctgga agacttggaa 840
gcacagtatt tgtagcaaat ctggattata aagttggctg gaagaaactg aaggaagtat 900
ttagtatggc tggtgtggtg gtccgagcag acattcttga agataaagat ggaaaaagtc 960
gtggaatagg cactgttact tttgaacagt ccattgaagc tgtgcaagct atatctatgt 1020
tcaatggcca gctgctattt gatagaccaa tgcacgtcaa gatggatgag agggccttac 1080
caaaaggaga tttcttccct cctgagcgtc cacaacaact tccccatggc cttggtggta 1140
ttggcatggg gttaggacca ggagggcaac ccattgatgc caatcacctg aataaaggca 1200
tcggaatggg aaacataggt cccgcaggaa tgggaatgga aggcatagga tttggaataa 1260
ataaaatggg aggaatggag gggccctttg gtggtggtat ggaaaacatg ggtcgatttg 1320
gatctgggat gaacatgggc aggataaatg aaatcctaag taatgcactg aagagaggag 1380
agatcattgc aaagcaggga ggaggtggag gtggaggaag cgtccctggg atcgagagga 1440
tgggtcctgg cattgaccgc ctcgggggtg ccggcatgga gcgcatgggc gcgggcctgg 1500
gccacggcat ggatcgcgtg ggctccgaga tcgagcgcat gggcctggtc atggaccgca 1560
tgggctccgt ggagcgcatg ggctccggca ttgagcgcat gggcccgctg ggcctcgacc 1620
acatggcctc cagcattgag cgcatgggcc agaccatgga gcgcattggc tctggcgtgg 1680

-continued

```
agcgcatggg tgccggcatg ggcttcggcc ttgagcgcat ggccgctccc atcgaccgtg   1740
tgggccagac cattgagcgc atgggctctg gcgtggagcg catgggccct gccatcgagc   1800
gcatgggcct gagcatggag cgcatggtgc ccgcaggtat gggagctggc ctggagcgca   1860
tgggccccgt gatggatcgc atggccaccg gcctggagcg catgggcgcc aacaatctgg   1920
agcggatggg cctggagcgc atgggcgcca acagcctcga gcgcatgggc ctggagcgca   1980
tgggtgccaa cagcctcgag cgcatgggcc ccgccatggg cccggccctg ggcgctggca   2040
ttgagcgcat gggcctggcc atgggtggcg gtggcggtgc cagctttgac cgtgccatcg   2100
agatggagcg tggcaacttc ggaggaagct tcgcaggttc ctttggtgga gctggaggcc   2160
atgctcctgg ggtggccagg aaggcctgcc agatatttgt gagaaatctg ccattcgatt   2220
tcacatggaa gatgctaaag gacaaattca acgagtgcgg ccacgtgctg tacgccgaca   2280
tcaagatgga gaatgggaag tccaaggggt gtggtgtggt taagttcgag tcgccagagg   2340
tggccgagag agcctgccgg atgatgaatg gcatgaagct gagtggccga gagattgacg   2400
ttcgaattga tagaaacgct taagcagttg ccttttttaa acatcgatac gagacctctg   2460
aatttgtatt ttttcttgtt aaccatttta atttgttggc tggatgtata aagatgttta   2520
aaaaattcag ttgctttttg gggtaatttg aattactttt ttaatgactg gggttccatt   2580
tgactgtttg cattgagatt gcaatgtgcg caattttttt tgtagttgtg gcatcttgtt   2640
gacatcgaat atgactttga taataaatac cggttcctga aaaaaaaaaa aaaaaaaaaa   2700
aaa                                                                 2703
```

<210> SEQ ID NO 163

<400> SEQUENCE: 163

000

<210> SEQ ID NO 164
<211> LENGTH: 5742
<212> TYPE: DNA
<213> ORGANISM: Rattus norvegicus

<400> SEQUENCE: 164

```
ggcggtgcaa gagagctgag ggaggcgcga gggcgcggag ttccaggtcg agcagttagg     60
ccgcgagcga ctgcggcgcc gagccgatga gtaacccgaa gcccctagag gagtggtcac    120
ctgcctgagg gcacttctgt cccaccagca tcagaccagg ccgcaccgag tccccggcac    180
catgtttggg aagaggaaga agcgggtgga gatctccgcg ccgtccaact tcgagcaccg    240
cgtgcacacg ggcttcgacc agcacgagca gaagttcacg ggcctgcccc gccagtggca    300
gagcctgatc gaggagtcgg ctcgccggcc caagcccctc gtcgaccccg cctgcatcac    360
ctccatccag cccggggccc ccaagggggga gcctcatgac gtggccccta acgggccatc    420
agcggggggc ctggccatcc cccagtcctc ctcctcctcc tcccggcctc ccacccgagc    480
ccgaggtgcc cccagccctg gagtgctggg accccacgcc tcagagcccc agctggcccc    540
tccagcctgc acccccgccg cccctgctgt tcctgggccc cctggccccc gctcaccaca    600
gcgggagcca cagcgagtat cccatgagca gttccgggct gccctgcagc tggtggtgga    660
cccaggcgac ccccgctcct acctggacaa cttcatcaag attggcgagg gctccacggg    720
catcgtgtgc atcgccaccg tgcgcagctc gggcaagctg gtggccgtca agaagatgga    780
cctgcgcaag cagcagaggc gcgagctgct cttcaacgag gtggtaatca tgagggacta    840
```

-continued ccagcacgag aatgtggtgg agatgtacaa cagctacctg gtgggggacg agctctgggt 900
ggtcatggag ttcctggaag gaggcgccct caccgacatc gtcacccaca ccaggatgaa 960
cgaggagcag atcgcggccg tgtgccttgc agtgctgcag gccctgtcgg tgctccacgc 1020
ccagggcgtc atccaccggg acatcaagag cgactcgatc ctgctgaccc atgatggcag 1080
ggtgaagctg tcagactttg ggttctgcgc ccaggtgagc aaggaagtgc cccgaaggaa 1140
gtcgctggtc ggcacgccct actggatggc cccagagctc atctcccgcc ttccctacgg 1200
gccagaggta gacatctggt cgctggggat aatggtgatt gagatggtgg acggagagcc 1260
cccctacttc aacgagccac ccctcaaagc catgaagatg attcgggaca acctgccacc 1320
ccgactgaag aacctgcaca aggtgtcgcc atccctgaag ggcttcctgg accgcctgct 1380
ggtgcgagac cctgcccagc gggccacggc agccgagctg ctgaagcacc cattcctggc 1440
caaggcaggg ccgcctgcca gcatcgtgcc cctcatgcgc cagaaccgca ccagatgagg 1500
cccagcgccc ttcccctcaa ccaaagagcc ccccgggtca cccccgcccc actgaggcca 1560
gtagggggcc aggcctccca ctcctcccag cccgggagat gctccgcgtg gcaccaccct 1620
ccttgctggg ggtagatgag accctactac tgaactccag ttttgatctc gtgactttta 1680
gaaaaacaca gggactcgtg ggagcaagcg aggctcccag gacccccacc ctctgggaca 1740
ggccctcccc catgttcttc tgtctccagg aagggcagcg gccctcccat cactggaagt 1800
ctgcagtggg ggtcgctggg ggtggagaga acactaagag gtgaacatgt atgagtgtgt 1860
gcacgcgtgt gagtgtgcat gtgtgtgtgt gcaaaggtcc agccaccccg tcctccagcc 1920
tgcaaggggt gtctggcgcc ttgcctgaca cccagccccc tctcccccctg agccattgtg 1980
ggggtcgatc atgaatgtcc gaagagtggc cttttcccgt agccctgcgc cccctttctg 2040
tggctggatg gggagacagg tcagggcccc ccaccctctc cagcccctgc agcaaatgac 2100
tactgcacct ggacagcctc ctcttttcta gaagtctatt tatattgtca ttttataaca 2160
ctctagcccc tgcccttatt gggggacaga tggtccctgt cctgcggggt ggccctggca 2220
gaaccactgc ctgaagaacc aggttcctgc ccggtcagcg cagccccagc ccgcccaccc 2280
ctgcctcgag ttagttttac aattaaaaca ttgtcttgtt ttgtgtctgt gtgcgatgtg 2340
tggggggcag gggccctgc ccggctgtct tgggtgggaa tttgcaggga gagggtctgg 2400
atctgggagc aaaccacgat tccagccaag gcagggcaag ggtggggtgg ggagtgggga 2460
gttcaggtca tagcagccag taagctcccc cagcctgcca ctccccagaa tggggcagga 2520
ttgtccccac ccctggaagc agccagtttg ccacagtcca tgtgcagact gatcccagtt 2580
tgccaaatct gcaatttcct ggaacctttt aaaggctgtc ttgagcgcgt ttggtgagta 2640
ggagctaacc caagttagta aattgaaggc catttggcaa attggtcagt gggcagatgg 2700
gcttttgggg attgactgag gctgactggc ctggagctgc tggcttcgga gagacaccct 2760
gtgaagtgtg tccttccacg caggagccca gagccgagcc cacgctgggg ggaatctgac 2820
tggcatggag gtggccatgc caccatcgct gctgcagctg catcctggca ctttgcgcct 2880
caggccctgt tgggctccac tttctgcatc ctccccagcc cccagggagg cagtggagtg 2940
gggagagagc caggagtgag cctccgtccc caaagccagc caggcgtcat cagcaccaga 3000
gacctcagcc tggtcctctc gggaagtgag tggccagggc agagattcca ggttagtcca 3060
cgcctcccac ccttcacagg tcctgacccc aagaatcaga gcactgtgtg tgtggcaggg 3120
cctatgccaa gtgcaaacac agcctagatg gatcatcaca gagtgaaacc cagcggtgca 3180
agcagctgtg ctctctgcga tgtattggag gcttaggtga ggtggatgcc tttctggaaa 3240

-continued aaaaaaaaat gctaacattg gcaaaagaag aaatagaaaa caagaccaaa ataactgtct 3300
cctcactgca cacacactcc agaataaata aaaggtttca ggcttgaatg cactttcaaa 3360
tgagattttt tttttttttt tgagacggag tatcgctctg tcgcccaggc tggagtgcgg 3420
tggcacggtc ttggctcgct gcaacttctg cctcctgggt tcaagcgatt ctcctgcctc 3480
agcctcccag gtggctggga ttgcaggcgc ttgccaccac gccgggctag ttttttgtat 3540
tttgggtaga gactgggttt cgccatcttg gccagactgg tcttgaactc ctgacctcgt 3600
gatccgccca cctcagcctc ccaaggtgct gggattgcag gcatgagcca ccatgcctgg 3660
cctcaaatga ggtttaccag actttgaagg agcaggtaat tccttctacc ttgtgaacaa 3720
gtcgttccag aaagatagca gctcaggagg cctctgtgac catggttcca gacccagata 3780
aggacggcaa agaacagagc atctcagaaa cgcaaggctc acagccaggg tgcccggcga 3840
ccccacgggc actgagaaca gctagctcta ggagctccac tctcctgctg aagaaaccac 3900
gggctcagag acggggagct ccctcgccca gccacatctg tgaccccacg gtaactctgc 3960
tggttttggt gccttcagtc actcactgca ggtttgtttt gttttgtttt gttttgtttt 4020
gagttttttt gtttttttgtt ttttgttttt agagacggga tgttgctatg ttgcctaggc 4080
tggtttcgaa ctcctggcct caggggatcc tccctccttg gccccgcaag gtgctgggat 4140
tgcaggcgtg agccgccgtg cccggcccgc tcactgcagt ttgaaggcat ggctttgggt 4200
ggcgtggggt gaaagctgcc cgaggccccg ttcctcccca cgtggctgcc tcctgccaga 4260
gccagtcagg aaaacagacc ccaactagag ttgtttcaaa tggcagggat ttggtaccgg 4320
tggttggatc atgacaaagc tctgagaagg ctggaggagc cacagagtgc caagtgccca 4380
gcaatcatta gaggaaggag gctgctgcca cctgtgtggc tagaggaaca gaggggccaa 4440
tggcattccc caaaccccac tctcgcctct gtctggccag agcagaatgg cttcttccag 4500
cttcccaccc tggactccca cccaggagcc tcctcctggc agacccttcc tgaccccacc 4560
ggcccggggg gtctacagat ccatgtttca ggcgtccgcc tggagcggaa caggggagtg 4620
cttaggacaa gggtggtgcc agaggatcca ctctgcccac atttagttga ccagctgagg 4680
cactccacgg gaatgaatga ctctcgacag gtgccggagg tgaggagggg cccggaggcc 4740
caggaggggc acagggatgg attcgtccgc ctgggggctg gaggtgtgtt tacagagccc 4800
caaaataaac aatgcaacca ggtcagacca gcggttctca cacagtgtgg ttcccagacc 4860
agcagcatca ctgggagctt actggacacg caaataaatc cctgtgtgcc accccagctg 4920
catcagatgc tggtggggcc cagtgatctg tatttaacac accctccggg ggatgccggt 4980
gcccactcac gtttgagaac ccctgcgatc cacgactgcc ctcccgtgta aaaggcccac 5040
ctctgtggga ctccaagtca tcagcaccct agggtccttc cgtctttttc cttcctcctg 5100
ggacacctgc ctctcccatg tcgtattaga gaattcctta tgctcccaag tgggcacggg 5160
gagaggaagg cactcctctt taaggaccga cccagaggtt ttgccattgc ttcactggcc 5220
agagcttagt cacgcagcct cacccagagg caagggaggt tggaaaatgt agtgtttgtg 5280
tgtgtctaac acaaattcta ttaccatgca gtcaggattc tccactcttg ctctttcatt 5340
agatttgctg ggcttcaccc tggactttct gatttagtga cagaacagag aacccagagg 5400
cagacccaga tgtgtacaag ggcttcatat acaatcagga gatttaataa tcatgctagg 5460
ggccgggtgc agtggctcac gcctgtaatc ccaagcactt tggggagccg aggcaggcgg 5520
atcacttgag gtcaggagtt tgagaccagc ctgggcaaca aagtgagacc ctgtctctac 5580

-continued

```
taaaaataac aaaaattagc cgggcgtggt ggtgggtgcc tgtaatccca gctcctcggg   5640
tggctgaggc atgagaatca cttgaaccca ggaggcagag gtttcagtga gctgagatca   5700
catcactgca ctccagcctg ggtgacagag tgagattccg tc                       5742
```

<210> SEQ ID NO 165
<211> LENGTH: 3709
<212> TYPE: DNA
<213> ORGANISM: Rattus norvegicus

<400> SEQUENCE: 165

```
gggctgcagg aattccccca cagagggagc atgacttcgg caacttcacc tatcattctg     60
aaatgggacc ccaaaagttt ggaaatccgg acgctaacag tggaaaggct gttggagcca    120
cttgttacac aggtgactac acttgtcaac acaagcaaca aaggcccatc tggtaaaaag    180
aaagggaggt caaagaaagc ccatgtacta gctgcctctg tagagcaagc cactcagaat    240
ttcctggaaa agggtgaaca gatcgctaag gagagtcaag atctcaaaga agagttggtg    300
gctgctgtag aggatgtgcg caaacaaggt gagacgatgc ggatcgcctc ctccgagttt    360
gcagatgacc cttgctcgtc ggtaaagcgc ggcaccatgg tacgggcggc aagggctttg    420
ctctccgcgg tgacacgctt actcatcctg gcggacatgg cagatgtcat gagactttta    480
tcccatctga aaattgtgga agaggccctg gaagctgtca aaaatgctac aaatgagcaa    540
gaccttgcaa accgttttaa agagtttggg aaaaagatgg tgaaacttaa ctatgtagca    600
gcaagaagac aacaggagct gaaggatcct cactgtcggg atgagatggc agccgcccga    660
ggggctctga agaagaatgc cacaatgctg tacacggcct ctcaagcatt tctccgccac    720
ccagatgtcg ccgctacgag agccaaccga gattatgtgt tcaaacaagt ccaggaggcc    780
atcgccggca tctccaatgc tgctcaagct acctcgccca ctgacgaagc caagggccac    840
acgggcatcg gcgagctggc tgcggctctt aatgagtttg acaataagat tatcctggac    900
cccatgacgt tcagcgaggc caggttccgg ccgtccctgg aggagaggct ggagagcatc    960
atcagcggcg cagcgctgat ggccgactcc tcctgcacgc gagacgaccg gcgcgagagg   1020
atcgtggcgg agtgcaacgc cgtgcggcag gcgctccagg acctgctcag cgagtacatg   1080
aataatactg gaaggaaaga aaaaggagat cctctcaaca ttgcgattga taagatgact   1140
aagaaaacaa gagatctaag gagacagctt cggaaagcag tgatggatca catatctgac   1200
tctttcctgg aaaccaatgt tcctttgcta gttctcattg aggctgcaaa gagcggaaat   1260
gaaaaggaag tgaaagaata tgcccaagtt ttccgtgagc atgccaacaa actggtagag   1320
gttgccaatt tggcctgttc catctccaac aatgaagaag ggtgaaatt agttcggatg    1380
gcagccaccc agattgacag cctgtgtccc caggtcatca atgccgctct gacactggct   1440
gcccggccac agagcaaagt tgctcaggat aacatggacg tcttcaaaga ccagtgggag   1500
aagcaggtcc gagtgttgac agaggccgtg gatgacatca cctcagtgga tgacttcctc   1560
tctgtctcag aaaatcacat cttggaggat gtgaacaagt gtgtgatagc cctccaagag   1620
ggcgatgtgg acactctgga ccggactgca ggggccatca ggggccgggc agctcgagtc   1680
atacacatca tcaatgctga gatggagaac tatgaagctg ggtttatac tgagaaggtg    1740
ttggaagcta caaaattgct ttctgaaaca gtgatgccac gcttcgctga acaagtagag   1800
gttgccattg aagccctgag tgccaacgtt cctcaaccgt ttgaggagaa tgagttcatc   1860
gatgcctctc gcctggtgta tgatggcgtt cgggacatca gaaaggctgt gctgatgatc   1920
aggaccccag aagaactaga ggatgattct gactttgagc aggaagatta tgatgtgcgt   1980
```

-continued agagggacaa gtgttcagac tgaggatgac cagctcattg cagggcagag cgcacgggcc 2040
atcatggcgc aactaccgca ggaggagaag gcaaaaatag ctgagcaggt ggagatattc 2100
catcaagaga aaagcaagct ggatgcagaa gtggccaaat gggacgacag cggcaatgat 2160
atcattgtac tggccaagca gatgtgtatg atcatgatgg aaatgacaga cttcacaaga 2220
ggcaaaggcc cattgaaaaa tacatctgat gtcattaatg ctgccaagaa aattgccgaa 2280
gcaggttctc gaatggacaa attagctcgt gctgtggctg atcagtgtcc tgattcagca 2340
tgtaagcagg atttattagc ctaccttcaa cgaattgcct tgtattgcca tcagcttaat 2400
atctgcagca aggtgaaggc agaagtgcag aatctgggag gagagctcat tgtgtcaggg 2460
acaggagttc agagcacttt cactaccttt tatgaggtag attgtgatgt catagatggg 2520
ggcagggcta gtcaactttc tacccacctc ccaacctgtg ctgagggagc tccgatcggg 2580
agtggaagca gtgattcctc catgctggac agtgccacat cgcttatcca ggcagctaaa 2640
aacctgatga atgctgttgt cctcacggtg aaagcatcct atgtggcctc aaccaaatac 2700
cagaaggtct atgggacagc agctgtcaac tcacctgttg tgtcttggaa gatgaaggct 2760
ccagagaaga agccccttgt gaagagagaa aagcctgaag aattccagac acgagttcga 2820
cgaggttctc agaagaaaca catttcgcct gtacaggctt taagtgaatt caaagcaatg 2880
gattccttct aggacgatag gttttaacaa gaaagctttt tctttctttt ctttctttct 2940
ttttcttttt aattccattt ttgtatgcat acctgccagc tcgtatgcct ctggcatggg 3000
gaaattaagg gaacagtgtc tgtttgcatg taagatgaga tgagatcaat actactgatc 3060
catctgtagc ctgggaagga gacaggacat tcctgtacta aggtggcaca gagctgtcct 3120
ttgcaacatt ctcataaaat tgggcacaga gttcgcattg gcgcaatatt tatgggagtg 3180
ggagggatgg ggaaaataaa cttaactcta caaaagcaaa ctctaatgca tgcaagaatc 3240
attaggttgg caggtatatg cataagtgaa aaatctggaa gtgtaatggt agaacataaa 3300
acttgtattg cttctgtttc agtgcaaaaa tgtactagcc aatacgctta agtgtgtggc 3360
ccatgaattg aacaatttaa ccttgaagtc tatatccgtg atattatgtc gatttttaac 3420
tgaggggaaa ttaactagtc cagcctaaaa tgcttctttt aatctgcatt ctgtttcctc 3480
ttctagttgt gccattacta gtgatcatgt ttttttcccc cctttaatga aaacaataaa 3540
catctatttg agacaattaa aatccttctg gggcactgg aagcacaata cggtgaccaa 3600
tcttgctttc atttttttt ctttttaatt tgaaccatga ttttgctaga aatagaaggc 3660
ccagtggtgg aatattagag ggaaggaaac tgacaacgtg tgaaagtta 3709

<210> SEQ ID NO 166
<211> LENGTH: 1874
<212> TYPE: DNA
<213> ORGANISM: Rattus norvegicus

<400> SEQUENCE: 166
ccggtgatgg cggctggtga tggggacgtg aagctaggca ccctggggag tggcagcgag 60
agcagcaacg acggcggcag cgagagtcca ggcgacgcgg gagcggcagc ggaaggggga 120
ggctgggcgg cggcggcgtt ggcgcttctg acggggggcg gggaaatgct gctgaacgtg 180
gcgctggtgg ctctggtgct gctgggggcc taccggctgt gggtgcgctg ggggcggcgg 240
ggtctggggg ccggggccgg ggcgggcgag gagagccccg ccacctctct gcctcgcatg 300
aagaagcggg acttcagctt ggagcagctg cgccagtacg acggctcccg caacccgcgc 360

-continued

```
atcctgctcg cggtcaatgg gaaagtcttc gacgtgacca aaggcagcaa gttctacggc    420
ccggcgggtc catatggaat atttgctggt agggatgcct ccagaggact ggccacattt    480
tgcctagata aagatgcact tagagatgaa tatgatgatc tctcagattt gaatgcagta    540
caaatggaga gtgttcgaga atgggaaatg cagtttaaag aaaaatatga ttatgtaggc    600
agactcctaa aaccaggaga agaaccatca gaatatacag atgaagaaga taccaaggat    660
cacaataaac aggattgaac tttgtaaaca accaaagtca ggggccttca gaactgcaat    720
tcttactccc tttcacagac tgtccggagt ctttgggttt gattcacctg ctgcgaaaaa    780
cattcaacaa attgtgtaca agataaatta atctcactat gaagatttga ataactagac    840
attatttatg ctgccaaact catttgttgc agttgtttgt aatgtctagt ggggcttcat    900
catcctgaaa agaaggagac agggattttt ttaaagagca agaaagtcac aatattactt    960
ctttccttcc ttttttcctt ctttcctttc ttctttctct ttctttcttt ttaaaatata   1020
ttgaagacaa ccagatatgt atttgctact caagtgtaca gatctcctca agaaacatca   1080
agggactcct gtgtcacata ctgtgttttt attttaacat gggtgaggga ggcgacctga   1140
tcaggggagg tgggggtaca catcaatttg agttgttcag gctactgaaa cattaaaatg   1200
tgaattccca aacttttctt tttggctttg tcagggaaaa gaaaaatatc tttataaaga   1260
aatctttgga aattaggaga aggaatttca ggtgggttta agtcagagct agttccccaa   1320
cagaaagatc atttgaaacc agtttttatc ccttctcttt ccttcccttt ccctaaatca   1380
aatcaatatt aattgtgcct tatttcactt aacatagact tgaattattt ttagggaaag   1440
cccctataat gaattcagaa atcactacaa gcagcattaa gactgaagtt ggaatattct   1500
gttgaccata aaaccttgat atcattctgt gtatatagaa tgtaaaagga atattacagt   1560
gttaactgcc atatatgtaa tatacacaaa ctcaattagc attgtaatgg ccaaatgcat   1620
tcccccatgc ttttctgttt tcaaaaaaat tgaaaaacaa atcaactctt atccccaaca   1680
gctgcctaat tttaggagtc tgaccctcca catctcactg gtgtgggtgc atggggctgt   1740
ggagtgggtg tcagtatgga tgtgtctgaa tgtgtgaggc cttggaaggg actctttctg   1800
cagatactgt aaatacaagt accattttaa taaagcatgt acaataaacc aaaaaaaaaa   1860
aaaaaaaaaa aaaa                                                     1874
```

<210> SEQ ID NO 167
<211> LENGTH: 2570
<212> TYPE: DNA
<213> ORGANISM: Rattus norvegicus

<400> SEQUENCE: 167

```
ggactcgagc gctccgattg gagttagggc ctgcttgtct gcgtgctgcg aagtccgcgg     60
ctgcccccgg ggccctagtc gttgggttcc agggtccttc acgttccatt cccaggctgg    120
tctgagctcc ggggccgtgg tcccgctgcc tcctccggtc gtcgtgcgga agctgcgacg    180
caggcagacc atggcagagt tctcccagaa acgggggaag cggcgtagcg acgaagggct    240
gggcagcatg gtggacttcc tcctggccaa tgcccgcctg gtgctgggcg tgggcggggc    300
tgctgtgctg ggcattgcca ccctggccgt gaagcggttc attgacaggg ccactagccc    360
gcgggatgag gatgacacca aggcagacag ctggaaggaa ctgagcctgc tcaaggccac    420
accacacctg cagccccggc ctccacctgc tgcccttagc cagccagtgt tgcccttggc    480
cccctcgtcg tctgccccag aagggcctgc agaaactgat cctgaggtga caccacagct    540
cagctcccca gcaccgctgt gtctgacact gcaggagagg ctgctggcct tcgagcggga    600
```

-continued ccgtgtgacc atcccagcag cccaggtggc tttggccaaa cagctggctg gcgacatcgc 660
cctggagctg caggcctact ttcggagcaa gttcccggaa ctgccctttg ggcattcgt 720 gcctgggggg ccgctctacg acgggctgca ggcgggggct gcggaccatg tgcgtctcct 780
ggtgccactg gtgctggagc cgggcctgtg gagcctggtg ccgggcgtgg acactgtggc 840
gagggaccct cgctgctggg ccgtgcgcag gacgcagctt gagttctgcc cccgtgggag 900
cagcccctgg gaccgcttcc tggtcggggg ctacttctcc tcccgcgtcc tgctggagct 960
actccgcaag gcgctggctg cttctgtcaa ctggccggcc attggcagcc ttctcgggtg 1020
cctgatccgg cccagcatgg cctcggagga gctgctgctc gaggtgcagc acgaacgcct 1080
ggagctcact gtggctgtgc ttgtggcagt ccctggggtc gatgctgacg accgcctcct 1140
cttggcctgg cccctggagg ggctggcggg gaacctctgg ctgcaggacc tgtatccagt 1200
ggaggctgct aggctgcgag ccctggacga ccatgacgct gggactcgcc ggcggctgct 1260
gctgctgctg tgtgctgtct gccgtggttg ctcggctctg ggcagctag gccggggtca 1320 cctgacccag gtggtcctgc gtctggggga ggacaacgtg gattggacgg aggaggcctt 1380
gggtgagcgc ttcctgcaag ccctggagct gctcatcggc agcctggagc aggccagcct 1440
gccctgccac ttcaacccca gcgtgaacct cttcagcagc ttgcgtgagg aggagattga 1500
cgacattggc tatgcgctat acagtggcct acaggagccc gaggggctgc tctaggtggg 1560
tggaaacggg tggttgccat gttttctaat gctggggagc tgcacccacc tcccttccag 1620
ggatttgaat agtggttttt ctctagcttt ttgccagaac aaaggagggt acattactta 1680
aacccagggc atcaggatgt gcttgggcta tggtggccat aaaccctgag cccagagagc 1740
ttgggtcact gtcacctgag tgcagctggg ctgcctcagg cagcttggag tgccagccat 1800
tcctgcaagc accgtttcag ctcttggggc caaccccagg acctttggct ctgtccatca 1860
ccagcaacca atccaccaac agaatgtggt ttctgccatc ctgggcagaa gctgaaggcc 1920
agcttcacat ttctgctgag agaaggtgac ttaacgcctt ttccggccct agctccaggc 1980
gttttgaggc gtctggtgcc tgatggtagg tatggtgtgt ttgttctgtc ccccaggggc 2040
tggagtcacc tggtgcccct gaaggacaga tttttggctg ttaaaggatg gcattttcct 2100
gctgtcttct gtgcgtttag ttttcttgct gagcgggagc tcagtatgac ttgccaccca 2160
cctgatacct cagggcaagg ccctttttcc ctccagccag gtgagtgttt tcttcaggca 2220
gctgagggtc ctgggggagc tgaggctctg tgctgcaccc ccagcccaca gctggggcat 2280
ctcactggag ctgttccagg ccccactgga gagcagagga cctgatcccc cactagagag 2340
gtccggtgtg cacagccggc ctcccagtgt gccaaaatga actgctctca gctgatggct 2400
gtattctgac tttgaagcct gttaagaggt agcaaggggg ctagaggagg gagattccac 2460
ctcccctccc aagtgaccct cctcctgcct ctggtatcct tccttttgaa acgaagctca 2520
gcttcgaaga tgtgaacaag aataaaagga aaaaattcta atgtatatat 2570

<210> SEQ ID NO 168
<211> LENGTH: 1755
<212> TYPE: DNA
<213> ORGANISM: Rattus norvegicus

<400> SEQUENCE: 168
acggagatct cgccggcttt acgttcacct cggtgtctgc agcaccctcc gcttcctctc 60
ctaggcgacg agacccagtg gctagaagtt caccatgtct attctcaaga tccatgccag 120

-continued

```
ggagatcttt gactctcgcg ggaatcccac tgttgaggtt gatctcttca cctcaaaagg    180
tctcttcaga gctgctgtgc ccagtggtgc ttcaactggt atctatgagg ccctagagct    240
ccgggacaat gataagactc gctatatggg gaagggtgtc tcaaaggctg ttgagcacat    300
caataaaact attgcgcctg ccctggttag caagaaactg aacgtcacag aacaagagaa    360
gattgacaaa ctgatgatcg agatggatgg aacagaaaat aaatctaagt ttggtgcgaa    420
cgccattctg gggtgtccc ttgccgtctg caaagctggt gccgttgaga agggggtccc     480
cctgtaccgc cacatcgctg acttggctgg caactctgaa gtcatcctgc cagtcccggc    540
gttcaatgtc atcaatggcg gttctcatgc tggcaacaag ctggccatgc aggagttcat    600
gatcctccca gtcggtgcag caaacttcag ggaagccatg cgcattggag cagaggttta    660
ccacaacctg aagaatgtca tcaaggagaa atatgggaaa gatgccacca atgtgggga     720
tgaaggcggg tttgctccca acatcctgga gaataaagaa ggcctggagc tgctgaagac    780
tgctattggg aaagctggct acactgataa ggtggtcatc ggcatggacg tagcggcctc    840
cgagttcttc aggtctggga agtatgacct ggacttcaag tctcccgatg accccagcag    900
gtacatctcg cctgaccagc tggctgacct gtacaagtcc ttcatcaagg actacccagt    960
ggtgtctatc gaagatccct ttgaccagga tgactgggga gcttggcaga agttcacagc   1020
cagtgcagga atccaggtag tgggggatga tctcacagtg accaacccaa agaggatcgc   1080
caaggccgtg aacgagaagt cctgcaactg cctcctgctc aaagtcaacc agattggctc   1140
cgtgaccgag tctcttcagg cgtgcaagct ggcccaggcc aatggttggg gcgtcatggt   1200
gtctcatcgt tcgggggaga ctgaagatac cttcatcgct gacctggttg tggggctgtg   1260
cactgggcag atcaagactg gtgccccttg ccgatctgag cgcttggcca agtacaacca   1320
gctcctcaga attgaagagg agctgggcag caaggctaag tttgccggca ggaacttcag   1380
aaaccccttg gccaagtaag ctgtgggcag gcaagccttc ggtcacctgt tggctacaca   1440
gacccctccc ctcgtgtcag ctcaggcagc tcgaggcccc cgaccaacac ttgcaggggt   1500
ccctgctagt tagcgcccca ccgccgtgga gttcgtaccg cttccttaga acttctacag   1560
aagccaagct ccctggagcc ctgttggcag ctctagcttt tgcagtcgtg taatgggccc   1620
aagtcattgt ttttctcgcc tcactttcca ccaagtgtct agagtcatgt gagcctcgtg   1680
tcatctccgg ggtggccaca ggctagatcc ccggtggttt tgtgctcaaa ataaaaagcc   1740
tcagtgaccc atgag                                                    1755
```

<210> SEQ ID NO 169
<211> LENGTH: 3800
<212> TYPE: DNA
<213> ORGANISM: Rattus norvegicus

<400> SEQUENCE: 169

```
gggggacggt gaaggttgcc tcccgcccgt ccgggctctg atcctccgtc tccccgtccc     60
ccggcggccg gcccatggcc tggcggaggc ccgaaccatg gacctccgca ccgccgtgta    120
caacgccgcc cgtgatggca agctgcagct gctccagaag ctgctcagcg gccggagccg    180
ggaggaactg gacgagctga cgggcgaggt ggccggcggg ggaacgccgc tactcatcgc    240
cgcccgctac ggccacctgg acgtggtgga gtacctggtg gaccggtgcg gcgcgagcgt    300
ggaggccggt ggctcggtgc acttcgatgg cgagaccatc gagggcgcgc cgccgctgtg    360
ggccgcctcc gcagccggcc acctggacgt ggtgcggagc ctgctgcgcc gcggggcctc    420
ggtgaaccgc accacgcgca ccaactccac gcctctccgc gccgcctgct tcgacggcca    480
```

-continued

```
cctggaggtg gtgcgctacc tggtcggcga gcaccaggcc gacctggagg tggccaaccg    540
gcacggccac acgtgcctca tgatctcgtg ctacaagggc caccgtgaga tcgcccgcta    600
cctgctggag cagggcgccc aggtgaaccg gcgcagcgcc aagggcaaca cggccctgca    660
tgactgcgcc gagtccggca gcctggagat cctgcagctg ctgctggggt gcaaggcccg    720
catggaacgt gacggctacg gcatgacccc gctgctcgcg gccagcgtga cgggccacac    780
caacatcgtg gagtacctca tccaggagca gcccggccag gagcaggtcg caggggggaga   840
ggctcagcct gggctgcccc aagaagaccc ctccaccagc caggggtgtg cgcagcctca    900
gggggctccg tgctgcagct cctccccaga ggaaccactg aacggggaat cttacgaaag    960
ctgctgtccc accagccggg aagctgccgt ggaagccttg gaattgctgg gagctacgta   1020
tgtggataag aaacgagatc tgcttggggc ccttaaacac tggaggcggg ccatggagct   1080
gcgtcaccag gggggcgagt acctgcccaa accggagccc ccacagctgg tcctggccta   1140
tgactattcc agggaggtca acaccaccga ggagctggag gcgctgatca ccgacccgga   1200
tgagatgcgc atgcaggccc tgttgatccg ggagcgcatc ctcggtccct cgcacccgga   1260
cacttcctat tacatccgtt acaggggtgc cgtgtacgcc gactcgggca atttcgagcg   1320
ctgcatccgc ttgtggaagt acgccctgga catgcaacag agcaacctgg agcctctgag   1380
ccccatgacc gccagcagct tcctctcctt cgcggaactc ttctcctacg tgcttcagga   1440
ccgggccgcc aaaggcagcc tgggcaccca gatcggcttt gcagacctca tgggggttct   1500
caccaaaggg gtccgggaag tggaacgggc cctgcagctg cccagggagc ccggagactc   1560
agcccagttc accaaggcgc tggccatcat cctccacctg ctctacctgc tggagaaagt   1620
ggagtgcacc cccagccagg agcacctgaa gcaccagacc gtctaccgcc tgctcaagtg   1680
cgcgcccagg ggcaagaacg gcttcacccc tctgcacatg gctgtggaca aggacaccac   1740
aaacgtgggc cgctatcccg tgggcagatt cccctccctg cacgtggtca aagtgctgct   1800
cgactgcggg gccgacccgg acagcaggga ttttgacaac aacaccccgc tacacatagc   1860
agcccagaac aactgcccgg ccatcatgaa tgccctgatc gaagcagggg cccacatgga   1920
cgccaccaat gccttcaaga agacggccta cgagctgctg gacgagaagc tgctggccag   1980
gggtaccatg cagcccttca actacgtgac cctgcagtgc cttgcggccc gggccctgga   2040
taagaacaag atcccttaca agggcttcat cccggaagat ctggaggcgt tcatcgaact   2100
gcactgacct gcccagaacg cctgcaccct cacctctccc ctctcctgct gagatggggg   2160
aaatccggct gcggcatagc agatgctcgt tcttgcctcc ttcaggcacc aatcaggaga   2220
agggttctgc ctcccatccc ctctacctgc agacagggtc ggaggtgtta gcgagccttt   2280
ggtgctagaa gcctgcgggg tcatgtgcta agaggacagt ctttctccgg gagcccgctc   2340
actcattctg agttaggaaa agacacaaga ccttccccac atcctgtctg cctgggttag   2400
ggaggccttt gccttgttac ctagaggcgg agggactgaa gccattgcgt tccttccctg   2460
ctagaaacac aggaagaagt tgaggactgt ctgccttccc tcgtcccttt acctggccag   2520
ataactccag ccgctgaata cagtgttagg actgggggct cctgagatga gagtttgaga   2580
ttcagggaat gagaccacct ctcatttctt ccagcatgat cgcgccctgc tcccgtgcca   2640
ccgtagtccc tggcagacag gcagggctct gcccagggca gcctgccact tgcatagctt   2700
tcggttggtt tggtgttctg tttatttaat aagtgggcag gttgcaagcg ttgcacagaa   2760
attctgagat tttactgcct tttttttttt ttttaagaaa gttgtttgtt ggactccata   2820
```

-continued agtgaatttc aagcagtgag gattttgtgg tgcctgagat ggccgagggc acagggagtg 2880
agctgtatgt gtgaggaatt tggtgagcga gataaaagtc cacggtgtca acccctaaaa 2940
catgggtgac cgtacatttt tatacatctc cactctacgg ccttttacag gctttccgat 3000
tttacaggcc tttccaagtt tccattctcc ttagagagag aactgtgctt ccaaacagaa 3060
atcaggagtg accacaaagc ctgaaaacac tttgccaccc agcaaagaac tggcacaatt 3120
ggtttgggtc tgcattgcca tagtgcccga gttaaaactg caggccactc tgccttgcag 3180
tggcctctga tttcattgtg ggtgcatcca caggtggccc gagctgttct ttcagctgct 3240
ccaaggattg agacccaagt catcatgaaa aaggcccaag tacagtctta atgcgataaa 3300
tccactagct aagacgtcga gtgccaagac cagccttcca gccgaggttt ggacaaagtc 3360
tcaggttccc gtgactcagg gtaaggtgct ggggctgcca gaggacctgc cccagcaaga 3420
tttttgtcaa gagcgagact ccatcagccc aggcagacgg gagcaggttc ttggccagcg 3480
tagacagcag caaacagcag cagggaagcc attctcactg catcctccct gcagtagcca 3540
cggccaggcc cttaggagga gcagtgaccg ggggtgtcca gaaatatcct gtccctggat 3600
ggaaactagg tctcgtttgg attttttttt ttttttgccg tgttaggaaa ttatttatta 3660
atttacaaga caggttttaa ctcagccgag gtgggaaatg gtgtccctgt ccctcccaaa 3720
gcacagagca cagaaatgag gccgtttaca tggcgagtct ccgtgctggt gtttaagtca 3780
ttaaaaagat actcaaagag 3800

<210> SEQ ID NO 170
<211> LENGTH: 1219
<212> TYPE: DNA
<213> ORGANISM: Rattus norvegicus

<400> SEQUENCE: 170
acaggatctg cttagtgaaa gaagtggcaa gcaatggatc ccaaatatca gcgtgtagag 60
ctaaatgatg gtcacttcat gcccgtattg ggatttggca cctatgcacc tccagaggtt 120
ccgaggaaca gagctgtaga ggtcaccaaa ttagcaatag aagctggctt ccgccatatt 180
gattctgctt atttatacaa taatgaggag caggttggac tggccatccg aagcaagatt 240
gcagatggca gtgtgaagag agaagacata ttctacactt caaagctttg gtgcactttc 300
tttcaaccac agatggtcca accagccttg gaaagctcac tgaaaaaact tcaactggac 360
tatgttgacc tctatcttct tcatttccca atggctctca agccaggtga gacgccacta 420
ccaaaagatg aaaatggaaa agtaatattc gacacagtgg atctctctgc cacatgggag 480
gtcatggaga agtgtaagga tgcaggattg gccaagtcca tcggggtgtc aaacttcaac 540
tacaggcagc tggagatgat cctcaacaag ccaggactca agtacaagcc tgtctgcaac 600
caggtagaat gtcatcctta cctcaaccag agcaaactgc tggatttctg caagtcaaaa 660
gacattgttc tggttgccca cagtgctctg ggaacccaac gacataaact atgggtggac 720
ccaaactccc cagttctttt ggaggaccca gttctttgtg ccttagcaaa gaaacacaaa 780
cgaaccccag ccctgattgc cctgcgctac cagctgcagc gtggggttgt ggtcctggcc 840
aagagctaca atgagcagcg gatcagagag aacatccagg tttttgaatt ccagttgaca 900
tcagaggata tgaaagttct agatggtcta aacagaaatt atcgatatgt tgtcatggat 960
tttcttatgg accatcctga ttatccattt tcagatgaat attagcatag agggtgttgc 1020
acgacatcta gcagaaggcc ctgtgtgtgg atggtgatgc agaggatgtc tctatgctgg 1080
tgactggaca cacggcctct ggttaaatcc ctcccctcct gcttggcaac ttcagctagc 1140

-continued

```
tagatatatc catggtccag aaagcaaaca taataaattt ttatcttgaa ctaaaaaaaa   1200

aaaaaaaaaa aaaaaaaaa                                                1219


<210> SEQ ID NO 171
<211> LENGTH: 3564
<212> TYPE: DNA
<213> ORGANISM: Rattus norvegicus

<400> SEQUENCE: 171

ggagcgcagt cgctccgcga tggactcgcc ggtcccggcc tctatgttcg cccccgagcc     60

cagctccccg ggggcggcca gggccgcggc ggccgccgcc cgactccacg gcggctttga    120

ctcggactgc agcgaggacg gcgaggcgct caacggcgag ccagagctgg acctcaccag    180

caagctggtt ctagtgagcc ctacatcaga gcagtatgac agcctacttc ggcagatgtg    240

ggagaggatg gacgagggat gcggagagac catatatgtc attgggcagg gatcagatgg    300

gactgagtat gggctgagtg aagctgacat ggaggcctcc tacgccacag tgaagagcat    360

ggcggaacag atagaggccg atgtcatcct tctgcgggaa cggcaagaag ctgggggccg    420

cgtgcgtgat tacctggtcc ggaaacgagt aggagacaat gacttcctgg aggtcagggt    480

agcagtggtg ggcaacgtgg atgctggcaa aagcacgctt ctgggggtcc tgacacatgg    540

ggagctggac aatggccgag gctttgcccg ccagaaactc ttccgccaca aacatgaaat    600

tgaatctggt cgcaccagca gtgtgggcaa cgacattctg ggctttgaca gtgaaggcaa    660

tgtagtgaac aagcctgaca gccacggcgg cagcctggag tggaccaaga tctgtgagaa    720

gtccacgaaa gtcattacct tcatcgactt ggctggtcat gagaagtacc tgaaaaccac    780

tgtcttcggc atgacaggcc atctgcctga cttctgcatg ctcatggtgg gcagcaatgc    840

tggcatcgtg ggatgacca aagaacacct gggcttggca ctggcactca atgtacctgt    900

ctttgtggta gtcaccaaga ttgacatgtg tcctgccaac atcctgcaag aaaccctgaa    960

gctgttacag cgcctgctga agtcaccagg ctgccggaag atccccgtgc tggtgcagag   1020

caaagatgat gtgattgtca cagcctccaa cttcagctct gaaaggatgt gcccgatatt   1080

ccagatctcc aacgttacag gcgagaacct agatctgctg aagatgttcc tcaacctcct   1140

ctccccccgc accagctaca gggaggagga gcctgctgag tttcagattg atgacaccta   1200

ctccgtcccg ggtgtgggga cagtggtttc ggggacaaca ctgagaggcc tgatcaagct   1260

gaatgacacg ctgctgctgg gcccagaccc cttgggtaac ttcctgtcca ttgctgtcaa   1320

atccatccat cgcaagcgca tgcctgtcaa ggaggtgcgg ggtggccaga cagcatcctt   1380

tgcgctgaag aagatcaagc gctcgtccat ccggaagggc atggtgatgg tttccccacg   1440

tttgaatccc caagcctcct gggagtttga ggccgagatt ctcgtcctcc accaccccac   1500

cacaattagc ccgcgctacc aggccatggt gcactgtggg agcatcaggc agacagccac   1560

cattctgagc atggacaagg actgtctgcg cactggggac aaggccactg tacacttccg   1620

cttcatcaag acccctgagt acctgcacat agaccagcgg ctggtgttcc gggaaggccg   1680

caccaaggct gtcggcacca tcaccaagct cctccagacc accaacaact ccccaatgaa   1740

ctccaagccg cagcagatta aaatgcagtc gacgaaaaag ggccccctga cgaaacgaga   1800

cgagggggc ccgtctggtg ggccagcagt aggagcaccc ccacctggag atgaagcctc   1860

ctctgtaggg gcagggcaac cagctgcgtc cagcaatctc cagcctcagc ctaagcccag   1920

cagtggaggc cggcgacgag gggccagcg ccacaaggtg aagtcccagg gggcctgtgt   1980
```

-continued

| | |
|---|---|
| gactcctgcc agcggctgct gaaccttccc ctggcccacc ctcaccaccc aaggggtcat | 2040 |
| catctctggc caccactcca ccagatgggc agagcagcta tgaccgccac ccagccctcc | 2100 |
| cgctcaggcc acagccggag cctccgcatt gcccccaccc ccattttcca ggggggttgt | 2160 |
| aatttataag ctgacgaagg tagccagact tccggaggac tgaccatctc tcactgtcct | 2220 |
| ccccaccttc ttcctcactc acacattttt tgtacatctg ggcccttagt ttttattctg | 2280 |
| tttattatat gtctctgtct ctctctattg tgtgtgtgtg tgtgtgtgtg tgtgtgtgtg | 2340 |
| tgtgtgtgtg gtgcaggagt gccaccccca gggccctgtc aacctctctt ttctcctcca | 2400 |
| tggctgtctg cctgcgtatc tgtctctgag aatcctcggg gcggtcaggg gatgtcagga | 2460 |
| ggggaaggag ccgccctccc tatcttgctg ctcctcttgg cactcagggg caccttccat | 2520 |
| ggagccagac cgggtggagg ggcttctggg atttggtgtc tgctgctgcc agagcaggaa | 2580 |
| cccccagtct aggacttggg cattttaaca gggagaaagt agtggcttcc cttttctctc | 2640 |
| tctcctcctt tttcccttta agcccacaga ttcaggtcat gccaaaagct ctctggttgt | 2700 |
| aacctggaga catgtggagg ggaatggcga tgggattata ggactctccc catctcgggc | 2760 |
| cctgaccctg acccttgcca ccaacccaaa gacagctggt gggtttcccc ttggagacaa | 2820 |
| tcctgcgttt gcctgggccg gccctggctg ccctcagctt tcgctgatct gcccggcctg | 2880 |
| gagcctccca tcaccccgct tcttgttggg cctcaggcac tggttaccag aagggggtct | 2940 |
| gggtctgctc aggatcatgt tttgtagcac ctcctgttgg aggggtggag ggatgttccc | 3000 |
| ctgagccagg ctgagactag aaccccatct tccctgagcc aggctgagac tagaacccca | 3060 |
| tcttccccac cacgccaccc ctgtggctgc tacaggagca cagtagtgaa ggcctgagct | 3120 |
| ccaggtttga aagacccaac tggagcgtgg ggcgggcagg caggggttag tgaaaggaca | 3180 |
| cttccagggt taggacagag catttagcct tctggaagaa cccctgcctg gggtgggact | 3240 |
| gtgcaggcca gagaaggtgg catgggcctg aacccacctg gactgacttc tgcactgaag | 3300 |
| ccacagatgg agggtaggct ggtgggtggg ggtggttcgt tctctagccg gggcagacac | 3360 |
| ccagctggct gggtccttcc tcagccttgc ctcctcctgt ccccaaccct ttcctttcct | 3420 |
| cctgcttgcg gactgctggt cccctctcct tccctccttc cagctgtttc tagttaccac | 3480 |
| ctacccctgg ccgtggactg atcagaccag cattcaaaat aaaagtttgt tccaaaaaaa | 3540 |
| aaaaaaaaaa aaaaaaaaaa aaaa | 3564 |

ZONE 3 NECROSIS ASSOCIATED MARKERS AND METHOD OF USE THEREOF

RELATED APPLICATION

This application claims priority to U.S. Ser. No. 60/410,763, filed Sep. 13, 2002. The contents of this application is incorporated herein by reference in its entirety.

FIELD OF THE INVENTION

The invention relates generally to the identification of genetic markers associated with toxicity.

BACKGROUND OF THE INVENTION

Necrotic cell death is a common response of the liver to hepatotoxic agents and represents an irreversible form of damage to individual liver cells. While the mechanisms by which hepatotoxic agents lead to necrosis remain to be fully understood, progress has been made in understanding the biochemical pathways involved. Necrotic cell death occurs when a chemical or it's metabolite react with critical cellular systems resulting in ion dysregulation, mitochondrial dysfunction and oxidative stress [1–3]. The acute disruption of these normal cellular events in effect leads to ATP depletion. This loss of energy within the cell distinguishes necrosis from the other classification of cell death known as apoptosis. When cells undergo apoptosis or programmed cell death, the cell requires an energy level capable of triggering special metabolic, signal transduction and gene regulation pathways that systematically shut down the cell. Necrosis occurs when the ATP levels falls below the threshold required for these processes and the cell is driven into a passive state of cellular chaos that culminates in cell death [4]. Thus, although these two forms of cell death are distinct, they can share initiating pathways depending on the how sharply the ATP levels decline. Such can be seen with the induction of the mitochondrial permeability transition (MPT), a mechanism that causes mitochondrial failure. The MPT will lead to necrosis if ATP is depleted or apoptosis if there are sufficient amounts available to initiate a caspase cascade [5].

Chemical insult that produces necrosis of the liver can be either nonzonal or zonal. Zonal necrosis is separated into zones 1, 2 and 3 based on the region of the lobule affected. Different hepatotoxic agents preferentially target specific zones [6]. This research project report specifically deals with those agents that produced zone 3 or centrilobular necrosis. This is the most commonly affected area of the liver for hepatotoxic agents producing zonal necrosis. Zones 1–3 are distinguishable in terms of blood flow, oxygen content, bile flow and ratio of intoxication versus detoxification pathways. Factors such as these explain the specificity of hepatotoxic agents for particular zones. Acetaminophen and carbon tetrachloride ($CCL_4$) are examples of agents that produce mainly zone 3 necrosis once they are converted to reactive metabolites. This can be attributed to the high degree of regional organization of agent specific cytochrome P450's within the liver [7]. The supply of oxygen available to the cell has also been shown to be a factor for zone 3 necrosis producing agents. Zone 3 is the region of the liver that is furthest from the arterial blood supply receiving the least supply of oxygen. When $CCl_4$ is metabolized to its reactive metabolite $CCl_3$, the reduction reaction is inhibited by oxygen, favoring a necrotic response in the centrilobular area [7].

Liver cell necrosis can evoke a range of responses within the liver that depend on the severity of insult. These responses range from regeneration of necrotic tissue with restoration of full liver function to concomitant loss of liver function, liver failure and death [8]. In the process, necrosis may trigger the development of other liver diseases. Recurring bouts of necrosis and repair may result in disruption of the structure of the liver and result in subacute hepatitis, chronic hepatitis or even cirrhosis [9]. In this process, inflammatory cells stimulate the deposition of collagen around hepatocytes causing alteration in hepatic function and blood flow [10]. There is also evidence that necrosis may play a role in the induction of early hepatocellular carcinoma through compensatory liver regeneration. Diethylnitrosamine and Fumonisin B(1) are two examples of compounds that show evidence of producing hepatocellular carcinoma in rats through a sequence of events that begin with necrosis [11–13]. Thus the benefit of obtaining marker genes predictive of hepatic zone 3 necrosis stem from its participation in the pathogenesis of other liver diseases as well as it being an early indicator of hepatic toxicity.

SUMMARY OF THE INVENTION

The invention is based in part on the discovery that certain nucleic acids are differentially expressed in liver cells or liver tissue of animals treated with toxic compounds. These differentially expressed nucleic acids include novel sequences and nucleic acids sequences that, while previously described, have not heretofore been identified as associated with toxicity and are collectively referred to herein as "TOXMARKER nucleic acids" or "TOXMARKER polynucleotides" and the corresponding encoded polypeptides are referred to as "TOXMARKER polypeptides" or "TOXMARKER proteins". The TOXMARKER genes are useful in high throughput screening of potential therapeutic compounds for toxicity.

In on aspect the invention provides methods of predicting the hepatotoxicity of a test agent. Hepatotoxicity is predicted by determining the level of expression of a toxicity-associated gene in a cell exposed to a test agent. The level of expression of the toxicity-associated gene is compared to the level of expression of the toxicity-associated gene in a control population exposed to a control agent. A test agent is predicted to be toxic if an alteration (e.g., increase or decrease) in the level of expression in the cell exposed to the test agent compared to the control population is identified.

Also provided by the invention are methods of screening a test agent for inducing changes in gene expression associated with a toxic agent. An agent is screened for inducing changes in gene expression associated with a toxic agent by determining the level of expression of a toxicity-associated gene in a cell exposed to a test agent. The level of expression of the toxicity-associated gene is compared to the level of expression of the toxicity-associated gene in a control population exposed to a control agent.

The alteration is statistically significant. By statistically significant is meant that the alteration is greater than what might be expected to happen by change alone. Statistical significance is determined by method known in the art. An alteration is statistically significant if the p-value is at least 0.05. Preferably, the p-value is 0.04, 0.03, 0.02, 0.01, 0.005, 0.001 or less.

By toxicity-associated gene is meant a gene that is characterized by a level of expression which differs in a cell exposed to a toxic compound compared to a control population. A toxicity-associated gene includes for example TOXMARKER 1–131. Preferably, the toxicity-associated gene is the genes listed on Table 5. More preferably, the toxicity-associated gene is TOXMARKER 42, 59, 65, 66, 71, 76, and 97.

A control population is a for example a cell not exposed to a toxic agent. Optionally, the control population is exposed to a control agent. A control agent is an agent that does not elicit a histology associated with a condition associated with liver toxicity such as Cholestasis; Steatosis; Reactive Inflamation; Necrosis, e.g., zone 3, general or multifocal; Genotoxic Carcinogenesis; Hepatocellular Hypertrophy; Non-Genotoxic Carcinogenesis; Appoptosis and Kupffer Cell Aggregation. Exemplary control agents are those listed in Table 1 and Table 2 below. A control level is a single expression pattern derived from a single control population or from a plurality of expression patterns. For example, the control level can be a database of expression patterns from previously tested cells.

The test cell is provided in vitro. Alternatively, the test cell is provided ex vivo or in vivo from a mammalian subject. The test cell is derived from liver tissue, such as for example a hepatocyte. Alternatively, the test cell is a subject derived cell sample. The subject derived tissue sample is any tissue from a test subject.

Expression is determined by for example detecting hybridization, e.g., on a chip, of a toxicity-associated gene probe to a gene transcript of the test cell.

The invention also provides a zone 3 necrosis reference expression profile of a gene expression level two or more of TOXMARKER 1–132. For example, the reference profile contains the expression levels of TOXMARKER 1–132. Alternatively, the reference profile contains the expression levels of TOXMARKER genes listed on Table 5. Preferably, the reference profile contains the expression levels of TOXMARKER 42, 59, 65, 66, 71, 76, and 97

The invention also provides a kit with a detection reagent which binds to two or more TOXMARKER nucleic acid sequences or which binds to a gene product encoded by the nucleic acid sequences. Also provided is an array of nucleic acids, e.g. oligonucleotides that binds to two or more TOXMARKER nucleic acids. For example, the array contains oligonucleotides that bind TOXMARKER 1–132. Alternatively, the array contains oligonucleotides that bind the TOXMARKER genes listed on Table 5. Preferably, the array contains oligonucleotides that bind TOXMARKER 42, 59, 65, 66, 71, 76, and 97 Most preferably, the array contains oligonucleotides that binds at least five TOXMARKER genes listed one Table 5, where the collection of TOXMARKER genes predict toxicity to a confidence level of a p-value of at least 0.05 or less.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

DETAILED DESCRIPTION OF THE INVENTION

Figure 1:
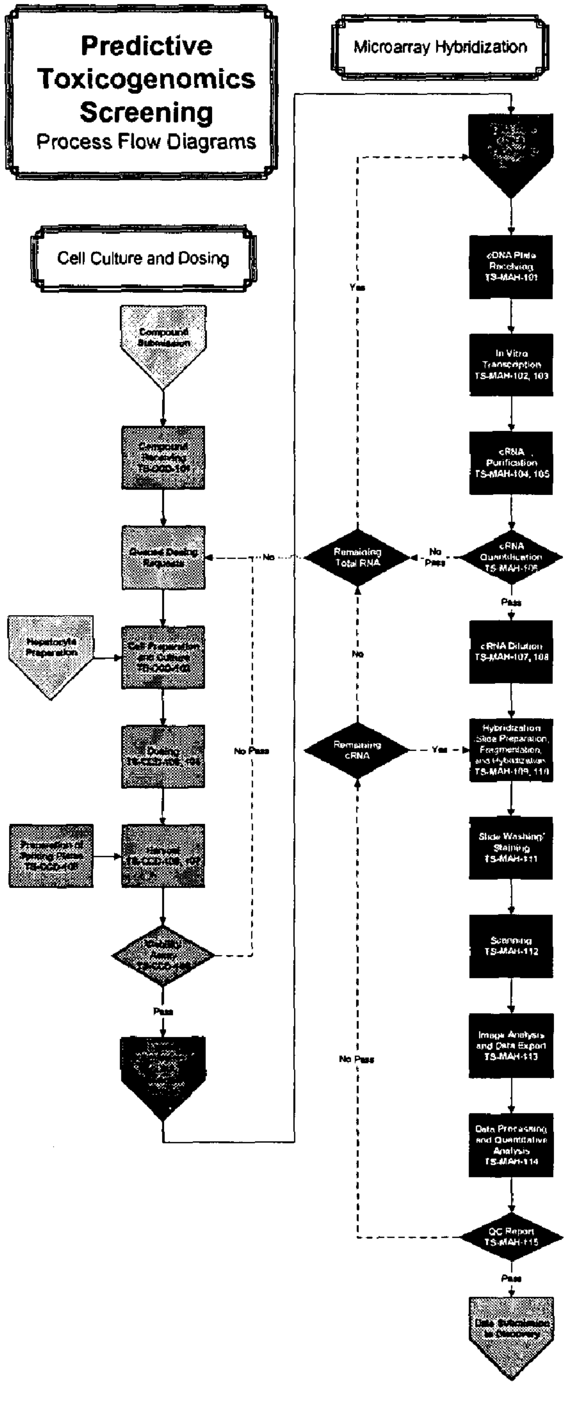
FIG. 1 is a schematic of the hepatotoxicity prediction screening method of the invention.
Figure 2:
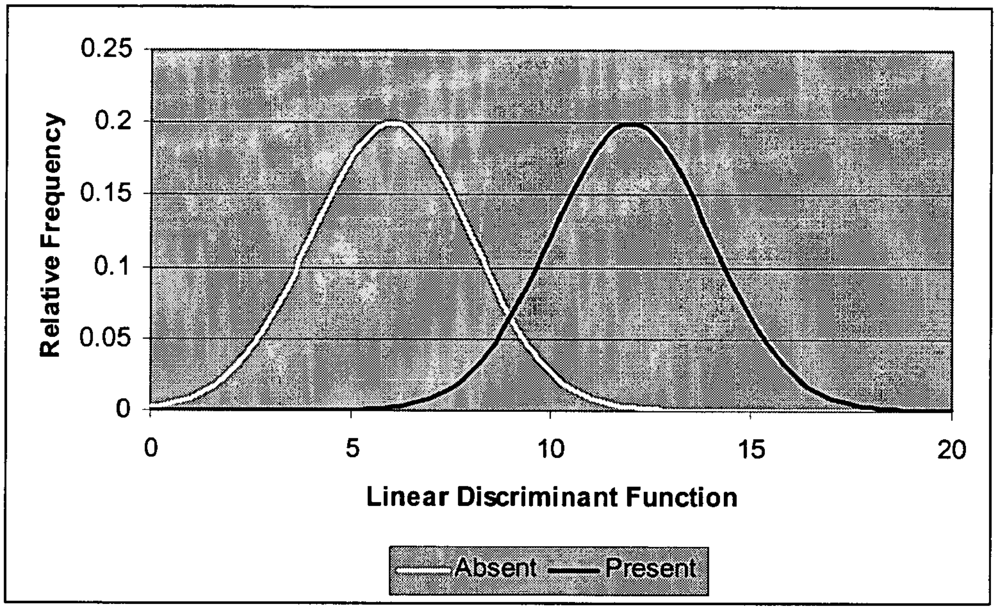
FIG. 2 is a illustration of a chart showing the linear discriminant model.

The present invention is based in part on the discovery of changes in expression patterns of multiple nucleic acid sequences in response to compounds known to elicit a histopathologic condition (i.e., a pathologic change to the liver visible on examination that causes the liver to function less effectively) associated with liver toxicity. The compounds are for example, compounds listed in Table 1 or 2 below. Examples of histopathologic conditions include, Cholestasis; Steatosis; Reactive Inflamation; Necrosis, e.g., zone 3, general or multifocal; Genotoxic Carcinogenesis; Hepatocellular Hypertrophy; Non-Genotoxic Carcinogenesis; Appoptosis and Kupffer Cell Aggregation. The histopathological conditions are identified by methods know in the art. For example, zone 3 necrosis is identified by choleastasis and hypertrophy. The identification of genes that are differentially expressed in response to toxic compounds are useful in screening potential therapeutic compositions for toxicity.

The genes whose expression levels are modulated (i.e., increased or decreased) in response to exposure to a toxic compound are summarized in Tables 3–5 (see EXAMPLES 4 and 5) and are collectively referred to herein as "toxicity-associated gene", "TOXMARKER nucleic acids" or "TOXMARKER polynucleotides" and the corresponding encoded polypeptides are referred to as "TOXMARKER polypeptides" or "TOXMARKER proteins." Unless indicated otherwise, "TOXMARKER" or "toxicity-associated gene" is meant to refer to any of the sequences disclosed herein.

For a given TOXMARKER sequence, its expression can be measured in the methods described herein. For previously described sequences, database accession numbers are provided. This information allows for one of ordinary skill in the art to deduce information necessary for detecting and measuring expression of the TOXMARKER nucleic acid sequences.

General Methods

The TOXMARKER nucleic acids and encoded polypeptides can be identified using the information provided in the EXAMPLES below. In some embodiments, the TOXMARKER nucleic acids and polypeptides correspond to the nucleic acids or polypeptides which include the various sequences (referenced by SEQ ID NOs) disclosed for each TOXMARKER.

The invention includes providing a test cell population which includes at least one cell that is capable of expressing one or more of the sequences TOXMARKER 1–132. By "capable of expressing" is meant that the gene is present in an intact form in the cell and can be expressed. Expression of one, some, or all of the TOXMARKER sequences is then detected, if present, and, preferably, measured to yield an expression profile, e.g., subject expression profile or a test cell expression profile. By "expression profile" is meant a pattern of the level of expression of at least two toxicity-associated genes.

"Similarity of expression profile" is a similarity of expression profile between two samples exists when the linear combination of the genes in the profile has a linear discriminant score that is more similar to one of the training classes than the other. Linear discriminant analysis (LDA) identifies a linear combination of markers that best separates the defined classes. In the training data (i.e., control population) of this invention linear discriminant score could be determined by the following equation:

$$\text{Linear disc. score}=a\text{Gene1}+b\text{Gene2}+\ldots+n\text{GeneN}$$

where a, b . . . n are the coefficients identified by least squares that best separate the phenotypes under investigation. Thus, similarity in expression profile is a similarity in gene combinations. Interpretation of raw data is difficult since the samples are plotted in more than 3 dimensions, one dimension for each gene, which makes it difficult to visualize the data. LDA compresses this information into a single dimension.

By "toxicity-associated gene" is meant a gene, which the level of expression differs in a cell or subject exposed to a known toxic compound as compared to a cell or subject not exposed to a toxic compound (i.e., control). Preferably, the TOXMARKER genes 42 (IFNAR-2), 59 (Transaldolase), 65 (Clp-1), 66 (Hex), 71 (cszr_204152648_191521095), 76 (scr_gb-aa899865_3), and 97 (scr_gb-bm986259_1).

Using sequence information provided by the database entries for the known sequences, or the sequence information provided herein for the newly described sequences, expression of the TOXMARKER sequences are detected (if present) and measured using techniques well known to one of ordinary skill in the art. For example, sequences within the sequence database entries corresponding to TOXMARKER sequences, or within the sequences disclosed herein, can be used to construct probes for detecting TOXMARKER RNA sequences in, e.g., northern blot hybridization analyses or methods which specifically, and, preferably, quantitatively amplify specific nucleic acid sequences. As another example, the sequences can be used to construct primers for specifically amplifying the TOXMARKER sequences in, e.g., amplification-based detection methods such as reverse-transcription based polymerase chain reaction. When alterations in gene expression are associated with gene amplification or deletion, sequence comparisons in test and reference populations can be made by comparing relative amounts of the examined DNA sequences in the test and reference cell populations.

Expression of the genes disclosed herein can be measured at the RNA level using any method known in the art. For example, northern hybridization analysis using probes which specifically recognize one or more of these sequences can be used to determine gene expression. Alternatively, expression can be measured using reverse-transcription-based PCR assays, e.g., using primers specific for the differentially expressed sequences.

Expression is also measured at the protein level, i.e., by measuring the levels of polypeptides encoded by the gene products described herein. Such methods are well known in the art and include, e.g., immunoassays based on antibodies to proteins encoded by the genes.

Expression levels of one or more of the TOXMARKER sequences in the test cell population are then compared to expression levels of the sequences in one or more cells from a reference (i.e., control) cell population. If desired, a reference expression profile is generated. A reference profile is a single expression pattern derived from a single reference population or from a plurality of expression patterns. For example, the reference cell population can be a database of expression patterns from previously tested cells for which one of the herein-described parameters or conditions (e.g., toxicity) is known.

The reference profile is obtained from the training data. Training data is a collection of data from the in vitro or in vivo samples that were exposed to compounds that produce a known pathology. (i.e., pathology present or pathology absent) Profile is defined here to indicate the absolute estimate of the expression level of any one TOXMARKER gene fragment (e.g. Intensity).

Expression of sequences in test and reference populations of cells are compared using any art-recognized method for comparing expression of nucleic acid sequences. For example, expression can be compared using GENECALLING® methods as described in U.S. Pat. No. 5,871,697 and in Shimkets et al., Nat. Biotechnol. 17:798–803.

In various embodiments, the expression of one or more sequences encoding genes of related function, as listed in Tables 3–5, is compared. In various embodiments, the expression of 2, 3, 4, 5, 6, 7, 8, 9, 10, 15, 20, 25, 35, 40, 50, 100 or all of the sequences represented by TOXMARKER 1–132 are measured. If desired, expression of these sequences can be measured along with other sequences whose expression is known to be altered according to one of the herein described parameters or conditions.

The reference cell population includes one or more cells for which the compared parameter is known. The compared parameter can be, e.g. toxic agent expression status. By "toxic agent expression status" is meant that it is known whether the reference cell has had contact with a toxic agent. Whether or not comparison of the gene expression profile in the test cell population to the reference cell population reveals the presence, or degree, of the measured parameter depends on the composition of the reference cell population. For example, if the reference cell population is composed of cells that have not been treated with a known toxic agent, a similar gene expression level in the test cell population and a reference cell population indicates the test agent is not a toxic agent. Conversely, if the reference cell population is made up of cells that have been treated with a toxic agent, a similar gene expression profile between the test cell population and the reference cell population indicates the test agent is a toxic agent.

In various embodiments, a TOXMARKER sequence in a test cell population is considered comparable in expression level to the expression level of the TOXMARKER sequence if its expression level varies within a factor of 2.0, 1.5, or 1.0 fold to the level of the TOXMARKER transcript in the reference cell population. In various embodiments, a TOXMARKER sequence in a test cell population can be considered altered in levels of expression if its expression level varies from the reference cell population by more than 3.0, 4.0, 5.0 or more fold from the expression level of the corresponding TOXMARKER sequence in the reference cell population.

If desired, comparison of differentially expressed sequences between a test cell population and a reference cell population can be done with respect to a control nucleic acid whose expression is independent of the parameter or condition being measured. Expression levels of the control nucleic acid in the test and reference nucleic acid can be used to normalize signal levels in the compared populations.

In some embodiments, the test cell population is compared to multiple reference cell populations. Each of the multiple reference populations may differ in the known parameter. Thus, a test cell population may be compared to a first reference cell population known to have been exposed to a toxic agent, as well as a second reference population known to have not been exposed to a toxic agent.

The test cell population that is exposed to, i.e., contacted with, the test toxic agent can be any number of cells, i.e., one or more cells, and can be provided in vitro, in vivo, or ex vivo. The test cell is obtained from a bodily fluid, e.g., biological fluid (such as blood, serum, urine, saliva, milk, ductal fluid, or tears). For example, the test cell is purified from blood or another tissue, i.e., liver tissue.

In other embodiments, the test cell population can be divided into two or more subpopulations. The subpopulations can be created by dividing the first population of cells to create as identical a subpopulation as possible. This will be suitable, in, for example, in vitro or ex vivo screening methods. In some embodiments, various subpopulations can be exposed to a control agent, and/or a test agent, multiple test agents, or, e.g., varying dosages of one or multiple test agents administered together, or in various combinations.

Preferably, cells in the reference cell population are derived from a tissue type as similar as possible to the test cell, e.g., liver tissue. Alternatively the cells are derived from an established cell line. Preferably, the cell is a hepatocyte. In some embodiments, the control cell is derived from the same subject as the test cell, e.g., from a region proximal to the region of origin of the test cell. In other embodiments, the reference cell population is derived from a plurality of cells. For example, the reference cell population can be a database of expression patterns from previously tested cells for which one of the herein-described parameters or conditions (toxic agent expression status) is known.

The test agent can be a compound not previously described or can be a previously known compound but which is not known to be a toxic agent.

The subject is preferably a mammal. The mammal can be, e.g., a human, non-human primate, mouse, rat, dog, cat, horse, or cow.

Prediction of Toxicity

In one aspect, the invention provides a method of predicting the toxicity e.g., hepatotoxicity of a test agent or identifying a toxic agents, e.g., a hepatotoxic agent. The method is an in vivo method. Alternatively, the method is an in vitro method.

Differences in the genetic makeup of individuals can result in differences in their relative abilities to metabolize various drugs. Accordingly, the differentially expressed TOXMARKER sequences disclosed herein allow for a putative therapeutic or prophylactic agent to be tested in a test cell population from a selected subject in order to predict if the agent causes toxicity in the subject.

By predicting the toxicity is meant that the test compound is more likely to be hepatotoxic that not be hepatotoxic. Hepatotoxicity is predicted by determining the level of expression of a toxicity-associated gene in a cell exposed to a test agent. The level of expression of the toxicity-associated gene is compared to the level of expression of the toxicity-associated gene in a control population exposed to a control agent. A test agent is predicted to be toxic if an alteration (e.g., increase or decrease) in the level of expression in the cell exposed to the test agent compared to the control population is identified.

The toxicity-associated gene is for example TOXMARKER 1–132. Alternatively, the toxicity-associated gene is the TOXMARKER genes listed on Table 5. Optionally, the toxicity-associated gene is TOXMARKER 42, 59, 65, 66, 71, 76, and 97 The toxicity-associated gene is a nucleic acid sequences homologous to those listed in Tables 3–5 as TOXMARKER 1–132. The sequences need not be identical to sequences including TOXMARKER 1–132, as long as the sequence is sufficiently similar that specific hybridization can be detected. Preferably, the cell includes sequences that are identical, or nearly identical to those identifying the TOXMARKER nucleic acids shown in Tables 3–5.

By hepatotoxicity is meant that that the compound causes a hispathological change in the live tissue associate with toxicity. By "toxicity" is meant that the agent is damaging or destructive to liver when administered to a subject. Damage to the liver is measured for example, histologically. Hepatotoxicity is determined, for example as described in the examples below.

The cell population is contacted in vitro, or in vivo. Optionally, the cell population is contacted ex vivo with the agent or activated form of the agent.

Expression of the nucleic acid sequences in the test cell population is then compared to the expression of the nucleic acid sequences in a control population, which is a cell population that has not been exposed to the test agent, or, in some embodiments, a cell population exposed to the test agent. Comparison can be performed on test and reference samples measured concurrently or at temporally distinct times. An example of the latter is the use of compiled expression information, e.g., a sequence database, which assembles information about expression levels of known sequences following administration of various agents. For example, alteration of expression levels following administration of test agent can be compared to the expression changes observed in the nucleic acid sequences following administration of a control agent. A control agent is a compound that elicits the histopathology. Alternatively, the control agent is a compound that does not elicit the histopathology. Exemplary control compounds are listed in Tables 1 and 2.

An alteration in expression of the nucleic acid sequence in the test cell population compared to the expression of the nucleic acid sequence in the control cell population that has not been exposed to the test agent indicates the test agent is a toxic agent.

The alteration is statistically significant. By statistically significant is meant that the alteration is greater than what might be expected to happen by change alone. Statistical significance is determined by method known in the art. For example statistical significance is determined by p-value. The p-values is a measure of probability that a difference between groups during an experiment happened by chance. ($P(z \geqq z_{observed})$). For example, a p-value of 0.01 means that there is a 1 in 100 chance the result occurred by chance. The lower the p-value, the more likely it is that the difference between groups was caused by treatment. An alteration is statistically significant if the p-value is at least 0.05. Preferably, the p-value is 0.04, 0.03, 0.02, 0.01, 0.005, 0.001 or less.

The invention also includes a toxic agent identified according to this screening method.

The differentially expressed TOXMARKER sequences identified herein also allow for the toxicity of a toxic agent to be determined or monitored. In this method, a test cell population from a subject is exposed to a test agent, i.e. a toxic agent. If desired, test cell populations can be taken from the subject at various time points before, during, or after exposure to the test agent. Expression of one or more of the TOXMARKER sequences, e.g., TOXMARKER: 1–132, in the cell population is then measured and compared to a control population which includes cells whose toxic agent expression status is known.

Kits

The invention also includes a TOXMARKER-detection reagent, e.g., nucleic acids that specifically identify one or more TOXMARKER nucleic acids by having homologous nucleic acid sequences, such as oligonucleotide sequences, complementary to a portion of the TOXMARKER nucleic acids or antibodies to proteins encoded by the TOXMARKER nucleic acids packaged together in the form of a kit. The oligonucleotides are fragments of the the TOXMARKER genes. For example the olignucleitides are 200, 150, 100, 50, 25, 10 or less nucleotides in length. The kit may contain in separate containers a nucleic acid or antibody (either already bound to a solid matrix or packaged separately with reagents for binding them to the matrix), control formulations (positive and/or negative), and/or a detectable label. Instructions (e.g., written, tape, VCR, CD-ROM, etc.) for carrying out the assay may be included in the kit. The assay may for example be in the form of a Northern hybridization or a sandwich ELISA as known in the art.

For example, TOXMARKER detection reagent, is immobilized on a solid matrix such as a porous strip to form at least one TOXMARKER detection site. The measurement or detection region of the porous strip may include a plurality of sites containing a nucleic acid. A test strip may also contain sites for negative and/or positive controls. Alternatively, control sites are located on a separate strip from the test strip. Optionally, the different detection sites may contain different amounts of immobilized nucleic acids, i.e., a higher amount in the first detection site and lesser amounts in subsequent sites. Upon the addition of test sample, the number of sites displaying a detectable signal provides a quantitative indication of the amount of TOXMARKER present in the sample. The detection sites may be configured in any suitably detectable shape and are typically in the shape of a bar or dot spanning the width of a test strip.

Alternatively, the kit contains a nucleic acid substrate array comprising one or more nucleic acid sequences. The nucleic acids on the array specifically identify one or more nucleic acid sequences represented by TOXMARKER 1–132. In various embodiments, the expression of 2, 3, 4, 5, 6, 7, 8, 9, 10, 15, 20, 25, 40 or 50 or more of the sequences represented by TOXMARKER 1–132. are identified by virtue of binding to the array. The substrate array can be on, e.g., a solid substrate, e.g., a "chip" as described in U.S. Pat. No. 5,744,305.

Arrays and Pluralities

The invention also includes a nucleic acid substrate array comprising one or more nucleic acid sequences. The nucleic acids on the array specifically identify one or more nucleic acid sequences represented by TOXMARKER 1–132. In various embodiments, the expression of 2, 3, 4, 5, 6, 7, 8, 9, 10, 15, 20, 25, 40 or 50 or more of the sequences represented by TOXMARKER 1–132 are identified.

The nucleic acids in the array can identify the enumerated nucleic acids by, e.g., having homologous nucleic acid sequences, such as oligonucleotide sequences, complementary to a portion of the recited nucleic acids. The substrate array can be on, e.g., a solid substrate, e.g., a "chip" as described in U.S. Pat. No. 5,744,305.

The invention also includes an isolated plurality (i.e., a mixture of two or more nucleic acids) of nucleic acid sequences. The nucleic acid sequence can be in a liquid phase or a solid phase, e.g., immobilized on a solid support such as a nitrocellulose membrane. The plurality typically includes one or more of the nucleic acid sequences represented by TOXMARKER 1–132. In various embodiments, the plurality includes 2, 3, 4, 5, 6, 7, 8, 9, 10, 15, 20, 25, 40 or 50 or more of the sequences represented by TOXMARKER 1–132.

Nucleic Acids

One aspect of the invention pertains to isolated nucleic acid molecules that encode TOXMARKER proteins or biologically active portions thereof, as well as nucleic acid fragments sufficient for use as hybridization probes to identify TOXMARKER-encoding nucleic acids (e.g., TOXMARKER mRNA) and fragments for use as PCR primers for the amplification or mutation of TOXMARKER nucleic acid molecules. As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule can be single-stranded or double-stranded, but preferably is double-stranded DNA.

"Probes" refer to nucleic acid sequences of variable length, preferably between at least about 10 nucleotides (nt), 100 nt, or as many as about, e.g., 6,000 nt, depending on use. Probes are used in the detection of identical, similar, or complementary nucleic acid sequences. Longer length probes are usually obtained from a natural or recombinant source, are highly specific and much slower to hybridize than oligomers. Probes may be single- or double-stranded and designed to have specificity in PCR, membrane-based hybridization technologies, or ELISA-like technologies.

An "isolated" nucleic acid molecule is one that is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated TOXMARKER nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g., testis, lung, B-cells). Moreover, an "isolated" nucleic acid molecule, such as a cDNA molecule, can be substantially free of other cellular material or culture medium when produced by recombinant techniques, or of chemical precursors or other chemicals when chemically synthesized.

A nucleic acid molecule of the present invention, e.g., a nucleic acid molecule having the nucleotide sequence of SEQ ID NO: 1–171 or a complement of any of these nucleotide sequences, can be isolated using standard molecular biology techniques and the sequence information provided herein. Using all or a portion of the nucleic acid sequences of SEQ ID NO: 1–171 as a hybridization probe, TOXMARKER molecules can be isolated using standard hybridization and cloning techniques (e.g., as described in Sambrook et al., (eds.), Molecular Cloning: A Laboratory Manual $2^{nd}$ Ed., Cold Spring Harbor Laboratory Press, Cold Spring Harbor, N.Y., 1989; and Ausubel, et al., (eds.), Current Protocols in Molecular Biology, John Wiley & Sons, New York, N.Y., 1993.)

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to TOXMARKER nucleotide sequences can be prepared by standard synthetic techniques, e.g., using an automated DNA synthesizer.

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides comprise portions of a nucleic acid sequence having about 10 nt, 50 nt, or 100 nt in length, preferably about 15 nt to 30 nt in length. In one embodiment, an oligonucleotide comprising a nucleic acid molecule less than 100 nt in length would further comprise at lease 6 contiguous nucleotides of SEQ ID NO: 1–171, or a complement thereof. Oligonucleotides may be chemically synthesized and may be used as probes.

In another embodiment, an isolated nucleic acid molecule of the invention comprises a nucleic acid molecule that is a complement of the nucleotide sequence shown in SEQ ID NO: 1–171. In another embodiment, an isolated nucleic acid molecule of the invention comprises a nucleic acid molecule that is a complement of the nucleotide sequence shown in SEQ ID NO: 1–171, or a portion of this nucleotide sequence. A nucleic acid molecule that is complementary to the nucleotide sequence shown in SEQ ID NO: 1–171 is one that is sufficiently complementary to the nucleotide sequence shown in SEQ ID NO: 1–171 that it can hydrogen bond with little or no mismatches to the nucleotide sequence shown in SEQ ID NO: 1–171, thereby forming a stable duplex.

As used herein, the term "complementary" refers to Watson-Crick or Hoogsteen base pairing between nucleotides units of a nucleic acid molecule, and the term "binding" means the physical or chemical interaction between two polypeptides or compounds or associated polypeptides or compounds or combinations thereof. Binding includes ionic, non-ionic, Von der Waals, hydrophobic interactions, etc. A physical interaction can be either direct or indirect. Indirect interactions may be through or due to the effects of another polypeptide or compound. Direct binding refers to interactions that do not take place through, or due to, the effect of another polypeptide or compound, but instead are without other substantial chemical intermediates.

Moreover, the nucleic acid molecule of the invention can comprise only a portion of the nucleic acid sequence of SEQ ID NO: 1–171, e.g., a fragment that can be used as a probe or primer or a fragment encoding a biologically active portion of TOXMARKER.

Fragments provided herein are defined as sequences of at least 6 (contiguous) nucleic acids or at least 4 (contiguous) amino acids, a length sufficient to allow for specific hybridization in the case of nucleic acids or for specific recognition of an epitope in the case of amino acids, respectively, and are at most some portion less than a full length sequence. Fragments may be derived from any contiguous portion of a nucleic acid or amino acid sequence of choice. Derivatives are nucleic acid sequences or amino acid sequences formed from the native compounds either directly or by modification or partial substitution. Analogs are nucleic acid sequences or amino acid sequences that have a structure similar to, but not identical to, the native compound but differs from it in respect to certain components or side chains. Analogs may be synthetic or from a different evolutionary origin and may have a similar or opposite metabolic activity compared to wild type. Homologs are nucleic acid sequences or amino acid sequences of a particular gene that are derived from different species.

Derivatives and analogs may be full length or other than full length, if the derivative or analog contains a modified nucleic acid or amino acid, as described below. Derivatives or analogs of the nucleic acids or proteins of the invention include, but are not limited to, molecules comprising regions that are substantially homologous to the nucleic acids or proteins of the invention, in various embodiments, by at least about 30%, 50%, 70%, 80%, or 95% identity (with a preferred identity of 80–95%) over a nucleic acid or amino acid sequence of identical size or when compared to an aligned sequence in which the alignment is done by a computer homology program known in the art, or whose encoding nucleic acid is capable of hybridizing to the complement of a sequence encoding the aforementioned proteins under stringent, moderately stringent, or low stringent conditions. See e.g. Ausubel, et al., Current Protocols in Molecular Biology, John Wiley & Sons, New York, N.Y., 1993, and below.

A "homologous nucleic acid sequence" or "homologous amino acid sequence," or variations thereof, refer to sequences characterized by a homology at the nucleotide level or amino acid level as discussed above. Homologous nucleotide sequences encode those sequences coding for isoforms of TOXMARKER polypeptide. Isoforms can be expressed in different tissues of the same organism as a result of, for example, alternative splicing of RNA. Alternatively, isoforms can be encoded by different genes. In the present invention, homologous nucleotide sequences include nucleotide sequences encoding for a TOXMARKER polypeptide of species other than humans, including, but not limited to, mammals, and thus can include, e.g., mouse, rat, rabbit, dog, cat cow, horse, and other organisms. Homologous nucleotide sequences also include, but are not limited to, naturally occurring allelic variations and mutations of the nucleotide sequences set forth herein. A homologous nucleotide sequence does not, however, include the nucleotide sequence encoding human TOXMARKER protein. Homologous nucleic acid sequences include those nucleic acid sequences that encode conservative amino acid substitutions (see below) in SEQ ID NO: 1–171, as well as a polypeptide having TOXMARKER activity. Biological activities of the TOXMARKER proteins are described below. A homologous amino acid sequence does not encode the amino acid sequence of a human TOXMARKER polypeptide.

An TOXMARKER polypeptide is encoded by the open reading frame ("ORF") of a TOXMARKER nucleic acid. An "open reading frame" ("ORF") corresponds to a nucleotide sequence that could potentially be translated into a polypeptide. A stretch of nucleic acids comprising an ORF is uninterrupted by a stop codon. An ORF that represents the coding sequence for a full protein begins with an ATG "start" codon and terminates with one of the three "stop" codons, namely, TAA, TAG, or TGA. For the purposes of this invention, an ORF may be any part of a coding sequence, with or without a start codon, a stop codon, or both. For an ORF to be considered as a good candidate for coding for a bona fide cellular protein, a minimum size requirement is often set, for example, a stretch of DNA that would encode a protein of 50 amino acids or more.

The nucleotide sequence determined from the cloning of the human TOXMARKER gene allows for the generation of probes and primers designed for use in identifying and/or cloning TOXMARKER homologues in other cell types, e.g. from other tissues, as well as TOXMARKER homologues from other mammals. The probe/primer typically comprises substantially purified oligonucleotide. The oligonucleotide typically comprises a region of nucleotide sequence that hybridizes under stringent conditions to at least about 12, 25, 50, 100, 150, 200, 250, 300, 350 or 400 consecutive sense strand nucleotide sequence of SEQ ID NO: 1–171, or an anti-sense strand nucleotide sequence of SEQ ID NO: 1–171 or of a naturally occurring mutant of SEQ ID NO: 1–171.

Probes based on the human TOXMARKER nucleotide sequence can be used to detect transcripts or genomic sequences encoding the same or homologous proteins. In various embodiments, the probe further comprises a label group attached thereto, e.g. the label group can be a radioisotope, a fluorescent compound, an enzyme, or an enzyme co-factor. Such probes can be used as a part of a diagnostic test kit for identifying cells or tissue which misexpress a TOXMARKER protein, such as by measuring a level of a TOXMARKER-encoding nucleic acid in a sample of cells from a subject e.g., detecting TOXMARKER mRNA levels or determining whether a genomic TOXMARKER gene has been mutated or deleted.

"A polypeptide having a biologically active portion of TOXMARKER" refers to polypeptides exhibiting activity similar, but not necessarily identical to, an activity of a polypeptide of the present invention, including mature forms, as measured in a particular biological assay, with or without dose dependency. A nucleic acid fragment encoding a "biologically active portion of TOXMARKER" can be prepared by isolating a portion of SEQ ID NO: 1–171 that encodes a polypeptide having a TOXMARKER biological activity (the biological activities of the TOXMARKER proteins are described below), expressing the encoded portion of TOXMARKER protein (e.g., by recombinant expression in vitro) and assessing the activity of the encoded portion of TOXMARKER.

TOXMARKER Variants

The invention further encompasses nucleic acid molecules that differ from the nucleotide sequence shown in SEQ ID NO: 1–171 due to degeneracy of the genetic code and thus encode the same TOXMARKER protein as that encoded by the nucleotide sequence shown in SEQ ID NO: 1–171.

In addition to the human TOXMARKER nucleotide sequence shown in SEQ ID NO: 1–171 it will be appreciated by those skilled in the art that DNA sequence polymorphisms that lead to changes in the amino acid sequences of TOXMARKER may exist within a population (e.g., the human population). Such genetic polymorphism in the TOXMARKER gene may exist among individuals within a population due to natural allelic variation. As used herein, the terms "gene" and "recombinant gene" refer to nucleic acid molecules comprising an open reading frame encoding a TOXMARKER protein, preferably a mammalian TOXMARKER protein. Such natural allelic variations can typically result in 1–5% variance in the nucleotide sequence of the TOXMARKER gene. Any and all such nucleotide variations and resulting amino acid polymorphisms in TOXMARKER that are the result of natural allelic variation and that do not alter the functional activity of TOXMARKER are intended to be within the scope of the invention.

Moreover, nucleic acid molecules encoding TOXMARKER proteins from other species, and thus that have a nucleotide sequence that differs from the human sequence of SEQ ID NO: 1–171 are intended to be within the scope of the invention. Nucleic acid molecules corresponding to natural allelic variants and homologues of the TOXMARKER cDNAs of the invention can be isolated based on their homology to the human TOXMARKER nucleic acids disclosed herein using the human cDNAs, or a portion thereof, as a hybridization probe according to standard hybridization techniques under stringent hybridization conditions. For example, a soluble human TOXMARKER cDNA can be isolated based on its homology to human membrane-bound TOXMARKER. Likewise, a membrane-bound human TOXMARKER cDNA can be isolated based on its homology to soluble human TOXMARKER.

Accordingly, in another embodiment, an isolated nucleic acid molecule of the invention is at least 6 nucleotides in length and hybridizes under stringent conditions to the nucleic acid molecule comprising the nucleotide sequence of SEQ ID NO: 1–171. In another embodiment, the nucleic acid is at least 10, 25, 50, 100, 250, 500, 750, 1000 or 1250 nucleotides in length. In another embodiment, an isolated nucleic acid molecule of the invention hybridizes to the coding region. As used herein, the term "hybridizes under stringent conditions" is intended to describe conditions for hybridization and washing under which nucleotide sequences at least 60% homologous to each other typically remain hybridized to each other.

Homologs (i.e., nucleic acids encoding TOXMARKER proteins derived from species other than human) or other related sequences (e.g., paralogs) can be obtained by low, moderate or high stringency hybridization with all or a portion of the particular human sequence as a probe using methods well known in the art for nucleic acid hybridization and cloning.

As used herein, the phrase "stringent hybridization conditions" refers to conditions under which a probe, primer or oligonucleotide will hybridize to its target sequence, but to no other sequences. Stringent conditions are sequence-dependent and will be different in different circumstances. Longer sequences hybridize specifically at higher temperatures than shorter sequences. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g., 10 nt to 50 nt) and at least about 60° C. for longer probes, primers and oligonucleotides. Stringent conditions may also be achieved with the addition of destabilizing agents, such as formamide.

Stringent conditions are known to those skilled in the art and can be found in Ausubel et al., (eds.), Current Protocols in Molecular Biology, John Wiley & Sons, N.Y. (1989), 6.3.1–6.3.6. Preferably, the conditions are such that sequences at least about 65%, 70%, 75%, 85%, 90%, 95%, 98%, or 99% homologous to each other typically remain hybridized to each other. A non-limiting example of stringent hybridization conditions are hybridization in a high salt buffer comprising 6× SSC, 50 mM Tris-HCl (pH 7.5), 1 mM EDTA, 0.02% PVP, 0.02% Ficoll, 0.02% BSA, and 500 mg/ml denatured salmon sperm DNA at 65° C., followed by one or more washes in 0.2× SSC, 0.01% BSA at 50° C. An isolated nucleic acid molecule of the invention that hybridizes under stringent conditions to the sequence of SEQ ID NO: 1–171 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In a second embodiment, a nucleic acid sequence that is hybridizable to the nucleic acid molecule comprising the nucleotide sequence of SEQ ID NO: 1–171, or fragments, analogs or derivatives thereof, under conditions of moderate stringency is provided. A non-limiting example of moderate stringency hybridization conditions are hybridization in 6× SSC, 5× Denhardt's solution, 0.5% SDS and 100 mg/ml denatured salmon sperm DNA at 55° C., followed by one or more washes in 1× SSC, 0.1% SDS at 37° C. Other conditions of moderate stringency that may be used are well-known in the art. See, e.g., Ausubel et al. (eds.), 1993, Current Protocols in Molecular Biology, John Wiley & Sons, NY, and Kriegler, 1990, Gene Transfer and Expression, A Laboratory Manual, Stockton Press, NY.

In a third embodiment, a nucleic acid that is hybridizable to the nucleic acid molecule comprising the nucleotide sequence of SEQ ID NO: 1–171, or fragments, analogs or derivatives thereof, under conditions of low stringency, is provided. A non-limiting example of low stringency hybridization conditions are hybridization in 35% formamide, 5× SSC, 50 mM Tris-HCl (pH 7.5), 5 mM EDTA, 0.02% PVP, 0.02% Ficoll, 0.2% BSA, 100 mg/ml denatured salmon sperm DNA, 10% (wt/vol) dextran sulfate at 40° C., followed by one or more washes in 2× SSC, 25 mM Tris-HCl (pH 7.4), 5 mM EDTA, and 0.1% SDS at 50° C. Other conditions of low stringency that may be used are well known in the art (e.g., as employed for cross-species hybridizations). See, e.g., Ausubel et al. (eds.), 1993, Current Protocols in Molecular Biology, John Wiley & Sons, NY, and Kriegler, 1990, Gene Transfer and Expression, A Laboratory Manual, Stockton Press, NY; Shilo and Weinberg, 1981, *Proc Natl Acad Sci USA* 78: 6789–6792.

EXAMPLES

Example 1

Induction of Zone 3 Necrosis In Vivo

Over 100 compounds were chosen based on evidence that they elicit one of eleven selected histopathology subtypes. The criteria for inclusion of a compound into the nongenotoxic carcinogens mode included evidence of parenchymal changes and an increase in mitosis in vivo. Compounds assigned to this group must also have strong historical documentation. Compounds from other pathology modes were not added to this histopathology subtype. The compounds included in nongenotoxic carcinogenesis can been seen in Table 1. Each compound was delivered orally on a daily basis at a high dose (tox dose) and a 1/10 low dose (mode dose) for up to 14 days. Five male rats/dose/time were randomly assigned to sacrifice on days 1, 3, 7, and 14. In order to best identify genes characteristic of the histopathology subtype, total RNA for all rat livers from a given dose time point were pooled and converted to mRNA and cDNA for GeneCalling®. In GeneCalling, the cDNA is cut with a battery of restriction enzyme pairs in different combinations followed by amplification by PCR using specific primers linked to specific adaptors. After gel electrophoresis, the resulting fragments are identified based on the inherent information in the cDNA fragment: The flanking restriction site sequences on the ends, the size of the fragment and the species (and sometimes the tissue) origin of the DNA. This information is used to query public and proprietary databases. The fragments that do not match any sequences in the database are isolated, sequenced and identified as novel.

TABLE 1

Zone 3 Necrosis in vivo

| Compound | Vehicle | Dose | Concentration | Time Points | Pathology Present | Pathology Absent |
|---|---|---|---|---|---|---|
| 1,3-Dibromobenzene | Corn Oil | High | 600 mg/kg/d | 1, 3, 7, 14 d | 1 d | |
| 1,3-Dibromobenzene | Corn Oil | Low | 60 mg/kg/d | 1, 3, 7, 14 d | | |
| 1,4-dichlorobenzene | Corn Oil | High | 300 mg/kg/d | 1, 3, 7, 14 d | | |
| 1,4-dichlorobenzene | Corn Oil | Low | 30 mg/kg/d | 1, 3, 7, 14 d | | 1, 3, 7, 14 d |
| 17α-Ethynyl-19-nortestosterone | Corn Oil | High | 30 mg/kg/d | 1, 3, 7, 14 d | | |
| 17α-Ethynyl-19-nortestosterone | Corn Oil | Low | 3 mg/kg/d | 1, 3, 7, 14 d | | |
| 2,4-diaminotoluene | Methylcellulose | High | 15 mg/kg/d | 1, 3, 7, 14 d | | |
| 2,4-diaminotoluene | Methylcellulose | Low | 1.5 mg/kg/d | 1, 3, 7, 14 d | | |
| 2-acetylaminofluorene | Methylcellulose | High | 12 mg/kg/d | 1, 3, 7, 14 d | | 1, 3, 7, 14 d |
| 2-acetylaminofluorene | Methylcellulose | Low | 1.2 mg/kg/d | 1, 3, 7, 14 d | | |
| 2-acetylaminofluorene | Methylcellulose | High | 120 mg/kg (ip) | 6, 12, 24, 48 h | | |
| 2-acetylaminofluorene | Methylcellulose | Low | 12 mg/kg (ip) | 6, 12, 24, 48 h | | |
| 2-nitrofluorene | Corn oil | High | 44 mg/kg/d | 1, 3, 7, 14 d | | |
| 2-nitrofluorene | Corn oil | Low | 4.4 mg/kg/d | 1, 3, 7, 14 d | | |
| 3-methyl-4-(dimethylamino) azobenzene | Methylcellulose | High | 36 mg/kg/d | 1, 3, 7, 14 d | | |
| 3-methyl-4-(dimethylamino) azobenzene | Methylcellulose | Low | 3.6 mg/kg/d | 1, 3, 7, 14 d | | 1, 3, 7, 14 d |
| 3-methylcholanthrene | Corn Oil | High | 25 mg/kg/d (ip) | 1, 3, 7, 14 d | | |
| 3-methylcholanthrene | Corn Oil | Low | 2.5 mg/kg/d (ip) | 1, 3, 7, 14 d | | 1, 3, 7, 14 d |
| Acetamide | Methylcellulose | High | 3000 mg/kg/d | 1, 3, 7, 14 d | | |
| Acetamide | Methylcellulose | Low | 300 mg/kg/d | 1, 3, 7, 14 d | | |
| Acetaminophen | Saline | High | 4.25 g/kg (po) | 6, 12, 24, 48 h | 24, 48 h | |

TABLE 1-continued

Zone 3 Necrosis in vivo

| Compound | Vehicle | Dose | Concentration | Time Points | Pathology Present | Pathology Absent |
|---|---|---|---|---|---|---|
| Acetaminophen | Saline | Low | 425 mg/kg (po) | 6, 12, 24, 48 h | | |
| Aflatoxin B1 | Methylcellulose | High | 0.24 mg/kg/d | 1, 3, 7, 14 d | | |
| Aflatoxin B1 | Methylcellulose | Low | 0.024 mg/kg/d | 1, 3, 7, 14 d | | |
| Allyl Alcohol | Methylcellulose | High | 36 mg/kg/d | 1, 3, 7, 14 d | | |
| Allyl Alcohol | Methylcellulose | Low | 3.6 mg/kg/d | 1, 3, 7, 14 d | | |
| Allyl Formate | Corn oil | High | 94.8 mg/kg (ip) | 3, 6, 12, 24 h | | |
| Allyl Formate | Corn oil | Low | 9.48 mg/kg (ip) | 3, 6, 12, 24 h | | |
| Amiodarone | Methylcellulose | High | 500 mg/kg/d | 1, 3, 7, 14 d | | |
| Amiodarone | Methylcellulose | Low | 50 mg/kg/d | 1, 3, 7, 14 d | | |
| ANIT | Corn Oil | High | 60 mg/kg/d | 1, 3, 7, 14 d | | |
| ANIT | Corn Oil | Low | 6 mg/kg/d | 1, 3, 7, 14 d | | |
| Azaserine | Saline | High | 100 mg/kg (ip) | 1, 3, 7, 14 d | 1,3 d | |
| Azaserine | Saline | Low | 10 mg/kg (ip) | 1, 3, 7, 14 d | | |
| BCNU | Corn Oil | High | 20 mg/kg/d | 1, 3, 7, 14 d | | |
| BCNU | Corn Oil | Low | 2 mg/kg/d | 1, 3, 7, 14 d | | |
| BHT | Corn Oil | High | 500 mg/kg/d | 1, 3, 7, 14 d | | |
| BHT | Corn Oil | Low | 50 mg/kg/d | 1, 3, 7, 14 d | | |
| Bromobenzene | Saline | High | 1200 mg/kg (ip) | 6, 12, 24, 48 h | 12, 48 h | |
| Bromobenzene | Saline | Low | 120 mg/kg (ip) | 6, 12, 24, 48 h | | |
| C.I. Direct Black | Corn oil | High | 146 mg/kg/d | 1, 3, 7, 14 d | | |
| C.I. Direct Black | Corn oil | Low | 14.6 mg/kg/d | 1, 3, 7, 14 d | | 1, 3, 7, 14 d |
| Cadmium chloride | Saline | High | 3.9 mg/kg (iv) | 6, 12, 24, 48 h | | |
| Cadmium chloride | Saline | Low | 0.39 mg/kg (iv) | 6, 12, 24, 48 h | | |
| Carbamazepine | Methylcellulose | High | 200 mg/kg/d | 1, 3, 7, 14 d | | |
| Carbamazepine | Methylcellulose | Low | 20 mg/kg/d | 1, 3, 7, 14 d | | |
| $CCl_4$ | Corn Oil | High | 50 mg/kg/d | 1, 3, 7, 14 d | 7 d | |
| $CCl_4$ | Methylcellulose | High | 956 mg/kg (ip) | 6, 12, 24, 48 h | 6, 12, 48 h | |
| $CCl_4$ | Corn Oil | Low | 5 mg/kg/d | 1, 3, 7, 14 d | | |
| $CCl_4$ | Methylcellulose | Low | 95.6 mg/kg (ip) | 6, 12, 24, 48 h | | |
| CCNU | Corn Oil | High | 20 mg/kg/d | 1, 3, 7, 14 d | | |
| CCNU | Corn Oil | Low | 2 mg/kg/d | 1, 3, 7, 14 d | | |
| Cefuroxime | Methylcellulose | Safe | 125 mg/kg/d | 1, 3, 7, 14 d | | 1, 3, 7, 14 d |
| Cerium (III) Chloride | Saline | High | 10 mg/kg (iv) | 1, 2, 3, 4 d | 1, 2, 3, 4 d | |
| Cerium (III) Chloride | Saline | Low | 1 mg/kg (iv) | 1, 2, 3, 4 d | | |
| Chlordane | Corn Oil | High | 25 mg/kg/d | 1, 3, 7, 14 d | | |
| Chlordane | Corn Oil | Low | 2.5 mg/kg/d | 1, 3, 7, 14 d | | 1, 3, 7, 14 d |
| Ciprofibrate | Corn Oil | High | 10 mg/kg/d | 1, 3, 7, 14 d | | |
| Ciprofibrate | Corn Oil | Low | 1 mg/kg/d | 1, 3, 7, 14 d | | |
| Ciprofloxacin | Methylcellulose | Safe | 40 mg/kg/d | 1, 3, 7, 14 d | | 1, 3, 7, 14 d |
| Clofibrate | Methylcellulose | High | 300 mg/kg/d | 1, 3, 7, 14 d | | |
| Clofibrate | Methylcellulose | Low | 30 mg/kg/d | 1, 3, 7, 14 d | | 1, 3, 7, 14 d |
| Clonidine | Methylcellulose | Safe | 0.1 mg/kg/d | 1, 3, 7, 14 d | | 1, 3, 7, 14 d |
| Colchicine | Saline | High | 5 mg/kg × 2 (ip) | 6, 12, 24, 48 h | | |
| Colchicine | Saline | Low | 0.5 mg/kg × 2 (ip) | 6, 12, 24, 48 h | | |
| Concanavalin A | Saline | High | 20 mg/kg (iv) | 6, 12, 24, 48 h | | |
| Concanavalin A | Saline | Low | 2 mg/kg (iv) | 6, 12, 24, 48 h | | |
| Corn Oil | | Control | | 1, 3, 7, 14 d | | 1, 3, 7, 14 d |
| Corn Oil (ip) | | Control | | 1, 3, 7, 14 d | | 1, 3, 7, 14 d |
| Corn Oil (ip) | | Control | | 3, 6, 12, 24 h | | 3, 6, 12, 24 h |
| Coumarin | Corn Oil | High | 150 mg/kg/d | 1, 3, 7, 14 d | 3 d | |
| Coumarin | Corn Oil | Low | 15 mg/kg/d | 1, 3, 7, 14 d | | |
| CTFT | Corn Oil | High | 1 g/kg/d | 1, 3, 7, 14 d | | |
| CTFT | Corn Oil | Low | 100 mg/kg/d | 1, 3, 7, 14 d | | |
| Cyclosporine A | Corn Oil | High | 50 mg/kg/day | 1, 3, 7, 14 d | | |
| Cyclosporine A | Corn Oil | Low | 5 mg/kg/d | 1, 3, 7, 14 d | | 1, 3, 7, 14 d |
| Cyproterone acetate | Corn Oil | High | 100 mg/kg/d | 1, 3, 7, 14 d | | |
| Cyproterone acetate | Corn Oil | Low | 10 mg/kg/d | 1, 3, 7, 14 d | | 1, 3, 7, 14 d |
| Dehydroepiandrosterone | Methylcellulose | High | 600 mg/kg/d | 1, 3, 7, 14 d | | |
| Dehydroepiandrosterone | Methylcellulose | Low | 60 mg/kg/d | 1, 3, 7, 14 d | | |
| Deoxycholic Acid | Methylcellulose | High | 300 mg/kg/d | 1, 3, 7, 14 d | | |
| Deoxycholic Acid | Methylcellulose | Low | 30 mg/kg/d | 1, 3, 7, 14 d | | |
| Dexamethasone | Corn oil | High | 50 mg/kg/d (ip) | 1, 3, 7, 14 d | | |
| Dexamethasone | Corn oil | Low | 5 mg/kg/d (ip) | 1, 3, 7, 14 d | | 1, 3, 7, 14 d |
| D-galactosamine | Saline | High | 500 mg/kg (ip) | 6, 12, 24, 48 h | | |
| D-galactosamine | Saline | Low | 50 mg/kg (ip) | 6, 12, 24, 48 h | | |
| Di(2-Ethylhexyl) phthalate | Methylcellulose | High | 1200 mg/kg/d | 1, 3, 7, 14 d | | |
| Di(2-Ethylhexyl) phthalate | Methylcellulose | Low | 120 mg/kg/d | 1, 3, 7, 14 d | | |
| Dibutyltin chloride | Corn oil | High | 20 mg/kg/d | 1, 3, 7, 14 d | | |
| Dibutyltin chloride | Corn oil | Low | 2 mg/kg/d | 1, 3, 7, 14 d | | |
| Dichloropropane | Corn oil | High | 1000 mg/kg/d | 1, 3, 7, 14 d | 1, 3 d | |
| Dichloropropane | Corn oil | Low | 100 mg/kg/d | 1, 3, 7, 14 d | | |
| Diethylnitrosamine | Saline | High | 150 mg/kg (ip) | 1, 3, 7, 14 d | 1, 3, 7 d | |

TABLE 1-continued

Zone 3 Necrosis in vivo

| Compound | Vehicle | Dose | Concentration | Time Points | Pathology Present | Pathology Absent |
|---|---|---|---|---|---|---|
| Diethylnitrosamine | Saline | Low | 15 mg/kg (ip) | 1, 3, 7, 14 d | | |
| Diethylstilbestrol | Methylcellulose | High | 10 mg/kg/d | 1, 3, 7, 14 d | | |
| Diethylstilbestrol | Methylcellulose | Low | 1 mg/kg/d | 1, 3, 7, 14 d | | |
| Dimethylformamide | Saline | High | 850 mg/kg (ip) | 6, 12, 24, 48 h | 48 h | |
| Dimethylformamide | Saline | Low | 85 mg/kg (ip) | 6, 12, 24, 48 h | | |
| Dimethylnitrosamine | Corn Oil | High | 4 mg/kg/d | 1, 3, 7, 14 d | 7, 14 d | |
| Dimethylnitrosamine | Corn Oil | Low | 0.4 mg/kg/d | 1, 3, 7, 14 d | | |
| Diquat | Saline | High | 36 mg/kg (ip) | 6, 12, 24, 48 h | | |
| Diquat | Saline | Low | 3.6 mg/kg (ip) | 6, 12, 24, 48 h | | 6, 12, 24, 48 h |
| Disopyramide | Methylcellulose | Safe | 20 mg/kg/d | 1, 3, 7, 14 d | | 1, 3, 7, 14 d |
| Endotoxin | Saline | High | 8 mg/kg (ip) | 6, 12, 24, 48 h | | |
| Endotoxin | Saline | Low | 0.8 mg/kg (ip) | 6, 12, 24, 48 h | | |
| Erythromycin Estolate (EE) | Methylcellulose | High | 800 mg/kg/d | 1, 3, 7, 14 d | | |
| Erythromycin Estolate (EE) | Methylcellulose | Low | 80 mg/kg/d | 1, 3, 7, 14 d | | 1, 3, 7, 14 d |
| Ethanol | Corn Oil | High | 15 g/kg/d | 1, 3, 7, 14 d | | |
| Ethanol | Corn Oil | Low | 1.5 g/kg/d | 1, 3, 7, 14 d | | 1, 3, 7, 14 d |
| Ethinylestradiol | Corn Oil | High | 15 mg/kg/d | 1, 3, 7, 14 d | | |
| Ethinylestradiol | Corn Oil | Low | 1.5 mg/kg/d | 1, 3, 7, 14 d | | |
| Ethionine | Methylcellulose | High | 200 mg/kg/d | 1, 3, 7, 14 d | 1, 3 d | |
| Ethionine | Methylcellulose | Low | 20 mg/kg/d | 1, 3, 7, 14 d | | |
| Ethosuximide | Methylcellulose | Safe | 100 mg/kg/d | 1, 3, 7, 14 d | | 1, 3, 7, 14 d |
| Ethylenethiourea | Saline | High | 920 mg/kg (po) | 6, 12, 24, 48 h | | |
| Ethylenethiourea | Saline | Low | 92 mg/kg (po) | 6, 12, 24, 48 h | | |
| Fenarimol | Corn Oil | High | 62.5 mg/kg/d | 1, 3, 7, 14 d | | |
| Fenarimol | Corn Oil | Low | 6.25 mg/kg/d | 1, 3, 7, 14 d | | |
| Fenbendazole | Methylcellulose | High | 3000 mg/kg/d | 1, 3, 7, 14 d | | |
| Fenbendazole | Methylcellulose | Low | 300 mg/kg/d | 1, 3, 7, 14 d | | 1, 3, 7, 14 d |
| Furan | Corn Oil | High | 15 mg/kg/d | 1, 3, 7, 14 d | | |
| Furan | Corn Oil | Low | 1.5 mg/kg/d | 1, 3, 7, 14 d | | 1, 3, 7, 14 d |
| Hydrazine | Methylcellulose | High | 100 mg/kg/d | 1, 3, 7, 14 d | | |
| Hydrazine | Methylcellulose | Low | 10 mg/kg/d | 1, 3, 7, 14 d | | |
| Ibuprofen | Methylcellulose | Safe | 94 mg/kg/d | 1, 3, 7, 14 d | | 1, 3, 7, 14 d |
| Ketoconazole | Methylcellulose | High | 100 mg/kg/d | 1, 3, 7, 14 d | | |
| Ketoconazole | Methylcellulose | Low | 10 mg/kg/d | 1, 3, 7, 14 d | | 1, 3 d |
| Lead nitrate | Saline | High | 33 g/kg (iv) | 1, 3, 7, 14 d | | |
| Lead nitrate | Saline | Low | 3.3 g/kg (iv) | 1, 3, 7, 14 d | | |
| Methapyrilene | Methylcellulose | High | 60 mg/kg/d | 1, 3, 7, 14 d | | |
| Methapyrilene | Methylcellulose | Low | 6 mg/kg/d | 1, 3, 7, 14 d | | |
| Methionine-choline deficient diet | In feed | High | 60 g/kg/d | 1, 3, 7, 14 d | | |
| Methyl Carbamate | Methylcellulose | High | 400 mg/kg/d | 1, 3, 7, 14 d | | |
| Methyl Carbamate | Methylcellulose | Low | 40 mg/kg/d | 1, 3, 7, 14 d | | |
| Methylcellulose | | Control | | 1, 3, 7, 14 d | | 1, 3, 7, 14 d |
| Methylcellulose (ip) | | Control | | 6, 12, 24, 48 h | | |
| Methylenedianiline | Corn Oil | High | 50 mg/kg/d | 1, 3, 7, 14 d | | |
| Methylenedianiline | Corn Oil | Low | 5 mg/kg/d | 1, 3, 7, 14 d | | |
| Methyleugenol | Methylcellulose | High | 1000 mg/kg/d | 1, 3, 7, 14 d | | |
| Methyleugenol | Methylcellulose | Low | 100 mg/kg/d | 1, 3, 7, 14 d | | |
| Methyl-tert-butyl ether | Corn Oil | High | 1500 mg/kg/d | 1, 3, 7, 14 d | | |
| Methyl-tert-butyl ether | Corn Oil | Low | 150 mg/kg/d | 1, 3, 7, 14 d | | |
| Microcystin-LR | Saline | High | 20 μg/kg (iv) | 6, 12, 24, 48 h | | |
| Microcystin-LR | Saline | Low | 2 μg/kg (iv) | 6, 12, 24, 48 h | | |
| Mirex | Corn Oil | High | 10 mg/kg/d | 1, 3, 7, 14 d | | |
| Mirex | Corn Oil | Low | 1 mg/kg/d | 1, 3, 7, 14 d | | |
| Molybdenum | Methylcellulose | High | 500 mg/kg/d | 1, 3, 7, 14 d | 3 d | |
| Molybdenum | Methylcellulose | Low | 50 mg/kg/d | 1, 3, 7, 14 d | | |
| Monocrotaline | $H_2O$ | High | 160 mg/kg/d | 1, 3, 7, 14 d | 1, 3 d | |
| Monocrotaline | $H_2O$ | Low | 16 mg/kg/d | 1, 3, 7, 14 d | | |
| N-diethylnitrosamine | Methylcellulose | High | 12 mg/kg/d | 1, 3, 7, 14 d | | |
| N-diethylnitrosamine | Methylcellulose | Low | 1.2 mg/kg/d | 1, 3, 7, 14 d | | |
| Nifedipine | Methylcellulose | Safe | 3 mg/kg/d | 1, 3, 7, 14 d | | 1, 3, 7, 14 d |
| Nitrofurantoin | Saline | High | 150 mg/kg (ip) | 1, 3, 7, 14 d | | |
| Nitrofurantoin | Saline | Low | 15 mg/kg (ip) | 1, 3, 7, 14 d | | 1, 3, 7, 14 d |
| Nitrosodiethanolamine | Methylcellulose | High | 200 mg/kg/d | 1, 3, 7, 14 d | | |
| Nitrosodiethanolamine | Methylcellulose | Low | 20 mg/kg/d | 1, 3, 7, 14 d | | 1, 3, 7, 14 d |
| Nitrosomethylethylamine | Methylcellulose | High | 75 mg/kg/d | 1, 3, 7, 14 d | 1, 3 d | |
| Nitrosomethylethylamine | Methylcellulose | Low | 7.5 mg/kg/d | 1, 3, 7, 14 d | 3, 7, 14 d | |
| N-nitrosodibutylamine | Methylcellulose | High | 25 mg/kg/d | 1, 3, 7, 14 d | | |
| N-nitrosodibutylamine | Methylcellulose | Low | 2.5 mg/kg/d | 1, 3, 7, 14 d | | 1, 3, 7, 14 d |
| N-nitrosomorpholine | Methylcellulose | High | 35 mg/kg/d | 1, 3, 7 d | 1, 3, 7, 14 d | |
| N-nitrosomorpholine | Methylcellulose | Low | 3.5 mg/kg/d | 1, 3, 7, 14 d | | |
| N-Nitrosopiperidine | Methylcellulose | High | 200 mg/kg/d | 1, 3, 7, 14 d | 1, 3 d | |

TABLE 1-continued

Zone 3 Necrosis in vivo

| Compound | Vehicle | Dose | Concentration | Time Points | Pathology Present | Pathology Absent |
|---|---|---|---|---|---|---|
| N-Nitrosopiperidine | Methylcellulose | Low | 20 mg/kg/d | 1, 3, 7, 14 d | | |
| NNK | Methylcellulose | High | 20 mg/kg/d | 1, 3, 7, 14 d | | |
| NNK | Methylcellulose | Low | 2 mg/kg/d | 1, 3, 7, 14 d | | |
| Pentachlorophenol | Methylcellulose | High | 50 mg/kg/d | 1, 3, 7, 14 d | | |
| Pentachlorophenol | Methylcellulose | Low | 5 mg/kg/d | 1, 3, 7, 14 d | | 1, 3, 7, 14 d |
| Phenobarbital | Methylcellulose | High | 80 mg/kg/d | 1, 3, 7, 14 d | | |
| Phenobarbital | Methylcellulose | Low | 8 mg/kg/d | 1, 3, 7, 14 d | | |
| Piperonyl Butoxide | Methylcellulose | High | 1200 mg/kg/d | 1, 3, 7, 14 d | | |
| Piperonyl Butoxide | Methylcellulose | Low | 120 mg/kg/d | 1, 3, 7, 14 d | | |
| Potassium bichromate | Methylcellulose | High | 10 mg/kg (ip) | 6, 12, 24, 48 h | | |
| Potassium bichromate | Methylcellulose | Low | 1 mg/kg (ip) | 6, 12, 24, 48 h | | |
| Prazosin | Methylcellulose | Safe | 1 mg/kg/d | 1, 3, 7, 14 d | | 1, 3, 7, 14 d |
| Pregnenolone-16α-Carbonitrile | Methylcellulose | High | 100 mg/kg/d | 1, 3, 7, 14 d | | |
| Pregnenolone-16α-Carbonitrile | Methylcellulose | Low | 10 mg/kg/d | 1, 3, 7, 14 d | | |
| Propranolol | Methylcellulose | Safe | 40 mg/kg/d | 1, 3, 7, 14 d | | 1, 3, 7, 14 d |
| Pyridine | Methylcellulose | High | 300 mg/kg/d | 1, 3, 7, 14 d | 14 d | |
| Pyridine | Methylcellulose | Low | 30 mg/kg/d | 1, 3, 7, 14 d | | |
| Ranitidine | Methylcellulose | Safe | 5 mg/kg/d | 1, 3, 7, 14 d | | 1, 3, 7, 14 d |
| Rifampicin | Methylcellulose | High | 250 mg/kg/d | 1, 3, 7, 14 d | | |
| Rifampicin | Methylcellulose | Low | 25 mg/kg/d | 1, 3, 7, 14 d | | 1, 3, 7, 14 d |
| Saline (ip) | | Control | | 6, 12, 24, 48 h | | 6, 12, 24, 48 h |
| Saline (ip) | | Control | | 1, 3, 7, 14 d | | 1, 3, 7, 14 d |
| Saline (iv) | | Control | | 6, 12, 24, 48 h | | 6, 12, 24, 48 h |
| Saline (iv) | | Control | | 1, 2, 3, 4 d | | 1, 2, 3, 4 d |
| Saline (iv) | | Control | | 1, 3, 7, 14 d | | 1, 3, 7, 14 d |
| Saline (po) | | Control | | 6, 12, 24, 48 h | | 6, 12, 24, 48 h |
| Terfenadine | Methylcellulose | Safe | 10 mg/kg/d | 1, 3, 7, 14 d | | 1, 3, 7, 14 d |
| Thioacetamide | Saline | High | 200 mg/kg (ip) | 6, 12, 24, 48 h | 12, 24, 48 h | |
| Thioacetamide | Saline | Low | 20 mg/kg (ip) | 6, 12, 24, 48 h | 6, 12, 24, 48 h | |
| Thioacetamide | Methylcellulose | High | 19.2 mg/kg/d | 1, 3, 7, 14 d | | |
| Thioacetamide | Methylcellulose | Low | 1.92 mg/kg/d | 1, 3, 7, 14 d | | |
| Thiobenzamide | In Feed | High | ad libitum 1 g/kg | 1, 3, 7, 14 d | 1, 3, 7, 14 d | |
| Thiobenzamide | In Feed | Low | ad libitum 0.1 g/kg | 1, 3, 7, 14 d | | |
| Untreated | | Control | | 1, 3, 7, 14 d | | 1, 3, 7, 14 d |
| Untreated | | Control | | 6, 12, 24, 48 h | | 6, 12, 24, 48 h |
| Untreated | | Control | | 1, 2, 3, 4 d | | 1, 2, 3, 4 d |
| WY-14643 | Methylcellulose | High | 60 mg/kg/d | 1, 3, 7, 14 d | | |
| WY-14643 | Methylcellulose | Low | 6 mg/kg/d | 1, 3, 7, 14 d | | |
| Xylidine | Corn Oil | High | 600 mg/kg/d | 1, 3, 7, 14 d | | |
| Xyidine | Corn Oil | Low | 60 mg/kg/d | 1, 3, 7, 14 d | | |

Example 2

Induction of Zone 3 Necrosis In Vitro

Over 100 compounds were chosen based on evidence that they elicit one of eleven selected histopathology subtypes. The criteria for inclusion of a compound into the zone 3 necrosis mode was necrosis or individual cell necrosis in centrilobular zone with an increase in some or all serum transaminases. The compounds included in the zone 3 necrosis mode can been seen in Table 2. Rat primary hepatocytes were treated with the same compounds used in the in vivo experiments. In all cases, compounds were run in any given two-day period with an untreated and DMSO vehicle as negative controls. Each compound was delivered daily at a reference dose derived from the literature (when available), a 10× high dose, and 1/10 and 1/100 low doses for up to 72 hours. Three hepatocyte cultures for each dose were randomly assigned for harvest at 6, 24, 48 and 72 hours. In order to best identify genes characteristic of zone 3 necrosis, total RNA for all hepatocyte cultures from a given dose time point were pooled and converted to mRNA and cDNA for GeneCalling®. In GeneCalling, the cDNA is cut with a battery of restriction enzyme pairs in different combinations followed by amplification by PCR using specific primers linked to specific adaptors. After gel electrophoresis, the resulting fragments are identified based on the inherent information in the cDNA fragment: The flanking restriction site sequences on the ends, the size of the fragment and the species (and sometimes the tissue) origin of the DNA. This information is used to query public and proprietary databases. The fragments that do not match any sequences in the database are isolated, sequenced and identified as novel.

TABLE 2

Zone 3 Necrosis in vitro

| Compound | Annotation | Concentration (microM) | Zone 3 Necrosis Pathology |
|---|---|---|---|
| 1,3-Dibromobenzene | | 63 | |
| 1,3-Dibromobenzene | | 250 | Present |
| 2AAF | | 10 | |
| 2AAF | | 50 | |
| 2-nitrofluorene | | 30 | |
| 2-nitrofluorene | | 150 | |
| Acetamide | | 500 | |
| Acetamide | | 2000 | |

TABLE 2-continued

Zone 3 Necrosis in vitro

| Compound | Annotation | Concentration (microM) | Zone 3 Necrosis Pathology |
|---|---|---|---|
| Acetaminophen | | 100 | |
| Acetaminophen | | 1000 | Present |
| Aflatoxin | | 0.008 | |
| Aflatoxin | | 0.04 | |
| Allylalcohol | | 16 | |
| Allylalcohol | | 80 | |
| Allylformate | | 0.06 | |
| Allylformate | | 0.3 | |
| Amiodarone | | 5 | |
| Amiodarone | | 20 | |
| ANIT | | 3.1 | |
| ANIT | | 13 | |
| Aspirin | non-toxic | 55.5 | Absent |
| Aspirin | non-toxic | 555 | |
| Atorvastatin | non-toxic | 0.0095 | Absent |
| Atorvastatin | non-toxic | 0.095 | |
| Azaserine | | 100 | |
| Azaserine | | 500 | Present |
| Azobenzene | | 1.6 | Absent |
| Azobenzene | | 8 | |
| BCNU | | 50 | |
| BCNU | | 250 | |
| Butylhydroxytoluene | | 75 | |
| Butylhydroxytoluene | | 150 | |
| Bretylium | non-toxic | 1.2 | Absent |
| Bretylium | non-toxic | 12 | |
| Bromobenzene | | 600 | |
| Bromobenzene | | 3000 | Present |
| Carbamate | | 300 | |
| Carbamate | | 1500 | |
| Carbamazepine | | 200 | |
| Carbamazepine | | 1000 | |
| CCNU | | 8 | |
| CCNU | | 40 | |
| CdCl | | 0.1 | |
| CdCl | | 0.5 | |
| CeCl3 | | 4 | |
| CeCl3 | | 20 | Present |
| Cefuroxime | non-toxic | 224 | Absent |
| Cefuroxime | non-toxic | 2240 | |
| Chlordane | | 8 | Absent |
| Chlordane | | 40 | |
| ClDirect | | 1 | |
| ClDirect | | 5 | |
| Ciprofibrate | | 100 | |
| Ciprofibrate | | 500 | |
| Clofibrate | | 100 | Absent |
| Clofibrate | | 400 | |
| Clonidine | non-toxic | 0.0165 | Absent |
| Clonidine | non-toxic | 0.165 | |
| Colchicine | | 500 | |
| Colchicine | | 2000 | |
| Concanavalin A | | 5000 | |
| Concanavalin A | | 20000 | |
| Coumarin | | 63 | |
| Coumarin | | 250 | Present |
| 4-chlorobenzotrifluoride | | 250 | |
| 4-chlorobenzotrifluoride | | 1000 | |
| Cyclosporine | | 3.1 | Absent |
| Cyclosporine | | 13 | |
| Cyproterone | | 10 | |
| Cyproterone | | 50 | |
| 2,4-diaminotoluene | | 0.8 | |
| 2,4-diaminotoluene | | 4 | |
| Di(2-Ethylhexyl)phthalate | | 500 | |
| Di(2-Ethylhexyl)phthalate | | 2000 | |
| Dehydroepiandosterone | | 1.2 | |
| Dehydroepiandosterone | | 6 | |
| Deoxycholate | | 6.3 | |
| Deoxycholate | | 25 | |
| Dexamethasone | | 100 | Absent |
| Dexamethasone | | 500 | |
| Dibutyltin | | 0.2 | |

TABLE 2-continued

Zone 3 Necrosis in vitro

| Compound | Annotation | Concentration (microM) | Zone 3 Necrosis Pathology |
|---|---|---|---|
| Dibutyltin | | 1 | |
| Dichlorobenzene | | 100 | Absent |
| Dichlorobenzene | | 500 | |
| Diethylnitrosamine | | 60 | |
| Diethylnitrosamine | | 300 | Present |
| Diethylstillbestrol | | 5 | |
| Diethylstillbestrol | | 50 | |
| Dimethylnitrosamine | | 200 | |
| Dimethylnitrosamine | | 1000 | Present |
| Disopyramide | non-toxic | 3 | Absent |
| Disopyramide | non-toxic | 30 | |
| Dimethylformamide | | 1000 | |
| Dimethylformamide | | 5000 | Present |
| DMSO | control | 0 | Absent |
| Doxorubicin | non-toxic | 0.5 | Absent |
| Doxorubicin | non-toxic | 5 | |
| Endotoxin | | 30 | |
| Endotoxin | | 100 | |
| Erythromycin | | 20 | Absent |
| Erythromycin | | 100 | |
| Ethanol | | 200 | Absent |
| Ethanol | | 1000 | |
| Ethinylestradiol | | 25 | |
| Ethinylestradiol | | 100 | |
| Ethionine | | 200 | |
| Ethionine | | 1000 | Present |
| Ethosuximide | non-toxic | 1000 | Absent |
| Ethosuximide | non-toxic | 10000 | |
| Ethylenethiourea | | 200 | |
| Ethylenethiourea | | 1000 | |
| Fenarimol | | 20 | Absent |
| Fenarimol | | 100 | |
| Fenbendazole | | 16 | |
| Fenbendazole | | 63 | |
| Fluconazole | non-toxic | 0.816 | Absent |
| Fluconazole | non-toxic | 8.16 | |
| Gabapentin | non-toxic | 2 | Absent |
| Gabapentin | non-toxic | 20 | |
| Galactosamine | | 12 | |
| Galactosamine | | 60 | |
| Hydrazine | | 20 | |
| Hydrazine | | 100 | |
| Ibuprofen | non-toxic | 50 | Absent |
| Ketoconazole | | 2 | Absent |
| Ketoconazole | | 10 | |
| Mephenytoin | non-toxic | 14.2 | Absent |
| Mephenytoin | non-toxic | 142 | |
| Methapyriline | | 30 | |
| Methapyriline | | 100 | |
| Methylcholanthrene | | 40 | Absent |
| Methylcholanthrene | | 200 | |
| Methylenedianiline | | 1.4 | |
| Methylenedianiline | | 7.8 | |
| Methylleugenol | | 100 | |
| Methylleugenol | | 500 | |
| Microcystin | | 0.005 | |
| Microcystin | | 0.025 | |
| Minoxidil | non-toxic | 0.166 | Absent |
| Minoxidil | non-toxic | 1.66 | |
| Mirex | | 50 | Absent |
| Mirex | | 100 | |
| Molybdenum | | 20 | |
| Molybdenum | | 50 | Present |
| Monocrotaline | | 30 | |
| Monocrotaline | | 100 | Present |
| Methyl-tert-butyl ether | | 1000 | |
| Methyl-tert-butyl ether | | 4000 | |
| Nifedipine | non-toxic | 0.335 | Absent |
| Nifedipine | non-toxic | 3.35 | |
| Nitrofurantoin | | 4 | Absent |
| Nitrofurantoin | | 20 | |
| Nitrosodibutylamine | | 200 | Absent |
| Nitrosodibutylamine | | 1000 | |

TABLE 2-continued

Zone 3 Necrosis in vitro

| Compound | Annotation | Concentration (microM) | Zone 3 Necrosis Pathology |
|---|---|---|---|
| Nitrosodiethanolamine | | 1000 | Absent |
| Nitrosodiethanolamine | | 5000 | |
| Nitrosomethylethylamine | | 200 | |
| Nitrosomethylethylamine | | 1000 | Present |
| Nitrosomorpholine | | 750 | |
| Nitrosomorpholine | | 3750 | Present |
| Nitrosopiperidine | | 640 | |
| Nitrosopiperidine | | 3200 | Present |
| NNK | | 200 | |
| NNK | | 1000 | |
| Norethindrone | | 40 | Absent |
| Norethindrone | | 200 | |
| Pentachlorophenol | | 19 | Absent |
| Pentachlorophenol | | 38 | |
| Piperonyl | | 20 | |
| Piperonyl | | 100 | |
| Prazosin | non-toxic | 0.0148 | Absent |
| Prazosin | non-toxic | 0.148 | |
| Pregnenolone | | 38 | Absent |
| Pregnenoione | | 150 | |
| Propranolol | non-toxic | 0.125 | Absent |
| Propranolol | non-toxic | 1.25 | |
| Pyridine | | 800 | |
| Pyridine | | 4000 | Present |
| Ranitidine | non-toxic | 0.128 | Absent |
| Ranitidine | non-toxic | 1.28 | |
| Rifampicin | | 20 | Absent |
| Rifampicin | | 100 | |
| Terfenadine | non-toxic | 0.15 | Absent |
| Terfenadine | non-toxic | 1.5 | |
| Thioacetamide | | 500 | |
| Thioacetamide | | 2000 | Present |
| Thiobenzamide | | 8 | |
| Thiobenzamide | | 40 | Present |
| Untreated | control | 0 | Absent |
| Verapamil | non-toxic | 0.1 | Absent |
| Verapamil | non-toxic | 1 | |
| WY14643 | | 20 | |
| WY14643 | | 100 | |
| Xylidine | | 13 | |
| Xylidine | | 50 | |

Example 3

Methods of Analysis

Data Preparation:

We used GeneCalling® to estimate the activity of several thousand transcripts simultaneously. These data generally have ~5% missing data and are log normally distributed. The data are log transformed and missing values are filled using k-nearest neighbor (knn) replacement [14]. The knn algorithm was initially validated using a complete data set and randomly eliminating constant percentages of the data. It was determined that using correlation as a similarity index and imputing missing values with 6 nearest neighbors resulted in the smallest error of prediction.

Initially our data sets contained between 6000 and 8000 genes, which poses two problems. These large numbers of genes make most marker selection procedures computationally intractable with most computer algorithms. Second, the inclusion of markers with low variation, or low association with pathology results in a significant risk of choosing markers that over fit the models. To eliminate these problems we imposed an initial filter on the data, requiring that there be a significant difference between negative control samples and positive control samples for each pathology mode (Kruskal-Wallis test, $p<0.001$). Depending on mode, this process reduced our gene set to a more tractable number of genes (approximately 200–800 genes depending on mode).

Initial Marker Selection:

We define a marker as a gene that helps to explain some variation in pathology. In order to avoid selecting markers that particularly fit our current data set well at the expense of predictability outside our training set, we employed a leave one out cross-validation method to identify markers that contribute some explanatory power to the data set. Specifically, after the Kruskal-Wallis filter, a series of leave one out models are created leaving out all of the samples for each compound until all compounds have been left out once. This process results in a marker list and a count of the number of leave-one out models the marker was used in. This marker list contains all of the genes that explain some portion of the variation in pathology but is almost certain to over fit the data because of its size. In order to refine this marker list a second series of leave one compound out models is created for each different count of markers within the marker list. For example, the initial leave one out model may produce a gene list consisting of 5 genes that occur at frequencies of 20, 19, 19, 2, and 1 leave one out models respectively. The first step will use all genes that occur in 1 or more leave one out models, the second step 2 or more, the third 19 or more and finally 20 or more. The genes that are considered to be markers will have been used in a majority of models and result in a highly sensitive model. In most cases the first modeling step resulted in a sharp cutoff (e.g. 19 or more in the above example), which guides the marker selection process. In a few cases, the change in frequency was so gradual that no clear cutoff was available. Marker selection then proceeded with the most sensitive model first, and then the most specific model and in the case of ties the least number of markers.

Models:

The above process is a general strategy that is applied to all of our marker selection models. The models we used covered a range of statistical power and assumption stringency. The most powerful model with the strongest assumptions is a linear discriminant analysis, followed by logistic regression and finally by classification trees, which is virtually devoid of assumptions but does have a cost in terms of predictivity. These modeling methods are common statistical procedures that need not be developed here [15] [16] for a more detailed discussion). All three methods went through the algorithm outlined above with the exception of discriminant analysis, which did not utilize a Kruskal-Wallis filter. Both discriminant analysis and logistic regression create poor models when too many intercorrelated variables are used. To minimize this problem, these methods utilized a stepwise selection procedure (incorporating both forward and reverse selection) to select the best discriminating set of markers.

In Vivo Pathology Annotation:

In order to construct in vivo models, the pathology of each sample had to be determined. Pathology was assigned to each liver sample by the pathologists at Bayer's Stillwell, Kans. facility. Criteria for inclusion of a compound into a particular mode included the following:

i. Zone-3 Necrosis: Necrosis or individual cell necrosis in centrilobular zone with an increase in some or all serum transaminases.

ii. Cholestasis: Increased plasma billirubin with bile duct necrosis or hyperplasia.

iii. Hypertrophy: Increase in cell size and liver weight.

iv. Genotoxic Carcinogens: Some evidence of mild parenchymal damage in vivo which may be associated with an increase in mitosis. Compounds assigned to this group must have strong historical documentation. Compounds from other pathology modes cannot be added to this list.

V. Non-genotoxic Carcinogens: Evidence of parenchymal changes and an increase in mitosis. Compounds assigned to this group must have strong historical documentation. Compounds from other pathology modes cannot be added to this list.

vi. Steatosis: Increase in lipid accumulation or "vacuolar degeneration."

vii. Zone 1 Necrosis: Necrosis or individual cell necrosis in the periportal zone, with an increase in some or all serum transaminases.

vii. Inflammation: Increase in inflammatory cells (e.g. Kupffer cells, neutrophils, macrophages, lymphocytes)

viii. Apoptosis: Shrinking or fragmentation of the nucleus and increased "blebbing."

In Vitro Pathology Annotation:

In order to construct in vitro models we need to make a decision about what pathology each sample represents. Two approaches were used. The first is to ascribe the in vivo compound annotation to the two highest concentrations in vitro (these are traditionally within five fold of each other). For example, clofibrate produced hypertrophy in vivo, so the two highest doses in vitro are used as a positive control for the model construction process. The second annotation strategy uses a nearest neighbor algorithm to assign annotation from in vivo samples to in vitro samples. Briefly, each in vitro sample was correlated, across in vivo markers, to all in vivo samples of the same compound. The annotation of the most correlated in vivo sample was used as the in vitro annotation.

Final Marker Selection:

This process resulted in 6 sets of models being generated for each mode of pathology (LDA, logistic, and classification trees for each annotation strategy, nearest neighbor and high dose). These markers are then correlated with the original data set (between 6000 and 8000 genes) and additional correlated markers (r>=0.60 across 329 samples, up to 3 per marker) were added back in to the final gene set for representation on a microarray.

Example 4

Identification of Zone 3 Necrosis Related Genes In Vivo

SP=Secreted Protein

NC=Novel Rat Composition

NU=Novel Rat Utility

TABLE 3

| | ACCNO | TOX MARKER ASSIGNMENT | SEQ ID NO: | Definition | Description | Bin |
|---|---|---|---|---|---|---|
| NU | scr_gb-af038870_4 | 1 | 1 | *Rattus norvegicus* betaine homocysteine methyltransferase (BHMT) [AF038870]. | Betaine-homocysteine methyltransferase (BHMT) catalyzes the transfer of an N-methyl group from betaine to homocysteine to produce dimethylglycine and methionine, respectively. The enzyme is found in the pathway of choline oxidation and is abundantly expressed in liver and kidney. It has been known for at least 50 years that alterations in methionine metabolism occur in human liver cirrhosis. Recently human BHMT had been shown to be a zinc metalloenzyme [14] [15]. | Amino Acid Metabolism |
| NC NU | scr_gb-z83053_3 | 2 | 2 | Rat gene fragment - 1984 bp. 88% SI (1241/1396) to *Mus musculus* betaine-homocysteine methyltransferase 2 (Bhmt2) [AF257474]. | Betaine-homocysteine methyltransferase (BHMT) catalyzes the transfer of an N-methyl group from betaine to homocysteine to produce dimethylglycine and methionine, respectively. The enzyme is found in the pathway of choline oxidation and is abundantly expressed in liver and kidney. It has been known for at least 50 years that alterations in methionine metabolism occur in human liver cirrhosis. Recently human BHMT had been shown to be a zinc metalloenzyme [14] [15]. | Amino Acid Metabolism |
| NU | scr_gb-x95189_4 | 3 | 3 | *Rattus norvegicus* Trihydroxycoprostanoyl-CoA Oxidase [X95189]. | Rat liver peroxisomes contain three acyl-CoA oxidases:palmitoyl-CoA oxidase, pristanoyl-CoA oxidase, and trihydroxycoprostanoyl-CoA oxidase. Mammalian liver peroxisomes are capable of beta-oxidizing a variety of substrates including very long chain fatty acids and the side chains of the bile acid intermediates di- and trihydroxycoprostanic acid. The first enzyme of peroxisomal beta-oxidation is acyl-CoA oxidase [16]. | Lipid Metabolism |
| NU | scr_gb-m59814_4 | 4 | 4 | *Rattus norvegicus* Ephrin type-B receptor 1 precursor (EphB1) [P09759] | Eph receptor tyrosine kinases and their membrane-bound ligands, ephrins, have thus emerged as mediators of cell-contact-dependent repulsion. The actin cytoskeleton is also a major target of the intracellular pathways activated by Eph receptors [17]. More specifically, activation of EphB1 by its ligand, ephrin-B1/Fc has been shown to recruit Nck to | Cell Cycle Regulation (Regulation Of Proliferation) |

TABLE 3-continued

| | ACCNO | TOX MARKER ASSIGNMENT | SEQ ID NO: | Definition | Description | Bin |
|---|---|---|---|---|---|---|
| | | | | | native receptor complexes and activate c-Jun kinase (JNK/SAPK) [18] | |
| NU | scr_gb-m29358_5 | 5 | 5 | *Rattus norvegicus* ribosomal protein S6 [M29358]. | It has been known for 20 years that the ribosomal protein S6 is rapidly phosphorylated when cells are stimulated to grow or divide [19]. S6 is phosphorylated in response to mitogens by activation of one or more protein kinase cascades. Members of the 90 kDa S6 kinases are activated in vitro by 42 kDa and 44 kDa MAP kinases, which are in turn activated by mitogen-dependent activators [20]. | Protein Metabolism |
| NU | aj297336 | 6 | 6 | *Rattus norvegicus* heat shock protein 86 (hsp86) [AJ428213]. | In addition to appearing in response to biological stresses, heat shock proteins are expressed as 'chaperones' by some cells living in physiological conditions. Among these proteins, the Hsp90 family, consisting of isoforms Hsp84 and Hsp86, seems to function under normal growth conditions in the pathways of numerous signal transducers, cell cycle and developmental regulators. [21, 22] | Protein Metabolism |
| NU | j00719 | 7 | 7 | *Rattus norvegicus* cytochrome p-450 isoform, (phenobarbital-inducible or 2B1) [J00719] [P04167]. | The cytochromes P-450 are among the major constituent proteins of the liver mixed function monooxygenases. They play a central role in the metabolism of steroids, the detoxification of drugs and xenobiotics, and the activation of procarcinogens. In liver microsomes, this enzyme is involved in an NADPH-dependent electron transport pathway. It oxidizes a variety of structurally unrelated compounds, including steroids, fatty acids, and xenobiotics [23]. | Detoxification Response/ Biotransformation-TOX |
| NU | j00720 | 8 | 8 | *Rattus norvegicus* cytochrome p-450 isoform, (phenobarbital-inducible or 2B2) [P04167] [J00719]. | The cytochromes P-450 are among the major constituent proteins of the liver mixed function monooxygenases. They play a central role in the metabolism of steroids, the detoxification of drugs and xenobiotics, and the activation of procarcinogens. In liver microsomes, this enzyme is involved in an NADPH-dependent electron transport pathway. It oxidizes a variety of structurally unrelated compounds, including steroids, fatty acids, and xenobiotics [23]. | Detoxification Response/ Biotransformation-TOX |
| NU | j00728 | 9 | 9 | *Rattus norvegicus* cytochrome p-450 isoform, (phenobarbital-inducible, 2B1, or 2B2) [P00176] [P04167] [Q64584]. | The cytochromes P-450 are among the major constituent proteins of the liver mixed function monooxygenases. They play a central role in the metabolism of steroids, the detoxification of drugs and xenobiotics, and the activation of procarcinogens. In liver microsomes, this enzyme is involved in an NADPH-dependent electron transport pathway. It oxidizes a variety of structurally unrelated compounds, including steroids, fatty acids, and xenobiotics [23]. | Detoxification Response/ Biotransformation-TOX |
| NU | l00320 | 10 | 10 | *Rattus norvegicus* cytochrome p-450 isoform (phenobarbital-inducible, 2B1, or 2B2) [J00719] [P00176] [P04167]. | The cytochromes P-450 are among the major constituent proteins of the liver mixed function monooxygenases. They play a central role in the metabolism of steroids, the detoxification of drugs and xenobiotics, and the activation of procarinogens. In liver microsomes, this enzyme is involved in an NADPH-dependent electron transport pathway. It oxidizes a variety of structurally unrelated compounds, including steroids, fatty acids, and xenobiotics [23]. | Detoxification Response/ Biotransformation-TOX |
| NU | m11251 | 11 | 11 | *Rattus norvegicus* cytochrome p-450 isoform (phenobarbital-inducible, 2B1, or 2B2) [Q64584] P00176] [P04167]. | The cytochromes P-450 are among the major constituent proteins of the liver mixed function monooxygenases. They play a central role in the metabolism of steroids, the detoxification of drugs and xenobiotics, and the activation of procarcinogens. In liver microsomes, this enzyme is involved in an NADPH-dependent electron transport pathway. It oxidizes a variety of structurally unrelated compounds, including steroids, fatty acids, and xenobiotics [23]. | Detoxification Response/ Biotransformation-TOX |
| NU | m26125 | 12 | 12 | *Rattus norvegicus* epoxide hydrolase [M26125]. | Epoxide formation from drugs, chemicals, food additives and environmental pollutants is catalyzed by cytochrome P-450 dependent monooxygenase(s). Epoxides are converted to glycols or dihydrodiols by epoxide hydrolase. | Detoxification Response/ Biotransformation-TOX |

TABLE 3-continued

| | ACCNO | TOX MARKER ASSIGNMENT | SEQ ID NO: | Definition | Description | Bin |
|---|---|---|---|---|---|---|
| | | | | | These enzymes are known to be present in the microsomes of different mammalian tissues and in the hepatic nuclei from rats and humans. The balance between the epoxide forming (AHH) and metabolizing (EH) enzyme activities may provide information about the "epoxide exposure" of a tissue [Kuklin, 1976 #2]. | |
| NU | m34452 | 13 | 13 | *Rattus norvegicus* cytochrome P450e-L (P450IIB2) [M34452]. | Epoxide formation from drugs, chemicals, food additives and environmental pollutants is catalyzed by cytochrome P-450 dependent monooxygenase(s). Epoxides are converted to glycols or dihydrodiols by epoxide hydrolase. These enzymes are known to be present in the microsomes of different mammalian tissues and in the hepatic nuclei from rats and humans. The balance between the epoxide forming (AHH) and metabolizing (EH) enzyme activities may provide information about the "epoxide exposure" of a tissue [Kuklin, 1976 #2]. | Detoxification Response/ Biotransformation-TOX |
| NU | u33546 | 14 | 14 | *Rattus norvegicus* CYP2B16P [CAB35441]. | CYP2B16P is an apparent pseudogene in the rat cytochrome P450 2B (CYP2B) subfamily [24]. | Detoxification Response/ Biotransformation-TOX |
| NU | x74673 | 15 | 15 | *Rattus norvegicus* aflatoxin B1 aldehyde reductase (AFAR) [X74673]. | Aflatoxin B1 aldehyde reductase/Succinic semialdehyde reductase is believed to be involved in the detoxification of xenobiotic carbonyl compounds [25]. | Detoxification Response/ Biotransformation-TOX |
| SP | scr_gb-x13044_4 | 16 | 16 | *Rattus norvegicus* MHC-associated invariant chain gamma (Ia antigen-associated invariant chain) (Ii) [X13044]. | MHC class II molecules at the surface of antigen presenting cells present antigenic peptides to CD4+ T helper cells. Ii plays a critical role in MHC class II antigen processing by stabilizing peptide-free class II alpha/beta heterodimers [26]. | Immunity And Defense |
| SP | scr_gb-x14254_5 | 17 | 17 | *Rattus norvegicus* MHC-associated invariant chain gamma (Ia antigen-associated invariant chain) (Ii) [X14254]. | MHC class II molecules at the surface of antigen presenting cells present antigenic peptides to CD4+ T helper cells. Ii plays a critical role in MHC class II antigen processing by stabilizing peptide-free class II alpha/beta heterodimers [26]. | Immunity And Defense |
| NU | scr_gb-bi275638_1 | 18 | 18 | *Rattus norvegicus* Ras-related protein Rab-2 [P05712]. | Rab proteins form the largest branch of the Ras superfamily of GTPases. They are localized to the cytoplasmic face of organelles and vesicles involved in the biosynthetic/secretory and endocytic pathways in eukaryotic cells [27]. | Intracellular Transport |
| | scr_gb-x66871_3 | 19 | 19 | *Rattus norvegicus* calpactin I heavy chain (annexin II) [X66871]. | The annexins are a family of proteins that bind acidic phospholipids in the presence of Ca2+. Because annexin II bridge secretory granules to plasma membrane it has suggested that this protein may play a role in Ca(2+)-dependent exocytosis. Annexin II tetramer has also been demonstrated on the extracellular face of some metastatic cells where it mediates the binding of certain metastatic cells to normal cells. Annexin II tetramer is a major cellular substrate of protein kinase C and pp60src [28]. | Intracellular Transport |
| NU | scr_gb-l49379_3 | 20 | 20 | *Rattus norvegicus* canalicular multispecific organic anion transporter (cMOAT) [L49379]. | cMOAT mediates the hepatobiliary excretion of numerous organic anions. It has been shown that both multidrug resistance-associated protein (MRP1) and canalicular multispecific organic anion transporter (cMOAT/MRP2) have the ability to extrude glutathione conjugates (GS-X pump activity) from cells [29] [30]. | Oxidative Stress-TOX |
| SP | scr_sc-132690501_1 | 21 | 21 | Rat gene fragment - 775 bp. 85% SI (618/722) to *Homo sapiens* inter-alpha-trypsin inhibitor heavy chain IIH1 [X63652]. | Inter-alpha-trypsin inhibitor (ITI) is a complex protein containing two heavy polypeptide chains (H1 and H2) and a light chain, which in the free state is known as bikunin [31]. ITI is a 220 kDa serine proteinase inhibitor found in human serum [32]. | Other |
| NC | scr_gb-aw141735_3 | 22 | 22 | Rat gene fragment - 1561 bp. 98% SI (1002/1022) to *Mus musculus* serine proteinase inhibitor mBM2A [U96701]. | Serine proteinase inhibitors (serpins) are classically regulators of extracellular proteolysis. Evidence suggests that some function intracellularly as well [33]. | Other |

TABLE 3-continued

| | ACCNO | TOX MARKER ASSIGNMENT | SEQ ID NO: | Definition | Description | Bin |
|---|---|---|---|---|---|---|
| SP | af18498 3 | 23 | 23 | *Rattus norvegicus* osteoactivin [AF184983]. | Osteoactivin cDNA was recently isolated from long bone and calvaria. In primary rat osteoblast cultures it was expressed at the highest levels during the later stages of matrix maturation and mineralization and correlated with the expression of alkaline phosphatase and osteocalcin. [34]. | Unknown |
| NU | scr_cg-2251067 4_1 | 24 | 24 | Unknown, 241 bp. | | Novel |
| NU | scr_cg-5721522 4_1 | 25 | 25 | Unknown, 283 bp. | | Novel |
| NU | scr_gb-aa85076 7_2 | 26 | 26 | Unknown, 642 bp. | | Novel |
| NU | scr_gb-ai01199 4_2 | 27 | 27 | Unknown, 866 bp. | | Novel |
| NU | scr_gb-aw1422 93_1 | 28 | 28 | Unknown, 629 bp. | | Novel |
| NU | scr_gb-bm3833 27_1 | 29 | 29 | Unknown, 1145 bp. | | Novel |
| NU | scr_gb-bm3866 25_1 | 30 | 30 | Unknown, 3087 bp. | | Novel |
| NU | scr_sc-1335569 69_1 | 31 | 31 | Unknown, 434 bp. | | Novel |
| NU | scr_sc-1701427 36_1 | 32 | 32 | Unknown, 221 bp. | | Novel |
| NU | scr_sc-2563586 _2 | 33 | 33 | Unknown, 581 bp. | | Novel |
| NU | scr_sc-8761825 7_1 | 34 | 34 | Unknown, 221 bp. | | Novel |

Example 5

Identification of Zone 3 Necrosis Related Genes In Vitro

SP=Secreted Protein
NC=Novel Rat Composition
NU=Novel Rat Utility

TABLE 4

| | ACCNO | TOX MARKER ASSIGN-MENT | SEQ ID NO | Definition | Description | Bin |
|---|---|---|---|---|---|---|
| NU | cszr_96561 134_837604 93 | 35 | 35 | *Rattus norvegicus* Carbamoyl-phosphate synthase [ammonia] (CPSASE I), mitochondrial precursor [P07756]. | Mitochondrial protein involved in the urea acid cycle of ureotelic animals where the enzyme plays an important role in removing excess ammonia from the cell. Catalytic Activity: 2 ATP + NH(3) + CO(2) + H(2)O = 2 ADP + ORTHOPHOSPHATE + CARBAMOYL PHOSPHATE [17]. | Amino Acid Metabolism |
| NU | scr_gb-x83855_1 | 36 | 36 | *Rattus norvegicus* hepatocyte EP3alpha receptor [X83855]. | EP3 receptors for Prostaglandin (PG) E(2) are primarily involved in inhibition of adenylyl cyclase via G(i) activation, and in Ca(2+)-mobilization through Gbetagamma from G(i). Along with G(i) | Carbohydrate Metabolism |

TABLE 4-continued

| | ACCNO | TOX MARKER ASSIGN-MENT | SEQ ID NO | Definition | Description | Bin |
|---|---|---|---|---|---|---|
| | | | | | activation, the EP3 receptor can stimulate cAMP production via G(s) activation [18]. | |
| NU | cszr_229800465_190907286 | 37 | 37 | *Rattus norvegicus* non-neuronal enolase (NNE) (alpha-alpha enolase, 2-phospho-D-glycerate hydrolase [X02610]. | Enolase is a vital enzyme of the glycolytic pathway. It exists mainly in two forms, non-neuronal enolase (NNE) and neuron specific enolase (NSE). Catalytic Activity: 2-phospho-D-glycerate = phosphoenolpyruvate + H(2)O [19]. | Carbohydrate Metabolism |
| SP | scr_gb-bi277612_1 | 38 | 38 | Rat gene fragment - 1381 bp. 89% SI (816/910) to *Mus musculus* for beta-hexosaminidase [Y00964]. | Two genes, HEXA and HEXB, encode the alpha- and beta-subunits, respectively, of human beta-hexosaminidase. In the mouse, the corresponding genes are termed Hexa and Hexb. The subunits have the capacity to degrade a variety of substrates including oligosaccharides, glycosaminoglycans, and glycolipids containing beta-linked N-acetylglucosaminyl or N-galactosaminyl residues [20]. | Carbohydrate Metabolism |
| NU | scr_gb-j05266_3 | 39 | 39 | *Rattus norvegicus* mitochondrial H+-ATP synthase alpha subunit [J05266]. | H+-ATP synthase catalyzes the synthesis and/or hydrolysis of ATP [21]. | Energy Metabolism |
| NU | scr_gb-m37394_5 | 40 | 40 | *Rattus norvegicus* epidermal growth factor receptor (Egfr) [M37394]. | Egfr is involved in the initiation of oncogenic effect such as DNA synthesis, enhanced cell growth, invasion, and metastasis. Specific abrogation of EGFR results in cell cycle arrest, apoptosis, or dedifferentiation of cancer cells [22]. | Cell Cycle Regulation (Regulation Of Proliferation) |
| NU | scr_gb-m64300_4 | 41 | 41 | *Rattus norvegicus* extracellular signal-related kinase (ERK2) [M64300]. | The Raf/MEK/ERK signaling was the first MAP kinase cascade to be characterized. It is probably one of the most well known signal transduction pathways among biologists because of its implication in a wide variety of cellular functions as diverse- and occasionally contradictory- as cell proliferation, cell-cycle arrest, terminal differentiation and apoptosis [23]. | Cell Cycle Regulation (Regulation Of Proliferation) |
| SP | scr_gb-bi294409_1 | 42 | 42 | Rat gene fragment - 526 bp. 88% SI (313/355) to *Mus musculus* type I interferon receptor soluble isoform precursor (IFNAR2) [AF013486]. | IFNAR-2, is expressed ubiquitously, and exists as both transmembrane and soluble forms. Recent evidence suggests murine IFNAR-2 as an efficient regulator of IFN responses. Type I interferons are cytokines that are important in defense against viral infections well as in the control of cell proliferation [24] [25]. | Cell Cycle Regulation (Regulation Of Proliferation) |
| NU | scr_gb-ab015747_3 | 43 | 43 | *Rattus norvegicus* interleukin-4 receptor (membrane-bound form) [AB015747]. | IL-4 is a pleiotropic cytokine which plays a pivotal role in shaping immune responses. The effects of IL-4 are mediated after binding to high affinity receptor complexes present on hematopoietic as well as non-hematopoietic cells. There is also evidence that IL-4 interaction with its receptor leads to signal transduction mechanisms that result in cellular proliferation and/or gene activation [26]. | Cell Cycle Regulation (Regulation Of Proliferation) |
| NU | scr_sc-191879433_1 | 44 | 44 | *Rattus norvegicus* Crk-associated substrate, p130 [D29766]. | The Crk-associated substrate (Cas) is a unique docking protein with a Src homology 3 (SH3) domain. Aberrant CAS tyrosine phosphorylation may contribute to cell transformation by certain oncoproteins, including v-Crk and v-Src, and to tumor growth and metastasis [27] [28]. | Cell Cycle Regulation (Regulation Of Proliferation) |
| NC | scr_sr-140438096_1 | 45 | 45 | Rat gene fragment - 383 bp. 98% SI (125/127) to *Homo sapiens* Diacylglycerol kinase, delta [Q16760]. | Diacylglycerol kinase (DGK) plays an important role in the signal transduction through modulating the balance between two signaling lipids, diacylglycerol and phosphatidic acid. Diacylglycerol is a protein kinase c activator. Thus, DGK is considered to regulate protein kinase C activity through the reduction of diacylglycerol [29] [30]. | Cell Cycle/ Proliferation (Basic Machinery) |
| NU | scr_gb-x87157_5 | 46 | 46 | *Rattus norvegicus* neurotensin endopeptidase [X87157]. | Neurotensin is a 13-amino acid hormonal peptide which was first isolated from bovine hypothalamus. It is present in the digestive tract as well as in the central nervous system. It has a variety of biological activities as a central neurotransmitter or neuromodulator, and a peripheral hormone [20]. | Cellular Communication |

TABLE 4-continued

| | ACCNO | TOX MARKER ASSIGN-MENT | SEQ ID NO | Definition | Description | Bin |
|---|---|---|---|---|---|---|
| NU | scr_gb-u66707_2 | 47 | 47 | *Rattus norvegicus* densin-180 [U66707]. | Densin-180 is a transmembrane protein that is strongly associated with the postsynaptic density in CNS neurons and is believed to function as a synaptic adhesion molecule [31]. | Cellular Communication |
| NU | scr_gb-af017393_2 | 48 | 48 | *Rattus norvegicus* cytochrome P4502F4 (CYP4502F4) [AF017393]. | The cytochromes P-450 are among the major constituent proteins of the liver mixed function monooxygenases. They play a central role in the metabolism of steroids, the detoxification of drugs and xenobiotics, and the activation of procarcinogens. In liver microsomes, this enzyme is involved in an NADPH-dependent electron transport pathway. It oxidizes a variety of structurally unrelated compounds, including steroids, fatty acids, and xenobiotics [32]. | Detoxification Response/ Biotransformation-TOX |
| NU | scr_sc-134241980_1 | 49 | 49 | *Rattus norvegicus* cytochrome P450 2B3 (CYP2B3) [U16214]. | The cytochromes P-450 are among the major constituent proteins of the liver mixed function monooxygenases. They play a central role in the metabolism of steroids, the detoxification of drugs and xenobiotics, and the activation of procarcinogens. In liver microsomes, this enzyme is involved in an NADPH-dependent electron transport pathway. It oxidizes a variety of structurally unrelated compounds, including steroids, fatty acids, and xenobiotics [32]. | Detoxification Response/ Biotransformation-TOX |
| NC | scr_sc-191609675_1 | 50 | 50 | Rat gene fragment - 217 bp. 94% SI (67/71) to *Streptococcus pneumoniae* DNA polymerase III, alpha subunit R6 [AAK99055]. | DNA polymerase III is a replicative enzyme known to be essential in the DNA synthesis of Gram-positive bacteria [33]. | DNA Metabolism |
| NU | scr_gb-x17037_2 | 51 | 51 | Rat OX40 antigen [X17037]. | OX40 is a member of the tumor necrosis factor family which is expressed by activated T lymphocytes [34]. | Immunity And Defense |
| SP | scr_gb-bi291805_1 | 52 | 52 | Rat gene fragment - 528 bp. 76% SI (290/380) to *Homo sapiens* IgG Fc binding protein [D84239]. | Fc gamma BP is widely expressed on mucosal surfaces and in external secretions lending support to the concept that Fc gamma BP is an important component of mucosal immunological defenses [35]. | Immunity And Defense |
| NU | scr_gb-aj000696_5 | 53 | 53 | *Rattus norvegicus* novel kinesin-related protein, KIF1D [AJ000696]. | The proteins of the kinesin superfamily (KIFs) are microtubule-based molecular motors whose functions include the transport of membrane-bound organelles. The KIF1 subfamily members are monomeric and contain a number of amino acid inserts in surface loops [36]. | Intracellular Transport |
| NU | scr_gb-d79221_3 | 54 | 54 | *Rattus norvegicus* r-sly1 [U35364]. | r-sly1 is a mammalian homologue to yeast Sly1p which plays a critical role in endoplasmic reticulum to Golgi apparatus vesicle trafficking [37]. | Intracellular Transport |
| NU | m61937 | 55 | 55 | *Rattus norvegicus* dihydrodiol dehydrogenase [M61937]. | Dihydrodiol dehydrogenase(s) (DD) have been implicated in the detoxication of proximate (trans-dihydrodiol) and ultimate carcinogenic (anti-diol-epoxide) metabolites of polycyclic aromatic hydrocarbons (PAHs). Although this pathway suppresses the formation of the PAH anti- and syn-diol epoxides (ultimate carcinogens), the process of autoxidation is anticipated to yield reactive oxygen species (ROS) [38]. | Oxidative Stress-TOX |
| NU | cszr_229602935_183895355 | 56 | 56 | *Rattus norvegicus* metallothionein-i (mt-1) [J00750]. | Metallothionein (MT) is a small, cysteine-rich, metal-binding protein. MT synthesis is induced by various stimuli such as heavy metals, oxidative stress, anticancer drugs and fasting stress. MT is capable of not only reducing metal toxicity but also scavenging free radicals [39]. | Oxidative Stress-TOX |
| NU | scr_gb-af106944_3 | 57 | 57 | *Rattus norvegicus* Peroxiredoxin III [AF106944]. | Peroxiredoxins are novel family of anti-oxidative proteins comprise six members in mammals. They share a common reactive Cys residue in the N-terminal region, and are capable of serving as a peroxidase and involve thioredoxin and/or glutathione as the electron donor [40]. | Oxidative Stress-TOX |
| NU | scr_gb-m11794_3 | 58 | 58 | *Rattus norvegicus* metallothionein-2 and | Metallothionein (MT) is a small, cysteine-rich, metal-binding protein. MT synthesis is induced by various stimuli such as heavy metals, oxidative stress, | Oxidative Stress-TOX |

TABLE 4-continued

| | ACCNO | TOX MARKER ASSIGN-MENT | SEQ ID NO | Definition | Description | Bin |
|---|---|---|---|---|---|---|
| | | | | metallothionein-1 genes [M11794]. | anticancer drugs and fasting stress. MT is capable of not only reducing metal toxicity but also scavenging free radicals [39]. | |
| NU | scr_gb-af069306_1 | 59 | 59 | *Rattus norvegicus* transaldolase [AF069306]. | Transaldolase is a key enzyme of the reversible nonoxidative branch of the pentose phosphate pathway (PPP) that is responsible for the generation of NADPH to maintain glutathione at a reduced state (GSH) and, thus, to protect cellular integrity from reactive oxygen intermediates (ROIs) [41]. | Oxidative Stress-TOX |
| NU | scr_gb-d17310_4 | 60 | 60 | *Rattus norvegicus* steroid 3-alpha-dehydrogenase [D17310]. | Steroid 3-alpha-dehydrogenase is an important multifunctional oxidoreductase capable of metabolizing steroid hormones, polycyclic aromatic hydrocarbons, and prostaglandins. It is also required for bile acid synthesis and has been suggested to play an important role in net bile acid transport across the hepatocyte [42]. | Oxidative Stress-TOX |
| NC | scr_gb-bf281368_2 | 61 | 61 | Rat gene fragment - 1086 bp. 80% SI (754/938) to Human Prt1 homolog [U62583]. | PRT1 is a component of translation initiation factor eIF-3 and originally discovered in *Saccharomyces cerevisiae* [43]. | Protein Metabolism |
| NU | scr_gb-u56407_3 | 62 | 62 | *Rattus norvegicus* ubiquitin conjugating enzyme [U56407]. | Ubiquitin-conjugating enzymes (UBC) catalyze the covalent attachment of ubiquitin to target proteins and are distinguished by the presence of a UBC domain required for catalysis [44]. | Protein Metabolism |
| NC | scr_gb-ai406674_1 | 63 | 63 | Rat gene fragment - 796 bp. 96% SI (634/660) *Mus musculus* heterogeneous nuclear ribonucleoprotein C, clone MGC:5715 IMAGE:3499283 [BC004706]. | Heterogeneous nuclear ribonucleoprotein (hnRNP) complexes, the structures that contain heterogeneous nuclear RNA and its associated proteins, constitute one of the most abundant components of the eukaryotic nucleus. hnRNPs appear to play important roles in the processing, and possibly also in the transport, of mRNA [45]. | RNA metabolism |
| NC | scr_gb-bf290678_2 | 64 | 64 | Rat gene fragment - 716 bp. 84% SI (542/643) to *Mus musculus* heterogeneous nuclear ribonucleoprotein G, splice variant 1 [AJ237847]. | Heterogeneous nuclear ribonucleoprotein (hnRNP) complexes, the structures that contain heterogeneous nuclear RNA and its associated proteins, constitute one of the most abundant components of the eukaryotic nucleus. hnRNPs appear to play important roles in the processing, and possibly also in the transport, of mRNA [45]. | RNA metabolism |
| NC | scr_gb-bi288503_1 | 65 | 65 | Rat gene fragment - 456 bp. 94% SI (430/456) to *Mus musculus* cardiac lineage protein 1 (Clp1) [AY090614]. | Mouse Clp-1 is a potential cardiac transcriptional regulatory factor [46]. | RNA Metabolism |
| NU | scr_gb-d86383_2 | 66 | 66 | *Rattus norvegicus* Hex [D86383]. | Hex is a homeobox protein which is believed to function as a transcriptional repressor and may be involved in the differentiation and/or maintenance of the differentiated state in hepatocytes [47]. | RNA metabolism |
| NU | scr_sc-133366194_1 | 67 | 67 | *Rattus norvegicus* thymosin beta-10 [M58405]. | Thymosin beta 10 is one of a small family of proteins closely related in sequence to thymosin beta 4, recently identified as an actin-sequestering protein [48]. | Structural Repair-TOX |
| NC | cszr_230290139_182026368 | 68 | 68 | Rat gene fragment - 249 bp. 91% SI (227/248) to *Mus musculus* sex-determination protein homolog Fem1a [AF064447]. | FEM-1 is a signal-transducing regulator in the *C. elegans* sex-determination pathway. The existence of FEM-1 homologs in the mouse raises the possibility that evolutionary conservation of ancient FEM-1 signaling interactions may play a role in vertebrate cell-fate determination [49]. | Other |
| NU | scr_gb-ai013477_2 | 69 | 69 | *Rattus norvegicus* VL30 element [M91234]. | VL30 elements constitute a family of retrotransposons that are associated with cancer by their overexpression in rodent malignancies, their | Other |

TABLE 4-continued

| | ACCNO | TOX MARKER ASSIGN-MENT | SEQ ID NO | Definition | Description | Bin |
|---|---|---|---|---|---|---|
| | | | | | induction in a fibroblast response to anoxia which shares features with the malignant phenotype, and their presence recombined into Harvey murine sarcoma virus (HaSV) and Kirsten murine sarcoma virus [50]. | |
| NU | scr_gb-m91235_3 | 70 | 70 | *Rattus norvegicus* VL30 element [M91235]. | VL30 elements constitute a family of retrotransposons that are associated with cancer by their overexpression in rodent malignancies, their induction in a fibroblast response to anoxia which shares features with the malignant phenotype, and their presence recombined into Harvey murine sarcoma virus (HaSV) and Kirsten murine sarcoma virus [50]. | Other |
| NU | cszr_204152648_191521095 | 71 | 71 | Unknown, 63 bp. | | Novel |
| NU | cszr_204152792_191517979 | 72 | 72 | Unknown, 133 bp. | | Novel |
| NU | cszr_204229614_191891958 | 73 | 73 | Unknown, 124 bp. | | Novel |
| NU | cszr_204229615_191892510 | 74 | 74 | Unknown, 124 bp. | | Novel |
| NU | scr_gb-aa801331_1 | 75 | 75 | Unknown, 1252 bp. | | Novel |
| NU | scr_gb-aa899865_3 | 76 | 76 | Unknown, 1241 bp. | | Novel |
| NU | scr_gb-aa997629_1 | 77 | 77 | Unknown, 396 bp. | | Novel |
| NU | scr_gb-aa997691_1 | 78 | 78 | Unknown, 473 bp. | | Novel |
| NU | scr_gb-ai411514_4 | 79 | 79 | Unknown, 1221 bp. | | Novel |
| NU | scr_gb-aw142560_3 | 80 | 80 | Unknown, 695 bp. | | Novel |
| NU | scr_gb-aw533305_2 | 81 | 81 | Unknown, 771 bp. | | Novel |
| NU | scr_gb-aw915573_2 | 82 | 82 | Unknown, 2262 bp. | | Novel |
| NU | scr_gb-be108509_1 | 83 | 83 | Unknown, 422 bp. | | Novel |
| NU | scr_gb-be111483_1 | 84 | 84 | Unknown, 445 bp. | | Novel |
| NU | scr_gb-be120910_1 | 85 | 85 | Unknown, 482 bp. | | Novel |
| NU | scr_gb-bf285287_1 | 86 | 86 | Unknown, 784 bp. | | Novel |
| NU | scr_gb-bf390383_1 | 87 | 87 | Unknown, 486 bp. | | Novel |
| NU | scr_gb-bf558463_2 | 88 | 88 | Unknown, 921 bp. | | Novel |
| NU | scr_gb-bf560709_1 | 89 | 89 | Unknown, 525 bp. | | Novel |
| NU | scr_gb-bg662990_2 | 90 | 90 | Unknown, 930 bp. | | Novel |
| NU | scr_gb-bi278552_1 | 91 | 91 | Unknown, 1060 bp. | | Novel |
| NU | scr_gb-bi278749_1 | 92 | 92 | Unknown, 1158 bp. | | Novel |
| NU | scr_gb-bi295938_1 | 93 | 93 | Unknown, 1241 bp. | | Novel |
| NU | scr_gb-bi296376_1 | 94 | 94 | Unknown, 2695 bp. | | Novel |
| NU | scr_gb-bm384392_1 | 95 | 95 | Unknown, 2423 bp. | | Novel |
| NU | scr_gb-bm387477_1 | 96 | 96 | Unknown, 610 bp. | | Novel |
| NU | scr_gb-bm986259_1 | 97 | 97 | Unknown, 1047 bp. | | Novel |
| NU | scr_gb-s69874_5 | 98 | 98 | Unknown, 1191 bp. | | Novel |

TABLE 4-continued

| | ACCNO | TOX MARKER ASSIGN-MENT | SEQ ID NO | Definition | Description | Bin |
|---|---|---|---|---|---|---|
| NU | scr_sc-119263563_1 | 99 | 99 | Unknown, 384 bp. | | Novel |
| NU | scr_sc-132556005_1 | 100 | 100 | Unknown, 181 bp. | | Novel |
| NU | scr_sc-132570828_1 | 101 | 101 | Unknown, 130 bp. | | Novel |
| NU | scr_sc-132947646_1 | 102 | 102 | Unknown, 50 bp. | | Novel |
| NU | scr_sc-133387221_1 | 103 | 103 | Unknown, 296 bp. | | Novel |
| NU | scr_sc-133555783_1 | 104 | 104 | Unknown, 321 bp. | | Novel |
| NU | scr_sc-133678871_1 | 105 | 105 | Unknown, 92 bp. | | Novel |
| NU | scr_sc-133725675_1 | 106 | 106 | Unknown, 94 bp. | | Novel |
| NU | scr_sc-133955481_1 | 107 | 107 | Unknown, 343 bp. | | Novel |
| NU | scr_sc-134521597_1 | 108 | 108 | Unknown, 238 bp. | | Novel |
| NU | scr_sc-172126480_1 | 109 | 109 | Unknown, 247 bp. | | Novel |
| NU | scr_sc-172130231_1 | 110 | 110 | Unknown, 196 bp. | | Novel |
| NU | scr_sc-172755010_1 | 111 | 111 | Unknown, 457 bp. | | Novel |
| NU | scr_sc-188295137_1 | 112 | 112 | Unknown, 85 bp. | | Novel |
| NU | scr_sc-190079504_1 | 113 | 113 | Unknown, 241 bp. | | Novel |
| NU | scr_sc-191455923_1 | 114 | 114 | Unknown, 388 bp. | | Novel |
| NU | scr_sc-195460151_1 | 115 | 115 | Unknown, 444 bp. | | Novel |
| NU | scr_sc-198205946_1 | 116 | 116 | Unknown, 135 bp. | | Novel |
| NU | scr_sc-2573087_1 | 117 | 117 | Unknown, 246 bp. | | Novel |
| NU | scr_sc-2585074_1 | 118 | 118 | Unknown, 203 bp. | | Novel |
| NU | scr_sc-8571871_2 | 119 | 119 | Unknown, 233 bp. | | Novel |
| NU | scr_sc-87731837_1 | 120 | 120 | Unknown, 300 bp. | | Novel |
| NU | scr_sc-87869413_1 | 121 | 121 | Unknown, 351 bp. | | Novel |
| NU | scr_gb-ai233262_2 | 122 | 122 | Unknown, 889 bp. | | Novel |
| NU | cgrrs0h0310.9_13952-135 | 123 | 123 | Unknown, 310 bp. | | Novel |
| NU | scr_gb-m13100.5_2 | 124 | 124 | Unknown, 100 bp. | | Novel |
| NU | scr_sc-170396977_1 | 125 | 125 | Unknown, 350 bp. | | Novel |

TABLE 4-continued

| | ACCNO | TOX MARKER ASSIGN-MENT | SEQ ID NO | Definition | Description | Bin |
|---|---|---|---|---|---|---|
| NU | scr_sc-14059147_2 | 126 | 126 | Rat gene patent WO0210453, 254 bp. | | Unknown |
| NU | scr_sc-87750810_1 | 127 | 127 | Rat gene patent WO0210453, 1063 bp. | | Unknown |
| NU | cszr_202034260_190929676 | 128 | 128 | *Rattus norvegicus* Tclone4 [U30788]. | | Unknown |

Using the TOXMARKER gene information listed in Table 4, zone 3 necrosis-related genes expressed in vitro were confirmed. Confirmed genes are listed in Table 5.

TABLE 5

| Gene ID | TOX Number | SEQ ID NO | Definition | Human Ortholog | SEQ ID NO: |
|---|---|---|---|---|---|
| | | | Amino Acid Metabolism | | |
| cszr_96561134_83760493 | 35 | 39 | *Rattus norvegicus* Carbamoyl-phosphate synthase [ammonia] (CPSASE I), mitochondrial precursor [P07756]. | CPS1: Carbamyl phosphate synthetase I [D90282, NM_001875] | 129 |
| | | | Carbohydrate Metabolism | | |
| scr_gb-bi277612_1 | 38 | 38 | Rat gene fragment - 1381 bp. 89% SI (816/910) to *Mus musculus* for beta-hexosaminidase [Y00964]. | NM_000521 >rshd:REFSEQHUMANDNA-ID:NM_000521\|acc:NM_000521 /geneName="HEXB" /definition="*Homo sapiens* hexosaminidase B (beta polypeptide) (HEXB), mRNA." /protein_id="NP_000512.1" /organism="*Homo sapiens*" /CDS="76 . . . 1746", 1857 bp. >gb:GENBANK-ID:AF378118\|acc:AF378118.1 *Homo sapiens* cervical cancer proto-oncogene 7 mRNA, complete cds - *Homo sapiens*, 1892 bp. | 130 |
| cszr_229800465_190907286 | 129 | 131 | Rat non-neuronal enolase (NNE) (alpha-alpha enolase, 2-phospho-D-glycerate hydrolase) [X02610]. | | |
| | | | Energy Metabolism | | |
| scr_gb-j05266_3 | 39 | .39 | *Rattus norvegicus* mitochondrial H+-ATP synthase alpha subunit [J05266]. | NM_004046 >rshd:REFSEQHUMANDNA-ID:NM_004046\|acc:NM_004046 /geneName="ATP5A1" /definition="*Homo sapiens* ATP synthase, H+ transporting, mitochondrial F1 complex, alpha subunit, isoform 1, cardiac muscle (ATP5A1), mRNA." /protein_id="NP_004037.1" /organism="*Homo sapiens*" /CDS=912 . . . 2573", 2725 bp. | 132 |
| | | | Cell Cycle Regulation (Regulation Of Proliferation) | | |
| scr_gb-ab015747_3 | 43 | 43 | Rat interleukin-4 receptor (membrane-bound form) (AB015747.1: | X52425.1 Human IL-4-R mRNA for the interleukin 4 receptor | 133 |

TABLE 5-continued

| Gene ID | TOX Number | SEQ ID NO | Definition | Human Ortholog | SEQ ID NO: |
|---|---|---|---|---|---|
| | | | 99%/3501, p = 0.000000), 3520 bp. | | |
| scr_gb-ai233262_2 | 122 | 122 | Rat gene fragment, 889 bp, 93% identical over 679 bp to mouse RANBP4 [AF123388]. | weakly similar to PUTATIVE IMPORTIN BETA-4 SUBUNIT [AK027871, NM_024658]. | 134 |
| scr_gb-bi294409_1 | 42 | 42 | Rat gene fragment, 526 bp, 89% SI (327/365) to mouse type I interferon receptor, IFNaR2 subunit, 1109 bp (Y09813). | Ifnar2: interferon receptor ifnar2-1 [L41944, NM_000874] | 135 |
| scr_gb-m37394_5 | 40 | 40 | *Rattus norvegicus* epidermal growth factor receptor (Egfr) [M37394]. | EGFR: epidermal growth factor receptor [K03193, NM_005228]. | 136 |
| scr_gb-m64300_4 | 41 | 41 | *Rattus norvegicus* extracellular signal-related kinase (ERK2) [M64300]. | MAPK1: Mitogen-activated protein kinase 1 [BC017832, NM_002745]. | 137 |
| scr_sc-191879433_1 | 44 | 44 | Rat Crk-associated substrate, p130 [D29766]. | BCAR1: breast cancer anti-estrogen resistance 1 [AK026121, NM_014567]. | 138 |
| | | | Cellular Communication | | |
| scr_gb-m13100.5_2 | 124 | 124 | *Rattus norvegicus* gene for histamine N-methyltransferase, exon 1 and 2 [AB007833]. | | |
| scr_gb-x87157_5 | 46 | 46 | *Rattus norvegicus* neurotensin endopeptidase [X87157]. | NLN: neurolysin [AJ300837, NM_020726]. | 139 |
| | | | Detoxification Response/Biotransformation-TOX | | |
| scr_gb-af017393_2 | 48 | 48 | *Rattus norvegicus* cytochrome P4502F4 (CYP4502F4) [AF017393]. | CYP2F1: cytochrome P450, subfamily IIF, polypeptide 1[J02906, NM_000774]. | 140 |
| scr-sc-134241980_1 | 49 | 49 | Rat cytochrome P450IIB3 (P450IIB subfamily) mRNA, complete cds (M20406.1: 100%/279, p = 5.0e−156), 367 bp. | MSRA: methionine sulfoxide reductase A [AJ242973, NM_012331]. | 141 |
| | | | DNA Metabolism | | |
| scr_gb-bi296376_1 | 94 | 94 | Rat ribosomal DNA external transcribed spacer 1 (ETS1) [X16321], Rat 45S rDNA gene transcription initiation region [X00677], and Rat ribosomal RNA 1.6 small subunit (SS1.6) | | |

TABLE 5-continued

| Gene ID | TOX Number | SEQ ID NO | Definition | Human Ortholog | SEQ ID NO: |
|---|---|---|---|---|---|
| | | | gene, 3' end [M30843] - 2695 bp. | | |
| | | | Immunity And Defense | | |
| scr_gb-x17037_2 | 51 | 51 | Rat OX40 antigen [X17037]. | TNFRSF4: tumor necrosis factor receptor superfamily, member 4 [AW293499, S76792, X75962, NM_003327]. | 142 |
| cgrrs0h0310.9_13952-135 | 123 | 123 | Rat lipocortin-V mRNA, complete cds (M21730.1: 99%/1419, p = 0.000000), 1744 bp. | | |
| | | | Intracellular Transport | | |
| scr_gb-aj000696_5 | 53 | 53 | *Rattus norvegicus* novel kinesin-related protein, KIF1D [AJ000696]. | KIF1C: kinesin family member 1C [AB014606, NM_006612]. | 143 |
| scr_gb-d79221_3 | 54 | 54 | *Rattus norvegicus* r-sly1 [U35364]. | Vesicle transport-related protein [AF110646, NM_016163]. | 144 |
| | | | Oxidative Stress-TOX | | |
| cszr_229602935_183895355 | 56 | 56 | Rat metallothionein-i (mt-1) | | |
| m61937 | 55 | 55 | *Rattus norvegicus* dihydrodiol dehydrogenase [M61937]. | | |
| scr_gb-af069306_1 | 59 | 59 | *Rattus norvegicus* transaldolase [AF069306]. | clone MGC:2838 IMAGE:2966784 [BC001517]. | 145 |
| scr_gb-af106944_3 | 57 | 57 | *Rattus norvegicus* Peroxiredoxin III [AF106944]. | | |
| scr_gb-d17310_4 | 60 | 60 | *Rattus norvegicus* steroid 3-alpha-dehydrogenase [D17310]. | MTCH2: mitochondrial carrier homolog 2 [AF085361, NM_014342] | 146 |
| scr_gb-m11794_3 | 58 | 58 | *Rattus norvegicus* metallothionein-2 and metallothionein-1 genes [M11794]. | MT2A: metallothionein 2A [S52379, NM_005953]. | 147 |
| | | | Protein Metabolism | | |
| scr_gb-bf281368_2 | 61 | 61 | Rat gene fragment - 1086 bp. 80% SI (754/938) to Human Prt1 homolog [U62583]. | eIF3: eukaryotic translation initiation factor 3 [U78525, NM_003751] | 148 |
| | | | RNA metabolism | | |
| scr_gb-ai406674_1 | 63 | 63 | Rat gene fragment, 796 bp. 91% SI to human heterogeneous nuclear ribonucleoprotein C (C1/C2), [XM_166936] | HNRPC: heterogeneous nuclear ribonucleoprotein C [BC003394, NM_004500]. | 149 |
| scr_gb-bi288503_1 | 65 | 65 | Rat gene fragment 456 bp. 94% SI (430/456) to *Mus* | HEMIX1 protein [AB021179, NM_006460]. | 150 |

TABLE 5-continued

| Gene ID | TOX Number | SEQ ID NO | Definition | Human Ortholog | SEQ ID NO: |
|---|---|---|---|---|---|
| | | | *musculus* cardiac lineage protein 1 (Clp1) (AY090614.1) | | |
| scr_gb-d86383_2 | 66 | 66 | *Rattus norvegicus* Hex [D86383]. | HHEX: hematopoietically expressed homeobox [BC015110, X67235, NM_002729]. | 151 |
| | | | Membrane Transport/Transporters | | |
| scr_sc-8571871_2 | 119 | 119 | *Rattus norvegicus* Na/Pi [AB025224.1]. | U90545.1\|HSU90545 Human sodium phosphate transporter (NPT4) mRNA, complete cds | 152 |
| | | | | Other | |
| scr_gb-af311311_2 | 130 | 153 | *Rattus norvegicus* P116RIP mRNA, complete cds (AF311311.1: 99%/3285, p = 0.000000), 3905 bp. | | |
| scr_bg-ai013477_2 | 69 | 69 | *Rattus norvegicus* VL30 element [M91234]. | | |
| scr_gb-bm986259_1 | 97 | 97 | Rat gene fragment, 1047 bp, 86% SI (647/748) to human CGI-126 protein mRNA, 1091 bp (AF151884). | HSPC155: hypothetical protein HSPC155 [AF161504, NM_016406] | 154 |
| cszr_230290139_182026368 | 131 | 155 | Similar to *Mus musculus,* feminization 1 a homolog (*C. elegans*), clone MGC:6309 IMAGE:2811079, mRNA, complete cds (BC009161.1: 91%/244, p = 3.4e-085), 249 bp. | | |
| scr_gb-m91235_3 | 70 | 70 | *Rattus norvegicus* VL30 element [M91235]. | | |
| | | | | Novel | |
| scr_gb-aa801331_1 | 75 | 75 | Unknown, 1252 bp. | | |
| scr_gb-aa899865_3 | 76 | 76 | Unknown, 1241 bp. | | |
| scr_gb-ai411514_4 | 79 | 79 | Unknown, 1221 bp. | KIAA0652 gene product [BC006191, NM_014741]. | 156 |
| scr_gb-bf558463_2 | 88 | 88 | Rat gene fragment, 921 bp. | Clone IMAGE:4052356, partial cds. [BC014348]. | 157 |
| scr_gb-bi278552_1 | 91 | 91 | Unknown, 1060 bp. | KIAA0427 gene product [AB007887, NM_014772]. | 158 |
| scr_gb-bi295938_1 | 83 | 83 | Unknown, 1241 bp. | Hypothetical protein FLJ13409 [BC015897, NM_024617]. | 159 |
| scr_gb-bm364392_1 | 85 | 85 | Unknown, 2423 bp. | Hypothetical protein MGC3067 [BC002457, NM_024295]. | 160 |
| scr_gb-s69874_5 | 98 | 98 | Unknown, 1191 bp. | COL4A1: collagen, type IV, alpha 1 [AH002741, NM_001845]. | 161 |
| scr_sc-132947646_1 | 102 | 102 | Rat gene fragment, 50 bp. | | |
| scr_sc-172126480_1 | 109 | 109 | Unknown, 247 bp. | | |
| scr_sc-188295137_1 | 112 | 112 | Unknown Gene, 85 bp. | | |
| scr_sc-191455923_1 | 114 | 114 | Unknown, 388 bp. | Heterogeneous nuclear ribonucleoprotein M [NM_005968]. | 162 |

TABLE 5-continued

| Gene ID | TOX Number | SEQ ID NO | Definition | Human Ortholog | SEQ ID NO: |
|---|---|---|---|---|---|
| scr_sc-195460151_1 | 115 | 115 | Unknown, 444 bp. | Unknown | |
| cszr_204152648_191521095 | 71 | 71 | UI-R-A1-ek-e-09-0-UI.s1 UI-R-A1 *Rattus norvegicus* cDNA clone UI-R-A1-ek-e-09-0-UI 3', 63 bp. | XM_114110 >rshd:REFSEQHUMANDNA-ID:XM_114110\|acc:XM_114110 /geneName = "LOC200081" /definition="*Homo sapiens* similar to muscle-derived protein MDP77 isoform 2 (LOC200081), mRNA." /protein id = "XP_114110.1" /organism = "*Homo sapiens*" /CDS = "94 . . . 873", 3962 bp. | 163 |
| cszr_204152792_191517979 | 72 | 72 | Rat gene fragment, 131 bp, 99% SI (130/131) to mouse IMAGE clone (BC030389), 2072 bp. | AB032968.1 *Homo sapiens* mRNA for KIAA1142 protein, partial cds | 164 |
| scr_gb-bf390383_1 | 87 | 87 | UI-R-CA1-bcg-d-03-0-UI.s1 UI-R-CA1 *Rattus norvegicus* cDNA clone UI-R-CA1-bcg-d-03-0-UI 3', 486 bp. [BF390383.1]. | | |
| scr_gb-bf560709_1 | 89 | 89 | UI-R-C1-kd-h-12-0-UI.r2 UI-R-C1 *Rattus norvegicus* cDNA clone UI-R-C1-kd-h-12-0-UI 5', mRNA sequence (BF560 709.1: 99%/464, p = 9.2e−264), 525 bp. | CTNNA2: Catenin (cadherin-associated protein), alpha 2 [M94151, NM_004389]. | 165 |
| scr_sc-14059147_2 | 126 | 126 | Rat gene fragment - 254 bp. 75% SI (190/252) to *Homo sapiens* mRNA for putative progesterone binding protein [AJ002030]. | >gb:GENBANK-ID:HSAJ2030\|acc:AJ002030.1 *Homo sapiens* mRNA for putative progesterone binding protein - *Homo sapiens,* 1874 bp. | 166 |
| scr_sc-172130231_1 | 110 | 110 | Rat gene fragment - 196 bp. 92% SI (181/196) to *Mus musculus* cDNA clone IMAGE:5051929 5'[BI146266.1]. | AK056165.1\|*Homo sapiens* cDNA FLJ31603 fis, clone NT2RI2002654 | 167 |

Example 6

Genes Involved in Zone 3 Necrosis In Vivo

There is ample evidence to support the importance of ATP depletion as a mechanism that leads to cell necrosis [3]. Rat trihydroxycoprostanoyl-CoA oxidase was selected as an in vivo marker for zone 3 necrosis and was found to be downregulated in the dataset. This enzyme is one of the three acyl-CoA oxidases found in rat liver peroxisomes and is responsible for the beta-oxidation of fatty acids [16]. Downregulation of an enzyme involved in beta-oxidation represents an interruption in a pathway that can lead to ATP production. Consistent with this is the downregulation of an enzyme involved in amino acid metabolism. Betaine-homocysteine methyltransferase (BHMT) catalyzes the transfer of an N-methyl group from betaine to homocysteine to form dimethylglycine and methionine, respectively [14]. Interestingly, alterations in methionine metabolism have been known to be associated with human liver cirrhosis for many years [15]. As discussed earlier, severe necrosis is involved in the pathogenesis of cirrhosis [9]. Thus, necrosis itself can lead to an inflammation mediated injury. A marker involved in an inflammation and defense response was found to be upregulated in this in vivo marker set. Rat MHC-associated invariant chain gamma stabilizes MHC class II molecules that are at the surface of antigen presenting cells [26]. Rat MHC-associated invariant chain gamma is predicted to be a secreted protein based upon PSORT, SIGNALP, and Hydropathic Profile (HP) analysis Rat ephrin type-B receptor 1 precursor (EphB1) was downregulated as compared to controls. Upon binding to its ligand, EphB1 has been shown to activate c-Jun kinase through recruitment of an intermediate protein Nck [18]. c-Jun is an oncogene involved in cell proliferation. Regulation of proliferation is an integral part of necrotic cell death, whether it results from compensatory liver regeneration of healthy cells or cell cycle arrest of unhealthy cells. Indeed, ribosomal protein S6 was selected as a marker and was found to be upregulated. It has been known for 20 years that the ribosomal protein S6 is quickly phosphorylated when cells are stimulated to grow or divide [19]. Phosphorylation of S6 occurs in response to mitogens by activation of one or more protein kinase cascades, including MAP kinases [20]. Rat annexin II belongs to a family of proteins that in the presence of $Ca^{2+}$ bind to acidic phospholipids. They may also cross-link plasma membrane phospholipids with actin and the cytoskeleton, and possibly play a part in exocytosis, since they are also involved in granule aggregation and membrane fusion [28]. Annexin II was found to be an upregulated marker and may be indicative of loss of structural integrity within the cell. Though annexin I and annexin II have also been identified as major substrates for the tyrosine kinase activity associated with epidermal growth factor receptor (Egfr). Rat Egfr signals through a number of pathways, including the MAP kinase pathway, to regulate proliferation [35].

Canalicular multispecific organic anion transporter (cMOAT), an upregulated gene in this in vivo marker set, has been shown to arbitrate the hepatobiliary elimination of many organic ions [29]. It has also been shown to remove glutathione conjugates from cells [30]. Glutathione conjugation is a cellular adaptation to the generation of reactive oxygen species (ROS) [36]. ROS occurs when oxidative phosphorylation becomes uncoupled during ATP generation. When molecular oxygen is reduced in such a manner damaging amounts of $O_2$—, $H_2O_2$ and OH are formed in the process. ROS are thought to participate in necrosis through their reaction with all forms of biological macromolecules including lipids, proteins, nucleic acids and carbohydrates [37–39].

Markers were chosen from other biochemical pathways as well. This includes the upregulation of rat heat shock protein 86 (hsp86) which may be indicative of cellular stress. Rat ras-related protein (Rab-2), a protein involved in intracellular transport, was also upregulated. Two protease inhibitors, rat homologue to human inter-alpha-trypsin inhibitor heavy chain (ITIH1) and rat homologue to mouse serine proteinase inhibitor mBM2A were down-regulated and upregulated, respectively. Human ITI is found in human serum and is predicted to be a secreted protein based upon PSORT, SIGNALP, and HP analysis [32]. Finally, numerous genes involved in xenobiotic metabolism were diminished after exposure to the zone 3 necrotic agents. However, two, rat epoxide hydrolase and rat aflatoxin B1 aldehyde reductase, were found to be upregulated.

There were 11 markers chosen for this PTS marker set that did not match any known genes in the database and have novel composition. One gene, rat osteoactivin has no known association to any of the histopathologically relevant biochemical or toxicological pathways but is predicted to be a secreted protein based upon PSORT, SIGNALP, and HP analysis.

Example 7

Genes Involved in Zone 3 Necrosis In Vitro

Several of the biochemical events consistent with necrosis are represented in the in vitro marker set that is predictive of zone 3 necrosis. There is ample evidence to support the importance of ATP depletion as a mechanism that leads to cell necrosis [3]. Included in this is documentation that the production of ATP via glycolysis can protect a cell from necrosis when oxidative phosphorylation is inhibited [51–53]. The alpha subunit of rat ATP synthase was found to be downregulated in the in vitro zone 3 necrosis marker set. ATP synthase is the final enzyme in the electron transport chain and is ultimately responsible for catalyzing the synthesis of ATP. Downregulation of such a key enzyme is indicative of loss of ATP within the cell. Rat nonneuronal enolase is another marker that was found to be downregulated. Enolase is a vital enzyme in the glycolysis pathway that converts glucose to pyruvate. Glucose is a preferred carbon source and generated the highest return of ATP per unit of expended energy. Downregulation of enolase may represent a depletion of glucose stores within the cell. The rat homologue to mouse beta-hexosaminidase is a protein involved in oligosaccharide and glycosaminoglycan degradation and was found to be upregulated in this marker set [20]. Upregulation of this marker may represent the cells attempt to maintain glucose supplies. The rat homologue of this gene was found to be a secreted protein based on protein based upon PSORT, SIGNALP, and HP analysis. Two markers related to ATP depletion were found to be upregulated in this marker set. Rat EP3 alpha receptors for prostaglandin has been found to be involved in the inhibition of adenylyl cyclase, which catalyzes the conversion of ATP to cAMP [18]. Inhibition of this process would be consistent with a lack of ATP within the cell. Carbamoylphosphate synthase is a mitochondrial protein that removes excess ammonia in the cell via the urea acid cycle. Upregulation of this rat enzyme may indicate a resort to utilize amino acids as a source of energy.

Uncoupling of electron transport during oxidative phosphorylation in the above process can lead to the formation of excessive amounts of Reactive Oxygen Species (ROS). When molecular oxygen is reduced in such a manner damaging amounts of $O_2$—, $H_2O_2$ and OH are formed in the process. ROS are thought to participate in necrosis through their reaction with all forms of biological macromolecules including lipids, proteins, nucleic acids and carbohydrates [54–56]. Cells have adapted to the generation ROS through an elaborate antioxidant defense system. Two such mechanisms of defense are found to be upregulated in this marker set. A rat metallothionein isoform represents one of these mechanisms. Metallothionein is a small cysteine-rich metal binding protein that mediates heavy metal response and can play a role in ion homeostasis has the ability to scavenge free radicals and has been found to be induced under oxidative stress conditions [39]. Transaldolase is a key enzyme in the nonoxidative branch of the pentose phosphate pathway that can reduce the amount of reactive oxygen intermediates though the maintenance of glutathione at a reduced state [41]. Glutathione is critical for scavenging mitochondrial ROS through glutathione reductase and peroxidase systems. Interestingly rat peroxiredoxin III, a member of a novel family of anti-oxidative proteins, was found to be downregulated in this marker set. Peroxiredoxins have the ability to reduce $H_2O_2$ by using thioredoxin or glutathione as an electron donor [40]. Downregulation of this protein may represent a preference to remove $H_2O_2$ through one of the other defense mechanisms available to the cell. Similarly rat metallothionein 1, another isoform of metallothionein, was down-regulated. The fact that there are two rat metallothionein isoforms found in this marker set modulated in opposite directions may also indicate a preference of one form over the other or may represent a redundancy in the pathway. Dihydrodiol dehydrogenase is a marker, which was found downregulated and may play a role in the amount of ROS generated in the cell. This enzyme is believed to yield ROS upon detoxification of polycyclic aromatic hydrocarbons [38]. Thus downregulation of this process may be an attempt to limit the overall amount of ROS within the cell.

As discussed earlier, hepatic regeneration is a response to cellular necrosis. This process involves re-entry of surviving liver cells into the cell cycle to replace lost tissue mass [57]. Though this normal reaction to liver injury can, if uncontrolled, lead to the early onset of hepatic carcinogenesis. Several markers predictive of in vitro zone 3 necrosis were found to be involved in the regulation of cellular proliferation in the cell. These markers were consistently upregulated and are represented by growth factor receptors (rat Egfr), cytokine receptors (rat IL-4r & a rat gene homologue to *Mus musculus* Inar-2 receptor), MAPK signaling cascades (rat Erk2), as well as a gene involved in the regulation of protein kinase C activity (rat homologue to human DGK-delta). Rat epidermal growth factor receptor signals through a number of pathways, including the MAP kinase pathway, to regulate proliferation. However, under certain conditions stimulation of this pathway can lead to cell growth arrest and the induction of apoptosis [22]. Interestingly rat extracellular signal-related kinase 2 (Erk2) was also found to be upregulated. Erk2 is a member of the Raf/MEK/ERK signaling pathway that was the first MAP kinase cascade to be characterized [23]. Rat interleukin-4 receptor (IL-4r) is an upregulated marker for in vitro zone 3 necrosis. While IL-4 is a cytokine that has immunomodulatory effects, there is evidence that IL-4 interaction with its receptor can lead to such downstream effects as gene activation and cellular proliferation [26]. A rat homologue to mouse soluble isoform precursor type I interferon receptor (Ifnar-2) represents the upregulation of another cytokine receptor. Recent data shows that murine Ifnar-2 is an effective regulator of interferon responses [24]. It is known that type I interferons play a role in cell proliferation [25]. Murine Ifnar-2 soluble form is predicted to be a secreted protein based upon PSORT, SIGNALP, and Hydropathic Profile (HP) analysis. A rat homologue to human diacylglycerol kinase, delta (DGK-delta) was found to be upregulated in this marker set. DGK is a signal transduction enzyme that mediates protein kinase C activity by modulating intracellular concentrations of two signaling lipids, diacylglycerol and phosphatidic acid [29]. Protein kinase C is a family of serine-threonine kinases that is known to regulate proliferation and apoptosis [30]. The only downregulated marker involved in regulation of cell proliferation was rat Crk-associated substrate (Cas) p130, a unique docking protein with a Src homology 3 (SH3) domain. Tyrosine phosphorylation of Cas has been implicated in integrin mediated activities including cell proliferation and survival [27]. Additionally, Cas, upon interaction with Src, has been shown to be involved in a $H_2O_2$ activation of cJun NH(2) terminal kinase (Jnk) pathway [28].

Some markers may have a less clear association with a necrosis specific pathway. This includes the upregulation of rat VL30 element, a retrotransposon that has been found to be upregulated in rodent malignancies but which a specific role has not been identified [50]. Rat OX40 antigen was found to be downregulated. OX40 is a member of the tumor necrosis factor family that is expressed by activated T lymphocytes and may indicate the presence of inflammatory events [34]. Also relevant to an immunological response is the upregulation rat homologue to *Homo sapiens* IgG Fc binding protein. This protein is widely expressed on mucosal surfaces and in external secretions [35]. The rat homologue to human IgG Fc binding protein is predicted to be a secreted protein based upon PSORT, SIGNALP, and HP analysis. This marker set includes two markers involved with protein metabolism. This includes the upregulation of rat ubiquitin-conjugating enzyme (UBC), which catalyzes the covalent attachment of ubiquitin to a target protein. The ubiquitin/proteasome pathway is the main non-lysosomal route for intracellular protein degradation in eukaryotes. It is important to many cell processes including cell-cycle progression and more recently has been found to target regulatory molecules found in the apoptotic cell death pathway [44]. Another protein that is involved with protein metabolism and was found to be downregulated is a rat homologue to human Prt1. Little is known of this protein, except that it a component of the translation initiation factor elf-3 [43]. Rat thymosin beta-10 is a marker that was downregulated. It is a protein that is believed to be involved in the sequestering of actin and may be indicative of loss of structural integrity of the cell [48].

Markers were chosen from several other biochemical pathways as well. A couple of genes involved in xenobiotic metabolism were induced after exposure to the zone 3 necrotic agents. These are rat cytochrome P-450's 2F4 and 2B3, which were both upregulated. Several genes that are involved with the synthesis or transport of RNA were also chosen as markers. These include the upregulation of the rat homologue to mouse heterogeneous ribonucleoprotein C, rat homologue to mouse cardiac lineage protein 1 and rat Hex. The rat homologue to mouse heterogeneous ribonucleoprotein G was also chosen as a marker but was found to be downregulated. Two markers involved in the intracellular trafficking were also selected. This includes the upregulation of a rat novel related kinesin protein which may be involved in the transport of membrane bound organelles and the downregulation of rat r-sly1 which plays a role in ER to Golgi trafficking [36, 37]. Two markers in this set are involved with cellular communication. Rat neurotensin endopeptidase was downregulated. Neurotensin is a hormonal peptide that functions as a central neurotransmitter or neuromodulator as well as a peripheral hormone [20]. Rat densin-180 has a strong association with the postsynaptic density in CNS neurons and is believed to function as a synaptic adhesion molecule. Densin-180 was found to be upregulated in this in vitro marker set [31]. Rat homologue to mouse sex-determination protein homologue Fem1a was upregulated in this marker set but has no known association to any of the histopathologically relevant biochemical or toxicological pathways. Fem1 is a known signal transducing regulator in the *C. elegans* sex-determination pathway [49].

There were 55 markers chosen for this PTS marker set that did not match any known genes in the database and have novel composition. There were also two genes that blasted to rat gene patents and have novel utility. One additional marker, rat Tclone4, had some similarity to a known gene but has no known function.

Example 8

Prediction of the Toxicity of a Test Compound

The following example describes the application of the TOXMARKER expression profiles generated, as described above, to identify hepatotoxic compounds.

Hepatocyte Culture

Animals. Male Wistar Han rats (Crl:WI[Glx/BRL/Han] IGS BR) were obtained from Charles River Laboratories, Inc. (Raleigh, N.C.). The animals were housed for 6 or 7 days in a temperature-, humidity-, light-controlled facility prior to hepatocyte preparation and were at this time 200–250 g in weight.

Hepatocyte isolation Hepatocytes were prepared by in situ liver perfusion according to a protocol used at the Yale Liver Center (Yale University School of Medicine, Yale University, New Haven, Conn.). To minimize the risk of contamination all equipment and solutions used during the perfusion procedure were autoclaved. The animals were anesthesized by sodium phenobarbital (approx. 50 mg/kg) and the abdomen opened to expose the liver. To perform the perfusion a catheter was attached to vena porta and secured by a ligature. After disrupting vena cava inferior 37° C. Hanks A buffer (120 mM NaCl, 5 mM KCl, 0.4 mM KH2PO4, 25 mM NaHCO3, 0.5 mM EGTA, 0.1% glucose) was circulated through the liver a 40 ml/min for 10 min. The perfusion was continued with 37° C. Hanks B buffer (120 mM NaCl, 5 mM KCl, 0.4 mM KH2PO4, 25 mM NaHCO30.4 mM MgSO4, 0.5 mM MgCl2, 3 mM $CaCl_2$, 0.1% glucose) supplemented with collagenase (Liberase Blendzyme 3, 120 mg/400 ml; Roche Diagnostics Corp., Indianapolis, Ind.) until clear signs of liver disintegration were visible (approx. 10 min). The liver was transfered into ice-cold Leibovitz L-15 media (Invitrogen, Carlsbad, Calif.) and the organ was disrupted mechanically with forceps. The cell suspension was filtered through a 80 μm mesh followed by a 45 μm mesh, and the medium replaced twice with fresh ice-cold L-15 medium following 5 min low speed centrifugations (30 G). Cell were transported on ice to Curagen's tissue culture facility and washed twice as above in William's E media (Sigma, St. Louis, Mo.) with supplements (10% fetal bovine serum (Gemini, Woodland, Calif.); 9.6 ug/ml prednisolon, glucagon 0.014 ug/ml, insulin 0.16 units/ml, glutamin and antibiotic-antimycotic solution (all purchased from Sigma, St. Louis, Mo.). Cells were counted and viability was measured in a hemacytometer after Trypan blue staining Hepatocyte culturing Cells were cultured in 12 or 24 well tissue culture plates coated with rat tail collagen (Becton-Dickinson, Bedford, Mass.) according to a protocol provided by Dr. Grazyna Wasinska-Kempka at Bayer (Wuppertal, Germany). Cells were seeded at a density of approximately 80,000 cells/$cm^2$ or 270,000 cells/well in 12 well plates and 140,000 cells/well in 24 well plates and incubated at 37° C., 5% $CO_2$ for 2 h. To suppress contamination the amount of antibiotic-mycotic solution was increased (3-fold) and gentamicin (44 ug/ml; Invitrogen, Carlsbad,) was added during the seeding stage. After 2 h the media was replaced with fresh William's E media (as above) supplemented with 75 ug/ml rat tail collagen (Becton-Dickinson). The media was replaced approximately 16 h later with fresh collagen-containing media, with or without test compound, and thereafter every 24 h.

Test compounds Test compounds were solubilized at 200-fold final concentration in 100% DMSO and diluted into hepatocyte culture media to final concentrations ranging from approximately 200 pM to 10 mM depending on the compound. Compound stock solutions in DMSO were prepared at the initiation of the dosing regimen and stored at 4° C. Compounds were added to the culture media immediately prior to addition to the cells.

Control compounds (compounds that do not elicit a toxic histopathogy, see for example Table 1 and 2)) are selected from the training set and dosed on each batch of hepatocytes along with the unknown compounds subjected to toxicity prediction. The data from these controls are used to determine hepatocyte quality over time RNA isolation Qiagen's (Valencia, Calif.) RNeasy 96 kit was used for isolation of RNA. For cell lysis the culture media was carefully removed and 400 ul/sample in 12 well plates and 200 ul/sample in 24 well plates of RLT lysis buffer supplemented with 10 mM DTT was added per well. The RLT buffer efficiently lysed cells and solubilized the collagen layer covering the cells. The lysates were homogenized by pipetting 12–15 times, snap frozen and stored at −80° C.

Cell viability In parallel with the compound dosing, a viability assay was performed to make sure that the concentrations used to treat the hepatocytes were not excessively toxic to the cells. Cell viability was monitored for each compound concentration using the CellTiter Assay (Promega, Madison, Wis.), a modified MTT assay. Cells were seeded in 96 well plates coated with rat-tail collagen (Becton-Dickinson) at a density of 27,000 cells/well. After 16 h in culture cells were treated in triplicate for each compound and concentration. Following 24, 48 or 72 h incubation in the presence of the drug, the MTS/PMS reagent of the CellTiter kit was diluted 1/6 in culture medium, added to the cells and after 60 min incubation of the cells optical density at 490 nm was measured using a PowerWaveX Select 96 well spectrophotometer (Bio-Tek Instruments, Winooski, Vt.). Viability was calculated in relation to no-drug control after subtraction of a no-cell background value. Only compound concentrations that showed 70% or more viability in this assay were used for gene expression profiling.

RNA Purification The hepatocytes are harvested in 200 μl of lysis buffer (RLT) provided with the Qiagen RNA isolation kit. Total RNA is isolated from the lysates using the Qiagen RNeasy 96® isolation kit following the manufacture's instructions with some modification. An equal volume of 70% ethanol is added to each of the lysates and the samples are added to the membrane on the 96 well plate. Membranes are then washed thoroughly (once with 800 μl of buffer RW1 and twice with 800 μl buffer RPE) to remove unbound material followed by DNase I treatment (50 units of DNase I from Promega (10 u/μl) in buffer RDD from Qiagen; total volume 60 ul) for 1 hr at room temperature to remove all traces of genomic DNA that might be co-purifying with the RNA. Following DNase I treatment, the membranes are again washed three times as before (once with 800 μl of buffer RW1 and twice with 800 μl buffer RPE), and dried with a centrifugation step (6000×g for 7 min; to remove all residual traces of ethanol from the washing buffers). RNA is then subsequently eluted from the columns with 40 μl of RNase/DNase-free water. This process has been automated using the Tecan Genesis Freedom robotic system.

Quantity of RNA is determined by fluorometry using Ribogreen dye from Molecular Probes and quantified using a fluorometer (Spectrafluor Plus instrument, Tecan). This procedure involves diluting each 2 μl sample ten-fold in Rnase-free water and then measuring fluorescence (after addition of dye). An average of triplicate subsamples is used to calculate the concentration and total RNA yield for each sample (by comparison to a standard curve generated from known amount of RNA standards). At this point the samples are evaluated as passed or failed based on a concentration criteria (60 ng/µl or more considered as "PASS"). The samples that have a concentration greater than 60 ng/µl are further diluted to 60 ng/µl with DEPC treated water.

cDNA Synthesis Double stranded cDNA is synthesized using the Roche cDNA synthesis kit, following the manufacturer's instructions, with some modifications. 600 ng of total RNA isolated from the hepatocytes (60 ng/µl), are spiked with 2 µl of reference mRNA ($7\times10^6$ copies of hyaB and $2.5\times10^7$ copies of mhpR) and this mix is incubated in the presence of 2 ug of oligo $[(dT)_{24}$ $T7prom]_{65}$ primer at 70° C. for 10 min, immediately followed by quick chilling on ice. To each sample first strand synthesis mix is added such that the final mix contains 1× AMV RT buffer, 8.1 mM DTT, 25 units of AMV reverse transcriptase, 12.5 units of RNase-inhibitor and a dNTP-mix (1 mM of each nucleotide). This mix is incubated at 42° C. for 1 hour followed by chilling on ice. The second strand synthesis involves the addition of the second strand buffer to a final concentration of 1×, a dNTP mix (80 µM each) and the second strand enzyme blend provided in the Roche cDNA synthesis kit. The mix is incubated at 16° C. for 2 hours. Adding 10 units of T4 DNA polymerase to each reaction and incubating at 16° C. for a further 5 minutes to terminate the elongation. The reactions are stopped by adding 11 µl of 0.2 M EDTA pH 8.0. The double stranded cDNA is purified using Qiagen's QIAquick™ Multiwell PCR Purification kit, following the manufacturer's instructions. The cDNA is then quantified by fluorometry using the Picogreen® dsDNA Quantification Kit (Molecular Probes) following manufacturers instructions.

Microarrays

In Vitro Transcription, cRNA Purification, and cRNA Quantitation The complete yield of double stranded cDNA (minimum 50 ng) is placed in a Centrivap Concentrator (Labconco) for 2 hours at 45° C. or until liquid is completely evaporated. In vitro transcription is performed using Ambion's MEGAscript™ T7 Kit, following the manufacturer's instructions, with the following modifications. Biotin labels are incorporated during cRNA synthesis by adding biotin 14-CTP (Invitrogen) and biotin 16-UTP (Roche Applied Science) to the in vitro transcription reaction to a final concentration of 1.5 mM. Transcription reactions are incubated at 37° C. during 16 to 18 hours. Reactions are stopped by adding 2 U of DNase 1, and incubating at 37° C. for 15 minutes. cRNA is purified using Qiagen's RNeasy 96™ kit, following the manufacturer's instructions. Purified labeled cRNA is recovered in 30 ul of DEPC-treated water (see STM TS-MAH-104). Labeled cRNA yield and quality are determined by measuring the 260/280 nm optical density ratio, using a Powerwave HT spectrophotometer (Bio-Tek). Labeled cRNA is then diluted to 0.225 ug/ul using DEPC-treated water.

Hybridization, and Fragmentation We use a format with two microarrays on each slide and dual hybridization chambers consisting of two 0.8 mm height, 22 $mm^2$ square chambers. Dual hybridization chambers are installed on glass arrays using a Slide-Chamber Alignment Tool (SCAT). The SCAT is linked to a vacuum pump to create pressure that makes the chamber and the microarray hold together. Once assembled, microarrays are incubated at 37° C. for 10 minutes. Slides are then placed chamber side down on a lint free paper towel (Texwipe Company LLC) on a flat surface, and using a finger, gentle pressure is applied along the periphery of the chamber.

Synthetic cRNAs (1 ng each of bacterial araA and ybiw) are combined with 9 ug hepatocyte-derived labeled cRNA prior to fragmentation. The cRNA mixtures are fragmented at 94° C. for 20 minutes in a 50 ul reaction containing 40 mM Tris-Acetate, 100 mM Potassium-Acetate, 31.5 mM Magnesium-Acetate, pH 8.1. After the fragmentation is complete, 300 ul of cold hybridization buffer (Mergen Ltd., proprietary composition) is added to the fragmented RNA, and kept on ice until ready for loading onto a microarray. 320 ul of cRNA are then loaded onto a barcoded microarray. After air bubbles have been removed from the liquid, loading ports of the chamber are tightly sealed using Mergen adhesive dots. Slides are incubated for 16–18 hours at 30° C. in a hybridization rotisserie oven set at 18 rpm (Robbins Scientific, model 400)

Microarray Washing and Staining After hybridization for 16 hours, the hybridization chambers are removed from the microarrays slowly using forceps. The microarrays are placed in a reservoir containing TNT (0.1 M Tris-HCl, pH 7.6, 0.15 M NaCl; 0.05% Tween-20) and incubated at 39° C. for 1 hour. The following staining procedure is light sensitive so all incubations are done under foil taking care to minimize light exposure. Following the TNT wash, the arrays are incubated in Buffer B (Mergen LTD, proprietary composition) at 4° C. with gentle agitation for 30 minutes. The slides are then placed in a 1:500 dilution of 1 mg/ml streptavidin-alexa 647 (Molecular Probes) in Buffer B at 4° C. with gentle shaking for 30 minutes. Following a TNT wash of three times 5 minutes each, the arrays are incubated in a 1:500 dilution of 0.5 mg/ml biotinylated anti-streptavidin antibody (Vector Labs) in Buffer B at 4° C. with gentle agitation for 30 minutes. The microarrays are washed three times in TNT for 5 minutes each. A 1:1 mix of streptavidin-alexa 647 and biotinylated anti-streptavidin antibody is incubated at 25° C. for 1 hour to encourage complex formation. This complex is diluted 1:267 in Buffer B and incubated with the microarrays for 30 minutes at 4° C. with gentle shaking. The slides are washed again in TNT three times for 5 minutes each followed by 2 washes of 5 seconds each in redistilled $H_2O$. The arrays are washed individually in redistilled $H_2O$ five times for 1 second each. The microarrays are placed in a slide holder and centrifuged for 15 minutes at 300 rpm to ensure complete dryness. The slides are placed in a clean dry box and stored at room temperature until being scanned.

Scanning and Analysis of Microarrays Each slide is individually scanned using a GenePix 4000B scanner (Axon Instruments Inc.), using the 630 nm laser at 100% power and a PMT setting of 600 volts.

Image QC and Data Export Tiff images from each slide are analyzed using the GenePix 4.0 software (Axon Instruments Inc.). The scanned image is first aligned with a grid consisting of an array of circular features, such that each spot on the image is contained within a feature. After the array is roughly aligned, the software conducts fine alignment of each feature with each spot on the array. Additionally the software calculates local median foreground and local median background for each feature. The microarray is then evaluated manually to determine whether the features found by the software were true data points and not false intensity due to a defect or contamination. If contamination affects more than 30% of a feature, the feature is flagged as bad. If contamination affects more than 30% of the local background area of a feature and the local foreground/local background intensity ratio is less than 3, the feature is flagged as bad. After flagging is complete, a GenePix output file is generated. The output file contains spot IDs, spot location information, median local foreground, median local background, and bad spot flag information.

A quality control log is kept for each array to document background levels, noise/contamination problems as well as the number of features flagged. A final Image QC pass or fail decision is made for each array and added to the log. An array must contain no more then 1% flagged spots in order to pass Image QC. If an array contains an area of contamination of >150 counts which covers more then 5% of the array then the array fails PTS Microarray Data Processing The GenePix output files generated during the Image QC and Data Export are processed using Microsoft excel. A macro is used to split the data from each of the two arrays, calculate spot intensities, and filter out low quality data. The following procedure is used to calculate gene intensity and filter the data.

A. Calculate Spot Intensity spot-intensity=median local foreground−median local background B. Calculate Threshold There are 15 probes on the array that are either yeast or mouse negative controls.

If (spot_intensity is from probe type “yeast_neg” or spot_intensity is from probe_type “mouse_neg”)

then spot_intensity=thres_value mean_thres=average (thres_value[1], thres_value[n])

stdev_thres=stdev (thres_value[1], thres_value[n])

If (thres_value<(mean_thres+3* stdev_thres) and thres_value>(mean_thres−3*stdev_thres)

then thres_value=good_thres_value else thres_value=bad_thres_value mean_good_thres=average (good_thres_value[1], good_thres_value[n])

if mean_good_thres>0 then threshold=mean_good_thres+5* stdev (local_bg_median[1], local_bg_median[n])

else threshold=5* stdev (local_bg_median[1], local_bg_median[n])

C. Data Filtration

If (spot_intensity has no problem spot flag then spot_intensity=good_spot_intensity Only data of type good_spot_intensity is passed to the Discovery department.

PTS Microarray Quantitative QC The array quality is assessed by calculating a set of descriptive statistics and testing if they pass set criteria. In order for array data to be accepted the following criteria must be met:

Toxicity marker spot intensity trim mean/threshold>8

Maximum spot intensity of blank spots<300

Number of marker spots above threshold>800

Labeling spike mean spot intensity/threshold>50

Hybridization spike mean spot intensity>50

Toxicity Prediction

The PTS presents a single overall likelihood of toxicity for unknown samples (i.e. the probability that a sample is toxic) that can be ranked to indicate severity of toxic insult. In order to compute the toxicity likelihood of an unknown we calculate a likelihood estimate from 3 different modeling types (Classification Trees, Discriminant Analysis, and Logistic Regression) using three independent gene lists for a total of 9 models per mode. These 9 models are then averaged to provide a likelihood (probability) of toxicity for each mode. The rationale behind combining the results of several models as opposed to relying on a single model that performs best for a given mode is to control for the risk of over-fit (a model that performs well on training data but inadequately on novel samples). The best performing model would be expected to be more over-fit than a weaker performer. In order to reconcile this we average the results of several models in order to determine the true likelihood of toxicity for an unknown. This section attempts to describe the methods we will use for model averaging, explain how compounds can be ranked, and how we can draw inferences about the severity of toxic insult.

Common Terms

Likelihood of Toxicity: A value between 0 and 1 indicating how confident we are that a given compound/dose combination is toxic.

Model: A statistical algorithm for prediction. This section focuses on Logistic Regression, Discriminant Analysis, and classification trees which are explained elsewhere.

Model Type: Logistic Regression, Discriminant Analysis, or classification trees

Mode: A specific type of hepatotoxicity (e.g. hypertrophy)

Present and Absent: Present means a compound produced a given toxicity in vivo absent means it did not.

Model Background

One obvious problem with model averaging is that different models provide different outputs. Discriminant Analysis produces a number without bounds, logistic regression produce a likelihood estimate with a value of 0 to 1, and classification trees a proportion of node impurity with a value between 0 and 1. Therefore an arithmetic mean of these three results may be misleading because the scale of discriminant analysis is so different than the other models. Our approach is to scale the results of all models to produce a single likelihood, $P^P$, the probability that this sample belongs to the toxicity class as opposed to $P^A$, the probability that the sample does not manifest itself as toxic for this mode. By definition:

$$P_j^P+P_j^A=1 \quad \text{Equation 1}$$

Where j is the $j^{th}$ model (the three models mentioned above). In order to proceed we first need to find $P^P$ for each model.

Equation 1 means that our classfications (present and absent) are mutually exclusive and collectively exhaustive. If a sample is absent for hypertrophy, it cannot also be present for hypertrophy (mutually exclusive) and if a sample is not hypertrophic it must be absent of hypertrophy (collectively exhaustive).

Logistic Regression: This model returns $P^P$ by design.

Discriminant Analysis: This model returns a linear discriminant that is a one-dimensional linear combination that establishes two separated normal distributions as follows:

where ‘Absent’ refers to the theoretical distribution of samples that did NOT produce pathology and ‘Present’ refers to the theoretical distribution of samples that did produce pathology. Let $M_P$=the mean of the linear discriminant function for the training samples annotated as present, and $M_A$=the mean of the linear discriminant function for the training samples annotated as absent. Let $G_P$ and $G_A$ denote the probability mass function for the Gaussian distributions of the linear discriminant values for the training samples annotated as present and absent, respectively. Having estimated these functions, calculations of percentiles is very straightforward. In the above figure, $M_P$>$M_A$, therefore, for an unknown sample with a linear discriminant value of ‘x’, we have:

Equation 2:

$$P^P = \frac{LowerTail(G_P(x))}{[UpperTail(G_A(x)) + LowerTail(G_P(x))]}$$

where Lower Tail $G_p(x)$ refers to the area under $G_p(y)$ for which y<x, and Upper Tail ($G_A(x)$) refers to the area under $G_A(Z)$ where z>x. When $M_A > M_P$ the above equation becomes:

Equation 3:

$$P^P = \frac{UpperTail(G_P(x))}{[LowerTail(G_A(x)) + UpperTail(G_P(x))]}$$

Equations 2 and 3 appear more complicated than they really are. They simply convert the percentile of (x) belonging to the "present" distribution to a conditional probability that it belongs to present and not absent. This is used to satisfy mutual exclusivity rule of equation 1.

Classification Trees. As mentioned above, classification trees return a probability of correct classification for each prediction. However, this probability is actually a proportion based on the node impurity of the classification tree (the fraction of training samples on that leaf that belong to the majority class, e.g. a leaf contains 9 samples with hypertrophy and 1 sample without, the probability returned is 0.9). This is not a good indication of the true probability of an unknown because the leaf may have very few members and because the confidences of branch decisions are not included in this calculation. In order to convert this proportion to likelihood, we simply construct many trees using a subset (n−1, where n=the number of compounds) of the compounds in the reference database until all compounds are NOT used once (this is identical to the leave one out cross validation described in the next section). This process is called a jack-knife estimate of confidence.

Summary

This section describes how we convery the results of the three different models to a likelihood estimate that satisfies the mutual exclusivity rule of equation 1. For logistic regression this is the result, for discriminant analysis we rely on the probability mass function of a normal distribution, and for classification trees we create a jack-knife estimate of node impurity. Having described these techniques the next section explains how we combine the results of the individual models.

Model Averaging

Each of the above models makes a decision as to whether a toxicity is "present" or "absent", and some models are expected to perform better than others. What remains to be explained is how we determine model quality and how we combine the results of individual models.

a) Model Quality:

In order to determine how confident a given model is in its decision, we perform jack-knife estimates of each prediction. A jack-knife estimate computes n different models, with n−1 compounds in the training set (where n is the number of compounds used for training a particular toxicity mode). Each jack-knife casts a single vote for absent or present. The best models confidently (likelihood is much greater or less than 0.5) make the same decision consistently, while poorer performing models tend to have equivalent "present" and "absent" votes.

b) Combining Models:

The number of present and absent votes are tallied across all the jack knife estimates for each unknown compound. Models that are more confident in there decision are naturally weighted heavier by an ability to cast more votes. The vote totals can then be evaluated using the binomial distribution as follows:

$$L_{Tox} = \sum_{i=0}^{P} \frac{\binom{N}{i}}{2^N}$$

Where $L_{Tox}$ is the likelihood that the observed vote distribution is greater than 0.5, P is the number of votes for "present" and N is the total number of votes cast.

Summary

This section explains how we use three different marker sets for each model and then compute a weighted average based on how consistent the prediction are within a given step. At the completion of this exercise each sample will have three sets of votes: one each for logistic regression, discriminant analysis, and classification trees. The likelihood for each mode is calculated from a binomial distribution, under the null hypothesis that voting is random.

Example 9

TOXMARKER Nucleic Acid Sequences

This example provides exemplary TOXMARKER nucleic acid sequences, useful in methods of screening compounds for hepatoxicity according to the invention.

TABLE 9A

>scr_gb-af038870_4 (TOXMARKER Assignment: 1; SEQ ID NO: 1)

tttttttttttttttttttgaaggttttcaaccggcatgtttttattaatgaaatggaa tggaagcagtcagaacagagattacagaattacagaatggatcagttatctgttaagttt tacagggctggtgtgtgttgtttctgcctaagggtcctgctcaaaagatcttggaatcca cttgggaagcatcttagatatagatggttgctgtgtcacttatgatacggtccctgaatg gttctatgtcactcgtggaggtggtgtcctatccccctatctgaaatgagattgacgtcg ggtgactttctcttcgctgcagtgactcctgtgcgcctgtaatgcgacaggcacgtagga TABLE 9A-continued aatgtgttcaggatttactgtggacttctcctttcttccttctaggtaaaattctaaagc
gtagttttgtaactgtgaaatgctatctgtgactccattttgtctaactagcaccaatca
caggtgtaagccggcatcaacacaaacgctggtttagagatgccttctccttccgggtgc
acactgtggcccggacctggaggaattcgccccgaaccgctggcctgtggctactgtgcg
gatttgaatttttgtttttcgaagagcgctctcagctgctgctcagtggtggcttccttc
tgctgcatcagctctgctgcccctttcgtcactccccaagcatccggcttggacatcgaa
ggattgtacggtctgccggaagctattcgaagattctgccagtattctttcctggccctt
gccctgatccagggtttggtgtgcatgtccaaaccacttccccagctgccatgtttttct
gaagctggtggtaaaaatcccctttctggggcgagctcctctgcaatggccctgatgtgg
tagggctcaaatccgcagcagccgccaatgtacctgacccccaggttgtaggcctctctg
gcgtatttttgaatatcccatctggtggcaactctgggttccaatccaaaggggaattct
gggagatcaataaatccctgtttgccacagtcaggggtgtggtaggccaggggctggctc
atcaagtaagccttcagccgagctgcttccagaccctccttcatgagctttattgtctgc
aagctggtgctggggtcgaagtggcagttcacaccgacaatggcggcacctgcttttacc
aaacgcactgcgcactctccaggagacacgccatgtagatctccttcaggtccgatgcac
atggtagccgctataggcttcccggatgtttttaaggcctcgactgcccacacggcttct
tcaacatgttcaaaatactctgcaatgaggaagtccacattcttcttcatgaagacctca
agctgttggtgaaatatctttttaacttccgtctcactcttgcagctgaggtaggaaggt
gtctgactcacacctcctgcaaccaatgcatccccttcgtcagcaacttgccgtgcaatg
tcacaagcagcttcattgaccttctgcccagatatcttctctgccacgtagttccctcgg
ttttccagcttgtcctcacttgcatagaaagtgaaggtctgcatgacgttcgatccagct
ctgaggaactcccgatgaagctgccgaactgcctcggggtgctccaccgcagcctctggg
gtccagggtccagcctttacgtagcccctcttttccagtgcaaagacaaatcccccatct
ccgatcacgacttcgccagcatttaagcgttctaagattcccctcttggccttcttgccg
gcaatcggtgccatctttccggtgtcctgagtggcgctgaacgcagctgcggactggaca
ggagcggtctccagcaaaggcttgactgctgagccgcttctggcctctttatatacagca
gctaggattccccagccttgaccgggtccaacacatggcctcaggcggggaacacgccca
ccagcctttgaaacaggcctggggctagctgggaattc >scr_gb-z83053_3 (TOXMARKER Assignment: 2; SEQ ID NO: 2)

gacatggcaccagccggaggcccacgagtcaagaagggtatcttggagcgtctggacagc
ggggaggttgtggttggggacggcggctttctcttcactctggaaaagagaggctttgtg
aaggcaggactttggactccagaagcagtggtagagtatccaagtgcagttcgtcagctt
cacacagaattcttgagagcgggagccgatgtcttgcagacattcaccttttcggctgct
gaagacagaatggaaagcaagtgggaagctgtgaatgcagctgcctgtgacctggcccag
gaggtggctgatggaggggctgctttggtggcagggggcatctgccagacatcactgtac
aagtaccacaaggatgaaactagaattaaaaacattttccgactacagctaggtgttttt
gccaggaaaaatgtggacttcttgattgcagagtattttgagcatgtggaagaagccgtg
tgggctgtggaagtcttgagagaggtgggggcacctgtggctgtgaccatgtgcatcggc
ccagaggggggacatgcacggcgtgacaccgggagagtgtgcggtgagactgtctcgtgca
ggggcgaacatcattggggtaaactgccggtttgggcctggaccagcttacaggaccatg TABLE 9A-continued agctcatgaaggagggcctcagggattgcggcctactagctcaccttatggtccagtgct
tgggttttctcacactgggactgtggcaagggagggttgtggacttcctgatatcctttt
cgcctggggcaagagttgccaccagatgggatattcaaaaatacgccagagaggcctaca
acctgggggtcaggtacattggcggctgctgcggatttgagccctaccacatcaggggcc
attgcagaggagctcgccccagaaaggggatttttgccaccagcttcagaaaaacatggc
atctggggaagtggtttggacatgcacaccaaaccctggatcagagcaagggctagacgg
gaatactgggaaactctgttgccagcttcgggaagacctttctgtccttccctatcaaag
ccagatgcttgagaagccatgaaagagacctctgaagtgacagaaaggaggaaacagcct
caagccccatctggaatcttcctggctgctgtcctcagcccgttcttctggctgttgagc
atcgatgagctgtcgtcccttccaattgagtgacatatcactcctgagtatgcccactag
atgcggtggagatgcagaggcatccggaccccacgccccaccccctcccctcacacactt
actctctgcctagtaatgccacagagcttccatccccatccaaaggtcatcaggcatggc
tatcagttggctctcagggtggatttgacattctcagatgattagaagttggcaagaagc
aaccttggtgaataactctggtgtctaaactctgtacttgagttacagtctcagtagagg
agacgccaaagctgttgcgagtgacggcagaattattgaacagtcatgatgcttggcttt
caaaggcgattatcgctttaaggtcttagaattagtaagtgcatctttataaccaggcat
agctagatcataaactactgatggccaaggaccatagaacgtgcttcttaccttcctctc
tagttagcattacgacaaacataatcaccaacgctcagggaaacacttgctgattcaagt
aaaatgcatgaaccttggaagacctttctagaagtcagagatcaagttcatcttgttcta
gcactttccacattcatgtttggtttgtatgctgcgccctacttttgttttttgctacaa
tgtaacaaattagtgagtaaccattagtgaaattgcgaataattttccttttctaaattt
tgatttctttggaacattgatttaaaaaaaatagtgtgttgcttgtcaaaaaaaaaaaaa
aaaa >scr_gb-x95189_4 (TOXMARKER Assignment: 3; SEQ ID NO: 3)

ccatagcgaagacttcatgaagactgtcccaggcatgctgtgacacaaactacagaaggt
gggaaaagatctttgtggtcaaaccatccggaccttggctaccgcagacagaacaatact
gaccgcattcactcatacacagttctcggcacctcccagtgctcagagcagaccctcaag
gagatgagcagatccaggatggggagcccaatgcaccgagtgtccctgggggacacctgg
agctggcaagtgcacccggacatagacagcgaaaggcactcaccgtccttcagtgtggag
cgactcaccaacatccttgatggaggcctcccaaacaccgtgctgcgaagaaaagtcgaa
agcatcatacaaagtgacccagtgtttaatttgaagaagctttacttcatgacccgagag
gagctatatgaggatgcgattcaaaagagattccatctcgagaagctagcctggagcctg
ggctggtcagaagatggtcctgaacgcatttatgctaacagagtccttgatggaaacgtc
aacttaagcttacatggtgttgccatgaatgctatccgaagcctgggctcagatgaacag
attgctaaatggggccaactctgcaaaaacttccaaatcatcacaacatacgcccagaca
gagctgggacacgggacatacctacagggcctggagactgaagccacctatgatgaagcc
aggcaggagcttgtgatacacagccctacgatgacttccaccaagtggtggcctggggac
ttgggatggtcggtcacccatgctgtggtcctagcccagttgacctgcttaggagtccgg
cacggcatgcacgccttcattgtgcccattcggagcctagaggatcacaccccactgcca TABLE 9A-continued ggaatcacagttggggacataggccccaagatgggtttggaacacatagacaatggcttc
ctgcaactgaaccacgtgcgggttcccagagaaaacatgctcagtcgctttgcagaggtc
ttgccagatggtacctaccagaggcttgggacgccacagagcaattatcttggcatgttg
gtgacccgggtgcagctgctgtgtaaaggaatcctaccctccctccagaaggcttgcatc
attgccacgcgctactcagtaatccgccatcagtctcgacttcggcccagtgacccagag
gcaaaaatcctggaataccagacgcagcagcagaaactccttcctcagcttgctgtgagc
tatgccttccacttcacggccaccagcctctcagaattcttccacagctcctacagtgct
attctgaagagagacttcagcctcctgcctgagctccatgcattgagcactggtatgaag
gccacgtttgcagacttctgtgcccagggcgccgagatctgtcgcagagcttgcgggggc
catggctactcaaagctgagcggcctgccgacactggttgctcgagcaacagcctcttgc
acatatgagggtgagaatacggtgctctacctgcaagtggccaggtttctgatgaagagc
tatctgcaggctcaagcgtccccaggcgccacaccacagaagcctctccctcagtccgtc
atgtatattgccacacaaaggccagccaggtgctcagcccagactgcagctgacttccgc
tgcccagatgtctataccacagcctgggcatatgtgtctaccaggctcataagagatgca
gcacaccgtacacagaccctcatgaagtccggggttgaccagcatgatgcctggaatcaa
actactgtcatccaccttcaggctgctaaggctcactgctacttcatcactgtgaagaat
ttcaaggaagctgtggagaaactagacaaggaaccagagattcagcgtgtgctccaacgc
ctctgtgacctctatgccttacacggtgttctgactaactcaggggactttctgcatgat
ggcttcctgtctggggcccaggtggacatggccagagaagccttcctagacctgcttccc
ttgatccggaaggatgccatcttgttaaccgatgcttttgacttctcggaccattgttta
aactcggcacttggctgttatgatggacacgtctacgaacgcctgtttgagtgggctcag
aagtacccagccaatactcaggagaaccctgcctataagaagtatatccgaccactgatg
ctcggctggagacacaagatgtgaaaagtcaaaggatttgggaccgagaagcaccacggc
cttactatggcacatatacatagagaatttaaagcacgggggggggggggggggggggtgc
tgctcggttaaatcaggtagtaaattggtacatgaatggatggtcatcctattagtctac
tattgagcatgtttgaaactttcccttgtccatctatagcatgtatttggctaaatgcta
aaatttttgttttacatacaggaaaagctaataaacttgtcagttacaaa
>scr_gb-m59814_4 (TOXMARKER Assignment: 4; SEQ ID NO: 4)
ttttttttttttttttttttttttttttttttttttttttttaacaatgagacatatacag
ctttatttaacctgtaaaaagtcacactctgcagagtgacacctttcttatctcagcaga
aagcaaggagtgtgtgaaaaacctttttcctcaggttgggaaccgtatgaccctggctggg
ctcacatgtggatccttccagagtccttgtgtgtggcagcttcttcccagaggtctccct
ggctggtgtgacccctcaccaacaacagacaggggggcaaaatatttctacctggacaag
gctgccctgagattgtccctttccctcctattaagggacattacatgcttaagaccttcc
cagaaaagtcaccttcaaggtgacttggctttcatcatgtctgctgacacttaggctcca
cttatttaccatgatggtgtgtgctaacggtccttcctcttccaataacctcaccatcga
tggcattttaaatatcactctgttctctgggaccgagggatggagaaccgctctccctca
gaccaggttttgactcaggagctgggttttattttgaagaaacttccctacatgagtcat
gagcaagggaaatggatgtgggggagggaggaggggctctgagggaggagtacgaatgga
ggaaagaaaagaatgtcattggcgagggagagcatggcacagcccagggcttccctctct TABLE 9A-continued tccctccacctccttcctttcttcctgcagacggggaactccagtccctctcagatggga actgagttcaccctggttcccaacgcatacggtttcagcttcgcttctgtttagcatcac ctttctctgtctttatcgtcaatcattacgcgtttggtttcccacggcttctacacactt ccatggccgagaaatggcggttgcccatgggcagcaggtccagttcattcttcacaggtg ggaagttgtttctcagccaagaagctgatctttctggcacattccaccgtggtcaacctc tgtttcccctttgaccctggtccttttcattcctctcctcccctaggaacatcgagttct catgccattaccgacggtgactggttcatctggaccctcatcgagtggatgctgctaaga atcttcttctgatggcctgccaaggtgacccctattctcaggaggtcttctgatgtcatc tgggtgaccagctggagggaggtgaagccagcggtgaggaagctgtccctgtactggacc attttgatggcacttagccagtcatccacggtggtaaaggccgtgaagtctgggatagag cggtcaagcaggggttgggaaggcacagcggtgatggttgccacagtcttgagactagct gggttccggatcatcttgtccagggtgttgacgatctctgcaaaacggggccggctattt cgatccttctgccaacagtccagcatgagctggtgcagggcagctgggcagtccatagga gggggcagccggtagtcctgctcaatggcattgatgacatcttgattggacatatcccag taaggtctctctccaaatgacattacttcccacatgacaatcccgtagctccagacatcg ctggctgacgtaaacttgcggtaggcgatggcctctggagctgtccatctaacaggtatc ttccctcccaaggagctggtgtaggtggggtctgaggtgtcatcctggaggtagcgagag aggccaaagtcagacactttgcacaccaggttgctgttcaccagaatgttcctagcagcc aggtcccggtgcacataattcatctcagataggtacttcatgccagcagcgatgcccctc agcatccccacaagctggatcacggtgaactgtccgtcattttgccggaggaaagagtct aaagcgccattctccatgaactccgtaatgatcatgacaggtcggctcttggtgacaaca ccctctaggcgaatgatgttgggatggtcaaactggcccatgatgctcgcctcgctcaga aaatcccgacgctgtttctctgagtacccagctttcagggtcttgatggccacatagatt tccctcttgcctggcagcttcaatcggcccttgtacacttctccaaactcccctgctccg atgacctcttcaattttcacaaaagacacatcaatctccttggcaaactcccggacagct tcattagggtcctcataagtgaacgggtcaatgtagatcttcatccctggggagcctcgg cctgtgctgtaatgctgaagtttatcactgtacacagcctctttgctgtaagctcgtttc ctgctgcagacaatggagatagccaccagagacacaacaaatacaaccccagctgctgca gagccagcgatcaggggtagctgctctctcagctccgacttgtaatcatcatctgtcaga gtctggaagcacatcttgccactgaacttgccatagccagccacggttcgagctcgtacc tggaccacatacaccatgccgggccgtagcccatcgatacgtgccgtgttggtctggctc ctggccatggaagagttgaactcattgtgctccttctcatagtaccggatctcatagtcc aggatgatgccattaggctgctccggctgaggccatgacaaggtgatgctcctcatggtg gcactgacctggtgcatgataggaacagtggagggggcagcttggtttgtggtgatgttg acagagacatgctgtgggggggaagggactcttgctagagactccattgatggcctggata tcaaaagtgtatggggtgtgggcccataggctactgatagagacacgacactcagtcaag cccagctgtctgggtacaaactccacattgtcatcgcagcgggagcaactccggcggtct gctctgcacttcttgcagatgatgttgtaggtcacatcatctcgcccaccggtctctctt ggagggtgccactctagaatgatagatgtctcattcacaatggagatgacatttcgaggg TABLE 9A-continued cctgatgggacactagtgcacgccacttctggggggatcaaagtctgctcggtaatagcca
gtccggcaggtgcagatgggagacgcctctgaaggggagcggctgttggaggggcagtgg
gagcagccttcagcttcctggctggccttgaaggttcccgcaggacaggccttgcaggcc
acgctgttctcaggttcatagccagccttacaggtgcagcgcccaatgggcaccatccac
tctccatctccattgcagtagagttttatgggcacatccacttcttctgcattagggatg
catgtgccccgagcaatcaccagagatgtgctctctgctcctgtcatggtttctgggaac
actgcaaaattttgcacaatgctgggacactttttgaagaagacacggacagaaagtaga
gacatacaggctccataatcctggaaagcgaggtaaaaaccattcctagtaagaggccca
aagctcctgacttctgtgttgaccttcatcaaccttcccccaaaatccacctgggagaag
ctctcatctgcagcaatggtgtcaactttgaggtagggggcttcagaccagaaggctgac
ttcttggtggcaatgacagagtcagtctcatagtagtataagttgaaggtctctttgcag
gagcctgggacatttggaaggctgctgcagtccctcacagtgaagcgcatctctgtatag
atgcgatgggcgccccgtctgttgataaaggtggtaagcagccagttgttctggttgggt
tcaaagacgttgcacacttggtaagtacggatggtgttcaggttttcatcgtagccactg
acttcttcccacccagaggcagggttggccgtccatcccaactctgcagtggcagtcctt
gtgtccatcaatgtttcttccatcgcggccactgcagatgccaggaggaacagcagcagg
caatccagggccatcgccggccagcggcccccaggccgagccccagcggagacgcgccgc
gtcccagggcgccgctgcgctcccggcgggtggcttctccgtgtcctttcgcgctctggc
cgggaccggactccccggagcgcggcgtgggcgtgggcgggagtgtgcgcgcgtggggcg
gtgcgggcgcgcgtggatgtgggtgtgcatgtgtgtgtgtgtgtttatgggagaggtggg
tgtgtgcgtgcgtgtgtgagagagggtgagggagagcgagccaaaccataaaaagatgga
gggggagttgtgggtgggcgaccctgctagtttcatagctggcattcttggggctggaaa
ccccatggcacaagacgttaggatggctggtctgctcaaccactgtgccgtgtgtgaggg
gtctctcggcttgtgtctctatcctgctctcattgagtcggatgacctgtacagctctgt
ctaccatggaggatgtattgtgaagtctctgtgctaaggactcacgtttgggtgctttgg
agatgaaatggatgacatgtacactggatatccccctcgtg >scr_gb-m29358_5 (TOXMARKER Assignment: 5; SEQ ID NO: 5)

cccccccctcgaggtgttttctttcatttcattccttgtctttagggctttttttttttc
aaggtctcattatttatttgttactctttaaagacttatttttgactggactcagattta
gaagtagaagctctcagcgaagacagcctacgtctcttggcaatctgttcctggcgcttc
tctttggcttccttcattctcttggccaaaagtttagcatattctgcagcctcctccttg
tttttcttagtgcgttgcttcttcagagcaatacgtcggcgtttgtgttgcaggacacgg
ggagtaacaagacgctgaatcttgggcgctttggtcctgggcttcttaccttctttgttt
aagggctttctgacaacatactggcggacatcatcttctttggagagattaaaaagcttt
cggattctactagctcttttaggtcccaaccgacgaggcacagtggtatctgtcagtcct
ggaatatccttctctcctttttttacaataaccaagttgagaacactcaggttggcatcc
acaatgcatcctcggacagacttgcgcttcctctctccagttctcctaggtctataacaa
gaatgccccttactcaaaagcaggcgcactctgccatgggtcaaaacgccttgcttcatg
ggaaaaccttgtttgtcattcccaccgctgatccggaccacataacccttccactcttca
ccaagagcatcagcagctacttctgtggccatgcgcttctcatagaacgtacgaagcttg TABLE 9A-continued cgttcgtcatccacttctatgagtttctgacagccagtggcagggaaggagatattcagc
ttcatcttgacacagccgaccgcctaggaggcgtgttaccattctgatgttggagcggcc
gc
>aj297736 (TOXMARKER Assignment: 6; SEQ ID NO: 6)
agttgcttcagtgtcccggtgcggttagtcacgtttcgtgcgtgctcattctgccaagat
gcctgaggaaacccagacccaagaccaaccaatggaggaagaggaggtcgaaacctttgc
ctttcaggcagaaattgcccagttaatgtccttgatcatcaacactttctactcgaacaa
agagatctttctgagggagctcatttccaactcctcagacgctctggataagatcagata
cgagagcttgaccgaccctagtaaactggactcggggaaggagctgcacattaatctcat
tcccaacaagcaagaccgaaccctcactattgtggatactggcattggaatgaccaaggc
tgacttgatcaataaccttggcactattgccaagtcaggcaccaaagccttcatggaggc
tttgcaggctggtgcagatatctctatgattggccagtttggtgttggtttttactctgc
gtatttggttgctgagaaagtgactgtcatcaccaagcataatgatgacgagcagtacgc
ctgggagtcctcagctggaggatccttcactgtgaggacagacacaggtgaaccaatggg
tcgtggaacaaaggttatcttgcatctaaaagaagaccaaactgagtatttggaggaaag
gagaataaaagaaattgtgaagaaacattctcagtttattggctaccccattactctctt
tgtggagaaggaacgtgacaaggaagtcagtgatgatgaggctgaagaaaaggaagagaa
agaggaagagaaagaaaaagaagaaaaggagtctgatgacaagcctgaaatagaagatgt
tggttctgatgaagaagaagaagagaagaaggatggtgacaagaagaaaaagaagaagat
aaaggaaaagtacattgatcaagaagaactcaacaaaacaaagccgatctggaccagaaa
tcctgatgacattacgaatgaagaatacggagagttctacaagagcttaaccaacgactg
ggaagaacatttggcagtaaagcatttttctgttgaaggacaattagaattccgggctct
tctttttgtcccaagacgcgctccttttgatctatttgaaaacagaaagaaaaagaacaa
catcaagttgtatgttcgcagagtttttatcatggataactgtgaggagttaatccccga
gtatctgaatttcatcagaggggtggtggattctgaggatctccctctaaatatttcccg
tgaaatgctgcaacaaagcaaaattctgaaagttatcaggaagaatttggtcaagaaatg
cctagaactatttactgaactggctgaagataaagagaactacaaaaagttttatgagca
gttctcaaaaaatataaagcttggaattcatgaagactctcaaaatcggaagaagctttc
agagctgttgagatactacacatctgcttctggggatgagatggtttctctgaaggacta
ctgcaccagaatgaaggaaaaccagaagcacatctattttatcacaggtgagaccaagga
ccaggttgctaactcagcctttgtggaacgtctccgaaagcatggcttagaagtaatcta
tatgattgagcccattgatgagtattgtgtgcaacagctgaaggaatttgagggcaagac
cttggtgtcagttaccaaagaaggactggaacttccagaagatgaagaggaaaagaagaa
acaggaagagaaaaagacaaaatttgagaacctctgcaaaattatgaaggatattttaga
gaaaaaggttgaaaaggtggttgtgtcaaaccgattggtgacatccccatgctgtattgt
cacaagcacatatggctggacagcaaacatggagagaatcatgaaagctcaagccctcag
agacaactcaacaatgggttacatggcagcaaagaaacacctggagataaaccctgatca
ctccattattgaaaccttaaggcaaaaggcagaggctgacaagaatgacaagtctgtgaa
agatctggtcatcttgctgtacgaaacagcactcctgtcttccggcttcagtctggaaga TABLE 9A-continued tccccagacccatgctaacaggatctacaggatgatcaagcttggtctaggtattgatga
ggatgatcctactgtggatgataccagtgctgctgtaactgaagaaatgccacccctgga
aggagatgatgacacatcacgcatggaagaagtagactaggcttcaccagaactatgtgt
ttgatgcttaccttcattccttctgataatatattttccatgatttttgtttattttttgt
taacatttaaaacatctgtgtggcatgaaaactaggggaaggtaaaaatttctacatgtg
atactgtgatactataggtttgactcaagaggttgatagaacgtttgttgtaagacgtaa
tgtaacctacggtacttgttaactatgggggtctgaaagtgtttagctgttgagctggat
tcctttagtagaccaaattaagatgacttaagtttcatct
>j00719 (TOXMARKER Assignment: 7; SEQ ID NO: 7)
ttgctcctccttgctctcctcgtgggcttcttgttactcttagtcaggggacacccaaag
tcccgtggcaacttcccaccaggacctcgtccccttcccctcttggggaacctcctgcag
ttggacagaggggggcctcctcaattccttcatgcagcttcgagaaaaatatggagatgtg
ttcacagtacacctgggaccaaggcctgtggtcatgctatgtgggacagacaccataaag
gaggctctggtgggccaagctgaggatttctctggtcggggaacaatcgctgtgattgag
ccaatcttcaaggaatatggtgtgatctttgccaatggggaacgctggaaggcccttcgg
cgattctctctggctaccatgagagactttgggatgggaaagaggagtgtggaagaacgg
attcaggaggaagcccaatgtttggtggaggaactgcggaaatcccagggagccccactg
gatcccaccttcctcttccagtgcatcacagccaacatcatctgctccattgtgtttgga
gagcgctttgactacacagaccgccagttcctgcgcctgttggagctgttctaccggacc
ttttccctcctaagttcattctccagccaggtgtttgagttcttctctgggttcctgaaa
tactttcctggtgcccacagacaaatctccaaaaacctccaggaaatcctcgattacatt
ggccatattgtggagaagcacagggccaccttagacccaagcgctccacgagacttcatc
gacacttaccttctgcgcatggagaaggagaagtcgaaccaccacacagagttccatcat
gagaacctcatgatctccctgctctctctcttctttgctggcactgagaccagcagcacc
acactccgctatggtttcctgctgatgctcaagtacccccatgtcgcagagagaaagtccaa
aaggagattgatcaggtgatcggctcacaccggctaccaacccttgatgaccgcagtaaa
atgccatacactgatgcagttatccacgagattcagaggttttcagatcttgtccctatt
ggagtaccacacagagtcaccaaagacaccatgttccgagggtacctgcttcccaagaac
actgaagtgtaccccatcctgagttcagctctccatgacccacagtactttgaccaccca
gacagcttcaatcctgaacacttcctggatgccaatggggcactgaaaaagagtgaagct
ttcatgcccttctccacaggaaagcgcatttgtcttggcgaaggcattgcccgaaatgaa
ttgttcctcttcttcaccaccatcctccagaacttctctgtgtcaagccatttggctccc
aaggacattgacctcacgcccaaggagagtggcattggaaaaatacctccaacgtaccag
atctgcttctcagctcggtgatccggctgaggcagccaggtgccccagttctgttgggaa
tggcctcatgtttctgcctctgggggacctgctgaaaaccaggctccaaggccactgctc
cacatct
>j00720 (TOXMARKER Assignment: 8; SEQ ID NO: 8)
cccagtgcccttttgtcctgtgtatctgtttcgtggtgtccttgccaacatctatggtgt
gggtaagggaatgaggagtgaatagccaaagcaggaggcgtgaacatctgaagttgcata
actgagtgtaggggcagattcagcataaaagatcctgctggagagcatgcactgaagtct TABLE 9A-continued accgtggttacaccaggaccatggagcccagtatcttgctcctccttgctctccttgtgg
gcttcttgttactcttagtcaggggacacccaaagtcccgtggcaacttcccaccaggac
ctcgtccccttcccctcttggggaacctcctgcagttggacagaggaggcctcctcaatt
ccttcatgcagcttcgcgaaaaatatggagatgtgttcacagtacacctgggaccaaggc
ctgtggtcatgctatgtgggacagacaccataaaggaggctctggtgggccaagctgagg
atttctctggtcggggaacaatcgctgtgattgagccaatcttcaaggaatatggtgtga
tctttgccaatggggaacgctggaaggcccttcggcgattctctctggctaccatgagag
actttgggatgggaaagaggagtgtggaagaacggattcaggaggaagcccaatgtttgg
tggaggaactgcggaaatcccagggagccccactggatcccaccttcctcttccagtgca
tcacagccaacatcatctgctccattgtgtttggagagcgctttgactacacagaccgcc
agttcctgcgcctgttggagctgttctaccggaccttttccctcctaagttcattctcca
gccaggtgtttgagttcttctctgggttcctgaaatactttcctggtgcccacagacaaa
tctccaaaaacctccaggaaatcctcgattacattggccatattgtggagaagcacaggg
ccaccttagaccccagcgctccacgagacttcatcgacacttaccttctgcgcatggaga
aggagaagtcgaaccaccacacagagttccatcatgagaacctcatgatctccctgctct
ctctcttctttgctggcactgagaccggcagcaccacactccgctatggtttcctgctca
tgctcaagtaccccccatgtcacagtgaaagtccaaaaggagattgatcaggtgattggct
ctcacaggccaccatcccttgatgatcgtaccaaaatgccatacactgatgcagtcatcc
acgagattcagaggtttgcagatcttgccccaattggtttaccacacagagtcaccaaag
acaccatgttccgagggtacctgctccccaagaacactgaggtgtatcccatcctgagtt
cagctctccatgacccacagtactttgaccatccagacaccttcaatcctgagcacttcc
tggatgccgatgggacactgaaaaagagtgaagcttttatgcccttctcccacaggaaagc
gcatttgtcttggcgaaggcattgcccgaaatgaattgttcctcttcttcaccaccatcc
tccagaacttctctgtgtcaagccatttggctcccaaggacattgacctcacgcccatgg
agagtggcattgcaaaaatacctccaacgtaccagatctgcttctcagctcggtgatcgg
gctgag >j00728 (TOXMARKER Assignment: 9; SEQ ID NO: 9)

atggagcccagtatcttgctcctccttgctctccttgtgggcttcttgttactcttagtc
aggggacacccaaagtcccgtggcaacttcccaccaggacctcgtccccttcccctcttg
gggaacctcctgcagttggacagaggaggcctcctcaattccttcatgcagcttcgcgaa
aaatatggagatgtgttcacagtacacctgggaccaaggcctgtggtcatgctatgtggg
acagacaccataaaggaggctctggtgggccaagctgaggatttctctggtcggggaaca
atcgctgtgattgagccaatcttcaaggaatatggtgtgatctttgccaatggggaacgc
tggaaggcccttcggcgattctctctggctaccatgagagactttgggatgggaaagagg
agtgtggaagaacggattcaggaggaagcccaatgtttggtggaggaactgcggaaatcc
cagggagccccactggatcccaccttcctcttccagtgcatcacagccaacatcatctgc
tccattgtgtttggagagcgctttgactacacagaccgccagttcctgcgcctgttggag
ctgttctaccggaccttttccctcctaagttcattctccagccaggtgtttgagttcttc
tctgggttcctgaaatactttcctggtgcccacagacaaatctccaaaaacctccaggaa TABLE 9A-continued atcctcgattacattggccatattgtggagaagcacagggccaccttagaccccagcgct
ccacgagacttcatcgacacttaccttctgcgcatggagaaggagaagtcgaaccaccac
acagagttccatcatgagaacctcatgatctccctgctctctctcttctttgctggcact
gagaccggcagcaccacactccgctatggtttcctgctcatgctcaagtacccccatgtc
acagtgaaagtccaaaaggagattgatcaggtgattggctctcacaggccaccatccctt
gatgatcgtaccaaaatgccatacactgatgcagtcatccacgagattcagaggtttgca
gatcttgccccaattggtttaccacacagagtcaccaaagacaccatgttccgagggtac
ctgctccccaagaacactgaggtgtatcccatcctgagttcagctctccatgacccacag
tactttgaccatccagacaccttcaatcctgagcacttcctggatgccgatgggacactg
aaaaagagtgaagcttttatgcccttctccacaggaaagcgcatttgtcttggcgaaggc
attgcccgaaatgaattgttcctcttcttcaccaccatcctccagaacttctctgtgtca
agccatttggctcccaaggacattgacctcacgcccatggagagtggcattgcaaaaata
cctccaacgtaccagatctgcttctcagctcggtga >l00320 (TOXMARKER Assignment: 10; SEQ ID NO: 10)

atggagcccagtatcttgctcctccttgctctccttgtgggcttcttgttactcttagtc
aggggacacccaaagtcccgtggcaacttcccaccaggacctcgtccccttcccctcttg
gggaacctcctgcagttggacagaggggggcctcctcaattccttcatgcagcttcgagaa
aaatatggagatgtgttcacagtacacctgggaccaaggcctgtggtcatgctatgtggg
acagacaccataaaggaggctctggtgggccaacctgaggatttctctggtcggggaaca
atcgctgtgattgagccaatcttcaaggaatatggtgtgatctttgccaatggggaacgc
tggaaggcccttcggcgattctctctggctaccatgagagactttgggatgggaaagagg
agtgtggaagaacggattcaggaggaagcccaatgtttggtggaggaactgcggaaatcc
cagggagccccactggatcccaccttcctcttccagtgcatcacagccaacatcatctgc
tccattgtgtttggagagcgctttgactacacagaccgccagttcctgcgcctgttggag
ctgttctaccggaggttttccctcctaagttcattctccagccaggtgtttgagttcttc
tctgggttcctgaaatactttcctggtgccccacagacaaatctccaaaaacctccaggaa
atcctcgattacattggccatattgtggagaagcacagggccaccttagacccaagcgct
ccacgagacttcatcgacacttaccttctgcgcatggagaaggagaagtcgaaccaccac
acagagttccatcatgagaacctcatgatctccctgctctctctcttctttgctggcact
gagaccagcagcaccacactccgctatggtttcctgctgatgctcaagtacccccatgtc
gcagagaaagtccaaaaggaggttgatcaggtgatcggttcacaccggctaccaaccctt
gatgaccgcagtaaaatgccatacactgatgcagttatccatgagattcataggttttca
gatcttgtccctattggagtaccacacagagtcaccaaagacaccatgttccgagggtac
ctgcttcccaagaacactgaagtgtaccccatccggagttcagctctccatgacccacag
tactttgaccacccagacagcttcaatcctgaacacttcctggacgttaacggggcactg
aaaaagagtgaagctttcatgcccttctccacaggaaagcacatttgtcttggcgaaggc
attgcccgaaatgaattgttcctcttcttcaccaccatcctccagaacttctctgtgtca
agccatttggctcccaaggacattgacctcacgcccaaggagagtggcattggaaaaata
cctccaacgtaccagatctgcttctcagctcggtga >m11251 (TOXMARKER Assignment: 11; SEQ ID NO: 11)

TABLE 9A-continued cccagtgcccttttgtcctgtgtatctgtttcgtggtgtccttgccaacatgtatggtgt
gggtaagggaatgaggagtgaatagctaaagcaggaggcgtgaacatctgaagttgcata
actgagtggaggggcggattcagcataaaagatcctgctggagagcatgcactgaagtct
accgtggttacaccaggaccatggagcccagtatcttgctcctccttgctctccttgtgg
gcttcttgttactcttagtcaggggacacccaaagtcccgtggcaacttcccaccaggac
ctcgtccccttcccctcttggggaacctcctgcagttggacagagggggcctcctcaatt
ccttcatgcagcttcgagaaaaatatggagatgtgttcacagtacacctgggaccaaggc
ctgtggtcatgctatgtgggacagacaccataaaggaggctctggtgggccaacctgagg
atttctctggtcggggaacaatcgctgtgattgagccaatcttcaaggaatatggtgtga
tctttgccaatggggaacgctggaaggcccttcggcgattctctctggctaccatgagag
actttgggatgggaaagaggagtgtggaagaacggattcaggaggaagcccaatgtttgg
tggaggaactgcggaaatcccagggagccccactggatcccaccttcctcttccagtgca
tcacagccaacatcatctgctccattgtgtttggagagcgctttgactacacagaccgcc
agttcctgcgcctgttggagctgttctaccggaggttttccctcctaagttcattctcca
gccaggtgtttgagttcttctctgggttcctgaaatactttcctggtgcccacagacaaa
tctccaaaaacctccaggaaatcctcgattacattggccatattgtggagaagcacaggg
ccaccttagacccaagcgctccacgagacttcatcgacacttaccttctgcgcatggaga
aggagaagtcgaaccaccacacagagttccatcatgagaacctcatgatctccctgctct
ctctcttctttgctggcactgagaccagcagcaccacactccgctatggtttcctgctga
tgctcaagtaccccatgtcgcagagaaagtccaaaaggaggttgatcaggtgatcggtt
cacaccggctaccaacccttgatgaccgcagtaaaatgccatacactgatgcagttatcc
atgagattcataggttttcagatcttgtccctattggagtaccacacagagtcaccaaag
acaccatgttccgagggtacctgcttcccaagaacactgaagtgtaccccatccggagtt
cagctctccatgacccacagtactttgaccacccagacagcttcaatcctgaacacttcc
tggacgttaacggggcactgaaaaagagtgaagctttcatgcccttctccacaggaaagc
acatttgtcttggcgaaggcattgcccgaaatgaattgttcctcttcttcaccaccatcc
tccagaacttctctgtgtcaagccatttggctcccaaggacattgacctcacgcccaagg
agagtggcattggaaaaatacctccaacgtaccagatctgcttctcagctcggtgatccg
gctgaggcagccatgtgccccagttctgttgggaatggcctcatgtttctgcctctgggg
gacctgctgaaaaccaggct >m26125 (TOXMARKER Assignment: 12; SEQ ID NO: 12)

gacttgggaggaaccagggcctacacttagccctggtaaacagcagagcatgctgggata
attcttcccagaaaaggaaaagcaggcacttctgttcccagggaaaacaacaggagcact
ttggacctccctgctgcagtcaggagtcatgtggctggaacttgtcctggcttcccttct
gggctttgtcatctactggtttgtctcccgggacaaggaggaaaccttaccactaggaga
tggatggtgggggccagggtcaaagccatcagccaaagaagatgagagcatccggccctt
caaggtggaaacatcagatgaggagatcaaggacttacaccagaggatagataggttccg
ggcatccccacctttggagggcagccgcttccactatggcttcaactccaactacatgaa
gaaagtggtgtcctactggaggaacgagtttgactggaggaagcaggtggagatcctcaa TABLE 9A-continued ccagtaccctcacttcaagaccaagatcgaagggcttgacatccacttcatccatgtgaa gcctccccagctgccctcagggcgcaccccaaagcccttgctgatggtgcatggctggcc tggatccttctatgagttttacaagatcatcccactactgactgaccccaagtcccacgg tctgagtgacgagcacgtgtttgaagtcatctgtccctcgattcctggctatggctactc agaggcatccagcaagaaaggtttaaattcggtggccactgcgaggattttctacaagct gatgacacggctgggcttccagaaattctacattcaaggcggggactgggggtccctcat ctgcaccaacatggcccagatggttcccaaccacgtgaaaggcctgcacttaaatatggc tttcatttcgagaagtttttacaccatgactcctctcctgggccaacgcttcgggagatt ccttggctacacagagaaggatatcgagctcttgtaccccctataaggagaaggttttcta cagcatcatgagggagagtggctacttacacatccaagccaccaagccagacactgtggg ctgtgctctcaatgactctcccgtgggcctggctgcctacatcttagagaagttctccac ctggaccaagtcagagtaccgtgaactggaggatggaggcctggagaggaagttctccct ggatgatctgctggttaacatcatgatctactggacgacaggaaccattgtctcctccca acgctactacaaggagaatttgggccagggcatcatggtccataaacatgaggggatgaa ggtctttgtgcccactggcttttcagccttcccttccgagctactgcatgccccagaaaa gtgggtgaaggtcaagtaccccaaactcatctcctattcctacatggaacgtgggggcca ctttgctgcctttgaagagcccaagcttctggcccaggacatccgcaagttcgtgtccct ggctgagctgcagtagtgacactggataccaactgtggctttagcagcagccctggttcc tcccaagtcacacttatggaagatgacccctttctgaggaataagtttgttccctgacca cactcgaggacccagacttaaactccacagagtcgtatgttacccccatatgcttcacct cactacatagctgtgttagctacatggctttaatgataaatggatttatttct >m34452 (TOXMARKER Assignment: 13; SEQ ID NO: 13)

tgagccaatcttcaaggaatatggtgtgttctttgccaatggggaacgctggaaggccct tcggcgattctctctggctaccatgagagactttgggatgggaaagaggagtgtggaaga acggattcaggaggaagcccaatgtttggtggaggaactgcggaaatcccagggagcccc actggatcccaccttcctcttccagtgcatcacagccaacatcatctgctccattgtgtt tggagagcgctttgactacacagaccgccagttcctgcgcctgttggagctgttctaccg gaccttttccctcctaagttcattctccagccaggtgtttgagttcttctctgggttcct gaaatactttcctggtgcccacagacaaatctccaaaaacctccaggaaatcctcgatta cattggccatattgtggagaagcacagggccaccttagaccccagcgctccacgagactt catcgacacttaccttctgcgcatggagaaagtgagtcctgcatggatgagagaggagaa gtcgaaccaccacacagagttccatcatgagaacctcatgatctccctgctctctctctt ctttgctggcactgagaccggcagcaccacactccgctatggtttcctgctcatgctcaa gtacccccatgtcacagagagaaagtccaaaaggagattgatcaggtgattggctctcacag gccaccatcccttgatgatcgtaccaaaatgccatacactgatgcagtcatccacgagat tcagagatttgcagatcttgccccaattggtttaccacacagagtcaccaaagacaccat gttccgagggtacctgctccccaagaacactgaggtgtatcccatcctgagttcagctct ccatgacccacagtactttgaccatccagacaccttcaatcctgagcacttcctggatgc cgatgggacactgaaaaagagtgaagcttttatgcccttctccacaggaaagcgcatttg tcttggcgaaggcattgcccgaaatgaattgttcctcttcttcaccaccatcctccagaa TABLE 9A-continued cttctctgtgtcaagccatttggctcccaaggacattgacctcacgcccaaggagagtgg
cattgcaaaaatacctccaacataccagatctgcttctcagctcggtgatcgggctgagg
cagccaggtgccccagttctgttgggaatggcctcatgtttctgcctctgggggacctgc
tgaaaaccaggctcaaggccactgctcacatcttcctattgcagttctccaaagtcccaa
ggcttgttcttattcctgtgaatggcactgaagaagtcaatcgactgtcttattttgaca
tgtgaacagagatttcatgagtacacatctcatgctgagtcacttccctcttcctcctaa
tagcccacgtccccacttatcagccctccatggtctgtgatctgtgctaatggactctgt
atatggtctcagtgctatgtctacagacttacatagtatgtatggttcaggtaaacagaa
tcacagagtgtgtg >u33546 (TOXMARKER Assignment: 14; SEQ ID NO: 14)

atggaacctagtgtcctacttctccttgctgtcctcctcagcttcttgctactcctggtc
aggggccatgcaaagatccatggtcgtcttccaccaggaccctgccctgtacccctttttg
ggaaatctcttgcagatggacagaagaggcctcctcaagtcttttattcagcttcaagaa
aaatatggagatgtgttcacagtgcacttaggactgaggccagtggtcgtgttatgtggg
acacagaccataagagaggctctggtggaccatgctgaggctttctctggccgggggaca
attgctgggcttgagccagttttccaggactatggtatattcttttccagtggagaacag
tggaagacccttcgacgattctctatggccaccatgagagactttgggatgagaaagaag
agtgtggaggagagaataaaggaagaatcccaatgtttggtggaggaactgaagaaatac
cagggagccccccctggatcccaccttcccttttccagtgcatcacatccaacatcatctgc
tccattgtctttggagagtgctttgactacacagatcaccaattcctgcacctgctggat
ctgatgtatcagacgttttcactcttaagctcaatcttcagtcaggtatttgaactcttc
cctggtgtcctgaagtactttcctggtgcccacagacaaatctccagaaacctccatgaa
atcctggacttcattggccagagtgtggagaagcacagggccactttggacccaaatgct
ccacgagactttatatatacttaccttctgcacatggagaaaaagtcaaaccattataca
gagttccatcactggaacctactgtcgtctgtactctctctcttctttgctggcactgag
actagcagcaccacactccgctatggcttcctgatcatgctcaagtaccctcatatcaca
gagaaagtccaaaaagagattgattgtgtgattggctcacaccggctacctaccctggat
gaccgcagcaaaatgccatacaccgaggcagttatccatgagattcagagattttcagat
cttgcccctattggaacaccacacagagtcatcaaagacaccattttccgagggtacctg
ctccctaagaacactgaggtgttccccatcctgagttcagttctccatgatccacagtac
tttgaacaaccagacatcttcaatcttcagcactttctggatgccaatggggcactgaag
ataattgaagcttttctgcccttctccacaggaaagcgaatttgtcttggtgaaagcatt
gcccgcaatgaattgttccttttcttcactaccatcctccagaacttctccgtgtccagc
cctgtggctcctaaagacattgatctcactcccaaagagagtggtattggaagaataccc
caagtgtaccagatctgcttcttggcccactga >x74673 (TOXMARKER Assignment: 15; SEQ ID NO: 15)

gaattccgcggccgccaacgtcctctcttacccgccaccttcttctgccacctctaccac
ggtcaccatgtcgcaagcccggcctgccactgtgctgggtgccatggagatgggtcgccg
catggatgtgacctccagctccgcgtcggtgcgcgccttcctgcagcgcggccacacgga TABLE 9A-continued gatagacaccgccttcgtgtatgcgaacggtcagtctgagaccatcctaggagacctggg
gctcggactgggccgcagcggctgcaaagtaaaaattgccaccaaggctgccccaatgtt
tgggaagacactgaagccagccgatgttcggttccagctggagacgtcactgaagaggct
gcagtgtccccgggtggacctcttctatttacactttccagaccacggcactcctataga
ggagaccctgcaggcctgccaccacgtgcatcaggagggcaagtttgtggagcttggtct
gtccaactatgtctcctgggaagtggctgagatttgtaccctctgcaagaaaaatggctg
gatcatgccaactgtgtaccagggcatgtacaacgccatcaccaggcaggtggagactga
gctcttcccctgcctcagacacttcggactaaggttctacgccttcaacccctttggctgg
gggcctgctgactggcagatataaataccaggataaggatgggaagaatcctgagagccg
cttctttgggaatccattttctcaactgtacatggaccgctactggaaggaggaacactt
caatggcatcgccttggtggagaaggctctgaagactacctatggccccactgcccccag
tatgatctcagctgccgtacggtggatgtaccatcactcacagctcaagggcacccaagg
ggatgcagtcattctgggcatgtccagtctggaacaactggagcagaacttggccttggt
cgaggaagggcctctggagccagctgttgtggatgcctttgaccaagcctggaacctagt
tgcccacgagtgtcccaactatttccgctaagatacatctgccttggggatggcgcagct
tactgcctgccccgccttgtcctgggctcgatctgatctggttctttcctttttagacag
gtcactgtctttttcttccctgctttctatacagccagttgctttcaaagtgagagctgg
ctgagccccaatacctcctgctgaataaaactgttccctgtcacagcctgggctacaact
ggcggccga >scr_gb-x13044_4 (TOXMARKER Assignment: 16; SEQ ID NO: 16)

tttttttttttttttttctaccttctaccttttattgtcacgtgaaccatggtcctaca
ggctgctgacaagcttggctgagcagggatcccaggggcgtcggcaggacatgaggaagg
gttgctgggagggcttggcctcttccttgagaagacagcaaatgtatccagcctagatta
agggtagggcatcccctatccctgtcagtgggcctagatctcagagccccacattaaaga
ctgctaatgggtcagaaatgggggtcccttagatgggggtaggcagcaaggccctccctc
cagtgttctcattctgttccggtttcatttgttgtgtccagggacggtgaagcagatacc
agtctcaagccccagggtgcaggaagacgggaaatggggtgtgatgttagggagtgtaag
aagggctgaggagcaggggagctgccgccgtgcagagctggcttctgtcttcacaagaac
atttggcccatatcctgcttggtcactcccaggccagaagatgggtcttccatgtccagt
ggctctttaggtggagtctgggtgggctgcttctcctccagggagttcttgctcatttca
aacaacagccactgtttcatccagctctcaaagaccttccagtccagaccattcatagag
ttcttaaggtgcttcagattctccgggaagctccccttcagctgtgggtagttcacgggt
ccagacttcgtaagcaggtgcatcacgtggtcctgggtcatgttgccatacttggtaaca
ttcttcacgggcgcttggagcatgttatccatggacagtgggcgcatcagcaagggagta
gccatgcgcatcgggctcacaggtttggcagatttcggaagcttcatgcgaaggttctcc
agttgcaggttctgggaggtgacggtcagcttgtccaggcggccctgctgctggtacagg
aagtaagcagtggtggcctgcccagccaagagcagagccaccaggacagagacactggtg
tacaggactccacggttgcaattgctttctggggctctagcacgctggcccaggatgggc
agctgctcatggttagagatgaggtcgcgctggtcatccatgactctagcctctagcttt
tcccccaagtgctgctggtgctgctgctgctgct TABLE 9A-continued >scr_gb-x14254_5 (TOXMARKER Assignment: 17; SEQ ID NO: 17)

tttttttttttttttgttctaccttctaccttttattgtcacgtgaaccatggtcctaca
ggctgctgacaagcttggctgagcagggatcccaggggcgtcggcaggacatgaggaagg
gttgctgggagggcttggcctcttccttgagaagacagcaaatgtatccagcctagatta
agggtagggcatcccctatccctgtcagtgggcctagatctcagagccccacattaaaga
ctgctaatgggtcagaaatgggggtcccttagatgggggtaggcagcaaggccctccctc
cagtgttctcattctgttccggtttcatttgttgtgtccagggacggtgaagcagatacc
agtctcaagccccagggtgcaggaagacgggaaatggggtgtgatgttagggagtgtaag
aagggctgaggagcaggggagctgccgccgtgcagagctggcttctgtcttcacaagaac
atttggcccatatcctgcttggtcactcccaggccagaagatgggtcttccatgtccagt
ggctcactgcagttatggcgcccgcggctcttggtgtgagggacctcagtgccgttgggg
aacacacaccagcagtagccagtgctcccatggcactggagtggcatatagttaccgttc
tcatcacacttgggacggaacgcccccgggtggacatcagggatgtggctgacttcttcc
tggcacttggtcaatactttaggtggagtctgggtgggctgcttctcctccagggagttc
ttgctcatttcaaacaacagccactgtttcatccagctctcaaagaccttccagtccaga
ccattcatagagttcttaaggtgcttcagattctccgggaagctccccttcagctgtggg
tagttcacgggtccagacttcgtaagcaggtgcatcacgtggtcctgggtcatgttgcca
tacttggtaacattcttcacgggcgcttggagcatgttatccatggacagtgggcgcatc
agcaagggagtagccatgcgcatcgggctcacaggtttggcagatttcggaagcttcatg
cgaaggttctccagttgcaggttctgggaggtgacggtcagcttgtccaggcggccctgc
tgctggtacaggaagtaagcagtggtggcctgcccagccaagagcagagccaccaggaca
gagacactggtgtacaggactccacggttgcaattgctttctggggctctagcacgctgg
cccaggatgggcagctgctcatggttagagatgaggtcgcgctggtcatccatgactcta
gcctctagcttttcccccaagtgctgctggtgctgctgctgctgctgctgctg >scr_gb-bi275638_1 (TOXMARKER Assignment: 18; SEQ ID NO: 18)

cggcacgaggcgcgctcggcgctgtcagttcgtcccgctgcccctcggcccttgctgctg
gctctgacggcgaccgacggcgggcggggcccgggttcgcggccgagcggcgccggtgag
ggcgcggaggaggcgcacagcgggaggaggagccgtgagcctggcacggagcggccgcgg
ccatggcgtacgcctatctcttcaagtacatcatcatcggcgacacaggtgttggtaaat
cgtgcttattgctacagtttacagacaagaggtttcagccggtgcatgacctcacaattg
gtgtagagtttggtgctcgaatgataaccattgatgggaaacagataaaactccagatct
gggatacagcagggcaggagtcctttcgttctatcacaaggtcatattacagaggtgcag
cgggggctttactagtgtatgatattacaaggagagacacgttcaaccacttgacaacct
ggttagaagacgcccgtcagcattccaattccaacatggtcatcatgcttattggaaata
aaagtgacttagaatctaggagagaagtgaaaaaggaagaaggtgaagcttttgcacgag
agcatggacttatcttcatggaaacttctgccaagactgcttctaatgtagaggaggcat
ttattaacacagcaaaagaaatttatgaaaaaatccaagaaggggtctttgacattaata
atgaggcaaacggcatcaaaattggccctcagcatgctgctaccaatgcatctcacggag
gcaaccaaggagggcagcaggcaggggggaggctgctgctgagtctgctgttgccggctag TABLE 9A-continued ctgcccagtggagccacgcactctgtcaccctctctcctcatgctcagctgagacatgaa
actattgaaatggctttgtgtcacaggagactttaatccttcagattcttgtataacttt
gaataaatggttaatgttcacttaaaaagacagattttggagattgtattcatatctatt
tgcatttgatttctaggtcaattg >scr_gb-x66871_3 (TOXMARKER Assignment: 19; SEQ ID NO: 19)

tttttttttttttttttttttttttttttttttttttttttttttttttttttttttcta
aagtaaaaatggtttattcacgacacatatgaggaagtgtctcatgtcacagacggtacg
tccaactccctggaatgttcatttctttggcataaaggagagaatgaggggaaagccagg
caaaggcagctaagatgggggatgggtcggcagctctgtcgtcatcttcacagggaggag
ttcaggggtccattagtggcaggctgattctctagaacattaggttggggcacaggtagg
gccacttctgggcaatccaccatgccaagcccttcagtcgtccccaccacacaggtacag
cagcgccttctggtagtcacccttagtgtcttgctggatgaagtagtacagggatttgcc
atatttcctcttgaattcagatctgattttcaacatgtccacttcactgcgagagaccat
gattctaatcaggaccttgtctcgagtccccttgcccttcatggagtcatacagccggtc
agcaaagtacaggggcttgttctgaatgcactgaaccaggttcaggaaggcgttctccag
gtctcctttgacctctttcctgatgctctccagcatgtcataaggactgtagctcttgta
cctttcgaacactttctggaggtggcacacactgcgctcagtcatgatgctgatccactt
ggggacatcggttcctttcctcttcaccccagcatcatagagctcccgggcatcctggtc
aatcagctcgtagtcaataacagaaccatcctctgcccgtttaccctttgcaagggcgac
caacagctttcggaattctccagatgtgtcagagatgatgtccttctccagatcggtctt
gtacatttccttatacactcggttaatctcctgcagctcctggttggttcttgagcagat
gatctcgatgagggagtcctcatcagtccccaggcccttcatggaggctttgagctcaga
ggcatcgtactgagcaggtgtcttcaacaggcctaacatcacggtctccaggtgaccaga
caaggccgacttcatcgccgatggcagttccttttggtcctcctctggtaggcgaaggc
aatgtcctgcctctgtgcattgctgcggttagtcagaatgttgacaatggtgacctcgtc
cacgcctttggtcttgattgctgtttcaatgttcaaagcatccctctcagcgtcgaagtt
ggtgtagggtttgaccgacccataggcacttgggggtgtagaatgctgagaatcaccctc
caagctgagcttgcacaggatttcgtggacagtagacattttgaaaaaaaagctgggccg
ggcacctattgcagagagcctcc >scr_gb-149379_3 (TOXMARKER Assignment: 20; SEQ ID NO: 20)

gggatgacatagagtacaacattcagagaagttaactattaagtcgtcaggatgaaaggt
caggaggcaggcctttaactgggctgtgagaatggagaaagcacggtgcactttaacatc
tgctttcccagaggaaaaagtaaaggagaaacagtacaatcatagaagagtcttcgtaac
agaagcgcgaggagagcattatggacaagttctgcaactctactttttgggatctctcat
tactggaaagtccagaggctgacctgcctctttgttttgagcaaactgttctggtgtgga
ttcccttgggctttctttggctcctggctccttggcaactttacagcgtgtacagatcca
ggaccaagagatcttctataaccaaattctaccttgccaagcaggtgttcgtcgtgtttc
ttcttattttagcagccatagacctgtctcttgcgctcacagaagatactggacaagcca
cagttcctcctgtcagatatacgaatccaatcctctacctgtgcacatggctcctggttt
tggcagtccagcacagcaggcaatggtgtgtacgaaagaactcttggttcctgtctctgt TABLE 9A-continued tctggatcctctcggtcttatgcggcgtattccagtttcagactctgatacgagcactcc
tgaaggacagcaagtccaacatggcctactcctacctgttcttcgtctcctacggtttcc
agattgtcctcctgattcttacagccttttcaggaccaagtgactcaacacaaactccat
cagtcacggcttcctttctgagtagcattacatttagttggtatgacaggactgttctga
aaggttacaagcatccactgacactagaagatgtctgggatatcgatgaagggtttaaaa
caaggtcagtcaccagcaagtttgaggcggccatgacaaaggacctgcagaaagccaggc
aggcttttcagaggcggctgcagaagtcccagcggaaacctgaggccacactacacggac
tgaacaagaagcagagtcagagccaagacgttctcgtcctggaagaagcgaaaaagaagt
ctgagaagaccaccaaagactatcccaaatcgtggttgatcaagtctctcttcaaaacct
tccacgtagtgatcctgaaatcatttatactgaaattaatacatgaccttttggtgtttc
tgaatcctcagctgctgaagttgctgatcggtttcgtgaagagctctaactcatacgtgt
ggtttggctatatctgtgcaatcctaatgtttgctgtgactctcatccaatctttctgcc
ttcagtcttactttcaacattgttttgtgttgggaatgtgcgtacggacaaccgtcatgt
cttcgatatataagaaggcattgaccctatctaacttggctaggaagcagtacaccattg
gagagacggtgaacttgatgtctgtagattcccagaagctaatggatgcgaccaactaca
tgcagttggtgtggtcaagtgttatacagattactttgtccatcttcttcctgtggagag
agttgggaccgtccatcttagcaggtgttggggttatggttctcctaatcccagttaatg
gagttctggctaccaagatcagaaatattcaggtccaaaatatgaagaataaagacaaac
gtttaaaaatcatgaatgagattctcagtggaatcaagatcctgaaatactttgcctggg
agccttcatttcaagagcaagtccagggcattcggaagaaagaactcaagaacttgctgc
ggttcggccagctgcagagtctgctgatcttcattttacagataactccaatcctggtgt
ctgtggtcacattttctgtctatgtcctggtggatagcgccaatgttttgaatgcggaga
aggcatttacctccatcaccctcttcaatatcctacgcttccctctgtccatgcttccca
tggtgacctcatcgatcctccaggccagtgtttctgtggaccggctggagaggtatttgg
gaggagacgatttagacacatctgccattcgccgcgtcagcaattttgataaagctgtga
agttttcagaggcctcttttacttgggacccggacttggaagccacaatccaagatgtga
acctggacataaagccaggccaactggtggctgtggtgggcactgtaggctctgggaaat
cctctttggtatcagccatgctgggagaaatggaaaacgttcacgggcacatcaccatcc
agggatccacagcctatgtccctcagcagtcctggattcagaatggaaccatcaaagaca
acatcctgtttgggtccgaatacaatgaaaagaagtaccagcaagttctcaaagcatgcg
ctctcctcccagacttggaaatattgcctggaggagacatggctgagatcggagagaagg
ggataaatctcagtggtggtcagaagcagcgagtcagcctggccagagctgcctatcaag
atgctgacatctatattctggacgatcccctgtcggctgtggatgctcatgtgggaaaac
acattttcaacaaggttgtgggccccaacggcctgttggctggcaagacgagaatctttg
ttactcatggtattcacttccttccccaagtggatgagattgtagttctggggaaaggca
ccatcttagagaaaggatcctatcgtgacctgttggacaagaagggagtgtttgctagga
actggaagaccttcatgaagcattcagggcctgaaggagaggccacagtcaataatgaca
gtgaggcggaagacgacgatgatgggctgattcccaccatggaggaaatccctgaggatg
cagcttccttggccatgagaagagaaaatagtcttcgccgtacactgagccgcagctcta TABLE 9A-continued ggtccagcagccgacgtgggaagtccctcaaaaactccttgaagattaaaaatgtgaatg
tcttgaaggagaaggaaaaagaagtggaaggacaaaaactaattaagaaagaatttgtgg
aaaccgggaaggtcaagttctccatctacctgaagtatctacaggcagtagggtggtggt
ccatacttttcatcatccttttctacggattgaataatgttgcttttatcggctctaacc
tctggctgagtgcttggaccagtgactctgacaacttgaatgggaccaacaattcgtctt
ctcatagggacatgagaattggggtctttggagctctgggattagcacaaggtatatgtt
tgcttatttcaactctgtggagcatatatgcttgcagaaatgcatcaaaagctttgcacg
ggcagctgttaaccaacatcctccgggcacccatgaggtttttttgacacaactcccacag
gccggattgtgaacagattttctggtgatatttctactgtggacgacttgctcccccaga
cacttcgaagctggatgatgtgtttctttggcatcgctggcactcttgtcatgatctgca
tggccaccccagtcttcgctatcatcatcattcctctcagcattctttatatttcggtgc
aggtttttatgtggctacttcccgccagctgagacggttggattctgtcaccaaatctc
cgatctattctcacttcagtgagactgtcacaggtttgcccattatccgtgcctttgagc
accagcagcgatttctagcttggaatgagaagcagattgacatcaaccagaaatgtgtct
tttcctggattacctccaacaggtggcttgcaattcggctggagctggttggaaacttgg
tcgtcttctgttccgccttgctgctggttatttatagaaaaaccttaaccggggacgttg
tgggctttgttctgtccaacgccctcaatatcacacaaaccttgaactggctagtgagga
tgacgtcagaagcagagaccaacattgtggcagttgagcgaataagtgaatacataaatg
tagagaatgaggcgccctgggtgactgacaagaggcctccggcagactggcccagacatg
gtgagatccagtttaacaactatcaagtgcggtatcggccggagctggatctggtactga
aagggatcacttgtaacatcaagagcggagagaaggtcggcgtagtgggcaggactgggg
ctgggaaatcatccctcacaaactgcctcttcagaatcttagagtctgcgggggggccaga
tcatcattgatgggatagatgttgcctccattggactgcacgaccttcgagagaggctga
ccatcattccccaggaccccattttgttctcggggagtctgaggatgaatctcgaccctt
tcaacaaatattcagatgaggaggtttggagggccctggagttggctcacctcagatcct
ttgtgtctggcctacagcttgggttgttatccgaagtgacagagggtggtgacaacctga
gcatagggcagaggcagctcctatgcctgggcagggctgtgcttcgaaaatccaaaatcc
tggtcctggatgaagccacggctgcagtggatctcgagacggatagcctcattcagacga
ccatccgaaaggagttctcccagtgcacggtcatcaccatcgctcacaggctgcacacca
tcatggacagtgacaagataatggtcctagacaacgggaagattgtcgagtatggcagtc
ctgaagaactgctgtccaacagaggttccttctatctgatggccaaggaagccggcattg
aaaatgtgaatcacacagagctctagcagctggttccgtggctggcggactataagaaca
gtttctattatttgctttggtttctgtgactgtgctctaggtgcaaagacacatattttg
ttcccgttgctcaggctggcctcaaactctaaggctccagcaatctctggtctcagccag
agacctgtaaaaatagacacttcaaagattatcatgaataaatatttaaataaatagtaa
aaaaaaaaaaaaaaaaaaa
>scr_sc-132690501_1 (TOXMARKER Assignment: 21; SEQ ID NO: 21)
gaattctctgggcccatccgttgttctcaatggacatgacctccaggaagctaaagtcca
ggtcgtgaccaaagccaaggttgtagagcgggaatctgccccggatagcgttgcggacat
tcttgaggatctgggaacggtccgtctccccttcagtgggctctccgtcggtcaacatga TABLE 9A-continued taagaattgaggcagggctgctgagttctgggtggcttccttgagctctgtttaagatct
cgattcctcggagcaagcctccattcaggtttgtggctccagccaaagaaaagcgcctca
caaagtcttgggctgcttgcaaattggcgtgagacgcgggtaccagtgagcccttccatg
actgcacttgagacccaaagaggaccaggtcaaagttgtctactggcttcatgtcccccca
atatcttaaggagcgcctcctttgtctgcttcactttctggccttccatggacccactga
tatcaatcacaaaaaccaggttcttgctcatgttggtcaggttttgggggggcaaagaaat
gtgtaaagtaattgttggccaccaggaggtcacagagcttgtctcggttcacatcgtagg
tcaccttgaagtctccattcagcaaggaggtagagcacgtggggcaggactgctgctggc
tcacagtggggcggaagagcacatgacccttcttccccgagaaagacttcttgatggttt
gagcacttgactggtgatgacgtagtgggcaaagcgagaggtgactttgcaattg
>scr_gb-aw141735_3 (TOXMARKER Assignment: 22; SEQ ID NO: 22)
ttttttttttttttttttactgtatatgtaatttaattcaaattggaacaatgacgtaga
tatataagccacaatccatgaaagtcttggaggaaaacataggagcagttatttctgtac
ttgattttagtggtgagattcttagctgtggcatggatacacatgatcagaacagtatta
aataaggagaacgtcactgaaaagagcaatctgtgtgcatcaaagaacattatcaagaaa
gcaaagaagcaatgtgtataaaacgtccctaataggtaaatctacatagataaagagaag
attggtggttagacaaccagagggaggaagaatggagagtcactgagtaatggttacagt
gtgtttgaaaggggataaagataagatcgtggcctgattttacccataaattgttgattc
tttacacaagaataatggttagaggaatgagccacaatagcagatattatccaaccatta
atgaaacttatgaccacttcttaaatttttatttatttttttaaaatttacttgtttctg
cataactttgagtgatgttacatgcttatacaggatgctggggccagtagtagccaaata
aaggcatcaagacatgggtggaaactggaatttccagaggttgtaagcagccatgtgggt
ggtgggaaatgtccctgtgtcctttgcaagatcagcaacttttcctagtatctgtccttc
tctccagcattcttacacattgattcagttctaccaggctgtaagttattggctataagt
tatgagtatcagcggcatagcaaaggctatatggcatcattagacataacctgcaaaagg
gcacaaatgcattcaggatagggagagctgaatgcaggcatcataagatcaggctggcag
gaagaaagtatcctcatcttggaacatggtttcccccctacttgcccatcctgacagagct
ttggagtggtggagatactgaagagaggactctccccatgtagtaaatgtgtctttatgg
agatgagaacctgccacagaacagaatgctgctggttttgttgtgcttgatgaagaaaag
gaaggggtggtcagcacagaatgttgggacaaaagcagcacagcagtattctatgacagc
ggaggctgctgcagcctctgtgccttcctcattgacctccactacgctcttgtgaacaat
cttggacacacacaggtttctctctggagacattgctgataagtcagccttggcctcttg
gaagacatccactattcccaagcgctgaaacacagactccatgtcataatcctcttgcag
tttaaattttggaaggaaaacctcaacattagtgttcttcataaagtctgggttggtcca
ggctgttaacttctcaaaagtgagattgctttccaccttgctgaggtccccgtcattatc
tgggagtaggaccacgaagctcagctccattccttcatatggcatcatgagcacttgcgc
ctgcacctcgttcacatgggcaaggttatatgtgtcctcacaacacatcatctgcactag
t
>af184983 (TOXMARKER Assignment: 23; SEQ ID NO: 23)

TABLE 9A-continued gtatttcataaaacagagaggatcgcaggaggccggcactctgactcctggtggatggga
ctagggagtcagagtcaagccctgactggctgagggcgggcgctccgagtcagcatggaa
agtctctgcggggtcctggtatttctgctgctggctgcaggactgccgctccaggcggcc
aagcggttccgtgatgtgctgggccatgagcagtatccggatcacatgagggagaacaac
caattacgtggctggtcttcagatgaaaatgaatgggatgaacagctgtatccagtgtgg
aggaggggagagggcagatggaaggactcctgggaaggaggccgtgtgcaggcagcccta
accagtgattcaccggccttggtgggttccaatatcaccttcgtagtgaacctggtgttc
cccagatgccagaaggaagatgccaacggcaatatcgtctatgagaggaactgcagaagt
gatttggagctggcttctgacccgtatgtctacaactggaccacaggggcagacgatgag
gactgggaagacaacaccagccaaggccagcacctcaggttccccgacgggaagcccttc
cctcgcccccacggacggaagaaatggaacttcgtctacgtcttccacacacttggtcag
tattttcaaaagctgggtcagtgttcagcacgagtttctataaacacagtcaacttgaca
gttggccctcaggtcatggaagtgattgtctttcgaagacacggccgggcatacattccc
atctccaaagtgaaagacgtgtatgtgataacagatcagatccctatattcgtgaccatg
taccagaagaatgaccggaactcgtctgatgaaaccttcctcagagacctccccattttc
ttcgatgtcctcattcacgatcccagtcatttcctcaactactctgccatttcctacaag
tggaactttggggacaacactggcctgtttgtctccaacaatcacactttgaatcacacg
tatgtgctcaatggaaccttcaactttaacctcaccgtgcaaactgcagtgccgggacca
tgcccctcacccacaccttcgccttcttcttcgacttctccttcgcctgcatcttcgcct
tcacccacattatcaacacctagtccctctttaatgcctactggctacaaatccatggag
ctgagtgacatttccaatgaaaactgccgaataaacagatatggttacttcagagccacc
atcacaattgtagatggaatcctagaagtcaacatcatccaggtagcagatgtcccaatc
cccacactgcagcctgacaactcactgatggacttcattgtgacctgcaaaggggccact
cccacggaagcctgtacgatcatctctgaccccacctgccagatcgcccagaacagggtg
tgcagcccggtggctgtggatgagctgtgcctcctgtccgtgaggagagccttcaatggg
tccggcacgtactgtgtgaatttcactctgggagacgatgcaagcctggccctcaccagc
gccctgatctctatccctggcaaagacctaggctcccctctgagaacagtgaatggtgtc
ctgatctccattggctgcctggccatgtttgtcaccatggttaccatcttgctgtacaaa
aaacacaagacgtacaagccaataggaaactgcaccaggaacgtggtcaagggcaaaggc
ctgagtgtttttctcagccatgcaaaagccccgttctcccgaggagaccgggagaaggat
ccactgctccaggacaagccatggatgctctaagtcttcactctcacttctgactgggaa
cccactcttctgtgcatgtatgtgagctgtgcagaagtacatgactggtagctgttgttt
tctacggattattgtaaaatgtatatcatggtttagggagtgtagttaattggcatttta
gtgaagggatgggaagacagtatttcttcgcatctgtattgtggtttttatactgttaat
agggtgggcacattgtgtctgaaggggggaggggaggtcactgctacttaaggtcctagg
ttaactgggagaggatgccccaggctccttagatttctacacaagatgtgcctgaaccca
gctagtcctgacctaaaggccatgcttcatcaactctatctcagctcattgaacatacct
gagcgcctgatggaattataatggaaccaagcttgttgtatggtgtgtgtgtgtacataa
gatactcattaaaaagacagtctattaaaaaaaaaaaaaa >scr_cg-22510674_1 (TOXMARKER Assignment: 24; SEQ ID NO: 24)

TABLE 9A-continued gaattcttgcagttacagagtatggctgttgtctactcgggagctcccagatcctcataa
ctcagggacgtgtccctatttatggacaaaaaagtttgacgccaggtcgggcctacatga
gctcttctctaccctgcaagtccccagtgtatctgaggaaggtgtattctgtcagagaag
caaggaagatcaatgcacacctttagtctcagccccataggaggcagagtcaagcagatc
t
>scr_cg-57215224_1 (TOXMARKER Assignment: 25; SEQ ID NO: 25)
aagctttatagtcaggcacagctggctgttgccaggcaactgtggggcagagcatacctg
gctgttgccaagtagctgtggggtggagcttagacagaatcccaacagatagtatagttg
gagagggtttcagtctgtcacagtggggaggcaggggcagtagttgagttcatggtgacc
agatcttgtgatggaggaaatttacatcatcatcccaggctagaaagcagtgagcagggc
agagacaggagcaggttatcaccttggaagacctgacactagt
>scr_gb-aa850767_2 (TOXMARKER Assignment: 26; SEQ ID NO: 26)
ttgcggccgcccaagtctgccacttcaacactgtatctaaaacttgaaaggcactgtcaa
aaaccctggtgggttcctagctttagggatccatcgttagagtcagtaaacatggcaact
ctgcctccgggcatgtgatacgtcgccagcagaggcttgctagcccttgccacacaacgc
tcagcttactcaaagcactgccaagacatggctgccctgagacggttgtctgggctcctt
ccttcctataccttagggcgccccccttcacagcactgggtaagcaatcagcccctcccgg
agaggagaagggaaggtaaaagacaaaggtatgttttacactatgcaaaacgttccagag
ggggaagatgaacgaagtaacaagtatccaacacagggttttaaaaagcaacgacatttc
aaatgagcttgtatgggagaaagaaaagcaggttttcaggaaaaatccaaacacattcag
gtgtgtcttttaagtcatgagtttatcatttattctaagttcattgggaggaaaactgga
gactatcagcatagctgtcttactggggaaggcattcccagtgaataaacatctccctta
cctgagctcttggcgagagattctgcccagcttgactctctc
>scr_gb-ai011994_2 (TOXMARKER Assignment: 27; SEQ ID NO: 27)
ttttttttttttttttccagaaatttgcccattcttttatttgaaggcaaaaattccca
tggaagtctggatgaagagagagacaaaggcttatagaaaataaattgaataactagaga
ttctctggatccagacatagttggttgataaatttgttacctatttctcattgtatttca
cattatttagacatagttcttgacatctctgttttgcatactgtctctggccaagagttt
tggtcttcctttctaaatatcaagaggaaaaatggcagaacaaaccagtaatgttacatg
gcatgtggttcctgagtatataatcaagcattagcagcagttgtagttatctgaatataa
tgcatagatataatacatgaccgaagagacacaccgatttaaacaaccaatgtcaacact
gaaacaaagaattttaatgctaaggcacccaatcacggtgtctttcagttatttgttgtt
ttctttaggagactggccatacacagcagggattcaaaattgtggcttgcagtcatgaat
caacatttgcatttgagtaacttacccatcttctttatgcttccacaaacatagtttcag
ttgggataatcactgaggtgtgcacagccctttcttcctgtagtttaggcaatatccaag
gctgtagaacttggggtaaggtgtaatggtgtcacaggaggagacatctactcactgtta
aatgttgctctgatgtaggttggccatagctccccatacgatctcacagggaagccgatg
ggtaatagcagcaggaagatcatggtctacataactgactctggaacttcttgacttata
acttattactttttgggtttcttttc TABLE 9A-continued >scr_gb-aw142293_1 (TOXMARKER Assignment: 28; SEQ ID NO: 28)

agggaacccggtttctgaggttaagaacctggtatgaggtagaaagcagaatcggacctt
aggcactcgagcgtcgtgtcgaagaaacattaaatagaatagaggagtaaaggggatgtt
tcggataagcgctaggtcgagtcaaagaagtcttgcaagaagagttaagggagcaagaat
ttctagaagcatctagataaggagtcgtagcatactgacgttactagtaataagtagggt
gagtcggagaatcatgcgctcgatggtcataagatagtatctatcgaggagtgtaggagg
cctcgtccttcggcggaaaagtaacgcgtagcggttaagaatcttgtcgttcattatctt
aagggtaaggagccatcagtttagaagtcgttcccgcggtagtaagttcgcgtcgatttt
aataagactttagattgcgtcgtttagtcgacgtagtagacggttaatagtaacggtctt
acttccttaagcgtttcgctagttcttaagcttaattcggctactctagattttaccttt
ggggttaagtttccgttagcgttgttggaatcggttttgcctgcggggtggacgcccgtc
taggagaacgcattcgctacgaacggtgc >scr_gb-bm383327_1 (TOXMARKER Assignment: 29; SEQ ID NO: 29)

ttttttttttttttttgatggccagtgacagtttttgcttttttttatatttataaacaa
aaccaacctccccccaagtaactccccaaacaaacaaaaaaaccagattaaataaaattt
acagtgaacccagcaaacatctgtatgtgcaattaaatactgtgtctgttactgtggtgg
cacgaacctcaaacaaacaatatacaagtgttctggggttggatcaggggtcgggggagt
cccaagttttaactctgtggggtttggggagacaaggtggggaattgaacgaatggggaa
atcaatttatttttcttaattctgtccatataaatatattcatgaagaccaaaagaggga
agggcagttgggctggtgatgaagtgggagaaggggagggcagagccctctcaactctac
tcagccaaaaatatgaaacaaattaatttcatggtgggagaagagatttaaaaaatgata
gaagatgggaaggagggggagacagaaggggaccaaccagggaaaaggggacccatggc
aagggagtcccatgtcaaggagtcctgtgccggtgtgagaatctgtctgcttctctcttc
agccataatgtggtaagctctggcccaatccgccttcggctcccggcttggcccttgctc
ctattgtgccagcccctcccgcctccagctattgagagctagctcgctccaggatcctca
ggtcgtagttctttttagctactcgaagtttgaagcgactcacagagttgttgaggcgaa
gggaggcattgtgggcagccaggggactggggaacacagccactatagtgtacaaggcag
cgaggtccgcatggcggccattctcagcagtcccactgttgtccccccccacctgcaccag
gcaacccctgagcatccttaagccactggatcttggcaccagacatggcaagctgtgtga
agagtttgtctgcctctgtgcgggtgattccttccgggagatcagtcacctccagtaccc
ttcccagcacaacatccgctgtccccaggtcagtggaggcagacttgagtgcttgtctct
tgcctcggtttccatgcttcaatccactctgtccctggtgcaccgtatacgttgactggc
catgg >scr_gb-bm386625_1 (TOXMARKER Assignment: 30; SEQ ID NO: 30)

ttttttttttttttttcacatgtcaacaactgctagctactattaaaatactgtcaccc
aaggaggtggaatgtttaacagaaaataggctttaacaattcatactggtcctcaataac
tgcagatgactagttcaagccaactgcaaaactgagcaagaaatgcagcttgaagaacag
gacaataaaatttaatcttgcaacttgatagacttggaggcattccggtcaatgtagaag
accttgcgggcctcagagttaaagcccaggccagcccctaggctgtacttccagctcatg
gcccggtcgtagtcctgctgcagactctgctggagcgtatctgaagacttcttgtccagg TABLE 9A-continued gccatgttggacctgacagtcatgctgggaggacggttgaatgacggggatagatgctta
aagccgcccataagtttcaggaaattttagtttctgtttcttcattttcaaagcccgcag
tgtcccactggccaaactgggttccctgatctatgcaggcctcatccatattgccttttt
tttccagtaccacctccaagtctgtgtctgactcctctttttcctcctgccaggggtctt
cctttactccgctctcttttctcctcttcttttcttccttttcacagccagcccttcac
caactggctgctccaccttttttttggatttcactttcttcttcccaggggccttcaggc
tgtctatcgggatgaaatccaacgcttcacttctgactgacttcttattccctttcttca
agctgttctccatggagatcttggagttgaccgggaggatgtctccctcctgatgagtct
ttttcttcttcttctttttcatgctgtgatctctggggctcccctgcttccttttgtgcc
ccaaggccgcctgctcttcggcctctgccccctctaagcatgagtgcaaagcatccccag
cctcagggatccaagagtcctggggaggaaaagcttccatgtccggaagcttcttctcct
tcctgtgctttttaggcttcctaccagctttgcttacctccttggcatgcttggagtctg
gggaagtcttcagccctgagccttgggaggcaacctttgataaggacttccgcctcttct
ttttcttctctctgatgaggccttctgctgactgctcaaggacctgccttctaaggctag
gtgactttatctgtcttgtccatgtaggctcatccttgcccaggtactcatccaagtgtg
tgctacaggactttttttctcttctttctcttgcccagtgacatctcagggacctgcacct
cacccacattgttaaaaggggatgtagcccttggaggagaaacatctatgaagtaatcat
tattgtttaagactgagtactgagtctctggttctgagacatttgccaccttctttttct
tcttcttctttttcttcttctctgggagccgtgggcccaggtcttctttctgagtcttgt
tgaccattactggtctattagcaggccaagcatccccacgtgagcacccgcgcagccgcg
acccggaagtcagcttcgaatttctggcccgccccctcgaaatcgttctccttccgggtc
gcagcttcgcggcgccctgggttgctgtagaaacggcgtccatggccgtgcctagacaag
catccagcctcagcgtgctgcgtgaggagacgggaggcgctgcggactcgccggtcacta
cacgaatgcccgggctcgcagggtcgcctgggtcccccgaagttctcgtgttacccgcgc
aggtcgccgagcctccggggaagaacctgtgggagcagatctgcgaggagtatgaagccg
agcagcctacctttccggaaggatataaagtgaagtttagtttcctgccttgcccggaat
gctacgctttcacgtggccatcttccccgcagttgttgacatgcctagtgaccgtgacct
ctgacacccgttttcccacttttgccaggatctgtattttaacttacttcagagtcctct
tagttgtcttggtttgggggtggtttgggggtgttgggataacagatggggcaaggctgt
agccctactgagctgtttccagaggccgttgtcaggaaggatttccagtgttacagcccc
agagtataacagcagcgccctgttagcttaatggtccccattggttctgtggctgcggct
caccaggattctcccattcaaaaggcccagacatggctgacagcctcctctgtaggtctg
actgacaagctaccacgcgtcttaggtaaatagtaaagcctttattttcttgttaagaac
agcattttgaaaataaaacctatctgcccatgcttaacaacctttaaagtctgtgatatt
ttatatacagccctgtacatactgattgtctggaaatttcttaaacagtttttgtttata
agtatgcaagtcagccaggatgaggggaagagtgagggtacattataaaatacacattaa
tacatttaataaatatatattatctatcaaaaacgagccatagctcttaatgaataaagc
acctgccaagggctctcatcagctcacagttgctacatccttggatgtgtaaatgccagt
gccccttctactttgccatttggcaaattcaaaagacaactcttccaccaccctgcact TABLE 9A-continued tgttccctggccttgacctcctctgtgtgggggtggggcagacaacaaccagatcttaac
tttagaaacagctgacacattggagcccctcccctctgccattgtcctgctaccttggca
actgactccagacctctatggagtcttcactcaggaggggacagagcggtggttatagtc
ccaatatggtattagtacccgggcatgccaagttgtgcttgcagtttggggttattcaca
gatgactttctagaccattttccccaaccaagtgttgggtgtatcaacacttaaacaggt
gccatgggattatgcatttcagccttgctctgtcagaagctggctgccacagtatctggg
tggagttgcctcgtggtcctcctcgtg >scr_sc-133556969_1 (TOXMARKER Assignment: 31; SEQ ID NO: 31)

tgtacaatgggggataaaagtgtcaaatgagatgttgctatagtttcatttcttttgccg
tgatagagcaccctgacaaaaagcagcacgagaggaaatgtatctggcttacgattccat
gttaaagcccgtcattgatgaggtgggtcggggagtcaaggtaagactgtaaacagctag
tcaatcacatccacagtcagagacagaaggacacaaattcatggatacttgctcctttgc
actcagctcagtttctccactcttacacagttttaaatgccctgcctagggagtgatgcc
acccacagtgggctggatgttcccacatcagttatgacaatctcccacctcatgcccata
ggccaacccaatgtagacaatctctcattgagactctcttcccaggccatgtcaagctga
cagttatagctagc >scr_sc-170142736_1 (TOXMARKER Assignment: 32; SEQ ID NO: 32)

agatctcttaagtgaaaatagaaaaatgattactaacgagaagatagacgcctacaacga
agctgcagtcagcattctgaacagcagcaccaggacatccaagtccaatgtcaagatgtt
cagtgtttccaaactcatcgcccaagaaaccatcatggagtctttgggtggcttacacct
tcctgaatcaagcagagaaactagtgcaatgattctcatga >scr_sc-2563586_2 (TOXMARKER Assignment: 33; SEQ ID NO: 33)

tcatgactcccagcattgacattcccctacaatagggctttgagccttcacaaaaccaag
ggcctctcctgccattgttgctcaacaaggccatcctctgcttgatatgcctctcgagtc
atgggtcattccatgtgtaatctttggtggtttagtacctggcagctctgcatggttgat
attgttgttcttactatggagtgacaagcctgttctgcttgttcaattatttgtctaact
ccttagttgagtaccctgtttgcagtccaatggttgggtgtcagaatctgcctctgtatt
tgtcaggctctggcagaggctctcaggagacagctatatctggctcctttcagccagcac
ttcttggcattagcaataatgtctaggtttgatgactataaatgggatggatccctaggt
gtgatagtttctggatggcctttccttcagtcactgctccacattaggtcttgatatttc
ctccttattttgtttccctttctgccccatcgttgtgcccttttgatagattttgcagtt
tagaaatacaatttacgtgcaggtttattgcattcagatct >scr_sc-87618257_1 (TOXMARKER Assignment: 34; SEQ ID NO: 34)

tcatgatgaagaaatgggttctcggcaataggcaaaggcaggatgagagcagaggggtcc
atgggggtcgaaggctgcccatgggggtggttctatgctctgaccattttgagatgaact
aataatgttccggcagtggctatcccctaacaaagatcacaagccgcctagtggagggaa
tggaatctgaactctggtaccagcctccaagatccagatct >cszr__96561134_83760493 (TOXMARKER Assignment: 35; SEQ ID NO: 35)

gaattcactagaccagcatattgctctatgctgcctttccagcgctgtactgcctgtagt
ggaacagactcttggagtccacagtacgagctttctgcacagcctcagcaaaaagtttgg TABLE 9A-continued tcacctggaaattggtgagcagagcaattccactgtccacagctgtcctccgaatcacat
aattatcatggacaaatttggtgttgttattggggaggttaatcactaggtcaatgcttc
cgtctcttatcaactttctgatggaagagaggctgggattctgtccttcctgagatggcc
aagccactggggtggcaggaacattgttggcgttgagccagtctgatgtggcttctgtgg
caaaaagctt >scr_gb-x83855_1 (TOXMARKER Assignment: 36; SEQ ID NO: 36)

ctagtccccgcagcctagcgcgggcggcggcgggcgatggaggagagcagagccccgggc
cccgccgtcctccagcgcgctccgctgcaaccccgcagctgagcccagaggctccggccc
tgtgcgccctaccgcggccccgccactatggccggcgtgtgggcgccggagcactcggtt
gaagcgcacagcaaccagtcaagtgctgccgacggctgcggctctgtgtccgtggccttc
cccatcaccatgatggtcactggcttcgtgggcaacgcgctggccatgttgcttgtgtcg
cgcagctatagacgccgggagagcaaacgcaaaaagtctttcctgctgtgcattggctgg
ctggcgctcaccgacttggtggggcagctcctgaccagtccggtggtcatcctcgtgtac
ctgtcgcagcgacgctgggagcaactcgacccatcggggcgcctgtgcaccttcttcggg
ctgaccatgacagtgttcggactgtcctcgctcttggtggccagcgccatggccgtggag
cgcgccctggctatccgtgcgccgcactggtatgccagccacatgaagactcgcgccacg
cgcgcggtactgctgggtgtgtggctgtctgtgctcgccttcgcgctgctgcctgtgctg
ggcgtgggccgctacagcgtgcagtggcccggcacgtggtgcttcatcagcaccgggccg
gcgggcaacgagacggactctgcgcgggagccgggcagcgtggcctttgcctccgccttc
gcctgtctaggcttgctggctctggtggtgacctttgcctgcaacctggcgaccatcaaa
gccctggtgtcccgctgccgggccaaagccgccgcctcgcagtccagcgcccagtggggc
cggatcaccacggagacggctatccagcttatggggatcatgtgtgtactgtccgtctgc
tggtcgccgctattgataatgatgctgaaaatgatcttcaatcagatgtcagtagagcaa
tgcaagacgcagatgggaaaggagaaggagtgcaattccttcctaatcgccgttcgcctg
gcttcgctgaaccagatcttggatccctgggtttatctgctgctaagaaagatccttctt
cgaaagttctgccagatcagggaccacaccaactatgcttccagctctacctccttgccc
tgcccaggcttctcagtcctgatgtggagtgaccagctagaaagatgatgaacaacctga
agcggagtttcattgcaatacctgcttccctgagtatgagaatttcttcccccagggaag
gataactgaatcattttggattgtatcttctttcggcctcatattttaagttttccttgc
cattaaacacaccgagacaagctt >cszr_229800465_190907286 (TOXMARKER Assignment: 37; SEQ ID NO: 37)

agatctctacaccgcaaaaggtctcttccgtgctgcggtgcccagcggtgcgtccactgg
catctacgaggccctagaactccgagacaatgataagacccgcttcatggggaagggtgt
ctcaaaggctgttgagcacatcaataaaactattgcacctgctctggttagcaagaaact
gaatgttgtggagcaggagaagattgaccagctgatgatcgagatggacggcacagagaa
taaatctaagtttggcgcacatgccatcctgggagtgtccctggctgtctgcaaggctgg
tgccgtggagaagggggtgcccctttaccgtcacattgccgacttggccggcaaccctga
agtcatcctgccggtcccagctttcaatgtgatcaacggcggttctcatgctggcgacaa
gttggccatgcaagagttcatga TABLE 9A-continued >scr_gb-bi277612_1 (TOXMARKER Assignment: 38; SEQ ID NO: 38)

gggcccctcctgctcgctgctgctggaggcgtttcggcgatattacaactatatttttgg
tttctacaagagacatcatggccctgctaaatttcaagataaaccacagttagagaagct
tctggtcttcattaacctcgaaccgcagtgtgatgccttccctagtatgtcatcagatga
gtcctattctctacttgtacaagaaccagtagctctcctcaaggccaacgaagtttgggg
agcactaagaggtttggagacctttagccagttggtttaccaggacgcttatgggacttt
taccatcaatgaatccactattgctgattctccaagattccctcatagaggaattctaat
tgatacatccagacactacctgcctgtgaagacaatttttaaaactctggatgtcatggc
ttttaataagtttaacgtccttcactggcacatagtggacgaccagtctttcccttatca
gagtatcacttttcctgagctaagcaacaagggaagctattctttgtctcatgtctatac
accaaacgacatccatatggtacttgaatatgcccggctccgagggattcgagtcatacc
agaattcgatagccccggccatacacagtcttgggggaaaggtcagaaaaaccttctaac
tccatgtttcattcaaaaaattagaactcaaaaggttggacctgtagacccaagtctaaa
tacaacatacgtattctttgacacattcttcaaagaaatcagcagggtgtttccagacca
gtttatccacttgggaggagatgaagtggaatttgaatgttgggcatcaaatccaaacat
ccaaaatttcatgaagaaaaagggctttggcaacaattttagaagactagaatcctttta
tatcaaaaagtaagtcatctgaaagcctaatcaccactgttttcatacaagtccaagctg
cgacttagctctctgctttacttctcatcttccccactgcttgcaagagtggagccaaga
acacctaggaggcagtaagcattttgcagtaactactgaaatagagggagaagccatgcg
cccgctaggagctctggctgccctttgtcttttgcactatccaggggctggaactcactc
cctttgtcctgagtgacctggggcatctctgctccttacacagtgcagtgacatttccaa
cattccacagccagggaattggtactgaagtggtggctgccttgttagaaaacacagaca
gaccacttcccaaaagtttggtggacagtctgttctctaagaatcagcacatttttcccc
atagggaccagaccacacttaggcatcatgggccatgtggagttgcaaatctcttttana
a >scr_gb-j05266_3 (TOXMARKER Assignment: 39; SEQ ID NO: 39)

ttttttttttttccagagcagaggtctttttaatcaatcacaaagtactttaaaatctc
ataggggacagccttgaatcatctatccacgctgattgtaccggtaagtagaacaggata
agagcaattcgccagctgcagcacagtctggtacacgagcagcccggggccagccatgcc
tggcgttacaatgtgctctcacaaaagtaactcatggaactcaacgtgaagtcgcgcttt
tttttttttggttctttttttttccggagctggggaccgaacccagggccttgcgcttcct
aggcaagcgctctaccactgagctaaatccccaacccctgaagtcgagctttaaataata
acctgagttaaattcccagggaaaggagggcactgactcctacaggctgctctctgacct
ccacaagtcccaggatacatctgagcccgtcccacacaaactagcactcaatatggaact
tttattcatgtgatttctgtacatcagggagtacaagagtaaacctttacaaatggtgct
gattttaccacaataaatgacaaaaccaaagcagtgtctggtgacagtggcagggcttta
aggttcaaacccagccaagaagtttgttacgatttccttcagctttgcatccgactgttc
tgagattttcccatcagacctgatattgcccaagaggctctggtgctggctcacaacatg
agacaagaaagcactctcgaactttgtgatcttactgggctccagtttatcaagataacc
ccggacgcctgcatagatgacagccacctgttcttcaatagccatgggagagtactgtcc TABLE 9A-continued ttgctttagcagctcggtcaggcgcacgccacggctcaagagctgctgagtggcagcatc
cagatcagaaccaaactgggcaaaagcagcgacctcccggtactgggccaactccagctt
catggtgcctgccacctgcttcatggctctggtctgggcggcagatccgacacgggacac
agacaagcccacattaatggcagggcggatgcctttatagaacaattctgtttccaagaa
gatctgtccatcggtgatggaaataacgtttgttggaatgtaggcggacacatcaccagc
ctgtgtttcaatgactggtaaggcagtcaaagagccaccaccaaaggaatcgttcatctt
ggctgctctctccagcaggcgagagtgtaggtaaaacacatcaccgggataggcctctcg
acccgggggtcggcggagcagcagagacatctggcggtaagcaacagcctgcttggataa
gtcgtcatagatgatcagagcgtgcttgccattatctcggaaatactctcccatggagca
gccggagtaaggagccaagtactgaagcggggcagcatcagaggcagtggctgacaccac
aatggtgtacttcatggcatctgcgtctgtcagtctcttcaccaactgagcaacggtgga
ccgtttctgaccaatagcaacgtagatgcagtacagtttcttcttctcgtcagtcccatc
attgaaacgcttctggttgatgattgtgtcaatagcaatcgaggttttcccggtctgtct
gtctccaataatcagctcacgctgacctcggccaatcggcaccaggctatccacagcctt
gatgcccgtctgcattggttcccgcacagagattcggggggataattccaggggctttcag
gcccactcgtctgcgaatcttggaaccaactggacccttcccatcaatggcatttcccag
ggcatcaactacacggcccaacagttcatcgccaactggaacgtccacgatggctcctgt
tctcttcacgatatcaccttctttaattagcttgtcattcccaaacacgacaactccaac
attgtcgggttccaagttcagggacatacccttaagccggaagaaaactctaccatctc
ctcagcttgaacgttcctcagtccatgcactcgggcaataccatcaccaatgcttaagac
acggccagtctcttcaaggtcaacagaagtatcagctccaaggatccgctcctcgagaat
ggaggacatctcggcagtgccagtcttctgaagtcgagtgttagaggcatggagatttct
tgtaccaacaaaagatgaccccaaggcatttttggagaccagtcccgcccgtcgagggag
ggcacggcg
>scr_gb-m37394_5 (TOXMARKER Assignment: 40; SEQ ID NO: 40)
ttttttttttttttttttgcttgtttgtttgtttgtttacttcatgaaatgaaaacagga
aagcatattaaaactcaaaacaatgaaacagaaaacataaaaggtagtctaatagtcaga
aaacactggtaaactagcgtgtgttaagtatcagggacatatttatacaaaaaagtaagt
ctgagggaaaattctacccagtcattcttctcccagtcccagtaagtaacaaagtggctt
atcctattgtacctgccatggtttaatgctgtacaagtgtggcctgctgagcacatccag
gacttcttgtgcatgtagttatcttgccatggaagtgtcttgatgcagagctgctagaac
caactgtctggtcagttggctccaggcaactctgtgtaatacacgctacgggcaagcttc
ttcctttatggaagagtgcatgaatcaaatcaataaagacaagaatcccagagttcccta
tgtcagcaagcgccataggtctgtttttttttcccccctatgtacctcaccatgaggcaacc
ttctgttccaaaaggacaatgttctcgatggatacctttcagtggaatcttcacagttcg
aagaccaatagatataccttcaacttcccaaagagcatcaggggagggggcccacttcttg
gctcagtgacaaagcccgtcagagttatgctttaaagccagtctgagggtttgacatttg
acacaatgtggacatggctgtcaggagcagaggtgctgccatggcttggtcctgggcctc
tggaaagtccggtttgtaactggtacaatgcctcttcaatgtcatgctccactaaactca TABLE 9A-continued ctgcttggcggtgccacccgcaggtactctgcattttcagctgtggggcccttaaagatg ccattcggcttggcttctttgggaaagaagtcctgctggtagtcagggttgtccaggctc atttggtggctgcctttctggatccagagggcagagctgtcaaacccactactgaggcag gtcggctgggcagtgttgagatactcagggttgctcaccgcattgctatggggattttga taatgcaggtctcttccaggagctggatgcaggggctgattgtgatagactgggttctgc acagagccagccggcctcttgggaacagattggtttatatattcaggcacgggaaggaat gtgtcatctatgttgtcctctgtcaggacgctggtgggatcggagctataccgttgcaag aaggcgtcttctttgacacggcagctcccatttctattaatgcaagccacagtggaactg ttgctatttgcactcagagagctcaagagtggagtccgtgacgtggatgggctgttgaag aagccttgctgtgggatgaggtattcatcagcatcaactacgtcttccatgtcctcctcc tccatcagggctcggtaaaagttggagtctgtagggctcggcaaatgcatcctttcatcc ccctggataacaaggtagcgctgtgggtctctggccattttggagaattcgagaatcaac tctcggaactttgggtggctatcagcatctatcatccagcacttgaccatgatcatgtag acgtcgatggtgcagataggtggctgtggaaggcgctctcctttctctaggatggatgag atctcacttgcagggatcccatcataaggcttggacccaaaggtcatcagttcccacacg gtgactccatagctccagacgtcgctttggtgtgtataaattcggtgtaaaattgattcc aaagccatccacttgataggcactttgccccccctctgcatggtattctttctcctcagca ccaagcagtttggccagtccaaaatctgtgatcttgacatgctgtggtgtctttaccagt acattcctggctgccaagtcacggtgtaccaaacgccggtcttccaggtagttcatgccc tttgcaatctgcacacaccagttgagtaggtactgggagccaatgttgtccttatgttct cggacatagtccaggaggcaaccatagggcatgagttgtgtaatgagctggacagtggag gtcagacagatgcccaggaggcggcatacatgagggttgtccacactggccatcacgtag gcttcatcaaggatttccttgttggctttgggagatgtggcttctcttaactccttgatg gccacagggattttcactttctcgccttctgggatccagagacccttatacactgtgcca aatgctcctgaacccagaactttgatctttttgaattctgtttcctttaatatcctcaag tgggcttggttcggagcttctccgctgggtgtgagaggttccacgagctctctctcttga agcaggcggcgtagtgtacgttttcggacaagctgacgtcgacgcatgaagaggccgatc ccaagggccaccactactatgaagaggaggccacccacaatcccagtggcgatggatggg atctttggcccttctggttgttgacatcctttaaggcctggcccagcacatccataggta cagtttgcatggcagaggtggcagacgttattggcatctgcaaacttccagaccagggtg ttgttctcccccatgatgcccgaagggcaggtcttgacacagtggggaccatcaacatag tgggcacacttgatgcagttgtctggcccccggcctgtacaggtgatgttcatggtctgg ggcagacattctggatggcactggatgcattcagaattttccacaaactccctcggttcc ccctccaggatgttgcacttgtccacgcactccctgcctctgctcacattctggcaggag acacagtccgtgggctcagggccccagcagccttccgaggagcataaaggattacagacg tggttcgtggccttgcagtccttttcagctctgttgttcatgattttggtcttttgattg ggcgtcccgaagagtttttccagtttatagtgtttgcgtagcacaaatttcggttccca gaaataatcacatccccatcactgatctccttgagggaacgcaaccccagcgatgttatg ttcaggccgacaaccgccagagaaaactgaccatgttgctttgttctgccacgaattatt tctaggttctcaaaagcatggaggtcagtccagttttcaggccaagcctgaatcagcaaa TABLE 9A-continued aaccctgttatttccttcacagttttgagaatttctagttcccgtgggtctagaggagga
gtgcgggtgaaagaatccccctttaaaggccactggcaggatgtggaggtccccactgatg
gcagtgcagtacttgaagtgtttgatgtttgtagcatttatggagagtgtgtctttaaat
tcaccaatgcctatgccattgcaaactttgcggcagggcccgtcacatttttttacacttg
ctgactccatcttcttctacttcatagtagtctggcccacaggcccggacacacgagccg
tgatctgtcaccacgtagtttctggggcatttcttcacacaggtggcaccaaagctgtac
ttcccctcagggttgacatccatctggtacgtggtggggttgtacagcatgagtggtggg
caggtgtctttgcacgtggcttcatctcggaacctgtggcagaccagacagtcactctct
ctgggccctgtacaccctgcggcacactggttgtggcagcagtcgctaggggacctgcca
cgacaacgccgggaacattgctgggcgcagatgattttggtcaatttctggcagttctcc
tctcctcttccccagcagcttccattgggacagctcggatcacatttcgggcagcccgtc
aggtggcgctgtacgtccattgacatgttgctcagaaagacatcttggacgatgtccctc
cactggatggtctccatattgcagaggatggggttgttgctaaatcgcacagcaccgatc
agaatttcctgtaagttccgcatgggcagttccctaagcccagttttgttggttccatag
ttggacaggacggctaaggcgtaggtgttttcgtagagagcatttcccctgatgatctgc
aggttctccaaagggattctctccacggtgttcagggcaatgagaacatagccagccacc
tcctggatggtctttaagaaggaaaggtcataattcctttgcacataggtgatttccaag
tttccaaggaccacttcacagttgttgaacatcctctggaggctcagaaagtggtcttca
aaggtgcctagttgggtgagcctgttacttgtgccttggcaaactttcttttcctccagc
gccccacctgcggcgcagagcgcagccagcagcagcagtagcttggttctcgcagtccct
gagggtcgcatcccggctcggcagtcgttggctctggctctccgggattaatccgagtca
gactgagtcccacggtcgtgcccggtgactgcgtcggcaacgacgacgggacccggactc
agactcgcgtccaggtgacccgtcgcctgtcttggtggcggtagcctccgggactggctc
cagacgctcgagcccaggaagagcgcacagt
>scr_gb-m64300_4 (TOXMARKER Assignment: 41; SEQ ID NO: 41)
tccgatctgagcagacagctacagccaacagatggcgtgtaagtttggagctgtcactga
cttaaggtgccttatgtcttagccttccctaatgtaaggtgggtgggcataactggaaca
agtctgttaagacttgctctgaggaggctgacagttcagtaggtgacatgtaggaaggat
tcagggcagggaggaaccactgcatctttcatccgacacagtagttactgactaaacaac
agtgagcacttgagtgcactgagtgcaactgtgcagggcctggtgcaggagaactctctg
gactgaagaattccgtgaaagtataaaagccactacgaccagaactgcccctcggaacgg
ctcaaaggagtcaagagtgggtaagctgagacgggctggagacaggaccagggtcaagaa
ctggggggacaccgacatctgaacgcgtccagtcctctgagcccttgtcctgaccaattt
aagatctgtatcctggctggaatcgagcagtctcttcaaaaatgagttctttgagcttct
ccttaggtaagtcgtccagctccatgtcaaacttgaatggtgcttcagcaatgggctcat
cacttgggtcataatactgctccaggtacgggtgggccagagcctgttcaacttcaatcc
tcttgtgagggttaaatgtcaacattttatccagtaaatccagagctttggagtcagcgt
ttgggaacaacctgttccacggcaccttatttttgtgcgggagagaaagcaaatagtttc
tagcttttaaatttattatacaattcagatcttcctgtgatggagatccaagaataccca

TABLE 9A-continued ggatgtgattcagctggtcaaggtaatgctttcctgggaagataggcctgttggatagca
tctctgccaggatgcagcccacagaccaaatatcaatggacttggtataacccttggaat
tcaacataatttctggagctctgtaccaacgcgtggctacatactctgtcaagaaccctg
tatgatcatggtctggatctgcaacacgggcaaggccaaagtcacagatcttgagatcac
aagtggtgttcagcaggaggttggaaggcttgaggtcacggtgcagaacattagctgaat
gtatatactttaatcctctcaggatctgataaagaaaatagcagatatgatacttgctga
ggtgctgtgtcttcaagagcttgtaaagatctgtctccatgaggtcctgtactatatata
catctttcatctgctcaatggttggtgcccggatgatgtcattgatgccgatgatgttct
catgtctgaagcgcagtaggattttttatctctctcagggttctctgacagtaggtctggt
gctcaaaaggactgattttcttgatagcaactcgaactttgttgagattatcataagcag
aacaaaccatgccgtaggcgccttctccgatgtacgagagattagtgtagcgcggcccca
cgtcgaacacctgcccgcggaccatctccgggcccgccgccgccgccgccgccatgttgg
ctgcacagcctccgccgcgttgggctcgacgcttcgcgttaccgctcgacttgtgctgcg
cttcccacaggaaccgcgccgccgcccgtgtagccggctggcggcgatcgggaacgagga
gggaggacaacacagaagagagaactaaccgccggtagaaccacgg
>scr_gb-bi294409_1 (TOXMARKER Assignment: 42; SEQ ID NO: 42)
gtgcacagaggggactcaacggtgtgccgctgctcagactacatctggcccacaaatgtt
cttctagagccaccagaatttaagattattggctttaaggaccacataaatgtgatgatg
gagtttccacctgccacttacaagctattcggggaaagcttatggaaaagactggagtct
acatccttcgtcatcgaggaacagacagaggacagcattagggtgcacaagccccaaatg
aataatgtcactgggaacttcacgtatgtccttagagacttacttccaaagacaaactac
tgtgtgtctgtttattttgatgatacacctgtaataaaatctcccttaaaatgcaccgtc
cttcagcctgaccaggaatcaggtatggctaggcttttaaaatttgcactgttgttttga
tggaaaacttgctgaaagaaaaaaaaaaactcaagttctggtacactaaatgtacttctt
ccaataaatgcacatcactgagctgtttaaaaaaaaaaaaaaaaaa
>scr_gb-ab015747_3 (TOXMARKER Assignment: 43; SEQ ID NO: 43)
ttttttttttttttttgacaagataaagagtctttattgacatagagctccacgtgacc
tcttctgtcctgccctccttgcaaacatactaggtgtcccaaaggtagggacacgagcag
acagtcctgagcctggtcccgtcctccagaatgcagtcagactgcagtctgccatctgcc
atccctatcatctggccaccaaccagaaccagccccacagttcccttgtggtctcgcctt
ggctgccagtggtggtgtccactgggacctgccactaggctgctgtgtttgtttactggg
atcccacttccacatcctgggagccctggcttctggccacatgtgggtaactggcagtga
ctttgggcaatcaagtttgcgttcttgttgctttccacaactgggccaagctgggacagc
aggctctgcttctagtctcagtccgagctgttcaatgaatagcctccttggggcagtatc
taccctcccttaactcaaaatttccactagttagggcctcccaagccactgccaggccag
ctgcgagtttctaggaccagcttccagctggagaacccgacagctatgccaggactgctg
tgagccttgggcaaacggtctattgggtggacagaatgggcctgagcaggtagggcaaca
agagctaggagagcccagggcttaagaatatcagcactgctgtgggagaaagcaaaatga
gtccctgaatcccttgtgagggaggagagcccaggccaacggtaggggagacagccaggc
tctgaacttctagggtcaggccaagttcacatcttcacttcaccattctttcgatttctg TABLE 9A-continued ggaaacctgccagctgggctgtctctcaggaagcacttccctggcttggaggaaccccgg ccttagcacagacctcagcaacaacagcacactcacctaagacacagtgacgcccagagt gcccacaggtacctcagtagtctggctgggaacaggagagtggccagggcccttgcccac ccctgacaaattggagggtgtcctgggtgctaaggtgaggttggcttcctgtgacatttc cccaggacagctctccaaggtccccgagagattccccaaggatggtgatttttcatcata gcaacagccgcagccagggctagcaacgacatggatctgaccatcttcctcctggctgtg gtgttgcttcaggtggccacacagatggcaggtgagggacgagtacacaatgccaaggcc caggtcatccccaaagggcttgggcacctgctctgaaggaggaggggccttcagccaggt gcctcctttgagccccagctctagaccaaggcattctggggtgctattgggtggggctga gttcaggggactgggtggcagctccatgtccagtccgaaggtgaataagggcatggagtt gggggactggttaggaacagggttctggaagggcttgtaccctccacatccactgtcagt ccctgctgctgctgtgtccgtgcagacgccactgctgctgagcaggctcgagaaagcctt gtaaccagtgtctccagaaggcccgacaccaggcacccacctggcctgggacgcaccctg cttcactgcctgcacaaactcttggtagccactggtaggggctggggtggagccagctgt cccgtgctgcaggacactcatgtgaaggatctgctcccagctctccgcttgctgcattgg tggccctgaagaatgggggtcaaccgggctcagaagatccccttcttccagatgtccagc ctgcttctgttctgaagccagctctccaggatttggggcggggctggagaagtcactaaa actccggtaggcaggattgtctgaaatgacaaggggggacctgtgtgcaggctgtgccagt tgctctctcagggtctgggtgtggaggctgctgccctgtgacctggcatgtggtctcact gggccccgtggggaagcaggcccaggacgtagaagcttgcccactttctgaaggcagaag ggaggatgactctgccatgctcgactggccaacgcctccattctcagcccccagcaagtc tgaaaacaggttctcagtgagccgggccatgatgtctgcctgactctcctggaagccccc tccgctgttctcaggtgacatgctcaggtccccctttgaccatctcatcctcttcctcctc cacattctgtactggggcctcaaacagctccatacagcgcaccacactgacatgaacgtt ctctggccagaggacggtcctgctgacctccgcaggataccagcctgctttttcaggact ctggagaggcttggttttggcagccttcggggattctctctctttcttcactctatgctc cagcaagcagggcagcagcttggttagacaagtcttccagtgccggctcttggttgactc ctggcttcgggtctgcttctcccagagggacaccttcgtgtcctgaatgatgatggctgc taagggactgcgtgctggagtgggaatctggtcccaccatatcttcttaatcttgataat gctgaagtaacaggtcaggcaaaacaataggatgcagatgcaggagatgctgacacccag cgggaggcgctgcagcaggggcagctggaagtggttgtaccacgtgatgctgggactcca ctcactccagatgccagggaagctctgggacaagaccctcacacgtgccctatagcgcac ccctgatgttagggtgttgactgggaagctcagcttgggttccgtgtaggtcacattata gactttgaattccgccgggttgtcctctctggagatgttgaccatgcagatgaggccttt gtgcaggaagttgttcgatgggtatgggttgctccacatcagcagcaggccattggagac attggtgtggagtgtgaggttgtctggagctgggggcttcacattgtcactaggcttgaa ggagccttgccacagctgtccccgctcagaccacagttccagccagtatgtgtctgcctg gatcggctcctctatggccatttggcacacacacacggtgtcggcactgttcttgggggt gcatgtgaggttttcagagaactcgaagagcagcctgtagtccaggaggagctgagaact TABLE 9A-continued gcagtccacagtgctatccagctgccactcacacgtagaagtgcggatgtagtcagagaa
gcaggtggggtcacccaggaccttgatgcccccagagccagtcacccatagcaaaatcag
acagctcacggaggacaggaacttggtgcaaagccgccccattgcggacacaaaggtgcc
tgggctatacagggagagactggaatgcagctcagtggcagcgtacctggcccccagatc
ctgggctccctctccagcacctgtgtgttcaggctccacgcgccgtgcggggctttcctg
cgcgaaggacctcgcccggtttcctacgccgcccggacgc >scr_sc-191879433_1 (TOXMARKER Assignment: 44; SEQ ID NO: 44)

gtgcactaagaatgacaaacttgctgtgtgccacaaagatcttgggtggctggttggtgg
ccagtggtcaggttggcctcacactgctccaagtagaagagcagcagctgtcggtctgaa
ggccccagtccccctgtccgccccggcacaaggggctgggctggtgtccagttggccagg
tcatggtctatgggacgagacacctcctgctccagtcgctcaaactgtttcagctgctgc
agctccagttggccttttccctgtcgcacgatgttgccctttttccagcagttccttctgg
gtcttctcaaattcctccttcccctgcagatgaacgtagtcatagtcctccatccaaccc
ccttcactgttctcatactggccatccgga >scr_sc-140438096_1 (TOXMARKER Assignment: 45; SEQ ID NO: 45)

tctagactttaacaacaagcgtgatgaacacccagagaaatgcaggagtcggactaagaa
catgatgtggtacggtgtccttgggaccaaagaactgcttcacagaacctacaggaacct
ggaacaaaaggtcctgctggagtgtgatgggcgcccgattcccctcccaagtcttcaggg
aattgctgtcctcaacattcccagctatgctggagggaccaacttctgggggggcaccaa
ggaagatgatacttttgcagctccatcattcgatgataagattctggaggtggtcgctgt
gttcggcagcatgcagatggctgtgtctcgtgtaattaagctacaacatcatcgaattgc
ccagtgtcgcacagtgaagatct >scr_gb-x87157_5 (TOXMARKER Assignment: 46; SEQ ID NO: 46)

ttttttttttttttttttaaccaagaggaggaatataattgtgataggaaactaagaatc
atgaagctcactacaaaagacaaacactactgaaacatgttgtgctggccttgacacacg
caggcagactgtcgcctagctctgaggcagagggtcaaggttgacacagggctcggagga
aatatttaccagagagaatgtggtgattcatttatcagtccagagatcgcaagtataaaa
cttcaagatataagaaggatcaaattatatcatgtatgtgattcaatttaaaatgtctta
gccctcttacattatattatctggattataactgtaaaaaaaatcaaattacattcatat
gaaacttttatcaaaagaaatcaaatccatttttatgaaactttatagtacaattatttt
tagttggtctttccttaggtcacagtatttataattccatttacatctgtataattttta
aaattaaaaaacaaaagcaaatcaatagaaatctaagttttcttttgtaaaactctcttc
agtctccaggccggcaccacatgacagtgttgacttgtcctccagacatggacaactccc
aggatccctggcttacgaaccattcaggcctcgactcattaggaatgctttttggtttgg
ctcacgttgcaagaaattctggagcatgtccatgccgtccagggacccccccaggcttcag
gattaagtttctgtatttcattccaacctctggattcatgatcccctctttttttaaaaca
gctgtgaaacatgtccatggaaaacacttcactccaaagatatccataatattggccatc
ataccctcctgccaagtgtccaaaagtagctggcatatttgtgcctggcgtagctgcaac
tcccagaatttctgtgcagtatttagcgtattcgctcgcggcatccagagtcgcattggt
atggagagattggtcaactttgctcaaaacaatttggcgcagcgtcagaagacctgtgtt TABLE 9A-continued gaccagcctagaagcaacaagcttctcgagcagctcgtctgtgatagggtgtccatcttt
ataatgctttgacagttttcgcagggaatcaacgtcccacacccagttttcaagcatttg
tgatggcacctctacaaagtcagtttccacgtttgttccactgaatcgtgcaaagtcagt
ctgcgcacagatctgatgcatgacgtgaccgaactcgtggaagtaagtccgcacttcatc
atgtctcaggagagagggccgacctgctacaggctgagagaagttgaccaccagggcggc
cacagacatcatccgactgccatcagggagaaggcagcctggctggagaccgaagcaggc
tgcatggttgtattttccttcccttggatagaggtccaggtagaactgccccaggacctc
tcctgtagctttatccttcacagtgtaaagtgaaacgctcttattccaaacatgagcatc
gggcacttgttcaaatgaaagtcccagcagctcctggtagatgcttagcaagccttccgt
gaccacctcaatggggaagtactccttaagggactcctggtccaccgagtacttgagctc
ctctgtctgtgtcatgtagtaatggaggtcccatgcattgatcttcccgtcgtattcaaa
acctcgctcttcacattccttcttcttcaggctcaaaataaactcccgttctgcctcacc
caagggtttcaatttctggcttaaatcatctagaaaggcggccacgcggctggtgctctt
cgcagtgttcagttcaaggacaaagtcagcatgggtgttatagcccagcagcttggccac
ttgagctcgcagcgggaggagctgttgcagaattgcggtgttttcctgtttgcacctggt
atgaaaagccatttccatcttccttcgagtttcagggacacagcatttcttcatgacagg
gaagtagtgaggatactttaaggtaactttgtacttgtcttcatctgttttttctaaact
gtcaatgaagtcatcaggaagagcaccaagttcagccttggagaatacaagggaagtgtc
gtcctcattgaggttcttgttgaagtcaatgcatagctcactcattctcttcttcattga
tttgatttcatttcttatgtgttctgaaagatggagtccattcctttttcccattttaat
tgacttttccaagtatcgcctggcttcaggctttatcttctccaaatcgcatgtttcttg
taaatgaacaattctctgaaacacatcttctctcatgctcatctcaatatcaaaacgaga
aagctttttgtctgcttctgtgcttgcagcccgcacttctctgtcagatgacacgtgctg
agggaagtccagcatggtcctttccactatgtacgtcacttctatgtcagccagcacctg
cagacagttctcataagttacttctttcagggcgattgtccccacggtgtcgtacacctg
cttggtctgtgctatgagctgctctgtcctcgtcttgatctgctctggagaaaggtccca
tctgagaacattcctgccagccgcagtgtaggaagacatagcttgaagaggagaagccag
ctcctttcccagtgtcattgtcagctgaagcctggagccaccagctctgtggaggcctcg
cagagtcgaaaggcacagggtgatcatgggcacgccgggaggccggcagcagctggcgcg
tcgtcctcccgcttgtaggtgcaggaggcaggcggtggtgtctgcgggcccggaagccag
gagtgggccaagccgaggagaccagatctcgagacggaggccgtcagtcc >scr_gb-u66707_2 (TOXMARKER Assignment: 47; SEQ ID NO: 47)

ttttttttttttgtttatatgccaacatataccttgtgctagaaatactttatggggtt
acaactctttatatacaattttttttgaggcagtatctctgatggagagcataacttgta
aagagcttgtgtgtgcttccgtgctccaaaatgataggaaatccactttgagaagacaac
ttatttgattttaaaaaaacaaaaacaaaaacaaaaacagaaacaaaaccgcaccaatgc
acagccagaggctccgctggaactgatacagaaccgcgcaaacgccgtgattataagtaa
cattttccagggtggtcaaggctaacgtacaatattatacacctggcactgatgtttgcc
attggtcagcaactggcaaaatttgtttctatgtataaatttatttttaaacattatctc TABLE 9A-continued

| |
|---|
| tggcctgacatatcttcactatttataaaaacatttagacagtgagctcacgttgaataa |
| ctaggtctactgtgttctggaagctcttcagtagtaaaacagctttttcgtgttccatat |
| gcacaaaactgtgtccatttgcctgaaggattttatccccgggctgtagaaggttggatg |
| ctggtccatcaggctgaaccctagtaacaaagatacccttgtcggaaggtttgaaaggat |
| ttccttgcccactaattccaccgctgatactaaatccaagcccagggttcttttctattc |
| tcacacagaactgctcgggataaccgtccatactcctctgccctttcgtttgaattaagc |
| accgtccaggctggggtccccgggtggcctgtgatgaggggatctggatgggcagtggcg |
| actggaactgctgaatggtcactttgttgatgttcccttcatatggctgctgctcccggc |
| tgcggtgctgaaggctctgtgaccccatcagggtctgaatgtggctgcctgcctttttag |
| taatggtgtccggaggtacatcccgcctcccaagtgggtaaggattccattggccactag |
| gagagacatcttcttgtccattgtctaaaatgttgctttgctgggacggggtcctgtcta |
| accttctagcttctatatgtctaagcagctgctgtctccagtctgccggcattttgccac |
| agctctcctctcccttcacaggggtgggccttgtctttatatcactgttatctgatgtct |
| tgtcaccatagttacccaagttatagtcagatggtattttttccaggagggctgccatgg |
| taggcctagctgaaactggcctggtttgggaggccccgtaactctctgtgctgtagctcc |
| tggcagacagtggcctcctctgggtaaggtttttagcaggaaaacttcccgcctgcgctt |
| tcacttcttgatatgaagggtgctcatcttcgtacctgccattcctcttgaggaattggg |
| gatcagtcattgaaacgctgctctggccttccagccctcccctataggctgctcggccat |
| acctgtcaccaggggggcagctcgtggggctcactgacccttctgaacatggccatctctg |
| tggagctggccagggagtcagccctccttaggaagcctgccctgggcccctggctggcga |
| actgagcattcaccatggcatcctcatttacagatggttgggaaaaggagaacatctgct |
| ccatgggtgggtatcctctataggctctggggctgacgagatccttggcgatgtttttac |
| cgggctgttgtacatactcagaattgtgtgcaaaaggggggtgggatcctcttctctgctt |
| ttacttccaccgctccttgtggattgaagctttggtcaaactgatagaccttcttagtca |
| tagatgctttttgttggggtgggcctttactacttccgtacatgagcatttcgtcatcca |
| gcatgggtaccgactggctcctggacatactggacatgccgtgctctggtcccaagaact |
| tgtctggccgctcgtggcttcctaagtgatcgcttccagaggcatagttttccagtggaa |
| tgttatagaccttgtaggtaccgacgtcaatctcatcaatactctgggactttttgaact |
| tgttggactttatatctttcatgagcggggaaagcctctccgtgcttttgctaattgcaa |
| taacacctttagacgaatctgggcggcagtggatttgagaaaagacattaccgagactcc |
| ggttgggggtggggtcgtggtactcccatggcactcccggagaaaagggacctggtgtct |
| ctgtaggctccttcatgtggtcttttctttcaggcaagggactggtagtaggggttgttt |
| ctaatttggagggaaaagcagtcctgtcctcaaatggactggggggttctggtccaattct |
| gccagggattggaaggaggcacttctgtttctggtgtgtgtctgtgggtggactgctcca |
| gttccaggggaacaccgacaatcctttcttgcctgattaaaggcctgcgcccatgagcag |
| gtacgcttctagccttggagcttaagagagggttattgttggcattctcgcctgtggctt |
| cctcggagacaaaacctgtgttatcgtaatgggagccatcggtccagttgtcagggaaag |
| catcactcattggcagccgatcaggacgctgggggaggttccctggagggacagcctccc |
| gttgggtgagtaatggctttgcatctagaggctgtgggaaaggtggtgcaatcctgttac |
| cccacaaagagttatgcacggcatctttagttgttggctgcaaggaccccactttcaccc |

TABLE 9A-continued gggtgttggaggatgctgaggaagcctgggagggcgagtagtctgagtaggtgcctgagg
agacactgttattcagacagtgagttttgtcaacttcagactcatcagttgattcttttt
tgtccttccctagcagaacaagtttgggtgggtacagaggggtctcagctaatgaagggt
gaagttccccaatcctcatttcattagctggatgaacaaaagaatcctccactgtaatct
cctttggggccaccggccacttgtgttcaaacttttctttcacagtttgctccgtgttag
ctgttgggtttgcgttctcaacgcgcactccatggcttggcttacccaccagattttgaa
cagattttaccatgttctttaaatcctccgggtaaggagttggatatcgttttaggttta
tttcaacctgtctgccacttagagagggaagagtggtggattgggctgccactggtaatg
gagcacacatgctcctctcctgctggaggccacttatacaaccccatgccagctgggggt
cactctggggggacgggcatatcttggatctgctgatcacacctggcccatggtgtgcagc
aatcgccagacagcctggcaggttggagagtaatcccacgctggcccctgtcccaggggg
cttggcaggagagagccttaactttcccagcactttcgtcatcttctttttttatcctcaa
attcaaaggcaacagtcatgcgctgttgtctctgctcctcccacagggtggggttgaagc
tgtcgctgtctgactggaaatcttcatcaccacggggctgctggggaaacatgtagttgg
tcagtaccctttgcttggtttctggatgggcttctgtttgcagagggatgagggccttgg
actgattgtcagaaagccacaatgctgcaagctctttgagtttggtgaaggagaatggca
agttcttcaacctattatcacttagatttaagactcgaagtctctgcatctgcccgattt
cttcaggaagaaattctagcttattggagcgtagagacataacggtgacgttcttacagc
ttccaatttctctgggcaactctgggaggaaattctcgtcccacagctaaggttcgcaggc
tgtgcaggtaaccaatggtgggagggagggactccagctcattgcaactgcagtcgaatt
cttctaataaagataagtttccgattgtgttgggtagcattgtaagctgattgtcatcta
cttttagagttgttaactttttcagcaatcctatagagtccggcagctgttgcaacatat
tggatgatagtaagaggtcctcgagggcttcacatccagaaatatccatgtcaaccgttt
ctatcctgtttttttgacatatccaggtataccaacatctttaacttccctatagacccag
gcagcacttgcaatgcgttgttatccatccacagctccctcaaattctgaatttgatcca
gaacttcaggcagctcgctgaattcattattgcctaggtcaagtctttccagctgggcca
gcttgtgcattgactttggtagagttttcaagtgattttctcttaactccaagattcgca
atttgacaagtcttccaaaattagctggaagaaattcgaggaaggcgtcattcaggtaga
gctgggtcaggttaagaagctgcgtgaagccatcgggtagtttagaaatgggattgacac
tggcttcaataatggttaaacacttacagcactttatgttttctggaaattcttgtacac
cgtttttactgatgtcgagttctttcagattaactaggctagcaatggaggtcggcagac
ttgagaggtcattatcaggaatgcttagtttccttagagcttgacagttgaacaattgct
tgggtagctcctcaatctgattggcatctagatagagctcttctagtgtacgttcgaagt
tgaagacctccttgggtacctgttgcaggctgcagtgggagtaatccaacaccgagatga
tctcttcctcgccacggaagcagcggcatggcaccaggcggccgatgagcttccgtttgg
tggtcatctccaggcactgcattgctagtcactcctgtctctgaagacttctaggctgtg
ggcactttgacttgcattcttttcatgtagcgggctcactcttcttcaggcctcttccga
agtgctgcacgggcctccttacaaggacttctctgatattgtgggggattccttccccgt
attaggttctccatcatcgcagaagca TABLE 9A-continued >scr_gb-af017393_2 (TOXMARKER Assignment: 48; SEQ ID NO: 48)

ttttttttttttttttttttactagtaaggtatttactaggaaatgatacaaacagccag
gaaaagggtgcatcgcagaacagggtctgtgcgtataagatgggtatttcccctttgtca
cgtcatttttttccatgaagatgcgcttaagataggaagggtaaagtaccgacacgtggca
ggccccgggtttagggaagggaacgtgagagagacgtcaatggaggcccacaacagtgaa
acccctggaagagggccagagcagtcccctggtgcagtactcagcgaatgcgcatacaca
actggaaaggccttggcaaattgcccagccctgagctgagcggggtcaggtcgatgtcct
caggctccaccagcggatgcaacgtgaagttctggagaatggaggtgaggtatatgaaca
gctccatgcgtgccagtggctctcccagacacagtcggcgtcccgccgaaaatggcatga
aggcggggctcttcttgaaggattgattggcatccagaaaatgctcaggattgaactcct
gaggggtcttgaattggtcggagtcatagtgcacggtgttaaggagcgtgatgacatctg
tgcccttgggtatcaggaagcccctgaaaggtgtgtcccgaatgacgcggtggggcaggt
tcatggggatgacgtctgcaaagcgctgcacttcgtggatcaccgcgtctgtgtaaggca
tggatgcacggtcctccagcgtgggcatccgcgaacgtcccaccacacaatcaatctctt
cctgcacacgggcttgcactttggggtacttcataagaatgaggaaggcatggcgtaaag
tggtgcccacagtctccgttccaccaaagagcaggttgtgtgtggtcatcagnagggtgt
ccatattgaagtggctcagtgggtcttgcttctcctgtaccatttttgtgaggaagcagt
cgatgaagtcccggggagagttggggtccagggagtcctggtgctcgcggacgctgcggg
cgatgagatctttcatgcccccaaagttccggaacacgcgtctgtgcggcccaggcaccc
agtccaggagactcgggaagatgttgtacatctcgccccaggggctgctcataatctgga
agttgtcattgataaagtggataatggtgagcagccgttcatcgtcataatcgaagcgac
tgccgaagatgacagagcaaataatgttggagaccgagcggctcaggataaacacggggt
caaagggcttgccttccgttttccgcagcacgtccagcaggaagctgccttcttccagga
tccgctcctcgatgcttctttttcccatgccaaagttcctcaggatttggacagagaacc
ttcggaggatcttccagcgttctccatcggagaaggcgatgccgttgcccttggtgaagt
tgaaaaagatggggtatgagcctcggccactgaactcctcccctttgtcccacaagagcct
ccttcacagtttgatatccgctgaggacaatcacacgcctgggccccaggtacaccgtga
acactgacccatagtccttgctaagcttggtgagtgaggtcagcaagtcttgggagcgaa
gctgcagcaggtttcctaggattgggagaggcttgggtcctggagggagctggcccttgc
cccatgaggtgaaggtcagggacagagagatgacagccaggaggagaagcaagatggctg
tgctcacaccatccatagtgaaggcagc >scr_sc-134241980_1 (TOXMARKER Assignment: 49; SEQ ID NO: 49)

actatatgatcctgtttacatgaaccatacatactaggcaaacctgtagacatagaattc
agaccttatacatagtccaatagcatagatcacagagcatggagacctgataaatgggga
ctgaggctgttgggaagaagtgaggaatgactcagcaaccttgggcctggtctccagcag
gtctcccagaatcagaaaaatggggccattttgaacagaagtgagtcggctgactgcctc
agcacaatcagcgggctacaaagcaaatcttgtacactgagtctacaagcaacactctct
gctatggattcctgctcatgctcaagtaccctcatgttgcagagaaagtccaaaaggaga
ttgatca >scr_sc-191609675_1 (TOXMARKER Assignment: 50; SEQ ID NO: 50)

TABLE 9A-continued gccggctcaaaggtctctgcgagcgcattggtgttttcaatgacaatcttgcgtgccaag
tcttctcccaaaaaggcgaattcatccagcatttcattggtggttctgaaatgcgctttt
ggcagtggcgctggctgggcatcttctccgtgcccaatggtccggttgatcatagcccct
tgaccgagactacggacaatgatctcccgatagatct
>scr_gb-x17037_2 (TOXMARKER Assignment: 51; SEQ ID NO: 51)
gaacacagacaaggatgtatgtgtgggttcagcagcccacagcatttctgctcctgggac
tctcacttggagttacagtgaagctcaactgtgttaaagatacctaccccagtggtcaca
agtgctgtcgtgagtgccagccaggccatggtatggtgagccgctgtgatcacaccaggg
acactgtatgtcatccatgtgagcctggcttctacaatgaggctgtcaattacgacacct
gcaagcagtgtacacagtgcaaccaccgaagtggaagtgaactcaagcagaactgcacac
ctactgaggatactgtctgccagtgtagaccaggcacccaaccccggcaagacagcagcc
acaagcttggagttgactgtgttccctgccccctggccacttttctccaggcagcaacc
aagcctgcaagccctggaccaattgtaccttatctggaaagcagatccgccacccagcca
gtaacagcttggacacagtctgtgaagacagaagcctcctggccacactgctctgggaga
cccagcgcactacattcaggccaaccactgtcccgtccaccacagtctggcccaggactt
ctcagttgccctctacacccaccttggtggctcctgagggccctgcatttgctgttatcc
taggcctaggcctgggcttgctggctcccttgactgtcctgctagccttgtacctgctcc
gaaaggcttggagatcgcccaacactcccaaaccttgttggggaaacagcttcaggaccc
ctatccaggaggagcagaccgacacacactttactctagccaagatctgagcaataccac
aggagtggattttatggggcacagacagcccatatcctgatgcctgcctgccagggccct
ccacaccgttctaggcgctgggctggctgtgcactctcccatgtatgctgtgcatactac
ctgcctggtggcactcctaataaacatgctcgcagctgtgagtctgtcactggccctaaa
aaaaaaaaaaaaaa
>scr_gb-bi291805_1 (TOXMARKER Assignment: 52; SEQ ID NO: 52)
ttttttttttttttttttccggggtcaagatatttactcgatgctttcaggtttgaattc
aggggctcagcaaggggggaggggcagggaagggacacacagggcatcttccaatcactgt
gacttctggcaggtctcgatgtcttcattgccagtggtgactgatcagttgggacatggg
gagaagtcctgtgccctccacgtctccattgaaatcttcttctgatatttatgcacatca
ttgctccggtccccgtcaaagtttccacaggccccacacaacatggccgcataatgctca
tcaaccatcacattcagatgcccatcctttccaagccacacctggactccggccttctgg
tggacaaacatggatccgtctgagatcttcctcacagacacagatgttaacacagtagct
gggagatccaactcggagaccattcacccatgcacccttgcttgggatcacagtcaccat
gccatcctggaagaagatgtggaccttgctcacgatcttgtcattgtt
>scr_gb-aj000696_5 (TOXMARKER Assignment: 53; SEQ ID NO: 53)
ttttttttttttttttttgttggtttggtttgtttttggagacagggtttctctgtgtag
tcctggctaccctggaactaactctgtagatgagactggcctctgactcaagagatctgc
ctatttctgtgaggattcaaagtgttcatcgcaatgcccggcttagaaaatgagtcttga
aatggcactcagaagggtggatgtggccttttgaacgggcaagtaacacaggtaaaatga
aaacacaacaggtgcagaagcctgatcaacactcaccgcccagacacctttcaaacaagg TABLE 9A-continued agctaagtcaatgaggtagaaccccaaatcctccacctaggcgctgacaggcttaaagac cccattgccccacacagccctccctcctttgtaaggtcactgagggtacaggacctgggc agagacccagagcaaacagaaatgaaagaacaggctttgtaccctgaagagaggaacagg aggttttcaactcaaggtaactggatggcagcatttgccggcttcgagtgctgagtggac acacgtgcagaaatgacgtgagatgacacgcttagtaaaacgatgatacactttactcgc acaacctgaacctctactaaaacccagccagccacaagctgtttgctatcctttattaag aggtcccacattcttgcgggactccagccaaaccagacaggtcccctaaatatagcagga ggcctggaggggaagggaatgacttaggatcccaccacaccaccctggaaacagaactcc accacagacagacggacagacggacggacaagagccggggaggagaacccacctcactct tggttctctccccgttgcatccactcaaaaagaaagtcaaacactggctatgcagacccc agcccacccacccacccatagcagcgtttgtgggactccccccctgaaacgggtagcccca agacaacttcctatggttcttccctgactttggtttgctcctggcaactccgcgccctct tccttccctcagcctccagctctctctcagcatcttctaccacctactcggaccttccct ctctcttgctctctgctttctggtctccctgccacgggcttcttggggaagcagcgggca cctttctcctagcaagggccccactaggccctgtctgcccagcgtgggactcacacagcc gccccactctctttgaggtcaggggctgagcgctgccttcgcattcgtggaggggtagtg tatggtgggtagcggggccctggccgctgggctgggtaaggttggggctgttggggataa gagttgtgcttctggggccgtaagtgctggggttctggctgtgtagaacccccctccccga gatcggctccctccatctagggaattcctgcgaggacggtggggccttcggggacttgga ggtctgcggttagggggaggagggggtgcagtgacctcttcaggggggttggggacctggg gcctcaccactccccattcctggccaggactccctgtgctgagggttgctcttgaagggg aagcgcagcttgcaatcatgcgggggtacaaagcgagctgggggcctgcgtagtccccca ccccggcccccggagccctgcagtccctgcagccgcagctgctcctgcttgagccagcga aggcgaccgcgacggaaggcagggtcctcttccatcagtcttgacacacgctcccagctg gactggggtggtgaggagggccggacagctggtgagtggtcattggacactgcctcctct actgcctctgacccttcgggtggggcccaggtgaccaaaccagattcttcattatcatcc tcaagatcctgggtcaacgggataaccctctccatgcggagcatccggtcccgcagggcc tgcagctcccggtccttgctgctgttttgcagcttcacttcctgcagaattcctgtcagc ttgtcaatatgagcccggaggtcttctacctctgccccacgggctccttcctcaccacca cctccaccacctccacatccttcttcttcacccacagtatcccagacatccctggccaca gctctccaggcgtctccaggaccctcaggcttgccgtaggtccggcacagctccctcatc ttgagagcagccagagcttcaatctctgcccgtccgtgacggaagtcggccagggccacc tcatagcagatctccttcactgcttgcatcttcaggtcagccatggtggcccaccggggg tctttgccctggagccgccgtcgctgagggatctggtaaactcttcgaggggccctgcgc ttcccactgctgggcaggccacagcgcttgacgatggtctggactgtgttagggggcagc tcgtcccgcaaggaggaaatcagccgccagctttcttcacaagagcgcttgtcagagtct tccccactgtcagaatctgcatacagccgctgctgctccagcaaaaggtcagcctcttcc ttttctttccggtactgattctccaagtcttgtagcctcttctccatctctagcttgatg tctatgccttgctgctccagccagtccttctgagcaaagttccagtccacaggctcagag ggaggtcctgggggtgggggacccctcgctctcgttccagccgtgcttgctccgggtga TABLE 9A-continued ttgaagcggaacacatggttcttgcccattacaatcctgttgcctgacttcagcaccagc
ggctccgtcacaagcttcccattgacatatgtctcagctccttcacaaggttccaatgtg
accatcacttctccatcaggctgagggatgctgcggaagaggcagtgctgctcccggatg
aactggccagtcaacttgatgtccacatctacctggccaaccctggtgacgccatctttg
atgtggtagagaaggcattcagacatcaaggggtcctcattcagatttaccaggtgggga
gtctttttggagagaagacacccacagtacgccatcctcccggagagcccatctcagcc
agcaatgcttctctctccatcctcagagcttctgtcttacggagcttctcctcccaagtc
tcattcagctcagctataattttctctgtttcctgcagcctctccatggcctcctcaggc
ccaatctggggctcagcactgggtgaaaatgacggctccagctcgccgttatgtggagga
ggagatgagggtgaagctggggcaggggggagatgatgcagcaggcagaacacctccagga
ctcccctcttccacctttagacctcctagagcagaggctgaaagcccctgagccatcagc
agttcccgcaaccgggccacctcctcctgcagctcccggataagccgggcattggggtcc
tcattgatgacagcattgcatcggatctgtttggtgcggtctgcgtacctgagagtgctg
agtgtctcctcgtaattgatgtcagcgggactcagggctgcaatcattgctgtgcgtgag
ttcccacccaaattctccttgagtagccaggtaagcacagagtctctgtaagggatgaag
tccgacttccgcttctttgattgcaaatctgccagggctgagatcaccttccctagagta
gtcagggacttattgatgtttgcaccttccttcagacgcatgccccgagcccctgaggag
tcggcccgctcgctcccggcaaggttcaccaagctgatcttactgaccttttctgaatcc
agtccagtaagctggtcatgggagcgctgggtaaagacgatagtaaagacagcgtgggag
cggctgctggtttcgttcatgttggtggcagcccacagttcttgccttatttccacagtcc
atgaggtcagcaatgtctgcataggaagtcacagccaacttagacaggtcttgtacatat
gggcccaggatggggtgctcccggacccgcagagagccccgactcttggggttcaagagg
tctcgtactcgttcgcaatagatctccatatagctcacctccacagagtaggaaagttga
gcactctggttcacattaactcgagagaagaggtcctcgcagagctgaggtacaatgccc
tgctgccccggttcctgccgccccatcatggtgtaggacttgccagcccccgtctgaccg
taagcaaagatgcacacgttgtagccttcaaaggcatgcagcagcatctcctctcctatg
tctcgatacacctgctgttgagatgcaaactgtgggtcctccaccgaagtatgtgaccag
taagaatagtcgaatgaagcttttaaaaacatcctgctctgtttgggattaatgatggag
gtggtgttgccctgcatgctgaccacacacttggcatcctggctggtctcacgggcatta
aagggccgaaccctcactgccactttcacggaggcaccagccatagcttcagaatctcct
gccctcctcagctggtgtcctggccccagatcagcggggctgtatcagttctggctgcca
ccggccctcgtatgggaagccccatcctacacttggggcctggccacaccagcaaggctc
ctcgcggcagactcccggcagagagcaaagggacaatactttgctggcgagtagtgctat
gaactctgcgctaccggtgtaagagacgcatcggggccagttcggggctgcccccgcccc
tcg >scr_gb-d79221_3 (TOXMARKER Assignment: 54; SEQ ID NO: 54)

atgggaaaaaaagataacccagggtgtgagcattctcgtgccgaattcggcacgagcagc
attcgggaaaggcaaacagtggctctgaagcggatgttgaatttcaatgtgcctcatgtt
aaaaacagtcctggagaacccgtatggaaggtactcatctatgacagatttggccaagat TABLE 9A-continued atcatctctcctctgctgtctgtgaaggagctgagagacatgggcatcaccctgcatctc
cttttgcactcagaccgagatccaattcgagatgttcctgcggtgtactttgtgatgcca
accgaagaaaatattgacagactgtgccaggatcttcgaaatcagctctatgaatcctat
tatttaaattttatttctgcgatttcaagaagtaaactggaagacattgcaaatgcagca
ttggccgctaatgcagtcacacaggttgccaaggtttttgaccagtatctcaattttatt
actttggaagaggacatgtttgtattatgtaatcaaaataaggaacttgtttcatatcgg
gccattaataggccagatatcacagacacagagatggagactgttatggacactattgtt
gacagcctcttctgctttttgttacattaggtgctgttcccatcatccgatgctcaaga
ggaacggcagcagaaatggtggcagtgaaactagataaaaaactgcgggagaatctaaga
gatgcaagaaacagccttttactggtgatccacttgggactggccagttcagcttccaa
aggcccttattagtccttgtggacagaaacattgacttggcaacgcctctgcaccatacg
tggacataccaagcgctggtacacgatgtcctggatttccacttaaacagagtaaatttg
gaagaatctacaggagtggaaaattctccaactggtgctagaccaaagaggaaaaacaag
aagtcttacgatttaactccagttgataaattttggcagaaacataaaggaagtccattc
ccagaagtcgcagaatcagtccaacaagaactagaatcttacagagcacaagaagatgag
gtcaaacgactgaagagcattatgggcctagaaggagaggacgaaggagccatcagcatg
ctttctgataacactgctaagctcacatcagctgtcagttctttgccagaactccttgaa
aaaaaaagacttatcgatctccatacaaatgtcgccactgctgttttagaacacataaag
gcaagaaaactggatgtatattttgaatatgaagaaaaaataatgagcaagactactctg
gataagtcccttctcgacgtcatatctgaccctgacgcagggactccggaagacaaaatg
aggctgtttcttatctactacataagcgctcagcaggcaccatctgaggttgatttggag
cagtataaaaaggctttaacagatgcaggatgcaaccttagccctttacagtatatcaaa
cagtggaaggcttttgccaagatggcctcaactcctgccagctacggaaacactaccact
aaaccaatgggtctcttgtcccgagtcatgaatacaggatcccagtttgtgatggaaggc
gtcaagaacctggtattgaagcagcagaatctacctgttactcggattttagacaatctc
atggagatgaagtcaaaccccgagactgatgattacagatattttgatcccaaaatgctg
cggagcaatgacagctcagttcctaggaacaaaagtccattccaagaggccattgtcttt
gtggtaggaggaggcaactatattgagtatcagaatcttgttgactacataaagggaaag
caaggcaagcatattttgtatggctgcagtgagatttttaatgctacacagttcataaaa
cagctgtcacagcttggacaaaagtaacacagaagagtcataatgggtgatcagtgtgga
cagatgtaaaaagccagacgtgtccttctccatagcagtgccctaacagtgcaacctgcg
gaatcagtcatttttaaagaaattctatacttcatatactgtacaatgattaaaataata
aaccatttcagaagtaaaaaaaaaaaaaaaaaaaaccc >m61937 (TOXMARKER Assignment: 55; SEQ ID NO: 55)

ctcaggtttctcacactcctggtaatactgtaaaactttaccatggaccacagttccaag
gactcctgaacacagtcttggagttaagcctgtgaacagcccacgcttcccatcgatgcg
taacaagcgatggattccatatctctgcgtgtagcactaaatgatggtaacttcattcct
gtactggggtttggaaccactgtgcctgagaaggttgctaaggatgaagttatcaaggct
actaaaatagctatagataatggattccgccattttgactctgcttatttgtacgaagta
gaagaggaagtgggccaagccattagaagcaagattgaagacggcactgtgaagagagaa TABLE 9A-continued gatatattctatacttcaaagctttggagcactttccatagaccagagctggtccgaact
tgcttggaaaagacactgaaaagcactcaactggactatgtggatctttatattattcat
ttcccaatggctttgcagcctggagatatatttttcccacgagatgagcatggaaaacta
ttgtttgaaacagtggatatctgtgacacatgggaggccatggaaaagtgtaaggatgca
ggattggccaagtctattggggtgtccaactttaactgcaggcagctggagaggattctg
aataagccagggctcaaatacaagcctgtgtgcaaccaggtggaatgtcacctttatctc
aaccagagcaaaatgctggactattgtaagtcaaaagacatcattctggtttcctactgc
acgctgggaagttcacgagacaaaacatgggtggatcagaaaagtccagttctcctagat
gatccagttctttgtgccatagcaaagaagtacaagcaaaccccagccctagttgccctt
cgctaccagctgcagcgtggggttgtgcccctgatcaggagtttcaacgcgaagcggatc
aaagagctaacacaggtttttgaattccagttggcttcagaggacatgaaagccctggat
ggcttgaacagaaatttcagatacaacaatgcaaaatattttgatgaccatcccaatcat
ccatttactgatgaatagtaacatggtggactttgtcagcatttctatcggaagatctgt
ttatgcattgtgatttgaaagatatcttggatactggtgactgaatgcatcagaccactg
tttctgttaattcacagtcagctggagcaatgtccacagtgctatgagggaagccatgtt
tttgtcacactctgaaatggaacatcacgttgcttttccttgtgtttttaaatattcatt
tattttgctttccatatatgaatattttccctacatgtatgtgtatctcatgaatgtcta
tgtccatgcagggttgaagagtgttgcaggtcacttggaaccggagttacattgattatg
gagttaccatgtgggtgctgggagccaaacctaggtcttctgtgagactagcaagtgcct
ttgaatgctgagccatctcattaggtccaaccctaaagatccttgcctgccactatttct
gtgatctcaatgttttgttttctcctgacttctgacaccaagctgatttgctagaagtct
tgggcatgaagtgggtgttgaggacagttattgcaaagggatttctgggtgggagttgaa
agaacgttcaacattcagggaattaattgttcgaggttattgattagtcaatattcccc
>cszr_229602935_183895355 (TOXMARKER Assignment: 56; SEQ ID NO: 56)
gtgcacttgtccgaggcacctttgcagacacagccctgggcacatttggagcagcccacg
gggcagcaggagcagcagctcttcttgcaggaggtgcatttgcagttcttgcagccgcag
gagctggagcaggtgcaggagccgccggtggagcaggagcagttggggtccattccgaga
tctggtgaatctggagcaacggtgtaagcgacaagaaggcagtttttttttttttttttt
taaaataaacaggcttttattttccacctgctcggtacaaaacggggtttattaaactgg
gtggaggtgtacggcaagactctgagttggtccgga
>scr_gb-af106944_3 (TOXMARKER Assignment: 57; SEQ ID NO: 57)
ttttttttttttttttttccaaaacaaattcttttataagttgtcttgtcatgttttgtc
acagcagaaagaaaagccactaagacacttgctaatcccccgttctgtttttttttctca
aaaccccaagatatatatatatatatatatatttacactcattttacatatgcaaaaata
gaaccagactcttctccctaaagacttccctgaaaaacctactcagaaccctgcaagtac
ctgatttctgtttattgagcttctcttccagaatcaagggaataaagacaaaggtttatt
tttcttcactccaatgcctccaggaccaacctggcatggttttcattccaggagctagca
aaataagggatgaaagtttaggtatcttgcctgctaatttcagtttcctaagggtggaga
cagctccgtgtaaatgcccagtaaacaggtacttgttgagctaagtcatcaaaggaggag TABLE 9A-continued cagtgccccagaataaattgacagttaatgatgtcaagtatcttaatgtttatttttatt
ctttacatccagcacttgaagaaaagaaaatgacatagtgttttagaaacatagtccttc
atgattataactcatcaataccttagaacacacaaggacactgtgagttaatgactacac
taaaaaataatgggaaattcagcataattaacaaaaatccaagaggaaatttcaggacct
tgatcagaagctttcactaagtgctggcactatatgctacttcatttcactaagtgctgg
cgctatgtgctacttcatttcactaagtactggtgctatgtgctacttcactgtagacca
agcttcagggcaggctaagaaatcttaaccctctgaagacatgatctaagaaatggggac
caagcacttgtagagaattggtagccatcaagaagtccctagtaaggacagctatggaag
gagctggccacctttaacctgaacctgtcttaaaattacaaagcccatggagcagtactt
ataaacacaagcatggtgaggttttgccattctataaataatcttcaggattccagctgg
ggctctcttttggcatgagaagcttcaggtaaaccagcagacataggatgacctattatt
gatggaccttctcaaagtactcttttgaagctgttggacttggcttgatcgtaggggact
ctggtgtccagttgggtgggcagacttctccatgggtctccacaaactggaacgccttta
ccaaacggagtggttcttccacacttcggcccaccggaaggtcattgacactcaggtgct
tgatgacaccattagggtcaataatgaagagacctctgagcgcaatgccagcactttcca
acagtactccgtagtctcgggatatctgcttagttaagtccgacaacagcgtgatgttca
tgtggcccaaaccaccattctttcttggcgtgttgatccaggcaagatgactgaagtggg
aatccacagaaaccgcaactacttcacagtttacgtcatgaaactcattggctttgtcac
tgaaagcaacaatttctgtaggacacacaaatgtgaaatccaaagggtagaagaaaagca
ccaagtatttccccttaaagtcgtcgagactcagctctttgaactctccattgacaacag
cagtacctttaaaatggggcgcatgctgggtgacagcaggggtgtggaatgaagaactgg
tgctaaaggcaaactttgcttggggacaggcagaccacagcatgtctgtcaagcaggttc
ttctagaagcaacaggcctaagaactgttgaggcagaaatactccggaaaatagtgctcg
caggccgagccaccgaggaccagagcaaccttcccgcagctgccgccatcttcagagaac
gcaagagccacgatagc
>scr_gb-m11794_3 (TOXMARKER Assignment: 58; SEQ ID NO: 58)
atgcccacatttgtgaccagtacatgtttctgcccaccatgttcgagactatcaaagtcc
agaggggtcatcaatccacttatcccaaatcaaggtgcaccaatcccatttcaacgcctc
tgccagccccttatttccaatgaacacagacaaagctgggttaatcaagtcaagtttttt
tattttattgtcagttacatgctttatagaaaaaagtgtggagaaccggtcagggttgta
caaaaaaaaggctaggttcctacgttgttttatttacaccattgtgaggacgcccccact
tcaggcgcagcagctgcacttgtccgaagcctctttgcagatgcagccctgggagcactt
cgcacagcccacggggcagcaggaacagcagcttttcttgcaggaggtgcatttgcattg
tttgcatttgcaggagccagcgcaggagcaggatccatctgtggcacaggagcagttggg
gtccatggcgaatggaggcggcagttggagatcaacgagagatcgctgtagagttctagg
agcgtgatggagagaagcacgcggagcgcgacctttatagcccagagtattgggtcgcgc
gcaaaagctccgcccgggtggcggggcgccacctgccctcctccccactgcctgcacacg
cccttcttctggctcaagggaaatgg
>scr_gb-af069306_1 (TOXMARKER Assignment: 59; SEQ ID NO: 59)
ttttttttttttttttttaggaaaagcgactgctttaatgaattagacaaaatttcacat TABLE 9A-continued gaaatcagaatcctataatccttcccttctgatcactaaaaaatgcaagattcattcgtt
acaagccatgtgcgattcggacccctcgaaggcagtgcaggtctgcggtccagcctcagg
tgctgcactatttcccattctcagcgctgaacattcgttctgtgagcatccgctccaact
ttatggcatcagcagcaaacttgcggatcccatcagagagcttctccacagccatttggt
cctcattgtgcagccaacggaaggccttctcgtccagatgtatcttctccaagtcactgg
tctgggctgctttgacggaaagcgtgggtgccagcttgctgctgtccttgagcagctccc
ccagaagcttgggtgagatggtgaggaaatcacagcctgccagcgctttgatctcacccg
tgttacggaaggaagcacccatgacaatggtcttgtagccaaactttttgtagtagttgt
agatttttgtgacactcttcaccccagggtcctcctggggttcgtaggatttcttgtctg
tgtttgccacatgccagtcaaggatgcgccccacaaagggagagatgagcgtcacgcccg
cttcagcgcaggccacggcctgggcgaaggagaaaagcagtgtcatgttgcagtggatgc
catgctgctcctccagctcctttccggcctggattccctcccaggttgatgataacttga
tgagaattctgtccttgctgatcccagcttctttgtaaagctctatgatgcgcctggctc
gggccaccatggcatccttatcaaaggaaagccttgcatcgacttctgtggatacacggc
ctagaatcttctttagtatttctgccccaaacagcacaaaaagtttatcaatggcatttt
taatctgctcctcttgtggcccacccagcttcttgccgtaggcaatggcctcctccacca
gctcttggtaggcaggcatctgtgctgcagccaggatcagggatgggttggtggtggcat
cctggggcttgtactcatcgatggcgttgaaatcacccgtgtcagccaccacggtggtga
actgcttgagctggtccaaggcggactccatcctctggcgctttaccggggaccccgaca
tggcgaaacgcgcacagctgaggcggtagctggt
>scr_gb-d17310_4 (TOXMARKER Assignment: 60; SEQ ID NO: 60)
gcactctccagcctctcaccgactttttttcaaggagacaattttattttttaccaag
gctgaatttataccataacatgggtaacagagggagggggaagtgtgaaacatttacac
aggccaagggcacagtatacatgtagtcagctgatgtcaacaggatgttggtttttcaga
aagcttacaggtcatcacattgggtatcttgatgtcagatgtatttctcagcaaggtcag
aactttatcatatcattattcatcctgaccaccagatttgtattagtcttctgcagctgg
ctggggattttccatgaacccagtcatacttaattctaaccataacatcaataatggagg
gtttcaagggcattgctcccaacatgtaattacaaaaagaaaaaagatgatatatttccc
aaaaagagagacacattcaaatttcctctcaaactccccacatctgaatcatgatgatgc
ttttaaattggttctcttcttaccaacattccaaccttcccacaagaacttgctctccag
gttcttggagctctggttcttgggctgttggagagaaccctgggtctcttggtcactcct
gccacaggtgccctacctcaaaactaagaaaaagggaaaatctatggagtactttcttct
tcctcaaagaatatggggaatattgactaatcaataacctcgaacaattaattccctgaa
tgttgaacgttctttcaactcccacccagaaatccctttgcaataactgtcctcaacacc
cacttcatgcccaagacttctagcaaatcagcttggtgtcagaagtcaggagaaaacaaa
acattgagatcacagaaatagtggcaggcaaggatctttagggttggacctaatgagatg
gctcagcattcaaaggcacttgctagtctcacagaagacctaggtttggctcccagcacc
cacatggtaactccataatcaatgtaactccggttccaagtgacctgcaacactcttcaa
ccctgcatggacatagacattcatgagatacacatacatgtagggaaaatattcatatat TABLE 9A-continued ggaaagcaaaataaatgaatatttaaaaacacaaggaaaagcaacgtgatgttccatttc
agagtgtgacaaaaacatggcttccctcatagcactgtggacattgctccagctgactgt
gaattaacagaaacagtggtctgatgcattcagtcaccagtatccaagatatctttcaaa
tcacaatgcataaacagatcttccgatagaaatgctgacaaagtccaccatgttactatt
catcagtaaatggatgattgggatggtcatcaaaatattttgcattgttgtatctgaaat
ttctgttcaagccatccagggctttcatgtcctctgaagccaactggaattcaaaaacct
gtgttagctctttgatccgcttcgcgttgaaactcctgatcaggggcacaaccccacgct
gcagctggtagcgaagggcaactagggctggggtttgcttgtacttctttgctatggcac
aaagaactggatcatctaggagaactggacttttctgatccacccatgttttgtctcgtg
aacttcccagcgtgcagtaggaaaccagaatgatgtcttttgacttacaatagtccagca
ttttgctctggttgagataaaggtgacattccacctggttgcacacaggcttgtatttga
gccctggcttattcagaatcttctccagctgcctgcggttaaagttggacaccccgatgg
acttggccaatcctgcatccttacacttctccatggcctcccatgtgtcacagatatcca
ctgtttcaaacaatagttttccatgctcatctcgtgggaaaaatatatctccaggctgca
aagccattgggaaatgaataatataaagatccacatagtccagttgagtgcttttcagtg
tcttttccaagcaagttcggaccagctctggtctatggaaagtgctccaaagctttgaag
tatagaatatatcttctctcttcacagtgccgtcttcaatcttgcttctaatggcttggc
ccacttcctcttctacttcgtacaaataagcagagtcaaaatggcggaatccattatcta
tagctattttagtagccttgataacttcatccttagcaaccttctcaggcacagtggttc
caaaccccagtacaggaatgaagttaccatcatttagtgctacacgcagagatatggaat
ccatcgcttgttactcatgcaaccaagcaggtcttgggtctggcgagggtcttctgactg
ttctgagacagccctgtgtgaggaatgcactttcacagggttggaggtacttccaagacg
ccataggaaccacacgtgggtcacagctatcagttcactgtgggcaagaaacctctttat
ggccacctggtaacaaaaatttttctgtctgtgaatttttttcttactatttaaa
>scr_gb-bf281368_2 (TOXMARKER Assignment: 61; SEQ ID NO: 61)
ttttttttttttttttttcacacagggttgcttttatttccacatccaacttgagcagag
gccctgccacaacctgaacagctgtgaggtgctgggtgcctccagagtttctggcacagt
aagtgttgggtgtgcagacttcctgatggccacatgacactggcccacacaggaacagca
agtccatgaatggaaatcccactgagctggaagtggaggctctggaaaccccatgggcag
cagcaggagttaaaggagccaccaggaacactgcagtgaggctccaatgcagacagggct
gataaaaacccaaacagggcattgtgagagcagaggctcgagtgtccccgctgaggaccc
ggggctgaaggcacagagctgtgtcgggatggaagaaccctgggtgcactcgcagtccag
agcacgaaagcacaggtgagaacccagcccgaggctctctgtgaagagtgtggccttgga
tcttgggcacggcacagtgacacacagtgctgaggtcactcctgacttcccagaggaatg
acctcttcagtgacaaaaaactcaatggtctcttcctcccagtcatccacgttgctgtcc
agctcgtcagtgtccacccctccccgtagctctagacgctcgttcttctgcttcatatag
agttcctgggccatttttcggtattgcctgaagtcctccatcatggtccgccttctttcc
accagttcctttgaagctttggactggctcaagcgatccttctgctcaaagatcttagag
tatttcttcagatcctttttaatttgctttatctgatcctgactgaggagtgttgggggc
cttggtctccagagcagctggcagaagcggtccttgttgttcttctggagaagacgacct TABLE 9A-continued tggaaggtccacagccaataagcattgtccaccttatggctccaccacgacacagaggta
accacatagcggccagttgggtcccattcgacgtcggaggccatgtagtgctctgcaatg
ttcatgacggtgcagtctgaagtgtcgacaaacgccaaggcgccattcatgctcctcagc
ctcgtg
>scr_gb-u56407_3 (TOXMARKER Assignment: 62; SEQ ID NO: 62)
ccaaaccaacaaggcagccacaggccgtcggtgcctgccgccttccaccaggggcccgcc
aagacaaccttccaccatggctttgaagagaatccacaaggaactgaacgacctggcgca
ggatcccccagcacagtgttcagcaggtcctgtcggggaagatatgttccattggcaagc
tacaatcatggggccaaatgacagtccctaccagggtggagcatttttcttgacaattga
tttcccaacagagtaccccttcaaaccacctaaggttgaatttacaacaagaatttatca
tccaaatgttaacagtaatggcagcatttgtcttgatattcttcggtcacagtggtctcc
agcactaactatttcaaaagtacttttgtccatcagttctctgttgtgtgatcccaatcc
cgatgatcccttagtgcctgagattgctcagatctacaaaacagatagagacaagtacaa
cagaacagctcgggaatggactcagaagtatgccatgtgactaaagagattattggatcc
tctgcgaataaaagctaggggaactctgaaagagaaagtccttttgattcccacttgact
gtttgctgtgaacccacgatgtaccggcctcgtcctccctggtgcacggtcttcatctga
tacagtactgttgcatgttgcacgcaccaaaaatactgtgtttctgtaccaacactgtct
cctagcagacgagccttctccaggcataacctaggtgtgagattaaaagttttccttatt
gacttaaatctggataacaaggtgtgagtgagggtggtgggtacaagatactgctcagaa
ggggtaaaggtccccaacctataagacaatgagatggcttttcagtggaagccatttaca
gctaaatgtttaaatgaatgaaaagctaggtgaagaacatgaatgttcctgtactcattt
tattccaaaagacctagagcttaaatgaacattaaagccaaccagactaagccaacccac
ctcctgtattttaaagtctaattggtcaacaaaaatagatcggcactatcggtccataaa
gtgtgcctggctttgttcccaaatcctttatacacggatgactcaacctattttctttca
cactttctctccatattctttggtttacttgcggtttctcagttgattcatcactaatag
ctcttatttttattatattaactgcttaatctatttggatgtaaaggtagacattcaact
tgatgaaaaaagcttgtgtatagagacctaattgctcctcttggagcttgtacagtcaag
aatgatgcatctgtgtaataaaccaattattctagccattat
>scr_gb-ai406674_1 (TOXMARKER Assignment: 63; SEQ ID NO: 63)
tgtacactacccctcacaaaccacaagccgcagcaacatggatgcccagtctggagcagc
aacagccaggatgacctggagccaggggggcttcggaacagatgtgcacccttcctgggt
gatgttttcagctttgtgagaaaccttactatcagaggagatggctagcaatgttaccaa
caagacagatcctcgatccatgaattcccgtgtattcattgggaatctcaacactctggt
ggtcaagaagtctgatgtggaggccatcttttcaaagtatggcaaaattgtgggttgctc
tgtgcataagggctttgcctttgtccagtatgttaatgaaagaaatgcccgagctgctgt
agctggagaggatggcagaatgattgctggccaggttttagatattaacctggctgcaga
gccaaaagtgaaccgaggaaaagcgggtgtgaaacgatctgcagcggagatgtacggttc
ctcatttgacttggactatgactttcaacgcgattattatgacaggatgtacagttaccc
agcacgtgttcctcctcctcctcccattgctcgagctgtggtgccttccaaacgccagcg TABLE 9A-continued tgtgtcggggaacacctcacgaaggggcaaaagtggattcaattcaaagagtggacaacg gggatcttcttccaaatctggaaagttgaaaggtgatgaccttcaggccattaaaaagga gctgactcagataaaacaaaaagtggattctctgctggaaagcctggaaaaaaaaaaaaa aaaaacccctcgtgcc >scr_gb-bf290678_2 (TOXMARKER Assignment: 64; SEQ ID NO: 64)

ttttttttttttttttttgattttggccaaactttttatttagtattttgtagttgttta acacacacttaaatggtcttactcggggagggggaagggaggttcttgtanattcccaag gaaaggtcagaaaagcaaaatatggccagcatccatttgctttttttgagggggggggt ttctgggtaaatagtacatgcctaggcatctgatctcagcttggtttgtttgtttgaata tatatatactgcgaacattgagatttcagttggaagacaccctgaaatcctcacacccca ccaaccctctctaatggctagcttgtctgcacaggcagggtgattcaactctcaatggag accaaaggacatctagatggctaaatgtttgtggaagatcttggggttgcttgcctcatt tgctgggaaaaatcaggaagtggccttcagggacacttttacttggaaaattacaacact agttacaagtcacgggttacacatctaacatttgcttgttgaaagcaactcataatagca aataaaattaaacatgtcttactttttccctcacaagaacataaaaattattaaggggaa caggaaattttaaaaaggtaacacaatttttcctttagtagtccttgggtagtttatgac agaaagtttccatttttttgtttgtttctttgaatggggattgttggtccctcgtg >scr_gb-bi288503_1 (TOXMARKER Assignment: 65; SEQ ID NO: 65)

tgtacagttgctagtttgaggctggtgttgatgttctgacaagagtggctcagccatggc tcagtagagtcctcttctggaagtttgagaaattctggcttacgggaaaaggtttttctt tcttttcaagatatgtccaacaaagtcctcttcggtcagtaatttctgcagtgacgcctt tcgtccgtcctgtcagcaaactccaatcgcaacttgggagtccagtcaataaagggttaa gcgcacacaagcgtggccaactagtaggtccgagaggttcaccggcaggcaccgtactta atatgcagaggggtgggcttcacgcctccccgccgagcgctcccacggtcgaggagttgg tgggcaaggagatgaggtttaagtccaatgggttaaacccaaccccgagagggttaaaac tacccgatgacgctgccacggagggggccgaatccac >scr_gb-d86383_2 (TOXMARKER Assignment: 66; SEQ ID NO: 66)

ttttttttttttttttttcacaccagatgacgaatgtatatgaaagttaattcattaaat taaaaaaaaaaatcaaacatttggggagggtttttttacaacgaataattctatacaca tgctatagacacggtttctataaaacacactatctacaatctacttacatttaattgtcc tgctatttctagttcatgtgagatcagtcacaagtgagtcagtttccctgcctgtagaga ctgcgtcatcccttaataccagggtcagaggcactggccgagcaaaacaagattgtaaga atcttatcaactatcttgcttatgagaacagacaccaggggccaagtgctctgaaccggc tttggagttaaggcagcaatgtaaggtgtcacgtaaaaaccaagtgtgctctttgaaagc attccatggatccccaaatgctggccccctttctaagtgcacctctgaagtcgagggaac agctacacatttgggaaaagtcattcgagaacagccgcccaaaacctttaaagttatagt ttaagcttcaggcaaaagttcaaattacttctcacaaatagaaagaattcacttttttaaa aacgaagtcacatttagccactttatcaaaacaacttaacaccggtacggaaaacgtacg ctaaaccaaaagtatggtttcaatgcacgccgtgccaaatattttcaaaacgctagaaga atggtacttctttctctcagaatttcccagtttgtctgtagcagaacggtattctaaagt TABLE 9A-continued ccagtctctgaacatggtcacggccgatgactgtcatccagcattaaaatagcctttatc
accctcgatgtccacttcctggtcggaatcctctgagatctctgattcagggtcttccgg
agaggctggggagggtgaacactgagaactgtccaaagaggcacctttattctgttcact
gggcaagtcttggccctggtcacaggaagtgtccaaactgtccaactcatcctttttatt
gctttgaggattctcctgcttcagtcgtctccatttagctctgcgattctgaaaccaggt
tttgacctgtctctcgctgagctgcaacatcttggccagacgctttctctcaggtgggga
gaggtatttctgagtctcgaacttcttctccagctcgatggtctggtcgttggaaaacct
cacttgaccgcctttccttttgtgcagaggtcgctgtaggaaggggttccagagcaaggg
cttgcccaggggggtcgtggcggagtagggcgtgcgtgtagtcgttcaccgtccgcgggaa
cgggtacagagggcctccgaagccaccggggccataggcagcggccagcgcggcggcggg
gtgatgcgagaaggcggggtggaccggcgtgggctcgtacaccggggtccggtaggagga
cacgaggctggtgaaggaggagttgggggacggcagcgtgggagtgggcgtgggagcggc
gggcccgcgacccaggatgtcgtcgatgtagaaaggcgtcgggtgagcgggctgcagcag
cggcgtgggcgcgtacagcgggactccgacggcgggcgcagccgcgggccccgggtgcgg
gaactgcatggctgctccgc
>scr_sc-133366194_1 (TOXMARKER Assignment: 67; SEQ ID NO: 67)
gctagcatctttttttctgccacgaggtgcgttttattttcatcaatcatacaaatgattt
tccatatcacagggcaagctgagtgcctgggtgtgttcacagtgtagcttgtcgcttgtg
tctgtccatcttccccgtcagaatggggtctcagaaatgatgaggtgaggtggagaaatc
ctcctaggcttgtaggaaattttactcctcttttcctgttgaatggtcttttggttggct
ggtgttcttctcatgctctttggttttctccagtgtggctttattgaagcttgtgatttc
ccccatggataacttgcctgccattttcttagaactcttggaatcttgctctgagctcat
gctccaattg
>cszr_230290139_182026368 (TOXMARKER Assignment: 68; SEQ ID NO: 68)
aagctttggagctgctaggtgctacctatgtcgataagaaaagggatctgcttggagccc
tgaagcattggagacgggcaatggaactccgccaccagggtggggactaccttcctaagc
ctgaaccccagcaactggttctagcctatgactattccagggaggtgagcacgccccaag
agttggaagccctcatcacagatcctgatgagatgcggatgcaggcactgctgatacggg
agaggatcc
>scr_gb-ai013477_2 (TOXMARKER Assignment: 69; SEQ ID NO: 69)
ttttttttttttttctaagaagctgttctcatctatgaaccagatggcatctaccccat
ctgttggctgatcagtccgatctttatgccactcctgtgctttagtgagcacctggtgac
agtcatgatggggggtgtctaggtcagggtccgggagcagggttgtagggtttagactcg
taggggcagtctgggatcacaaggaacaagtgggatacccggcccacgccaaggtccacc
gttcttcgggtagtccatgagtatcatttgttgtcagtagccccttgtactcaaggtctt
ttgcttgacactagcccatttggacgtaggagcacagagtgttgggcccccgtattcaca
caacaactgggcgggcttcccttctatctttttgcatagccagcactctaggaccaagag
gcttgccttccaggctgctggagaggcccctcttgttcttcctggggcagtccctgaccc
agtgtcctttttctttgcattaggcacactgatctttagccaggaattctcttctgttgc TABLE 9A-continued caggtactgtcttcctaggttccctaactactgtggccagtatatgttcctctcttgtct
tttatctctctttagctctctagcttcctcttctttttgtctcttttcttccctagcttc
ctgctctttttaccttcttttctctttctctttgtttaaccttactttctctgtaactta
tactaactctcagcaacttagcttaacccttcaaatttctgtaactttctcttcataccc
tttccttatcttagccagattggtggggcattttccagcccctaggagacccaccctcgg
agcctgggggcagacctggagcactccctaccttcaggggcattgaagtcaacagtcagg
agccttccatccatgtctggaacattctttctggcctctagcaggattctgtctttcctc
agtggtaaagaagatctgtaacagttactaacaagcatctcacgtgggatggtgagaaaa
caagaagggaatctagaggagagaggtccactgaagaggacaaatagcatttagtcacac
agctaaaccaggaggcctttttttggacaaaaaggccactgtaaatataagcacaagctt
tgtctatgaaacagaaaggcgagcagagaggcagcctagctgttaccggctgtctctctg
ggcttagattttcccttaaggagtacctacctcccttcagtgtcagcttggtggctttgc
ctctcaagagaaccagcctccaaatgacactaggcttctagtaacaactaataacaaaag
gatggagagatggttagaacctgggtgctagatactaagcagctgacaaaagaattgtaa
ccagttcacctggggctttcaggactttagtaacagccctttaccaaactgtctcagtgg
gctataggcccatggaaaagaaaacattaatcctgaccttgtccaccaccaaagcctgaa
ttctaacctcgtgccg >scr_gb-m91235_3 (TOXMARKER Assignment: 70; SEQ ID NO: 70)

aaaaaaaaaaaaaaaaaaaaaaaaaaaaaaacagtctctctgcatcttcttctacagcta
ttaggtgctgtccacttttctgcacagaccctgaaccacgcatcaacttattttctctgc
aacttacaataactctctcagtgacttagctttacccttcaagtttctgtaactttctct
tcatatcctttccttatcttagccagatccagattggcgggggattttccagcccctagg
agacccaccctcggagcctgggggagacctggagcactccctaccttcaggggcattgaa
gtcaacagtcaggagccttccatccatgtctggaacattctttctggcctctagcaggat
ctgtctttcctcagtggtaaagaagatctgtaacagttactaacaagcatctcacgtggg
atggtgagaaaacaagaagggaatctagaggagagaggtccactgaagaggacaaatagc
atttagtcacacagctaaaccaggaggcctttttttggacaaaaaggccactgtaaata
taagcacaagctttgtctatgaaacagaaaggcgagcagagaggcagcctagctgttacc
ggctgtctctctggacttagattttcccttaaggagtacctacctcccttcagtgtcagc
ttggtggctttgcctctcaagagaaccagcctccaaatgacactaggcttctagtaacaa
ctaataacaaaaggatggagagatggttagaacctgggtgctagatactaagcagctgac
aaaagaattgtaaccagttcacctggggctttcaggactttagtaacagccctttaccaa
actgtctcagtgggctataggcccatggaaaagaaaacattaatcctgactggcaaaaca
aagttcttcacagttgtagattctttgaaactattttaggggctctttttgtcccccaac
ctggggcattttaaccataggggcaggaactggctgctgtggggataggaccaaaggcac
tctccatgttaatgatgatcagtggagaaaagtaattttgatgttggagactactcctcc
ttggataggacagcagataaggaggcttcttaagactcttaatgagcgctctcctacttg
agcgaaattcctttcctgttctgttttcctatagccccactagctctccagcctttttag
tcattcttccttgacgatttctaacacagcctgtcctttttttatagcctgttaacagca
tttctgatcttttaggcagctatcgactaagtgccataccgggtgaaactccgcctttaa TABLE 9A-continued gattccttactcccaaggaaaatttaaatctttcccagttcatcacagctggctgcgagc
ataagcacagaataaaacactatatgtttttgttttgtttttctttcctttttttcactag
gctggggcccgaacccagggccttgcgcttgctaggcaagagctctaccactgagctaaa
tccccaacccccaaaacactatgttttaaaaattaactttggctatcaaccaacacactg
ccactagagcggggtctctacaaaattaagtttcttactcactaagcgttaaggggacca
agtaaaactcttcgacgaacaaagcaaacagtttcatgatttcaaacacagtcgtcggtc
caagattttaaacacagtcgtcagtccaaattcaaacacgaaacaaaagtcaaaaagaca
ctaacagacacaacacgtccagaaaaccacagtcaggtcacaaagaagacaaacaattcc
aacagtcaaacaagtaacaagcagacgcgccgcgcagcttcggtaccaaactgaaaccaa
aaaattcagacggagtcatcaagggtgcggatccctccgaaaacggacggaggtgccacg
gatccggatctccctctcctccaaccacccttggaacgtcttccagggctgcgggggaga
agtccgagctcgtcagctccttctctggcccgcccagatagtccccagatctgagcctat
tgatcgatcgttcacaggacaagacaccctcgtgcc
>cszr_204152648_191521095 (TOXMARKER Assignment: 71; SEQ ID NO: 71)
tcatgacctcattttaggaccaagagctgtgttggtttcttagattgttagctttttctc
taga
>cszr_204152792_191517979 (TOXMARKER Assignment: 72; SEQ ID NO: 72)
tctagaaaacggaggctgtctggatgcagtagtcatttgctgcagaggttggggaagggg
aggccccatgtttctcctgtggaaagagggtgtggggctctgggaaaaggccactcttca
aacattcatga
>cszr_204229614_191891958 (TOXMARKER Assignment: 73; SEQ ID NO: 73)
gctagccttatgccagcctgccactgtcaacatattctgttcccattggttacatgcttg
atacatacactcttgtgtttttggctaattgagctttttaattctattgtaatattttca
attg
>cszr_204229615_191892510 (TOXMARKER Assignment: 74; SEQ ID NO: 74)
caattgaaaatattacaatagaattaaaaatctcaattagccaaaaacacaagagtgtat
gtatcaagcatgtaaccaatgggaacagaatatgttgacagtggcaggctggcataaggc
tagc
>scr_gb-aa801331_1 (TOXMARKER Assignment: 75; SEQ ID NO: 75)
tttttttttttttttatgaagacacgaaatgcatttattcacataacaaaaaacaaaaac
aaaaacgaaaaaaacactcactccctcttcacttgaaatgtgtcagtaatgactcaaagt
gtcatgatttaccaggtggtgaattcttctgacaaccaggtgaagaattaggaaaacata
cagttccagtctttatattctgaccctagaaatcggttcatttgtagctcttgggggtac
acagtaaagcaggcaagcaactgtccacactgtttcattccacatacttagtgagtgccc
ttattcagggcctaacttcactccaggcacaaaaacaaggcaggattgcctggtaagtct
gaacatgagaaaagaaaacgatttattacacaacagatatatccatttatgtgagtgttg
acatctaggaattctctgctttatagacaattagaagcagcatcctttctttagaatatt
tctatgccctcactaaacccatgagtaagtatcttgcttgggagtcatacccagagctaa
ttacaattcaatattctccctgtacatgcaatccttgaaaaacgttatatgtattttatc TABLE 9A-continued tcattttcataaaagaattacaaagaccccaaaaaggtttagtgtttgtttgcatattaa
ggttgcaattctccagaaacccaaagttcggatagtatgtgacgttgtgcagacaatagt
ttacctcatgctacaggctataaatgtcagaacagagcttaaacactcacattagtgaac
gcattggcactacttgtactctttattttaagggctaagaaaaagcacacttctactcag
ccctatggaagttatcagtgagcacattctctatcgctcactgtacagtaaactatgtac
aacaggcactataacaaacagaattttagagtcaggtatgacatgaaactttttcaattt
tttatatttacactgtgggtttatcctcatcttaagatcagtttttcattttgttttgtt
cttctgtttttttggtttttttttctgcctaaacggtatgctcaagtagcatggataaatc
ttccagaatatgcactgagtaactccttggctcttcccagagccttgccttcagcacagc
atgatgttaaaagatggtctcattgtagacatcaaagtaggtagaagaacaattgtgtct
gtatcagaggctctatgaagagacctggagtctcgaagttccttcttactac
>scr_gb-aa899865_3 (TOXMARKER Assignment: 76; SEQ ID NO: 76)
aaattttggctggatccacagcaagagtcctcagtattatttatttgttttgttttgtgt
tctgttttgtttttactgcaacttgacaataaaagatgtttggcattggaagagaataga
acattaggtctgggcccagcgctctgactccgtcttgtttaatagtttaacctgaagtcg
caagactgggataaacaggagagctgacatgaaggacatcatcgcacatgtttcggctta
ctgtgtcagaactacacgtgcttggccttatttctttgagcctgtggcagaagagtgtat
cgaggcagaaagcagaaaggtccaacctccctttctagaaaatgtcccttgatgtcctga
ttctcttccactagtcctcactactaaaggtcctgtcacctctcagtaacactgtgggcc
gggaaccaagcctcagggcacaggcctttgggagctgtattagagttctcgagaagaata
aacagcacttgcagaaggaattcccagaagaagaatgacttacaggcttctgtccagcta
atccaacagtgagcagaaagtccaaaaatccagcagttcgggccatgaggctgggtgtct
cggctggtcttcagtagactctggaatcccaatgacgtaggctctaacgccagtgaagga
atggacttgccaacaaggtgaggccaagcaggcaaagagcaaaagctcccttcgtcctgt
cctcaagtagacttctagcagaaggcgtggcccagactagaggtgtgtcttcccacctca
agatcaggattaaagaagatctactgacttcaaattaagcaaaactccctcccaggtgtg
ccctctgtcattagattttagttcattcaagatggagtcaagttgacaaccaagaatggc
catcaccggggacactccacatataaactgtataccaagcttcatatttcagacatgttt
cttaatgtcatccacgtctccagcccctgtagtgtgtatgtgttgtattctctgcagaat
ttagcatgcccgtgtttcctgtccttcacataaacgcctttgtgtgaagcttgcttgatc
ctccactcccctctccagcccccacccctgtgacactgcccagtaataactgttcgttgt
ttacctgttgcttgtaagtgcaagtattaaagcaatttgaaagctaaactcacctgtaag
actataataaatacctgtaatccaataaaaaaaaaaaaaaa
>scr_gb-aa997629_1 (TOXMARKER Assignment: 77; SEQ ID NO: 77)
ttttttttttttttttaaataataatgttactgtcgtgttggctgtatatcattgcata
tacttcaggaaaagttttcttgttcttgctaaataacaaagcacaattggtaagttccat
ggacagcaggctccctcagaacgtagccagttctgtgaggcaccccatatcccaaggaca
agcttgtggcatgccagatgaacagcagccttggcttacacgcacacctgtacataaaag
ctcatctttccaaccacgtgcagccaagagattaccacagacttgacacagggaccctaa
caggctcctatagacagtcctgccgctccatgaagtggggaaggaacaaatgcagtgacc TABLE 9A-continued gcatctaatgcacttcctttgaaaatgtttgcttat >scr_gb-aa997691_1 (TOXMARKER Assignment: 78; SEQ ID NO: 78)

agatctgagcggccgcccacggtcctgatgacagaagagctctcctccccgaaaggggca
gtccggagcccaccagtggataccgccaggaaggagataaaggcagctgagcacaatggt
gctccagaacgcacagaggagatgaggacaccggagcccctggaggagggtctagcagag
gaagctggcagggctgagcgcagtgacagcaggggcagcccacagggtggccggcgctat
gtgcaggtgatgggcagcgggctgctggcggagatgaaggctaaacaggagcggagagca
gcatgtgcgcagaagaagcttggcaacgatgtcatctcccaggatccctccagcccagtc
atgagcaacacagagcgattagatggaggggcaacagtgcctaaactgcaaccaggtctt
ccagaggcccgctttggtttgggaacaccagaaaagaatgccaaagctgaacc >scr_gb-ai411514_4 (TOXMARKER Assignment: 79; SEQ ID NO: 79)

ttttttttttttttgtttgtgaaagtacagaaaactttattggaaatctcttgattatat
ttccaagtgtagctctcatttcctaacaaagcactggaggaggggcttcacagccacctg
gtcccagcctgagcttggctgcgggagttgtctagagcccgtttcttccattgtgtagga
ctgaggggcacaggccaccttgaaggatgcttcgctcagcttccctggcctctttcttaa
gaatctgggacataaaggctgctgtctagaggccactggctgagccctgaaaagaatccg
tgccctcaccccccttttagtgctggccctggggggtaaatcctgttcagtaggctatga
atgtgcccctgacccaaaggctgcaatggcacttggccaccactgctgggcacatttctc
tgtggcagcaaaagcatgcacaggggaaaggctccagtgttacatgcagattactaacag
cagttgagagccacctgctccaatgcgtaacggctgctgccagtgaggatccagggacaa
gaacaggacaggctggcagaggcacttgactgactcaagcaacaatacctgaaggtttaa
gtcaaccataggctcagctttggtttctcaaaagggaaccaatccagcttgtaagcccag
ggccatgtacagactctggaattagagggagggagagagggaggaacagctccctagtcc
tgctccagctcaggggctggagcagcaggttatacagtgctcctctgggcaccatgggca
acacacctctgaggagtcctcacactgaacacacctgagacctcctgggctgctagaaca
gagctagtcacattacagatgctgtgtcaacagagtatgctcggcaggagcacgcagcat
gccgggaagcctgatgcctgctcagttccatacacacagtttgagggggctactttgcct
ttgccagacccattgctgatctctccttaggtgtgacaggaagatcctcagagcagtagc
acaggttctgagtaatcttcaccggaggcctacagcccagagaaaccctcctccttcccc
agcagaactgctaaccccaaacatacttcttttataaaatatctgatttctctgacagta
ataaatatttaccatgttctatatccacgcagcagcgatcgagggaaaacgaggaggaaa
aaagatcctacaggcggccgc >scr_gb-aw142560_3 (TOXMARKER Assignment: 80; SEQ ID NO: 80)

ttttttttttttttttttgattgaaaatgtttaatttgtaaggcacacagtttatgatca
ttttaatatctaaaagaacgaaattaacaggactaaaacctgattgtcgaatcatttacc
aagtttggatgtcacgttgtaaaagcaggcttaaaaagatgactccttacaaaggagtga
ggtggacctgggtgggacaggctagacatggccctgaaaaccttcttgggtgacaaagaa
acagactactggactgaagccacagcttccaagaaacaagaaaatgtagtggccaccaca
ttgggctttgtttccttatgagacattttccacctcatctcgggatcttactgttaccct TABLE 9A-continued tgcccaaactgcttatggcatgagggttccagagcccagcgccccagccaagtgtacaaa
agacgtttcctgtagagtgtgcctgtgagggacaagcttgaggagtcctgtagagcgtcc
agacaagctcacatttcctcattcatggatgatgaaggggatgtcacaagcagaccagaa
actcctcaatgtctcaggaaaggaccgttttccagagcggcttacaagtgggactttctg
ggtttccatctggagtttggttttcctgcttggcctcagactgagatagaagagcagtga
gacagaaagtagacagagaatgagctagcctccgg
>scr_gb-aw533305_2 (TOXMARKER Assignment: 81; SEQ ID NO: 81)
tttttttttttttttttagaggttaaaggtgttcatttgccaaccggacagcctgagttg
gatcccctgagccccccatggtggaaggaaaggattggctcctgtaagttgtccactcttc
tgaagtatgtgcactgcggtgtgtacctgcccacatacacaaacaggctaggtagagaag
aaaagggaaaccattaatagtcaacactgatacttatcaaaaatggcactagatggtgat
ggtttaaaagcttcacttagaagccaacagtgacagcagagacagacctctgttaaccat
tgcaggcaaaactgaaagacatgctcacacaggaagcaagcacaggcggctttgttgacg
gcttagctgaaacagactcaagacaaagcgtgttaacagacagacgcacttcacggtgac
acgaggggccagctaccaagaagacattgaccccaaaacatgtatacacgccaacagaat
cccaaaaggcacagtgagaaaggacagaaggaaagttcgaaatagaactttgtgctgccg
aggtaggagattaacttcccctggagatttccacagtggccaaaacttcggtgaggatat
ggaagacggaggtaccatctgagcttgatcagactctctaaggtgtgatattgcaaatag
tgcaagccaaacgactcagcgggcacatcacaggttcaagaccagcctgagaaacttagc
agggccctgtctcaaaattaaaagaggttgtttttaaggaccagcctcgtg
>scr_gb-aw915573_2 (TOXMARKER Assignment: 82; SEQ ID NO: 82)
cacgagggatcaccagatgctgccaggtgctggttgccaaggttgaaatgagaagtttct
gttaactgggtacagagtttcagttttacaaggtgaagaagttgggcagacagatggtag
ggatggtcacacaaagatatgaatgtatttactgccactgaagcaacactaaggtggtta
atctgagaagttatgtttattatttaaaggactaaattgtcaagctaacttcaataactg
ttttattttgtacaactgacatattcatatagatgacatctctaaagatgtctttatcag
tatttaaaactgtgttacatctcttaggaatttgacacacagtttcacttgtaaggccag
ataaccaattgtagggtgcgttattacccagaatgtggtgggtccaagagcttgaactca
cgatcaagtttggtgacacttgcctttacccactgagccttctcatcaacccaagtttcc
caggaattaagtaatctgtttccctaattccccttaagcaaacatggcagtcaagtgtac
agcaggagacaggttatgatttgcatgatgtaatttaataatgtaaccatctttggggaa
tctaattagtaccaaaagagaaaaaaaaaaccaacaggaaacagctgtctctctcacaca
gtgttgagagctttccctcccactcattgccaatcagtgtcctggtgtcccctcaccctg
cctctgtctctgcaacctgccagcctccaactgaacagacttccattcctgtgcaatcta
agtcagtctctccagtctcttcctccctccctccctcgctctccctctctcttataaagg
aaagaaagcactcactgggtataattgatgtctatatgcaggtgagggcaggtacaagat
aaggcaagacctgtgattgggcagtgaaaaaagaaaggcgggggcagaggttttgtaagg
caggagagatgaggaggtagaagaaccaagaaaaaggcagagaaggacgacccagatctg
cgtggctttaaccgggcaaaggtagctatgaatatttcataagggacagatttatatagg
acaatttgtcttacctaggtgggcagtttacatcaataccaattggttgtgactttattg TABLE 9A-continued tgtggacgttttgtggactgagaatttgctgatatgaatctgactgctaaattacaagct
ttgggttttgattttaactggctactgggagttgtgactgtagccacaggggcagatgct
gggattgtgagcagggttcacagcacagtcccaggatggcagctgctgctgggcccagag
aggagccagtgccaacatggggctagccatggaggtggagagatcgctggggacagagaa
gagcaggaggcagtgtggcttggtgcctggtgccccacccaccccctgcatccattttaat
tatttactgctacaactgggtgcttgcttttagtttcagagggttagtccattagcatcc
tgaggagaagcatgcaggcaggcagacaggcatggtgctagaagggtagctgagagcttt
aaatcgtgatccgcacgctgcagagagagaaaaaggaaacagagatggagggatgactgt
ccctggcaaggactttcaaaccttaaaagccacctctagggacacacctcttccaacaag
gccacacccctactccttcccaacagtccaccaactgtgaacaaagcatccaaatgtatg
ggccgatggggccattcctattcaagccacctcactgaaggaataaattaacatgtccca
aagtattaaatgtagtcatttttctcagtactgagacaaaatatctcaagaaataaaaaa
acactgaaggacgtatttcgtttggctcccccctttaaaagaaacagtccaccatggccgg
gaaggcatgtggctggtcagagtgcaccctcatgcaggaagcagagagtgggggagtgct
cctcgaagccttttcctttttatttagcatgcaccccaagcccacaggagctggctaacc
cagcaagccttgctggcctggaagccacccccaacaaccatcatcaccccagtgcctccc
tacagtggggattatgagttgccaccatgctgtttttcacatgggtgcaggggatttgaa
accacagcctcctgcttgtacagaaagcatcctgaggagccatctctctggattcaccct
tcacttttggctgactgggcctgagctggagtcacctgggct
>scr_gb-be108509_1 (TOXMARKER Assignment: 83; SEQ ID NO: 83)
ttttttttttttttttggtttgttttgttttgtttttctttgcttttctaaggatagtt
taaaatacaaacaaattaaagtatgtgatatgtcaacatgatcatgcccctcccagacac
agcctttaactgtccagctcaaataagagaaatgctgaagcttaagatgtctttgtcctc
aggaagacatcacatgtgtggttgtcctgacactgcacatggcagcttccccacaacatg
ggcccttcgccttcacactgacaagaagtgtatgcccttcacactgacaagaactgtgtg
ctcactacaacttgtattggttgtaccttccccaaaagcagtaatgtatttctcaagatg
tcctaaatcaagtggagactctcctctggaaggaactggactcagcctcgtgccgaattc
tt
>scr_gb-be111483_1 (TOXMARKER Assignment: 84; SEQ ID NO: 84)
ttttttttttttttttcagacaaggatggtttattgaatggacccccctgagactgatca
atcagggccagggccgcagcctcagaattcaggggctgagccatgactctgaccatttct
cagggccggcttataaagggaaaaccccacaaagccacaatgagctcgcatgcaggtgct
gccggatggttggctctgactcaagccatttcagacagaacagctcatatttacctttaa
tgtggtgggccatatgtaaagctttgtgtaatttattaagttgaacaaacctcacagcat
gaccttgctctgagtcgagtcattttctgtatcaatgatggcaggcatggaacaaaatgg
ctatagctatgctaggtggggtagacctcaacaggataagaaactaaaaagtaacaaaga
tgagaagacaattgggcatcctggt
>scr_gb-be120910_1 (TOXMARKER Assignment: 85; SEQ ID NO: 85)
tctttttttttcggagctggggaccgaacccagggccttgcgcttcctaggcaagcgctct TABLE 9A-continued accactgagctaaatccccagccccaggaacaagccttcttaaacaaccaccccatctct
ccagtccctgatcaatattttatgactacgtttactctgtaaaacaaaggattaaaatct
aatccgattaccagtcttactagacaaaccttccaaatctgagttttctcaagtataaac
acttcacaacaccttctgagaaatgtccacatcactcaaagacaacacatttgggaggtt
tttatgggcttcttttcatacagaacctttcaaagcttgtaaaacttcgaacctagggac
atttgggagttcttctcggtctcacacaaaacggacttgctttcaaagatcccttcggat
tctatttgacttagcaaaaacacagcgcaaaacacaccccctgtaagaacaaaggtgcaat
tg >scr_gb-bf285287_1 (TOXMARKER Assignment: 86; SEQ ID NO: 86)

agttcatgtgcattggtgtttgctcacatgcatgtctgtgacgtatgcctgtaggagggc
atcagatccctgcaactggagttattgacagttgtgagctaccatgtgggctgtgggaat
taaacctcgaaaagcagccagtgctcttaaccactgagccatctttccagccacctcaac
tcattcttaaatccacttaagacatagaggaaacactattccttctattctgtttgctga
tatctgtaaaagtagacagacttgcagagtggtggtggcagacacctttaatgtcagcac
tcaagaggcagaggaagacagatctgagttcaaggctaccctgatctacagatagagttt
caggtcagtcagagctttatagagagacctgtctcaaaatacaaaaaacaaaaccaaatt
aagtagacagactcccacttacacgaaacgtaaacactgtttcacacacttcagaatcac
atttaaactaccaatcaacaagaactgacagaaccaatatcaggaaacctcatccatata
aagcaacgtcacagcaccaagcagttaacagcttttggctcgctctaatcgaggatccca
aacacaaatcttacacagacatggggaggtacatcctacatctcatctcggtcgcagctc
atcgtcagtcctagggatcttttgggtccccacaaagatggaggcatagccttgctcttc
ttgcccgacaaggaggccagcaggccaggaagttaaactgccaatacctgccaatgctgg
tctc >scr_gb-bf390383_1 (TOXMARKER Assignment: 87; SEQ ID NO: 87)

ttttttttttttttttanagnagctgtattttctttatattctgcatgggatatgaaat
aggggttttgctccacagggagcctggtcaatatagacaggatgtantcagggtgtgtct
tccaaggtcatctccatttccaggcagatggaaaaaaaatcatgaacaatcatgttgatg
attttgaaagatgagtataggcaatagcatgtgtcctctgtcctgagcaacagatctcag
ggatgtgagggtgtgcgctttctggatggttcaccatacgcatcttcagcaccaaggcta
tgcaagctttgttcagtaaggcagaacatcaggaactcaggagagtggctcccggaaggt
gatcatgtggcttgacccctgattatccatcttcctcaccaatggtttgcttacattcga
agcttaaagccttaaagttaacttcgtcttgtgatgctgttaaatgttttcaattacagc
acgatc >scr_gb-bf558463_2 (TOXMARKER Assignment: 88; SEQ ID NO: 88)

tttttttttttttttttaagagaaacattttaatatctgcaggctcacgcaggattcaa
ctgtgtgtggtacagtctagagtgacttgcttctatttacttccacacacggtgactttc
gatgagatggttaagctgagcagtatacattcctgaacagtgccaaggatcctgttttca
aacagctttatcaatcgaaacatcctcaaagagccattggaggcagtgtggctgggccat
ctgcactaaaatcgcttattcagaaggtgtcaaagcagccgagggccttgagccacaggt
tgctggtgttcacatctcagctgggacgtgataaagactgcatgagctgcagatccgcaa TABLE 9A-continued acagccttgcaggctggctctgctcctgcaaagtcaatggagccacaaggtacttcttaa
tggtgtcatctgttcaggttctccagggagttaagggaagcactgtctttgcacacagtc
tctatcacaagggctctggctagcagcatgagagttccctctcagccaggctgccacagt
gagccatctattgtcctcactgcagagtgcacaggatgaagatgtccactttcctcatca
gacttgctgacagcctcatttcctgccaaacggatcagaccacactttcaaccctggtgg
ctgcacatcttcctggacgataccagctcgatttacagcctgctccttctggtattcttc
cagccgcagaaggggccggaagtagatagggtagaaggcggctccgaccatagagatgaa
gcctccgaatatgagcgcggtgcgcaggttccgggccgcggccatggtgagaaagggggc
tgcagggcgggcgaaggcccggcacgctccgaaacccgactcccagccttaaggtcgcga
cccggctcggaagaggcggag
>scr_gb-bf560709_1 (TOXMARKER Assignment: 89; SEQ ID NO: 89)
ttttttttttttttttacatttatgaatttttaatactcctgtcaagatcttacaagga
gaaattactttgggaggtgggtatggaggttagaggtaggttggaaagtggatcatgatc
tcaaaatagtaaatgctagctgagtggctttcccagagagaagcgacatgccctgacgag
actggagaacatgtgtaaaggagagcttattttcaggtctccgctggcctccatcctctt
caaaaacctcagctcctgggttctgctcaacccacattctgtaatacttgctcaagtagg
cctgtagcaccttgtaggatacagacagttccaaatggatgtccactccagtctctggct
gctctattctgtacttctcttgaatcacagcttttatccatgtaagtagatgcctttacc
tgggcacttgaagttcagaggagacaggtctttagatagaaatgtgcaaattacttatgt
ggttattgacaatcaatgactgttctcccgtagtctcccctcgtg
>scr_gb-bg662990_2 (TOXMARKER Assignment: 90; SEQ ID NO: 90)
ttttttttttttttttttacataaactattttatttaaataaaaccaggactgaccctct
cccacacgcaccagcacatgcactcgcacaatcatgtcctccgtttctgttcctcctgaa
cagccacctcaaaccccacaggttttcattgtgaccatccttgaaacctgaaaattggga
gatcccatgcgaaacactggcactcttcccccaaccctgggcaagcattctcctcatcct
cctggtgggacaggagctcagctcttccaaggcacccagatctggtgtggtttcccttca
cacaacccgggaacaccaatacccagagctgctctttgaggctgggacccctcgcttcag
gtcaactcctctcacacaacagaggaggctttgtaaccatgcttaagcgctctccaaagg
ttcctggcataggtaccgtctggtatgaggaagagcgacagagagcaattgagcaccaag
ttccctaatgccaccctgaaggagggtgccaagctccagttcagtctgtaccaagaaaaa
gcaagcctagcgccacacatggggaaggtggggatggcaaggtctcagccttgagaatct
cacatctctaccctccagcatagatcccatgagggacccactagcaccttggcgattgta
agggctcagcccaactggagacacaccacacaaacagtggccatttggagttggcccaaa
tgcctgtgtcggtaacagggtttgactcccgcatctaacactgactgaaggacacacagc
acagcagctaaggtcacgagaggtgcactgacagaaggtgttgtcttccagaggcacatg
gacatttcacacactgctcacaggcaagctgggacaggagaagagcacaggctgccaggg
actcagcagcgtatctagggcatgccctct
>scr_gb-bi278552_1 (TOXMARKER Assignment: 91; SEQ ID NO: 91)
tttttttttttttttttggggtttggtatcatttattttttttcttaaacccacttgta TABLE 9A-continued gtttgggttcagctgggaagcaggatatacgggtagagggaaggggacggtgcgagcagg
attggcccatagctttgggggcaatctccaaaccctgctccagggaggtaggtcctgttg
tcaggctcccagctggctcaggtgaggctccaaatggatcttctggagcaagtgtcctga
gcagaggagaatttccattctctccaacccacctcctcaaagacccagtcagaaggtttt
ccaacacagtgccaggcagttgaggggacatcaggccacgggcaggcctgagtgggtggg
acaaggaacactgtctggcttctggttccaggtaacaacctaggatgtggctacccagag
gctgccatctagagtgacctccgggagctgcttctcttgcttcctgggctgcctgggatc
caaacctgcagctgccctggttgcaaccagtggtatacttcccaccccccacccctcaga
caaaataaaataaaataaaatacaataaaaattagaataaataccaatcgggtcaacatt
tacatttacacaaatggacaagatgatcccccaaaccgtagaagtttacagactggatgg
gaaggatacgcagatgaagatggttttggggaggaagaggttcgccgtggtggttgatgg
tggggggtcctggccctgtccaggggagggccagagccctgcaggaactgtggtctcaga
gcttaggcaatacggccagttcatgaggagaacagtgacctgcaggccacttgagtagaa
aacaaggaccaacttgtcctgacaggtaggggagcctaaaaaggctcaatatgagatcgc
catggccagcaggacaccacagtttgggagaggcttcgcctcctgttcatccattcagag
gcggctttgataggccgtccctctggcagcgggagagcctctggcctggggaggtcaggg
tctgtgggtacctgcaacgcccctacttcccctcgtgccg
>scr_gb-bi278749_1 (TOXMARKER Assignment: 92; SEQ ID NO: 92)
tggctcagtggtcgagcacagtaacaacatggagattctaaaaacagagaaagagaaaag
caagaagatagtggagggagacaagaagaaaggctgggggccagttttgttatttttgt
tttggttcagctatatgctccacacttccaaagcagcaaatgtgttgcatcaccacccaa
acctgagaaagctacagcatcactggcaaggacaagctagcgcacgggtgacatcctcta
accctgccattgtaaattatacaactgcagtttccagcacacaccattgcctccgacact
attggagagcccgtgacactccaaaaactgctaaggcctttacagtatctgaccttcaat
ggccccgaaaactggtaggccgcttctccccattccaacccaaaaattacatgcgagcaa
cggaagagaaaagcttttaagcccgcgcggacgaagagaccagcggacgctgctgaagac
cacagaccaggtaagccagctgaggctggagtttattgccgatgagcgctgagtcctggg
gaggagcggggaaggataaggtcgggcaggatcaggaccttggctaggagaggcggcgcc
acgaaggcgaggccgggaggtgcagacagacaggcgcaggccacggtgggggcgggccag
gctatccaggcactcggtgagcggtctccggcgtcgctcccggagctgggtggcggctgt
ggcggcggctccgcggcagtcctggctgcggtcgtggcccaccggaggccccaagcaagc
aggacgcggcgggaggcggggcgggtggtgctgctcgagcacacggagcagctgcagcgc
tgggcaaggggtcggcggggcccgcaggcggccgcgtggggacccagatgagcccgtagt
ataccgcaagcaacacagcagccaaggatacacacaggaagtaggcgcagacaggggcga
gccgcagccatcgggcgcggggcccctcgctcagccccgtaccacctgggctctcgccac
cactgcccacgcagctcgagcccccgcatgcgctgcccactcagcctgtaccgaccccgc
ccccaccccgccgcttctagcaagccacgccccttctagagtcacgccctatcagaccgc
caccccccctcgtgccgaa
>scr_gb-bi295938_1 (TOXMARKER Assignment: 93; SEQ ID NO: 93)
aaaaatctcgatgccctcaactgttaggttaaagcctgacctgtgtcactatgtgctgtg TABLE 9A-continued acacgaacctaattcccaagtggacagggacacctgagtggcatttcgtgcttcagttcc
ttccctcatgattcttgctgggtcctcttcactgaggctctcccctgagtcatatattta
ctggaaaggctacctggagagcctttgaattgtgggcattcctttttaatgtgtccctct
cttccacagatgaaacagcgcttttctcttgagtctctgtcatcctgtctcttccacttt
tcggctggtgtcctgacaagtttctcccggcccaggtcaacagctgccctcattggcttg
gctttggcagctgtgcacggtgcagccttgtcttcttttgctgacacttccttttctgtg
tacttgttctgaatttctttgtcctctttgcttctttttttctttgctctctgtgtacctt
tggtttggggtatcttcctggtctcgccgccgcctcacttttctcctcatgggacagtcc
ttcatgaagtggccaattttcccacagatccggcagcacctgtcatttggggccagttct
ccctcagtcaggacatccggatcaaagaagtatgccaggatgtcctttggaaatcctttg
actggaattccaaatactcttctaccattgataaaagctttcattataaaatttgtcatt
ttccttgataatccagcaccaagattgtggttcaaatcaaagggatcttcaatgacgatg
tattttgaggtccactgtttcttaaaagttgtaagcagactttttcttctgatgctgatt
acgtgttccttaaagtcaaactcctcagtgtagaagcgtagaagtcccaaccacagctgc
ccaacagattctgtatttttttccatattctggccaacaagtgggcagttcatttatttga
tcgaaaaagtagatattccagccatcaacaagtatttctggtttcttttcacctttgtat
atctcctgaagcacagggatgacagggggggaccgctgctggaggaagtacagcaccata
agagtgtaagcgtatgatgacaagctgcctctggacgcgtcaccgatgtcacacatcttt
gtgaacactttcatggtgtagcacaggtatttcactctggggtcaatggctgagtatgca
aacaggagccgcgtgttgtgaagagccagtgtgtcctcgtg
>scr_gb-bi296376_1 (TOXMARKER Assignment: 94; SEQ ID NO: 94)
ttttttttttttttttttccaggagtcccttcggtccctgatagcgggagcctggacctc
tgaggccgagagggtgctgtgtccccggcctccgagccgaggtggcccggctagggggcg
ccacggagtttttttttttttttctttttcttttccaggagtcccttcggtcccagccag
cgggaccatagacacttttgaggccgagagggtgctgtgtccccggcctccgagccgagg
tggcccggctaggtggcgccacggatttttttttttcttttccaggagtcccttcggtccc
tgatagcgggagcctggacctctgaggccgagagggtgctgtgtccccggcctccgagcc
gaggtggcccggctagggggcgcctccgaggctttatttttttccaggatcctccccggtc
cctgccagcgggagcatggacttctgaggccgaggggaagctgtgttccaggctatctac
catggcctcctcggtctgtgagcactcagggttctaaggtcgaccagttgttcctttgcg
gtccggttctctttctacatggggacctcttggggacacgtcaccgaacatgacttccag
acgttccgtgtggcctgtcatgtttatccctgtgtcttttacacttttcatctttgctat
ctgtccttattgtacctggagatatatgctgacacgctgtccttttgactctttttgtca
ttaaaggacgttggaagaggcttgcaccaaggctgtttgcttgtccagccctagctcttt
tcttctgcgcatgggcctcttcgatgcttgaagcttagcgtccccccatgagtacgcgct
tcctgctttcccgtgcttgcttgcctgtgctctgtggggcagctttatgacaaccgtccc
gcgtgtcaggcgttcccgatttccccgtggtggttgtcgtccgttaccggtaggagtcgt
tggtgccgagtgcgactgaaagggttttcccgtttggtgctagtgaccccctggcgtgct
cctctgcggccgaccggtttttttatttgtttttttttttttttgttttttttttgttttt TABLE 9A-continued tttttgttttttggaaggagttcccgaacctccgctgcttggtggtgtgtccctttctt
tcctgctgtgtgcctcccgagttgcaccttttctccttcgaaggggattttattttttta
tttttatttttttttattttttatttttttgaaggagttcccgaacctccgctgcccgt
tgagtcccgttcttccacgccacgtgcctcccgagtgcaacgcttcctttttttttctcgc
cctcgagaagggtaaatttttttttgtgtgtgtgtgtggcagtgttagcgacttcttcc
cgtgctctctctcgctcttctcgctcgtattcccgtccagtgcgtgttagaaagctctca
cgcccgttgttcccgatgcatggcgtgtctcgctcccgttggatcgatgtggtgctgccg
cgttctcttcgggccggggcctaagccgcgccaggcgagggacggacattcatggcgaat
ggtcattcagcgcgaatggcgaccgctcttctcgttctgccagcgggcccctcgtctctc
ctccccattcctttgcagggtggtgtgtggaagtcaggggtgcggctgtccggcacgagc
gctgacccgcgcacacttgctgctgtggttcgcggtgtccctgtggacgtgtcgggggcg
cttgcccccacgccgttcactgcttcgcggccctcttcccccgtgccgggggaaggtggt
agacccgctgcggtgcatacccttcccgaatggtgtgtgcacgcgccctgctttgtgtga
gccttgcggtgctcctggagcgttccgggctttgaccaccaaggtgcccgcttctgagtt
ggcggtggcgcttcccgctccccggcgtgcctcctgtgctccatggtgcttgtgccttta
cgctttcccttgtcctagttgccggctttctgcacggtgacagaaaggggggggtcgag
gagttgagtgtgcggttaaaaggctccttccgttgggtgagcgcccaccccgtgcctatg
tttttggtgccttcacccgcgggccctgcgcggttagggtggtgctgagcgatcgcggct
ggccctttttaaagaccggactccctcaagtcaaggctcctcctttgtgtgcgccttgaa
gaggcctggccctcggcggggacctgtcgcaggtccccccggtccgcgaatgctcaagaa
gaccccggagaaagagacctttgccgataccgcagaccccccaccagctggcgcgtggtc
cttcccgttctgtcccgcgcctgttgctcgtttcccgttgcgtgcacggagcccttggct
gctcgtcggtgttgggttcgtcccgccctcagtgaggaatttgccttctctagctatctt
cggaaagggctttacgatctccgaggggcttctcccggatggtcccctcggctgcccgcc
ctgacctcagccttctgcgcgcagcgtttgctctctcgcctaccgcgacccgcgcctccc
cgctccgagtacgaggagggatcacgcgggacggggctctgtcgacctgccgctgtgcgg
agcttgtgggggagattgggtttctggtggcaggtggcggggaagggccgtgcac
>scr_gb-bm384392_1 (TOXMARKER Assignment: 95; SEQ ID NO: 95)
ttttttttttttgtttttcaagttgcacattttaatttacaatgtttaccagtaaaaagg
attagttacaaaaaggaaagctgtctgtacaaaataagggttttttttttcacattcat
aaagagaacccactgtgaattcttaccttgtgaagtcaatactcaaacagctcactttgg
taaaactatcttggaaggactagtaatccaggcaagataataaaattatcagcttcccaa
tcatgtccaggagaaagaattttctgaacattttccctgtacagaaaagctctctgtact
tgcagatccttagaaaagccagtgctctcaggagacagcctggtaccaggacgaagcata
atctcctgctcactcaaatggcaatccttcctgaatctgacagacacacatttatcatag
cctcaggtcagcaggagaaccagatggttcaggatcagcctctctccactcaatagttta
tcatataaattaaatatggagaggtacacatgagaaagggggagctctttttcaaactcc
cacttcctaatataatacacatcacagttttaatgagcagagaagggtaagtcaccctgg
tttgggcacatttcctcaagggaaaaaccaaagtatcaaaagccttcaaagcatactggc
ccgtcccactgcagccagcagcctgattccagaatgaaagcatacagtagctgtaaagcc TABLE 9A-continued ctggagccttcagaaagctttatttagtgataagctgagctctgctggcaaaagcccacc
tataaaaagggagcaggtctgattcacaaagtgtatacatgcatgacccaaggtaatgaa
gaccttcaaatgcaaatgatcctaaagctattggaacctctaattacgagtgacccgttc
agatgtgcctccattagccttaaaaactgaccaacacacatctgaagaggcacttccctt
agcattaacataaacacttgaccagaaaaggcatggtccaaaaaacagttaactaaaaat
ttagagtctaaacctctcttctccaccgactgaatgaacacacccgcaatgaggaccaaa
cagaatcagtgcctccagggacgtgtgtctgtctggccatgtgatcaggaacctcctaac
atagcacagcacagcacagctgctctgggcacacaaagccagttcaccccatgaagaaac
acaagggattgtgattaaacccatcccctgtgtcaggagcaactccactatggttttgat
cactcagctcagagggataggagtgcctagcaacaagtcctaatcctcgttactcccagt
ccgggccctcactgactcagaggtgcctttgtgtataaatatgtgagaggcagcaaatgg
cagcactgctgacaggctaatgcaggccccacagcggagaaagttcttcctctgctgctc
caatcttctccctacagttacagtcctgccagtgatggccaaggaccatgtgtgagccag
ctctttgtgaccaagctttggcaagtcagtaagtttgtcaaaggcaaaatccttctgtgg
acaatgctagctgcagctctggggacgtgtgagagaggagagggtcctctgacgggattg
gggacgtgtgagagaggagagggtcctctgagaggatttgactcatcagcccctcttgcc
cagttcattaatcagaaggaaggggagaggagaagacagcagaacatgagtcagttgtga
aatctgcacagctgacatttgctcttcacagcagaaaggacttgaatgagaatcatgaaa
cttgaggaacacttgtattttccttcgggatttaaaaatgtgtcttgtaccaaaagacta
cattcagtgtgggtcaggtccaagagcggcagcaagagctcggccattaagcgtgcccag
cactgggaggagactgtcatctgcttagcatggctggtgagcaggccagggctgctcctc
actggtctccaagtcggaagccctggccccagttgtgtctcccacctccgccattctgat
cagcagctcgcctcatgcttgcaggggggcacaccgaagcccgacacccctcctctcctgc
tgggtagccagcggtacaaaaactgaggtgtggacagaaaattccttcctcccaaatcca
ttgggtatctgaacatcaggaagaaataaagatgtccgacaaggtttccaatgagctcat
tgatgaccgagcctccaatgatatagttgaatccgaggataacccaaggtaagtaacagg
ccttaaatcgtgttccaaaccaaaatgatacaatcaggtctctgttcagctgggcccaga
cgtaaagtactgacatgattagaggaatcatcagcaactgcatatccatggctaagccag
taataacaatgcagatccagttg
>scr_gb-bm387477_1 (TOXMARKER Assignment: 96; SEQ ID NO: 96)
aaatttcaagaggtcagagtggggcttagattaagtaactaatgcacagcaaaacgctgt
gagattaggtgtgaaggagctggctgccctcctgtctcttcccttctctatcccacagga
gctacagagagagcacagcagccagacgctggccaaacagggaacactctttatgccaag
tcgcaaagatgacaagcggcatgaggaggacccagggccctcctttgtgtggaaggacgg
agaggttctgggagggctgggaagggtatgggaggatcctttgtgtgggaggattgagga
aggcctgggcaggctgggaagggctaggaccgctctcctttgtgttagaggtctgggaaa
gtctgggaggatcctcctttgtgtgggaggactgaggggctctgggagggctgggagggc
cctcctttgcttcacagttttagatgttgttccatctgctctcggagtttgaatttctgg
atctttcctgagacagtgagaggatagccttccacaaacacgatgtatcggggaatctta TABLE 9A-continued aaatgggaaatctttcctttgcagaaagctttgatctcctcctccgtggtggtctctccg
cctcgtgcca
>scr_gb-bm986259_1 (TOXMARKER Assignment: 97; SEQ ID NO: 97)
gtaacccacctccattctgttcttcggacgcttgcgccagtgggtcaattttattttctt
tcaaaaataaaagtcgagtgcattcagagacggccttaaggcaatacgcctcatcttccc
acagtaaagatggcgacgccgtgagtaagttacaagtaactccacttccgcaattttctt
gagccctggtccaagatggcggacgaggccacccggcgggtcgtgtctgagatcccggtg
ctgaagactaacgccggaccccgagatcgggaattgtgggtgcagcgactaaaggaggaa
tatcagtcccttatccggtatgtcgaaaacaacaagaatgcggacaatgattggttccga
ctggagtccaacaaggaagggacccggtggtttggaaaatgctggtacatccacgacttc
ctcaaatacgagtttgacatcgagtttgaaattcctatcacatatcccactactgctcca
gaaattgcagtccctgagctggatgggaaaacggcaaagatgtacaggggtggcaaaata
tgtctaactgatcatttcaaacctttgtgggccaggaatgtgcccaagtttggactagct
cacctcatggccctggggctgggtccttggctggcagtggaagtccctgatctgattcag
aagggtgtgatccagcacaaagaaaaatgcaaccaatgaaggatgaagcttctgaggcag
gacagagggactgttgctagactctgattctgtttcctcctttctcatgattccttcaag
ggtcacctctggccattacaaagtagctggagggacaaataacaaaacccaacaaaaggg
caaggtcacaaagttgctaaattaagctgtacagagaggtgaaagatttgggccttgaaa
gaggcggtttgtatcccttctccaagcagagccctggaggcattttggagacctggggtg
taactgacagcatatagctttttgatttctggagacaacctgtcaataaaagctgcttcc
catggtgtgaaaaaaaaaaaaaaaaaa
>scr_gb-s69874_5 (TOXMARKER Assignment: 98; SEQ ID NO: 98)
tttgctatctgcacagcccatcgagggacctgaggtggcaaaccctggacagtgggtcag
gcggcgctcacgtctggggtgacaggatgaagcgggctgtgggctgtgtggagcaccgtg
cacccctagcacctttgggtttcttgtggagttctcgccccagacatcagtgcactggat
tgcaaaaggcaattcatcttttattggatcaggagcgccatttggagtgtgccattatgg
gaggctcgtagctgtctgtccctcgtgccgaattcggcacgagcccccctttttttttt
ttttttttttttttttttttttttttttgaattagcacaaacgcatttatttactaa
ccaaaggaatgatcctgggtaaaccaacggtctgacatgggtttcgggtaaagtgtctat
gatgaaaagtcatgaaaaataaaaccaaagaagtgaagcagtgtggttctgtacgacctg
ctcattgaattgagcttattccctcagccagctgactgctgtccaggatgacgagttagc
cagtcctcattgtaccttctcatagacccgagtacagatggcattgttcatgacgcactc
caccaccatcttcccgtccttcagttttctcgttatcgtgctttctttcccttcccactt
ctggtgctggaccagggcaccgtctgtgaaggtgcagaccgtctcagttttcctgccatc
agctgtggtttcatcaaacttctctcccaaggtgcaagaaaacacggtcgtcttcaccgt
gctctcagttttgacggtgaggttgttgccgtcgagggtaatgatgcagtctggtttggc
catggcacccatcttcctaagagccagccctactcctagttccttcatgtagtcctcaaa
cccgtggctttccaccagacgccacttcccttccaggtccttaaggctggccatggcgag
cgggagagcacaaaagcagcaaggagacgcggtggcgggggcgctgagggaataagctca
attcaatgagcaggtcgtacagaaccacactgcttcacttctttggttttatttttcatg TABLE 9A-continued acttttcatcatagacactttacccgaaacccatgtcagaccgttggtttacccaggatc
attcctttggttagtaaataaatgcgtttgtgctaaaaaaaaaaaaaaaa
>scr_sc-119263563_1 (TOXMARKER Assignment: 99; SEQ ID NO: 99)
ncctagcagaacgcttgttaggagtctgtgggacaagatagcctctgataaaataaactc
taaacatgaactccttcaagaaaaaggactggactccaccactgttcaataaagtcacag
cgagggatgctagaggcggtagacagaaattaagacattctagatacggggagtggccac
ttggttgggccaccacttgccttagcataggtaccataggctaagcatggaaggcagtaa
gggtggatgtcattttaatgagagcagcaaatttagtacatggtttatcaaataaaaggt
aaaggagtccaagatcaatctgacaaatagatctatcagctgaattgtaatcttggggtg
gaggggtcagaggtccggcaattg
>scr_sc-132556005_1 (TOXMARKER Assignment: 100; SEQ ID NO: 100)
caattgctgctctaggatagtcagagtgtgttctctgtctcctgggaaacagtggaccag
gaatgaaagcttcaacctggtacccagattttagatgttttagggacaatcagtcaaatt
tttgtgtgaatgtatgggtttatatgactataactgtgtaagacagagaaatggatgtac
a
>scr_sc-132570828_1 (TOXMARKER Assignment: 101; SEQ ID NO: 101)
ccatggacataactacctcctgattaagtccgttaattgagacctaatcagtctgttaga
ttattgaaacaggtcctgttagcagactgcagggagaaaacacggtcatgaaccaaagag
tgagtccgga
>scr_sc-132947646_1 (TOXMARKER Assignment: 102; SEQ ID NO: 102)
aagcttcctccatttcccagtagtgccatacgctggcaaccataggatcc
>scr_sc-133387221_1 (TOXMARKER Assignment: 103; SEQ ID NO: 103)
aagcttcaactgtctatttattcacagtcacactggctgagatgtcctacactgtgtcca
gtgcaagtgctgacactggacattgatgtcttcttctgtatcttagaggaaaggtcggta
gaggtagagcctggcttccggcttgtcatacatgaccccctaagtgattatttctactgta
ccttattctcagaggaattttatcatgaaaggggtccaggagtctccccacaaaccttag
gaacaccaatctcagtcagacagggatgttttgaatgcacacctaaagtctgatca
>scr_sc-133555783_1 (TOXMARKER Assignment: 104; SEQ ID NO: 104)
gctagccatttggtatttattagataacaagttagggaactcatgccttggaaaggtgtt
gttggttgcttgtagttctttgtctggcacagggaagctacagctattatctcaataaaa
tagctgtcccttggatttttttttttaaataattgcttattcgagccaacatctaaata
aggtgcatgcattgtatttgcttgatacgtttgttgtgtctctttttcttcttctgtaag
tttcttcccctccttatttttctttcctcgtattgtatttactggaaaaaccagatcgcg
cgccctgcaggcttctgtaca
>scr_sc-133678871_1 (TOXMARKER Assignment: 105; SEQ ID NO: 105)
agatctgaaagttaggcaaaatataagagcagccctctgaagaggggacctgccagctca
cttgggactcaacattctactgtagagctagc
>scr_sc-133725675_1 (TOXMARKER Assignment: x106; SEQ ID NO: 106)
agatcttggggtttcaggcttgtttggcattcaattttaccttctgagcccaggagcgag TABLE 9A-continued aatcttgaactaaagagggcttgacagtgctagc >scr_sc-133955481_1 (TOXMARKER Assignment: 107; SEQ ID NO: 107)

caattgaacagtagtctgtaagtagtgcaacactgtaaaatgttctctttagttcagaga gaaaattcccaagcattattccaactgctgctaaaatagatgttataattatcagtttaa tgccagttccaaacccctaaataagcaaatattactgttattgccagcaacttcctgaaa ctacacaaattcagtgtatccctccctccctcttttcctttcagtcatgaagggagcaga tacaacccagggtccaagataggtaagtgatccttagatgattttagatagcaggtggtg caaacttttaatcccagcacttgggaggtaaacaggtggatcc >scr_sc-134521597_1 (TOXMARKER Assignment: 108; SEQ ID NO: 108)

nctaacaaagatggtttagagatccaggtcaccaatcctcttctcagacagacccatttc tggggtcaacagccattactgcatgtagagtaaagggaagtaagacagagagagttcatg ggcagtcctaactggctgtgtggaaacagctttccaattgttctgggaatgaatgtagag tcagtgtccctgcatgggtcatgataagagtgcctgcaagtgaggcgctcacaagctt >scr_sc-172126480_1 (TOXMARKER Assignment: 109; SEQ ID NO: 109)

ctcaggttggccttaaactcactatatactcaaggatgaggttgaacctatcttcctatc tctgtctcctgagtgtactgggattgtacacatgtgccaccatacctggcttacgtgatg ttgtggatcaaacccatggctttatgtatgctaagcaagcactttatcaactcaaccaca attcatctctatattttaaatgtaatattcctaatatgtctttacattttccagctacat tcctagg >scr_sc-172130231_1 (TOXMARKER Assignment: 110; SEQ ID NO: 110)

tgatcaagagtcccaaacccagagagtctggggtgctgacatctgaatgtggctggcctg ccctggctgactgctttcagtgccagccacactgatgccccttagccctctggggttaat ttaggaacttgggctcaggccaccgtcaccagcaatgaactcacaaagaatgagatgtgg ctgttgatttcctagg >scr_sc-172755010_1 (TOXMARKER Assignment: 111; SEQ ID NO: 111)

agatcttccggagcaatggggttcagcttttgcagcgcctactggacacgggagagactg acctcatgctggcagccctgcgcacactggtcggcatttgctctgagcaccagtctcgga cagtggcgaccctgagtgtcctaggaactcggagagtcgtctccatcctgggtgtggaaa accaggctgtgtcgctggcagcctgccacctgctgcaggttatgtttgatgccctcaagg aaggtgtcaagaaaggcttccgaggcaaagaaggtgccattatcgtggatcctgcccggg agctgaaggttctcatcagtaacctcttggagcttctgactgagatgggggtctctggcc aaggccgggacaatgccctgaccctcctcattaaaatggtacctcggaagtcaccgaaag atcccaacaacagcctcacactctgggtcattgatca >scr_sc-188295137_1 (TOXMARKER Assignment: 112; SEQ ID NO: 112)

gctagcttaagggttcttctgtaggccgcctcatttcctggtttaattttactttatgta tatgatgttgcctggatgtagatct >scr_sc-190079504_1 (TOXMARKER Assignment: 113; SEQ ID NO: 113)

agatctttttgcttcccttccttttattgatccttaggaataaatcctcccaaactctg ttgtttttaaagttttttgaaagacctgattttttttccattttctttgcccttgcaaat aaccatcagtgtaattagttgtccatgctgcaagggaatactttgtgaggggaaataagca TABLE 9A-continued agaattgagtgttgtttactaagaggtcacgcggatggtttttgggtaattatttactag
t
>scr_sc-191455923_1 (TOXMARKER Assignment: 114; SEQ ID NO: 114)
tccggagctggggactgaacccagggccttgtgcttcctaggcaagcgctctaccactga
gctaaatccccaaccccgtcaaaggccatttttatcctcatcaaacaattataccttact
ttttgagttggaaatgtaattcagtaatagtctgttttcctagtatgtacaaagtcttgg
gctccctcactaacaccaaaggaaaggggaaaaaagagctcacttctttgactttcagtg
gccttccactcagactatgcttgtttagaacttcggcagctttttttcatgctctcctcca
tcttgaactcaacaacactataaaaaagaaaagccaaaaacaaatgaataaaaccagtct
tacttggaaaattgaacttggaaaattt
>scr_sc-195460151_1 (TOXMARKER Assignment: 115; SEQ ID NO: 115)
tctagagaaatatacatagacagcaaggctggagttgagccaggcaacctaagctgggcc
accggagtcaggcagctgcagaaggtcacgtgagcaggcccagtgctagcctgtgacgga
gtgatgtagacactcagccacaccagggagccaatctccaagttgtcttggctagactgt
ggactctgcccttcatgggtctgccacacaggcattctggaactgtctagctagctcttg
gggaaacagctaaaaggactttggcttttctggggtttgcagggagggtaacagtgtctg
cgcccttgttctctacttctgaatgtagtaacctcaccctctggggtagcatatgacagg
tacccaactccttttcgtgggcaagcctctggcaggggagctctttctgttgcaatgtaa
cagaggcattgcctctttcaattg
>scr_sc-198205946_1 (TOXMARKER Assignment: 116; SEQ ID NO: 116)
gtgcacagaagtatgtgttctgggtcggaggaaagatggtaggtgtttgtcccaacacag
tgaaaaggaacagacatgtgaagtcttcagactgtgggcctttgatttacccctcagttg
gtctatgtgtgtaca
>scr_sc-2573087_1 (TOXMARKER Assignment: 117; SEQ ID NO: 117)
caattgcattgcaaaattttaaaggttacattgaaaacacttgaaaataagccaccaata
aatgagatgacgataataagagcccctaaataaagaggctaagaaggagttaagtgtaaa
ggaagagggaagaaatagttaaggcatttataagacactagaaagtctagaagagagaat
gttagcagtacggagtcacagctaaaaatctgcatcttgccctttaaaacccaagagaga
aagctt
>scr_sc-2585074_1 (TOXMARKER Assignment: 118; SEQ ID NO: 118)
agatctgctggtgtttgcctccacagtggtgaggttgcatgtacatgccgaccatgctcc
tatctttcacatgagtgctgtggaatgctcaggtcttagtgcttgtacaagcaccttact
caactgaaccattgtcttagcccaatagtgaaacactgaaaagttattttacccatgatc
agaagctttaacaatcaactagt
>scr_sc-8571871_2 (TOXMARKER Assignment: 119; SEQ ID NO: 119)
cctaggtctgccagtgaataagaagacccctccccggaaagtcccgagtttatgttccat
gcgctattcaatagccttcatcgcacatatctgcaacttcacattgatagcacagaattc
catcataagcatcaccatggtagccatggtcaacaacacggaccagccatcccacctcaa
tagctctactgaatggtttcctgatggtttaaacggtgatcaacatgaagctt TABLE 9A-continued >scr_sc-87731837_1 (TOXMARKER Assignment: 120; SEQ ID NO: 120)
tgtacacaggtagtcttaggatttctgttgctgaaaccgtgggaagggaacagttcaatg
agtaaaaccaagacagaagtcaacctggttagaagctggaggcaggagaagatgcagagg
ctgtggaggggtgctgcttactggcttgctccccatggcttattcctgctttcttataga
acccaggaccaccggcccaagggttacaccatctgtggtgatctgggccctcctccatca
accactaattaagaaagtgtccaagtttggctatatcttacagagatgttttctcaattg
>scr_sc-87869413_1 (TOXMARKER Assignment: 121; SEQ ID NO: 121)
cctagggaatttgccattgtttagtttaagctaacactccaaaggtaatctcctatttcc
tcttttcctttctgtcctccatgtggctgtcatgggcatgcagcataccagttctcaggt
gcctggaacactggccagtgctctagcccagccactgtgccctgaaatccttccctgtgt
tcaatgctacagcacatcctccagactgcctccccacccccagcaaccgaattgagcagg
gacactaagacagtcctttggagacttccactggtctgttgaaactttggctgctctcac
agcatagctcctcttagcctgtaacttagtgctgctcaggctgactgatca
>scr_gb-ai233262_2 (TOXMARKER Assignment: 122; SEQ ID NO: 122)
tttttttttttttttttaaggggccaagcagaagacaagctgcctttattatagttgatg
tcacagctctgcttgtaatagattcagccccagaaacaccccggttaaaacagcacggtt
gacttcaatggatagagtctttggtaaggtgaaccagaccagggctgaccgacaatcttc
gggcccctggcccaggggtagcctgtagtcttacgtgaggcccagcatggcctgaagttc
ccgagctttatcatctggcagagagcccagggctgtgtggaagctgtcgctgtgctgctt
ggccaggaacgtcagtagtagtagcagtgcggccttggtgtctgggggggatcctgttgtc
tggcaggatcaggctgcagatgcgcaggagctctgaagccacacccacaacctggtcagg
gttgttctggtgcaggaagctgaagaggtgacctatagtgacccattcctccatgtcttc
cttcaggggcagggcatgtagcagggtagctagcacctggggctctgtttttcctgccgg
actggccatcagcagacgggcaagagccccacagatgttatcacggactcgatcatgccg
ctcccttgccaggaggggcaaaaggaggcccagtagcttagggaagtggtcctgagcagg
gcagcccccatgctctgcaagtacgcccagcccaaagatggcattgctccgcacctcggg
gtctgcttcccgggcattgtttaacagcacaggaaacagccgggacacaaattgggctga
ggcagcacctagaccctgaatggattctgccagtgtccccactgcaaaggacttctctgc
cactgtacagctctgtttcgtcttacacagcaataatggcaacctcgtg
>cgrrs0h0310.9_13952-135 (TOXMARKER Assignment: 123; SEQ ID NO: 123)
tgatcaagggcgacacatctggagactataagaaggccctgctgctcctctgtggaggcg
aggatgactgaggagctgcctggagtgccctgggcccgcctgctgcccaccatcagcttc
cttcagcaccacgcctacttacgttcaatgcctgcctgcctgccacgctgccttactcac
acgagtgtgtgctaatgaccaaagctgtctcgaatgaaagcagtgttctgctgttctgtc
tgacatagaccttcccacgtctctcagtctagtatctctaagttgcgttttctatcctct
tctaaagctt
>scr_gb-m13100.5_2 (TOXMARKER Assignment: 124; SEQ ID NO: 124)
aagctctggttgcttgacattgttgtacatatagggtctcgagccccttagagctcgtcc
agttctttctctgattccttcaacgggggtcctattctcagttcagtggtttgctgctgg
cattcacctctgtatttgctgtattctggctgtgtctctcaggagagatctacatccggc TABLE 9A-continued tcctgttggtctgcacttctttgcttcatccatcttgtctaattgggtggctgtatatgt
atgggccacatgtggggcaggctctgaatgggtgttccttctgcctctgttttaatcttt
gcctctctcttccctgccaagggtattcttgttcccctttttaaagaaggagtgaagcatt
cacattttgatcatccgtcttgagtttcatttgttctgtgcatctagggtaattcaagca
tttgggctaatagccacttatcaatgagtgcataccatgtatgtctttctgtgattgggt
tagctcactcaggatgatattttccagttccaaccatttgcctacgaatttcataaactc
gttgtttttgatagctgagtaatattccattgtgtagatgtaccacattttctgtatcca
ttcctctgttgaagggcatctgggttctttccagcttctggctattatataaataaggctgc
aatgaacatagtggagcacgtgtctcttttatatgttggggcatcttttgggtatatgcc
caagagaggtatagctggatcctcaggcagttcaatgtccaattttctgaggaacctcca
gactgatttccagaatggttgtaccagtttgcaatcccaccaacaatggaggagtgttcc
tctttctccacatcctcgccagcatctgttgtcccctgagtttttgatcatagccattct
cactggtgtgaggtgaaatctcacggttgttttgatttgcatttcccttatgactaaaga
tgttgaacatttctttaggtgtttctcagccatttggcattcctcagctgtgaattcttt
gtttagctctgaaccccatttttttaatagggttatttgtttccctgcggtctaacttctt
gagttctttgtatattttggatataaggcctctatctgttgtaggattggtaaagatatt
ttcccaatctgttggttgccgttttgtcctaaccacagtgtcctttgccttacagaagct
ttgcagttttatgagatcccatttgtcgattcttgatcttagagcataagccattggtgt
tttgttcaggaaatttttttccagtgcccatgtgttccagatgcttccctagtttttcttc
tattagtttgagtgtgtctggtttgatgtggaggtccttgatccacttggacttaagctt
tgtacagggtgataagcatggatcgatctgcattcttctacatgttgccctccagttgaa
ccagcaccatttgctgaaaatgctatcttttttccattggatggttttggctcctttgtc
aaaaatcaagtgaccataggtgtgtgggttcatttctgggtcttcagttctattccattg
gtctatctgtctgtctctgtaccaatcaccatgcagtttttatcactattgctctgtaat
actgcttgagttcagggatagtgattccccctgaagtccttttattgttgaggatagctt
tagctatcctgggtttttttgttattccagatgaatttgcaaattgttctgtct
>scr_sc-170396977_1 (TOXMARKER Assignment: 125; SEQ ID NO: 125)
tgatcacgctcagcccttggtaggacattctacagagtctcttgctgcccctccgtctgt
gccagtggtaccacacggggcagcctccgtggaagtttctagttcacagtatgcagctca
gagtgaaagtgtggtgcatcaagactccagtgtccctggaatgccagtacaaactccagg
cccagtccaaggacagaattacagtgtctgggattcaaaccaacagtctgtcagtgtaca
gccccagtattctcctgcccaatctcaagcaaccatatattaccaaggacagacatgttc
aactgtctacggtgtgacctctccttattcacagacaactcctccaattg
>scr_sc-14059147_2 (TOXMARKER Assignment: 126; SEQ ID NO: 126)
gctagcatcgtgatggccaagtgcatccctgtgctttttttcttttctaagaaagattgaa
aaccaacagttcttccccaacagctgcctaaattttaaggggtctgacccttacatttca TABLE 9A-continued attggggggaatgaagggggcccaaccggcttaattgctgtgggagagtgagtctggatgt ctgagagagcaccttgggagggactcttcctgcaatgctgtaaatacgagtaccgtttta ataaagcatgtaca >scr_sc-87750810_1 (TOXMARKER Assignment: 127; SEQ ID NO: 127)

tttttttttttttttttggctcctgccatctttttttattggtctgggctgtgggctgggg gaggcaggtgggctcacatctttatgcaagcagcaaggagacggttcacatgctcaggag actccaggaaggccttgagcttgggtcgggctttgagacgcgctacataggcggagagca gggggaagtctttcaagtaaccagggaacaggagctctaggttcagaagtaaatccagta ggcggtagtcggcgaaggagatctggtcaccaacaatgaagcattggccacccttgttct gggccagaagagtttcaaatggcttcaggtgtcctggaagctccttcctatattggccct tgtcctccttacagatatggagatagtgccatgcaatgcgcctgaacacgtcttccagtc cgtcgttcaccatgtccaccagtgctgcctcttgctggtctttgccgtagagcccgaagg agtggcccaggtgccgtaggatggcattcgattggtacagagtgagctttccatcctgga acttggggatctgcccaaacagacaggaagccttgaatgtgccttgctcccaaacatcca aggtcaccacctcctccttccaactctggccctggtcggctagcagcatgcgcataacct cacagcgcccagtgttggggtgcaggatggggatgaggccacagcgaagagacccaccct cagagcatcctgggagagtttgggagactggaaagctgacaagtggactaaactagcttg ggagcctcgaagggagggaaaaaatgtggtggtagaggccatgtcctaacattatcttgg caagccaagacccagccccaccggcacagggaaggaggaaaagtgacagacagtgtagct gcctatggaggctaagaggtcagtcctggccccaccaaccacaattgtagtcccgcccca agtctcggtcttgcccccaacgtggtcttggccacatccctccagcaccagtgttgaggg ggccccaggagtgactatggcttgtgcccttcatcttgaaaac >cszr_2 02034260_190929676 (TOXMARKER Assignment: 128; SEQ ID NO: 128)

gtgcaccagtacctgatgctgggagatgaatggcttagcgctgttctacttggaacatat cactcctgccagccgggcactaacaattatcacccaatccaggacttaaactgtgataga ctggctgatgtttgcctttgaatagagtgtcccaaaagatgggaccactggtcagctgcc atggactagattctccacctgttgggggcaatctggtcaccttgctgcccaatccgacct ggagccaccacagcacgagtgtcaagcactggcagaagcccatgggtggaggaaagacct ctgcgactggctgattgacccctgctgaaagccgaggctaccttgtccacagacgggaac agttctcttcatga Example 10

Identification of a TOXMARKER 76, 135, 147, 151, 152, 154, and 162 for Accurate Prediction of Hepatotoxcity In order to determine the minimal number of markers required for prediction, backward selection from a larger set of putative markers was used. Each set of smaller markers was evaluated on cross-validation by linear regression and the smallest set that was significantly accurate ($p<0.001$, Fisher's exact test) was selected. The TOXMARKER genes that make up the TOXMARKER 76, 135, 147, 151, 152, 154, and 162 is listed in Table 6 below

TABLE 6

TOXMARKER 76, 135, 147, 151, 152, 154, and 162

| PTS Code | Rat ID No. | TOXMARKER | SEQ ID NO | Gene Name | Accuracy | P. Value |
|---|---|---|---|---|---|---|
| pts2.3014511.1 | scr_gb-bi294409_1 | 42 | 42 | IFNAR-2 | 0.771552 | 4.12E−13 |
| pts2.3013420.1 | scr_gb-af069306_1 | 59 | 59 | Transaldolase | | |
| pts2.3015170.1 | scr_gb-bi288503_1 | 65 | 65 | Clp-1 | | |
| pts2.3011880.1 | scr_gb-d86383_2 | 66 | 66 | Hex | | |
| pts2.3015871.2 | scr_gb-bm986259_1 | 97 | 97 | Novel | | |
| pts2.3012511.2 | scr_gb-aa899865_3 | 76 | 76 | Novel | | |
| pts2.3017180.2 | cszr_204152648_1915 21095 | 71 | 71 | Novel | | |

"P.value" is the probability level that the observed classification is random.

"Accuracy" is the number of correct predictions divided by the number of samples (total number of predictions). It is a proportion of how often the disclosed TOXMARKER 76, 135, 147, 151, 152, 154, and 162s are accurate in screening for toxicity.

REFERENCES IN VIVO

1. Kedderis, G. L., *Biochemical basis of hepatocellular injury*. Toxicol Pathol, 1996. 24(1): p. 77–83.
2. Seeman, P., *The membrane actions of anesthetics and tranquilizers*. Pharmacol Rev, 1972. 24(4): p. 583–655.
3. Rosser, B. G. and G. J. Gores, *Liver cell necrosis: cellular mechanisms and clinical implications*. Gastroenterology, 1995. 108(1): p. 252–75.
4. Neuman, M. G., *Apoptosis in diseases of the liver*. Crit Rev Clin Lab Sci, 2001. 38(2): p. 109–66.
5. Kaplowitz, N., *Cell death at the millennium. Implications for liver diseases*. Clin Liver Dis, 2000. 4(1): p. 1–23, v.
6. Oinonen, T. and K. O. Lindros, *Zonation of hepatic cytochrome P*-450 *expression and regulation*. Biochem J, 1998. 329(Pt 1): p. 17–35.
7. Zimmerman, H. J., *Hepatotoxicity: The adverse effects of drugs and other chemicals on the liver*. Second Edition ed. 1999.
8. Horn, K. D., et al., *Biomarkers of liver regeneration allow early prediction of hepatic recovery after acute necrosis*. Am J Clin Pathol, 1999. 112(3): p. 351–7.
9. Cotran R S, K. V., Robbins SL, *Robbins Pathological Basis of Disease*, W.B. Saunders, Editor. 1994. p. 833.
10. Achord, J. L., *Cirrhosis of the liver: new concepts*. Compr Ther, 1989. 15(2): p. 11–6.
11. Dragan, Y. P., et al., *Implications of apoptosis for toxicity, carcinogenicity, and risk assessment: fumonisin B*(1) as an example. Toxicol Sci, 2001. 61(1): p. 6–17.
12. Newberne, P. M., et al., *The role of necrosis in hepatocellular proliferation and liver tumors*. Arch Toxicol Suppl, 1987. 10: p. 54–67.
13. Troyanskaya, O., et al., *Missing value estimation methods for DNA microarrays*. Bioinformatics, 2001. 17(6): p. 520–5.
14. Breksa, A. P., 3rd and T. A. Garrow, *Recombinant human liver betaine-homocysteine S-methyltransferase: identification of three cysteine residues critical for zinc binding*. Biochemistry, 1999. 38(42): p. 13991–8.
15. Avila, M. A., et al., *Reduced mRNA abundance of the main enzymes involved in methionine metabolism in human liver cirrhosis and hepatocellular carcinoma*. J Hepatol, 2000. 33(6): p. 907–14.
16. Schepers, L., et al., *Presence of three acyl-CoA oxidases in rat liver peroxisomes. An inducible fatty acyl-CoA oxidase, a noninducible fatty acyl-CoA oxidase, and a noninducible trihydroxycoprostanoyl-CoA oxidase*. J Biol Chem, 1990. 265(9): p. 5242–6.
17. Wilkinson, D. G., *Eph receptors and ephrins: regulators of guidance and assembly*. Int Rev Cytol, 2000. 196: p. 177–244.
18. Stein, E., et al., *Nck recruitment to Eph receptor, EphB1/ELK, couples ligand activation to c-Jun kinase*. J Biol Chem, 1998. 273(3): p. 1303–8.
19. Stewart, M. J. and G. Thomas, *Mitogenesis and protein synthesis: a role for ribosomal protein S6 phosphorylation*? Bioessays, 1994. 16(11): p. 809–15.
20. Sturgill, T. W. and J. Wu, *Recent progress in characterization of protein kinase cascades for phosphorylation of ribosomal protein S6*. Biochim Biophys Acta, 1991. 1092 (3): p. 350–7.
21. Vanmuylder, N., et al., *Heat shock protein HSP86 expression during mouse embryo development, especially in the germ-line*. Anat Embryol (Berl), 2002. 205(4): p. 301–6.
22. Dale, E. C., et al., *Murine 86-kDa heat shock protein gene and promoter*. Cell Stress Chaperones, 1997. 2(2): p. 87–93.
23. Kanamura, S. and J. Watanabe, *Cell biology of cytochrome P-450 in the liver*. Int Rev Cytol, 2000. 198: p. 109–52.
24. Trottier, E., et al., *Identification of CYP2B14P and CYP2B16P, two apparent pseudogenes in the rat cytochrome P450 2B (CYP2B) subfamily*. Biochem Pharmacol, 1996. 52(6): p. 963–5.
25. Schaller, M., et al., *Cloning and expression of succinic semialdehyde reductase from human brain. Identity with aflatoxin B1 aldehyde reductase*. Eur J Biochem, 1999. 265(3): p. 1056–60.

26. Weenink, S. M. and A. M. Gautam, *Antigen presentation by MHC class II molecules*. Immunol Cell Biol, 1997. 75(1): p. 69–81.

27. Martinez, O. and B. Goud, *Rab proteins*. Biochim Biophys Acta, 1998. 1404(1–2): p. 101–12.

28. Waisman, D. M., *Annexin II tetramer: structure and function*. Mol Cell Biochem, 1995. 149–150: p. 301–22.

29. Paulusma, C. C., et al., *Congenital jaundice in rats with a mutation in a multidrug resistance-associated protein gene*. Science, 1996. 271(5252): p. 1126–8.

30. Suzuki, H. and Y. Sugiyama, *Excretion of GSSG and glutathione conjugates mediated by MRP*1 *and cMOAT/MRP*2. Semin Liver Dis, 1998. 18(4): p. 359–76.

31. Balduyck, M., et al., *Human leucocyte elastase* (*HLE*) *preferentially cleaves the heavy chain H*2 *of inter-alpha-trypsin inhibitor* (*ITI*). Biol Chem Hoppe Seyler, 1993. 374(9): p. 895–901.

32. Diarra-Mehrpour, M., et al., *Human inter-alpha-trypsin inhibitor: full-length cDNA sequence of the heavy chain H*1. Biochim Biophys Acta, 1992. 1132(1): p. 114–8.

33. Sun, J., et al., *A new family of* 10 *murine ovalbumin serpins includes two homologs of proteinase inhibitor* 8 *and two homologs of the granzyme B inhibitor* (*proteinase inhibitor* 9). J Biol Chem, 1997. 272(24): p. 15434–41.

34. Safadi, F. F., et al., *Cloning and characterization of osteoactivin, a novel cDNA expressed in osteoblasts*. J Cell Biochem, 2001. 84(1): p. 12–26.

35. Oldak, M. and J. Malejczyk, [*Signal transduction mechanisms induced by epidermal growth factor receptor* (*EGFR*) *and their role in apoptosis regulation*]. Postepy Hig Med Dosw, 1999. 53(2): p. 315–29.

36. Hayes, J. D. and L. I. McLellan, *Glutathione and glutathione-dependent enzymes represent a co-ordinately regulated defence against oxidative stress*. Free Radic Res, 1999. 31(4): p. 273–300.

37. Kaas GEN, J. M., Orrenius S., *Cyclosporine A protects hepatocytes against prooxidant-induced killing*. Biochem Pharmacol, 1992. 44: p. 1995–2003.

38. Schulte-Frohlinde D, S. C., Radiolysis of DNA and model systems in the presence of oxygen, in Oxidative Stress. 1985: Orlando. p. 11–40.

39. Tribble, D. L., T. Y. Aw, and D. P. Jones, The pathophysiological significance of lipid peroxidation in oxidative cell injury. Hepatology, 1987. 7(2): p. 377–86.

REFERENCES IN VITRO

1. Kedderis, G. L., *Biochemical basis of hepatocellular injury*. Toxicol Pathol, 1996. 24(1): p. 77–83.

2. Seeman, P., *The membrane actions of anesthetics and tranquilizers*. Pharmacol Rev, 1972. 24(4): p. 583–655.

3. Rosser, B. G. and G. J. Gores, *Liver cell necrosis: cellular mechanisms and clinical implications*. Gastroenterology, 1995. 108(1): p. 252–75.

4. Neuman, M. G., *Apoptosis in diseases of the liver. Crit Rev Clin Lab Sci,* 2001. 38(2): p. 109–66.

5. Kaplowitz, N., *Cell death at the millennium. Implications for liver diseases*. Clin Liver Dis, 2000. 4(1): p. 1–23, v.

6. Oinonen, T. and K. O. *Lindros, Zonation of hepatic cytochrome P*-450 *expression and regulation*. Biochem J, 1998. 329(Pt 1): p. 17–35.

7. Zimmerman, H. J., *Hepatotoxicity: The adverse effects of drugs and other chemicals on the liver*. Second Edition ed. 1999.

8. Horn, K. D., et al., *Biomarkers of liver regeneration allow early prediction of hepatic recovery after acute necrosis*. Am J Clin Pathol, 1999. 112(3): p. 351–7.

9. Cotran RS, K. V., Robbins SL, *Robbins Pathological Basis of Disease*, W.B. Saunders, Editor. 1994. p. 833.

10. Achord, J. L., *Cirrhosis of the liver: new concepts*. Compr Ther, 1989. 15(2): p. 11–6.

11. Ying, T. S., D. S. Sarma, and E. Farber, *Role of acute hepatic necrosis in the induction of early steps in liver carcinogenesis by diethylnitrosamine*. Cancer Res, 1981. 41(6): p. 2096–102.

12. Dragan, Y. P., et al., *Implications of apoptosis for toxicity, carcinogenicity, and risk assessment: fumonisin B*(1) *as an example*. Toxicol Sci, 2001. 61(1): p. 6–17.

13. Newberne, P. M., et al., *The role of necrosis in hepatocellular proliferation and liver tumors*. Arch Toxicol Suppl, 1987. 10: p. 54–67.

14. Troyanskaya, O., et al., *Missing value estimation methods for DNA microarrays. Bioinformatics,* 2001. 17(6): p. 520–5.

15. Hastie, T., R. Tibshirani, and J. H. Friedman, *The elements of statistical learning: data mining, inference, and prediction*. Springer series in statistics. 2001, New York: Springer. xvi, 533.

16. Venables, W. N. and B. D. Ripley, *Modern applied statistics with S-PLUS*. 3rd ed. Statistics and computing. 1999, New York: Springer. xi, 501.

17. Shambaugh, G. E., 3rd, *Urea biosynthesis I. The urea cycle and relationships to the citric acid cycle*. Am J Clin Nutr, 1977. 30(12): p. 2083–7.

18. Hatae, N., Y. Sugimoto, and A. Ichikawa, *Prostaglandin Receptors: Advances in the Study of EP*3 *Receptor Signaling*. J Biochem (Tokyo), 2002. 131(6): p. 781–4.

19. Pancholi, V., *Multifunctional alpha-enolase: its role in diseases*. Cell Mol Life Sci, 2001. 58(7): p. 902–20.

20. Norflus, F., S. Yamanaka, and R. L. Proia, *Promoters for the human beta-hexosaminidase genes*, HEXA and HEXB. DNA Cell Biol, 1996. 15(2): p. 89–97.

21. Vinogradov, A. D., *Mitochondrial ATP synthase: fifteen years later*. Biochemistry (Mosc), 1999. 64(11): p. 1219–29.

22. Oldak, M. and J. Malejczyk, [*Signal transduction mechanisms induced by epidermal growth factor receptor* (*EGFR*) *and their role in apoptosis regulation*]. Postepy Hig Med Dosw, 1999. 53(2): p. 315–29.

23. Peyssonnaux, C. and A. Eychene, *The Raf/MEK/ERK pathway: new concepts of activation*. Biol Cell, 2001. 93(1–2): p. 53–62.

24. Hardy, M. P., et al., *The soluble murine type I interferon receptor Ifnar*-2 *is present in serum, is independently regulated, and has both agonistic and antagonistic properties*. Blood, 2001. 97(2): p. 473–82.

25. Prejean, C. and O. R. Colamonici, *Role of the cytoplasmic domains of the type I interferon receptor subunits in signaling*. Semin Cancer Biol, 2000. 10(2): p. 83–92.

26. Nelms, K., et al., *The IL*-4 *receptor: signaling mechanisms and biologic functions*. Annu Rev Immunol, 1999. 17: p. 701–38.

27. Ruest, P. J., et al., *Mechanisms of CAS substrate domain tyrosine phosphorylation by FAK and Src*. Mol Cell Biol, 2001. 21(22): p. 7641–52.

28. Yoshizumi, M., et al., *Src and Cas mediate JNK activation but not ERK*1/2 *and p*38 *kinases by reactive oxygen species*. J Biol Chem, 2000. 275(16): p. 11706–12.

29. Sakane, F. and H. Kanoh, *Molecules in focus: diacylglycerol kinase*. Int J Biochem Cell Biol, 1997. 29(10): p. 1139–43.

30. Swannie, H. C. and S. B. Kaye, *Protein kinase C inhibitors*. Curr Oncol Rep, 2002. 4(1): p. 37–46.

31. Walikonis, R. S., et al., *Densin*-180 *forms a ternary complex with the* (*alpha*)-*subunit of Ca*2+/*calmodulin-dependent protein kinase II and* (*alpha*)-*actinin.* J Neurosci, 2001. 21(2): p. 423–33.

32. Kanamura, S. and J. Watanabe, *Cell biology of cytochrome P*-450 *in the liver*. Int Rev Cytol, 2000. 198: p. 109–52.

33. Ali, A., et al., *Design and synthesis of novel antibacterial agents with inhibitory activity against DNA polymerase III*. Bioorg Med Chem Lett, 2001. 11(16): p. 2185–8.

34. Weinberg, A. D., A. T. Vella, and M. Croft, *OX*-40*: life beyond the effector T cell stage*. Semin Immunol, 1998. 10(6): p. 471–80.

35. Kobayashi, K., et al., *Distribution and partial characterisation of IgG Fc binding protein in various mucin producing cells and body fluids*. Gut, 2002. 51(2): p. 169–76.

36. Miki, H., et al., *All kinesin superfamily protein, KIF, genes in mouse and human*. Proc Natl Acad Sci USA, 2001. 98(13): p. 7004–11.

37. Peterson, M. R., S. C. Hsu, and R. H. Scheller, *A mammalian homologue of SLY*1*, a yeast gene required for transport from endoplasmic reticulum to Golgi*. Gene, 1996. 169(2): p. 293–4.

38. Penning, T. M., et al., *Generation of reactive oxygen species during the enzymatic oxidation of polycyclic aromatic hydrocarbon trans-dihydrodiols catalyzed by dihydrodiol dehydrogenase*. Chem Res Toxicol, 1996. 9(1): p. 84–92.

39. Coyle, P., et al., *Metallothionein: the multipurpose protein*. Cell Mol Life Sci, 2002. 59(4): p. 627–47.

40. Kang, S. W., et al., *Mammalian peroxiredoxin isoforms can reduce hydrogen peroxide generated in response to growth factors and tumor necrosis factor-alpha*. J Biol Chem, 1998. 273(11): p. 6297–302.

41. Banki, K., et al., *Glutathione levels and sensitivity to apoptosis are regulated by changes in transaldolase expression*. J Biol Chem, 1996. 271(51): p. 32994–3001.

42. Stolz, A., et al., *Molecular structure of rat hepatic* 3 *alpha-hydroxysteroid dehydrogenase. A member of the oxidoreductase gene family*. J Biol Chem, 1991. 266(23): p. 15253–7.

43. Methot, N., et al., *The human homologue of the yeast Prt*1 *protein is an integral part of the eukaryotic initiation factor* 3 *complex and interacts with p*170. J Biol Chem, 1997. 272(2): p. 1110–6.

44. Jesenberger, V. and S. Jentsch, *Deadly encounter: ubiquitin meets apoptosis*. Nat Rev Mol Cell Biol, 2002. 3(2): p. 112–21.

45. Singh, O. P., *Functional diversity of hnRNP proteins*. Indian J Biochem Biophys, 2001. 38(3): p. 129–34.

46. Huang, F., M. Wagner, and M. A. Siddiqui, *Structure, expression, and functional characterization of the mouse* CLP-1 *gene*. Gene, 2002. 292(1–2): p. 245–59.

47. Tanaka, T., et al., *cDNA cloning and expression of rat homeobox gene, Hex, and functional characterization of the protein*. Biochem J, 1999. 339(Pt 1): p. 111–7.

48. Yu, F. X., et al., *Effects of thymosin beta* 4 and thymosin beta 10 *on actin structures in living cells*. Cell Motil Cytoskeleton, 1994. 27(1): p. 13–25.

49. Ventura-Holman, T., et al., *The murine fem*1 *gene family: homologs of the Caenorhabditis elegans sex-determination protein FEM*-1. Genomics, 1998. 54(2): p. 221–30.

50. Anderson, G. R. and D. L. Stoler, *Anoxia, wound healing, VL*30 *elements, and the molecular basis of malignant conversion*. Bioessays, 1993. 15(4): p. 265–72.

51. Anundi, I., et al., *Fructose prevents hypoxic cell death in liver*. Am J Physiol, 1987. 253(3 Pt 1): p. G390–6.

52. Kane, A. B., et al., *ATP depletion and loss of cell integrity in anoxic hepatocytes and silica-treated P*388*D*1 *macrophages*. Am J Physiol, 1985. 249(3 Pt 1): p. C256–66.

53. Pastorino, J. G., et al., *Cyclosporin and carnitine prevent the anoxic death of cultured hepatocytes by inhibiting the mitochondrial permeability transition*. J Biol Chem, 1993. 268(19): p. 13791–8.

54. Kaas GEN, J. M., Orrenius S., *Cyclosporine A protects hepatocytes against prooxidant-induced killing*. Biochem Pharmacol, 1992. 44: p. 1995–2003.

55. Schulte-Frohlinde D, S. C., *Radiolysis of DNA and model systems in the presence of oxygen*, in Oxidative Stress. 1985: Orlando. p. 11–40.

56. Tribble, D. L., T. Y. Aw, and D. P. Jones, *The pathophysiological significance of lipid peroxidation in oxidative cell injury*. Hepatology, 1987. 7(2): p. 377–86.

57. Bisgaard, H. C. and S. S. Thorgeirsson, *Hepatic regeneration. The role of regeneration in pathogenesis of chronic liver diseases*. Clin Lab Med, 1996. 16(2): p. 325–39.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An in vitro method of predicting the association of a test agent with zone 3 necrosis, comprising:

a) determining the level of expression of each of the genes listed in Table 5 in a cell exposed to said test agent;

b) comparing said level of expression to the level of expression of said genes in a control population exposed to at least one control agent;

c) identifying a statistically significant alteration in the level of expression of said genes in the presence of the test agent;

wherein, if present, said alteration indicates that said test agent is predicted to be associated with zone 3 necrosis.

2. The method of claim 1, wherein said level of expression is determined by detecting a gene transcript.

3. An in vitro method of predicting the association of a test agent with zone 3 necrosis, comprising:

a) determining the level of expression of each of the TOXMARKER 42, 59, 65, 66, 71, 76, and 97 genes in a cell exposed to said test agent;

b) comparing said level of expression to the level of expression of said genes in a control population exposed to at least one control agent;

c) identifying a statistically significant alteration in the level of expression of said genes in the presence of the test agent;

wherein, if present, said alteration indicates that said test agent is predicted to be associated with zone 3 necrosis.

4. The method of claim 3, wherein said level of expression is determined by detecting a gene transcript.

5. An in vivo method of predicting the association of a test agent with zone 3 necrosis, comprising:

a) providing a cell from a subject exposed to said test agent;

b) determining the level of expression of each of the TOXMARKER 42, 59, 65, 66, 71, 76, and 97 genes in said cell;

c) comparing said level of expression to the level of expression of said genes in a control population exposed to at least one control agent;

d) identifying a statistically significant alteration in the level of expression of said genes in the presence of the test agent;

wherein, if present, said alteration indicates that said test agent is predicted to be associated with zone 3 necrosis.

6. The method of claim 5, wherein said level of expression is determined by detecting a gene transcript.

7. A method for screening for changes in gene expression associated with a toxic agent, comprising:

a) determining the level of expression of each of the genes listed in Table 5 in a cell exposed to a test agent;

b) comparing said level of expression to the level of expression of said genes in a control population exposed to at least one control agent;

c) identifying a statistically significant alteration in the level of expression of said genes in the presence of the test agent thereby screening for changes in gene expression associated with a toxic agent.

8. A method of predicting the association of a test agent with zone 3 necrosis, comprising:

a) determining the level of expression of TOXMARKER 71 in a cell exposed to said test agent;

b) determining the level of expression of at least one TOXMARKER selected from the group consisting of TOXMARKERS 1–70 and 72–129 in said cell;

c) comparing the level of expression in said cell of TOXMARKER 71 and the TOXMARKER(s) selected in step (b) to the level of expression in a control population exposed to at least one control agent; and d) identifying a statistically significant alteration in the level of expression of said genes in the presence of the test agent, wherein, if present, said alteration indicates that said test agent is predicted to be associated with zone 3 necrosis.

9. The method of claim 8, wherein the TOXMARKERs selected in step (b) are TOXMARKERs 42, 59, 65, 66, 76 and 97.

10. The method of claim 8, wherein said level of expression is determined by detecting a gene transcript.

* * * * *